United States Patent
Shinoda et al.

(10) Patent No.: US 6,884,821 B1
(45) Date of Patent: Apr. 26, 2005

(54) CARBOXYLIC ACID DERIVATIVES AND DRUGS CONTAINING THE SAME

(75) Inventors: Masanobu Shinoda, Ibaraki (JP); Eita Emori, Ibaraki (JP); Fumiyoshi Matsuura, Ibaraki (JP); Toshihiko Kaneko, Ibaraki (JP); Norihito Ohi, Ibaraki (JP); Shunji Kasai, Ibaraki (JP); Hideki Yoshitomi, Ibaraki (JP); Kazuto Yamazaki, Ibaraki (JP); Sadakazu Miyashita, Ibaraki (JP); Taro Hibara, Ibaraki (JP); Takashi Seiki, Ibaraki (JP); Richard Clark, Ibaraki (JP); Hitoshi Harada, Ibaraki (JP)

(73) Assignee: Eisai Co., Ltd., Tokyo (JP)

( * ) Notice: Subject to any disclaimer, the term of this patent is extended or adjusted under 35 U.S.C. 154(b) by 54 days.

(21) Appl. No.: 10/088,916
(22) PCT Filed: Sep. 29, 2000
(86) PCT No.: PCT/JP00/06788
§ 371 (c)(1),
(2), (4) Date: Mar. 25, 2002
(87) PCT Pub. No.: WO01/25181
PCT Pub. Date: Apr. 12, 2001

(30) Foreign Application Priority Data

| Oct. 1, 1999 | (JP) | ................................ 11-282079 |
| Dec. 27, 1999 | (JP) | ................................ 11-369442 |
| Feb. 16, 2000 | (JP) | ................................ 2000-038795 |
| Apr. 6, 2000 | (JP) | ................................ 2000-104260 |

(51) Int. Cl.[7] ............... A61K 31/192; C07C 59/64
(52) U.S. Cl. ............... 514/563; 514/252.1; 514/265; 514/27; 514/307; 514/311; 514/357; 514/365; 514/374; 514/378; 514/399; 514/400; 514/406; 514/469; 514/529; 514/538; 514/557; 544/335; 544/336; 546/147; 546/172; 546/331; 546/335; 548/204; 548/214; 548/236; 548/335.5; 548/341.1; 548/375.1; 548/376.1; 549/467; 549/471; 560/12; 560/42; 560/125; 560/126; 562/430; 562/451; 562/507; 562/508
(58) Field of Search ............... 562/442, 451, 562/430, 507, 508; 564/155, 158; 514/563, 616; 560/12, 42, 125, 126

(56) References Cited

U.S. PATENT DOCUMENTS 5,773,646 A * 6/1998 Chandrakumar et al. ... 562/439

6,528,525 B1 3/2003 Yanagisawa et al. ....... 514/307

FOREIGN PATENT DOCUMENTS

| EP | 516069 A1 | 12/1992 |
| EP | 763524 A1 | 3/1997 |
| EP | 911025 A1 | 4/1999 |
| GB | 1436502 A | 5/1976 |
| JP | 9048771 A | 2/1997 |
| JP | WO 99/04815 | 2/1999 |
| WO | 96/31492 A1 | 10/1996 |
| WO | 97/36862 A1 | 10/1997 |
| WO | 99/19300 A1 | 4/1999 |
| WO | 99/20275 A1 | 4/1999 |

OTHER PUBLICATIONS

Chandrakumar et al., Chemical Abstracts, vol. 129:108912, 1998.*
English abstract of WO99/18066 (Apr. 15, 1999).
Lehmann et al., *The Journal of Biological Chemistry*, vol. 270, No. 22, Jun. 2, 1995, pp. 12953–12956.
Hulin et al., *Current Pharmaceutical Design*, vol. 2, No. 1, 1996, pp. 85–102.
Buckle et al., *Bioorganic & Medicinal Chemistry Letters*, vol. 6, No. 17, pp. 2121–2126, 1996.
Bastie et al., *The Journal of Biological Chemistry*, vol. 274, No. 31, Jul. 30, 1999. pp. 21920–21925.

* cited by examiner

*Primary Examiner*—Richard L. Raymond
(74) *Attorney, Agent, or Firm*—Birch, Stewart, Kolasch & Birch, LLP

(57) ABSTRACT

Novel carboxylic acid derivatives of general formula (I), salts of the same, esters thereof, or hydrates of them, which are useful as insulin resistance improvers; and drugs containing the derivatives as the active ingredient. In said formula, $R^1$ is hydrogen, hydroxyl, alkyl, or the like; L is a single bond, a double bond, alkylene, or the like; M is a single bond, alkylene, or the like; T is a single bond, alkylene, or the like; W is carboxyl, $-CON(R^{W1})R^{W2}$, or the like; ═══ represents a single or double bond; X is oxygen, alkenylene, or the like; Y is an aromatic hydrocarbon group which may contain a heteroatom, or the like; and Z is an aromatic hydrocarbon group which may contain a heteroatom.

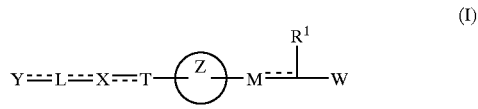

(I)

19 Claims, No Drawings

US 6,884,821 B1

CARBOXYLIC ACID DERIVATIVES AND DRUGS CONTAINING THE SAME

This application is the national phase under 35 U.S.C. § 371 of PCT International Application No. PCT/JP00/06788 which has an International filing date of Sep. 29, 2000, which designated the United States of America.

TECHNICAL FIELD

The present invention relates to a novel carboxylic acid compound useful for prevention or treatment of hyperglycemia and hyperlipemia, a salt thereof, an ester thereof or a hydrate of them, and to a medicament comprising the compound.

PRIOR ART

Diabetes mellitus refers to a durable hyperglycemic condition attributable to the absolute or relative shortage of intrinsic insulin (blood sugar-depressing hormone produced and secreted from Langerhans islet β cells in the pancreas), and in this disease, metabolic abnormalities caused by this condition appear as various morbid states.

Diabetes mellitus is classified roughly into insulin dependent diabetes mellitus (IDDM) that is diabetes mellitus of first type, for treatment of which insulin administration is absolutely necessary, non insulin dependent diabetes mellitus (NIDDM) that is diabetes mellitus of second type, and other diabetes mellitus (secondary diabetes mellitus; diabetes mellitus occurs as one symptom of other diseases).

In particular, as life-style is modernized, NIDDM is rapidly increased due to overeating and lack of exercise, thus causing a social problem. While IDDM occurs mainly in infants, NIDDM occurs in middle-aged or elderly persons, to account for the majority of diabetes mellitus in Japan. It is said that NIDDM occurs owing to insulin function-suppressing factors (insulin resistance) such as overeating, lack of exercise, obesity and stress in addition to hereditary factors.

Since excessive intake of calories and obesity resulting from lack of exercise are related to diabetes mellitus as described above, the therapy is based on 3 kinds of therapies, that is, dietary therapy, exercise therapy and chemotherapy.

However, there are not a few cases where dietary therapy and exercise therapy are hardly to conduct because of an increase in the number of persons of advanced age in this aging society in recent years.

In chemotherapy of NIDDM, sulfonyl urea (SU) medicines such as tolbutamide, chlorpropamide and tolazamide and biguanide (BG) medicines such as metformin and buformin have been used as oral blood sugar depressants, but the morbid state of NIDDM is characterized by insulin deficiency and insulin resistance, and it cannot be said that the SU medicines stimulating insulin secretion from pancreatic β cells are effective therapeutic medicines for the insulin resistance of NIDDM because the sufficient insulin secretion induced by the medicines cannot be well controlled in a target organ, thus permitting high blood sugar levels. Further, the BG medicines may permit the onset of lactic acid acidosis, so use of such medicines is limited to a certain extent. Further, these chemicals often caused severe low blood sugar as a side effect.

To solve these problems, development of chemicals with a new working mechanism is advancing, and thiazolidine derivatives such as Troglitazone, Pioglitazone and Rosiglitazone are called insulin-resistant improvers, and these chemicals recently attract attention because they can ameliorate insulin resistance (or enhance the action of insulin) and lower blood sugar without promoting secretion of insulin from the pancreas.

It has been revealed that these thiazolidine-type chemicals are related to differentiation of adipocytes, and exhibit their action via an intranuclear receptor PPARγ (peroxisome proliferator-activated receptor gamma: a transcriptional factor important for differentiation of adipocytes) (J. Biol. Chem., 270, 12953–12956, 1995). By the differentiation of pre-adipocytes, immature and small adipocytes with less secretion of TNFα, FFA and leptin are increased thus resulting in amelioration of insulin resistance.

Thiazolidine derivatives such as the above Troglitazone, Pioglitazone and Rosiglitazone also act as agonists for PPARγ, to exhibit the effect of ameliorating insulin resistance.

Besides PPARγ, PPAR subtypes such as α, β etc. have been found, any of which regulate expression of genes involved in lipid metabolism. The homology of each subtype among different biological species is higher than the homology of these subtypes in the same species, and with respect to distribution of each subtype in tissues, PPARγ is located substantially in adipose tissues while PPARα occurs mainly in the liver, heart and kidney, and therefore it was considered that each subtype has an independent function. In recent years, it has been revealed that PPARγ mainly mediates lipid anabolism by promoting expression of a group of genes for LPL, acyl-CoA carboxylase, GPDH etc. to convert sugar into lipid and storing the lipid, while PPARα mediates lipid catabolism by regulating expression of a gene group involved in intake of fatty acids into cells and oxidation thereof to decompose lipid.

As thiazolidine derivatives acting as PPARγ and α dual agonists, compounds disclosed in e.g. JP-A 9-48771 are known.

Further, some compounds are known as insulin-resistant improvers having a carboxylic acid moiety in their structure (Current Pharmaceutical Design, 2, No. 1, pp. 85–102, 1996; Bioorganic & Medicinal Chemistry Letters, 6, No. 17, pp. 2121–2126, 1996).

However, it has been reported that some chemicals acting as PPARγ agonists cause hepatic damage and thus should be carefully used, so chemicals satisfactory in both therapeutic effects and side effects such as toxicity are still not obtained.

Further, compounds having a thiazolidine moiety replaced by a carboxylic acid derivative are merely presented in literatures and not marketed. Further, there is no report showing that such compounds can be used as PPARγ and α dual agonists, and as a matter of course, their γ, α and β triple agonist action is not known. However, it is also estimated that the toxicity of PPARγ agonists described above is the unique one derived from the thiazolidine moiety, and if a compound exhibiting the above action with a new structure in place of the above structure can be found, the compound can be expected to solve the problem of toxicity, and is thus very useful.

The conventional chemicals are still unsatisfactory in respect of neutral fat (triglyceride (TG)) related closely to arteriosclerosis.

Further, the action gf PPARβ to induce differentiation of adipocytes is known (J. Biol. Chem., 274, No. 31, pp. 21920–21925), and by this action, cholesterol levels are reported to be lowered (WO9904815), and if a compound having an agonist action for this subtype can be found, this compound can be expected to exhibit a higher activity than that of the conventional insulin-resistant improvers and to reduce side effects such as hepatic toxicity.

From the foregoing aspects, there is demand for development of excellent chemicals.

DISCLOSURE OF INVENTION

For the purpose of providing a medicament effective in prevention or treatment of hyperglycemia, which satisfies these various requirements, the present inventors made extensive study and, as a result, they found that a carboxylic acid derivative having a novel structure has an excellent anti-hyperglycemia and anti-hyperlipemia action, thus completing the present invention.

That is, the present invention relates to a carboxylic acid derivative represented by the formula:

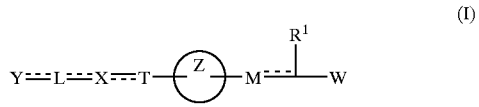
(I)

(wherein $R^1$ represents hydrogen atom, hydroxyl group or a $C_{1-6}$ alkyl group, $C_{1-6}$ alkoxy group, $C_{1-6}$ alkylthio group, $C_{1-6}$ hydroxyalkyl group, $C_{1-6}$ hydroxyalkoxy group, $C_{1-6}$ hydroxyalkylthio group, $C_{1-6}$ aminoalkyl group, $C_{1-6}$ aminoalkoxy group, $C_{1-6}$ aminoalkylthio group, $C_{1-6}$ halogenated alkyl group, $C_{1-6}$ halogenated alkoxy group, $C_{1-6}$ halogenated alkylthio group, $C_{2-12}$ alkoxyalkyl group, $C_{2-12}$ alkoxyalkoxy group, $C_{2-12}$ alkoxyalkylthio group, $C_{3-7}$ cycyloalkyl group, $C_{3-7}$ cycloalkyloxy group, $C_{3-7}$ cycloalkylthio group, $C_{2-6}$ alkenyl group, $C_{2-6}$ alkenyloxy group, $C_{2-6}$ alkenylthio group, $C_{2-6}$ alkynyl group, $C_{2-6}$ alkynyloxy group, $C_{2-6}$ alkynylthio group, $C_{6-12}$ aryl group, $C_{6-12}$ aryloxy group, $C_{6-12}$ arylthio group, $C_{7-18}$ alkylaryl group, $C_{7-18}$ alkylaryloxy group, $C_{7-18}$ alkylarylthio group, $C_{7-18}$ aralkyl group, $C_{7-18}$ aralkyloxy group or $C_{7-18}$ aralkylthio group, each of which may have one or more substituents; L represents a single or double bond or a $C_{1-6}$ alkylene group, $C_{2-6}$ alkenylene group or $C_{2-6}$ alkynylene group, each of which may have one or more substituents; M represents a single bond or a $C_{1-6}$ alkylene group, $C_{2-6}$ alkenylene group or $C_{2-6}$ alkynylene group, each of which may have one or more substituents; T represents a single bond or a $C_{1-3}$ alkylene group, $C_{2-3}$ alkenylene group or $C_{2-3}$ alkynylene group, each of which may have one or more substituents; W represents a 2,4-dioxothiazolidine-5-yl group, 2,4-dioxothiazolidine-5-ylidene group, carboxyl group or a group represented by —CON($R^{w1}$)$R^{w2}$ (wherein $R^{w1}$ and $R^{w2}$ are the same as or different from each other and each represents hydrogen atom, formyl group or a $C_{1-6}$ alkyl group, $C_{2-7}$ aliphatic acyl group or $C_{7-19}$ aromatic acyl group, each of which may have one or more substituents), provided that the case where T is a single bond; and W is 2,4-dioxothiazolidine-5-yl group or 2,4-dioxothiazolidine-5-ylidene group in the above definition is excluded; === represents a single or double bond; X represents an oxygen atom, a $C_{2-6}$ alkenylene group which may have one or more substituents, hydroxymethylene group, or a group represented by the formula —CQ— (wherein Q represents oxygen atom or sulfur atom), —CQNR$^x$— (wherein Q represents the same group as defined above; $R^x$ represents hydrogen atom, formyl group or a $C_{1-6}$ alkyl group, $C_{2-7}$ aliphatic acyl group or $C_{7-19}$ aromatic acyl group, each of which may have one or more substituents), —NR$^x$CQ— (wherein Q and $R^x$ each represent the same group as defined above), —SO$_2$NR$^x$— (wherein R represents the same group as defined above), —NR$^x$SO$_2$— (wherein $R^x$ represents the same group as defined above) or —NR$^{x1}$CQNR$^{x2}$— (wherein Q represents the same group as defined above; and $R^{x1}$ and $R^{x2}$ are the same as or different from each other and each represents hydrogen atom, formyl group or a $C_{1-6}$ alkyl group, $C_{2-7}$ aliphatic acyl group or $C_{7-19}$ aromatic acyl group, each of which may have one or more substituents), provided that the case where T is a single bond; and X is oxygen atom in the above definition is excluded; Y represents a $C_{5-12}$ aromatic hydrocarbon group or $C_{3-7}$ alicyclic hydrocarbon group which may have one or more substituents and which may further have one or more heteroatoms; and ring Z represents a $C_{5-6}$ aromatic hydrocarbon group which may have 0 to 4 substituents and which may have one or more heteroatoms, provided that a group represented by the formula:

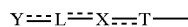

(wherein each symbol has the same meaning as defined above) and a group represented by the formula:

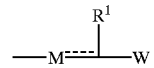

(wherein each symbol has the same meaning as defined above) are bound to each other via 3 atoms on ring Z), a salt thereof, an ester thereof or a hydrate of them, and to a medicament comprising it. Specifically, it relates to the medicament which is based on PPAR α and γ dual agonism; the medicament based on PPAR α, β and γ triple agonism; the medicament which is an insulin-resistant improver; the medicament which is an agent for preventing or treating diabetes; and the medicament which is an agent for preventing or treating X syndromes.

The present invention provides a method for preventing, treating or ameliorating diseases against which PPAR α and γ dual agonism or PPAR α, β and γ triple agonism is effective, by administering a pharmacologically effective amount of the compound represented by the above formula (I), a salt thereof, an ester thereof or a hydrate of them to a patient. Further, the present invention also provides use of the compound represented by the above formula (I), a salt thereof, an ester thereof. or a hydrate of them, for producing an agent for preventing, treating or ameliorating diseases against which PPAR α and γ dual agonism or PPAR α, β and γ triple agonism is effective.

Hereinafter, the present invention is described in detail.

The present invention is as described above, and it is preferable that in the formula (I), W is a carboxylic acid for the compound of the present invention, a salt thereof, an ester thereof or a hydrate of them; in the formula (I), $R^1$ is a $C_{1-6}$ alkyl group or $C_{1-6}$ alkoxy group, each of which may have one or more substituents, for the carboxylic acid derivative of the present invention, a salt thereof, an ester thereof or a hydrate of them; in the formula (I), ring Z is a benzene ring which may further have 0 to 4 substituents, for the carboxylic acid derivative of the present invention, a salt thereof, an ester thereof or a hydrate of them; in the formula (I), X is a group represented by —CQNR$^x$— (wherein Q and $R^x$ each represent the same group as defined above) or —NR$^x$CQ— (wherein Q and $R^x$ each represent the same group as defined above), for the carboxylic acid derivative of the present invention, a salt thereof, an ester thereof or a hydrate of them; in the formula (I), Y is a $C_{5-12}$ aromatic hydrocarbon group which may have one or more substituents for the carboxylic acid derivative of the present invention, a salt thereof, an ester thereof or a hydrate of them; in the formula (I), L or M is a $C_{1-6}$ alkylene group for the carboxylic acid derivative of the present invention, a salt thereof, an ester thereof or a hydrate of them; in the formula (I), $R^1$ is a $C_{1-6}$ alkyl group or $C_{1-6}$ alkoxy group, each of which may have one or more substituents, and ring Z is a benzene ring which may further have 0 to 4 substituents, for the carboxylic acid derivative of the present invention, a salt thereof, an ester thereof or a hydrate of them; and in the formula (I), X is a group represented by —CQNR$^x$— (wherein Q and R$^x$ each represent the same group as defined above) or —NR$^x$CQ— (wherein Q and R$^x$ each represent the same group as defined above), and Y is a $C_{5-12}$ aromatic hydrocarbon group which may have one or more substituents, for the carboxylic acid derivative of the present invention, a salt thereof, an ester thereof or a hydrate of them; and it is more preferable that in the formula (I), $R^1$ represents a $C_{1-6}$ alkyl group or $C_{1-6}$ alkoxy group, each of which may have one or more substituent, ring Z is a benzene ring which may further have 0 to 4 substituents, and X is a group represented by —CQNR$^x$— (wherein Q and R$^x$ each represent the same group as defined above) or —NR$^x$CQ— (wherein Q and R$^x$ each represent the same group as defined above), and Y is a $C_{5-12}$ aromatic hydrocarbon group which may have one or more substituents, for the carboxylic acid derivative of the present invention, a salt thereof, an ester thereof or a hydrate of them.

In this specification, the structural formulae of the compounds may, for convenience' sake, indicate a certain isomer, but the present invention encompasses every possible isomer such as geometric isomer, optical isomer based on asymmetric carbon, stereoisomer and tautomer, which can occur in the structures of the compounds of the present invention, and mixtures of these isomers, and therefore, the compounds of the present invention are not limited by the formulae shown for convenience' sake.

Now, the terms used in this specification are described in detail.

When $R^1$, W, $R^x$, $R^{x1}$ and $R^{x2}$ each represents a $C_{1-6}$ alkyl group which may have one or more substituents, the alkyl group means a $C_{1-6}$ linear or branched alkyl group, and specific examples thereof include methyl group, ethyl group, n-propyl group, i-propyl group, n-butyl group, i-butyl group, sec-butyl group, t-butyl group, n-pentyl group, i-pentyl group, sec-pentyl group, t-pentyl group, neopentyl group, 1-methylbutyl group, 2-methylbutyl group, 1,1-dimethylpropyl group, 1,2-dimethylpropyl group, n-hexyl group, i-hexyl group, 1-methylpentyl group, 2-methylpentyl group, 3-methylpentyl group, 1,1-dimethylbutyl group, 1,2-dimethylbutyl group, 2,2-dimethylbutyl group, 1,3-dimethylbutyl group, 2,3-dimethylbutyl group, 3,3-dimethylbutyl group, 1-ethylbutyl group, 2-ethylbutyl group, 1,1,2-trimethylpropyl group, 1,2,2-trimethylpropyl group, 1-ethyl-1-methylpropyl group and 1-ethyl-2-methylpropyl group, preferably methyl group, ethyl group, n-propyl group, i-propyl group, n-butyl group, i-butyl group, sec-butyl group, t-butyl group, n-pentyl group, i-pentyl group, sec-pentyl group, t-pentyl group, neopentyl group, 1-methylbutyl group, 2-methylbutyl group, 1,1-dimethylpropyl group, 1,2-dimethylpropyl group, n-hexyl group and i-hexyl group, more preferably methyl group, ethyl group, n-propyl group, i-propyl group, n-butyl group, i-butyl group, sec-butyl group, t-butyl group, n-pentyl group, i-pentyl group, sec-pentyl group, t-pentyl group, neopentyl group, 1-methylbutyl group, 2-methylbutyl group, 1,1-dimethylpropyl group and 1,2-dimethylpropyl group, further preferably methyl group, ethyl group, n-propyl group, i-propyl group, n-butyl group, i-butyl group, sec-butyl group and t-butyl group, and most preferably methyl group, ethyl group, n-propyl group and i-propyl group.

Herein, the phrase "which may have a substituent" specifically means that the group may be substituted with a substituent such as hydroxyl group; thiol group; nitro group; morpholino group; thiomorpholino group; a halogen atom such as fluorine atom, chlorine atom, bromine atom and iodine atom; nitrile group; azide group; formyl group; alkyl group such as methyl group, ethyl group, propyl group, isopropyl group and butyl group; alkenyl group such as vinyl group, allyl group and propenyl group; alkynyl group such as ethynyl group, butynyl group and propargyl group; alkoxy group such as methoxy group, ethoxy group, propoxy group and butoxy group corresponding to the lower alkyl group; halogenoalkyl group such as fluoromethyl group, difluoromethyl group, trifluoromethyl group and fluoroethyl group; hydroxyalkyl group such as hydroxymethyl group, hydroxyethyl group and hydroxypropyl group; guanidino group; formimidoyl group; acetoimidoyl group; carbamoyl group; thiocarbamoyl group; carbamoyl alkyl group such as carbamoyl methyl group and carbamoyl ethyl group; alkyl carbamoyl group such as methyl carbamoyl group and dimethyl carbamoyl group; carbamide group; alkanoyl group such as acetyl group; amino group; alkyl amino group such as methyl amino group, ethyl amino group and isopropyl amino group; dialkyl amino group such as dimethyl amino group, methyl ethyl amino group and diethyl amino group; amino alkyl group such as amino methyl group, amino ethyl group and amino propyl group; carboxy group; alkoxycarbonyl group such as methoxycarbonyl group, ethoxycarbonyl group and propoxycarbonyl group; alkoxycarbonyl alkyl group such as methoxycarbonyl methyl group, ethoxycarbonyl methyl group, propoxycarbonyl methyl group, methoxycarbonyl ethyl group, ethoxycarbonyl ethyl group and propoxycarbonyl ethyl group; alkyloxyalkyl group such as methyloxymethyl group, methyloxyethyl group, ethyloxymethyl group and ethyloxyethyl group; alkylthioalkyl group such as methylthiomethyl group, methylthioethyl group, ethylthiomethyl group and ethylthioethyl group; aminoalkyl aminoalkyl group such as aminomethyl aminomethyl group and aminoethyl aminomethyl group; alkyl carbonyloxy group such as methyl carbonyloxy group, ethyl carbonyloxy group and isopropyl carbonyloxy group; arylalkoxy alkoxy alkyl group such as oxymethyl group and benzyloxy ethyloxy ethyl group; hydroxyalkoxyalkyl group such as hydroxyethyloxymethyl group and hydroxyethyloxyethyl group; arylalkoxyalkyl group such as benzyloxymethyl group, benzyloxyethyl group and benzyloxypropyl group; quaternary ammonio group such as trimethyl ammonio group, methyl ethyl methyl ammonio group and triethyl ammonio group; cycloalkyl group such as cyclopropyl group, cyclobutyl group, cyclopentyl group and cyclohexyl group; cycloalkenyl group such as cyclopropenyl group, cyclobutenyl group, cyclopentenyl group and cylohexenyl group; aryl group such as phenyl group, pyridinyl group, thienyl group, furyl group and pyrolyl group; alkyl thio group such as methyl thio group, ethyl thio group, propyl thio group and butyl thio group; aryl thio group such as phenyl thio group, pyridinyl thio group, thienyl thio group, furyl thio group and pyrolyl thio group; aryl lower alkyl group such as benzyl group, trityl group and dimethoxy trityl group; substituted sulfonyl group such as sulfonyl group, mesyl group and p-toluene sulfonyl group; aryloyl group such as benzoyl group; halogenoaryl group such as fluorophenyl group and bromophenyl group; and oxyalkoxy group such as methylene dioxy group.

The phrase "which may have one or more substituents" means that the group may have one or more of these groups in an arbitrary combination, and includes e.g. an alkyl group, alkenyl group, alkynyl group and alkoxy group substituted with hydroxyl group, thiol group, nitro group, morpholino group, thiomorpholino group, a halogen atom, nitrile group, azide group, formyl group, amino group, alkyl amino group, dialkyl amino group, carbamoyl group and sulfonyl group.

Hereinafter, the phrases "which may have a substituent" and "which may have one or more substituents" in the present invention have the meanings as defined above.

When $R^1$ represents a $C_{1-6}$ alkoxy group which may have one or more substituents, the alkoxy group means a $C_{1-6}$ linear or branched alkoxy group and refers to a group having an oxygen atom bound to the end of the alkyl group. Specific examples thereof include methoxy group, ethoxy group, n-propoxy group, i-propoxy group, n-butoxy group, i-butoxy group, sec-butoxy group, t-butoxy group, n-pentyloxy group, i-pentyloxy group, sec-pentyloxy group, t-pentyloxy group, neopentyloxy group, 1-methylbutoxy group, 2-methylbutoxy group, 1,1-dimethylpropoxy group, 1,2-dimethylpropoxy group, n-hexyloxy group, i-hexyloxy group, 1-methylpentyloxy group, 2-methylpentyloxy group, 3-methylpentyloxy group, 1,1-dimethylbutoxy group, 1,2-dimethylbutoxy group, 2,2-dimethylbutoxy group, 1,3-dimethylbutoxy group, 2,3-dimethylbutoxy group, 3,3-dimethylbutoxy group, 1-ethylbutoxy group, 2-ethylbutoxy group, 1,1,2-trimethylpropoxy group, 1,2,2-trimethylpropoxy group, 1-ethyl-1-methylpropoxy group and 1-ethyl-2-methylpropoxy group; preferably methoxy group, ethoxy group, n-propoxy group, i-propoxy group, n-butoxy group, i-butoxy group, sec-butoxy group, t-butoxy group, n-pentyloxy group, i-pentyloxy group, sec-pentyloxy group, t-pentyloxy group, neopentyloxy group, 1-methylbutoxy group, 2-methylbutoxy group, 1,1-dimethylpropoxy group, 1,2-dimethylpropoxy group, n-hexyloxy group and i-hexyloxy group; more preferably methoxy group, ethoxy group, n-propoxy group, i-propoxy group, n-butoxy group, i-butoxy group, sec-butoxy group, t-butoxy group, n-pentyloxy group, i-pentyloxy group, sec-pentyloxy group, t-pentyloxy group, neopentyloxy group, 1-methylbutoxy group, 2-methylbutoxy group, 1,1-dimethylpropoxy group and 1,2-dimethylpropoxy group; further preferably methoxy group, ethoxy group, n-propoxy group, i-propoxy group, n-butoxy group, i-butoxy group, sec-butoxy group and t-butoxy group, and most preferably a methoxy group, ethoxy group, n-propoxy group and i-propoxy group.

When $R^1$ represents a $C_{1-6}$ alkylthio group which may have one or more substituents, the alkylthio group represents a $C_{1-6}$ linear or branched alkylthio group and refers to a group having a sulfur atom bound to the end of the alkyl group. Specific examples thereof include methylthio group, ethylthio group, n-propylthio group, i-propylthio group, n-propylthio group, i-butylthio group, sec-butylthio group, t-butylthio group, n-pentylthio group, i-pentylthio group, sec-pentylthio group, t-pentylthio group, neopentylthio group, 1-methylbutylthio group, 2-methylbutylthio group, 1,1-dimethylpropylthio group, 1,2-dimethylpropylthio group, n-hexylthio group, i-hexylthio group, 1-methylpentylthio group, 2-methylpentylthio group, 3-methylpentylthio group, 1,1-dimethylbutylthio group, 1,2-dimethylbutylthio group, 2,2-dimethylbutylthio group, 1,3-dimethylbutylthio group, 2,3-dimethylbutylthio group, 3,3-dimethylbutylthio group, 1-ethylbutylthio group, 2-ethylbutylthio group, 1,1,2-trimethylpropylthio group, 1,2,2-trimethylpropylthio group, 1-ethyl-1-methylpropylthio group and 1-ethyl-2-methylpropylthio group; preferably methylthio group, ethylthio group, n-propylthio group, i-propylthio group, n-butylthio group, i-butylthio group, sec-butylthio group, t-butylthio group, n-pentylthio group, i-pentylthio group, sec-pentylthio group, t-pentylthio group, neopentylthio group, 1-methylbutylthio group, 2-methylbutylthio group, 1,1-dimethylpropylthio group, 1,2-dimethylpropylthio group, n-hexylthio group and i-hexylthio group; more preferably methylthio group, ethylthio group, n-propylthio group, i-propylthio group, n-butylthio group, i-butylthio group, sec-butylthio group, t-butylthio group, n-pentylthio group, i-pentylthio group, sec-pentylthio group, t-pentylthio group, neopentylthio group, 1-methylbutylthio group, 2-methylbutylthio group, 1,1-dimethylpropylthio group and 1,2-dimethylpropylthio group; further preferably methylthio group, ethylthio group, n-propylthio group, i-propylthio group, n-butylthio group, i-butylthio group, sec-butylthio group and t-butylthio group; and most preferably a methylthio group, ethylthio group, n-propylthio group and i-propylthio group.

When $R^1$ represents a $C_{1-6}$ hydroxyalkyl group which may have one or more substituents, the hydroxyalkyl group represents a group having the $C_{1-6}$ linear or branched alkyl group substituted at a substitutable site with a hydroxy group. Specific examples thereof include hydroxymethyl group, 2-hydroxyethyl group and 1-hydroxyethyl group.

Similarly, when $R^1$ represents a $C_{1-6}$ hydroxyalkoxy group which may have one or more substituents, the hydroxyalkoxy group represents a group having the $C_{1-6}$ linear or branched alkoxy group substituted at a substitutable site with a hydroxy group. Specific examples thereof include hydroxymethoxy group, 2-hydroxyethoxy group and 1-hydroxyethoxy group.

Similarly, when $R^1$ represents a $C_{1-6}$ hydroxyalkylthio group which may have one or more substituents, the hydroxyalkylthio group represents a group having the $C_{1-6}$ linear or branched alkylthio group substituted at a substitutable site with a hydroxy group. Specific examples thereof include hydroxymethylthio group, 2-hydroxyethylthio group and 1-hydroxyethylthio group.

When $R^1$ represents a $C_{1-6}$ aminoalkyl group which may have one or more substituents, the aminoalkyl group represents a group having the $C_{1-6}$ linear or branched alkyl group substituted at a substitutable site with an amino group. Specific examples thereof include aminomethyl group, 2-aminoethyl group and 1-aminoethyl group.

Similarly, when $R^1$ represents a $C_{1-6}$ aminoalkoxy group which may have one or more substituents, the aminoalkoxy group represents a group having the $C_{1-6}$ linear or branched alkoxy group substituted at a substitutable site with an amino group. Specific examples thereof include aminomethoxy group, 2-aminoethoxy group and 1-aminoethoxy group.

Similarly, when $R^1$ represents a $C_{1-6}$ aminoalkylthio group which may have one or more substituents, the aminoalkylthio group represents a group having the $C_{1-6}$ linear or branched alkylthio group substituted at a substitutable site with an amino group. Specific examples thereof include aminomethylthio group, 2-aminoethylthio group and 1-aminoethylthio group.

When $R^1$ represents a $C_{1-6}$ halogenated alkyl group which may have one or more substituents, the halogenated alkyl group represents a group having the $C_{1-6}$ linear or branched alkyl group substituted at substitutable sites with one or more halogen atoms. Herein, the halogen atoms refer to fluorine atom, chlorine atom, bromine atom and iodine atom. Specific examples of such a group include fluoromethyl group, trifluoromethyl group, 2-fluoroethyl group and 1-fluoroethyl group.

Similarly, when $R^1$ represents a $C_{1-6}$ halogenated alkoxy group which may have one or more substituents, the halogenated alkoxy group represents a group having the $C_{1-6}$ linear or branched alkoxy group substituted at substitutable sites with one or more halogen atoms. Specific examples thereof include fluoromethoxy group, trifluoromethoxy group, 2-fluoroethoxy group and 1-fluoroethoxy group.

Similarly, when $R^1$ represents a $C_{1-6}$ halogenated alkylthio group which may have one or more substituents, the halogenated alkylthio group represents a group having the $C_{1-6}$ linear or branched alkylthio group substituted at substitutable sites with one or more halogen atoms. Specific examples thereof include fluoromethylthio group, trifluoromethylthio group, 2-fluoroethylthio group and 1-fluoroethylthio group.

When $R^1$ represents a $C_{2-12}$ alkoxyalkyl group which may have one or more substituents, the alkoxyalkyl group represents a group having the $C_{1-6}$ linear or branched alkyl group substituted at a substitutable site with the $C_{1-6}$ linear or branched alkoxy group. Specific examples thereof include methoxymethyl group, ethoxymethyl group, 1-methoxyethyl group, 2-methoxyethyl group, 1-ethoxyethyl group and 2-ethoxyethyl group.

Similarly, when $R^1$ represents a $C_{2-12}$ alkoxyalkoxy group which may have one or more substituents, the alkoxyalkoxy group represents a group having the $C_{1-6}$ linear or branched alkoxy group substituted at a substitutable site with the $C_{1-6}$ linear or branched alkoxy group. Specific examples thereof include methoxymethoxy group, ethoxymethoxy group, 1-methoxyethoxy group, 2-methoxyethoxy group, 1-ethoxyethoxy group and 2-ethoxyethoxy group.

Similarly, when $R^1$ represents a $C_{2-12}$ alkoxyalkylthio group which may have one or more substituents, the alkoxyalkylthio group represents a group having the $C_{1-6}$ linear or branched alkylthio group substituted at a substitutable site with the $C_{1-6}$ linear or branched alkoxy group. Specific examples thereof include methoxymethylthio group, ethoxymethylthio group, 1-methoxyethylthio group, 2-methoxyethylthio group, 1-ethoxyethylthio group and 2-ethoxyethylthio group.

When $R^1$ represents a $C_{3-7}$ cycloalkyl group which may have one or more substituents, the cycloalkyl group means a $C_{3-7}$ cyclic alkyl group, and specific examples thereof include cyclopropyl group, cyclobutyl group, cyclopentyl group, cyclohexyl group and cycloheptyl group.

Similarly, when $R^1$ represents a $C_{3-7}$ cycloalkyloxy group which may have one or more substituents, the cycloalkyloxy group refers to a group having an oxygen atom bound to the end of the $C_{3-7}$ cyclic alkyl group, and specific examples thereof include cyclopropyloxy group, cyclobutyloxy group, cyclopentyloxy group, cyclohexyloxy group and cycloheptyloxy group.

Similarly, when $R^1$ represents a $C_{3-7}$ cycloalkylthio group which may have one or more substituents, the cycloalkylthio group refers to a group having a sulfur atom bound to the end of the $C_{3-7}$ cycloalkyl group, and specific examples thereof include cyclopropylthio group, cyclobutylthio group, cyclopentylthio group, cyclohexylthio group and cycloheptylthio group.

When $R^1$ represents a $C_{2-6}$ alkenyl group which may have one or more substituents, the alkenyl group is a $C_{2-6}$ linear or branched alkenyl group and refers to a compound residue having a double bond in the alkyl group containing 2 or more carbon atoms. Specific examples of there of include ethenyl group, 1-propene-1-yl group, 2-propene-1-yl group, 3-propene-1-yl group, 1-butene-1-yl group, 1-butene-2-yl group, 1-butene-3-yl group, 1-butene-4-yl group, 2-butene-1-yl group, 2-butene-2-yl group, 1-methyl-1-propene-1-yl group, 2-methyl-1-propene-1-yl group, 1-methyl-2-propene-1-yl group, 2-methyl-2-propene-1-yl group, 1-methyl-1-butene-1-yl group, 2-methyl-1-butene-1-yl, 3-methyl-1-butene-1-yl group, 1-methyl-2-butene-1-yl group, 2-methyl-2-butene-1-yl group, 3-methyl-2-butene-1-yl group, 1-methyl-3-butene-1-yl group, 2-methyl-3-butene-1-yl group, 3-methyl-3-butene-1-yl group, 1-ethyl-1-butene-1-yl group, 2-ethyl-1-butene-1-yl group, 3-ethyl-1-butene-1-yl group, 1-ethyl-2-butene-1-yl group, 2-ethyl-2-butene-1-yl group, 3-ethyl-2-butene-1-yl group, 1-ethyl-3-butene-1-yl group, 2-ethyl-3-butene-1-yl group, 3-ethyl-3-butene-1-yl group, 1,1-dimethyl-1-butene-1-yl group; 1,2-dimethyl-1-butene-1-yl group, 1,3-dimethyl-1-butene-1-yl group, 2,2-dimethyl-1-butene-1-yl group, 3,3-dimethyl-1-butene-1-yl group, 1,1-dimethyl-2-butene-1-yl group, 1,2-dimethyl-2-butene-1-yl group, 1,3-dimethyl-2-butene-1-yl group, 2,2-dimethyl-2-butene-1-yl group, 3,3-dimethyl-2-butene-1-yl group, 1,1-dimethyl-3-butene-1-yl group, 1,2-dimethyl-3-butene-1-yl group, 1,3-dimethyl-3-butene-1-yl group, 2,2-dimethyl-3-butene-1-yl group, 3,3-dimethyl-3-butene-1-yl group, 1-pentene-1-yl group, 2-pentene-1-yl group, 3-pentene-1-yl group, 4-pentene-1-yl group, 1-pentene-2-yl group, 2-pentene-2-yl group, 3-pentene-2-yl group, 4-pentene-2-yl group, 1-pentene-3-yl group, 2-pentene-3-yl group, 1-pentene-1-yl group, 2-pentene-1-yl group, 3-pentene-1-yl group, 4-pentene-1-yl group, 1-pentene-2-yl group, 2-pentene-2-yl group, 3-pentene-2-yl group, 4-pentene-2-yl group, 1-pentene-3-yl group, 2-pentene-3-yl group, 1-methyl-1-pentene-1-yl group, 2-methyl-1-pentene-1-yl group, 3-methyl-1-pentene-1-yl group, 4-methyl-1-pentene-1-yl group, 1-methyl-2-pentene-1-yl group, 2-methyl-2-pentene-1-yl group, 3-methyl-2-pentene-1-yl group, 4-methyl-2-pentene-1-yl group, 1-methyl-3-pentene-1-yl group, 2-methyl-3-pentene-1-yl group, 3-methyl-3-pentene-1-yl group, 4-methyl-3-pentene-1-yl group, 1-methyl-4-pentene-1-yl group, 2-methyl-4-pentene-1-yl group, 3-methyl-4-pentene-1-yl group, 4-methyl-4-pentene-1-yl group, 1-methyl-1-pentene-2-yl group, 2-methyl-1-pentene-2-yl group, 3-methyl-1-pentene-2-yl group, 4-methyl-1-pentene-2-yl group, 1-methyl-2-pentene-2-yl group, 2-methyl-2-pentene-2-yl group, 3-methyl-2-pentene-2-yl group, 4-methyl-2-pentene-2-yl group, 1-methyl-3-pentene-2-yl group, 2-methyl-3-pentene-2-yl group, 3-methyl-3-pentene-2-yl group, 4-methyl-3-pentene-2-yl group, 1-methyl-4-pentene-2-yl group, 2-methyl-4-pentene-2-yl group, 3-methyl-4-pentene-2-yl group, 4-methyl-4-pentene-2-yl group, 1-methyl-1-pentene-3-yl group, 2-methyl-1-pentene-3-yl group, 3-methyl-1-pentene-3-yl group, 4-methyl-1-pentene-3-yl group, 1-methyl-2-pentene-3-yl group, 2-methyl-2-pentene-3-yl group, 3-methyl-2-pentene-3-yl group, 4-methyl-2-pentene-3-yl group, 1-hexene-1-yl group, 1-hexene-2-yl group, 1-hexene-3-yl group, 1-hexene-4-yl group, 1-hexene-5-yl group, 1-hexene-6-yl group, 2-hexene-1-yl group, 2-hexene-2-yl group, 2-hexene-3-yl group, 2-hexene-4-yl group, 2-hexene-5-yl group, 2-hexene-6-yl group, 3-hexene-1-yl group, 3-hexene-2-yl group and 3-hexene-3-yl group; preferably ethenyl group, 1-propene-1-yl group, 2-propene-1-yl group, 3-propene-1-yl group, 1-butene-1-yl group, 1-butene-2-yl group, 1-butene-3-yl group, 1-butene-4-yl group, 2-butene-1-yl group, 2-butene-2-yl group, 1-methyl-1-propene-1-yl group, 2-methyl-1-propene-1-yl group, 1-methyl-2-propene-1-yl group, 2-methyl-2-propene-1-yl group, 1-methyl-1-butene-1-yl group, 2-methyl-1-butene-1-yl group, 3-methyl-1-butene-1-yl group, 1-methyl-2-butene-1-yl group, 2-methyl-2-butene-1-yl group, 3-methyl-2-butene-1-yl group, 1-methyl-3-butene-1-yl group, 2-methyl-3-butene-1-yl group, 3-methyl-3-butene-1-yl group, 1-ethyl-1-butene-1-yl group, 2-ethyl-1-butene-1-yl group, 3-ethyl-1-butene-1-yl group, 1-ethyl-2-butene-1-yl group, 2-ethyl-2-butene-1-yl group, 3-ethyl-2-butene-1-yl group, 1-ethyl-3-butene-1-yl group, 2-ethyl-3-butene-1-yl group, 3-ethyl-3-butene-1-yl group, 1,1-dimethyl-1-butene-1-yl group, 1,2-dimethyl-1-butene-1-yl group, 1,3-dimethyl-1-butene-1-yl group, 2,2-dimethyl-1-butene-1-yl group, 3,3-dimethyl-1-butene-1-yl group, 1,1-dimethyl-2-butene-1-yl group, 1,2-dimethyl-2-butene-1-yl group, 1,3-dimethyl-2-butene-1-yl group, 2,2-dimethyl-2-butene-1-yl group, 3,3-dimethyl-2-butene-1-yl group, 1,1-dimethyl-3-butene-1-yl group, 1,2-dimethyl-3-butene-1-yl group, 1,3-dimethyl-3-butene-1-yl group, 2,2-dimethyl-3-butene-1-yl group and 3,3-dimethyl-3-butene-1-yl group; more preferably ethenyl group, 1-propene-1-yl group, 2-propene-1-yl group, 3-propene-1-yl group, 1-butene-1-yl group, 1-butene-2-yl group, 1-butene-3-yl group, 1-butene-4-yl group, 2-butene-1-yl group, 2-butene-2-yl group, 1-methyl-1-propene-1-yl group, 2-methyl-1-propene-1-yl group, 1-methyl-2-propene-1-yl group, 2-methyl-2-propene-1-yl group, 1-methyl-1-butene-1-yl group, 2-methyl-1-butene-1-yl group, 3-methyl-1-butene-1-yl group, 1-methyl-2-butene-1-yl group, 2-methyl-2-butene-1-yl group, 3-methyl-2-butene-1-yl group, 1-methyl-3-butene-1-yl group, 2-methyl-3-butene-1-yl group, and 3-methyl-3-butene-1-yl group; and most preferably ethenyl group, 1-propene-1-yl group, 2-propene-1-yl group, 3-propene-1-yl group, 1-butene-1-yl group, 1-butene-2-yl group, 1-butene-3-yl group, 1-butene-4-yl group, 2-butene-1-yl group and 2-butene-2-yl group.

Similarly, when $R^1$ represents a $C_{2-6}$ alkenyloxy group which may have one or more substituents, the alkenyloxy group refers to a group having an oxygen atom bound to the end of the $C_{2-6}$ linear or branched alkenyl group. Specific examples thereof include ethenyloxy group, 1-propene-1-yloxy group, 2-propene-1-yloxy group, 3-propene-1-yloxy group, 1-butene-1-yloxy group, 1-butene-2-yloxy group, 1-butene-3-yloxy group, 1-butene-4-yloxy group, 2-butene-1-yloxy group, 2-butene-2-yloxy group, 1-methyl-1-propene-1-yloxy group, 2-methyl-1-propene-1-yloxy group, 1-methyl-2-propene-1-yloxy group, 2-methyl-2-propene-1-yloxy group, 1-methyl-1-butene-1-yloxy group, 2-methyl-1-butene-1-yloxy group, 3-methyl-1-butene-1-yloxy group, 1-methyl-2-butene-1-yloxy group, 2-methyl-2-butene-1-yloxy group, 3-methyl-2-butene-1-yloxy group, 1-methyl-3-butene-1-yloxy group, 2-methyl-3-butene-1-yloxy group, 3-methyl-3-butene-1-yloxy group, 1-ethyl-1-butene-1-yloxy group, 2-ethyl-1-butene-1-yloxy group, 3-ethyl-1-butene-1-yloxy group, 1-ethyl-2-butene-1-yloxy group, 2-ethyl-2-butene-1-yloxy group, 3-ethyl-2-butene-1-yloxy group, 1-ethyl-3-butene-1-yloxy group, 2-ethyl-3-butene-1-yloxy group, 3-ethyl-3-butene-1-yloxy group, 1,1-dimethyl-1-butene-1-yloxy group, 1,2-dimethyl-1-butene-1-yloxy group, 1,3-dimethyl-1-butene-1-yloxy group, 2,2-dimethyl-1-butene-1-yloxy group, 3,3-dimethyl-1-butene-1-yloxy group, 1,1-dimethyl-2-butene-1-yloxy group, 1,2-dimethyl-2-butene-1-yloxy group, 1,3-dimethyl-2-butene-1-yloxy group, 2,2-dimethyl-2-butene-1-yloxy group, 3,3-dimethyl-2-butene-1-yloxy group, 1,1-dimethyl-3-butene-1-yloxy group, 1,2-dimethyl-3-butene-1-yloxy group, 1,3-dimethyl-3-butene-1-yloxy group, 2,2-dimethyl-3-butene-1-yloxy group, 3,3-dimethyl-3-butene-1-yloxy group, 1-pentene-1-yloxy group, 2-pentene-1-yloxy group, 3-pentene-1-yloxy group, 4-pentene-1-yloxy group, 1-pentene-2-yloxy group, 2-pentene-2-yloxy group, 3-pentene-2-yloxy group, 4-pentene-2-yloxy group, 1-pentene-3-yloxy group, 2-pentene-3-yloxy group, 1-pentene-1-yloxy group, 2-pentene-1-yloxy group, 3-pentene-1-yloxy group, 4-pentene-1-yloxy group, 1-pentene-2-yloxy group, 2-pentene-2-yloxy group, 3-pentene-2-yloxy group, 4-pentene-2-yloxy group, 1-pentene-3-yloxy group, 2-pentene-3-yloxy group, 1-methyl-1-pentene-1-yloxy group, 2-methyl-1-pentene-1-yloxy group, 3-methyl-1-pentene-1-yloxy group, 4-methyl-1-pentene-1-yloxy group, 1-methyl-2-pentene-1-yloxy group, 2-methyl-2-pentene-1-yloxy group, 3-methyl-2-pentene-1-yloxy group, 4-methyl-2-pentene-1-yloxy group, 1-methyl-3-pentene-1-yloxy group, 2-methyl-3-pentene-1-yloxy group, 3-methyl-3-pentene-1-yloxy group, 4-methyl-3-pentene-1-yloxy group, 1-methyl-4-pentene-1-yloxy group, 2-methyl-4-pentene-1-yloxy group, 3-methyl-4-pentene-1-yloxy group, 4-methyl-4-pentene-1-yloxy group, 1-methyl-1-pentene-2-yloxy group, 2-methyl-1-pentene-2-yloxy group, 3-methyl-1-pentene-2-yloxy group, 4-methyl-1-pentene-2-yloxy group, 1-methyl-2-pentene-2-yloxy group, 2-methyl-2-pentene-2-yloxy group, 3-methyl-2-pentene-2-yloxy group, 4-methyl-2-pentene-2-yloxy group, 1-methyl-3-pentene-2-yloxy group, 2-methyl-3-pentene-2-yloxy group, 3-methyl-3-pentene-2-yloxy group, 4-methyl-3-pentene-2-yloxy group, 1-methyl-4-pentene-2-yloxy group, 2-methyl-4-pentene-2-yloxy group, 3-methyl-4-pentene-2-yloxy group, 4-methyl-4-pentene-2-yloxy group, 1-methyl-1-pentene-3-yloxy group, 2-methyl-1-pentene-3-yloxy group, 3-methyl-1-pentene-3-yloxy group, 4-methyl-1-pentene-3-yloxy group, 1-methyl-2-pentene-3-yloxy group, 2-methyl-2-pentene-3-yloxy group, 3-methyl-2-pentene-3-yloxy group, 4-methyl-2-pentene-3-yloxy group, 1-hexene-1-yloxy group, 1-hexene-2-yloxy group, 1-hexene-3-yloxy group, 1-hexene-4-yloxy group, 1-hexene-5-yloxy group, 1-hexene-6-yloxy group, 2-hexene-1-yloxy group, 2-hexene-2-yloxy group, 2-hexene-3-yloxy group, 2-hexene-4-yloxy group, 2-hexene-5-yloxy group, 2-hexene-6-yloxy group, 3-hexene-1-yloxy group, 3-hexene-2-yloxy group and 3-hexene-3-yloxy group; preferably ethenyloxy group, 1-propene-1-yloxy group, 2-propene-1-yloxy group, 3-propene-1-yloxy group, 1-butene-1-yloxy group, 1-butene-2-yloxy group, 1-butene-3-yloxy group, 1-butene-4-yloxy group, 2-butene-1-yloxy group, 2-butene-2-yloxy group, 1-methyl-1-propene-1-yloxy group, 2-methyl-1-propene-1-yloxy group, 1-methyl-2-propene-1-yloxy group, 2-methyl-2-propene-1-yloxy group, 1-methyl-1-butene-1-yloxy group, 2-methyl-1-butene-1-yloxy group, 3-methyl-1-butene-1-yloxy group, 1-methyl-2-butene--1-yloxy group, 2-methyl-2-butene-1-yloxy group, 3-methyl-2-butene-1-yloxy group, 1-methyl-3-butene-1-yloxy group, 2-methyl-3-butene-1-yloxy group, 3-methyl-3-butene-1-yloxy group, 1-ethyl-1-butene-1-yloxy group, 2-ethyl-1-butene-1-yloxy group, 3-ethyl-1-butene-1-yloxy group, 1-ethyl-2-butene-1-yloxy group, 2-ethyl-2-butene-1-yloxy group, 3-ethyl-2-butene-1-yloxy group, 1-ethyl-3-butene-1-yloxy group, 2-ethyl-3-butene-1-yloxy group, 3-ethyl-3-butene-1-yloxy group, 1,1-dimethyl-1-butene-1-yloxy group, 1,2-dimethyl-1-butene-1-yloxy group, 1,3-dimethyl-1-butene-1-yloxy group, 2,2-dimethyl-1-butene-1-yloxy group, 3,3-dimethyl-1-butene-1-yloxy group, 1,1-dimethyl-2-butene-1-yloxy group, 1,2-dimethyl-2-butene-1-yloxy group, 1,3-dimethyl-2-butene-1-yloxy group, 2,2-dimethyl-2-butene-1-yloxy group, 3,3-dimethyl- 2-butene-1-yloxy group, 1,1-dimethyl-3-butene-1-yloxy group, 1,2-dimethyl-3butene-1-yloxy group, 1,3-dimethyl-3-butene-1-yloxy group, 2,2-dimethyl-3-butene-1-yloxy group and 3,3-dimethyl-3-butene-1-yloxy group; more preferably ethenyloxy group, 1-propene-1-yloxy group, 2-propene-1-yloxy group, 3-propene-1-yloxy group, 1-butene-1-yloxy group, 1-butene-2-yloxy group, 1-butene-3-yloxy group, 1-butene-4-yloxy group, 2-butene-1-yloxy group, 2-butene-2-yloxy group, 1-methyl-1-propene-1-yloxy group, 2-methyl-1-propene-1-yloxy group, 1-methyl-2-propene-1-yloxy group, 2-methyl-2-propene-1-yloxy group, 1-methyl-1-butene-1-yloxy group, 2-methyl-1-butene-1-yloxy group, 3-methyl-1-butene-1-yloxy group, 1-methyl-2-butene-1-yloxy group, 2-methyl-2-butene-1-yloxy group, 3-methyl-2-butene-1-yloxy group, 1-methyl-3-butene-1-yloxy group, 2-methyl-3-butene-1-yloxy group and 3-methyl-3-butene-1-yloxy group; further preferably ethenyloxy group, 1-propene-1-yloxy group, 2-propene-1-yloxy group, 3-propene-1-yloxy group, 1-butene-1-yloxy group, 1-butene-2-yloxy group, 1-butene-3-yloxy group, 1-butene-4-yloxy group, 2-butene-1-yloxy group and 2-butene-2-yloxy group; and most preferably ethenyloxy group, 1-propene-1-yloxy group, 2-propene-1-yloxy group and 3-propene-1-yloxy group.

Similarly, when $R^1$ represents a $C_{2-6}$ alkenylthio group which may have one or more substituents, the alkenylthio group refers to a group having sulfur atom bound to the end of the $C_{2-6}$ linear or branched alkenyl group, and specific examples thereof include ethenylthio group, 1-propene-1-ylthio group, 2-propene-1-ylthio group, 3-propene-1-ylthio group, 1-butene-1-ylthio group, 1-butene-2-ylthio group, 1-butene-3-ylthio group, 1-butene-4-ylthio group, 2-butene-1-ylthio group, 2-butene-2-ylthio group, 1-methyl-1-propene-1-ylthio group, 2-methyl-1-propene-1-ylthio group, 1-methyl-2-propene-1-ylthio group; 2-methyl-2-propene-1-ylthio group, 1-methyl-1-butene-1-ylthio group, 2-methyl-1-butene-1-yl, 3-methyl-1-butene-1-ylthio group, 1-methyl-2-butene-1-ylthio group, 2-methyl-2-butene-1-ylthio group, 3-methyl-2-butene-1-ylthio group, 1-methyl-3-butene-1-ylthio group, 2-methyl-3-butene-1-ylthio group, 3-methyl-3-butene-1-ylthio group, 1-ethyl-1-butene-1-ylthio group, 2-ethyl-1-butene-1-ylthio group, 3-ethyl-1-butene-1-ylthio group, 1-ethyl-2-butene-1-ylthio group, 2-ethyl-2-butene-1-ylthio group, 3-ethyl-2-butene-1-ylthio group, 1-ethyl-3-butene-1-ylthio group, 2-ethyl-3-butene-1-ylthio group, 3-ethyl-3-butene-1-ylthio group, 1,1-dimethyl-1-butene-1-ylthio group, 1,2-dimethyl-1-butene-1-ylthio group, 1,3-dimethyl-1-butene-1-ylthio group, 2,2-dimethyl-2-butene-1-ylthio group, 3,3-dimethyl-1-butene-1-ylthio group, 1,1-dimethyl-2-butene-1-ylthio group, 1,2-dimethyl-2-butene-1-ylthio group, 1,3-dimethyl-2-butene-1-ylthio group, 2,2-dimethyl-2-butene-1-ylthio group, 3,3-dimethyl-2-butene-1-ylthio group, 1,1-dimethyl-3-butene-1-ylthio group, 1,2-dimethyl-3-butene-1-ylthio group, 1,3-dimethyl-3-butene-1-ylthio group, 2,2-dimethyl-3-butene-1-ylthio group, 3,3-dimethyl-3-butene-1-ylthio group, 1-pentene-1-ylthio group, 2-pentene-1-ylthio group, 3-pentene-1-ylthio group, 4-pentene-1-ylthio group, 1-pentene-2-ylthio group, 2-pentene-2-ylthio group, 3-pentene-2-ylthio group, 4-pentene-2-ylthio group, 1-pentene-3-ylthio group, 2-pentene-3-ylthio group, 1-pentene-1-ylthio group, 2-pentene-1-ylthio group, 3-pentene-1-ylthio group, 4-pentene-1-ylthio group, 1-pentene-2-ylthio group, 2-pentene-2-ylthio group, 3-pentene-2-ylthio group, 4-pentene-2-ylthio group, 1-pentene-3-ylthio group, 2-pentene-3-ylthio group, 1-methyl-1-pentene-1-ylthio group, 2-methyl-1-pentene-1-ylthio group, 3-methyl-1-pentene-1-ylthio group, 4-methyl-1-pentene-1-ylthio group, 1-methyl-2-pentene-1-ylthio group, 2-methyl-2-pentene-1-ylthio group, 3-methyl-2-pentene-1-ylthio group, 4-methyl-2-pentene-1-ylthio group, 1-methyl-3-pentene-1-ylthio group, 2-methyl-3-pentene-1-ylthio group, 3-methyl-3-pentene-1-ylthio group, 4-methyl-3-pentene-1-ylthio group, 1-methyl-4-pentene-1-ylthio group, 2-methyl-4-pentene-1-ylthio group, 3-methyl-4-pentene-1-ylthio group, 4-methyl-4-pentene-1-ylthio group, 1-methyl-1-pentene-2-ylthio group, 2-methyl-1-pentene-2-ylthio group, 3-methyl-1-pentene-2-ylthio group, 4-methyl-1-pentene-2-ylthio group, 1-methyl-2-pentene-2-ylthio group, 2-methyl-2-pentene-2-ylthio group, 3-methyl-2-pentene-2-ylthio group, 4-methyl-2-pentene-2-ylthio group, 1-methyl-3-pentene-2-ylthio group, 2-methyl-3-pentene-2-ylthio group, 3-methyl-3-pentene-2-ylthio group, 4-methyl-3-pentene-2-ylthio group, 1-methyl-4-pentene-2-ylthio group, 2-methyl-4-pentene-2-ylthio group, 3-methyl-4-pentene-2-ylthio group, 4-methyl-4-pentene-2-ylthio group, 1-methyl-1-pentene-3-ylthio group, 2-methyl-1-pentene-3-ylthio group, 3-methyl-1-pentene-3-ylthio group, 4-methyl-1-pentene-3-ylthio group, 1-methyl-2-pentene-3-ylthio group, 2-methyl-2-pentene-3-ylthio group, 3-methyl-2-pentene-3-ylthio group, 4-methyl-2-pentene-3-ylthio group, 1-hexene-1-ylthio group, 1-hexene-2-ylthio group, 1-hexene-3-ylthio group, 1-hexene-4-ylthio group, 1-hexene-5-ylthio group, 1-hexene-6-ylthio group, 2-hexene-1-ylthio group, 2-hexene-2-ylthio group, 2-hexene-3-ylthio group, 2-hexene-4-ylthio group, 2-hexene-5-ylthio group, 2-hexene-6-ylthio group, 3-hexene-1-ylthio group, 3-hexene-2-ylthio group and 3-hexene-3-ylthio group; preferably ethenylthio group, 1-propene-1-ylthio group, 2-propene-1-ylthio group, 3-propene-1-ylthio group, 1-butene-1-ylthio group, 1-butene-2-ylthio group, 1-butene-3-ylthio group, 1-butene-4-ylthio group, 2-butene-1-ylthio group, 2-butene-2-ylthio group, 1-methyl-1-propene-1-ylthio group, 2-methyl-1-propene-1-ylthio group, 1-methyl-2-propene-1-ylthio group, 2-methyl-2-propene-1-ylthio group, 1-methyl-1-butene-1-ylthio group, 2-methyl-1-butene-1-ylthio group, 3-methyl-1-butene-1-ylthio group, 1-methyl-2-butene-1-ylthio group, 2-methyl-2-butene-1-ylthio group, 3-methyl-2-butene-1-ylthio group, 1-methyl-3-butene-1-ylthio group, 2-methyl-3-butene-1-ylthio group, 3-methyl-3-butene-1-ylthio group, 1-ethyl-1-butene-1-ylthio group, 2-ethyl-1-butene-1-ylthio group, 3-ethyl-1-butene-1-ylthio group, 1-ethyl-2-butene-1-ylthio group, 2-ethyl-2-butene-1-ylthio group, 3-ethyl-2-butene-1-ylthio group, 1-ethyl-3-butene-1-ylthio group, 2-ethyl-3-butene-1-ylthio group, 3-ethyl-3-butene-1-ylthio group, 1,1-dimethyl-1-butene-1-ylthio group, 1,2-dimethyl-1-butene-1-ylthio group, 1,3-dimethyl-1-butene-1-ylthio group, 2,2-dimethyl-1-butene-1-ylthio group, 3,3-dimethyl-1-butene-1-ylthio group, 1,1-dimethyl-2-butene-1-ylthio group, 1,2-dimethyl-2-butene-1-ylthio group, 1,3-dimethyl-2-butene-1-ylthio group, 2,2-dimethyl-2-butene-1-ylthio group, 3,3-dimethyl-2-butene-1-ylthio group, 1,1-dimethyl-3-butene-1-ylthio group, 1,2-dimethyl-3-butene-1-ylthio group, 1,3-dimethyl-3-butene-1-ylthio group, 2,2-dimethyl-3-butene-1-ylthio group and 3,3-dimethyl-3-butene-1-ylthio group; more preferably ethenylthio group, 1-propene-1-ylthio group, 2-propene-1-ylthio group, 3-propene-1-ylthio group, 1-butene-1-ylthio group, 1-butene-2-ylthio group, 1-butene-3-ylthio group, 1-butene-4-ylthio group, 2-butene-1-ylthio group, 2-butene-2-ylthio group, 1-methyl-1-propene-1-ylthio group, 2-methyl-1-propene-1-ylthio group, 1-methyl-2-propene-1-ylthio group, 2-methyl-2-propene-1-ylthio group, 1-methyl-1-butene-1-ylthio group, 2-methyl-1- butene-1-ylthio group, 3-methyl-1-butene-1-ylthio group, 1-methyl-2-butene-1-ylthio group, 2-methyl-2-butene-1-ylthio group, 3-methyl-2-butene-1-ylthio group, 1-methyl-3-butene-1-ylthio group, 2-methyl-3-butene-1-ylthio group and 3-methyl-3-butene-1-ylthio group; further preferably ethenylthio group, 1-propene-1-ylthio group, 2-propene-1-ylthio group, 3-propene-1-ylthio group, 1-butene-1-ylthio group, 1-butene-2-ylthio group, 1-butene-3-ylthio group, 1-butene-4-ylthio group, 2-butene-1-ylthio group and 2-butene-2-ylthio group; and most preferably ethenylthio group, 1-propene-1-ylthio group, 2-propene-1-ylthio group and 3-propene-1-ylthio group.

When $R^1$ represents a $C_{2-6}$ alkynyl group which may have one or more substituents, the alkynyl group is a $C_{2-6}$ linear or branched alkynyl group and refers to a compound residue having a triple bond in the alkyl group containing 2 or more carbon atoms. Specific examples thereof include ethynyl group, 1-propyn-1-yl group, 2-propyn-1-yl group, 3-propyn-1-yl group, 1-butyn-1-yl group, 1-butyn-2-yl group, 1-butyn-3-yl group, 1-butyn-4-yl group, 2-butyn-1-yl group, 2-butyn-2-yl group, 1-methyl-1-propyn-1-yl group, 2-methyl-1-propyn-1-yl group, 1-methyl-2-propyn-1-yl group, 2-methyl-2-propyn-1-yl group, 1-methyl-1-butyn-1-yl group, 2-methyl-1-butyn-1-yl group, 3-methyl-1-butyn-1-yl group, 1-methyl-2-butyn-1-yl group, 2-methyl-2-butyn-1-yl group, 3-methyl-2-butyn-1-yl group, 1-methyl-3-butyn-1-yl group, 2-methyl-3-butyn-1-yl group, 3-methyl-3-butyn-1-yl group, 1-ethyl-1-butyn-1-yl group, 2-ethyl-1-butyn-1-yl group, 3-ethyl-1-butyn-1-yl group, 1-ethyl-2-butyn-1-yl group, 2-ethyl-2-butyn-1-yl group, 3-ethyl-2-butyn-1-yl group, 1-ethyl-3-butyn-1-yl group, 2-ethyl-3-butyn-1-yl group, 3-ethyl-3-butyn-1-yl group, 1,1-dimethyl-1-butyn-1-yl group, 1,2-dimethyl-1-butyn-1-yl group, 1,3-dimethyl-1-butyn-1-yl group, 2,2-dimethyl-1-butyn-1-yl group, 3,3-dimethyl-1-butyn-1-yl group, 1,1-dimethyl-2-butyn-1-yl group, 1,2-dimethyl-2-butyn-1-yl group, 1,3-dimethyl-2-butyn-1-yl group, 2,2-dimethyl-2-butyn-1-yl group, 3,3-dimethyl-2-butyn-1-yl group, 1,1-dimethyl-3-butyn-1-yl group, 1,2-dimethyl-3-butyn-1-yl group, 1,3-dimethyl-3-butyn-1-yl group, 2,2-dimethyl-3-butyn-1-yl group and 3,3-dimethyl-3-butyn-1-yl group, 1-pentyn-1-yl group, 2-pentyn-1-yl group, 3-pentyn-1-yl group, 4-pentyn-1-yl group, 1-pentyn-2-yl group, 2-pentyn-2-yl group, 3-pentyn-2-yl group, 4-pentyn-2-yl group, 1-pentyn-3-yl group, 2-pentyn-3-yl group, 1-pentyn-1-yl group, 2-pentyn-1-yl group, 3-pentyn-1-yl group, 4-pentyn-1-yl group, 1-pentyn-2-yl group, 2-pentyn-2-yl group, 3-pentyn-2-yl group, 4-pentyn-2-yl group, 1-pentyn-3-yl group, 2-pentyn-3-yl group, 1-methyl-1-pentyn-1-yl group, 2-methyl-1-pentyn-1-yl group, 3-methyl-1-pentyn-1-yl group, 4-methyl-1-pentyn-1-yl group, 1-methyl-2-pentyn-1-yl group, 2-methyl-2-pentyn-1-yl group, 3-methyl-2-pentyn-1-yl group, 4-methyl-2-pentyn-1-yl group, 1-methyl-3-pentyn-1-yl group, 2-methyl-3-pentyn-1-yl group, 3-methyl-3-pentyn-1-yl group, 4-methyl-3-pentyn-1-yl group, 1-methyl-4-pentyn-1-yl group, 2-methyl-4-pentyn-1-yl group, 3-methyl-4-pentyn-1-yl group, 4-methyl-4-pentyn-1-yl group, 1-methyl-1-pentyn-2-yl group, 2-methyl-1-pentyn-2-yl group, 3-methyl-1-pentyn-2-yl group, 4-methyl-1-pentyn-2-yl group, 1-methyl-2-pentyn-2-yl group, 2-methyl-2-pentyn-2-yl group, 3-methyl-2-pentyn-2-yl group, 4-methyl-2-pentyn-2-yl group, 1-methyl-3-pentyn-2-yl group, 2-methyl-3-pentyn-2-yl group, 3-methyl-3-pentyn-2-yl group, 4-methyl-3-pentyn-2-yl group, 1-methyl-4-pentyn-2-yl group, 2-methyl-4-pentyn-2-yl group, 3-methyl-4-pentyn-2-yl group, 4-methyl-4-pentyn-2-yl group, 1-methyl-1-pentyn-3-yl group, 2-methyl-1-pentyn-3-yl group, 3-methyl-1-pentyn-3-yl group, 4-methyl-1-pentyn-3-yl group, 1-methyl-2-pentyn-3-yl group, 2-methyl-2-pentyn-3-yl group, 3-methyl-2-pentyn-3-yl group, 4-methyl-2-pentyn-3-yl group, 1-hexyn-1-yl group, 1-hexyn-2-yl group, 1-hexyn-3-yl group, 1-hexyn-4-yl group, 1-hexyn-5-yl group, 1-hexyn-6-yl group, 2-hexyn-1-yl group, 2-hexyn-2-yl group, 2-hexyn-3-yl group, 2-hexyn-4-yl group, 2-hexyn-5-yl group, 2-hexyn-6-yl group, 3-hexyn-1-yl group, 3-hexyn-2-yl group and 3-hexyn-3-yl group; preferably ethynyl group, 1-propyn-1-yl group, 2-propyn-1-yl group, 3-propyn-1-yl group, 1-butyn-1-yl group, 1-butyn-2-yl group, 1-butyn-3-yl group, 1-butyn-4-yl group, 2-butyn-1-yl group, 2-butyn-2-yl group, 1-methyl-1-propyn-1-yl group, 2-methyl-1-propyn-1-yl group, 1-methyl-2-propyn-1-yl group, 2-methyl-2-propyn-1-yl group, 1-methyl-1-butyn-1-yl group, 2-methyl-1-butyn-1-yl group, 3-methyl-1-butyn-1-yl group, 1-methyl-2-butyn-1-yl group, 2-methyl-2-butyn-1-yl group, 3-methyl-2-butyn-1-yl group, 1-methyl-3-butyn-1-yl group, 2-methyl-3-butyn-1-yl group, 3-methyl-3-butyn-1-yl group, 1-ethyl-1-butyn-1-yl group, 2-ethyl-1-butyn-1-yl group, 3-ethyl-1-butyn-1-yl group, 1-ethyl-2-butyn-1-yl group, 2-ethyl-2-butyn-1-yl group, 3-ethyl-2-butyn-1-yl group, 1-ethyl-3-butyn-1-yl group, 2-ethyl-3-butyn-1-yl group, 3-ethyl-3-butyn-1-yl group, 1,1-dimethyl-1-butyn-1-yl group, 1,2-dimethyl-1-butyn-1-yl group, 1,3-dimethyl-1-butyn-1-yl group, 2,2-dimethyl-1-butyn-1-yl group, 3,3-dimethyl-1-butyn-1-yl group, 1,1-dimethyl-2-butyn-1-yl group, 1,2-dimethyl-2-butyn-1-yl group, 1,3-dimethyl-2-butyn-1-yl group, 2,2-dimethyl-2-butyn-1-yl group, 3,3-dimethyl-2-butyn-1-yl group, 1,1-dimethyl-3-butyn-1-yl group, 1,2-dimethyl-3-butyn-1-yl group, 1,3-dimethyl-3-butyn-1-yl group, 2,2-dimethyl-3-butyn-1-yl group and 3,3-dimethyl-3-butyn-1-yl group; more preferably ethynyl group, 1-propyn-1-yl group, 2-propyn-1-yl group, 3-propyn-1-yl group, 1-butyn-1-yl group, 1-butyn-2-yl group, 1-butyn-3-yl group, 1-butyn-4-yl group, 2-butyn-1-yl group, 2-butyn-2-yl group, 1-methyl-1-propyn-1-yl group, 2-methyl-1-propyn-1-yl group, 1-methyl-2-propyn-1-yl group, 2-methyl-2-propyn-1-yl group, 1-methyl-1-butyn-1-yl group, 2-methyl-1-butyn-1-yl group, 3-methyl-1-butyn-1-yl group, 1-methyl-2-butyn-1-yl group, 2-methyl-2-butyn-1-yl group, 3-methyl-2-butyn-1-yl group, 1-methyl-3-butyn-1-yl group, 2-methyl-3-butyn-1-yl group and 3-methyl-3-butyn-1-yl group; further preferably ethynyl group, 1-propyn-1-yl group, 2-propyn-1-yl group, 3-propyn-1-yl group, 1-butyn-1-yl group, 1-butyn-2-yl group, 1-butyn-3-yl group, 1-butyn-4-yl group, 2-butyn-1-yl group and 2-butyn-2-yl group; and most preferably ethynyl group, 1-propyn-1-yl group, 2-propyn-1-yl group and 3-propyn-1-yl group.

Similarly, when $R^1$ represents a $C_{2-6}$ alkynyloxy group which may have one or more substituents, the alkynyloxy group refers to a group having oxygen atom bound to the end of the $C_{2-6}$ linear or branched alkynyl group, and specific examples thereof include ethynyloxy group, 1-propyn-1-yloxy group, 2-propyn-1-yloxy group, 3-propyn-1-yloxy group, 1-butyn-1-yloxy group, 1-butyn-2-yloxy group, 1-butyn-3-yloxy group, 1-butyn-4-yloxy group, 2-butyn-1-yloxy group, 2-butyn-2-yloxy group, 1-methyl-1-propyn-1-yloxy group, 2-methyl-1-propyn-1-yloxy group, 1-methyl-2-propyn-1-yloxy group, 2-methyl-2-propyn-1-yloxy group, 1-methyl-1-butyn-1-yloxy group, 2-methyl-1-butyn-1-yl group, 3-methyl-1-butyn-1-yloxy group, 1-methyl-2-butyn-1-yloxy group, 2-methyl-2-butyn-1-yloxy group, 3-methyl-2-butyn-1-yloxy group, 1-methyl-3-butyn-1-yloxy group, 2-methyl-3-butyn-1-yloxy group, 3-methyl-3-butyn-1-yloxy group, 1-ethyl-1-butyn-1-yloxy group, 2-ethyl-1-butyn-1- yloxy group, 3-ethyl-1-butyn-1-yloxy group, 1-ethyl-2-butyn-1-yloxy group, 2-ethyl-2-butyn-1-yloxy group, 3-ethyl-2-butyn-1-yloxy group, 1-ethyl-3-butyn-1-yloxy group, 2-ethyl-3-butyn-1-yloxy group, 3-ethyl-3-butyn-1-yloxy group, 1,1-dimethyl-1-butyn-1-yloxy group, 1,2-diethyl-1-butyn-1-yloxy group, 1,3-dimethyl-1-butyn-1-yloxy group, 2,2-dimethyl-1-butyn-1-yloxy group, 3,3-dimethyl-1-butyn-1-yloxy group, 1,1-dimethyl-2-butyn-1-yloxy group, 1,2-dimethyl-2-butyn-1-yloxy group, 1,3-dimethyl-2-butyn-1-yloxy group, 2,2-dimethyl-2-butyn-1-yloxy group, 3,3-dimethyl-2-butyn-1-yloxy group, 1,1-dimethyl-3-butyn-1-yloxy group, 1,2-dimethyl-3-butyn-1-yloxy group, 1,3-dimethyl-3-butyn-1-yloxy group, 2,2-dimethyl-3-butyn-1-yloxy group, 3,3-dimethyl-3-butyn-1-yloxy group, 1-pentyn-1-yloxy group, 2-pentyn-1-yloxy group, 3-pentyn-1-yloxy group, 4-pentyn-1-yloxy group, 1-pentyn-2-yloxy group, 2-pentyn-2-yloxy group, 3-pentyn-2-yloxy group, 4-pentyn-2-yloxy group, 1-pentyn-3-yloxy group, 2-pentyn-3-yloxy group, 1-pentyn-1-yloxy group, 2-pentyn-1-yloxy group, 3-pentyn-1-yloxy group, 4-pentyn-1-yloxy group, 1-pentyn-2-yloxy group, 2-pentyn-2-yloxy group, 3-pentyn-2-yloxy group, 4-pentyn-2-yloxy group, 1-pentyn-3-yloxy group, 2-pentyn-3-yloxy group, 1-methyl-1-pentyn-1-yloxy group, 2-methyl-1-pentyn-1-yloxy group, 3-methyl-1-pentyn-1-yloxy group, 4-methyl-1-pentyn-1-yloxy group, 1-methyl-2-pentyn-1-yloxy group, 2-methyl-2-pentyn-1-yloxy group, 3-methyl-2-pentyn-1-yloxy group, 4-methyl-2-pentyn-1-yloxy group, 1-methyl-3-pentyn-1-yloxy group, 2-methyl-3-pentyn-1-yloxy group, 3-methyl-3-pentyn-1-yloxy group, 4-methyl-3-pentyn-1-yloxy group, 1-methyl-4-pentyn-1-yloxy group, 2-methyl-4-pentyn-1-yloxy group, 3-methyl-4-pentyn-1-yloxy group, 4-methyl-4-pentyn-1-yloxy group, 1-methyl-1-pentyn-2-yloxy group, 2-methyl-1-pentyn-2-yloxy group, 3-methyl-1-pentyn-2-yloxy group, 4-methyl-1-pentyn-2-yloxy group, 1-methyl-2-pentyn-2-yloxy group, 2-methyl-2-pentyn-2-yloxy group, 3-methyl-2-pentyn-2-yloxy group, 4-methyl-2-pentyn-2-yloxy group, 1-methyl-3-pentyn-2-yloxy group, 2-methyl-3-pentyn-2-yloxy group, 3-methyl-3-pentyn-2-yloxy group, 4-methyl-3-pentyn-2-yloxy group, 1-methyl-4-pentyn-2-yloxy group, 2-methyl-4-pentyn-2-yloxy group, 3-methyl-4-pentyn-2-yloxy group, 4-methyl-4-pentyn-2-yloxy group, 1-methyl-1-pentyn-3-yloxy group, 2-methyl-1-pentyn-3-yloxy group, 3-methyl-1-pentyn-3-yloxy group, 4-methyl-1-pentyn-3-yloxy group, 1-methyl-2-pentyn-3-yloxy group, 2-methyl-2-pentyn-3-yloxy group, 3-methyl-2-pentyn-3-yloxy group, 4-methyl-2-pentyn-3-yloxy group, 1-hexyn-1-yloxy group, 1-hexyn-2-yloxy group, 1-hexyn-3-yloxy group, 1-hexyn-4-yloxy group, 1-hexyn-5-yloxy group, 1-hexyn-6-yloxy group, 2-hexyn-1-yloxy group, 2-hexyn-2-yloxy group, 2-hexyn-3-yloxy group, 2-hexyn-4-yloxy group, 2-hexyn-5-yloxy group, 2-hexyn-6-yloxy group, 3-hexyn-1-yloxy group, 3-hexyn-2-yloxy group and 3-hexyn-3-yloxy group; preferably ethynyloxy group, 1-propyn-1-yloxy group, 2-propyn-1-yloxy group, 3-propyn-1-yloxy group, 1-butyn-1-yloxy group, 1-butyn-2-yloxy group, 1-butyn-3-yloxy group, 1-butyn-4-yloxy group, 2-butyn-1-yloxy group, 2-butyn-2-yloxy group, 1-methyl-1-propyn-1-yloxy group, 2-methyl-1-propyn-1-yloxy group, 1-methyl-2-propyn-1-yloxy group, 2-methyl-2-propyn-1-yloxy group, 1-methyl-1-butyn-1-yloxy group, 2-methyl-1-butyn-1-yloxy group, 3-methyl-1-butyn-1-yloxy group, 1-methyl-2-butyn-1-yloxy group, 2-methyl-2-butyn-1-yloxy group, 3-methyl-2-butyn-1-yloxy group, 1-methyl-3-butyn-1-yloxy group, 2-methyl-3-butyn-1-yloxy group, 3-methyl-3-butyn-1-yloxy group, 1-ethyl-1-butyn-1-yloxy group, 2-ethyl-1-butyn-1-yloxy group, 3-ethyl-1-butyn-1-yloxy group, 1-ethyl-2-butyn-1-yloxy group, 2-ethyl-2-butyn-1-yloxy group, 3-ethyl-2-butyn-1-yloxy group, 1-ethyl-3-butyn-1-yloxy group, 2-ethyl-3-butyn-1-yloxy group, 3-ethyl-3-butyn-1-yloxy group, 1,1-dimethyl-1-butyn-1-yloxy group, 1,2-dimethyl-1-butyn-1-yloxy group, 1,3-dimethyl-1-butyn-1-yloxy group, 2,2-dimethyl-1-butyn-1-yloxy group, 3,3-dimethyl-1-butyn-1-yloxy group, 1,1-dimethyl-2-butyn-1-yloxy group, 1,2-dimethyl-2-butyn-1-yloxy group, 1,3-dimethyl-2-butyn-1-yloxy group, 2,2-dimethyl-2-butyn-1-yloxy group, 3,3-dimethyl-2-butyn-1-yloxy group, 1,1-dimethyl-3-butyn-1-yloxy group, 1,2-dimethyl-3-butyn-1-yloxy group, 1,3-dimethyl-3-butyn-1-yloxy group, 2,2-dimethyl-3-butyn-1-yloxy group and 3,3-dimethyl-3-butyn-1-yloxy group; more preferably ethynyloxy group, 1-propyn-1-yloxy group, 2-propyn-1-yloxy group, 3-propyn-1-yloxy group, 1-butyn-1-yloxy group, 1-butyn-2-yloxy group, 1-butyn-3-yloxy group, 1-butyn-4-yloxy group, 2-butyn-1-yloxy group, 2-butyn-2-yloxy group, 1-methyl-1-propyn-1-yloxy group, 2-methyl-1-propyn-1-yloxy group, 1-methyl-2-propyn-1-yloxy group, 2-methyl-2-propyn-1-yloxy group, 1-methyl-1-butyn-1-yloxy group, 2-methyl-1-butyn-1-yloxy group, 3-methyl-1-butyn-1-yloxy group, 1-methyl-2-butyn-1-yloxy group, 2-methyl-2-butyn-1-yloxy group, 3-methyl-2-butyn-1-yloxy group, 1-methyl-3-butyn-1-yloxy group, 2-methyl-3-butyn-1-yloxy group and 3-methyl-3-butyn-1-yloxy group; further preferably ethynyloxy group, 1-propyn-1-yloxy group, 2-propyn-1-yloxy group, 3-propyn-1-yloxy group, 1-butyn-1-yloxy group, 1-butyn-2-yloxy group, 1-butyn-3-yloxy group, 1-butyn-4-yloxy group, 2-butyn-1-yloxy group and 2-butyn-2-yloxy group; and most preferably ethynyloxy group, 1-propyn-1-yloxy group, 2-propyn-1-yloxy group and 3-propyn-1-yloxy group.

Similarly, when $R^1$ represents a $C_{2-6}$ alkynylthio group which may have one or more substituents, the alkynylthio group refers to a group having sulfur atom bound to the end of the $C_{2-6}$ linear or branched alkynyl group, and specific examples thereof include ethynylthio group, 1-propyn-1-ylthio group, 2-propyn-1-ylthio group, 3-propyn-1-ylthio group, 1-butyn-1-ylthio group, 1-butyn-2-ylthio group, 1-butyn-3-ylthio group, 1-butyn-4-ylthio group, 2-butyn-1-ylthio group, 2-butyn-2-ylthio group, 1-methyl-1-propyn-1-ylthio group, 2-methyl-1-propyn-1-ylthio group, 1-methyl-2-propyn-1-ylthio group, 2-methyl-2-propyn-1-ylthio group, 1-methyl-1-butyn-1-ylthio group, 2-methyl-1-butyn-1-ylthio group, 3-methyl-1-butyn-1-ylthio group, 1-methyl-2-butyn-1-ylthio group, 2-methyl-2-butyn-1-ylthio group, 3-methyl-2-butyn-1-ylthio group, 1-methyl-3-butyn-1-ylthio group, 2-methyl-3-butyn-1-ylthio group, 3-methyl-3-butyn-1-ylthio group, 1-ethyl-1-butyn-1-ylthio group, 2-ethyl-1-butyn-1-ylthio group, 3-ethyl-1-butyn-1-ylthio group, 1-ethyl-2-butyn-1-ylthio group, 2-ethyl-2-butyn-1-ylthio group, 3-ethyl-2-butyn-1-ylthio group, 1-ethyl-3-butyn-1-ylthio group, 2-ethyl-3-butyn-1-ylthio group, 3-ethyl-3-butyn-1-ylthio group, 1,1-dimethyl-1-butyn-1-ylthio group, 1,2-dimethyl-1-butyn-1-ylthio group, 1,3-dimethyl-1-butyn-1-ylthio group, 2,2-dimethyl-1-butyn-1-ylthio group, 3,3-dimethyl-1-butyn-1-ylthio group, 1,1-dimethyl-2-butyn-1-ylthio group, 1,2-dimethyl-2-butyn-1-ylthio group, 1,3-dimethyl-2-butyn-1-ylthio group, 2,2-dimethyl-2-butyn-1-ylthio group, 3,3-dimethyl-2-butyn-1-ylthio group, 1,1-dimethyl-3-butyn-1-ylthio group, 1,2-dimethyl-3-butyn-1-ylthio group, 1,3-dimethyl-3-butyn-1-ylthio group, 2,2-dimethyl-3-butyn-1-ylthio group, 3,3-dimethyl-3-butyn-1-ylthio group, 1-pentyn-1-ylthio group, 2-pentyn-1-ylthio group, 3-pentyn-1-ylthio group, 4-pentyn-1-ylthio group, 1-pentyn-2-ylthio group, 2-pentyn-2-ylthio group, 3-pentyn-2-ylthio group, 4-pentyn-2-ylthio group, 1-pentyn-3-ylthio group, 2-pentyn-3-ylthio group, 1-pentyn-1-ylthio group, 2-pentyn-1-ylthio group, 3-pentyn-1-ylthio group, 4-pentyn-1-ylthio group, 1-pentyn-2-ylthio group, 2-pentyn-2-ylthio group, 3-pentyn-2-ylthio group, 4-pentyn-2-ylthio group, 1-pentyn-3-ylthio group, 2-pentyn-3-ylthio group, 1-methyl-1-pentyn-1-ylthio group, 2-methyl-1-pentyn-1-ylthio group, 3-methyl-1-pentyn-1-ylthio group, 4-methyl-1-pentyn-1-ylthio group, 1-methyl-2-pentyn-1-ylthio group, 2-methyl-2-pentyn-1-ylthio group, 3-methyl-2-pentyn-1-ylthio group, 4-methyl-2-pentyn-1-ylthio group, 1-methyl-3-pentyn-1-ylthio group, 2-methyl-3-pentyn-1-ylthio group, 3-methyl-3-pentyn-1-ylthio group, 4-methyl-3-pentyn-1-ylthio group, 1-methyl-4-pentyn-1-ylthio group, 2-methyl-4-pentyn-1-ylthio group, 3-methyl-4-pentyn-1-ylthio group, 4-methyl-4-pentyn-1-ylthio group, 1-methyl-1-pentyn-2-ylthio group, 2-methyl-1-pentyn-2-ylthio group, 3-methyl-1-pentyn-2-ylthio group, 4-methyl-1-pentyn-2-ylthio group, 1-methyl-2-pentyn-2-ylthio group, 2-methyl-2-pentyn-2-ylthio group, 3-methyl-2-pentyn-2-ylthio group, 4-methyl-2-pentyn-2-ylthio group, 1-methyl-3-pentyn-2-ylthio group, 2-methyl-3-pentyn-2-ylthio group, 3-methyl-3-pentyn-2-ylthio group, 4-methyl-3-pentyn-2-ylthio group, 1-methyl-4-pentyn-2-ylthio group, 2-methyl-4-pentyn-2-ylthio group, 3-methyl-4-pentyn-2-ylthio group, 4-methyl-4-pentyn-2-ylthio group, 1-methyl-1-pentyn-3-ylthio group, 2-methyl-1-pentyn-3-ylthio group, 3-methyl-1-pentyn-3-ylthio group, 4-methyl-1-pentyn-3-ylthio group, 1-methyl-2-pentyn-3-ylthio group, 2-methyl-2-pentyn-3-ylthio group, 3-methyl-2-pentyn-3-ylthio group, 4-methyl-2-pentyn-3-ylthio group, 1-hexyn-1-ylthio group, 1-hexyn-2-ylthio group, 1-hexyn-3-ylthio group, 1-hexyn-4-ylthio group, 1-hexyn-5-ylthio group, 1-hexyn-6-ylthio group, 2-hexyn-1-ylthio group, 2-hexyn-2-ylthio group, 2-hexyn-3-ylthio group, 2-hexyn-4-ylthio group, 2-hexyn-5-ylthio group, 2-hexyn-6-ylthio group, 3-hexyn-1-ylthio group, 3-hexyn-2-ylthio group and 3-hexyn-3-ylthio group; preferably ethynylthio group, 1-propyn-1-ylthio group, 2-propyn-1-ylthio group, 3-propyn-1-ylthio group, 1-butyn-1-ylthio group, 1-butyn-2-ylthio group, 1-butyn-3-ylthio group, 1-butyn-4-ylthio group, 2-butyn-1-ylthio group, 2-butyn-2-ylthio group, 1-methyl-1-propyn-1-ylthio group, 2-methyl-1-propyn-1-ylthio group, 1-methyl-2-propyn-1-ylthio group, 2-methyl-2-propyn-1-ylthio group, 1-methyl-1-butyn-1-ylthio group, 2-methyl-1-butyn-1-ylthio group, 3-methyl-1-butyn-1-ylthio group, 1-methyl-2-butyn-1-ylthio group, 2-methyl-2-butyn-1-ylthio group, 3-methyl-2-butyn-1-ylthio group, 1-methyl-3-butyn-1-ylthio group, 2-methyl-3-butyn-1-ylthio group, 3-methyl-3-butyn-1-ylthio group, 1-ethyl-1-butyn-1-ylthio group, 2-ethyl-1-butyn-1-ylthio group, 3-ethyl-1-butyn-1-ylthio group, 1-ethyl-2-butyn-1-ylthio group, 2-ethyl-2-butyn-1-ylthio group, 3-ethyl-2-butyn-1-ylthio group, 1-ethyl-3-butyn-1-ylthio group, 2-ethyl-3-butyn-1-ylthio group, 3-ethyl-3-butyn-1-ylthio group, 1,1-dimethyl-1-butyn-1-ylthio group, 1,2-dimethyl-1-butyn-1-ylthio group, 1,3-dimethyl-1-butyn-1-ylthio group, 2,2-dimethyl-1-butyn-1-ylthio group, 3,3-dimethyl-1-butyn-1-ylthio group, 1,1-dimethyl-2-butyn-1-ylthio group, 1,2-dimethyl-2-butyn-1-ylthio group, 1,3-dimethyl-2-butyn-1-ylthio group, 2,2-dimethyl-2-butyn-1-ylthio group, 3,3-dimethyl-2-butyn-1-ylthio group, 1,1-dimethyl-3-butyn-1-ylthio group, 1,2-dimethyl-3-butyn-1-ylthio group, 1,3-dimethyl-3-butyn-1-ylthio group, 2,2-dimethyl-3-butyn-1-ylthio group and 3,3-dimethyl-3-butyn-1-ylthio group; more preferably ethynylthio group, 1-propyn-1-ylthio group, 2-propyn-1-ylthio group, 3-propyn-1-ylthio group, 1-butyn-1-ylthio group, 1-butyn-2-ylthio group, 1-butyn-3-ylthio group, 1-butyn-4-ylthio group, 2-butyn-1-ylthio group, 2-butyn-2-ylthio group, 1-methyl-1-propyn-1-ylthio group, 2-methyl-1-propyn-1-ylthio group, 1-methyl-2-propyn-1-ylthio group, 2-methyl-2-propyn-1-ylthio group, 1-methyl-1-butyn-1-ylthio group, 2-methyl-1-butyn-1-ylthio group, 3-methyl-1-butyn-1-ylthio group, 1-methyl-2-butyn-1-ylthio group, 2-methyl-2-butyn-1-ylthio group, 3-methyl-2-butyn-1-ylthio group, 1-methyl-3-butyn-1-ylthio group, 2-methyl-3-butyn-1-ylthio group and 3-methyl-3-butyn-1-ylthio group; further preferably ethynylthio group, 1-propyn-1-ylthio group, 2-propyn-1-ylthio group, 3-propyn-1-ylthio group, 1-butyn-1-ylthio group, 1-butyn-2-ylthio group, 1-butyn-3-ylthio group, 1-butyn-4-ylthio group, 2-butyn-1-ylthio group and 2-butyn-2-ylthio group; and most preferably ethynylthio group, 1-propyn-1-ylthio group, 2-propyn-1-ylthio group and 3-propyn-1-ylthio group.

When $R^1$ represents a $C_{6-12}$ aryl group which may have one or more substituents, the aryl group refers to an aromatic cyclic group, and specific examples thereof include phenyl group, 1-naphthyl group, 2-naphthyl group, as-indacenyl group, s-indacenyl group and acenapthylenyl group. The group is preferably phenyl group, 1-naphthyl group or 2-naphthyl group, more preferably phenyl group.

Similarly, when $R^1$ represents a $C_{6-12}$ aryloxy group which may have one or more substituents, the aryloxy group refers to a group having an oxygen atom bound to the end of the $C_{6-12}$ aryl group, and specific examples thereof include phenyloxy group, 1-naphthyloxy group, 2-naphthyloxy group, as-indacenyloxy group, s-indacenyloxy group and acenapthylenyloxy group. The group is preferably phenyloxy group, 1-naphthyloxy group or 2-naphthyloxy group, more preferably phenyloxy group.

Similarly, when $R^1$ represents a $C_{6-12}$ arylthio group which may have one or more substituents, the arylthio group refers to a group having a sulfur atom bound to the end of the $C_{6-12}$ aryl group, and specific examples thereof include phenylthio group, 1-naphthylthio group, 2-naphthylthio group, as-indacenylthio group, s-indacenylthio group and acenapthylenylthio group. The group is preferably phenylthio group, 1-naphthylthio group or 2-naphthylthio group, more preferably phenylthio group.

When $R^1$ represents a $C_{7-18}$ alkylaryl group which may have one or more substituents, the alkylaryl group refers to a group having the $C_{6-12}$ aryl group substituted at a substitutable site with the $C_{1-6}$ alkyl group. Specific examples thereof include tolyl group, xylyl group, cumenyl group, mesityl group, cymenyl group and styryl group; preferably tolyl group, xylyl group, cumenyl group, mesityl group, cymenyl group and styryl group; more preferably tolyl group, xylyl group, cumenyl group and mesityl group; and further preferably tolyl group, xylyl group and cumenyl group.

Similarly, when $R^1$ represents a $C_{7-18}$ alkylaryloxy group which may have one or more substituents, the alkylaryloxy group refers to a group having an oxygen atom bound to the end of the $C_{7-18}$ alkylaryl group. Specific examples thereof include o-tolyloxy group, m-tolyloxy group, p-tolyloxy group, 2,3-xylyl-1-oxy group, 2,4-xylyl-1-oxy group, 2,5-xylyl-1-oxy group, o-cumenyloxy group, m-cumenyloxy group, p-cumenyloxy group, mesityloxy group, 2,3-cymenyl-1-oxy group, 2,4-cymenyl-1-oxy group, 2,5-cymenyl-1-oxy group, o-styryloxy group, m-styryloxy group and p-styryloxy group; preferably o-tolyloxy group, m-tolyloxy group, p-tolyloxy group, 2,3-xylyl-1-oxy group, 2,4-xylyl-1-oxy group, 2,5-xylyl-1-oxy group, o-cumenyloxy group, m-cumenyloxy group, p-cumenyloxy group, mesityloxy group, 2,3-cymenyl-1-oxy group, 2,4-cymenyl-1-oxy group, 2,5-cymenyl-1-oxy group, o-styryloxy group, m-styryloxy group and p-styryloxy group; more preferably o-tolyloxy group, m-tolyloxy group, p-tolyloxy group, 2,3-xylyl-1-oxy group, 2,4-xylyl-1-oxy group, 2,5-xylyl-1-oxy group, o-cumenyloxy group, m-cumenyloxy group, p-cumenyloxy group, mesityloxy group, o-styryloxy group, m-styryloxy group and p-styryloxy group; more preferably o-tolyloxy group, m-tolyloxy group, p-tolyloxy group, 2,3-xylyl-1-oxy group, 2,4-xylyl-1-oxy group, 2,5-xylyl-1-oxy group and mesityloxy group; and most preferably o-tolyloxy group, m-tolyloxy group and p-tolyloxy group.

Similarly, when $R^1$ represents a $C_{7-18}$ alkylarylthio group which may have one or more substituents, the alkylarylthio group refers to a group having a sulfur atom bound to the end of the $C_{7-18}$ alkylaryl group. Specific examples thereof include o-tolylthio group, m-tolylthio group, p-tolylthio group, 2,3-xylyl-1-thio group, 2,4-xylyl-1-thio group, 2,5-xylyl-1-thio group, o-cumenylthio group, m-cumenylthio group, p-cumenylthio group, mesitylthio group, 2,3-cymenyl-1-thio group, 2,4-cymenyl-1-thio group, 2,5-cymenyl-1-thio group, o-styrylthio group, m-styrylthio group and p-styrylthio group; preferably o-tolylthio group, m-tolylthio group, p-tolylthio group, 2,3-xylyl-1-thio group, 2,4-xylyl-1-thio group, 2,5-xylyl-1-thio group, o-cumenylthio group, m-cumenylthio group, p-cumenylthio group, mesitylthio group, 2,3-cymenyl-1-thio group, 2,4-cymenyl-1-thio group, 2,5-cymenyl-1-thio group, o-styrylthio group, m-styrylthio group and p-styrylthio group; more preferably o-tolylthio group, m-tolylthio group, p-tolylthio group, 2,3-xylyl-1-thio group, 2,4-xylyl-1-thio group, 2,5-xylyl-1-thio group, o-cumenylthio group, m-cumenylthio group, p-cumenylthio group, mesitylthio group, o-styrylthio group, m-styrylthio group and p-styrylthio group; further preferably o-tolylthio group, m-tolylthio group, p-tolylthio group, 2,3-xylyl-1-thio group, 2,4-xylyl-1-thio group, 2,5-xylyl-1-thio group and mesitylthio group; and most preferably o-tolylthio group, m-tolylthio group and p-tolylthio group.

When $R^1$ represents a $C_{7-18}$ aralkyl group which may have one or more substituents, the aralkyl group refers to a group having the $C_{1-6}$ alkyl group substituted at a substitutable site with the $C_{6-12}$ aryl group. Specific examples thereof include benzyl group, phenetyl group, 3-phenyl propyl group, 4-phenyl butyl group, 5-phenyl pentyl group, 6-phenyl hexyl group, 1-naphthyl methyl group, 2-naphthyl methyl group, 1-naphthyl ethyl group, 2-naphthyl ethyl group, 1-naphthyl propyl group and 2-naphthyl propyl group; preferably benzyl group, phenetyl group, 3-phenyl propyl group, 4-phenyl butyl group, 5-phenyl pentyl group, 6-phenyl hexyl group, 1-naphthyl methyl group, 2-naphthyl methyl group, 1-naphthyl ethyl group, 2-naphthyl ethyl group, 1-naphthyl propyl group and 2-naphthyl propyl group; more preferably benzyl group, phenetyl group, 3-phenyl propyl group, 4-phenyl butyl group, 5-phenyl pentyl group, 6-phenyl hexyl group, 1-naphthyl methyl group and 2-naphthyl methyl group; further preferably benzyl group, phenetyl group, 3-phenyl propyl group and 4-phenyl butyl group; and most preferably benzyl group and phenetyl group.

Similarly, when $R^1$ represents a $C_{7-18}$ aralkyloxy group which may have one or more substituents, the aralkyloxy group refers to a group having an oxygen atom bound to the $C_{7-18}$ aralkyl group. Specific examples thereof include benzyloxy group, phenetyloxy group, 3-phenylpropyloxy group, 4-phenylbutyloxy group, 5-phenylpentyloxy group, 6-phenylhexyloxy group, 1-naphthylmethyloxy group, 2-naphthylmethyloxy group, 1-naphthylethyloxy group, 2-naphthylethyloxy group, 1-naphthylpropyloxy group and 2-naphthylpropyloxy group; preferably benzyloxy group, phenetyloxy group, 3-phenylpropyloxy group, 4-phenylbutyloxy group, 5-phenylpentyloxy group, 6-phenylhexyloxy group, 1-naphthylmethyloxy group, 2-naphthylmethyloxy group, 1-naphthylethyloxy group, 2-naphthylethyloxy group, 1-naphthylpropyloxy group and 2-naphthylpropyloxy group; more preferably benzyloxy group, phenetyloxy group, 3-phenylpropyloxy group, 4-phenylbutyloxy group, 5-phenylpentyloxy group, 6-phenylhexyloxy group, 1-naphthylmethyloxy group and 2-naphthylmethyloxy group; further preferably benzyloxy group, phenetyloxy group, 3-phenylpropyloxy group and 4-phenylbutyloxy group; and most preferably benzyloxy group and phenetyloxy group.

Similarly, when $R^1$ represents a $C_{7-18}$ aralkylthio group which may have one or more substituents, the aralkylthio group refers to a group having a sulfur atom bound to the end of the $C_{7-18}$ aralkyl group. Specific examples thereof include benzylthio group, phenetylthio group, 3-phenyl propylthio group, 4-phenyl butylthio group, 5-phenyl pentylthio group, 6-phenyl hexylthio group, 1-naphthyl methylthio group, 2-naphthyl methylthio group, 1-naphthyl ethylthio group, 2-naphthyl ethyl thio group, 1-naphthyl propylthio group and 2-naphthyl propylthio group; preferably benzylthio group, phenetylthio group, 3-phenyl propylthio group, 4-phenyl butylthio group, 5-phenyl pentylthio group, 6-phenyl hexylthio group, 1-naphthyl methylthio group, 2-naphthyl methylthio group, 1-naphthyl ethylthio group, 2-naphthyl ethylthio group, 1-naphthyl propylthio group and 2-naphthyl propylthio group; more preferably benzylthio group, phenetylthio group, 3-phenyl propylthio group, 4-phenyl butylthio group, 5-phenyl pentylthio group, 6-phenyl hexylthio group, 1-naphthyl methylthio group and 2-naphthyl methylthio group; further preferably benzylthio group, phenetylthio group, 3-phenyl propylthio group and 4-phenyl butylthio group; and most preferably benzylthio group and phenetylthio group.

When L represents a single bond, the compounds of the invention are exemplified by carboxylic acid derivatives having group X bound via a single bond to the group Y, represented by the following formula:

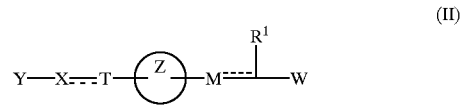

(II)

(wherein each symbol has the same meaning as defined above), a salts thereof, an ester thereof or a hydrate of them.

Similarly, when L represents a double bond, the compounds of the invention are exemplified by carboxylic acid derivatives having group X bound via a single bond to the group Y, represented by the following formula:

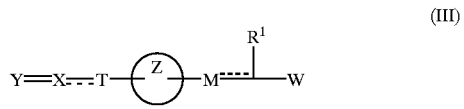

(III)

(wherein each symbol has the same meaning as defined above), a salt thereof, an ester thereof or a hydrate of them.

Similarly, when M represents a single bond, the compounds of the invention are exemplified by carboxylic acid derivatives represented by the following formula:

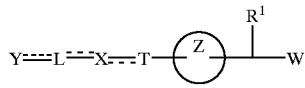

(IV)

(wherein each symbol has the same meaning as defined above), a salt thereof, an ester thereof or a hydrate of them.

When T represents a single bond, the compounds of the invention are exemplified by carboxylic acid derivatives represented by the following formula:

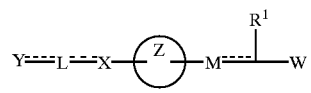

(V)

(wherein each symbol has the same meaning as defined above), a salt thereof, an ester thereof or a hydrate of them.

When L and M each represent a $C_{1-5}$ alkylene group which may have one or more substituents, the alkylene group refers to a divalent group derived by removing one hydrogen atom from the above-mentioned $C_{1-6}$ alkyl group. Specific examples thereof include methylene group, ethylene group, methyl ethylene group, propylene group, ethyl ethylene group, 1,1-dimethyl ethylene group, 1,2-dimethyl ethylene group, trimethylene group, 1-methyl trimethylene group, 1-ethyl trimethylene group, 2-methyl trimethylene group, 1,1-dimethyl trimethylene group, tetramethylene group, pentamethylene group and hexamethylene group; preferably methylene group, ethylene group, methyl ethylene group, propylene group, ethyl ethylene group, 1,1-dimethyl ethylene group, 1,2-dimethyl ethylene group, trimethylene group, 1-methyl trimethylene group, 1-ethyl trimethylene group, 2-methyl trimethylene group, 1,1-dimethyl trimethylene group, tetramethylene group, pentamethylene group and hexamethylene group; more preferably methylene group, ethylene group, methyl ethylene group, propylene group, ethyl ethylene group, 1,1-dimethyl ethylene group, 1,2-dimethyl ethylene group, trimethylene group, 1-methyl trimethylene group, 1-ethyl trimethylene group, 2-methyl trimethylene group and 1,1-dimethyl trimethylene group; further preferably methylene group, ethylene group, methyl ethylene group, propylene group, ethyl ethylene group, 1,1-dimethyl ethylene group, 1,2-dimethyl ethylene group and trimethylene group; more further preferably a methylene group, ethylene group, methyl ethylene group and propylene group; and most preferably methylene group or ethylene group.

Similarly, when T represents a $C_{1-3}$ alkylene group which may have one or more substituents, the alkylene group refers to a divalent group derived by removing one hydrogen atom from the $C_{1-3}$ alkyl group. Specific examples thereof include the $C_{1-3}$ alkylene group described above; preferably methylene group, ethylene group and propylene group; further preferably methylene group and ethylene group; and most preferably methylene group.

When L, M and X each represent a $C_{2-6}$ alkenylene group which may have one or more substituents, the alkenylene group refers to a divalent group derived by removing one hydrogen atom from the $C_{2-6}$ alkenyl group. Specific examples thereof include vinylene group, propenylene group, butenylene group, pentenylene group and hexenylene group; preferably vinylene group, propenylene group, butenylene group and pentenylene group; more preferably vinylene group, propenylene group and butenylene group; further preferably vinylene group and propenylene group; and most preferably vinylene group.

Similarly, when T represents a $C_{2-3}$ alkenylene group which may have one or more substituents, the alkenylene group refers to a divalent group derived by removing one hydrogen atom from the $C_{2-3}$ alkenyl group. Specific examples thereof include the $C_{2-3}$ alkenylene group described above; preferably vinylene group or propenylene group; and further preferably vinylene group.

When L and M each represent a $C_{2-6}$ alkynylene group which may have one or more substituents, the alkynylene group refers to a divalent group derived by removing one hydrogen atom from the $C_{2-6}$ alkynyl group. Specific examples thereof include ethynylene group, propynylene group, butynylene group, pentynylene group and hexynylene group; preferably ethynylene group, propynylene group, butynylene group and pentynylene group; more preferably ethynylene group, propynylene group and butynylene group; further preferably ethynylene group and propynylene group; and most preferably ethynylene group.

Similarly, when T represents a $C_{2-3}$ alkynylene group which may have one or more substituents, the alkynylene group refers to a divalent group derived by removing one hydrogen atom from the $C_{2-3}$ alkynyl group. Specific examples thereof include the $C_{2-3}$ alkynylene group described above; preferably ethynylene or propynylene group; and further preferably ethynylene group.

When $R^{w1}$, $R^{w2}$, $R^{x}$, $R^{x1}$ and $R^{x2}$ each represent a $C_{2-7}$ aliphatic acyl group which may have one or more substituents, the aliphatic acyl group refers to a group having a carbonyl group added to the end of the $C_{1-6}$ alkyl foup, the $C_{2-6}$ alkenyl or the $C_{2-6}$ alkynyl group. Specific examples thereof include acetyl group, propionyl group, butyryl group, isobutyryl group, valeryl group, isovaleryl group, pivaloyl group, hexanoyl group, octanoyl group, acryloyl group, methacryloyl group and crotonyl group; preferably acetyl group, propionyl group, butyryl group, isobutyryl group, valeryl group, isovaleryl group, pivaloyl group, hexanoyl group, octanoyl group, acryloyl group, methacryloyl group and crotonyl group; more preferably acetyl group, propionyl group, butyryl group, isobutyryl group, valeryl group, isovaleryl group, pivaloyl group, hexanoyl group and octanoyl group; further preferably acetyl group, propionyl group, butyryl group and isobutyryl group; and most preferably acetyl group and propionyl group.

When $R^{w1}$, $R^{w2}$, $R^{x}$, $R^{x1}$ and $R^{x2}$ each represent a $C_{7-19}$ aromatic acyl group which may have one or more substituents, the aromatic acyl group refers to a group wherein a carbonyl group or a group derived by removing one hydrogen atom from the $C_{2-7}$ aliphatic acyl group has been added to the end of the $C_{5-12}$ aryl group. Specific examples thereof include benzoyl group, o-toluoyl group, m-toluoyl group, p-toluoyl group, cinnamoyl group, 1-naphthoyl group and 2-naphthoyl group; preferably benzoyl group, o-toluoyl group, m-toluoyl group, p-toluoyl group, cinnamoyl group, 1-naphthoyl group and 2-naphthoyl group; more preferably benzoyl group, o-toluoyl group, m-toluoyl group, p-toluoyl group and cinnamoyl group; further preferably benzoyl group and cinnamoyl group; and most preferably benzoyl group.

═══ represents a single or double bond. Accordingly, the compounds of the present invention represented by the following formula (I):

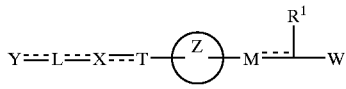
(I)

(wherein each symbol has the same meaning as defined above) also encompass the carboxylic acid derivatives represented by the the following formulae:

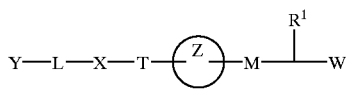
(Ia)

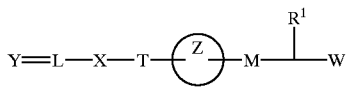
(Ib)

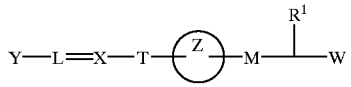
(Ic)

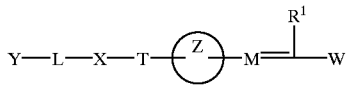
(Id)

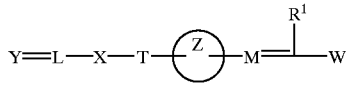
(Ie)

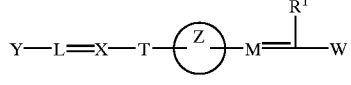
(If)

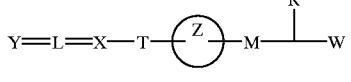
(Ig)

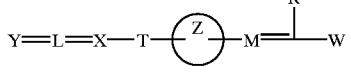
(Ih)

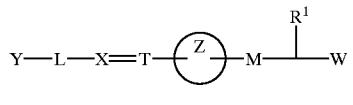
(Ii)

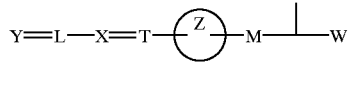
(Ij)

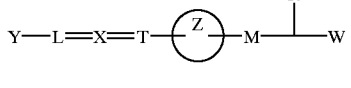
(Ik)

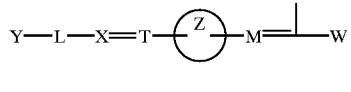
(Il)

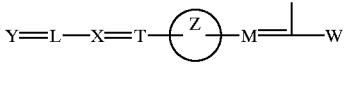
(Im)

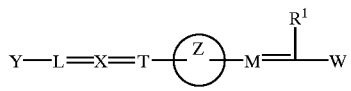
(In)

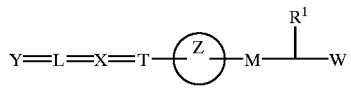
(Io)

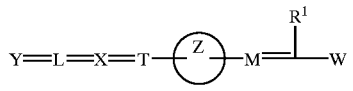
(Ip)

(wherein each symbol has the same meaning as defined above), a salt thereof, an ester thereof or a hydrate of them.

Q represents oxygen or sulfur atom. Accordingly, the formula —CQ— refers to a carbonyl group or thiocarbonyl group.

Y represents a $C_{5-12}$ aromatic hydrocarbon group which may have one or more substituents, and which may have one or more heteroatoms, the aromatic hydrocarbon group refers to the $C_{6-12}$ aryl group or a group having the $C_{6-12}$ aryl group substituted at a substitutable site with the $C_{1-6}$ aliphatic hydrocarbon group, provided that the number of carbon atoms in the aromatic hydrocarbon group does not exceed 12, and the aliphatic hydrocarbon group includes a monovalent to polyvalent group. Specifically, this group includes phenyl group, o-tolyl group, m-tolyl group, p-tolyl group, 2,3-xylyl group, 2,4-xylyl group, 2,5-xylyl group, mesityl group, cymenyl group, o-cumenyl group, m-cumenyl group, p-cumenyl group, benzyl group, phenetyl group, α-methyl benzyl group, benzhydryl group, tolytyl group, benzylidene group, styryl group, cinnamyl group, cinnamylidene group, 3-phenyl propyl group, 4-phenyl butyl group, 5-phenyl pentyl group, 6-phenyl hexyl group, 1-naphthyl group, 2-naphthyl group, 1-naphthyl methyl group, 2-naphthyl methyl group, 1-naphthyl ethyl group, 2-naphthyl ethyl group, as-indacenyl group, s-indacenyl group and acenapthylenyl group; preferably phenyl group, o-tolyl group, m-tolyl group, p-tolyl group, 2,3-xylyl group, 2,4-xylyl group, 2,5-xylyl group, mesityl group, cymenyl group, o-cumenyl group, m-cumenyl group, p-cumenyl group, benzyl group, phenetyl group, α-methyl benzyl group, benzhydryl group, tolytyl group, benzylidene group, styryl group, cinnamyl group, cinnamylidene group, 3-phenyl propyl group, 4-phenyl butyl group, 5-phenyl pentyl group, 6-phenyl hexyl group, 1-naphthyl group, 2-naphthyl group, 1-naphthyl methyl group, 2-naphthyl methyl group, 1-naphthyl ethyl group, 2-naphthyl ethyl group, as-indacenyl group, s-indacenyl group and acenapthylenyl group; more preferably phenyl group, o-tolyl group, m-tolyl group, p-tolyl group, 2,3-xylyl group, 2,4-xylyl group, 2,5-xylyl group, mesityl group, cymenyl group, o-cumenyl group, m-cumenyl group, p-cumenyl group, benzyl group, phenetyl group, α-methyl benzyl group, benzhydryl group, tolytyl group, benzylidene group, styryl group, cinnamyl group, cinnamylidene group, 3-phenyl propyl group, 4-phenyl butyl group, 5-phenyl pentyl group, 6-phenyl hexyl group, 1-naphthyl group, 2-naphthyl group, 1-naphthyl methyl group and 2-naphthyl methyl group; further preferably phenyl group, o-tolyl group, m-tolyl group, p-tolyl group, 2,3-xylyl group, 2,4-xylyl group, 2,5-xylyl group, mesityl group, cymenyl group, o-cumenyl group, m-cumenyl group, p-cumenyl group, benzyl group, phenetyl group, α-methyl benzyl group, benzhydryl group, tolytyl group, benzylidene group, styryl group, cinnamyl group and cinnamylidene group; further more preferably phenyl group, o-tolyl group, m-tolyl group, p-tolyl group, 2,3-xylyl group, 2,4-xylyl group, 2,5-xylyl group, mesityl group, cymenyl group, o-cumenyl group, m-cumenyl group, p-cumenyl group, benzyl group or phenetyl group; and most preferably phenyl group, o-tolyl group, m-tolyl group, p-tolyl group, 2,3-xylyl group, 2,4-xylyl group, 2,5-xylyl group and benzyl group.

As used herein, the heteroatom is for example oxygen atom, sulfur atom, nitrogen atom, phosphorus, arsenic, antimony, silicon, germanium, tin, lead, boron or mercury; preferably oxygen atom, sulfur atom, nitrogen atom and phosphorus; more preferably oxygen atom, sulfur atom and nitrogen atom; and further preferably sulfur atom or nitrogen atom.

Hereinafter, the heteroatoms in the phrase "may have one or more heteroatoms" in the specification have the meaning as defined above.

Accordingly, when Y represents a $C_{5-12}$ aromatic hydrocarbon group having one or more heteroatoms, this group includes e.g. pyridine, thiophene, furan, pyrrole, oxazole, isoxazole, thiazole, isothiazole, imidazole, triazole, pyrazole, furazane, thiadiazole, oxadiazole, pyridazine, pyrimidine, pyrazine, indole, isoindole, indazole, chromene, quinoline, isoquinoline, cinnoline, quinazoline, quinoxaline, naphthylidine, phthalazine, purine, pteridine, thienofurane, imidazothiazole, benzofuran, benzothiophene, benzoxazole, benzthiazole, benzthiadiazole, benzimidazole, imidazopyridine, pyrrolopyridine, pyrrolopyrimidine and pyridopyrimidine; preferably pyridine, thiophene, furan, pyrrole, oxazole, isoxazole, thiazole, isothiazole, imidazole, triazole, pyrazole, furazane, thiadiazole, oxadiazole, pyridazine, pyrimidine, pyrazine, indole, isoindole, indazole, chromene, quinoline, isoquinoline, cinnoline, quinazoline, quinoxaline, naphthylidine, phthalazine, purine, pteridine, thienofurane, imidazothiazole, benzofuran, benzothiophene, benzoxazole, benzthiazole, benzthiadiazole, benzimidazole, imidazopyridine, pyrrolopyridine, pyrrolopyrimidine and pyridopyrimidine; more preferably pyridine, thiophene, furan, pyrrole, oxazole, isoxazole, thiazole, isothiazole, imidazole, triazole, pyrazole, furazane, thiadiazole, oxadiazole, pyridazine, pyrimidine, pyrazine, indole, isoindole, indazole, benzoxazole, benzthiazole and benzthiadiazole; further preferably thiophene, furan, pyrrole, oxazole, isoxazole, thiazole, isothiazole, imidazole, triazole, pyrazole, furazane, thiadiazole, oxadiazole, indole, isoindole and indazole; further more preferably thiophene, furan, pyrrole, oxazole, thiazole, imidazole and indole; and most preferably oxazole and indole.

When Y represents a $C_{3-7}$ alicyclic hydrocarbon group which may have one or more substituents, and which may have one or more heteroatoms, the alicyclic hydrocarbon group refers to a $C_{3-7}$ cyclic aliphatic hydrocarbon group. Specific examples thereof include cyclopropyl group, cyclobutyl group, cyclopentyl group, cyclohexyl group, cycloheptyl group, cyclopropenyl group, cyclobutenyl group, cyclopentenyl group, cylohexenyl group and cycloheptenyl group; preferably cyclopropyl group, cyclobutyl group, cyclopentyl group, cyclohexyl group, cycloheptyl group, cyclopropenyl group, cyclobutenyl group, cyclopentenyl group, cylohexenyl group, and cycloheptenyl group; more preferably cyclopropyl group, cyclobutyl group, cyclopentyl group, cyclohexyl group and cycloheptyl group; further preferably cyclopropyl group, cyclobutyl group, cyclopentyl group and cyclohexyl group; and most preferably cyclopropyl group, cyclobutyl group and cyclopentyl group.

When the ring Z represents a $C_{5-6}$ aromatic hydrocarbon group which may have 0 to 4 substituents, and which may have one or more heteroatoms, this group refers to $C_{5-6}$ aromatic hydrocarbon groups out of the above $C_{5-12}$ aromatic hydrocarbon groups, and includes phenyl group The $C_{5-6}$ aromatic hydrocarbon group which has one or more heteroatoms, which is represented by Z, includes e.g. pyridine, thiophene, furan, pyrrole, oxazole, isoxazole, thiazole, isothiazole, imidazole, triazole, pyrazol, furazane, thiadiazole, oxadiazole, pyridazine, pyrimidine and pyrazine. The group is preferably pyridine, thiophene, furan, pyrrole, oxazole, isoxazole, thiazole, isothiazole, imidazole, triazole, pyrazol, furazane, thiadiazole, oxadiazole, pyridazine, pyrimidine or pyrazine, more preferably pyridine, pyridazine, pyrimidine or pyrazine.

Herein, the group represented by the formula:

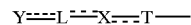

(wherein each symbol has the same meaning as defined above) and the group represented by the formula:

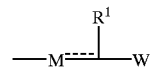

(wherein each symbol has the same meaning as defined above) are bound to each other via 3 atoms on ring Z. Specifically, when ring z is e.g. a benzene ring, it is the compound represented by the formula:

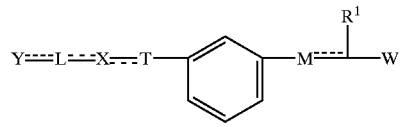

(wherein each symbol has the same meaning as defined above) and accordingly, when ring Z is a benzene ring, the above-mentioned two groups are bound to each other at the m-position on the ring. When ring Z is e.g. a furan ring, the two groups are bound to each other via 3 atoms therebetween, as shown in the compound represented by the formula:

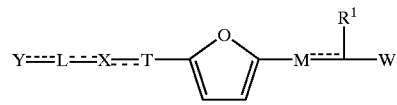

(wherein each symbol has the same meaning as defined above), provided that the position of the oxygen atom is not limited to the position in the above compound.

In the present invention, the salt includes, but is not limited to, inorganic acid addition salts such as hydrofluorate, hydrochloride, sulfate, nitrate, perchlorate, phosphate, carbonate, bicarbonate, hydrobromate and hydroiodate; organic carboxylic acid addition salts such as acetate, maleate, fumarate, oxalate, lactate, tartrate and trifluoroacetate; organic sulfonic acid addition salts such as methane sulfonate, trifluoromethane sulfonate, ethane sulfonate, hydroxymethane sulfonate, hydroxyethane sulfonate, benzene sulfonate, toluene sulfonate and taurine salt; amine addition salts such as trimethyl amine salt, triethylamine salt, pyridine salt, procaine salt, picoline salt, dicyclohexylamine salt, N,N'-dibenzyl ethylene diamine salt, N-methyl glucamine salt, diethanolamine salt, triethanolamine salt, tris(hydroxymethylamino)methane salt and phenetyl benzyl amine salt; alkali metal addition salts such as sodium salt and potassium salt; alkaline earth metal addition salts such as magnesium salt and calcium salt; and amino acid addition salts such as arginine salt, lysine salt, serine salt, glycine salt, aspartate and glutamate. Preferably, these salts are pharmaceutically acceptable salts.

The pharmaceutically acceptable salts include, but are not limited to, inorganic acid addition salts such as hydrochloride, sulfate, carbonate, bicarbonate, hydrobromate and hydroiodate; organic carboxylic acid addition salts such as acetate, maleate, lactate, tartrate and trifluoroacetate; organic sulfonic acid addition salts such as methanesulfonate, hydroxymethanesulfonate, hydroxyethanesulfonate, benzenesulfonate, toluenesulfonate and taurine salt; amine addition salts such as trimethyl amine salt, triethylamine salt, pyridine salt, procaine salt, picoline salt, dicyclohexylamine salt, N,N'-dibenzyl ethylene diamine salt, N-methyl glucamine salt, diethanolamine salt, triethanolamine salt, tris (hydroxymethylamino)methane salt and phenetyl benzyl amine salt; alkali metal addition salts such as sodium salt and potassium salt; and amino acid addition salts such as arginine salt, lysine salt, serine salt, glycine salt, aspartate and glutamate.

In the present invention, the ester refers to an ester formed by a carboxyl group represented by W in the formula (I). This ester is not particularly limited insofar as it is usually used in organic synthesis, and includes physiologically acceptable ester groups hydrolyzed under physiological conditions. Specific examples thereof include a $C_{1-6}$ alkyl group, a $C_{6-12}$ aryl group, a $C_{7-20}$ aralkyl group such as benzyl group, a $C_{7-20}$ heteroarylalkyl group, 4-methoxybenzyl group, an alkanoyloxy alkyl group such as acetoxy methyl group, propionyloxy methyl group and pivaloxy methyl group, an alkoxycarbonyloxy alkyl group such as methoxycarbonyloxy methyl group, ethoxycarbonyloxy methyl group and 2-methoxycarbonyloxy ethyl group, and (5-methyl-2-oxo-1,3-dioxo-4-yl)-methyl group.

In the present invention, when the carboxylic acid derivatives of the above formula (I), a pharmacologically acceptable salt thereof or a pharmacologically acceptable ester thereof form solvates, these solvates also fall under the scope of the present invention.

The compounds of the present invention represented by the formula (I):

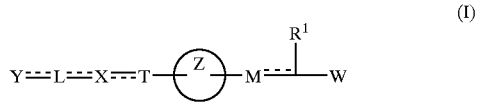

(I)

(wherein each symbol represents the same group as defined above) can be synthesized in a conventional method, and for example, these compounds can be synthesized in the following methods.

A. Process for Producing the Compounds of the Present Invention Represented by the Formula

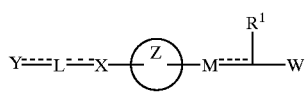

(wherein each symbol represents the same group as defined above), in which in the formula (I), T is a single bond.

Specifically, in the present invention, the compounds represented by the following formula:

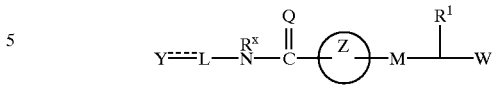

(wherein each symbol represents the same group as defined above) can be synthesized for example by the following general production method A(1) or A(2).

General Production Method A(1)

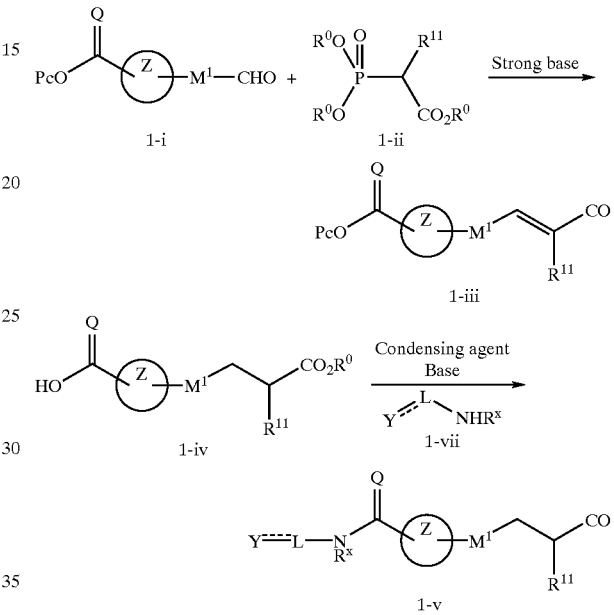

wherein each symbol represents the same group as defined above; Pc is a carboxy-protecting group; $M^1$ is a single bond or a $C_{1-5}$ alkylene group, $C_{2-5}$ alkenylene group or $C_{2-5}$ alkynylene group, each of which may have one or more substituents; $R^0$ is a $C_{1-6}$ alkyl group; and $R^{11}$ is hydrogen atom, hydroxyl group protected with a protective group or a $C_{1-6}$ alkyl group, $C_{1-6}$ hydroxy alkyl group protected at the hydroxy group with a protective group, $C_{1-6}$ aminoalkyl group protected at the amino group with a protective group, $C_{1-6}$ halogenated alkyl group, $C_{2-12}$ alkoxy alkyl group, $C_{3-7}$ cycloalkyl group, $C_{2-6}$ alkenyl group, $C_{2-6}$ alkynyl group, $C_{6-12}$ aryl group, $C_{7-18}$ alkyl aryl group or $C_{7-18}$ aralkyl group, each of which may have one or more substituents, respectively, provided that the group represented by the formula PcOCQ— (wherein each symbol represents the same group as defined above) and the group represented by the formula —$M^1$CHO (wherein each symbol represents the same group as defined above) are bound to each other via 3 atoms on the ring Z.

The compound of the formula (1-iii) can be produced by reacting the compound of the formula (1-ii) with the compound of the formula (1-i).

The reaction of the compound of the formula (1-ii) with the compound of the formula (1-i) can be carried out in the presence of sodium hydride, potassium hydride, t-butoxy potassium etc. in an organic solvent such as tetrahydrofuran and N,N-dimethylformamide. The reaction can be carried out at a temperature under ice-cooling to 50° C.

The compound of the formula (1-iv) can be produced by reducing the compound of the formula (1-iii) in the presence of a catalyst such as palladium-carbon in a solvent such as ethanol, ethyl acetate and tetrahydrofuran.

The compound of the formula (1-v) can be produced by allowing the compound of the formula (1-vii) to act on the compound of the formula (1-iv).

The reaction can be carried out by treating with a condensing agent such as 1-ethyl-3-(3'-dimethylaminopropyl) carbodiimide and diethyl cyanophosphate in an organic solvent such as dimethyl sulfoxide and N,N-dimethylformamide. If necessary, an organic base such as triethylamine may be added. The reaction can be carried out at a temperature under ice-cooling to room temperature.

The compound of the formula (1-vi) can be produced by hydrolyzing the compound of the formula (1-v) with an inorganic base such as sodium hydroxide and potassium hydroxide in an ethanol solvent. The reaction may be carried out at room temperature to a temperature under heating reflux.

General Production Method A(2)

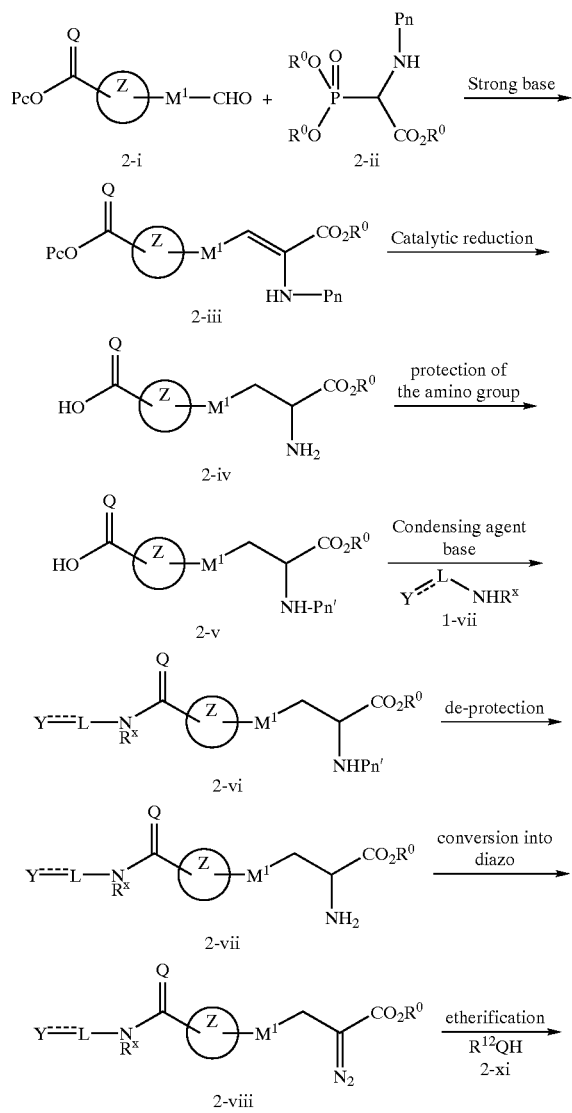

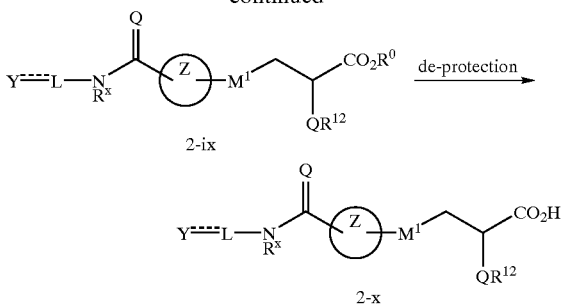

wherein each symbol represents the same group as defined above; Pn and Pn' are different from each other and each represents an amino-protecting group; and $R^{12}$ represents hydrogen atom, a hydroxyl group protected with a protective group or a $C_{1-6}$ alkyl group, $C_{1-6}$ hydroxyalkyl group protected at the hydroxy group with a protective group, $C_{1-6}$ aminoalkyl group protected at the amino group with a protective group, $C_{1-6}$ halogenated alkyl group, $C_{2-12}$ alkoxyalkyl group, $C_{3-7}$ cycloalkyl group, $C_{2-6}$ alkenyl group, $C_{2-6}$ alkynyl group, $C_{6-12}$ aryl group, $C_{7-18}$ alkyl aryl group or $C_{7-18}$ aralkyl group, each of which may have one or more substituents, respectively, provided that the group represented by the formula PcOCQ— (wherein each symbol represents the same group as defined above) and the group represented by the formula —$M^1$CHO (wherein each symbol represents the same group as defined above) are bound to each other via 3 atoms on the ring Z.

The compound of the formula (2-iii) can be produced by reacting the compound of the formula (2-ii) with the compound of the formula (2-i).

The reaction of the compound of the formula (2-ii) with the compound of the formula (2-i) can be carried out in the presence of sodium hydride, potassium hydride, t-butoxy potassium etc. in an organic solvent such as tetrahydrofuran and N,N-dimethylformamide. The reaction can be carried out at a temperature under ice-cooling to 50° C.

The compound of the formula (2-iv) can be produced by reducing the compound of the formula (2-iii) in the presence of a catalyst such as palladium-carbon in a solvent such as ethanol, ethyl acetate or tetrahydrofuran. The reaction can be carried out at a temperature under ice-cooling to room temperature.

The compound of the formula (2-v) can be produced by reacting the compound of the formula (2-iv) with di-t-butyl dicarbonate.

The reaction of the compound of the formula (2-iv) with di-t-butyl dicarbonate can be carried out in the presence of an organic base such as triethylamine etc. in an organic solvent such as ethanol or methanol. The reaction can be carried out at a temperature under ice-cooling to 50° C.

The compound of the formula (2-vi) can be produced by allowing the compound of the formula (1-vii) to act on the compound of the formula (2-v).

The reaction can be carried out by treating with a condensing agent such as 1-ethyl-3-(3'-dimethylaminopropyl) carbodiimide and diethyl cyanophosphate in an organic solvent such as dimethyl sulfoxide and N,N-dimethylformamide. If necessary, an organic base such as triethylamine may be added. The reaction can be carried out at a temperature under ice-cooling to room temperature.

The compound of the formula (2-vii) can be produced by reacting the compound of the formula (2-vi) with hydrochloric acid etc. in an organic solvent such as methanol, tetrahydrofuran, acetone and ethyl acetate. The reaction may be carried out at a temperature ice-cooling to room temperature.

The compound of the formula (2-viii) can be produced by reacting the compound of the formula (2-vii) with isoamyl nitrite.

The reaction can be conducted by adding isoamyl nitrite to the compound of the formula (2-vii) in the presence of an organic acid such as acetic acid in an organic solvent such as chloroform. The reaction can be carried out at a temperature under ice-cooling to 50° C.

The compound of the formula (2-ix) can be produced by heating the compound of the formula (2-viii) and the compound of the formula (2-xi) under reflux in the presence of rhodium acetate.

The compound of the formula (2-x) can be produced by hydrolyzing the compound of the formula (2-ix) with an inorganic base such as sodium hydroxide and potassium hydroxide in an ethanol solvent. The reaction may be carried out at room temperature to a temperature under heating reflux.

In the present invention, the compounds represented by the following formula:

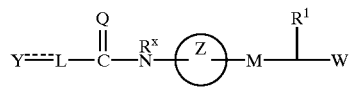

(wherein each symbol represents the same group as defined above) can be synthesized by the following general production method A(3).

General Production Method A(3)

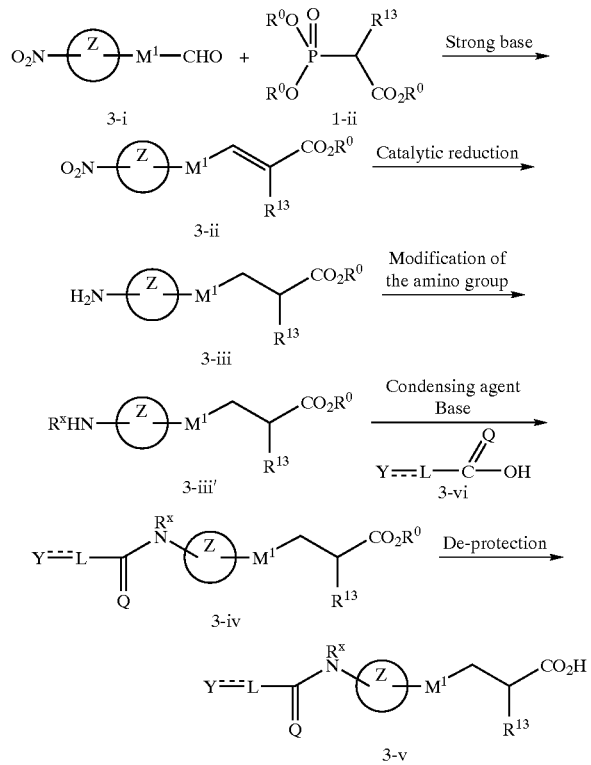

wherein each symbol represents the same group as defined above; and $R^{13}$ represents hydrogen atom, hydroxyl group protected with a protective group or a $C_{1-6}$ alkyl group, $C_{1-6}$ hydroxy alkyl group protected at the hydroxy group with a protective group, $C_{1-6}$ aminoalkyl group protected at the amino group with a protective group, $C_{1-6}$ halogenated alkyl group, $C_{2-12}$ alkoxy alkyl group, $C_{3-7}$ cycloalkyl group, $C_{2-6}$ alkenyl group, $C_{2-6}$ alkynyl group, $C_{6-12}$ aryl group, $C_{7-18}$ alkyl aryl group or $C_{7-18}$ aralkyl group, each of which may have one or more substituents, respectively, provided that the group represented by the formula $O_2N$— (wherein each symbol represents the same group as defined above) and the group represented by the formula —$M^1$CHO (wherein each symbol represents the same group as defined above) are bound to each other via 3 atoms on the ring Z.

The compound of the formula (3-ii) can be produced by reacting the compound of the formula (1-ii) with the compound of the formula (3-i).

The reaction of the compound of the formula (1-ii) with the compound of the formula (3-i) can be carried out in the presence of sodium hydride, potassium hydride, t-butoxy potassium etc. in an organic solvent such as tetrahydrofuran and N,N-dimethylformamide. The reaction can be carried out at a temperature under ice-cooling to 50° C.

The compound of the formula (3-iii) can be produced by reducing the compound of the formula (3-ii) in the presence of a catalyst such as palladium-carbon in a solvent such as ethanol, ethyl acetate and tetrahydrofuran.

The compound of the formula (3-iv) can be produced by allowing the compound of the formula (3-vi) to act on the compound of the formula (3-iii).

The reaction can be carried out by treating with a condensing agent such as 1-ethyl-3-(3'-dimethylaminopropyl)carbodiimide and carbonyl diimidazole in an organic solvent such as tetrahydrofuran If necessary, an organic base such as triethylamine may be added. The reaction can be carried out at a temperature under ice-cooling to 50° C.

The compound of the formula (3-v) can be produced by hydrolyzing the compound of the formula (3-iv) with an inorganic base such as sodium hydroxide and potassium hydroxide in an ethanol solvent. The reaction may be carried out at room temperature to a temperature under heating under reflux.

In the present invention, the compounds represented by the following formula:

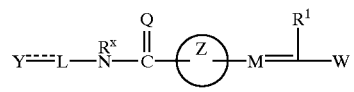

(wherein each symbol represents the same group as defined above) can be synthesized for example by the following general production method A(4).

General Production Method A(4)

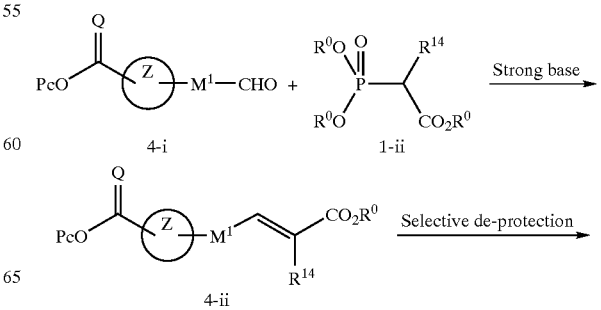

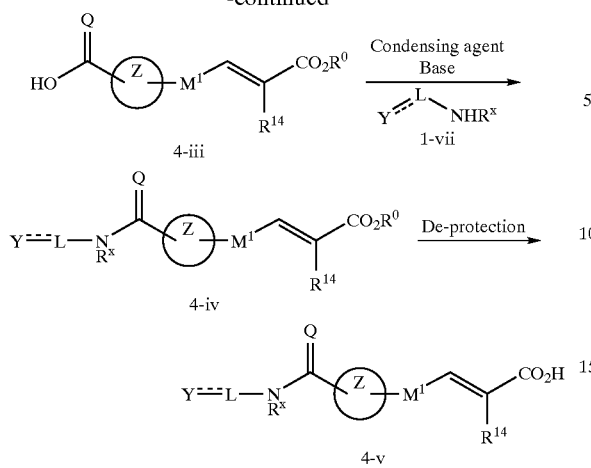

4-iii 4-iv 4-v wherein each symbol represents the same group as defined above; and $R^{14}$ represents hydrogen atom, hydroxyl group protected with a protective group or a $C_{1-6}$ alkyl group, $C_{1-6}$ hydroxy alkyl group protected at the hydroxy group with a protective group, $C_{1-6}$ aminoalkyl group protected at the amino group with a protective group, $C_{1-6}$ halogenated alkyl group, $C_{2-12}$ alkoxy alkyl group, $C_{3-7}$ cycloalkyl group, $C_{2-6}$ alkenyl group, $C_{2-6}$ alkynyl group, $C_{6-12}$ aryl group, $C_{7-18}$ alkyl aryl group or $C_{7-18}$ aralkyl group, each of which may have one or more substituents, respectively, provided that the group represented by the formula PcOCQ— (wherein each symbol represents the same group as defined above) and the group represented by the formula —$M^1$CHO (wherein each symbol represents the same group as defined above) are bound to each other via 3 atoms on the ring Z.

The compound of the formula (4-ii) can be produced by reacting the compound of the formula (1-ii) with the compound of the formula (4-i).

The reaction of the compound of the formula (1-ii) with the compound of the formula (4-i) can be carried out in the presence of sodium hydride, potassium hydride, t-butoxy potassium etc. in an organic solvent such as tetrahydrofuran and N,N-dimethylformamide. The reaction can be carried out at a temperature under ice-cooling to 50° C.

The compound of the formula (4-iii) can be produced by treating the compound of the formula (4-ii) with an organic acid such as trifluoroacetic acid in an organic solvent such as tetrahydrofuran and dichloromethane.

The compound of the formula (4-iv) can be produced by allowing the compound of the formula (1-vii) to act on the compound of the formula (4-iii).

The reaction can be conducted by treatment with a condensing agent such as 1-ethyl-3-(3'-dimethylaminopropyl)carbodiimide and diethyl cyanophosphate in an organic solvent such as dimethyl sulfoxide and N,N-dimethylformamide. If necessary, an organic base such as triethylamine may be added. The reaction can be carried out at a temperature under ice-cooling to room temperature.

The compound of the formula (4-v) can be produced by hydrolyzing the compound of the formula (4-iv) with an inorganic base such as sodium hydroxide and potassium hydroxide in an ethanol solvent. The reaction may be carried out at room temperature to a temperature under heating under reflux.

In the present invention, the compounds represented by the following formula:

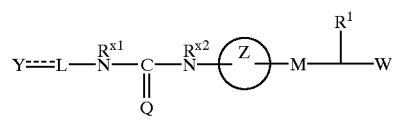

(wherein each symbol represents the same group as defined above) can be synthesized for example by the following general production method A(5)

Production Method A(5)

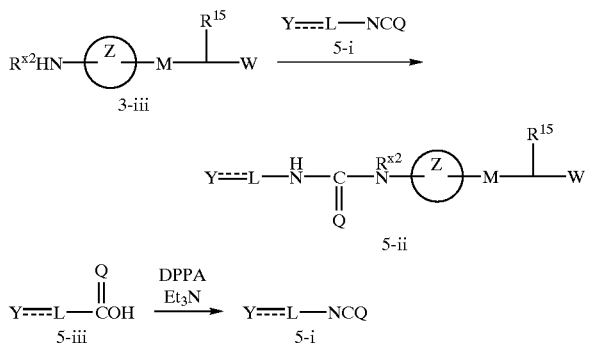

3-iii 5-ii 5-iii    5-i wherein each symbol represents the same group as defined above; and $R^{15}$ represents hydrogen atom, hydroxyl group protected with a protective group or a $C_{1-6}$ alkyl group, $C_{1-6}$ hydroxy alkyl group protected at the hydroxy group with a protective group, $C_{1-6}$ aminoalkyl group protected at the amino group with a protective group, $C_{1-6}$ halogenated alkyl group, $C_{2-12}$ alkoxy alkyl group, $C_{3-7}$ cycloalkyl group, $C_{2-6}$ alkenyl group, $C_{2-6}$ alkynyl group, $C_{6-12}$ aryl group, $C_{7-18}$ alkyl aryl group or $C_{7-18}$ aralkyl group, each of which may have one or more substituents, respectively, provided that the group represented by the formula $R^{x2}$HN— (wherein each symbol represents the same group as defined above) and the group represented by the formula —MCH($R^{15}$)W (wherein each symbol represents the same group as defined above) are bound to each other via 3 atoms on the ring Z.

The compound of the formula (5-ii) can be produced by reacting the compound of the formula (3-iii) with the compound of the formula (5-i) in a solvent such as tetrahydrofuran. The reaction can be carried out at room temperature to 50° C.

The compound of the formula (5-i) can be synthesized by reacting diphenyl phosphoryl azide (DPPA) with the compound of the formula (5-iii).

The reaction can be carried out in the presence of an organic base such as triethylamine in an organic solvent such as toluene and tetrahydrofuran. The reaction can be carried out at room temperature to a temperature under heating under reflux.

Hereinafter, the general processes for synthesizing the compounds of the present invention are described in more detail. The compounds of the present invention can be produced by the following general synthesis methods or by usual organic synthesis means.

Production Method A(1)

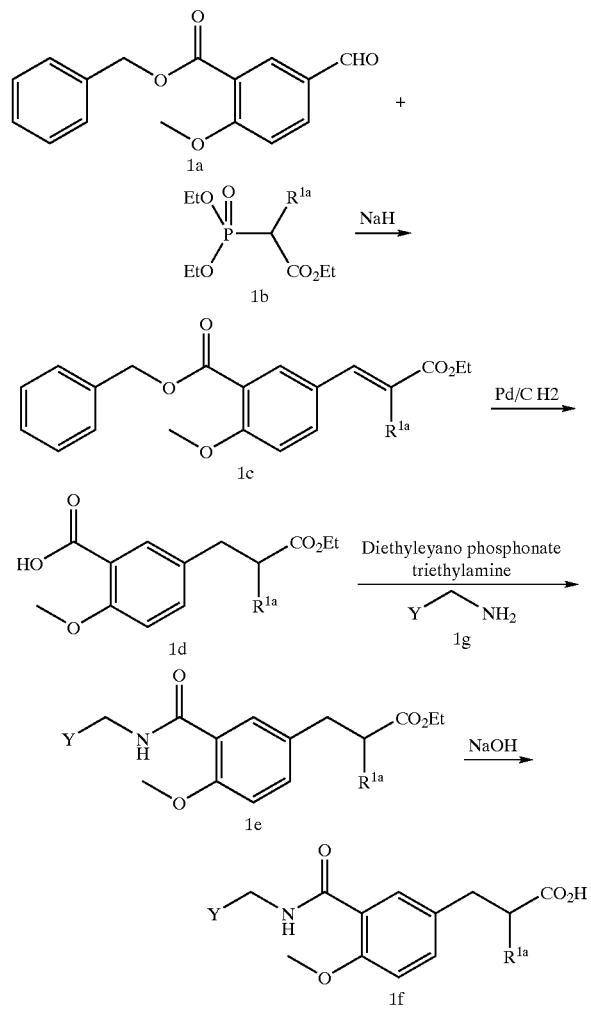

wherein symbols represent the same groups as defined above; $R^{1a}$ represents hydrogen atom, hydroxyl group protected with a protective group or a $C_{1-6}$ alkyl group, $C_{1-6}$ hydroxyalkyl group protected at the hydroxy group with a protective group, $C_{1-6}$ aminoalkyl group protected at the amino group with a protective group, $C_{1-6}$ halogenated alkyl group, $C_{2-12}$ alkoxy alkyl group, $C_{3-7}$ cycloalkyl group, $C_{2-6}$ alkenyl group, $C_{2-6}$ alkynyl group, $C_{6-12}$ aryl group, $C_{7-18}$ alkyl aryl group or $C_{7-18}$ aralkyl group, each of which may have one or more substituents.

The compound of the formula (1c) can be produced by reacting the compound of the formula (1b) with the compound of the formula (1a).

The reaction of the compound of the formula (1b) with the compound of the formula (1a) can be carried out in the presence of sodium hydride, potassium hydride, t-butoxy potassium etc. in an organic solvent such as tetrahydrofuran and N,N-dimethylformamide. The reaction can be carried out at a temperature under ice-cooling to 50° C.

The compound of the formula (1d) can be produced by reducing the compound of the formula (1c) in the presence of a catalyst such as palladium-carbon in a solvent such as ethanol, ethyl acetate and tetrahydrofuran.

The compound of the formula (1e) can be produced by allowing the compound of the formula (1g) to act on the compound of the formula (1d).

The reaction can be carried out by treating with a condensing agent such as 1-ethyl-3-(3'-dimethylaminopropyl) carbodiimide and diethyl cyanophosphate in an organic solvent such as dimethyl sulfoxide and N,N-dimethylformamide. If necessary, an organic base such as triethylamine may be added. The reaction can be carried out at a temperature under ice-cooling to room temperature.

The compound of the formula (1f) can be produced by hydrolyzing the compound of the formula (1e) with an inorganic base such as sodium hydroxide and potassium hydroxide in an ethanol solvent. The reaction may be carried out at room temperature to a temperature under heating under reflux.

Production Method A(2)

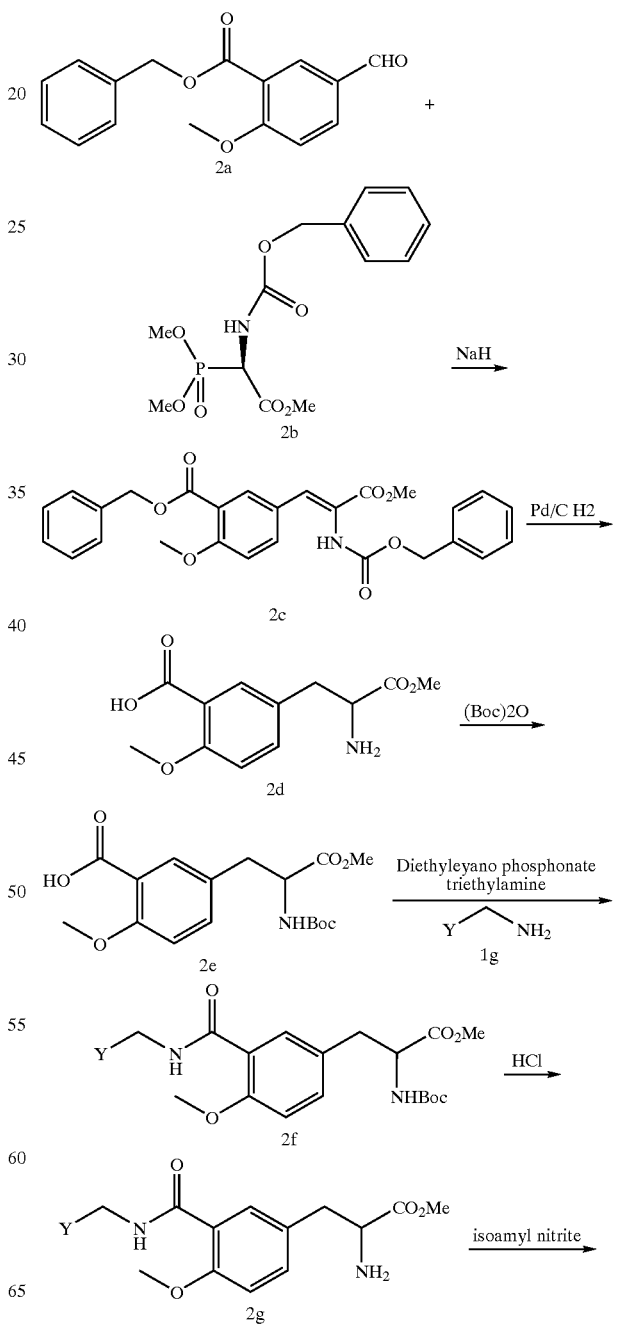

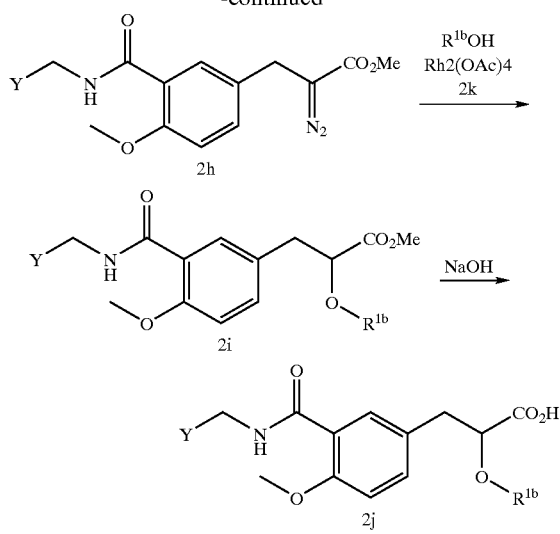

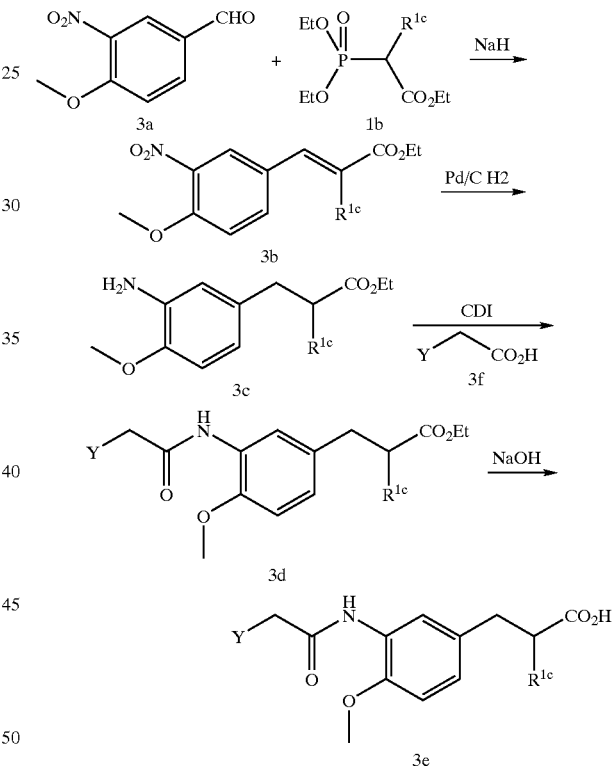

wherein symbols represent the same groups as defined above; $R^{1b}$ represents hydrogen atom, hydroxyl group protected with a protective group or a $C_{1-6}$ alkyl group, $C_{1-6}$ hydroxyalkyl group protected at the hydroxy group with a protective group, $C_{1-6}$ aminoalkyl group protected at the amino group with a protective group, $C_{1-6}$ halogenated alkyl group, $C_{2-12}$ alkoxy alkyl group, $C_{3-7}$ cycloalkyl group, $C_{2-6}$ alkenyl group, $C_{2-6}$ alkynyl group, $C_{6-12}$ aryl group, $C_{7-18}$ alkyl aryl group or $C_{7-18}$ aralkyl group, each of which may have one or more substituents.

The compound of the formula (2c) can be produced by reacting the compound of the formula (2b) with the compound of the formula (2a).

The reaction of the compound of the formula (2b) with the compound of the formula (2a) can be carried out in the presence of sodium hydride, potassium hydride, t-butoxy potassium etc. in an organic solvent such as tetrahydrofuran and N,N-dimethylformamide. The reaction can be carried out at a temperature under ice-cooling to 50° C.

The compound of the formula (2d) can be produced by reducing the compound of the formula (2c) in the presence of a catalyst such as palladium-carbon in a solvent such as ethanol, ethyl acetate or tetrahydrofuran. The reaction can be carried out at a temperature under ice-cooling to room temperature.

The compound of the formula (2e) can be produced by reacting the compound of the formula (2d) with di-t-butyl dicarbonate.

The reaction of the compound of the formula (2d) with di-t-butyl dicarbonate can be carried out in the presence of an organic base such as triethylamine in an organic solvent such as ethanol and methanol. The reaction can be carried out at a temperature under ice-cooling to 50° C.

The compound of the formula (2f) can be produced by allowing the compound of the formula (1g) to act on the compound of the formula (2e).

The reaction can be carried out by treating with a condensing agent such as 1-ethyl-3-(3'-dimethylaminopropyl) carbodiimide and diethyl cyanophosphate in an organic solvent such as dimethyl sulfoxide and N,N-dimethylformamide. If necessary, an organic base such as triethylamine may be added. The reaction can be carried out at a temperature under ice-cooling to room temperature.

The compound of the formula (2g) can be produced by reacting the compound of the formula (2f) with hydrochloric acid in an organic solvent such as methanol, tetrahydrofuran, acetone and ethyl acetate. The reaction may be carried out at a temperature ice-cooling to room temperature.

The compound of the formula (2h) can be produced by reacting the compound of the formula (2g) with isoamyl nitrite.

The reaction can be conducted by adding isoamyl nitrite to the compound of the formula (2g) in the presence of an organic acid such as acetic acid in an organic solvent such as chloroform. The reaction can be carried out at a temperature under ice-cooling to 50° C.

The compound of the formula (2i) can be produced by heating the compound of the formula (2h) and the compound of the formula (2k) under reflux in the presence of rhodium acetate.

The compound of the formula (2j) can be produced by hydrolyzing the compound of the formula (2i) with an inorganic base such as sodium hydroxide and potassium hydroxide in an ethanol solvent. The reaction may be carried out at room temperature to a temperature under heating under reflux.

Production Method A(3)

wherein symbols represent the same groups as defined above; $R^{1c}$ represents hydrogen atom, hydroxyl group protected with a protective group or a $C_{1-6}$ alkyl group, $C_{1-6}$ hydroxyalkyl group protected at the hydroxy group with a protective group, $C_{1-6}$ aminoalkyl group protected at the amino group with a protective group, $C_{1-6}$ halogenated alkyl group, $C_{2-12}$ alkoxy alkyl group, $C_{3-7}$ cycloalkyl group, $C_{2-6}$ alkenyl group, $C_{2-6}$ alkynyl group, $C_{6-12}$ aryl group, $C_{7-18}$ alkyl aryl group or $C_{7-18}$ aralkyl group, each of which may have one or more substituents.

The compound of the formula (3b) can be produced by reacting the compound of the formula (1b) with the compound of the formula (3a).

The reaction of the compound of the formula (1b) with the compound of the formula (3a) can be carried out in the presence of sodium hydride, potassium hydride and t-butoxy potassium in an organic solvent such as tetrahydrofuran and N,N-dimethylformamide. The reaction can be carried out at a temperature under ice-cooling to 50° C.

The compound of the formula (3c) can be produced by reducing the compound of the formula (3b) in the presence of a catalyst such as palladium-carbon in a solvent such as ethanol, ethyl acetate and tetrahydrofuran.

The compound of the formula (3d) can be produced by allowing the compound of the formula (3f) to act on the compound of the formula (3c).

The reaction can be carried out by treating with a condensing agent such as 1-ethyl-3-(3'-dimethylaminopropyl) carbodiimide and carbonyl diimidazole in an organic solvent such as tetrahydrofuran. If necessary, an organic base such as triethylamine may be added. The reaction can be carried out at a temperature under ice-cooling to 50° C.

The compound of the formula (3e) can be produced by hydrolyzing the compound of the formula (3d) with an inorganic base such as sodium hydroxide and potassium hydroxide in an ethanol solvent. The reaction may be carried out at room temperature to a temperature under heating under reflux.

Production Method A(4)

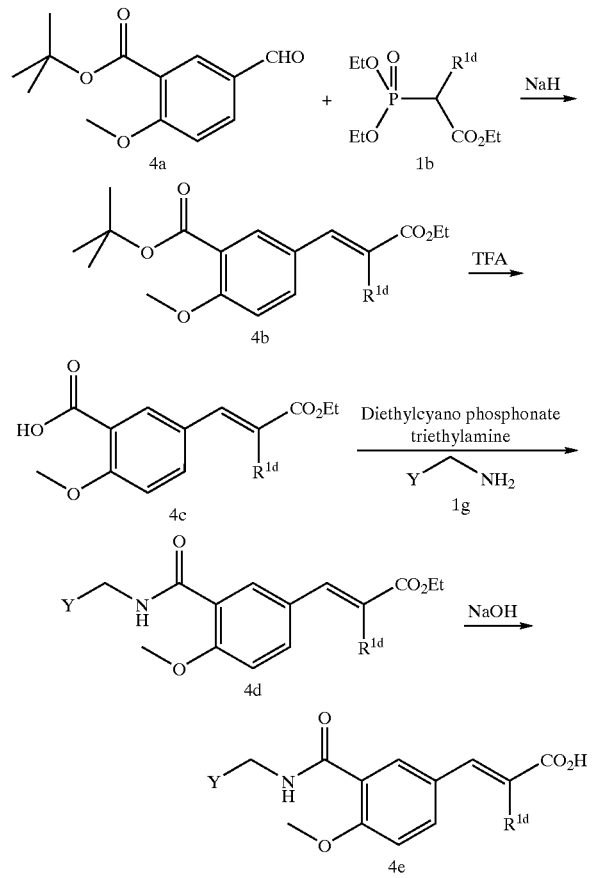

wherein symbols represent the same groups as defined above; $R^{1d}$ represents hydrogen atom, hydroxyl group protected with a protective group or a $C_{1-6}$ alkyl group, $C_{1-6}$ hydroxyalkyl group protected at the hydroxy group with a protective group, $C_{1-6}$ aminoalkyl group protected at the amino group with a protective group, $C_{1-6}$ halogenated alkyl group, $C_{2-12}$ alkoxy alkyl group, $C_{3-7}$ cycloalkyl group, $C_{2-6}$ alkenyl group, $C_{2-6}$ alkynyl group, $C_{6-12}$ aryl group, $C_{7-18}$ alkyl aryl group or $C_{7-18}$ aralkyl group, each of which may have one or more substituents.

The compound of the formula (4b) can be produced by reacting the compound of the formula (1b) with the compound of the formula (4a).

The reaction of the compound of the formula (1b) with the compound of the formula (4a) can be carried out in the presence of sodium hydride, potassium hydride and t-butoxy potassium in an organic solvent such as tetrahydrofuran and N,N-dimethylformamide. The reaction can be carried out at a temperature under ice-cooling to 50° C.

The compound of the formula (4c) can be produced by treating the compound of the formula (4b) with an organic acid such as trifluoroacetic acid in an organic solvent such as tetrahydrofuran and dichloromethane.

The compound of the formula (4d) can be produced by allowing the compound of the formula (1g) to act on the compound of the formula (4c).

The reaction can be conducted by treatment with a condensing agent such as 1-ethyl-3-(3'-dimethylaminopropyl)carbodiimide and diethyl cyanophosphate in an organic solvent such as dimethyl sulfoxide and N,N-dimethylformamide. If necessary, an organic base such as triethylamine may be added. The reaction can be carried out at a temperature under ice-cooling to room temperature.

The compound of the formula (4e) can be produced by hydrolyzing the compound of the formula (4d) with an inorganic base such as sodium hydroxide and potassium hydroxide in an ethanol solvent. The reaction may be carried out at room temperature to a temperature under heating under reflux.

Production Method A(5)

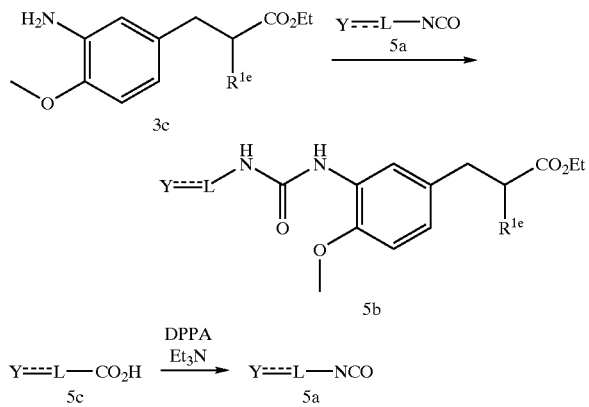

wherein each symbol represents the same group as defined above; $R^{1c}$ represents hydrogen atom, hydroxyl group protected with a protective group or a $C_{1-6}$ alkyl group, $C_{1-6}$ hydroxyalkyl group protected at the hydroxy group with a protective group, $C_{1-6}$ aminoalkyl group protected at the amino group with a protective group, $C_{1-6}$ halogenated alkyl group, $C_{2-12}$ alkoxy alkyl group, $C_{3-7}$ cycloalkyl group, $C_{2-6}$ alkenyl group, $C_{2-6}$ alkynyl group, $C_{6-12}$ aryl group, $C_{7-18}$ alkyl aryl group or $C_{7-18}$ aralkyl group, each of which may have one or more substituents.

The compound of the formula (5b) can be synthesized by reacting the compound of the formula (3c) with the compound of the formula (5a) in a solvent such as tetrahydrofuran. The reaction can be carried out at room temperature to 50° C.

The compound of the formula (5a) can be synthesized by reacting diphenyl phosphoryl azide (DPPA) with the compound of the formula (5c).

The reaction can be carried out in the presence of an organic base such as triethylamine in an organic solvent such as toluene and tetrahydrofuran. The reaction can be carried out at room temperature to a temperature under heating under reflux.

B. Process for Producing the Compounds of the Present Invention Represented by the Formula

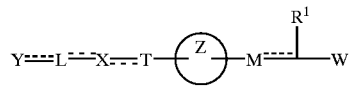

(wherein each symbol represents the same group as defined above) wherein in the formula (I) T is not a single bond.

Hereinafter, the general methods for synthesizing the compounds of the present invention are described.

Specifically, in the present invention, the compounds represented by the following formula:

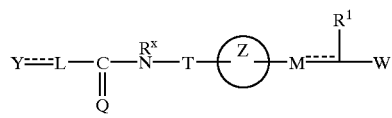

(wherein each symbol represents the same group as defined above) can be synthesized by the following production method B(1), B(6) or B(7).

Specifically, in the present invention, the compounds represented by the following formula:

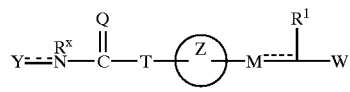

(wherein each symbol represents the same group as defined above) can be synthesized for example by the following production method B(3).

Specifically, in the present invention, the compounds represented by the following formula:

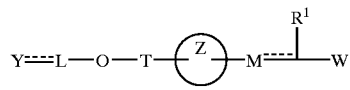

(wherein each symbol represents the same group as defined above) can be synthesized for example by the following production methods B(4) or B(5).

Production Method B(1)

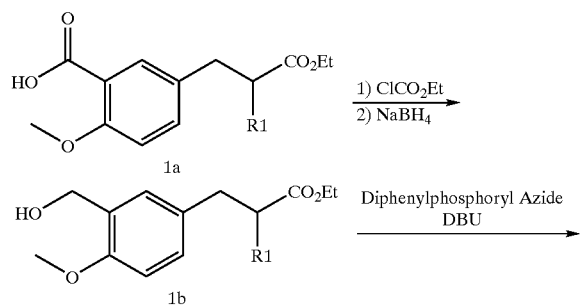

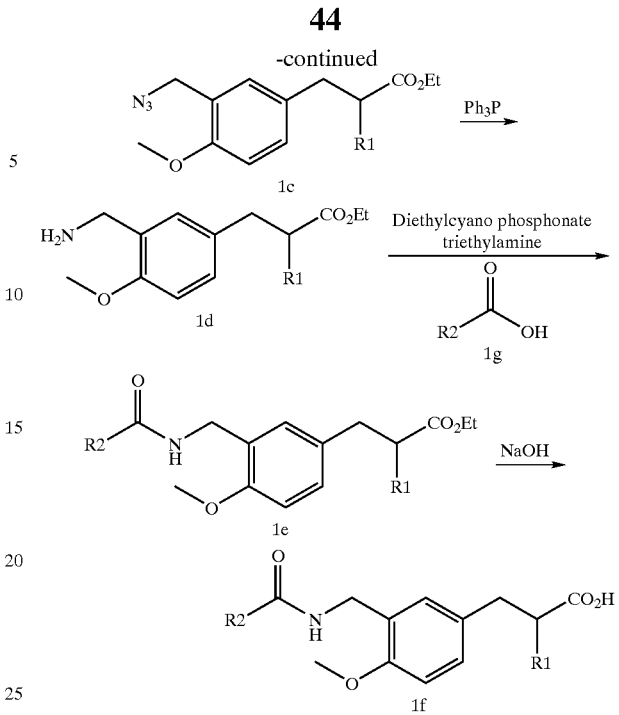

wherein each symbol represents the same group as defined above; and $R^2$ represents a group corresponding to the Y—L— group or Y=L— group described above.

The compound of the formula (1b) can be produced by reacting methyl chloroformate, ethyl chloroformate etc. with the compound of the formula (1a) in an organic solvent such as tetrahydrofuran to convert it into an acid hydride, followed by reducing with sodium borohydride, potassium borohydride etc.

The compound of the formula (1c) can be produced by reacting the compound of the formula (1b) with diphenylphosphoryl azide in the presence of an organic base such as azabicyclo[5.4.0]undecene in an organic solvent such as toluene.

The compound of the formula (1d) can be produced by allowing triphenylphosphine to act on the compound of the formula (1c) in an organic solvent such as tetrahydrofuran.

The compound of the formula (1e) can be produced by allowing the compound of the formula (1g) to act on the compound of the formula (1d). The reaction can be carried out by treating with a condensing agent such as 1-ethyl-3-(3'-dimethylaminopropyl)carbodiimide and diethyl cyanophosphate in an organic solvent such as dimethyl sulfoxide and N,N-dimethylformamide. If necessary, an organic base such as triethylamine may be added. The reaction can be carried out at a temperature under ice-cooling to room temperature.

The compound of the formula (1f) can be produced by hydrolyzing the compound of the formula (1e) with an inorganic base such as sodium hydroxide and potassium hydroxide in an ethanol solvent. The reaction may be carried out at room temperature to a temperature under heating reflux.

Production Method B(2)

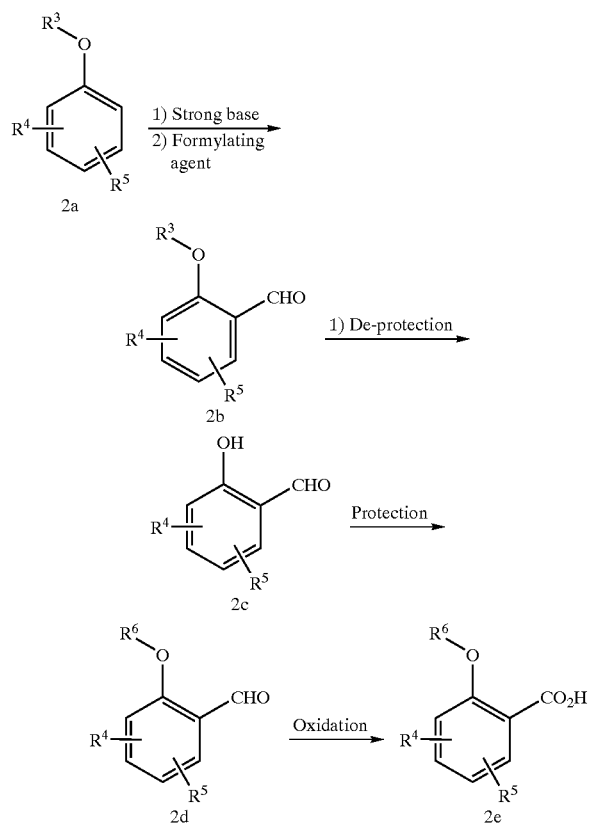

Production Method B(3)

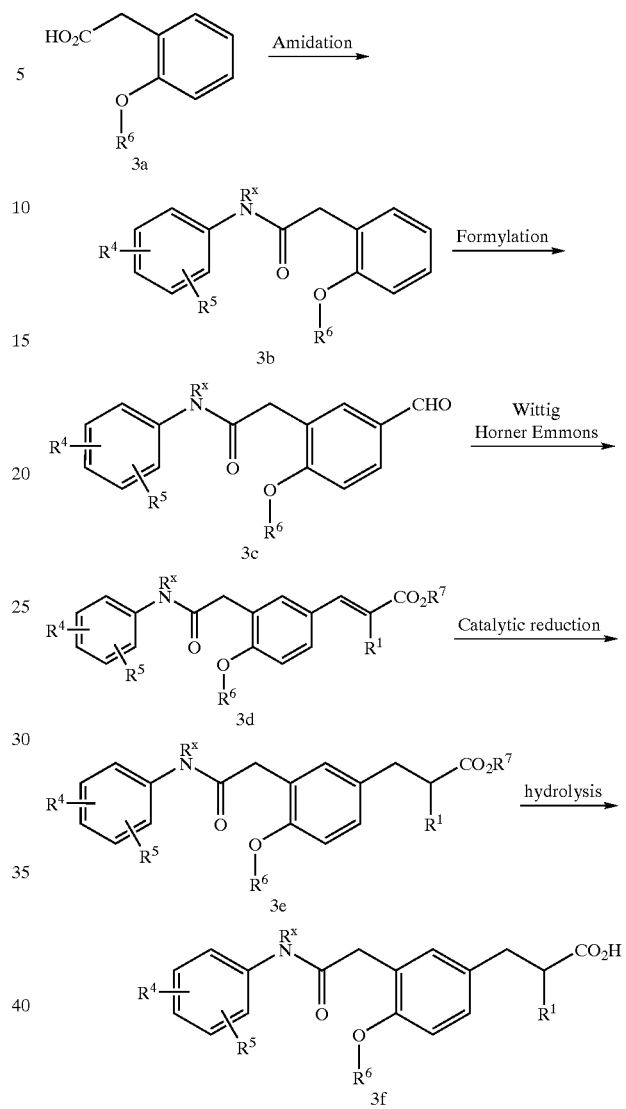

wherein $R^3$ represents a hydroxyl-protecting group; and $R^4$ and $R^5$ each represent a substituent on Y described above.

The compound of the formula (2b) can be produced by allowing a strong base such as n-butyl lithium, sec-butyl lithium and lithium diisopropylamide to act on the compound of the formula (2a) in a solvent such as anhydrous diethyl ether or tetrahydrofuran to lithate the ortho-position of the alkoxy group, followed by reacting with a formylating agent such as N,N-dimethylformamide. The reaction can be carried out at −78° C. to 50° C.

When $R^1$ in the compound of the formula (2b) is e.g. methoxymethyl group, the compound of the formula (2c) can be obtained by allowing an acid such as hydrochloric acid, sulfuric acid, p-toluenesulfonic acid and methanesulfonic acid to act in a solvent such as acetone and tetrahydrofuran.

The compound of the formula (2d) can be obtained by allowing a base such as sodium hydride and potassium tert-butoxide to act on the compound of the formula (2c) in a solvent such as N,N-dimethylformamide, tetrahydrofuran and N-methylpyrrolidone, followed by reacting with alkyl halide such as methyl iodide. The reaction can be carried out in the range of −78° C. to 100° C.

The compound of the formula (2e) can be obtained by allowing an oxidizing agent such as sodium chlorite to act on the compound of the formula (2d) in a mixed solvent of dimethyl sulfoxide and an aqueous solution of sodium dihydrogen phosphate.

wherein each symbol represents the same group as defined above; the $R^6O-$ group represents a substituent on the ring Z; and $R^7$ represents a carboxyl-protecting group.

The compound of the formula (3b) can be produced by allowing an acid halogenating agent such as thionyl chloride and oxalyl dichloride to act on the compound of the formula (3a) in a solvent such as dichloromethane, carbon tetrachloride and chloroform, and then allowing a suitable aniline derivative to act on the product. The reaction can be carried out at −20° C. to 100° C.

The compound of the formula (3c) can be produced by allowing hexamethylene tetramine to act on the compound of the formula (3b) in a solvent such as trifluoroacetic acid in the range of 50 to 100° C. or by allowing dichloromethyl methyl ether and titanium tetrachloride to act in dichloromethane at −20° C. to 50° C.

The compound of the formula (3d) can be produced by allowing a suitable phosphorane or phosphonate to act on the compound of the formula (3c) in N,N-dimethylformamide, N-methylpyrrolidone or tetrahydrofuran.

The compound of the formula (3e) can be produced by subjecting the compound of the formula (3d) to hydrogenation reaction in the presence of a catalyst such as palladium-carbon in a solvent such as ethanol, ethyl acetate, methanol and tetrahydrofuran.

The compound of the formula (3f) can be produced by hydrolyzing the compound of the formula (3e) with an inorganic base such as sodium hydroxide and potassium hydroxide in a solvent such as ethanol, methanol and tetrahydrofuran.

Production Method B(4)

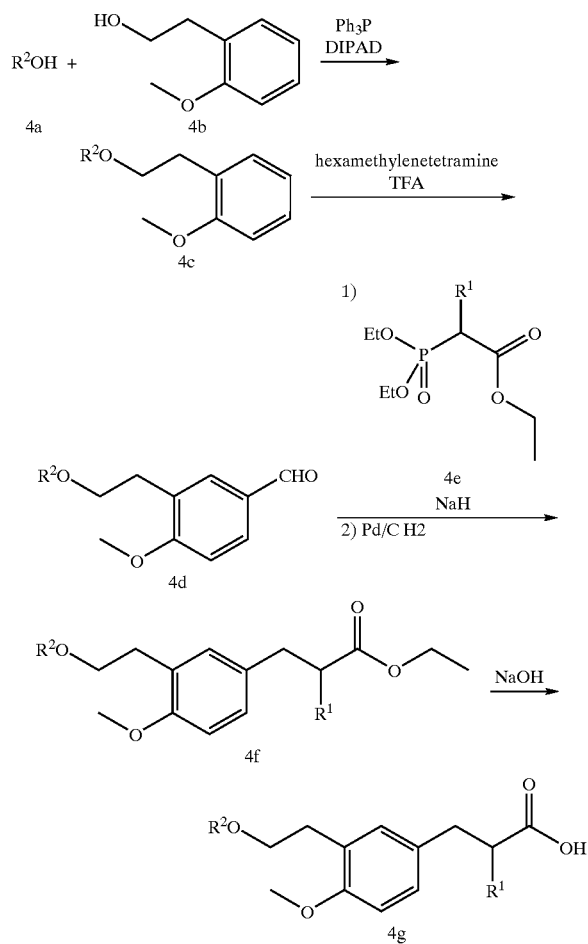

wherein each symbol represents the same group as defined above.

The compound of the formula (4c) can be produced by reacting the compound of the formula (4b) with the compound of the formula (4a). The reaction can be conducted by treating the compound of the formula (4b) and the compound of the formula (4a) with diethyl azodicarboxylate, diisopropyl azodicarboxylate etc. in the presence of triphenylphosphine.

The compound of the formula (4d) can be produced by allowing hexamethylene tetramine to act on the compound of the formula (4c) in a solvent such as trifluoroacetic acid in the range of 50 to 100° C.

The compound of the formula (4f) can be produced by reacting the compound of the formula (4e) with the compound of the formula (4d) in the presence of sodium hydride or potassium hydride in an organic solvent such as tetrahydrofuran, and then reducing the product in the presence of a catalyst such as palladium-carbon in a solvent such as ethanol and ethyl acetate.

The compound of the formula (4g) can be produced by. hydrolyzing the compound of the formula (4f) with an inorganic base such as sodium hydroxide and potassium hydroxide in an ethanol solvent. The reaction can be carried out at room temperature to a temperature under heating reflux.

Production Method B(5)

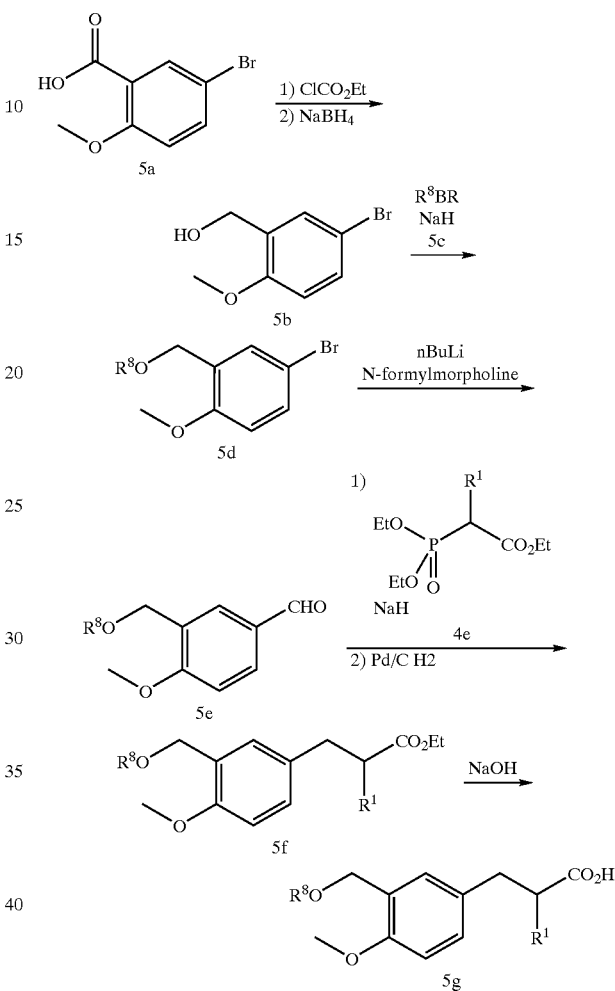

wherein each symbol represents the same group as defined above; and $R^8$ represents a group corresponding to the Y—L— group or Y=L— group described above.

The compound of the formula (5b) can be produced by reacting methyl chloroformate, ethyl chloroformate etc. with the compound of the formula (5a) in an organic solvent such as tetrahydrofuran to convert it into an acid hydride and then reducing the product with sodium borohydride, potassium borohydride etc.

The compound of the formula (5d) can be produced by reacting the compound of the formula 5(c) with the compound of the formula 5(b) in the presence of sodium hydride, potassium hydride etc. in an organic solvent such as tetrahydrofuran.

The compound of the formula (5e) can be produced by reacting N,N-dimethylformamide, N-formylmorpholine etc. with the compound of the formula (5d) in the presence of n-butyl lithium etc. in an organic solvent such as tetrahydrofuran.

The compound of the formula (5f) can be produced by reacting the compound of the formula (4e) with the compound of the formula (5e) in the presence of sodium hydride, potassium hydride etc. in an organic solvent such as tetrahydrofuran, and then reducing the product in the presence of a catalyst such as palladium-carbon in a solvent such as ethanol or ethyl acetate.

The compound of the formula (5g) can be produced by hydrolyzing the compound of the formula (5f) with an inorganic base such as sodium hydroxide and potassium hydroxide in an ethanol solvent. The reaction can be carried out at room temperature to a temperature under heating reflux.

Production Method B(6)

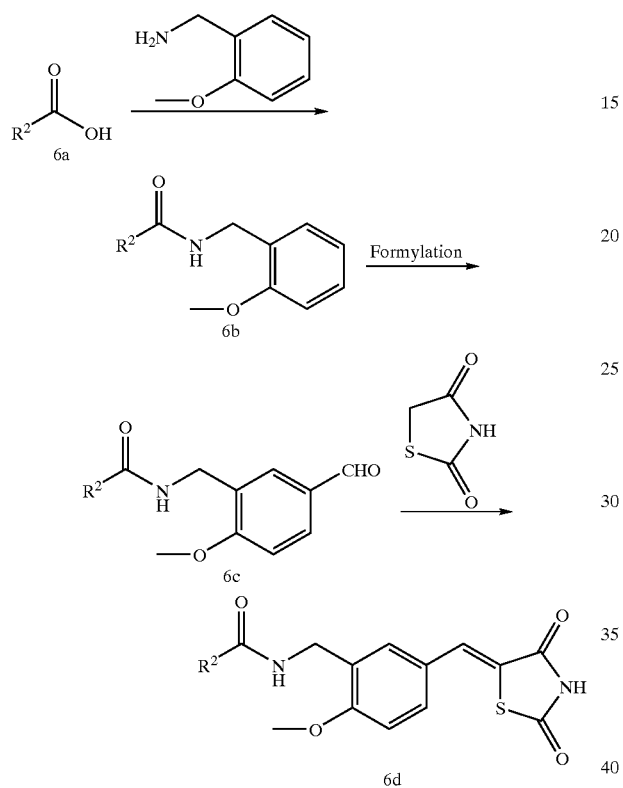

wherein each symbol represents the same group as defined above; and $R^2$ represents a group corresponding to the Y—L— group or Y=L— group described above.

The compound of the formula (6b) can be produced by allowing 2-methoxybenzyl alcohol to act on the compound of the formula (6a). The reaction can be carried out by treating with a condensing agent such as 1-ethyl-3-(3'-dimethylaminopropyl)carbodiimide and diethyl cyanophosphate in an organic solvent such as dimethyl sulfoxide and N,N-dimethylformamide. If necessary, an organic base such as triethylamine may be added. The reaction can be carried out at a temperature under ice-cooling to room temperature.

The compound of the formula (6c) can be produced by allowing hexamethylene tetramine to act on the compound of the formula (6b) in a solvent such as trifluoroacetic acid in the range of 50° C. to 100° C. or by allowing dichloromethyl methyl ether and titanium tetrachloride to act in dichloromethane at −20° C. to 50° C.

The compound of the formula (6d) can be produced by allowing 2,4-thiazolidine dione to act on the compound of the formula (6c). The reaction can be carried out by heating under reflux in the presence of a secondary amine (such as piperidine and pyrrolidine) and an organic acid (such as acetic acid and benzoic acid) as catalysis in an organic solvent such as benzene and toluene.

Production Method B(7)

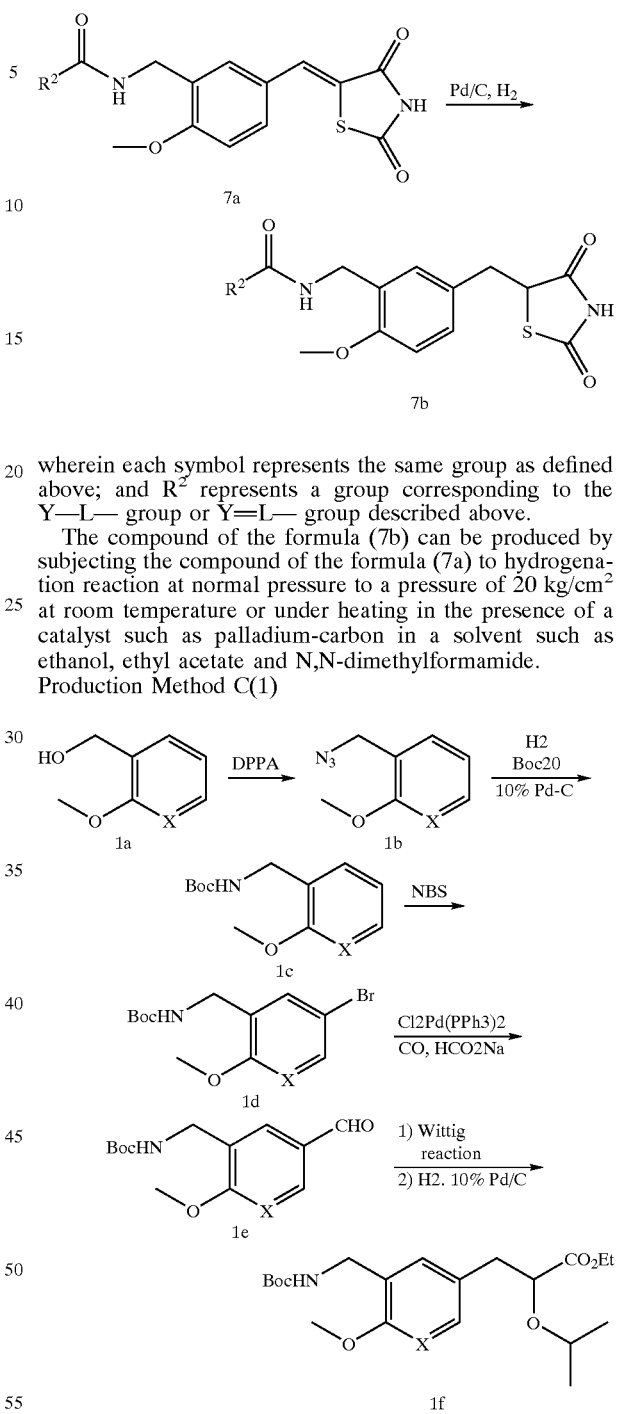

wherein each symbol represents the same group as defined above; and $R^2$ represents a group corresponding to the Y—L— group or Y=L— group described above.

The compound of the formula (7b) can be produced by subjecting the compound of the formula (7a) to hydrogenation reaction at normal pressure to a pressure of 20 kg/cm² at room temperature or under heating in the presence of a catalyst such as palladium-carbon in a solvent such as ethanol, ethyl acetate and N,N-dimethylformamide.

Production Method C(1)

The compound of the formula (1b) can be produced by reacting the compound of the formula (1b) with diphenyl phosphorylazide in the presence of an organic base such as diazabicyclo[5.4.0]undecene in an organic solvent such as toluene. The reaction temperature is preferably −20° C. to 50° C.

The compound of the formula (1c) can be produced by subjecting the compound of the formula (1b) to catalytic hydrogenation reduction in the presence of 10% palladium-carbon and tertiary butyl dicarbonate in an organic solvent such as ethyl acetate.

The compound of the formula (1d) can be produced by reacting the compound of the formula (1c) with N-bromosuccimide in an organic solvent such as N,N-dimethylformamide and acetonitrile. The reaction temperature is preferably −20° C. to 50° C.

The compound of the formula (1e) can be produced by reacting the compound of the formula (1c) with carbon monoxide in the presence of a metal catalyst such as dichlorobistriphenylphosphine palladium and a reducing agent such as sodium formate in an organic solvent such as N,N-dimethylformamide. The reaction temperature is preferably 80° C. to 150° C.

The compound of the formula (1f) can be produced by allowing a suitable phosphorane and phosphonate to act on the compound of the formula (1e) in N,N-dimethylformamide, N-methylpyrrolidine or tetrahydrofuran, followed by conducting hydrogenation reaction in the presence of a catalyst such as palladium-carbon in a solvent such as ethanol, ethyl acetate, methanol or tetrahydrofuran. The reaction temperature is preferably 0 to 50° C.

Production Method C(2)

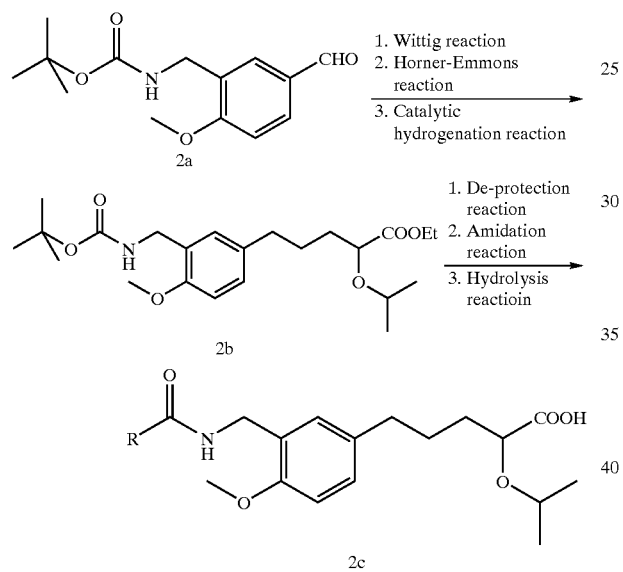

wherein R represents a group corresponding to the Y—L— group or Y=L— group described above.

The compound of formula (2b) can be produced by allowing (triphenylphosphoranilidene)acetaldehyde to act on the compound of formula (2a) in a solvent such as toluene, preferably at 80 to 100° C., then allowing a suitable phosphonate to act on the product in the presence of a base such as sodium hydride in a solvent such as N,N-dimethylformamide, N-methylpyrrolidone and tetrahydrofuran, followed by conducting hydrogenation reaction thereof in the presence of a catalyst such as palladium-carbon in a solvent such as methanol, ethanol, ethyl acetate and tetrahydrofuran.

The compound of the formula (2c) can be produced by de-protecting the tert-butoxy carbonyl group as an amino-protecting group for the compound of formula (2b) under acid conditions, then condensing RCOOH with the formed amino group, and hydrolyzing the resulting ester group with a base. The de-protection reaction is carried out by using an acid such as hydrochloric acid and trifluoroacetic acid in a solvent such as dichloromethane, 1,4-dioxane, methanol and ethanol. The condensation reaction can be conducted by using 1-ethyl-3-(3-dimethylaminopropyl)carbodiimide or diethyl cyanophosphate as a condensing agent in an organic solvent such as dimethyl sulfoxide and N,N-dimethylformamide. If necessary, a base such as triethylamine may be added. The hydrolysis reaction can be conducted by using a base such as sodium hydroxide and potassium hydroxide in a solvent such as methanol and ethanol.

Production Method C(3)

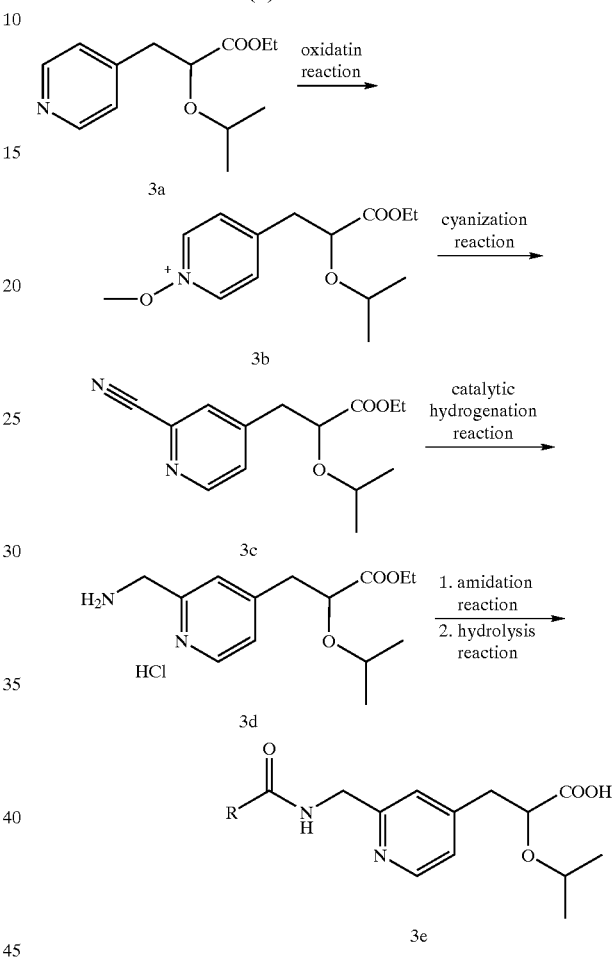

wherein R represents a group corresponding to the Y—L— group or Y=L— group described above.

The compound of formula (3b) can be produced by allowing an organic peroxide such as m-chloroperbenzoic acid to act on the compound of formula (3a) in a solvent such as dichloromethane. This compound can also be produced by allowing hydrogen peroxide to act thereon in a solvet such as acetic acid and water.

The compound of formula (3c) can be produced by allowing dimethyl carbamoyl chloride and trimethyl silyl cyanide to act on the compound of the formula (3b) in a solvent such as dichloromethane.

The compound of formula (3d) can be produced by subjecting the compound of formula (3c) to hydrogenation reaction in the presence of a catalyst such as palladium-carbon in a solvent such as methanol, ethanol, ethyl acetate and tetrahydrofuran. When an acid represented by hydrochloric acid is added in this step, the reaction is promoted.

The compound of the formula (3e) can be produced by condensing RCOOH with the amino group of the compound of formula (3d), and then hydrolyzing the resulting ester group with a base. The condensation reaction can be carried out by using 1-ethyl-3-(3-dimethylaminopropyl) carbodiimide or diethyl cyanophosphate as a condensing agent in an organic solvent such as dimethyl sulfoxide and N,N-dimethylformamide. If necessary, a base such as triethylamine may be added. The hydrolysis reaction can be conducted by using a base such as sodium hydroxide and potassium hydroxide in a solvent such as methanol and ethanol.

Production Method C(4)

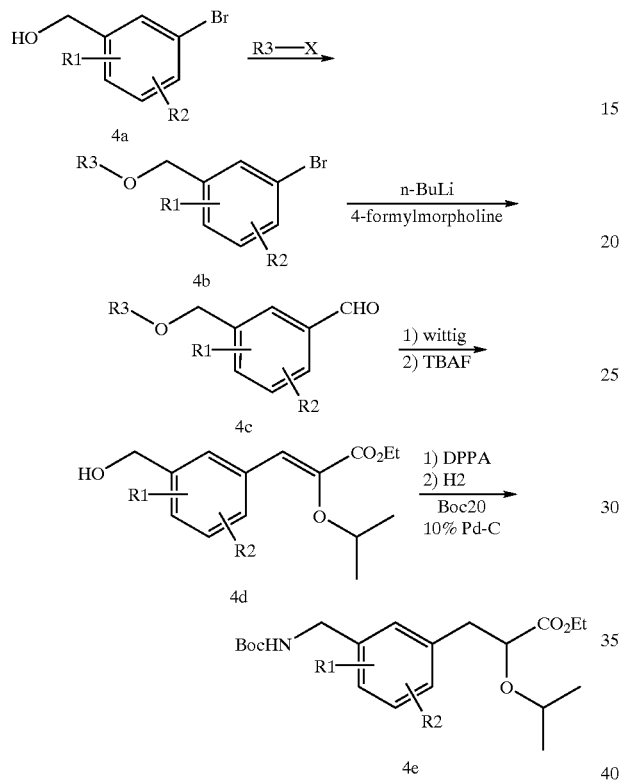

toluene, followed by conducting catalytic hydrogenation reduction in the presence of 10% palladium-carbon and tert-butyl dicarbonate in an organic solvent such as ethyl acetate. The reaction temperature is preferably −20° C. to 50° C.

Production Method C(5)

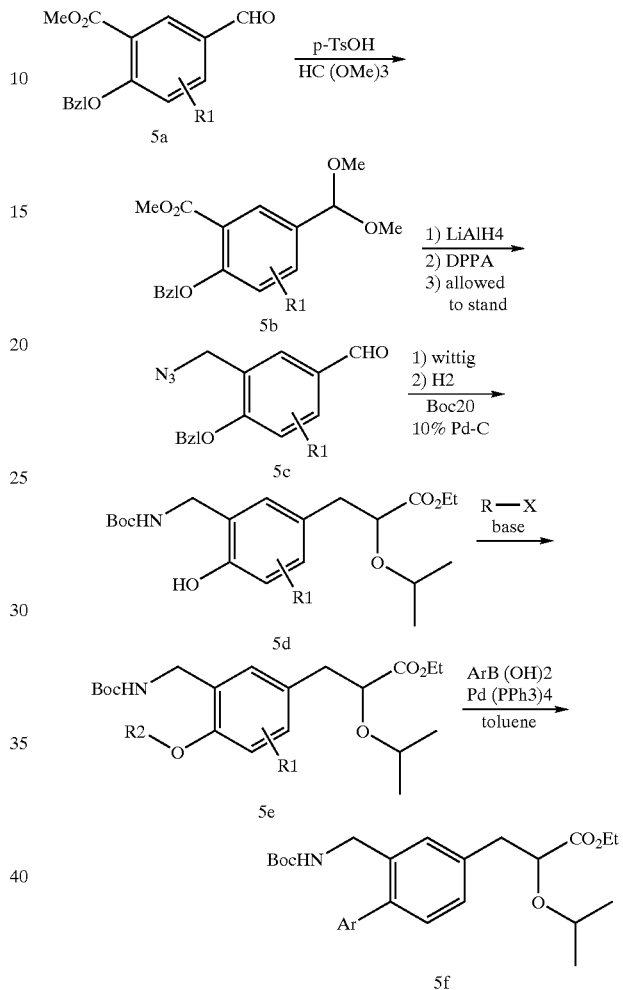

The compound of the formula (4a) can be obtained by reducing its corresponding benzoic acid or benzaldehyde derivative with sodium borohydride, diborane etc. The reaction temperature is preferably −20° C. to 50° C.

The compound of the formula (4b) can be obtained by reacting an alkylating agent such as trialkyl silyl halide with the compound of the formula (4b) in a solvent such as tetrahydrofuran. The reaction temperature is preferably 0° C. to 50° C.

The compound of the formula (4c) can be produced by allowing a strong base such as butyl lithium to act on the compound of the formula (4b) in a solvent such as tetrahydrofuran to lithate it, and then reacting the product with a formylating agent such as 4-formyl morpholine. The reaction temperature is suitably −78° C.

The compound of the formula (4d) can be obtained by allowing a suitable phosphorane and phosphonate to act on the compound of the formula (4c) in N,N-dimethylformamide, N-methylpyrrolidine or tetrahydrofuran, and then reacting the product with tetrabutyl ammonium fluoride. The reaction temperature is preferably 0 to 50° C.

The compound of the formula (4e) can be produced by reacting the compound of the formula (4d) with diphenyl phosphoryl azide in the presence of an organic base such as diazabicyclo[5.4.0]undecene in an organic solvent such as The compound of the formula (5b) can be obtained by reacting the compound of the formula (5a) with a dehydrating agent such as trimethyl orthoformate in the presence of an acid catalyst such as toluenesulfonic acid in a solvent such as methanol at a temperature of 0 to 80° C.

The compound of the formula (5c) can be obtained by reacting the compound of the formula (5b) with a reducing agent such as lithium aluminum hydride in a solvent such as tetrahydrofuran, diethyl ether etc., then reacting the resulting alcohol with diphenyl phosphoryl azide in the presence of an organic base such as diazabicyclo[5.4.0]undecene in an organic solvent such as toluene, and allowing an acid such as hydrochloric acid to act on the product.

The compound of the formula (5d) can be produced by allowing a suitable phosphorane or phosphonate to act on the compound of the formula (5c) in N,N-dimethylformamide, N-methylpyrrolidone or tetrahydrofuran, and then subjecting the product to hydrogenation reaction in the presence of a catalyst such as palladium-carbon in a solvent such as ethanol, ethyl acetate, methanol and tetrahydrofuran. The reaction temperature is preferably 0° C. to 50° C.

The compound of the formula (5e) can be produced by reacting the compound of the formula (5d) with an alkylating agent such as iodomethane, ethane, propane and trifluoromethane sulfonyl chloride in an organic solvent such as N,N-dimethylformamide, acetonitrile and pyridine at 0 to 50° C.

The compound of the formula (5f) can be obtained by reacting the compound of the formula (5e) (R2= trifluoromethanesulfonic acid derivative) with an allylboric acid derivative at 80 to 150° C. in the presence of a metal catalyst such as tetrakistriphenylphosphine palladium and an inorganic base such as potassium carbonate in an organic solvent such as toluene.

Production Method C(6)

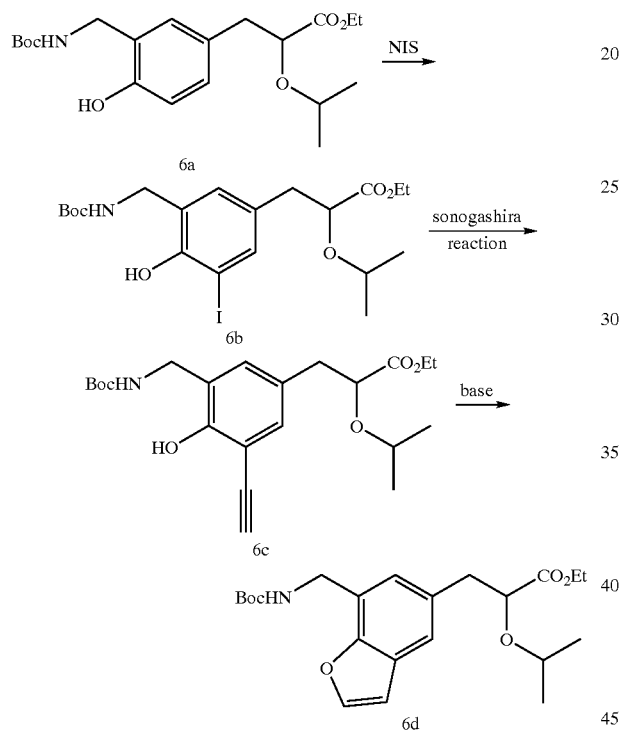

The compound of the formula (6b) can be produced by reacting the compound of the formula (6a) with N-iodosuccimide in an organic solvent such as N,N-dimethylformamide and acetonitrile. The reaction temperature is preferably −0° C. to 50° C.

The compound of the formula (6c) can be obtained by reacting the compound of the formula (6b) with acetylene in the presence of a metal catalyst such as dichlorobistriphenylphosphine palladium, and of an organic base such as copper iodide and triethylamine in an organic solvent such as N,N-dimethylformamide. The reaction temperature is preferably 80° C. to 150° C.

The compound of the formula (6d) can be obtained by heating the compound of the formula (6c) in the presence of an inorganic base such as potassium carbonate in an organic solvent such as N,N-dimethylformamide. The reaction temperature is preferably 80° C. to 150° C.

Production Method C(7)

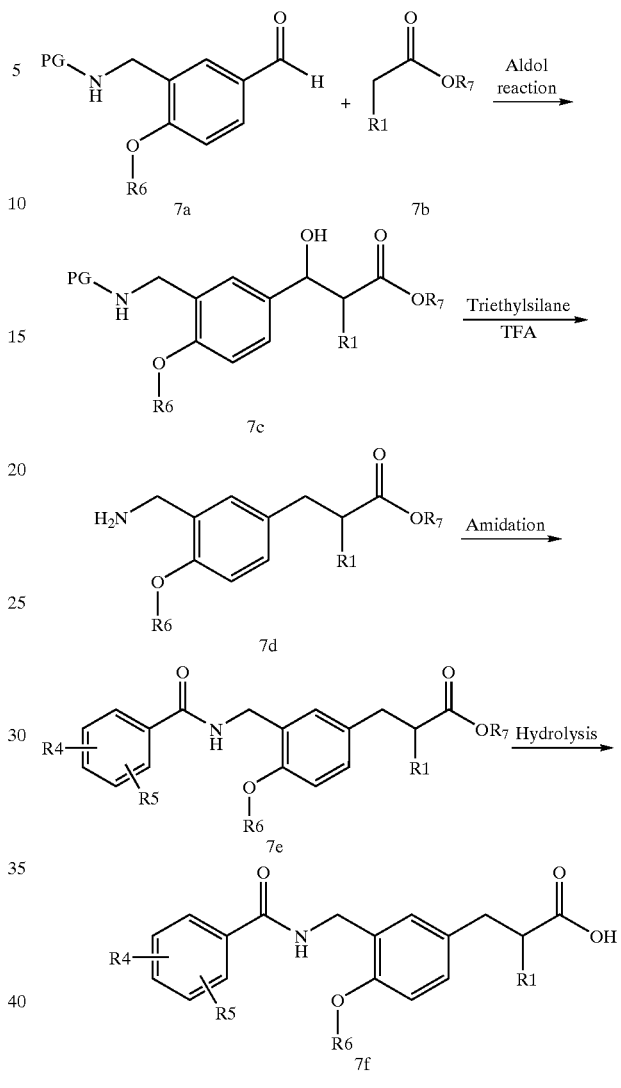

The compound of the formula (7c) can be produced by reacting the compound of the formula (7b) with hexamethyl silazane sodium, lithium diisopropylamide etc. in an anhydrous solvent such as tetrahydrofuran in the range of −78° C. to 0° C., and then reacting the product with the compound of the formula (7a) (PG means a protective group eliminated with an acid).

The compound of the formula (7d) can be produced by reacting trifluoroacetic acid and triethylsilane with the compound of the formula (7c) in the range of 0° C. to room temperature.

The compound of the formula (7e) can be produced by reacting the compound of the formula (7d) with a suitable acid chloride, activated ester etc. in the presence of a base such as pyridine and triethylamine in an anhydrous solvent such as N,N-dimethylformamide, dichloromethane and diethyl ether in the range of −78° C. to room temperature.

The compound of the formula (7f) can be produced by hydrolyzing the compound of the formula (7e) with an inorganic base such as sodium hydroxide and lithium hydroxide in a solvent such as ethanol, methanol and tetrahydrofuran.

Alternatively, the intermediate (7e) can also be produced in the following route.

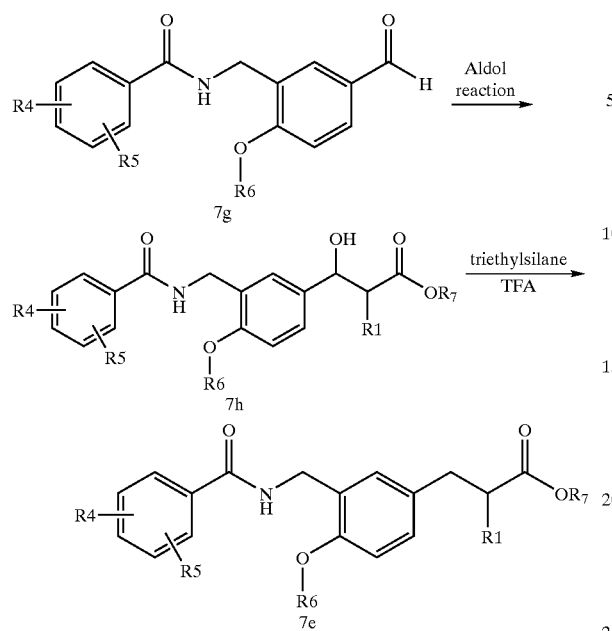

The compound of the formula (7h) can be produced by reacting hexamethyl silazane sodium, lithium diisopropylamide etc. with the compound of the formula (7b) in an anhydrous solvent such as tetrahydrofuran in the range of −78° C. to 0° C., followed by reacting with the compound of the formula (7g).

The compound of the formula (7e) can be produced by reacting trifluoroacetic acid and triethylsilane with the compound of the formula (7h) in the range of 0° C. to room temperature.

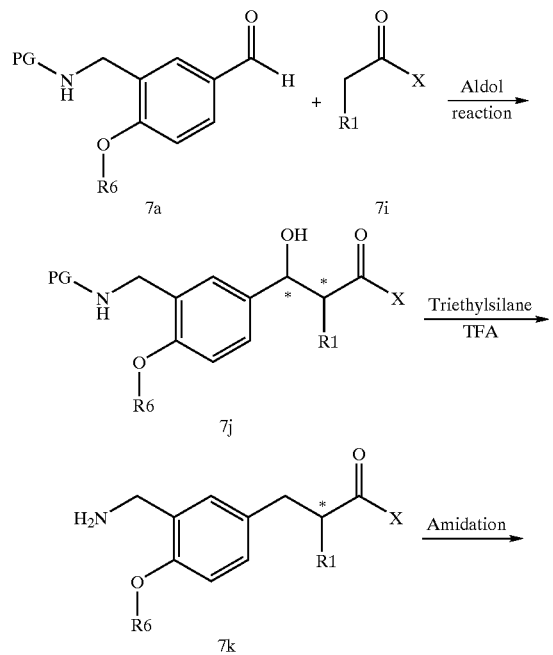

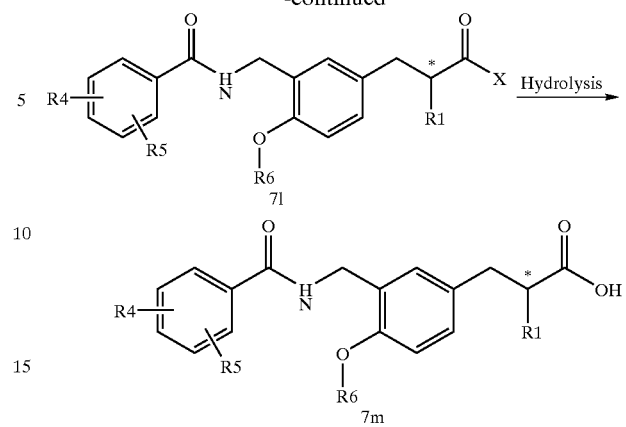

The compound of the formula (7j) can be produced diastereo-selectively by reacting a dialkyl borane compound such as dibutyl boron triflate with the compound of the formula (7i) (X means an asymmetric assistant group such as oxazolidinone) in an anhydrous solvent such as toluene and dichloromethane in the range of −78° C. to room temperature, and then reacting the product with the compound of the formula (7a) (PG means a protective group eliminated with an acid) in the range of −78° C. to room temperature.

The compound of the formula (7k) can be produced by reacting trifluoroacetic acid and triethylsilane with the compound of the formula (7j) in the range of 0° C. to room temperature.

The compound of the formula (7l) can be produced by reacting the compound of the formula (7k) with a suitable acid chloride, activated ester etc. in the presence of a base such as pyridine and triethylamine in an anhydrous solvent such as N,N-dimethylformamide, dichloromethane and diethyl ether in the range of −78° C. to room temperature.

The compound of the formula (7m) can be produced by reacting the compound of the formula (7l) with an inorganic base such as lithium hydroxide/hydrogen peroxide, or sodium hydroxide, or by reacting it successively with sodium methoxide and sodium hydroxide, in a solvent such as ethanol, methanol or tetrahydrofuran or in a mixed solvent of one of such solvents and water, in the range of −30° C. to room temperature.

Alternatively, the intermediate (7l) can also be produced in the following route.

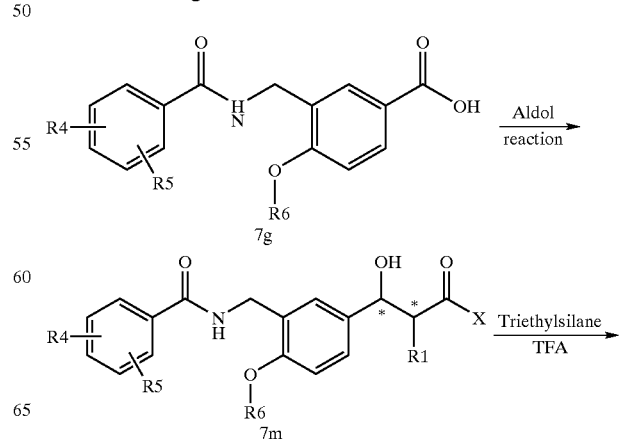

-continued

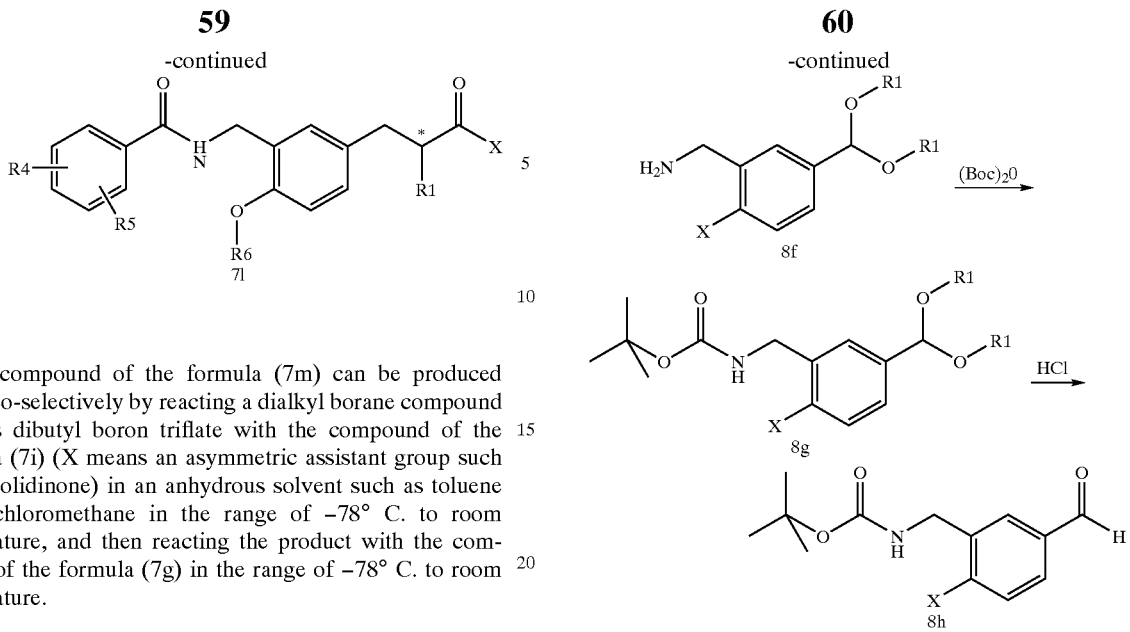

The compound of the formula (7m) can be produced diastereo-selectively by reacting a dialkyl borane compound such as dibutyl boron triflate with the compound of the formula (7i) (X means an asymmetric assistant group such as oxazolidinone) in an anhydrous solvent such as toluene and dichloromethane in the range of −78° C. to room temperature, and then reacting the product with the compound of the formula (7g) in the range of −78° C. to room temperature.

The compound of the formula (7l) can be produced by reacting trifluoroacetic acid and triethylsilane with the compound of the formula (7m) in the range of 0° C. to room temperature.

Production Method C(8)

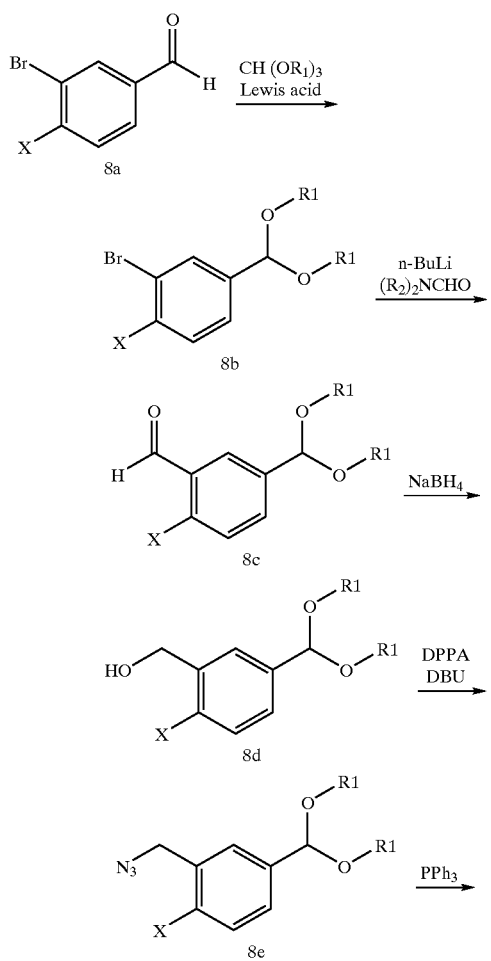

The compound of the formula (1b) can be produced by allowing an ortho-ester to act on the compound of the formula (1a) in the presence of a Lewis acid. The reaction can be carried out in an organic solvent such as methanol, ethanol and toluene. As the Lewis acid, p-toluenesulfonic acid, hydrochloric acid etc. can be used, and as the ortho-ester, methyl ortho-formate, ethyl ortho-formate etc. can be used. The reaction can be carried out at room temperature to 100° C.

The compound of the formula (8c) can be produced by allowing a base such as n-butyl lithium to act on the compound of the formula (8b) and then reacting the product with N,N-dimethylformamide, N-formyl morpholine etc. The reaction can be carried out in an organic solvent such as diethyl ether and tetrahydrofuran, and at a temperature of −80° C. to 0° C.

The compound of the formula (8d) can be produced by reacting sodium borohydride with the compound of the formula (8c) in a solvent such as methanol and ethanol. The reaction can be carried out at a temperature of 0° C. to room temperature.

The compound of the general formula (8e) can be produced by reacting diphenyl phosphoryl azide with the compound of the formula (8d) in the presence of 1,8-diazabicyclo[5.4.0]-7-undecene. The reaction can be carried out in toluene at a temperature of 0° C. to room temperature.

The compound of the formula (8f) can be produced by allowing triphenylphosphine to act on the compound of the formula (8e) The reaction can be carried out in an organic solvent such as tetrahydrofuran or in water at a reaction temperature of 0 to 50° C.

The compound of the formula (8g) can be produced by allowing tert-butyl dicarbonate to act on the compound of the formula (8f). The reaction can be carried out in an organic solvent such as tetrahydrofuran and dichloromethane at a temperature of 0° C. to room temperature.

The compound of the formula (8h) can be produced by treating the compound of the formula (8g) with an acid such as hydrochloric acid. The reaction can be conducted in an organic solvent such as tetrahydrofuran and acetone at a temperature of 0° C. to room temperature.

Production Method C(9)

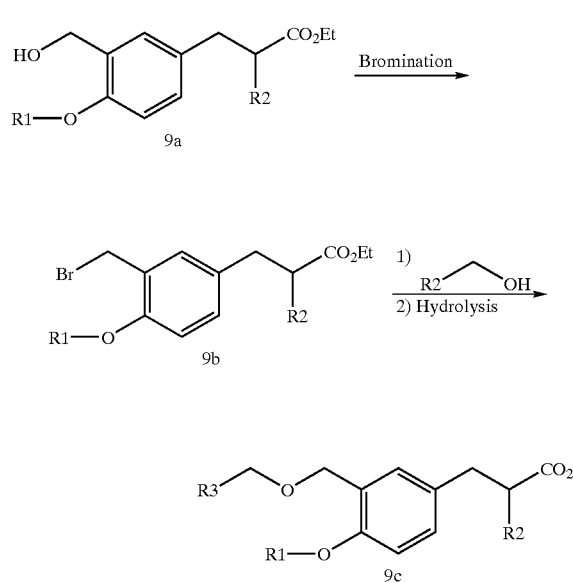

The compound of the formula (9b) can be produced by allowing phosphorus tribromide, thionyl bromide etc. to act on the compound of the formula (9a) in a solvent such as dichloromethane.

The compound of the formula (9c) can be produced by allowing an alcohol to act on the compound of the formula (9b) in the presence of a base such as sodium hydride in a solvent such as tetrahydrofuran to convert it into an ether and then hydrolyzing the product with an inorganic base such as sodium hydroxide and potassium hydroxide in ethanol or methanol.

Production method C(10)

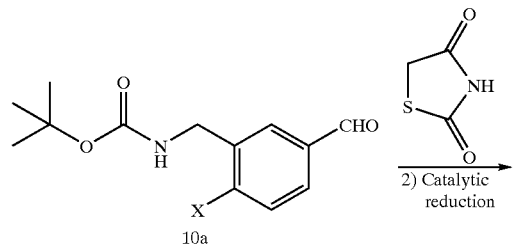

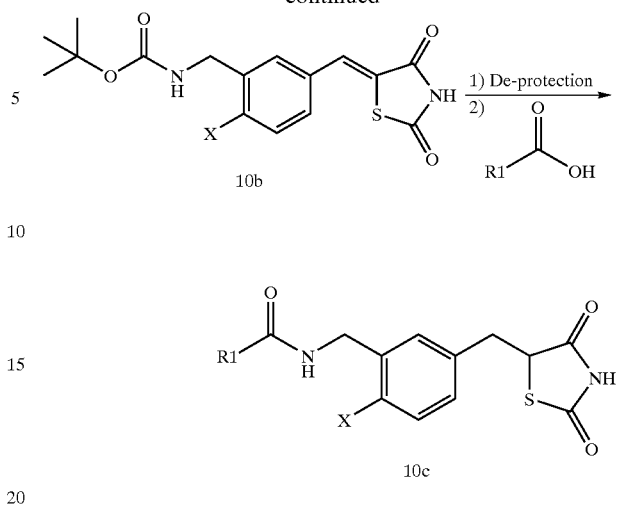

The compound of the formula (10b) can be produced by allowing 2,4-thiazolidine dione on the compound of the formula (9b) in the presence of an organic acid (such as acetic acid and benzoic acid) and a secondary amine (such as piperidine and pyrrolidine) under heating under reflux in an organic solvent such as benzene and toluene, and then subjecting the product to hydrogenation reaction at room temperature to temperature under heating under normal pressure to a pressure of 20 kg/cm$^2$ in the presence of a catalyst such as palladium-carbon in a solvent such as ethanol, ethyl acetate and N,N-dimethylformamide.

The compound of the formula (10c) can be produced by de-protecting the tert-butoxycarbonyl group as an amino-protecting group for the compound of the formula (10b) under acid conditions, and then condensing a carboxylic acid with the formed amino group. The de-protection reaction is conducted by using an acid such as hydrochloric acid and trifluoroacetic acid in a solvent such as dichloromethane, 1,4-dioxane, methanol and ethanol. The de-protection reaction can be conducted by using a condensing agent such as 1-ethyl-3-(3'-dimethylaminopropyl) carbodiimide and diethyl cyanophosphate in an organic solvent such as dimethyl sulfoxide and N,N-dimethylformamide. If necessary, a base such as triethylamine may be added.

Production Method C(11)

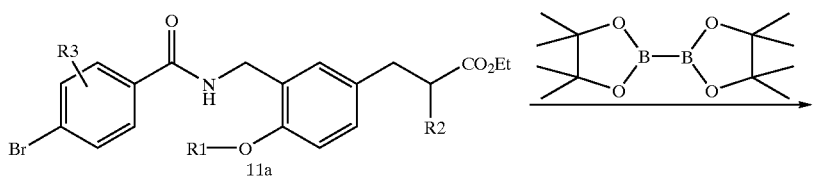

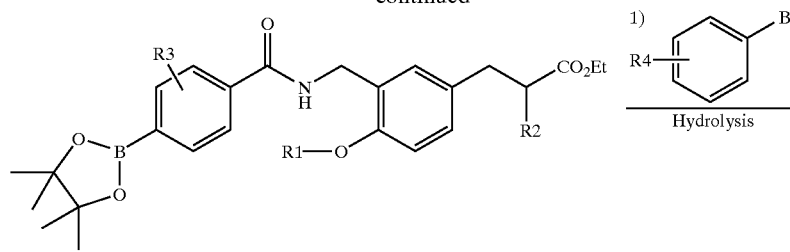

11b

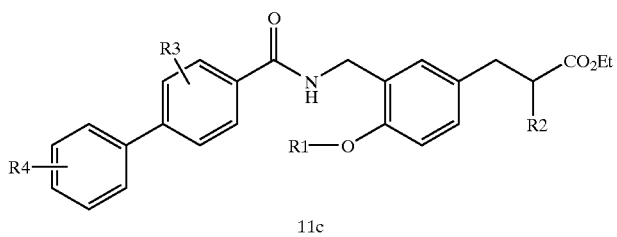

11c

The compound of the formula (11b) can be produced by reacting the compound of the formula (11a) with bis(pinacolate)diboron at room temperature to under heating reflux in the presence of a catalyst such as 1,1-bis(diphenylphosphino)ferrocene dichloropalladium and of an inorganic base such as potassium acetate in a solvent such as dimethyl sulfoxide.

The compound of the formula (11c) can be produced by reacting the compound of the formula (11b) with aryl bromide at room temperature to under heating reflux in the presence of a catalyst such as 1,1-bis(diphenylphosphino)ferrocene dichloropalladium and of an inorganic base such as potassium carbonate in a solvent such as dimethyl ethane, and then hydrolyzing the product with an inorganic base such as sodium hydroxide and potassium hydroxide in ethanol or methanol.

In the synthesis methods described above, the hydroxyl group protected with a protective group means a hydroxyl group protected with a hydroxyl-protecting group, and may be any group and is not particularly limited insofar as it is a hydroxyl group protected with a group usually known as a hydroxyl-protecting group in organic synthesis. Examples of the hydroxyl-protecting group include a lower alkylsilyl group such as trimethylsilyl group and t-butyl dimethylsilyl group; a lower alkoxymethyl group such as methoxymethyl group and 2-methoxyethoxymethyl group; tetrahydropyranyl group; an aralkyl group such as benzyl group, p-methoxybenzyl group, 2,4-dimethoxybenzyl group, o-nitrobenzyl group, p-nitrobenzyl group and trityl group; an acyl group such as formyl group and acetyl group; a lower alkoxycarbonyl group such as t-butoxycarbonyl group, 2-iodoethoxycarbonyl group and 2,2,2-trichloroethoxycarbonyl group; an alkenyloxycarbonyl group such as 2-propenyloxycarbonyl group, 2-chloro-2-propenyloxycarbonyl group, 3-methoxycarbonyl-2-propenyloxycarbonyl group, 2-methyl-2-propenyloxycarbonyl group, 2-butenyloxycarbonyl group and cinnamyloxycarbonyl group; and an aralkyloxy carbonyl group such as benzyloxycarbonyl group, p-methoxybenzyloxycarbonyl group, o-nitrobenzyloxycarbonyl group and p-nitrobenzyloxy carbonyl group.

Elimination of such a protective group can be carried out in a conventional method such as hydrolysis and reduction, depending on the type of the protective group used.

In the amino group protected with a protective group, the protective group is not particularly limited and may be any group insofar as it is a group usually known as an amino-protecting group in organic synthesis. Examples thereof include a substituted or unsubstituted lower alkanoyl group such as formyl group, acetyl group, chloroacetyl group, dichloroacetyl group, propionyl group, phenyl acetyl group, phenoxy acetyl group and thienyl acetyl group; a substituted or unsubstituted lower alkoxy carbonyl group such as benzyloxycarbonyl group, t-butoxycarbonyl group and p-nitrobenzyloxycarbonyl group; a substituted lower alkyl group such as methyl group, t-butyl group, 2,2,2-trichloroethyl group, trityl group, p-methoxybenzyl group, p-nitrobenzyl group, diphenylmethyl group and pivaloyloxymethyl group; a substituted silyl group such as trimethylsilyl group and t-butyldimethylsilyl group; a substituted silyl alkoxyalkyl group such as trimethylsilyl methoxymethyl group, trimethylsilyl ethoxymethyl group, t-butyldimethylsilyl methoxymethyl group and t-butyldimethylsilyl ethoxymethyl group; and a substituted or unsubstituted benzylidene group such as benzylidene group, salicylidene group, p-nitrobenzylidene group, m-chlorobenzylidene group, 3,5-di(t-butyl)-4-hydroxybenzylidene group and 3,5-di(t-butyl)benzylidene group.

Elimination of such a protective group can be carried out in a conventional method such as hydrolysis and reduction, depending on the type of the protective group used.

The carboxyl-protecting group is not particularly limited and may be any group insofar as it is a carboxyl group protected with a group usually known as a carboxyl-protecting group in organic synthesis. Examples of the carboxyl-protecting group include a linear or branched $C_{1-4}$ lower alkyl group such as methyl group, ethyl group, isopropyl group and t-butyl group; a halogeno lower alkyl group such as 2-iodoethyl group and 2,2,2-trichloroethyl group; a lower alkoxy methyl group such as methoxymethyl group, ethoxymethyl group and isobutoxymethyl group; a lower aliphatic acyloxy methyl group such as butyryloxymethyl group and pivaloyloxymethyl group; 1-lower alkoxy carbonyloxyethyl group such as 1-methoxycarbonyloxyethyl group and 1-ethoxycarbonyloxyethyl group; an aralkyl group such as benzyl, p-methoxybenzyl group, o-nitrobenzyl group and p-nitrobenzyl group; benzhydride group; and phthalidyl group.

Elimination of such a protective group can be carried out in a conventional method such as hydrolysis and reduction etc, depending on the type of the protective group used.

As described above, the solvent usable in the present invention is not particularly limited, and may be any solvent ordinarily used in organic synthesis and not inhibiting the reaction. Specific examples include mixed solvents in any ratio of one or more solvents such as lower alcohols such as methanol, ethanol, propanol and butanol; polyalcohols such as ethylene glycol and glycerin; ketones such as acetone, methyl ethyl ketone, diethyl ketone and cyclohexanone; ethers such as diethyl ether, isopropyl ether, tetrahydrofuran, dioxane, 2-methoxyethanol and 1,2-dimetehoxyethane; nitriles such as acetonitrile and propionitrile; esters such as methyl acetate, ethyl acetate, isopropyl acetate, butyl acetate and diethyl phthalate; halogenated hydrocarbons such as dichloromethane, chloroform, carbon tetrachloride, 1,2-dichloroethane, trichloroethylene and tetrachloroethylene; aromatics such as benzene, toluene, xylene, monochlorobenzene, nitrobenzene, indene, pyridine, quinoline, collidine and phenol; hydrocarbons such as pentane, cyclohexane, hexane, heptane, octane, isooctane, petroleum benzine and petroleum ether; amines such as ethanolamine, diethylamine, triethylamine, pyrrolidine, piperidine, piperazine, morpholine, aniline, dimethylaniline, benzylamine and toluidine; amides such as formamide, N-methylpyrrolidone, N,N-dimethylimidazolone, N,N-dimethylacetamide and N,N-dimethylformamide; phosphoric acid amides such as hexamethylphosphoric acid triamide and hexamethylphosphorous acid triamide; water; and other generally used solvents.

As described above, the base usable in the present invention is not particularly limited, and may be any base usually known as a base in organic synthesis and not inhibiting the reaction. Specific examples include sodium carbonate, sodium hydrogencarbonate, potassium carbonate, sodium hydride, potassium hydride, t-butoxy potassium, pyridine, dimethylaminopyridine, trimethylamine, triethylamine, N,N-diisopropylethylamine, N-methylmorpholine, N-methylpyrrolidine, N-methylpiperidine, N,N-dimethylaniline, 1,8-diazabicyclo[5,4,0]undeca-7-ene (DBU), pyridine, 4-dimethylaminopiperidine, picoline, lutidine, quinoline, isoquinoline, sodium hydroxide, potassium hydroxide, lithium hydroxide, butyl lithium, and sodium or potassium alcolates such as sodium methylate, potassium methylate and sodium ethylate.

As described above, the reducing agent usable in the present invention is not particularly limited, and may be any reducing agent ordinarily used in organic synthesis and not inhibiting the reaction, and specific examples include $NaBH_4$, $LiBH_4$, $Zn(BH_4)_2$, $Me_4NBH(OAc)_3$, $NaBH_3CN$, selectride, super hydride ($LiBHEt_3$), $LiAlH_4$, DIBAL, $LiAlH(t-BuO)_3$, Red-al, binap, and catalytic hydrogenation catalysts such as platinum, palladium, rhodium, ruthenium and nickel.

After the reaction is completed, the product can be purified if necessary by usual treatment methods such as column chromatography on silica gel or adsorption resin, or by re-crystallization from a suitable solvent.

The medicament according to the present invention improves insulin resistance by the agonism of PPAR as described above, and the present invention can be applied not only as an insulin-resistant improver but also as various medicaments based on PPAR ($\alpha$, $\beta$, $\gamma$) agonism (based on e.g. PPAR $\alpha$ and $\gamma$ dual agonism or on PPAR $\alpha$, $\beta$ and $\gamma$ triple agonism).

For example, the relationship of PPAR not only with insulin resistance but also with blood lipid or inflammatory diseases is known (Current Opinion in Lipidol. 10:245–257, 1999; Jiang, C., et al., PPAR-gamma agonists inhibit production of monocyte inflammatory cytokines, Nature 391:82–86 (1998); Jackson, S. M., et al., Peroxisome proliferator-activated receptor activators target human endothelial cells to inhibit leukocyte-endothelial cell interaction., Arterioscler. Thromb. Vasc. Biol. 19: 2094–2104 (1999); Su, C. G., et al., A novel therapy for colitis utilizing PPAR-gamma ligands to inhibit the epithelial inflammatory response., J Clin Invest 1999 August;104 (4):383–9; Ricote, M., et al., The peroxisome proliferator-activated receptor-gamma is a negative regulator of macrophage activation., Nature 1998 Jan. 1;391(6662): 79–82), and the medicament of the present invention can be applied to diseases against which it is reported to be effective in these literatures.

The dose of the pharmaceutical preparation of the present invention, though being varied depending on the severeness of symptom, age, sex, bodyweight, administration form and the type of disease, is usually 100 $\mu$g to 10 g/day/adult, and this dose is administered in one or divided portions.

The administration form of the medicament of the present invention is not particularly limited, and it can be administered orally or parenterally by an ordinarily used method.

For manufacturing of the medicament, ordinarily used fillers, binders, lubricants, coloring agents, flavoring agents and if necessary stabilizers, emulsifiers, absorption promoters, surfactants etc. can be used, and ingredients used generally as starting materials for medicament are compounded in a usual manner.

These ingredients include e.g. animal and vegetable oils (such as soybean oil, tallow and synthetic glyceride), hydrocarbons (such as liquid paraffin, squalene and solid paraffin), ester oils (such as octyldodecyl myristate and isopropyl myristate), higher alcohols (such as cetostearyl alcohol and behenyl alcohol), silicon resin, silicon oil, surfactants (polyoxyethylene fatty ester, sorbitan fatty ester, glycerin fatty ester, polyoxyethylene sorbitan fatty ester, polyoxyethylene hardened castor oil and polyoxyethylene-polyoxypropylene block copolymer), water-soluble polymers (such as hydroethyl cellulose, polyacrylic acid, carboxyvinyl polymer, polyethylene glycol, polyvinyl pyrrolidone and methyl cellulose), alcohols (such as ethanol and isopropanol), polyvalent alcohols (such as glycerin, propylene glycol, dipropylene glycol and sorbitol), sugars (such as glucose and sucrose), inorganic powder (such as silicic anhydride, aluminum magnesium silicate and aluminum silicate), and pure water. For pH adjustment, it is possible to use inorganic acids (such as hydrochloric acid and phosphoric acid), alkali metal salt of inorganic acid (such as sodium phosphate), inorganic bases (such as sodium hydroxide), organic acids (such as lower fatty acids, citric acid and lactic acid), alkali metal salts of organic acid (such as sodium citrate and sodium lactate) and organic bases (such as arginine and ethanolamine). If necessary, preservatives, antioxidants etc. can be added.

Hereinafter, pharmacological experiment examples are shown to show the usefulness of this invention.

Experiment Example 1

Measurement of Blood Sugar Reduction, Blood Triglyceride Reduction and Blood Free Fatty Acid Reduction A chemical suspended in 0.5% methyl cellulose was orally administered via a sonde into male db/db mice (Nippon Charles River, Yokohama, JP) once a day (30 mg/kg/day; *however, in Examples 36g) and 37e), 1 mg/kg/day). Blood, was collected through a tail vein after the mice were fasted for 1 hour, before administration, and on Day 4 and Day 9 after administration, respectively. On Day 10, an oral glucose loading test was conducted; in this test, the mice were fasted overnight from the previous day, and in the next morning, 2 g/kg glucose was given to the mice. Plasma glucose, triglycerides (TG), free fatty acid (NEFA) were measured by using commercial kits, that is, Glucose C-II Test Wako (trade name) (Wako Pure Chemical Industries, Ltd., Tokyo), Deteminer L TG II (trade name) (Kyowa Medex, Tokyo) and NEFA C-Test Wako (Wako Pure Chemical Industries, Ltd., Tokyo), respectively. The determined blood sugar reduction, blood tridglyceride reduction and blood free fatty acid reduction are shown in Table 1.

TABLE 1 in vivo db/db mice day 9 after administration

|  | Blood sugar reduction (%) | Blood triglycerides reduction (%) | Blood free fatty acid reduction (%) |
| --- | --- | --- | --- |
| Example 2d) | 44.6 | 71.6 | 46.7 |
| Example 3d) | 27.5 | 63.8 | 47 |
| Example 5d) | 53.6 | 58.8 | 65.5 |
| Example 9d) | 46.1 | 80.4 | 62.9 |
| Example 36g)* | 51.5 | 55.2 | 54.0 |
| Example 37e)* | 48.1 | 68.3 | 70.2 |

Experiment Example 2
Measurement of Transcriptional Activity

A GAL4-PPAR LBD chimera expression vector was constructed by ligating human PPAR 167–468 (PPARα), 138–440 (NUC-1) and 174–475 (PPARγ) amino acid regions (LBD: Ligand Binding Domain) to a yeast transcriptional factor GAL4 1–147 amino acid region. As the reporter gene, PLAP (Placental Alkaline Phosphatase) was used, and this was ligated downstream of a TK promoter containing a 5-copy GAL4 DNA binding element to construct a vector. As host cells, CV-1 (ATCC CCL-70D) was used. That is, CV-1 cells were spread at a density of $5 \times 10^5$ cells on a 35-mm dish and cultured in 10% FCS/DMEM for 24 hours, and using FuGENE 6 transfection reagent, the cells were co-transfected with the GAL4-PPAR LBD expression vector and GAL4 DBD-TK-PLAP expression vector. 24 hours after this transfection, the cells were spread again on a 96-well plate at a density of $1 \times 10^4$/well and further cultured for 24 hours. After 24 hours, the medium was exchanged with DMEM containing 10% FCS, which was previously treated at 65° C. for inactivating intrinsic alkaline phosphatase, and a test compound was added at an arbitrary concentration. The transcriptional activity was determined in terms of PLAP activity secreted 24 hours after addition of the compound, to calculate $EC_{50}$. The PLAC activity was determined after adding 50 μl assay buffer and 50 μl chemoluminescence substrate to 10 μl culture supernatant and incubating the mixture at room temperature for 1 hour. The transcriptional activities for PPARα, PPARβ and PPARγ are shown respectively in Table 2.

TABLE 2

| Transcriptional activities $EC_{50}$ (Unit: μM) | | |
| --- | --- | --- |
| PRAR α | PRAR β | PRAR γ |
| Example 2d) | 0.08 | 2.513 | 0.382 |
| Example 3d) | 0.087 | 5.072 | 0.217 |
| Example 5d) | 0.394 | 0.789 | 0.254 |
| Example 9d) | 0.701 | >30 | 0.746 |

TABLE 2-continued

| Transcriptional activities $EC_{50}$ (Unit: μM) | | |
| --- | --- | --- |
| PRAR α | PRAR β | PRAR γ |
| Example 18d) | 0.162 | 8.054 | >10 |
| Example 36g) | 0.012 | 0.037 | 0.047 |
| Example 37e) | 0.028 | 0.432 | 0.016 |

As described above, the compounds of the present invention have an excellent blood sugar- and blood lipid-ameliorating action and are very useful as anti-diabetes agents, anti-hyperlipemia agents and insulin-resistant improvers.

EXAMPLES

Hereinafter, the present invention is described in more detail by reference to the following Examples, which are however not intended to limit the present invention.

Example 1

Production Example 1a)

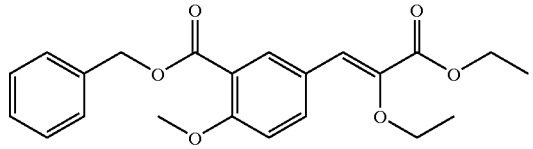

1.5 g of ethyl 2-(diethylphosphoryl)-2-ethylacetate was dissolved in 30 ml tetrahydrofuran, and 0.26 g of 60% sodium hydride was added thereto under ice-cooling. The reaction solution was stirred for 30 minutes under ice-cooling and 1.5 g of benzyl 5-formyl-2-methoxybenzoate was added thereto, and the mixture was stirred at room temperature for 20 hours. Aqueous ammonium chloride solution was added to the reaction mixture, followed by extracting with ethyl acetate. The organic layer was washed with brine, dried over anhydrous magnesium sulfate, and the solvent was evaporated. The residue was subjected to silica gel column chromatography, to give 1.6 g of benzyl 5-(3-ethoxy-2-ethoxy-3-oxo-1-propenyl)-2-methoxybenzoate as an E-Z mixture from fractions eluted with hexane-ethyl acetate (4:1).

$^1$H-NMR(Z-isomer, CDCl$_3$) δ: 1.25 (t, J=6.8 Hz, 3H) 1.36 (t, J=7.2 Hz, 3H) 3.96 (s, 3H) 3.98 (q, J=6.8 Hz, 2H) 4.27 (q, J=7.2 Hz, 2H) 6.92 (s, 1H) 6.98 (d, J=8.0 Hz, 1H) 7.30–7.43 (m, 5H) 7.90 (dd, J=2.4, 8.0 Hz, 1H) 8.32 (d, J=2.4 Hz, 1H)

Production Example 1b)

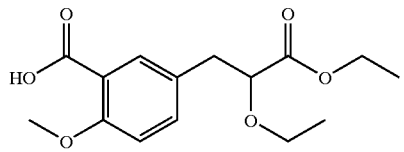

1.6 g of benzyl 5-(3-ethoxy-2-ethoxy-3-oxo-1-propenyl)-2-methoxybenzoate was dissolved in 30 ml ethanol, 0.35 g of 10% palladium-carbon was added, and the mixture was stirred for 16 hours in a hydrogen atmosphere. The catalyst was filtered through Celite and the solvent was evaporated. Then, the residue was subjected to silica gel column chromatography, and from fractions eluted with hexane-ethyl acetate (2:1), 1.2 g of 5-(3-ethoxy-2-ethoxy-3-oxopropyl)-2-methoxybenzoic acid was obtained.

$^1$H-NMR(CDCl$_3$) δ:1.16 (t, J=6.8 Hz, 3H) 1.25 (t, J=7.2 Hz, 3H) 2.98 (dd, J=8.0, 14.0 Hz, 1H) 3.04 (dd, J=4.8, 14.0 Hz, 1H) 3.34 (dq, J=6.8, 9.2 Hz, 1H) 3.61 (dq, J=6.8, 9.2 Hz, 1H) 3.98 (dd, J=4.8, 8.0 Hz, 1H) 4.05 (s, 3H) 4.18 (q, J=7.2 Hz, 2H) 6.97 (d, J=8.0 Hz, 1H) 7.47 (dd, J=2.4, 8.0 Hz, 1H) 8.06 (d, J=2.4 Hz, 1H)

Example 1c)

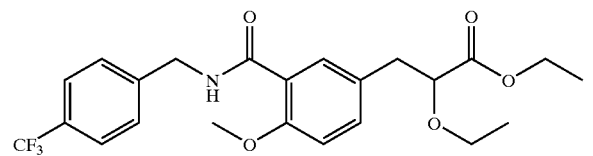

0.58 g of 5-(3-ethoxy-2-ethoxy-3-oxopropyl)-2-methoxybenzoic acid and 0.34 g of 4-(trifluoromethyl)benzylamine were dissolved in 7 ml N,N-dimethylformamide, and 0.30 ml diethyl cyanophosphonate and 0.27 ml triethylamine were added thereto under ice-cooling. The reaction mixture was stirred at room temperature for 16 hours, then poured into iced water and extracted with ethyl acetate. The organic layer was washed with 1N hydrochloric acid and brine in this order, dried over anhydrous magnesium sulfate, and the solvent was evaporated. The residue was subjected to silica gel column chromatography, and from fractions eluted with hexane-ethyl acetate (3:1), 0.64 g of ethyl 2-ethoxy-3-(4-methoxy-3-(([4-(trifluoromethyl)benzyl]amino)carbonyl)phenyl)propanoate was obtained.

$^1$H-NMR(CDCl$_3$) δ:1.16 (t, J=6.8 Hz, 3H) 1.25 (t, J=7.2 Hz, 3H) 2.98 (dd, J=8.0, 14.0 Hz, 1H) 3.04 (dd, J=4.8, 14.0 Hz, 1H) 3.34 (dq, J=6.8, 9.2 Hz, 1H) 3.61 (dq, J=6.8, 9.2 Hz, 1H) 3.93 (s, 3H) 4.01 (dd, J=4.8, 8.0 Hz, 1H) 4.18 (q, J=7.2 Hz, 2H) 4.73 (d, J=6.0 Hz, 2H) 6.91 (d, J=8.0 Hz, 1H) 7.37 (dd, J=2.4, 8.0 Hz, 1H) 7.47 (d, J=8.0 Hz, 2H) 7.59 (d, J=8.0 Hz, 2H) 8.12 (d, J=2.4 Hz, 1H) 8.29 (m, 1H)

Example 1d)

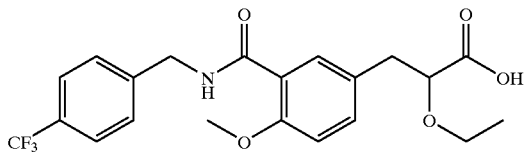

0.25 g of ethyl 2-ethoxy-3-(4-methoxy-3-({[4-(trifluoromethyl)benzyl]amino}carbonyl)phenyl)propanoate was dissolved in 7 ml ethanol, and 3 ml of 1 N sodium hydroxide was added, and the mixture was stirred at room temperature for 14 hours. The reaction mixture was ice-cooled, neutralized with 1N hydrochloric acid, and then extracted with ethyl acetate. The organic layer was washed with brine, dried over anhydrous sodium sulfate and the solvent was evaporated, to give 0.18 g of 2-ethoxy-3-(4-methoxy-3-({[4-(trifluoromethyl)benzyl]amino}carbonyl)phenyl)propanoic acid.

$^1$H-NMR(DMSO-d$_6$) δ:1.02 (t, J=7.2 Hz, 3H) 2.82 (dd, J=8.0, 14.4 Hz, 1H) 2.91 (dd, J=5.2, 14.4 Hz, 1H) 3.30 (dq, J=7.2, 9.6 Hz, 1H) 3.50 (dq, J=7.2, 9.6 Hz, 1H) 3.86 (s, 3H) 3.94 (dd, J=5.2, 8.0 Hz, 1H) 4.55 (d, J=6.0 Hz, 2H) 7.05 (d, J=8.0 Hz, 1H) 7.32 (dd, J=2.4, 8.0 Hz, 1H) 7.52. (d, J=8.0 Hz, 2H) 7.61 (d, J=2.4 Hz, 1H) 7.68 (d, J=2.4 Hz, 2H) 8.78 (t, J=6.0 Hz, 1H)

Example 2

Production Example 2b)

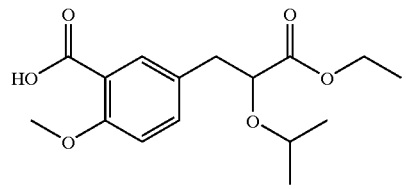

5-(3-Ethoxy-2-isopropoxy-3-oxypropyl)-2-methoxybenzoic acid was obtained in the same method as in Production Example 1b).

$^1$H-NMR(CDCl$_3$) δ:0.94 (d, J=6.0 Hz, 3H) 1.15 (d, J=6.0 Hz, 3H) 1.26 (t, J=7.2 Hz, 3H) 2.93 (dd, J=8.0, 14.0 Hz, 1H) 3.02 (dd, J=4.8, 14.0 Hz, 1H) 3.52 (sept, J=6.0 Hz, 1H) 4.03 (dd, J=4.8, 8.0 Hz, 1H) 4.06 (s, 3H) 4.15–4.22 (m, 2H) 6.98 (d, J=8.0 Hz, 1H) 7.47 (dd, J=2.4, 8.0 Hz, 1H) 8.08 (d, J=2.4 Hz, 1H)

Example 2c)

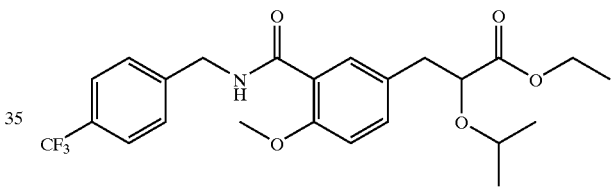

Ethyl 2-isopropoxy-3-(4-methoxy-3-({[4-(trifluoromethyl)benzyl]amino}carbonyl)phenyl)propanoate was obtained in the same method as in Example 1c).

$^1$H-NMR(CDCl$_3$) δ:0.96 (d, J=6.0 Hz, 3H) 1.15 (d, J=6.0 Hz, 3H) 1.25 (t, J=7.2 Hz, 3H) 2.92 (dd, J=8.0, 14.0 Hz, 1H) 3.01 (dd, J=4.8, 14.0 Hz, 1H) 3.51 (sept, J=6.0 Hz, 1H) 3.93 (s, 3H) 4.05 (dd, J=4.8, 8.0 Hz, 1H) 4.14–4.21 (m, 2H) 4.73 (d, J=6.0 Hz, 2H) 6.90 (d, J=8.0 Hz, 1H) 7.37 (dd, J=2.4, 8.0 Hz, 1H) 7.47 (d, J=8.0 Hz, 2H) 7.59 (d, J=8.0 Hz, 2H) 8.13 (d, J=2.4 Hz, 1H) 8.30(m, 1H)

Example 2d)

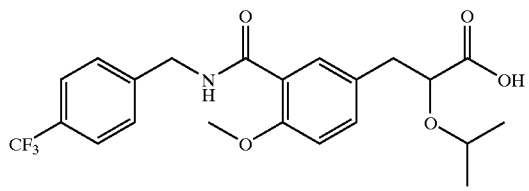

2-Isopropoxy-3-(4-methoxy-3-({[4-(trifluoromethyl)benzyl]amino}carbonyl)phenyl)propanoic acid was obtained in the same method as in Example 1d).

$^1$H-NMR(DMSO-d$_6$) δ:0.89 (t, J=6.0 Hz, 3H) 1.03 (t, J=6.0 Hz, 3H) 2.76 (dd, J=8.0, 14.0 Hz, 1H) 2.88 (dd, J=4.8, 14.0 Hz, 1H) 3.48 (sept, J=6.0 Hz, 1H) 3.86 (s, 3H) 3.99 (dd, J=4.8, 8.0 Hz, 1H) 4.55 (d, J=6.0 Hz, 2H) 7.04 (d, J=8.0 Hz, 1H) 7.32 (dd, J=2.4, 8.0 Hz, 1H) 7.52 (d, J=8.0 Hz, 2H) 7.62 (d, J=2.4 Hz, 1H) 7.68 (d, J=8.0 Hz, 2H) 8.77 (t, J=6.0 Hz, 1H)

Example 3

Production Example 3b)

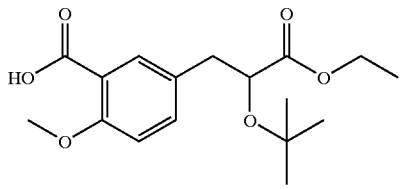

5-(3-Ethoxy-2-tert-butoxy-3-oxypropyl)-2-methoxybenzoic acid was obtained in the same method as in Production Example 1b).

$^1$H-NMR(CDCl$_3$) δ:1.02 (s, 9H) 1.25 (t, J=7.2 Hz, 3H) 2.85 (dd, J=8.0, 14.0 Hz, 1H) 2.95 (dd, J=4.8, 14.0 Hz, 1H) 4.06 (s, 3H) 4.10 (dd, J=4.8, 8.0 Hz, 1H) 4.18 (q, J=7.2 Hz, 2H) 6.98 (d, J=8.0 Hz, 1H) 7.47 (dd, J=2.4, 8.0 Hz, 1H) 8.07 (d, J=2.4 Hz, 1H)

Production Example 3c)

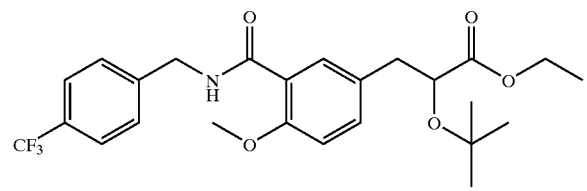

Ethyl 2-tert-butoxy-3-(4-methoxy-3-({[4-(trifluoromethyl)benzyl]amino}carbonyl)phenyl)propanoate was obtained in the same method as in Example 1c).

$^1$H-NMR(CDCl$_3$) δ:1.02 (s, 9H) 1.25 (t, J=7.2 Hz, 3H) 2.85 (dd, J=8.0, 14.0 Hz, 1H) 2.95 (dd, J=4.8, 14.0 Hz, 1H) 3.93 (s, 3H) 4.10 (dd, J=4.8, 8.0 Hz, 1H) 4.18 (q, J=7.2 Hz, 2H) 4.73 (d, J=6.0 Hz, 2H) 6.90 (d, J=8.0 Hz, 1H) 7.37 (dd, J=2.4, 8.0 Hz, 1H) 7.47 (d, J=8.0 Hz, 2H) 7.59 (d, J=8.0 Hz, 2H) 8.13 (d, J=2.4 Hz, 1H) 8.29 (m, 1H)

Example 3d)

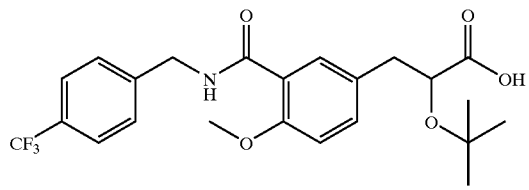

2-tert-Butoxy-3-(4-methoxy-3-({[4-(trifluoromethyl)benzyl]amino}carbonyl)phenyl)propanoic acid was obtained in the same method as in Example 1d).

$^1$H-NMR(DMSO-d$_6$) δ:0.94 (s, 9H) 2.70 (dd, J=8.8, 13.2 Hz, 1H) 2.83 (dd, J=4.4, 13.2 Hz, 1H) 3.86 (s, 3H) 4.01 (dd, J=4.4, 8.8 Hz, 1H) 4.56 (d, J=6.0 Hz, 2H) 7.04 (d, J=8.0 Hz, 1H) 7.31 (dd, J=2.0, 8.0 Hz, 1H) 7.52 (d, J=8.0 Hz, 2H) 7.63 (d, J=2.0 Hz, 1H) 7.68 (d, J=8.0 Hz, 2H) 8.77 (t, J=6.0 Hz, 1H)

Example 4

Production Example 4b)

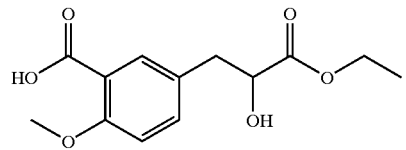

5-(3-Ethoxy-2-hydroxy-3-oxopropyl)-2-methoxybenzoic acid was obtained in the same method as in Production Example 1b).

$^1$H-NMR(CDCl$_3$) δ: 1.31 (t, J=7.2 Hz, 3H) 2.95 (dd, J=8.0, 14.0 Hz, 1H) 3.12 (dd, J=4.8, 14.0 Hz, 1H) 4.06 (s, 3H) 4.23 (q, J=7.2 Hz, 2H) 4.40 (dd, J=4.8, 8.0 Hz, 1H) 6.98 (d, J=8.0 Hz, 1H) 7.47 (dd, J=2.4, 8.0 Hz, 1H) 8.01 (d, J=2.4 Hz, 1H)

Example 4c)

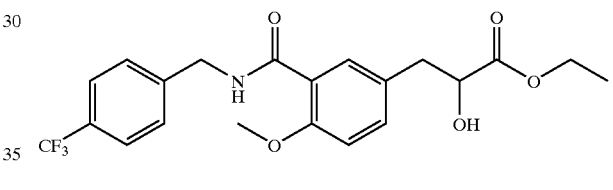

Ethyl 2-hydroxy-3-(4-methoxy-3-({[4-(trifluoromethyl)benzyl]amino}carbonyl)phenyl)propanoate was obtained in the same method as in Example 1c).

$^1$H-NMR(CDCl$_3$) δ: 1.31 (t, J=7.2 Hz, 3H) 2.95 (dd, J=8.0, 14.0 Hz, 1H) 3.15 (dd, J=4.8, 14.0 Hz, 1H) 3.92 (s, 3H) 4.23 (q, J=7.2 Hz, 2H) 4.40–4.43 (m, 1H) 4.73 (d, J=6.0 Hz, 2H) 6.92 (d, J=8.0 Hz, 1H) 7.37 (dd, J=2.4, 8.0 Hz, 1H) 7.47 (d, J=8.0 Hz, 2H) 7.59 (d, J=8.0 Hz, 2H) 8.08 (d, J=2.4 Hz, 1H) 8.28 (m, 1H)

Example 4d)

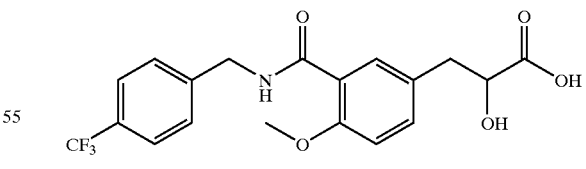

2-Hydroxy-3-(4-methoxy-3-({[4-(trifluoromethyl)benzyl]amino}carbonyl)phenyl)propanoic acid was obtained in the same method as in Example 1d).

$^1$H-NMR(DMSO-d$_6$) δ: 2.75 (dd, J=8.0, 14.0 Hz, 1H) 2.90 (dd, J=4.8, 14.0 Hz, 1H) 3.86 (s, 3H) 4.08 (dd, J=4.8, 8.0 Hz, 1H) 4.55 (d, J=6.0 Hz, 2H) 7.05 (d, J=8.0 Hz, 1H) 7.32 (dd, J=2.4, 8.0 Hz, 1H) 7.52 (d, J=8.0 Hz, 2H) 7.62 (d, J=2.4 Hz, 1H) 7.68 (d, J=8.0 Hz, 2H) 8.77 (t, J=6.0 Hz, 1H)

Example 5

Production Example 5b)

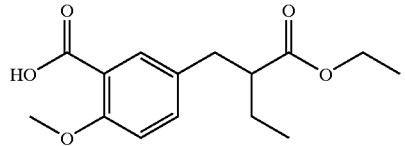

5-[2-(Ethoxycarbonyl)butyl]-2-methoxybenzoic acid was obtained in the same method as in Production Example 1b).

$^1$H-NMR(CDCl$_3$) δ:0.92 (t, J=7.6 Hz, 3H) 1.17 (t, J=6.8 Hz, 3H) 1.51–1.70 (m, 2H) 2.54–2.60 (m, 1H) 2.75 (dd, J=6.4, 13.6 Hz, 1H) 2.91 (dd, J=8.4, 13.6 Hz, 1H) 4.02–4.10 (m, 2H) 4.05 (s, 3H) 6.96 (d, J=8.0 Hz, 1H) 7.37 (dd, J=2.4, 8.0 Hz, 1H) 8.00 (d, J=2.4 Hz, 1H)

Example 5c)

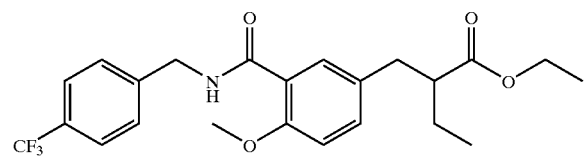

Ethyl 2-[4-methoxy-3-({[4-(trifluoromethyl)benzyl]amino}carbonyl)benzyl)butanoate was obtained in the same method as in Example 1c).

$^1$H-NMR(CDCl$_3$) δ:0.91 (t, J=7.6 Hz, 3H) 1.18 (t, J6.8 Hz, 3H) 1.51–1.70 (m, 2H) 2.54–2.61 (m, 1H) 2.75 (dd, J=6.4, 13.6 Hz, 1H) 2.92 (dd, J=8.4, 13.6 Hz, 1H) 3.92 (s, 3H) 4.04–4.15 (m, 2H) 4.73 (d, J=6.0 Hz, 2H) 6.89 (d, J=8.0 Hz, 1H) 7.26 (dd, J=2.4, 8.0 Hz, 1H) 7.47 (d, J=8.0 Hz, 2H) 7.59 (d, J=8.0 Hz, 2H) 8.05 (d, J=2.4 Hz, 1H) 8.30 (m, 1H)

Example 5d)

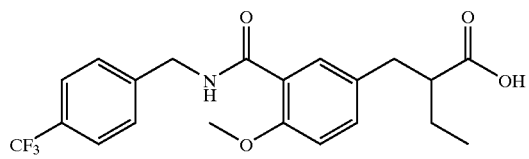

2-[4-Methoxy-3-({[4-(trifluoromethyl)benzyl]amino}carbonyl)benzyl)butanoic acid was obtained in the same method as in Example 1d).

$^1$H-NMR(DMSO-d$_6$) δ:0.84 (t, J=7.2 Hz, 3H) 1.43–1.49 (m, 2H) 2.38–2.43 (m, 1H) 2.64 (dd, J=6.0, 13.6 Hz, 1H) 2.75 (dd, J=8.8, 13.6 Hz, 1H) 3.85 (s, 3H) 4.54 (d, J=6.4 Hz, 2H) 7.04 (d, J=8.0 Hz, 1H) 7.27 (dd, J=2.4, 8.0 Hz, 1H) 7.52 (d, J=8.0 Hz, 2H) 7.55 (d, J=2.4 Hz, 1H) 7.68 (d, J=8.0 Hz, 2H) 8.78 (t, J=6.4 Hz, 1H)

Example 6

Production Example 6b)

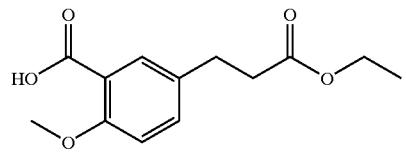

5-[2-(Ethoxycarbonyl)ethyl]-2-methoxybenzoic acid was obtained in the same method as in Production Example 1b).

$^1$H-NMR(CDCl$_3$) δ: 1.14 (t, J=6.8 Hz, 3H) 2.56 (t, J=7.2 Hz, 2H) 2.88 (t, J=7.2 Hz, 2H) 3.98 (s, 3H) 4.06 (q, J=6.8 Hz, 2H) 6.92 (d, J=8.0 Hz, 1H) 7.37 (dd, J=2.4, 8.0 Hz, 1H) 7.98 (d, J=2.4 Hz, 1H)

Example 6c)

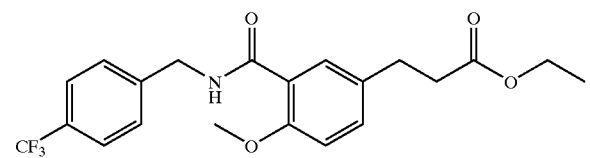

Ethyl 3-[4-methoxy-3-({[4-(trifluoromethyl)benzyl]amino}carbonyl)phenyl]propanoate was obtained in the same method as in Example 1c).

$^1$H-NMR(CDCl$_3$) δ: 1.12 (t, J=6.8 Hz, 3H) 2.60 (t, J=7.2 Hz, 2H) 2.95 (t, J=7.2 Hz, 2H) 3.92 (s, 3H) 4.11 (q, J=6.8 Hz, 2H) 4.73 (d, J=6.0 Hz, 2H) 6.90 (d, J=8.0 Hz, 1H) 7.26 (dd, J=2.4, 8.0 Hz, 1H) 7.47 (d,J=8.0 Hz,2H) 7.59 (d,J=8.0 Hz,2H) 8.07 (d,J=2.4 Hz,1H) 8.30 (m, 1H)

Example 6d)

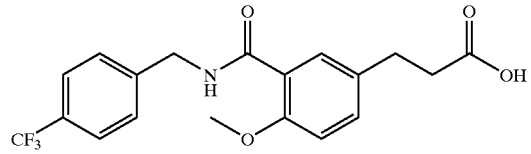

3-[4-Methoxy-3-({[4-(trifluoromethyl)benzyl]amino}carbonyl)phenyl]propanoic acid was obtained in the same method as in Example 1d).

$^1$H-NMR(DMSO-d$_6$) δ:2.48 (t, J=7.2 Hz, 2H) 2.76 (t, J=7.2 Hz, 2H) 3.85 (s, 3H) 4.54 (d, J=6.4 Hz, 2H) 7.04 (d, J=8.0 Hz, 1H) 7.31 (dd, J=2.4, 8.0 Hz, 1H) 7.51 (d, J=8.0 Hz, 2H) 7.57 (d, J=2.4 Hz, 1H) 7.68 (d, J=8.0 Hz, 2H) 8.78 (t, J=6.4 Hz, 1H)

Example 7

Example 7c)

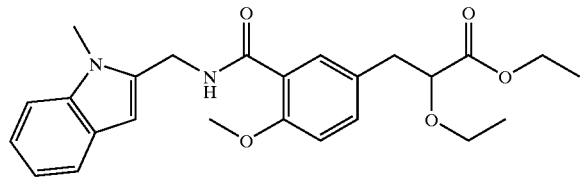

Ethyl 2-ethoxy-3-[4-methoxy-3-({[(1-methyl-1H-2-indolyl)methyl]amino}carbonyl)phenyl]propanoate was obtained in the same method as in Example 1c).

$^1$H-NMR(CDCl$_3$) δ:1.16 (t, J=6.8 Hz, 3H) 1.25 (t, J=7.2 Hz, 3H) 2.98 (dd, J=8.0, 14.0 Hz, 1H) 3.04 (dd, J=4.8, 14.0 Hz, 1H) 3.34 (dq, J=6.8, 9.2 Hz, 1H) 3.61 (dq, J=6.8, 9.2 Hz, 1H) 3.74 (s, 3H) 3.84 (s, 3H) 4.01 (dd, J=4.8, 8.0 Hz, 1H) 4.18 (q, J=7.2 Hz, 2H) 4.87 (d, J=6.0 Hz, 2H) 6.87 (d, J=8.0 Hz, 1H) 6.90 (s, 1H) 7.11 (dd, J=0.8, 8.0 Hz, 1H) 7.20 (dd, J=0.8, 8.0 Hz, 1H) 7.30 (d, J=8.0 Hz, 1H) 7.37 (dd, J=2.4, 8.0 Hz, 1H) 7.59 (d, J=8.0 Hz, 1H) 8.10 (m,1H) 8.12 (d, J=2.4 Hz, 1H)

Example 7d)

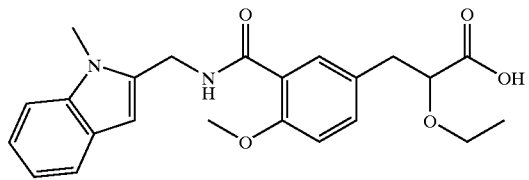

2-Ethoxy-3-[4-methoxy-3-({[(1-methyl-1H-2-indolyl)methyl]amino}carbonyl)phenyl]propanoic acid was obtained in the same method as in Example 1d).

$^1$H-NMR(DMSO-d$_6$) δ:1.03 (t, J=6.8 Hz, 3H) 2.83 (dd, J=7.2, 14.0 Hz, 1H) 2.91 (dd, J=4.8, 14.0 Hz, 1H) 3.30 (dq, J=6.8, 9.6 Hz, 1H) 3.50 (dq, J=6.8, 9.6 Hz, 1H) 3.74 (s, 3H) 3.84 (s, 3H) 3.94 (dd, J=4.8, 7.2 Hz, 1H) 4.67 (d, J=5.6 Hz, 2H) 6.35 (s, 1H) 6.97 (dd, J=0.8, 8.0 Hz, 1H) 7.04 (d, J=8.0 Hz, 1H) 7.09 (dd, J=0.8, 8.0 Hz, 1H) 7.31 (dd, J=2.0, 8.0 Hz, 1H) 7.39 (d, J=8.0 Hz, 1H) 7.46 (d, J=8.0 Hz, 1H) 7.61 (d, J=2.0 Hz, 1H) 8.57 (t, J=5.6 Hz, 1H)

Example 8

Example 8c)

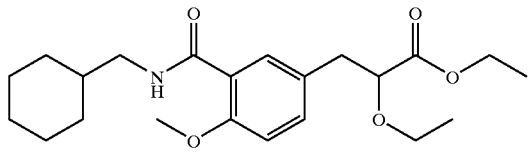

Ethyl 3-[3-({[cyclohexylmethyl]amino}carbonyl)-4-methoxyphenyl]-2-ethoxypropanoate was obtained in the same method as in Example 1c).

$^1$H-NMR(CDCl$_3$) δ:0.95–1.07 (m, 2H) 1.16 (t, J=6.8 Hz, 3H) 1.16–1.25 (m, 3H) 1.25 (t, J=7.2 Hz, 3H) 1.50–1.80 (m, 6H) 2.98 (dd, J=8.0, 14.0 Hz, 1H) 3.04 (dd, J=4.8, 14.0 Hz, 1H) 3.30 (t, J=6.4 Hz, 2H) 3.34 (dq, J=6.8, 9.2 Hz, 1H) 3.61 (dq, J=6.8, 9.2 Hz, 1H) 3.94 (s, 3H) 4.01 (dd, J=4.8, 8.0 Hz, 1H) 4.18 (q, J=7.2 Hz, 2H) 6.87 (d, J=8.0 Hz, 1H) 7.37 (dd, J=2.4, 8.0 Hz, 1H) 7.90 (m, 1H) 8.08 (d, J=2.4 Hz, 1H)

Example 8d)

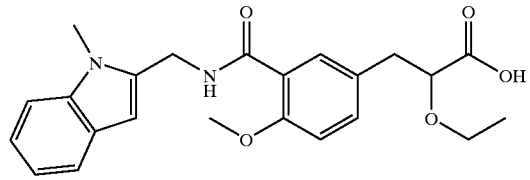

3-[3-[{(Cyclohexylmethyl]amino}carbonyl]-4-methoxyphenyl)-2-ethoxypropanoic acid was obtained in the same method as in Example 1d).

$^1$H-NMR(DMSO-d$_6$) δ:0.89–0.95 (m, 2H) 1.03 (t, J=7.2 Hz, 3H) 1.14–1.20 (m, 3H) 1.45–1.70 (m, 6H) 2.81 (dd, J=8.0, 14.0 Hz, 1H) 2.90 (dd, J=5.2, 14.0 Hz, 1H) 3.10 (dd, J=6.4, 6.4 Hz, 2H) 3.30 (dq, J=7.2, 9.6 Hz, 1H) 3.50 (dq, J=7.2, 9.6 Hz, 1H) 3.83 (s, 3H) 3.93 (dd, J=5.2, 8.0 Hz, 1H) 7.02 (d, J=8.0 Hz, 1H) 7.28 (dd, J=2.4, 8.0 Hz, 1H) 7.57 (d, J=2.4 Hz, 1H) 8.07 (t,J=6.4 Hz,1H)

Example 9

Example 9a)

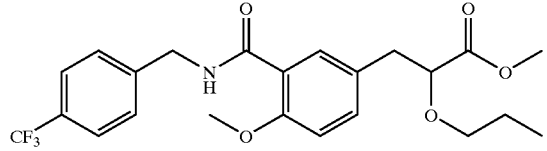

0.25 g of methyl 2-amino-3-methoxy({[4-(trifluoromethyl)benzyl]amino}carbonyl)phenyl]propanoate and 0.12 ml acetic acid were dissolved in 8 ml chloroform, and 0.10 ml isoamyl nitrite was added at room temperature. The reaction solution was heated under reflux for 30 minutes, then cooled to room temperature and diluted with ethyl acetate. The organic layer was successively washed with a saturated aqueous sodium hydrogencarbon solution and brine, and then dried over anhydrous magnesium sulfate. The solvent was evaporated, and the residue was dissolved in 8 ml 1-propanol, and 13 mg rhodium acetate was added at room temperature. The reaction solution was heated under reflux for 5 hours and the solvent was evaporated. Then, the residue was subjected to silica gel column chromatography, and from fractions eluted with hexane-ethyl acetate (2:1), 0.18 g of methyl 3-[4-methoxy-3-({[4-(trifluoromethyl)benzyl]amino}carbonyl)phenyl]-2-propoxypropanoate was obtained.

$^1$H-NMR(CDCl$_3$) δ:0.84 (t, J=7.2 Hz, 3H) 1.55 (tq, J=6.8, 7.2 Hz, 2H) 2.98 (dd, J=8.0, 14.0 Hz, 1H) 3.04 (dd, J=4.8, 14.0 Hz, 1H) 3.21 (dt, J=6.8, 8.8 Hz, 1H) 3.53 (dt, J=6.8, 8.8 Hz, 1H) 3.73 (s, 3H) 3.93 (s, 3H) 4.02 (dd, J=4.8, 8.0 Hz, 1H) 4.73 (d, J=6.0 Hz, 2H) 6.91 (d, J=8.0 Hz, 1H) 7,.36 (dd, J=2.4, 8.0 Hz, 1H) 7.47 (d, J=8.0 Hz, 2H) 7.59 (d, J=8.0 Hz, 2H) 8.10 (d, J=2.4 Hz,1H) 8.29 (m, 1H)

Example 9b)

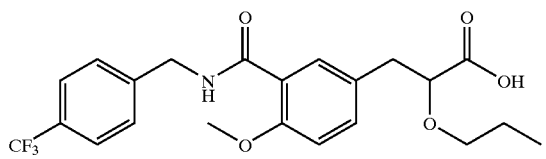

0.18 g of methyl 3-[4-methoxy-3-({[4-(trifluoromethyl)benzyl]amino}carbonyl)phenyl]-2propoxypropanoate was dissolved in 2 ml methanol, and 2 ml of 1 N sodium hydroxide was added, and the mixture was stirred at room temperature for 4 hours. The reaction mixture was ice-cooled, neutralized with 1N hydrochloric acid, and then extracted with ethyl acetate. The organic layer was washed with brine, dried over anhydrous sodium sulfate and the solvent was evaporated, to give 0.15 g of 3-[4-methoxy-3-({[4-(trifluoromethyl)benzyl]amino}carbonyl)phenyl]-2-propoxypropanoic acid.

$^1$H-NMR(DMSO-d$_6$) δ:0.76 (t, J=7.2 Hz, 3H) 1.41 (tq, J=6.4, 7.2 Hz, 2H) 2.82 (dd, J=8.0, 14.4 Hz, 1H) 2.91 (dd, J=4.8, 14.4 Hz, 1H) 3.17 (dt, J=6.4, 9.2 Hz, 1H) 3.43 (dt, J=6.4, 9.2 Hz, 1H) 3.86 (s, 3H) 3.92 (dd, J=4.8, 8.0 Hz, 1H) 4.55 (d, J=6.0 Hz, 2H) 7.05 (d, J=8.0 Hz, 1H) 7.32 (dd, J=2.4, 8.0 Hz, 1H) 7.52 (d, J=8.0 Hz, 2H) 7.61(d,J=2.4 Hz,1H) 7.68(d,J=8.0 Hz,2H) 8.78(t,J=6.0 Hz,1H)

Example 10

Example 10a)

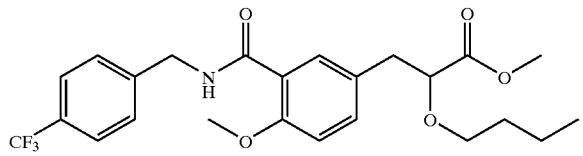

Methyl 2-butoxy-3-[4-methoxy-3-({[4-(trifluoromethyl)benzyl]amino}carbonyl)phenyl]propanoate was obtained in the same method as in Example 9a).

$^1$H-NMR(CDCl$_3$) δ: 0.84 (t, J=7.2 Hz, 3H) 1.25–1.32 (m, 2H) 1.46–1.55 (m, 2H) 2.98 (dd, J=8.0, 14.0 Hz, 1H) 3.04 (dd, J=4.8, 14.0 Hz, 1H) 3.25 (dt, J=6.8, 8.8 Hz, 1H) 3.55 (dt, J=6.8, 8.8 Hz,1H) 3.73 (s, 3H) 3.93 (s, 3H) 4.01 (dd, J=4.8, 8.0 Hz, 1H) 4.73 (d, J=6.0 Hz, 2H) 6.91 (d, J=8.0 Hz, 1H) 7.35 (dd, J=2.4, 8.0 Hz, 1H) 7.47 (d, J=8.0 Hz, 2H) 7.59 (d, J=8.0 Hz, 2H) 8.10 (d, J=2.4 Hz, 1H) 8.29 (m, 1H)

Example 10b)

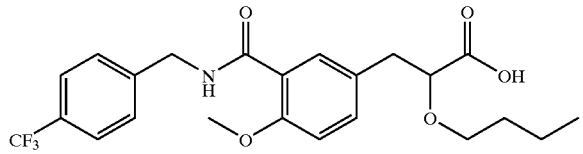

2-Butoxy-3-[4-methoxy-3-({[4-(trifluoromethyl)benzyl]amino}carbonyl)phenyl]propanoic acid was obtained in the same method as in Example 9b).

$^1$H-NMR(DMSO-d$_6$) δ:0.77 (t, J=7.2 Hz, 3H) 1.15–1.25 (m, 2H) 1.32–1.41 (m, 2H) 2.82 (dd, J=8.4, 14.0 Hz, 1H) 2.91 (dd, J=4.8, 14.0 Hz, 1H) 3.20 (dt, J=6.4, 9.2 Hz, 1H) 3.46 (dt, J=6.4, 9.2 Hz, 1H) 3.86 (s, 3H) 3.90 (dd, J=4.8, 8.4 Hz, 1H) 4.55 (d, J=6.0 Hz, 2H) 7.05 (d, J=8.0 Hz, 1H) 7.32 (dd, J=2.4, 8.0 Hz, 1H) 7.52 (d, J=8.0 Hz, 2H) 7.61 (d, J=2.4 Hz, 1H) 7.68 (d, J=8.0 Hz, 2H) 8.77 (t, J=6.0 Hz, 1H)

Example 11

Example 11a)

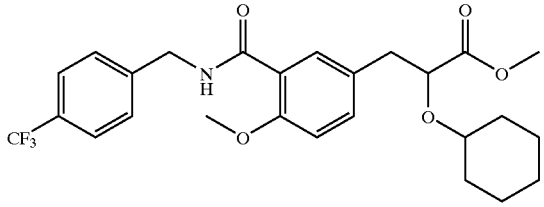

Methyl 2-cyclohexyloxy-3-[4-methoxy-3-({[4-(trifluoromethyl)benzyl]amino}carbonyl)phenyl]propanoate was obtained in the same method as in Example 9a).

$^1$H-NMR(CDCl$_3$) δ:0.80 (dd, J=6.4, 16.0 Hz, 1H) 1.08–1.90 (m, 9H) 2.96 (dd, J=8.0, 14.0 Hz, 1H) 3.02 (dd, J=4.8, 14.0 Hz, 1H) 3.14–3.21 (m, 1H) 3.73 (s, 3H) 3.93 (s, 3H) 4.10 (dd, J=4.8, 8.0 Hz, 1H) 4.73 (d, J=6.0 Hz, 2H) 6.91 (d, J=8.0 Hz, 1H) 7.36 (dd, J=2.4, 8.0 Hz, 1H) 7.47 (d, J=8.0 Hz, 2H) 7.59 (d, J=8.0 Hz, 2H) 8.10 (d, J=2.4 Hz, 1H) 8.29 (m, 1H)

Example 11b)

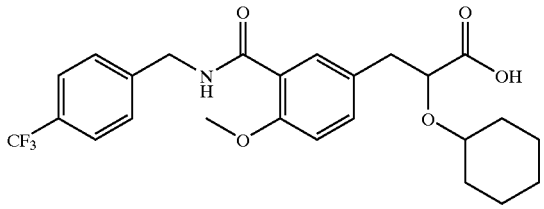

2-Cyclohexyloxy-3-[4-methoxy-3-({[4-(trifluoromethyl)benzyl]amino}carbonyl)phenyl]propanoic acid was obtained in the same method as in Example 9b).

$^1$H-NMR(DMSO-d$_6$) δ:0.75 (dd, J=6.4, 16.0 Hz, 1H) 1.00–1.71 (m, 9H) 2.78 (dd, J=8.0, 14.0 Hz, 1H) 2.89 (dd, J=4.8, 14.0 Hz, 1H) 3.18–3.23 (m, 1H) 3.86 (s, 3H) 4.03 (dd, J=4.8, 8.0 Hz, 1H) 4.55 (d, J=6.0 Hz, 2H) 7.05 (d, J=8.0 Hz, 1H) 7.33 (dd, J=2.4, 8.0 Hz, 1H) 7.52 (d, J=8.0 Hz, 2H) 7.63 (d, J=2.4 Hz, 1H) 7.67 (d, J=8.0 Hz, 2H) 8.77 (t, J=6.0 Hz, 1H)

Example 12

Example 12a)

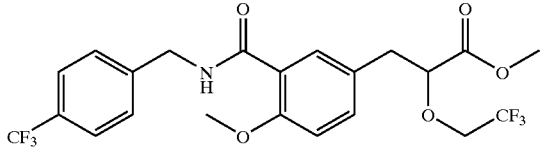

Methyl 3-[4-methoxy-3-({[4-(trifluoromethyl)benzyl]amino}carbonyl)phenyl]-2-(2,2,2-trifluoroethoxy)propanoate was obtained in the same method as in Example 9a).

¹H-NMR(CDCl₃) δ: 3.04 (dd, J=8.0, 14.0 Hz, 1H) 3.15 (dd, J=4.8, 14.0 Hz, 1H) 3.67 (dd, J=8.8, 12.0 Hz, 1H) 3.73 (s, 3H) 3.93 (s, 3H) 4.03 (d, J=8.8, 12.0 Hz, 1H) 4.20 (dd, J=4.8, 8.0 Hz, 1H) 4.73 (d, J=6.0 Hz, 2H) 6.91 (d, J=8.0 Hz, 1H) 7.36 (dd,J=2.4,8.0 Hz,1H) 7.47 (d, J=8.0 Hz, 2H) 7.59 (d, J=8.0 Hz, 1H) 8.10(d,J=8.0 Hz,2H) 8.29 (m, 1H)

Example 12b)

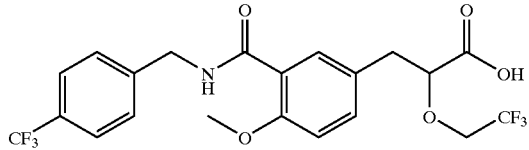

3-[4-Methoxy-3-([{4-(trifluoromethyl)benzyl]amino}carbonyl)phenyl]-2-(2,2,2-trifluoroethoxy)propanoic acid was obtained in the same method as in Example 9b).

¹H-NMR(DMSO-d₆) δ:2.92 (dd, J=8.0, 14.0 Hz, 1H) 3.01 (dd, J=4.8, 14.0 Hz, 1H) 3.87 (s, 3H) 4.03 (dd, J=8.8, 12.0 Hz, 1H) 4.11 (d, J=8.8, 12.0 Hz, 1H) 4.26 (dd, J=4.8, 8.0 Hz, 1H) 4.55 (d, J=6.4 Hz, 2H) 7.06 (d, J=8.0 Hz, 1H) 7.31 (dd, J=2.4, 8.0 Hz, 1H) 7.52 (d, J=8.0 Hz, 2H) 7.61 (d, J=2.4 Hz, 1H) 7.68 (d, J=8.0 Hz, 2H) 8.78 (t, J=6.4 Hz, 1H)

Example 13

Example 13a)

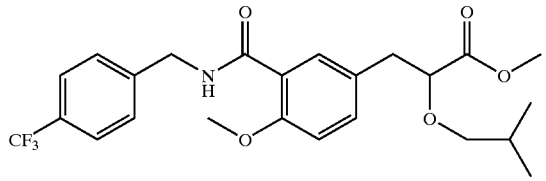

Methyl 2-isobutoxy-3-[4-methoxy-3-({[4-(trifluoromethyl)benzyl]amino}carbonyl)phenyl]propanoate was obtained in the same method as in Example 9a).

¹H-NMR(CDCl₃) δ:0.82 (d, J=6.4 Hz, 6H) 1.80 (tq, J=6.4, 6.4 Hz, 1H) 2.98 (dd, J=8.0, 14.0 Hz, 1H) 2.99 (dd, J=6.4, 8.8 Hz, 1H) 3.04 (dd, J=4.8, 14.0 Hz, 1H) 3.36 (dd, J=6.4, 8.8 Hz, 1H) 3.72 (s, 3H) 3.93 (s, 3H) 4.00 (dd, J=4.8, 8.0 Hz, 1H) 4.73 (d, J=6.0 Hz, 2H) 6.91 (d, J=8.0 Hz, 1H) 7.36 (dd, J=2.4, 8.0 Hz, 1H) 7.47 (d, J=8.0 Hz, 2H) 7.59 (d, J=8.0 Hz, 2H) 8.10 (d, J=2.4 Hz, 1H) 8.29 (m, 1H)

Example 13b)

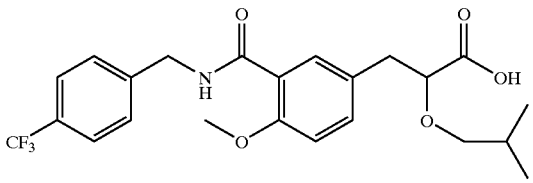

2-Isobutoxy-3-[4-methoxy-3-({[4-(trifluoromethyl)benzyl]amino}carbonyl)phenyl]propanoic acid was obtained in the same method as in Example 9b).

¹H-NMR(DMSO-d₆) δ:0.74 (d, J=6.4 Hz, 6H) 1.67 (tq, J=6.4, 6.4 Hz, 1H) 2.82 (dd, J=8.0, 14.4 Hz, 1H) 2.92 (dd, J=4.8, 14.4 Hz, 1H) 2.96 (dd, J=6.4, 8.8 Hz, 1H) 3.26 (dd, J=6.4, 8.8 Hz, 1H) 3.86 (s, 3H) 3.90 (dd, J=4.8, 8.0 Hz, 1H) 4.55 (d, J=6.0 Hz, 2H) 7.04 (d, J=8.0 Hz, 1H) 7.32 (dd, J=2.4, 8.0 Hz, 1H) 7.51(d,J=8.0 Hz,2H) 7.62 (d, J=2.4 Hz, 1H) 7.67 (d, J=8.0 Hz, 2H) 8.76(t,J=6.0 Hz,1H)

Example 14

Production Example 14a)

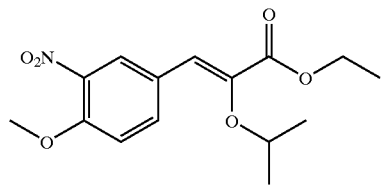

1.5 g of ethyl 2-(diethylphospholyl)-2-isopropylacetate was dissolved in 10 ml tetrahydrofuran, and 0.22 g of 60% sodium hydride was added under ice-cooling. After the reaction solution was stirred for 20 minutes under ice-cooling, 0.88 g of 4-methoxy-3-nitrobenzaldehyde was added, and the mixture was stirred at room temperature for 2 hours. Aqueous ammonium chloride solution was added to the reaction product which was then extracted with ethyl acetate. The organic layer was washed with brine, dried over anhydrous magnesium sulfate and the solvent was evaporated. The residue was subjected to silica gel column chromatography, and from fractions eluted with hexane-ethyl acetate (9:1), 0.85 g of ethyl 2-isopropoxy-3-(4-methoxy-3-nitrophenyl)-2-propanoate was obtained as an E-Z mixture.

¹H-NMR(CDCl₃) δ:1.17+1.37(t, J=6.0 Hz, 3H) 1.27+1.31 (d, J=6.0 Hz, 6H) 3.94+3.98(s, 3H) 4.17+4.28(q, J=6.0 Hz, 2H) 6.10+6.88(s, 1H) 7.00+7.06(d, J=8.0 Hz, 1H) 7.40+7.91 (dd, J=38.0, 2.0 Hz, 1H) 7.75+8.37(d, J=2.0 Hz, 1H)

Production Example 14b)

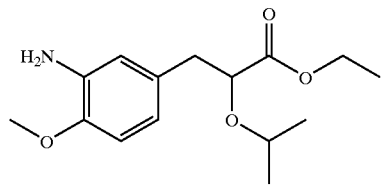

0.85 g of ethyl 2-isopropoxy-3-(4-methoxy-3-nitrophenyl)-2-propanoate was dissolved in 15 ml ethanol, and 0.3 g of 10% palladium-carbon was added, and the mixture was stirred for 4 hours in a hydrogen atmosphere. The catalyst was filtered off, then the solvent was evaporated, the residue was subjected to silica gel column chromatography, and from fractions eluted with hexane-ethyl acetate (6:1), 0.72 g of ethyl 3-(3-amino-4-methoxyphenyl)-2-isopropoxypropanoate was obtained.

¹H-NMR(CDCl₃) δ:1.00(d, J=6.0 Hz, 3H) 1.15(d, J=6.0 Hz, 3H) 1.24(t, J=6.0 Hz, 3H) 2.83(m, 2H) 3.50(dq, J=6.4, 6.4 Hz, 1H) 3.81(s, 3H) 4.00(dd, J=8.4, 4.8 Hz, 1H) 4.17(q, J=6.0 Hz, 2H) 6.60(dd,J=8.0,2.0 Hz,1H) 6.67(d,J=2.0 Hz,1H) 6.70(d,J=8.0 Hz,1H)

Example 14c)

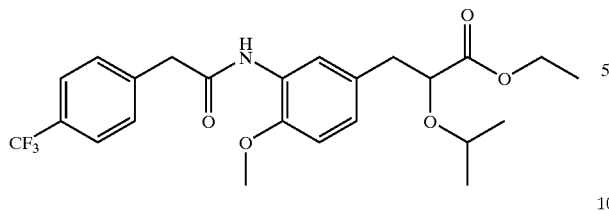

0.3 g of ethyl 3-(3-amino-4-methoxyphenyl)-2-isopropoxypropanoate and 0.218 g of (α,α,α-trifluoro-p-tolyl)acetic acid were dissolved in 7 ml tetrahydrofuran, and 0.22 g of carbonyldiimidazole and 0.23 ml triethylamine were added thereto, and the mixture was stirred at 50° C. for 2 hours. The reaction mixture was ice-cooled, and water was added followed by extraction with ethyl acetate. The organic layer was washed with brine, dried over anhydrous magnesium sulfate and the solvent was evaporated. The residue was subjected to silica gel column chromatography, and from fractions eluted with hexane-ethyl acetate (6:1), 0.34 g of ethyl 2-isopropoxy-3-[4-methoxy-3-(4-trifluoromethylphenylacetylamino)phenyl]propanoate was obtained.

$^1$H-NMR(CDCl$_3$) δ:0.95(d, J=6.0 Hz, 3H) 1.10(d, J=6.0 Hz, 3H) 1.22(t, J=7.2 Hz, 3H) 2.83(dd, J=14.0, 6.0 Hz, 1H) 2.93(dd, J=14.0, 4.4 Hz, 1H) 3.48(dq, J=6.0, 6.0 Hz, 1H) 3.73(s, 3H) 3.78(s, 2H) 4.02(dd, J=7.6, 4.4 Hz, 1H) 4.15(q, J=8.0 Hz, 2H) 6.72(d,J=8.0 Hz,1H) 6.91(dd,J=8.0,2.0 Hz,1H) 7.46(d,J=8.0 Hz,2H) 7.64(d,J=8.0 Hz,2H) 7.73(s, 1H) 8.24(d,J=2.0 Hz,1H)

Example 14d)

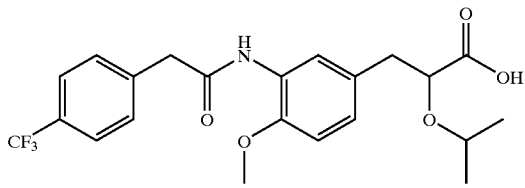

0.34 g of ethyl 2-isopropoxy-3-(4-methoxy-3-(4-trifluoromethylphenylacetylamino)phenyl)propanoate was dissolved in 5 ml ethanol, and 0.28 ml of 5N sodium hydroxide was added, and the mixture was stirred at room temperature for 4 hours. The reaction mixture was ice-cooled and neutralized with 1N hydrochloric acid, followed by extracting with ethyl acetate. The organic layer was washed with brine, dried over anhydrous sodium sulfate and the solvent was evaporated, to give 0.28 g of 2-isopropoxy-3-(4-methoxy-3-{[2-(4-trifluoromethyl)phenyl]acetyl}amino)phenylpropanoic acid.

$^1$H-NMR(CDCl$_3$) δ:1.06(d,J=6.0 Hz,3H) 1.15(d,J=6.0 Hz, 3H) 2.89(dd, J=14.0, 6.0 Hz, 1H) 3.06(dd, J=14.0, 4.4 Hz, 1H) 3.58(dq, J=6.0, 6.0 Hz, 1H) 3.75(s, 3H) 3.80(s, 2H) 4.13(dd, J=7.6, 4.4 Hz, 1H) 6.74(d, J=8.0 Hz, 1H) 6.90(dd, J=8.0, 2.0 Hz, 1H) 7.48(d, J=8.0 Hz, 2H) 7.65(d, J=8.0 Hz, 2H) 7.73(s,1H) 8.26(d, J=2.0 Hz,1H)

Example 15

Example 15c)

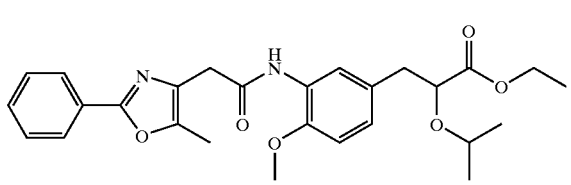

Ethyl 2-isopropoxy-3-(4-methoxy-3-{[2-(5-methyl-2-phenyl-1,3-oxazolyl-4-yl)acetyl]amino}phenyl)propanoate was obtained in the same method as in Example 14c).

$^1$H-NMR(CDCl$_3$) δ:0.96(d, J=6.0 Hz, 3H) 1.13(d, J=6.0 Hz, 3H) 1.24(t, J=7.2 Hz, 3H) 2.40(s, 3H) 2.87(dd, J=14.0, 8.8 Hz, 1H) 2.95(dd, J=14.0, 8.8 Hz, 1H) 3.50(dq, J=6.4, 6.4 Hz, 1H) 3.63(s, 2H) 3.75(s, 3H) 4.04(dd, J=8.4, 4.8 Hz, 1H) 4.17(q, J=7.2 Hz, 2H) 6.73(d, J=8.0 Hz, 1H) 6.90(dd, J=8.0, 2.0 Hz, 1H) 7.47(m, 3H) 8.08(m, 2H) 8.33(d, J=2.0 Hz, 1H) 9.42(s, 1H)

Example 15d)

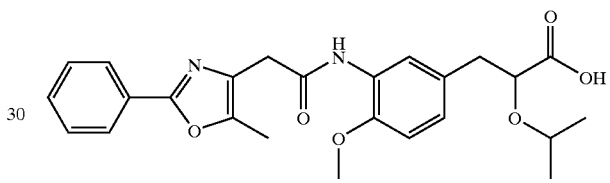

2-Isopropoxy-3-(4-methoxy-3-{[2-(5-methyl-2-phenyl-1,3-oxazole-4-yl)acetyl]amino}phenyl)propanoic acid was obtained in the same method as in Example 14d).

$^1$H-NMR(CDCl$_3$) δ:1.07(d, J=6.0 Hz, 3H) 1.15(d, J=6.0 Hz, 3H) 2.40(s, 3H) 2.89(dd, J=14.0, 8.8 Hz, 1H) 3.09(dd, J=14.0, 8.8 Hz, 1H) 3.58(dq, J=6.4, 6.4 Hz, 1H) 3.63(s, 2H) 3.75(s, 3H) 4.14(dd, J=8.4, 4.8 Hz, 1H) 6.75(d, J=8.0 Hz, 1H) 6.88(dd, J=8.0, 2.0 Hz, 1H) 7.46(m, 3H) 8.08(m, 2H) 8.33(d, J=2.0 Hz, 1H) 9.46(s, 1H)

Example 16

Production Example 16a)

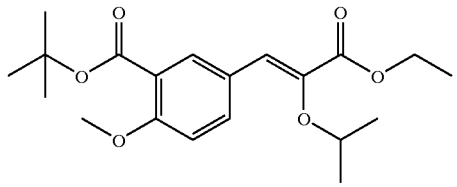

1.6 g of ethyl 2-(diethylphosphoryl)-2-isopropylacetate was dissolved in 30 ml tetrahydrofuran, and 0.24 g of 60% sodium hydride was added thereto under ice-cooling. After stirring the reaction solution for 30 minutes under ice-cooling, 1.2 g of tert-butyl 5-formyl-2-methoxybenzoate was added, followed by stirring at room temperature for 3 hours. Aqueous ammonium chloride solution was added to the reaction mixture, followed by extracting with ethyl acetate. The organic layer was washed with brine, dried over anhydrous magnesium sulfate and the solvent was evaporated. The residue was subjected to silica gel column chromatography, and from fractions eluted with hexane-ethyl acetate (3:1), 1.5 g of tert-butyl 5-(3-ethoxy-2-isopropoxy-3-oxo-1-propenyl)-2-methoxybenzoate was obtained as an E-Z mixture.

$^1$H-NMR(Z-isomer, CDCl$_3$) δ:1.28 (d, J=6.4 Hz, 6H) 1.36 (t, J=7.2 Hz, 3H) 1.59 (s, 9H) 3.91 (s, 3H) 4.29 (q, J=7.2 Hz, 2H) 4.41 (sept, J=6.4 Hz, 1H) 6.92 (d, J=8.0 Hz, 1H) 6.96 (s, 1H) 7.85 (dd, J=2.4, 8.0 Hz, 1H) 8.26 (d, J=2.4 Hz, 1H)

Production Example 16b)

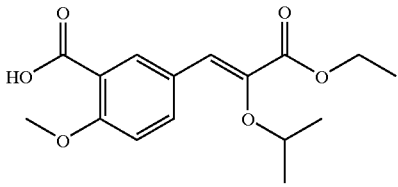

0.3 g of tert-butyl 5-(3-ethoxy-2-isopropoxy-3-oxo-1-propenyl)-2-methoxybenzoate was dissolved in 2.5 ml dichloromethane, and 1.2 ml trifluoroacetic acid was added under ice-cooling, and the mixture was stirred as such under ice-cooling for 2 hours. 30 ml toluene was added to the reaction mixture and the solvent was evapoarated; this procedure was repeated twice. Then, the residue was subjected to silica gel column chromatography, and from fractions eluted with hexane-ethyl acetate (2:1), 65 mg of 5-[(Z)-3-ethoxy-2-isopropoxy-3-oxo-1-propenyl]-2-methoxybenzoic acid was obtained.

$^1$H-NMR(CDCl$_3$) δ:1.30 (d, J=6.4 Hz, 6H) 1.36 (t, J=?7.2 Hz, 3H) 4.09 (s, 3H) 4.29 (q, J=7.2 Hz, 2H) 4.47 (sept, J=6.4 Hz, 1H) 6.96 (s, 1H) 7.05 (d, J=8.0 Hz, 1H) 8.18 (dd, J=2.4, 8.0 Hz, 1H) 8.57 (d, J=2.4 Hz, 1H)

Example 16c)

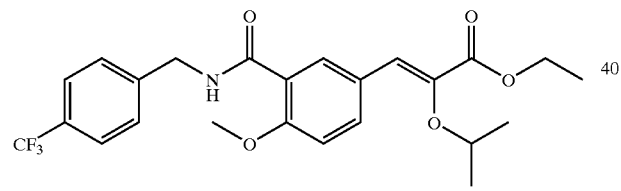

65 mg of 5-[(Z)-3-ethoxy-2-isopropoxy-3-oxo-1-propenyl]-2-methoxybenzoic acid and 37 mg of 4-(trifluoromethyl)benzylamine were dissolved in 1 ml N,N-dimethylformamide, and 33 μl diethyl cyanophosphonate and 30 μl triethylamine were added under ice-cooling. After stirring the reaction mixture at room temperature for 16 hours, it was poured into ice-water and extracted with ethyl acetate. The organic layer was successively washed with 1N hydrochloric acid and brine, dried over anhydrous magnesium sulfate and the solvent was evaporated. The residue was subjected to silica gel column chromatography, and from fractions eluted with hexane-ethyl acetate (5:1), 77 mg of ethyl (Z)-2-isopropoxy-3-[4-methoxy-3-({[4-(trifluoromethyl)benzyl]amino}carbonyl)phenyl]-2-propenoate was obtained.

$^1$H-NMR(CDCl$_3$) δ:1.30 (d, J=6.4 Hz, 6H) 1.36 (t, J=7.2 Hz, 3H) 3.97 (s, 3H) 4.29 (q, J=7.2 Hz, 2H) 4.47 (sept, J=6.4 Hz, 1H) 4.75 (d, J=6.0 Hz, 2H) 6.99 (d, J=8.0 Hz, 1H) 7.01.(s, 1H) 7.47 (d, J=8.0 Hz, 2H) 7.60 (d, J=8.0 Hz, 2H) 8.12 (dd, J=2.4, 8.0 Hz, 1H) 8.18 (m, 1H) 8.57 td, J=2.4 Hz, 1H)

Example 16d)

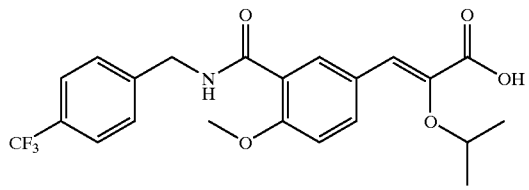

77 mg of ethyl (Z)-2-isopropoxy-3-[4-methoxy-3-({[4-(trifluoromethyl)benzyl]amino}carbonyl)phenyl]-2-propenoate was dissolved in 2 ml methanol, and 1 ml of 1N sodium hydroxide was added, and the mixture was stirred at room temperature for 22 hours. The reaction mixture was ice-cooled and neutralized with 1N hydrochloric acid, followed by extracting with ethyl acetate. The organic layer was washed with brine, dried over anhydrous sodium sulfate and the solvent was evaporated, to give 44 mg of (Z)-2-isopropoxy-3-[4-methoxy-3-({[4-(trifluoromethyl)benzyl]amino}carbonyl)phenyl]-2-propenoic acid.

$^1$H-NMR(DMSO-d$_6$) δ: 1.17 (d, J=6.4 Hz, 6H) 3.90 (s, 3H) 4.46 (sept, J=6.4 Hz, 1H) 4.56 (d, J=6.4 Hz, 2H) 6.90 (s, 1H) 7.15 (d, J=8.8 Hz, 1H) 7.53 (d, J=8.0 Hz, 2H) 7.68 (d, J=8.0 Hz, 2H) 7.87 (dd, J=2.4, 8.8 Hz, 1H) 8.30 (d, J=2.4 Hz, 1H) 8.82 (m, 1H)

Example 17

Production Example 17a)

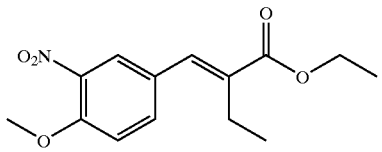

Ethyl 2-ethyl-3-(4-methoxy-3-nitrophenyl)-2-propenoate was obtained as an E-Z mixture in the same method as in Production Example 14a).

$^1$H-NMR(CDCl$_3$) δ:1.15+1.35(m, 6H) 2.45+2.53(q, J=6.0 Hz, 2H) 3.95+3.98(s, 3H) 4.18+4.27(d, J=6.0 Hz, 2H) 6.52+7.53(d, 1H) 7.01+7.11(d, J=8.0 Hz, 1H) 7.44+7.55(dd, J=8.0, 2.0 Hz, 1H) 7.79+7.89(d, J=2.0 Hz, 1H)

Production Example 17b)

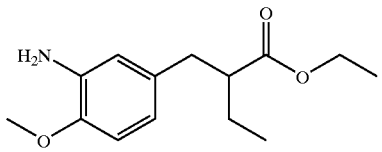

Ethyl 2-(3-amino-4-methoxybenzyl)butanoate was obtained in the same method as in Production Example 14b).

$^1$H-NMR(CDCl$_3$) δ: 0.88(t, J=6.0 Hz, 3H) 1.17(t, J=6.0 Hz, 3H) 1.56(m, 2H) 2.52(m, 1H) 2.59(dd, J=13.5,7.0 Hz, 1H) 2.80(dd, J=13.5, 8.0 Hz, 1H) 3.81(s, 3H) 4.08(q, J=6.0 Hz, 2H) 6.50(dd, J=8.0, 2.0 Hz, 1H) 6.54(d, J=2.0 Hz, 1H) 6.68(d, J=8.0 Hz, 1H)

Example 17c)

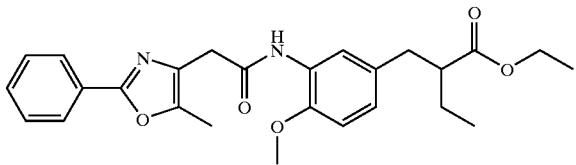

Ethyl 2-(4-methoxy-3-{[2-(5-methyl-2-phenyl-1,3-oxazole-4-yl)acetyl]amino}benzyl)butanoate was obtained in the same method as in Example 14c).

$^1$H-NMR(CDCl$_3$) δ: 0.89(t, J=6.0 Hz, 3H) 1.18(t, J=6.0 Hz, 3H) 1.58(m, 2H) 2.56(m, 1H) 2.68(dd, J=13.5, 7.0 Hz, 1H) 2.88(dd, J=13.5, 8.0 Hz, 1H) 3.63(s, 2H) 3.74(s, 3H) 4.08(q, J=6.0 Hz, 2H) 6.71(d, J=8.0 Hz, 2H) 6.79(dd, J=8.0, 2.0 Hz, 2H) 7.46(m, 3H) 8.07(m, 2H) 8.25(d, J=2.0 Hz, 1H) 9.40(bs, 1H)

Example 17d)

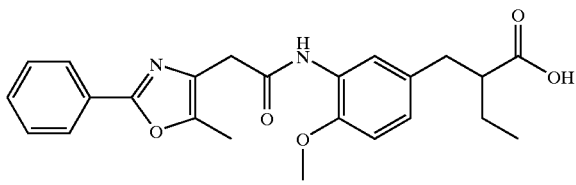

2-(4-Methoxy-3-{[2-(5-methyl-2-phenyl-1,3-oxazole-4-yl)acetyl]amino}benzyl)butanoic acid was obtained in the same method as in Example 14d).

$^1$H-NMR(CDCl$_3$) δ:0.94(t, J=6.0 Hz, 3H) 1.60(m, 2H) 2.61(m, 1H) 2.72(dd, J=13.5, 7.0 Hz, 1H) 2.90(dd, J=13.5, 8.0 Hz, 1H) 3.62(s, 2H) 3.74(s, 3H) 6.73(d, J=8.0 Hz, 2H) 6.83(dd, J=8.0, 2.0 Hz, 2H) 7.46(m, 3H) 8.06(m, 2H) 8.26(d, J=2.0 Hz, 1H) 9.40(bs, 1H)

Example 18

Example 18c)

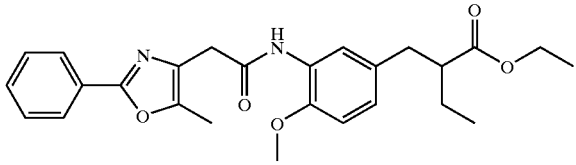

Ethyl 2-(4-methoxy-3-{[2-(3-fluoro-4-trifluoromethylphenyl)acetyl]amino}benzyl)butanoate was obtained in the same method as in Example 17c).

$^1$H-NMR(CDCl$_3$) δ: 0.88(t, J=6.0 Hz, 3H) 1.17(t, J=6.0 Hz, 3H) 1.58(m, 2H) 2.54(m, 1H) 2.67(dd, J=13.5, 7.0 Hz, 1H) 2.86(dd, J=13.5, 8.0 Hz, 1H) 3.77(s, 2H) 3.79(s, 3H) 4.08(q, J=6.0 Hz, 2H) 6.73(d, J=8.0 Hz, 2H) 6.83(dd, J=8.0, 2.0 Hz, 1H) 7.24(m, 2H) 7.61(t, J=7.5 Hz, 1H) 7.77(bs, 1H) 8.17(d, J=2.0 Hz, 1H)

Example 18d)

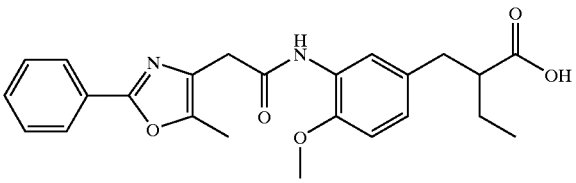

2-(4-Methoxy-3-{[2-(3-fluoro-4-trifluoromethylphenyl)acetyl]amino}benzyl)butanoic acid was obtained in the same method as in Example 17d).

$^1$H-NMR(CDCl$_3$) δ:0.93(t, J=6.0 Hz, 3H) 1.59(m, 2H) 2.59(m, 1H) 2.70(dd, J=13.5, 7.0 Hz, 1H) 2.89(dd, J=13.5, 8.0 Hz, 1H) 3.70+3.77(s, 2H) 3.79+3.81(s, 3H) 6.74(d, J=8.0 Hz, 1H) 6.86(dd, J=8.0, 2.0 Hz, 1H) 7.17(d, J=8.0 Hz, 1H) 7.22(d, J=10.5 Hz, 1H) 7.60(t, J=7.5 Hz, 1H) 7.78(bs, 1H) 8.17(d, J=2.0 Hz, 1H)

Example 19

Production Example 19a)

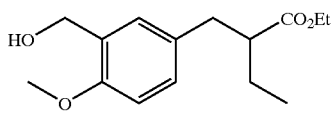

0.50 g of 5-[2-(ethoxycarbonyl)butyl]-2-methoxybenzoic acid was dissolved in 8 ml tetrahydrofuran, and 0.20 ml ethyl chloroformate and 0.29 ml triethylamine were added under ice-cooling. After the reaction solution was stirred for 10 minutes under ice-cooling, insoluble matters were filtered off. The mother liquor was ice-cooled again, and 10 L water and 136 mg sodium borohydride were added, and the mixture was stirred at room temperature for 2 hours. Water was added to the reaction product, followed by extracting with ethyl acetate. The organic layer was washed with brine, dried over anhydrous magnesium sulfate and the solvent was evapoarated. The residue was subjected to silica gel column chromatography, and from fractions eluted with hexane-ethyl acetate (3:1), 0.47 g of ethyl 2-[3-(hydroxymethyl)-4-methoxybenzyl]butanoate was obtained.

$^1$H-NMR(CDCl$_3$) δ:0.90 (t, J=7.2 Hz, 3H) 1.17 (t, J=6.8 Hz, 3H) 1.50–1.64 (m, 2H) 2.51–2.57 (m, 1H) 2.68 (dd, J=6.8, 14.0 Hz, 1H) 2.87 (dd, J=8.0, 14.0 Hz, 1H) 3.84 (s, 3H) 4.04–4.10 (m, 2H) 4.65 (s,2H) 6.78 (d,J=9.2 Hz,1H) 7.05 (d,J=9.2 Hz,1H) 7.07(s,1H)

Production Example 19b)

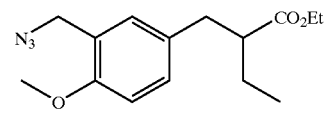

0.47 g of ethyl 2-[3-(hydroxymethyl)-4-methoxybenzyl]butanoate was dissolved in 6 ml toluene, and 0.54 ml diphenyl phosphoryl azide and 0.37 ml diazabicyclo[5.4.0]undecene were added and the mixture was stirred at room temperature for 16 hours. Water was added to the reaction mixture, and then extracted with ethyl acetate. The organic layer was washed with brine, dried over anhydrous magnesium sulfate and the solvent was evaporated. The residue was subjected to silica gel column chromatography, and from fractions eluted with hexane-ethyl acetate (5:1), 0.47 g of 1-{5-[2-(ethoxycarbonyl)butyl]-2-methoxybenzyl}-1,2-triazadiene-2-ium.

$^1$H-NMR(CDCl$_3$) δ: 0.90 (t, J=7.2 Hz, 3H) 1.17 (t, J=6.8 Hz, 3H) 1.50–1.64 (m, 2H) 2.51–2.57 (m, 1H) 2.68 (dd, J=6.8, 14.0 Hz, 1H) 2.87 (dd, J=8.0, 14.0 Hz, 1H) 3.82 (s, 3H) 4.02–4.12 (m, 2H) 4.30 (s, 2H) 6.81 (d, J=8.0 Hz, 1H) 7.03 (s, 1H) 7.11 (d, J=8.0 Hz, 1H)

Production Example 19c)

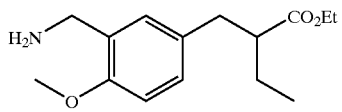

0.47 g of 1-{5-[2-(ethoxycarbonyl)butyl]-2-methoxybenzyl}-1,2-triazadiene-2-ium was dissolved in 6 ml tetrahydrofuran, and 0.4 ml water and 0.55 g triphenyl phosphine were added and the mixture was stirred at room temperature for 20 hours. After evaporating the solvent, the residue was subjected to silica gel column chromatography, and from fractions eluted with ethyl acetate-methanol-triethylamine (10:1:0.1), 0.40 g of ethyl 2-[3-(aminomethyl)-4-methoxybenzyl]butanoate was obtained.

$^1$H-NMR(CDCl$_3$) δ:0.90 (t, J=7.2 Hz, 3H) 1.17 (t, J=6.8 Hz, 3H) 1.50–1.64 (m, 2H) 2.49–2.56 (m, 1H) 2.67 (dd, J=6.8, 14.0 Hz, 1H) 2.86 (dd, J=8.0, 14.0 Hz, 1H) 3.77 (s, 2H) 3.81 (s, 3H) 4.04–4.10 (m, 2H) 6.76 (d, J=8.8 Hz, 1H) 7.00 (d, J=8.8 Hz, 1H) 7.01 (s, 1H)

Example 19d)

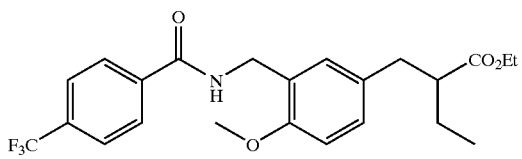

0.40 g of ethyl 2-[3-(aminomethyl)-4-methoxybenzyl]butanoate and 0.29 g of 4-(trifluoromethyl)benzoic acid were dissolved in 5 ml N,N-dimethylformamide, and 0.24 ml diethyl cyanophosphonate and 0.21 ml triethylamine were added under ice-cooling. After stirring the reaction mixture at room temperature for 16 hours, the mixture was poured into ice-water and extracted with ethyl acetate. The organic layer was successively washed with 1N hydrochloric acid and brine, dried over anhydrous magnesium sulfate and the solvent was evapoarated. The residue was subjected to silica gel column chromatography, and from fractions eluted with hexane-ethyl acetate (3:1), 0.59 g of ethyl 2-[4-methoxy-3-({[4-(trifluoromethyl)benzoyl]amino}methyl)benzyl]butanoate was obtained.

$^1$H-NMR(CDCl$_3$) δ:0.91 (t, J=7.2 Hz, 3H) 1.16 (t, J=6.8 Hz, 3H) 1.50–1.67 (m, 2H) 2.49–2.56 (m, 1H) 2.68 (dd, J=6.4, 14.0 Hz, 1H) 2.86 (dd, J=8.6, 14.0 Hz, 1H) 3.86 (s, 3H) 4.01–4.10 (m, 2H) 4.61 (d, J=6.0 Hz, 2H) 6.67–6.72 (m, 1H) 6.81 (d, J=8.0 Hz, 1H) 7.08 (dd, J=2.4, 8.0 Hz, 1H) 7.13 (d, J=2.4 Hz, 1H) 7.68 (d, J=8.0 Hz, 2H) 7.86 (d, J=8.0 Hz, 2H)

Example 19e)

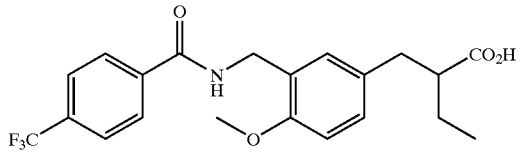

0.59 g of ethyl 2-[4-methoxy-3-({[4-(trifluoromethyl)benzoyl]amino}methyl)benzyl]butanoate was dissolved in 5 ml ethanol, and 2 ml of 1 N sodium hydroxide was added, and the mixture was stirred at 70° C. for 4 hours. The reaction mixture was ice-cooled and neutralized with 1N hydrochloric acid, followed by extracting with ethyl acetate. The organic layer was washed with brine, dried over anhydrous sodium sulfate and the solvent was evaporated, to give 0.50 g of 2-[4-methoxy-3-({[4-(trifluoromethyl)benzoyl]amino}methyl)benzyl]butanoic acid.

$^1$H-NMR(DMSO-d$_6$) δ:0.80 (t, J=7.2 Hz, 3H) 1.39–1.46 (m, 2H) 2.33–2.40 (m, 1H) 2.55 (dd, J=6.4, 14.0 Hz, 1H) 2.72 (dd, J=8.0, 14.0 Hz, 1H) 3.77 (s, 3H) 4.42 (d, J=5.6 Hz, 2H) 6.88 (d, J=8.0 Hz, 1H) 7.01 (s, 1H) 7.03 (d, J=8.0 Hz, 1H) 7.85 (d, J=8.0 Hz, 2H) 8.07 (d, J=8.0 Hz, 2H) 9.03 (t, J=5.6 Hz, 1H)

Example 20

Production Example 20a)

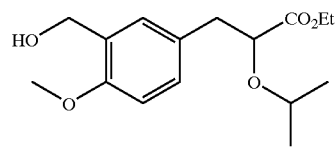

Ethyl 3-[3-(hydroxymethyl)-4-methoxyphenyl]-2-isopropoxypropanoate was obtained in the same method as in Production Example 19a).

$^1$H-NMR(CDCl$_3$) δ:0.97 (d, J=6.0 Hz, 3H) 1.15 (d, J=6.0 Hz, 3H) 1.24 (t, J=7.2 Hz, 3H) 2.88 (dd, J=8.4, 14.0 Hz, 1H) 2.95 (dd, J=5.2, 14.0 Hz, 1H) 3.50 (sept, J=6.0 Hz, 1H) 3.85 (s, 3H) 4.00 (dd, J=5.2, 8.4 Hz, 1H) 4.11–4.21 (m, 2H) 4.65 (d, J=6.4 Hz, 2H) 6.79 (d, J=8.8 Hz, 1H) 7.14 (d, J=8.8 Hz, 1H) 7.15 (s, 1H)

Production Example 20b)

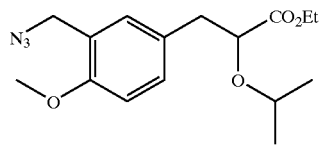

1-[5-(3-Ethoxyisopropoxyoxopropyl)-2-methoxybenzyl]-1,2-triazadiene-2-ium was obtained in the same method as in Production Example 19b).

$^1$H-NMR(CDCl$_3$) δ:0.96 (d, J=6.0 Hz, 3H) 1.15 (d, J=6.0 Hz, 3H) 1.25 (t, J=7.2 Hz, 3H) 2.88 (dd, J=8.8, 13.6 Hz, 1H) 2.95 (dd, J=4.8, 13.6 Hz, 1H) 3.50 (sept, J=6.0 Hz, 1H) 3.84 (s, 3H) 4.00 (dd, J=4.8, 8.8 Hz, 1H) 4.15–4.21 (m, 2H) 4.32 (s, 2H) 6.83 (d, J=8.0 Hz, 1H) 7.14 (d, J=2.0 Hz, 1H) 7.20 (dd, J=2.0, 8.0 Hz, 1H)

Production Example 20c)

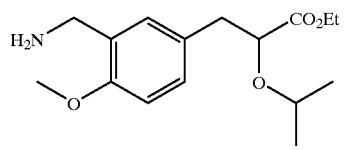

Ethyl 3-[3-(aminomethyl)-4-methoxyphenyl]-2-isopropoxypropanoate was obtained in the same method as in Production Example 19c).

$^1$H-NMR(CDCl$_3$) δ: 0.96 (d, J=6.0 Hz, 3H) 1.15 (d, J=6.0 Hz, 3H) 1.25 (t, J=7.2 Hz, 3H) 2.88 (dd, J=8.8, 13.6 Hz, 1H) 2.95 (dd, J=4.8, 13.6 Hz, 1H) 3.50 (sept, J=6.0 Hz, 1H) 3.84 (s, 3H) 4.00 (dd, J=4.8, 8.8 Hz, 1H) 4.15–4.21 (m, 2H) 4.32 (s, 2H) 6.83 (d, J=8.0 Hz, 1H) 7.14 (d, J=2.0 Hz, 1H) 7.20 (dd, J=2.0, 8.0 Hz, 1H)

Example 20d)

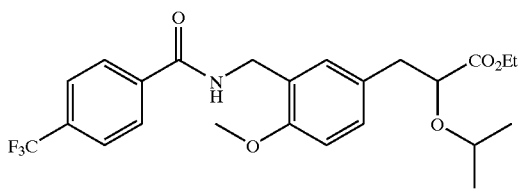

Ethyl 2-isopropoxy-3-[4-methoxy-3-({[4-(trifluoromethyl)benzoyl]amino}methyl)phenyl]propanoate was obtained in the same method as in Example 19d).

$^1$H-NMR(CDCl$_3$) δ:0.96 (d, J=6.0 Hz, 3H) 1.14 (d, J=6.0 Hz, 3H) 1.24 (t, J=7.2 Hz, 3H) 2.88 (dd, J=8.4, 14.0 Hz, 1H) 2.95 (dd, J=4.8, 14.0 Hz, 1H) 3.51 (sept, J=6.0 Hz, 1H) 3.87 (s. 3H) 4.01 (dd, J=4.8, 8.4 Hz, 1H) 4.12–4.20 (m, 2H) 4.62 (d, J=6.0 Hz, 2H) 6.65–6.70 (m, 1H) 6.82 (d, J=8.0 Hz, 1H) 7.17 (dd, J=2.0, 8.0 Hz, 1H) 7.22 (d, J=2.0 Hz, 1H) 7.68 (d, J=8.4 Hz, 2H) 7.86 (d, J=8.4 Hz, 2H)

Example 20e)

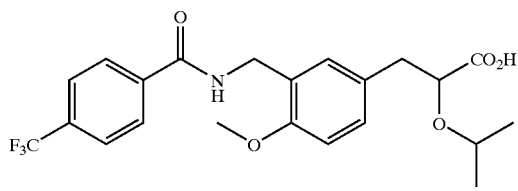

2-Isopropoxy-3-[4-methoxy-3-({[4-(trifluoromethyl)benzoyl]amino}methyl)phenyl]propanoic acid was obtained in the same method as in Example 19e).

$^1$H-NMR(DMSO-d$_6$) δ:0.78 (d, J=6.0 Hz, 3H) 0.93 (d, J=6.0 Hz, 3H) 2.68 (dd, J=8.0, 14.0 Hz, 1H) 2.81 (dd, J=4.0, 14.0 Hz, 1H) 3.41 (sept, J=6.0 Hz, 1H) 3.78 (s, 3H) 3.92 (dd, J=4.8, 8.4 Hz, 1H) 4.43 (d, J=6.0 Hz, 2H) 6.88 (d, J=8.0 Hz, 1H) 7.07 (s, 1H) 7.08 (d, J=8.0 Hz, 1H) 7.85 (d, J=8.0 Hz, 2H) 8.09 (d, J=8.0 Hz, 2H) 9.06 (t, J=6.0 Hz, 1H)

Example 21

Production Example 21a)

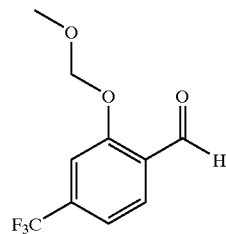

7.0 g of 1-(methoxymethyl)-3-(trifluoromethyl)benzene was dissolved in 300 ml anhydrous diethyl ether, and 19 ml n-butyl lithium (2.5 M solution in hexane) was added dropwise at −78° C. The reaction mixture was stirred at room temperature for 3 hours and cooled again at −78° C., and 10 ml N,N-dimethylformamide was added. The reaction solution was returned to room temperature, poured into water, extracted with ethyl acetate. The extract was washed with brine, dried over anhydrous magnesium sulfate and the solvent was evapoarated. The residue was subjected to silica gel column chromatography, and from fractions eluted with hexane-ethyl acetate (9:1), 5.0 g of 1-(methoxymethyl)-3-(trifluoromethyl)benzaldehyde was obtained as a reddish orange oil.

$^1$H-NMR(CDCl$_3$) δ:3.54(s,3H) 5.35(s,2H) 7.34(d,J=8 Hz,1H) 7.49(s,1H) 7.94(d,J=8 Hz,1H) 10.52(s,1H)

Production Example 21b)

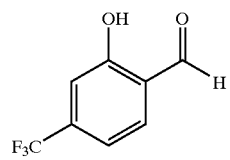

5.0 g of 1-(methoxymethyl)-3-(trifluoromethyl)benzaldehyde was dissolved in 25 ml acetone, and 22 ml of 6 N hydrochloric acid was added. The mixture was reacted at room temperature for 3 hours, and water was added thereto, followed by extracting with ethyl acetate. The extract was washed with brine, dried over anhydrous magnesium sulfate and the solvent was evapaorated, to give 4.5 g of 2-hydroxy-4-(trifluoromethyl)benzaldehyde as a pale reddish orange oil.

$^1$H-NMR(CDCl$_3$) δ:7.2–7.3 (m,2H) 7.70(d,J=8 Hz, 1H) 10.0(s,1H) 11.1(s,1H)

Production Example 21c)

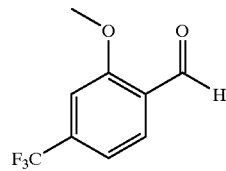

4.5 g of 2-hydroxy-4-(trifluoromethyl)benzaldehyde was dissolved in 20 ml N,N-dimethylformamide. 1.0 g of sodium hydride (60% oily) was added, followed by stirring at room temperature for 30 minutes. 1.8 ml methyl iodide was added dropwise thereinto, follwed by reacting for 1 hour. Water was added to the reaction solution, and the mixture was extracted with ethyl acetate, washed with brine, dried over anhydrous magnesium sulfate and the solvent was evaporated. The residue was subjected to silica gel column chromatography, to give 3.0 g of 2-methoxy-4-(trifluoromethyl)benzaldehyde as a colorless oil from fractions eluted with hexane-ethyl acetate (9:1).

$^1$H-NMR(CDCl$_3$) δ4.00(s,3H) 7.22(s,1H) 7.29(d,J=8 Hz,1H) 7.93(d,J=8 Hz,1H) 10.50(s,1H)

Production Example 21d)

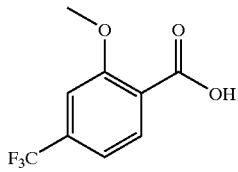

3.0 g of 2-methoxy-4-(trifluoromethyl)benzaldehyde was dissolved in 50 ml dimethyl sulfoxide and an aqueous solution (20 ml) of 1.6 g sodium dihydrogenphosphate, followed by adding dropwise an aqueous solution (30 ml) of 8.0 g sodium chlorite thereinto. After stirring at room temperature for 3 days, water was added thereto, followed by extracting with ethyl acetate. The extract was washed with brine, dried over anhydrous magnesium sulfate and the solvent was evaporated. The residue was subjected to silica gel column chromatography, to give 0.8 g of 2-methoxy-4-(trifluoromethyl)benzoic acid as a colorless solid from fractions eluted with hexane-ethyl acetate (3:7).

$^1$H-NMR(CDCl$_3$) δ4.14(s,3H) 7.29(s,1H) 7.41(d,J=8 Hz,1H) 8.30 (d, J=8 Hz, 1H)

Example 21e)

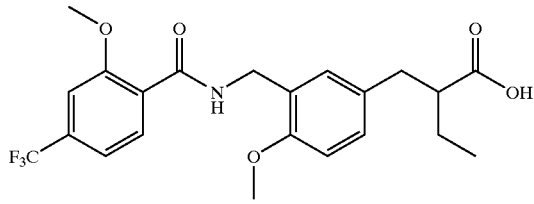

0.24 g of 2-methoxy-4-(trifluoromethyl)benzoic acid and 0.3 g of ethyl 2-[3-(aminomethyl)-4-methoxybenzyl] butanoate were treated in the same manners as in Example 19d) and then in Example 19e), to give 0.3 g of 2-[4-methoxy-3-({[2-methoxy-4-(trifluoromethyl)benzoyl] amino}methyl)benzyl]butanoic acid as a pale yellow oil.

$^1$H-NMR(CDCl$_3$) δ:0.93(t,J=7 Hz,3H) 1.5–1.7(m,2H) 2.5–2.6(m,1H) 2.69(dd,J=7,14 Hz,1H) 2.89(dd,J=8,14 Hz,1H) 3.87(s,3H) 3.98(s,3H) 4.62(d,J=6 Hz,2H) 6.80(d, J=8 Hz,1H) 7.08(dd,J=2.8 Hz,1H) 7.16(s,2H) 7.28–7.34(m, 1H) 8.26–8.40(m,1H) 8.36(t,J=6 Hz,1H)

Example 22

Production Example 22a)

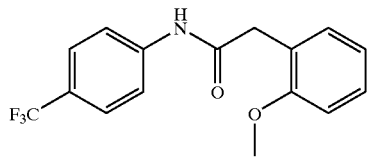

5.0 g of 2-methoxyphenylacetic acid was dissolved in 20 ml dichloromethane, and 4.6 g of oxalyl dichloride was added, and the mixture was stirred at room temperature for 3 hours. The solvent and an excessive oxalyl dichloride were evapoarated, and the residue was dissolved in 20 ml dichloromethane. Under ice-cooling, 14 g of 4-trifluoromethyl aniline was added thereto, followed by stirring at room temperature for 12 hours. Water was added to the reaction solution, and the mixture was extracted with ethyl acetate, washed with 1N hydrochloric acid and brine, dried over anhydrous magnesium sulfate and then the solvent was evpoarated. The resulting solid was collected by filtration and washed with diethyl ether, to give 8.0 g of N-[4-(trifluoromethyl)phenyl]-2-(2-methoxyphenyl)acetamide as a colorless solid.

$^1$H-NMR(CDCl$_3$) δ:3.73(s,2H) 4.95(s,3H) 6.98(d,J=8 Hz,1H) 7.00(d,J=8 Hz,1H) 7.28–7.35(m,2H) 7.50–7.60(m, 4H) 7.91(s,1H)

Production Example 22b)

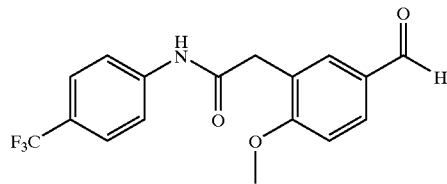

1.0 g of N-[4-(trifluoromethyl)phenyl]-2-(2-methoxyphenyl)acetamide was dissolved in 10 mg trifluoroacetic acid, and 0.46 g hexamethylene tetramine was added, and the mixture was reacted at 85° C. for 3 hours. The reaction solution was returned to room temperature, water and ethyl acetate were added, and sodium bicarbonate was further added until the pH reached 8. The reaction solution was extracted with ethyl acetate, washed with brine and dried over anhdydrous magnesium sulfate and the solvent was evaporated. The residue was subjected to silica gel column chromatography, to give 0.7 g of N-[4-(trifluoromethyl)phenyl]-2-(5-formyl-2-methoxyphenyl) acetamide as a colorless oil from fractions eluted with hexane-ethyl acetate (1:1).

$^1$H-NMR(CDCl$_3$) δ:3.78(s,2H) 4.00(s,3H} 7.07(d,J=8 Hz,1H) 7.54(d,J=9 Hz,2H) 7.57(d,J=9 Hz,2H) 7.85(d,J=2 Hz,1H) 7.83–7.90(m,1H) 9.91(s,1H)

Example 22c)

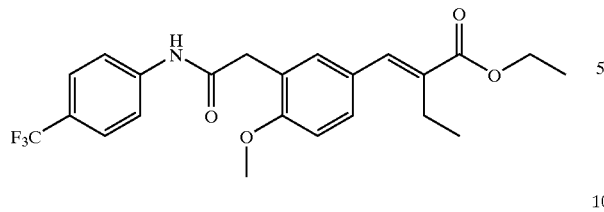

0.7 g of N-[4-(trifluoromethyl)phenyl]-2-(5-formyl-2-methoxyphenyl)acetamide and 1.6 g of ethyl 2-phosphonobutanoate were treated in the same manner as in Production Example 1a), to give 0.8 g of ethyl 2-ethyl-3-(4-methoxy-3-{2-oxo-2-[4-(trifluoromethyl)anilino]ethyl}phenyl)-2-propenoate as a colorless oil.

$^1$H-NMR(CDCl$_3$) δ:1.18(t,J=7 Hz,3H) 1.34(t,J=7 Hz,3H) 2.55(q,J=7 Hz,2H) 3.74(s,2H) 3.97(s,3H) 4.26(q,J=7 Hz,2H) 6.99(d,J=9 Hz,1H) 7.34(d,J=9 Hz,1H) 7.38(dd,J=2,8 Hz,1H) 7.48–7.62(m,5H) 7.82(s,1H)

Example 22d)

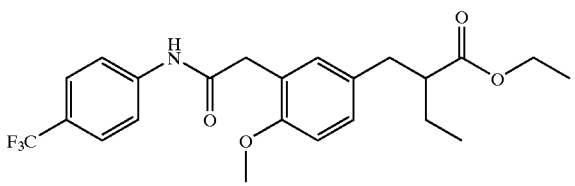

0.3 g of ethyl 2-ethyl-3-(4-methoxy-3-{2-oxo-2-[4-(trifluoromethyl)anilino]ethyl}phenyl)-2-propenoate was treated in the same manner as in Production Example 1b), to give 0.3 g of ethyl 2-(4-methoxy-3-{2-oxo-2-[4-(trifluoromethyl)anilino]ethyl}benzyl)butanoate as a colorless oil.

$^1$H-NMR(CDCl$_3$) δ:0.91(t,J=7 Hz,3H) 1.14(t,J=7 Hz,3H) 1.5–1.8(m,2H) 2.48–2.60(m,1H) 2.71(dd,J=6,14 Hz,1H) 2.87(dd,J=4,14 Hz,1H) 3.68(s,2H) 3.91(s,3H) 3.95–4.10(m,2H) 6.86(d,J=9 Hz,1H) 7.09(s,1H) 7.06–7.12(m,1H) 7.51(d,J=9 Hz,2H) 7.56(d,J=9 Hz,2H) 7.94(s,1H)

Example 22e)

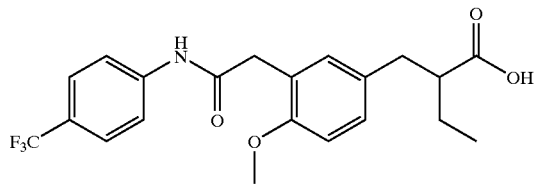

0.3 g of ethyl 2-(4-methoxy-3-{2-oxo-2-[4-(trifluoromethyl)anilino]ethyl}benzyl)butanoate was treated in the same manner as in Production Example 19e), to give 0.11 g of 2-(4-methoxy-3-{2-oxo-2-[4-(trifluoromethyl)anilino]ethyl}benzyl)butanoic acid as a colorless solid.

$^1$H-NMR(DMSO-d$_6$) δ:0.84(t,J=8 Hz,3H) 1.46(sept,J=8 Hz,2H) 2.35–2.60(m,1H) 2.57(dd,J=6,14 Hz,1H) 2.74(dd,J=8,14 Hz,1H) 3.61(s,2H) 3.71(s,3H) 6.86(d,J=8 Hz,1H) 7.02(s,1H) 7.03(d,J=8 Hz,1H) 7.64(d,J=9 Hz,2H) 7.79(d,J=9 Hz,2H) 10.4(s,1H) 12.1(s,1H)

Example 23

Example 23a)

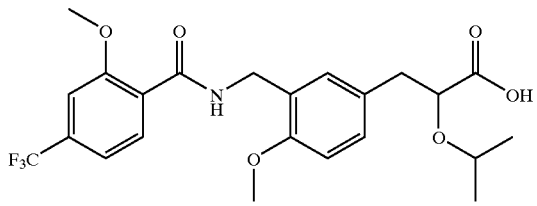

0.15 g of ethyl 3-[3-(aminomethyl)-4-methoxyphenyl]-2-isopropoxypropanoate and 0.24 g of 2-methoxy-4-(trifluoromethyl)benzoic acid were treated in the same manners as in Example 19d) and then in Example 1d), to give 0.15 g of 2-isopropoxy-3-[4-methoxy-3-({[2-methoxy-4-(trifluoromethyl)benzoyl]amino}methyl)phenyl]propanoic acid as a pale yellow oil.

$^1$H-NMR(CDCl$_3$) δ:1.00(d,J=6 Hz,3H) 1.14(d,J=6 Hz,3H) 2.90(dd,J=8.14 Hz,1H) 3.03(dd,J=4.14 Hz,1H) 3.56(sept,J=6 Hz,1H) 3.88(s,3H) 4.00(s,3H) 4.08(dd,J=4.8 Hz,1H) 4.63(d,J=6 Hz,2H) 6.81(d,J=8 Hz,1H) 7.14(dd,J=2.8 Hz,1H) 7.17(s,1H) 7.22(d,J=2 Hz,1H) 7.32(d,J=8 Hz,1H) 8.30(d,J=8 Hz,1H) 8.35(t,J=8 Hz,1H)

Example 24

Example 24a)

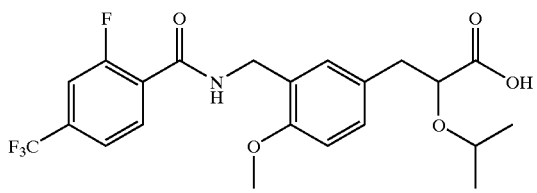

0.15 g of ethyl 3-[3-(aminomethyl)-4-methoxyphenyl]-2-isopropoxypropanoate was dissolved in 5 ml N,N-dimethylformamide, and 0.2 ml pyridine and 0.24 g of 2-fluoro-4-(trifluoromethyl)benzoate chloride were added, followed by stirring at room temperature for 12 hours. Water was added to the reaction solution, followed by extracting with ethyl acetate The extract was washed with brine, dried over anhydrous magnesium sulfate and the solvent was evapoarated. The residue was subjected to silica gel column chromatography, and from fractions eluted with ethyl acetate-hexane (1:2), 0.2 g of ethyl 2-isopropoxy-3-[4-methoxy-3-({[2-fluoro-4-(trifluoromethyl)benzoyl]amino}methyl)phenyl]propanoate was obtained as a pale yellow oil. This product was treated in the same manner as in Example 1d), to give 0.15 g of 2-isopropoxy-3-[4-methoxy-3-{[2-fluoro-4-(trifluoromethyl)benzoyl]amino}methyl)phenyl]propanoic acid as a pale yellow solid.

$^1$H-NMR(CDCl$_3$) δ:1.00(d,J=6 Hz,3H) 1.15(d,J=6 Hz,3H) 2.91(dd,J=8,14 Hz,1H) 3.04(dd,J=4,14 Hz,1H) 3.56(sept,J=6 Hz,1H) 3.87(s,3H) 4.09(dd,J=4,8 Hz,1H) 4.64(d,J=6 Hz,2H) 6.82(d,J=8 Hz,1H) 7.16(dd,J=2,8 Hz,1H) 7.22(d,J=2 Hz,1H) 7.37(d,J=12 Hz,1H) 7.51(d,J=8 Hz,1H) 7.34–7.5(m,1H) 8.22(t,J=8 Hz,1H)

Example 25

Example 25a)

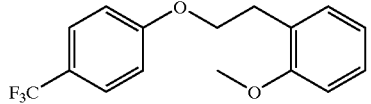

1.1 g of 4-hydroxybenzotrifluoride and 1.0 g of 2-methoxyphenetyl alcohol were dissolved in 200 ml tetrahydrofuran. 2.6 g of triphenyl phosphine and 2.0 g of diisopropyl azodicarboxylate were added thereto, followed by stirring at room temperature for 24 hours. After evaporating the solvent, the residue was subjected to silica gel column chromatography, to give 1.6 g of 1-methoxy-2-{2-[4-(trifluoromethyl)phenoxy]ethyl}benzene was obtained from fractions eluted with hexane-ethyl acetate (10:1).

$^1$H-NMR(CDCl$_3$) δ: 3.14 (t, J=7.2 Hz, 2H) 3.85 (s, 3H) 4.20 (t, J=7.2 Hz, 2H) 6.85–6.92 (m, 2H) 6.96 (d, J=8.0 Hz, 2H) 7.20–7.27 (m, 2H) 7.51 (d, J=8.0 Hz, 2H)

Example 25b)

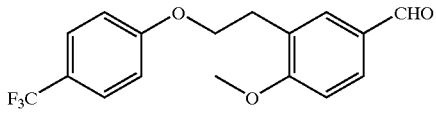

1.6g of 1-methoxy-2-{2-[4-(trifluoromethyl)phenoxy]ethyl}benzene was treated in the same manner as in Example 22b), to give 0.20 g of 4-methoxy-3-{2-[4-(trifluoromethyl)phenoxy]ethyl}benzaldehyde.

$^1$H-NMR(CDCl$_3$) δ: 3.18 (t, J=7.2 Hz, 2H) 3.93 (s, 3H) 4.20 (t, J=7.2 Hz, 2H) 6.95 (d, J=8.0 Hz, 2H) 6.99 (d, J=8.0 Hz, 1H) 7.52 (d, J=8.0 Hz, 2H) 7.78 (s, 1H) 7.80 (d, J=8.0 Hz, 1H) 9.89 (s,1H)

Example 25c)

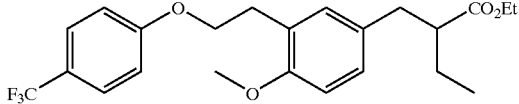

0.20 g of 4-methoxy-3-{2-[4-(trifluoromethyl)phenoxy]ethyl}benzaldehyde was treated in the same manners as in Production Example 1a) and then in Production Example 1b), to give 0.22 g of ethyl 2-(4-methoxy-3-{2-[4-(trifluoromethyl)phenoxy]ethyl}benzyl)butanoate.

$^1$H-NMR(CDCl$_3$) δ: 0.91 (t, J=6.8 Hz, 3H) 1.16 (t, J=7.2 Hz, 3H) 1.52–1.67 (m, 2H) 2.48–2.56 (m, 2H) 2.6) (dd, J=6.8, 13.6 Hz, 1H) 2.86 (dd, J=8.4, 13.6 Hz, 1H) 3.07 (t, J=7.2 Hz, 2H) 3.81 (s, 3H) 4.04–4.10 (m, 2H) 4.16 (t, J=7.2 Hz, 2H) 6.77 (d, J=8.0 Hz, 1H) 6.96 (d, J=8.0 Hz, 2H) 7.00 (s, 1H) 7.01 (d, J=8.0 Hz, 1H) 7.52 (d, J=8.0 Hz, 2H)

Example 25d)

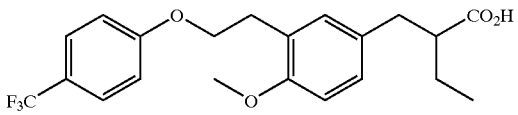

0.22 g of ethyl 2-(4-methoxy-3-{2-[4-(trifluoromethyl)phenoxy]ethyl}benzyl)butanoate was treated in the same manner as in Example 19e), to give 0.20 g of 2-(4-methoxy-3-{2-[4-(trifluoromethyl)phenoxy]ethyl}benzyl)butanoic acid.

$^1$H-NMR(CDCl$_3$) δ: 0.95 (t, J=7.2 Hz, 3H) 1.53–1.67 (m, 2H) 2.52–2.60 (m, 1H) 2.69 (dd, J=6.8, 14.0 Hz, 1H) 2.90 (dd, J=8.0, 14.0 Hz, 1H) 3.07 (t, J=7.2 Hz, 2H) 3.81 (s, 3H) 4.16 (t, J=7.2 Hz, 2H) 6.78(d, J=8.0 Hz, 1H) 6.96 (d, J=8.0 Hz, 2H) 7.02 (s, 1H) 7.03 (d, J=8.0 Hz, 1H) 7.52 (d, J=8.0 Hz, 2H)

Example 26

Production Example 26a)

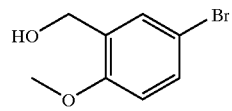

3.0 g of 5-bromo-2-methoxybenzoic acid was treated in the same manner as in Production Example 19a), to give 1.7 g of 5-bromo-2-methoxyphenyl methanol.

$^1$H-NMR(CDCl$_3$) δ: 2.20 (m, 1H) 3.82 (s, 3H) 4.64 (d, J=6.0 Hz, 2H) 6.77 (d, J=8.0 Hz, 1H) 7.37 (dd, J=2.0, 8.0 Hz, 1H) 7.52 (d, J=2.0 Hz, 1H)

Production Example 26b)

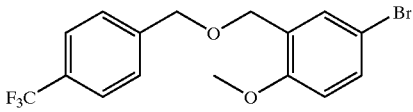

0.8 g of 5-bromo-2-methoxyphenyl methanol was dissolved in 30 ml tetrahydrofuran. 2.6 g of 4-(trifluoromethyl)benzyl bromide and 0.22 g of sodium hydride (60% oily) were added thereto, followed by stirring at room temperature for 16 hours. Water was added to the reaction solution, followed by extracting with diethyl ether. The organic layer was washed with brine, dried over anhydrous magnesium sulfate and the solvent was evaporated. The residue was subjected to silica gel column chromatography, to give 1.4 g of 4-bromo-1-methoxy-2-({[4-(trifluoromethyl)benzyl]oxy}methyl)benzene from fractions eluted with hexane-ethyl acetate (9:1).

$^1$H-NMR(CDCl$_3$) δ: 3.80 (s, 3H) 4.57 (s, 2H) 4.64 (s, 2H) 6.77 (d, J=8.0 Hz, 1H) 7.37 (dd, J=2.0, 8.0 Hz, 1H) 7.50 (d, J=8.0 Hz, 2H) 7.52 (d, J=2.0 Hz, 1H) 7.61 (d, J=8.0 Hz, 2H)

Example 26c)

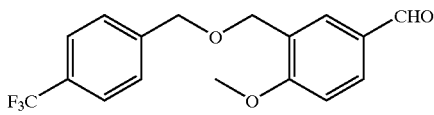

1.4 g of 4-bromo-1-methoxy-2-({[4-(trifluoromethyl)benzyl]oxy}methyl)benzene was dissolved in 15 ml tetrahydrofuran and cooled at −78° C., and 3.0 ml n-butyl lithium (1.5 M solution in pentane) was added. After stirring the reaction mixture at −78° C. for 30 minutes, 0.45 ml N-formyl morpholine was added, and the mixture was stirred at −78° C. for 1 hour. 1N hydrochloric acid was added to the reaction solution, followed by extracting with ethyl acetate. The organic layer was washed with brine, dried over anhydrous magnesium sulfate and the solvent was evaporated. The residue was subjected to silica gel column chromatography, and from fractions eluted with hexane-ethyl acetate (3:1), 0.42 g of 4-methoxy-3-({[4-(trifluoromethyl)benzyl]oxy}methyl)benzaldehyde was obtained.

$^1$H-NMR(CDCl$_3$) δ: 3.92 (s, 3H) 4.63 (s, 2H) 4.70 (s, 2H) 6.99 (d, J=8.0 Hz, 1H) 7.51 (d, J=8.0 Hz, 2H) 7.62 (d, J=8.0 Hz, 2H) 7.84 (dd, J=2.0, 8.0 Hz, 1H) 7.98 (d, J=2.0 Hz, 1H) 9.90 (s, 1H)

Example 26d)

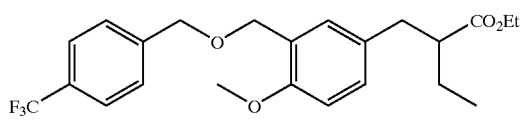

0.42 g of 4-methoxy-3-({[4-(trifluoromethyl)benzyl]oxy}methyl)benzaldehyde was treated in the same manners as in Production Example 1a) and then in Production Example 1b), to give 0.33 g of ethyl 2-[4-methoxy-3-({[4-(trifluoromethyl)benzyl]oxy}methyl)benzyl]butanoate.

$^1$H-NMR(CDCl$_3$) δ: 0.91 (t, J=7.6 Hz, 3H) 1.16 (t, J=7.2 Hz, 3H) 1.52–1.68 (m, 2H) 2.50–2.57 (m, 1H) 2.70 (dd, J=6.8, 14.0 Hz, 1H) 2.88 (dd, J=8.4, 14.0 Hz, 1H) 3.80 (s, 3H) 4.01–4.10 (m, 2H) 4.57 (s, 2H) 4.64 (s, 2H) 6.78 (d, J=8.0 Hz, 1H) 7.06 (dd, J=2.0, 8.0 Hz, 1H) 7.19 (d, J=2.0 Hz, 1H) 7.50 (d, J=8.0 Hz, 2H) 7.61 (d, J=8.0 Hz, 2H)

Example 26e)

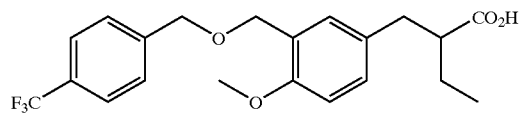

0.33 g of ethyl 2-[4-methoxy-3-({[4-(trifluoromethyl)benzyl]oxy}methyl)benzyl]butanoate was treated in the same manner as in Example 19e), to give 0.30 g of 2-[4-methoxy-3-({[4-(trifluoromethyl)benzyl]oxy}methyl)benzyl]butanoic acid.

$^1$H-NMR(CDCl$_3$) δ: 0.95 (t, J=7.2 Hz, 3H) 1.54–1.68 (m, 2H) 2.55–2.62 (m, 1H) 2.71 (dd, J=6.8, 13.6 Hz, 1H) 2.92 (dd, J=8.0, 13.6 Hz, 1H) 3.79 (s, 3H) 4.57 (s, 2H) 4.63 (s, 2H) 6.78 (d, J=8.0 Hz, 1H) 7.08 (dd, J=2.0, 8.0 Hz, 1H) 7.21 (d, J=2.0 Hz, 1H) 7.49 (d, J=8.0 Hz, 2H) 7.61 (d, J=8.0 Hz, 2H)

Example 27

Example 27a)

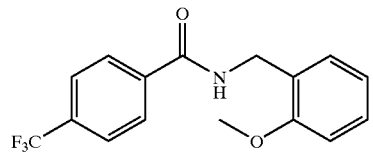

5.7 g of 4-(trifluoromethyl)benzoic acid and 4.0 g of 2-methoxybenzylamide were dissolved in 100 ml N,N-dimethylformamide, and 4.8 ml diethyl cyanophosphonate and 4.2 ml triethylamine were added under ice-cooling. The reaction mixture was stirred at room temperature for 16 hours, then poured into ice-water and extracted with ethyl acetate. The organic layer was successively washed with 1N hydrochloric acid and brine, dried over anhydrous magnesium sulfate and the solvent was evapoarated. The residue was subjected to silica gel column chromatography, and from fractions eluted with hexane-ethyl acetate (2:1), 8.7 g of N1-(2-methoxybenzyl)-4-(trifluoromethyl)benzamide was obtained.

$^1$H-NMR(CDCl$_3$) δ:3.89(s,3H) 4.65(d, J=5.6 Hz,2H) 6.70 (br, 1H) 6.92(d,J=8.4 Hz,1H) 6.95(t,J=7.6 Hz,1H) 7.28–7.36 (m,2H) 7.68(d,J=8.4 Hz,2H) 7.86(d,J=8.4 Hz,2H)

Production Example 27b)

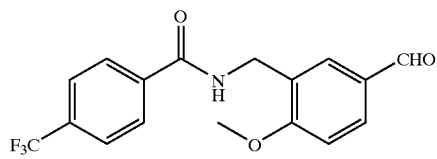

8.7 g of N1-(2-methoxybenzyl)-4-(trifluoromethyl)benzamide was dissolved in 20 ml trifluoroacetic acid, and 3.9 g of hexamethylene tetramine was added, and the mixture was reacted at 85° C. for 3 hours. The reaction solution was returned to room temperature, and water and ethyl acetate were added, and further sodium bicarbonate was added until the pH reached 8. After extracting with ethyl acetate, the extract was washed with brine, dried over anhydrous magnesium sulfate and the solvent was evapoarated. The residue was subjected to silica gel column chromatography, and from fractions eluted with hexane-ethyl acetate (2:1), 4.2 g of N1-(5-formyl-2-methoxybenzyl)-4-(trifluoromethyl)benzamide was obtained.

$^1$H-NMR(CDCl$_3$) δ: 3.99 (s, 3H) 4.72 (d, J=5.6 Hz, 2H) 6.70(br, 1H) 7.02 (d, J=8.4 Hz, 1H) 7.68 (d, J=8.4 Hz, 2H) 7.83–7.90 (m, 4H) 9.89 (s,1H)

Example 27c)

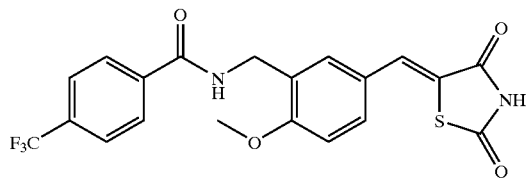

1.5 g of N1-(5-formyl-2-methoxybenzyl)-4-(trifluoromethyl)benzamide was dissolved in 15 ml toluene, and 0.52 g of 2,4-thiazolidine dione, 36 mg pyrrolidine and 30 mg acetic acid were added thereto, and the mixture was heated under reflux for 2 hours with a Dean-Stark apparatus. After cooling to room temperature, the precipitated crystals were collected by filtration, washed with ethyl acetate and then dried, to give 1.4 g of N1-[5-[(2,4-dioxo-1,3-thiazolane-5-ylidene)methyl]-2-methoxybenzyl)-4-(trifluoromethyl)benzamide.

$^1$H-NMR(DMSO-$d_6$) δ: 3.90 (s, 3H) 4.47 (d, J=5.6 Hz, 2H) 6.70(br, 1H) 7.17 (d, J=8.8 Hz, 1H) 7.40 (s, 1H) 7.54 (d, J=8.8 Hz, 1H) 7.70 (s, 1H) 7.87 (d, J=8.0 Hz, 2H) 8.13 (d, J=8.0 Hz, 2H) 9.23 (t, J=5.6 Hz, 1H)

Example 28

Production Example 28a)

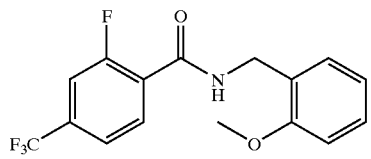

1.5 g of 2-fluoro-4-(trifuluoromethyl)benzoic acid and 0.90 g of 2-methoxybenzylamine were treated in the same manner as in Production Example 27a), to give 2.0 g of N1-(2-methoxybenzyl)-2-fluoro-4-(trifluoromethyl)benzamide.

$^1$H-NMR(CDCl$_3$) δ:3.90 (s, 3H) 4.67 (d, J=4.8 Hz, 2H) 6.90–6.96(m, 2H) 7.25–7.39 (m, 4H) 7.52 (d, J=8.0 Hz, 1H) 8.24 (t,J=8.0 Hz,1H)

Production Example 28b)

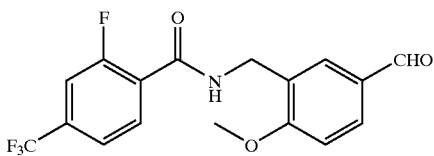

2.0 g of N1-(2-methoxybenzyl)-2-fluoro-4-(trifluoromethyl)benzamide was treated in the same manner as in Production Example 27b), to give 1.1 g of N1-(5-formyl-2-methoxybenzyl)-2-fluoro-4-(trifluoromethyl)benzamide.

$^1$H-NMR(CDCl$_3$) δ: 4.00 (s, 3H) 4.72 (d, J=5.6 Hz, 2H) 7.03 (d, J=8.0 Hz, 1H) 7.32(br, 1H) 7.40 (d, J=12.0 Hz, 1H) 7.53 (d, J=8.0 Hz, 1H) 7.84–7.88 (m, 2H) 8.25 (t, J=8.0 Hz, 1H) 9.89 (s,1H)

Example 28c)

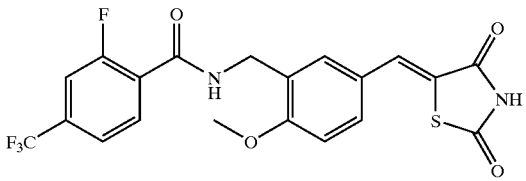

1.1 g of N1-(5-formyl-2-methoxybenzyl)-2-fluoro-4-(trifluoromethyl)benzamide was treated in the same manner as in Example 27c), to give 0.70 g of N1-(5-[(2,4-dioxo-1,3-thiazolane-5-ylidene)methyl]-2-methoxybenzyl)-2-fluoro-4-(trifluoromethyl)benzamide.

$^1$H-NMR(DMSO-$d_6$) δ: 3.89 (s, 3H) 4.45 (d, J=5.6 Hz, 2H) 7.18 (d, J=8.8 Hz, 1H) 7.44 (d, J=2.0 Hz, 1H) 7.55 (dd, J=2.0, 8.8 Hz, 1H) 7.68 (d, J=8.0 Hz, 1H) 7.71 (s, 1H) 7.83–7.90 (m, 2H) 9.02 (t, J=5.6 Hz, 1H)

Example 29

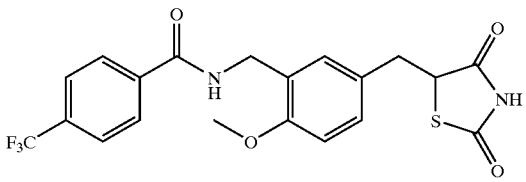

0.55 g of N1-(5-[(2,4-dioxo-1,3-thiazolane-5-ylidene)methyl]-2-methoxybenzyl)-4-(trifluoromethyl)benzamide was suspended in 20 ml N,N-dimethylformamide, and 0.60 g of 10% palladium-carbon was added, and the mixture was stirred at 50° C. under pressure at 15 kg/cm$^2$ hydrogen for 16 hours. After the reaction, the catalyst was filtered off, and after the solvent was evapoarated. Water was added to the residue, followed by extracting with ethyl acetate. The organic layer was washed with brine, dried over anhydrous magnesium sulfate and the solvent was evapoarated. The residue was subjected to silica gel column chromatography, and from fractions eluted with hexane-ethyl acetate (1:1), 1.2 g of N1-{5-[(2,4-dioxo-1,3-thiazolane-5-yl)methyl]-2-methoxybenzyl}-4-(trifluoromethyl)benzamide was obtained.

$^1$H-NMR(DMSO-$d_6$) δ: 2.99 (dd, J=9.2, 17.5 Hz, 1H) 3.28 (dd, J=4.0, 17.5 Hz, 1H) 3.79 (s, 3H) 4.42 (d, J=5.6 Hz, 2H) 4.79 (dd, J=4.0, 9.2 Hz, 1H) 6.93 (d, J=8.4 Hz, 1H) 7.08 (d, J=2.0 Hz, 1H) 7.10 (dd, J=2.0, 8.4 Hz, 1H) 7.84 (d, J=8.0 Hz, 2H) 8.08 (d, J=8.0 Hz, 2H) 9.05 (t, J=5.6 Hz,1H)

Example 30

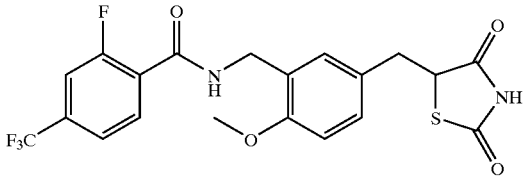

0.70 g of N1-{5-[(2,4-dioxo-1,3-thiazolane-5-ylidene)methyl]-2-methoxybenzyl}-2-fluoro-4-(trifluoromethyl)benzamide was treated in the same manner as in Production Example 29), to give 0.47 g of N1-{5-[(2,4-dioxo-1,3- thiazolane-5-yl)methyl]-2-methoxybenzyl)-2fluoro-4-(trifluoromethyl)benzamide.

$^1$H-NMR(DMSO-d$_6$) δ: 3.01(dd,J=9.6,18.0 Hz,1H) 3.31 (dd,J=4.0,18.0 Hz,1H) 3.79 (s, 3H) 4.40 (d, J=5.6 Hz, 2H) 4.81 (dd, J=4.0, 9.6 Hz, 1H) 6.94 (d, J=9.2 Hz, 1H) 7.12 (m, 2H) 7.66 (d, J=7.2 Hz, 1H) 7.80–7.84 (m, 2H) 8.88 (t, J=5.6 Hz, 1H)

Example 31

Production Example 31a)

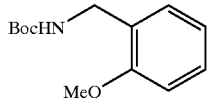

13.0 g of 2-methoxybenzylamine was dissolved in 80 ml tetrahydrofuran, and a solution of 16 g tertiary butyl dicarbonate in tetrahydrofuran (20 ml) was added. After the mixture was stirred at room temperature for 1 hour, the solvent was evaporated. The residue was dissolved in ethyl acetate and successively washed with 1N hydrochloricacid and brine. After the organic layer was dried over anhydrous magnesium sulfate, the solvent was evaporated, to give 19.0 g of tertiary butyl N-(2-methoxybenzyl)carbamate was obtained.

$^1$H-NMR(CDCl$_3$) δ: 1.45 (s, 9H) 3.84 (s, 3H) 4.27–4.33 (m, 2H) 5.01 (br, 1H) 6.84 (d, J=8.8 Hz, 1H) 6.94 (t, J=8.8 Hz, 1H) 7.23–7.29 (m, 2H)

MS m/e (ESI) 440 (MH$^+$)

Production Example 31b)

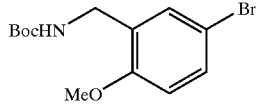

6.04 g of tertiary butyl N-(2-methoxybenzyl)carbamate was dissolved in 50 ml acetonitrile, followed by adding 4.6 g of N-bromosuccinimide thereto. After stirring at room temperature for 3 hours, the solvent was evaporated. The residue was dissolved in ethyl acetate and successively-washed with water and brine. The organic layer was dried over anhydrous magnesium sulfate and the solvent was evapoarated. The residue was washed with a mixture of methyl tertiary butyl methyl ether and hexane, to give 6.97 g of tertiary butyl N-(5-bromo-2-methoxybenzyl)carbamate.

$^1$H-NMR(CDCl$_3$) δ: 1.45 (s, 9H) 3.62 (s, 3H) 4.26 (d, J=6.4 Hz, 2H) 4.97 (br, 1H) 6.72 (d, J=8.8 Hz, 1H) 7.34 (dd, J=2.8, 11.2 Hz) 7.35 (s, 1H)

Production Example 31c)

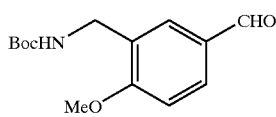

1.015 g of tertiary butyl N-(5-bromo-2-methoxybenzyl) carbamate, 45 mg of dichlorobis(triphenylphosphine) palladium (II), 330 mg of sodium formate and 17 mg of triphenyl phosphine were dissolved in anhydrous N,N-dimethylformamide and stirred at 110° C. for 2 hours in a carbon monoxide atmosphere. The reaction mixture was diluted with ethyl acetate, and successively washed with water and saturated aqueous sodium bicarbonate. The organic layer was dried over anhydrous magnesium sulfate and the solvent was evapoarated. The residue was purified by silica gel column chromatography, and from fractions eluted with hexane-ethyl acetate (3:1), 640 mg of tertiary butyl N-(5-formyl-2-methoxybenzyl)carbamate was obtained.

$^1$H-NMR(CDCl$_3$) δ: 1.45 (s, 9H) 3.94 (s. 3H) 4.36 (d, J=6.0 Hz, 2H) 5.00 (br, 1H) 6.98 (d, J=8.4 Hz, 1H) 7.80–7.83 (m, 2H) 9.88 (s, 1H)

Production Example 31d)

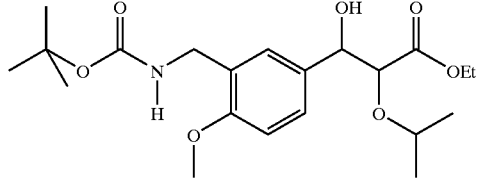

80 ml sodium hexamethyl disilazane (1 M solution in tetrahydrofuran) was diluted with 40 ml tetrahydrofuran in a nitrogen atmosphere and cooled at −78° C., and then a solution of 11.68 g ethyl 2-isopropoxyacetatein tetrahydrofuran (10 ml) was added. After stirring for 30 minutes, a solution of 10.73 g tert-butyl N-(5-formyl-2-methoxybenzyl)carbamate in tetrahydrofuran (10 ml) was added. After the mixture was further stirred for 1 hour, 100 ml saturated aqueous ammonium chloride solution was added. The reaction solution was poured into 400 ml water and 500 ml ethyl acetate, and the organic layer was dried over anhydrous magnesium sulfate. The solvent was evaporated, and the residue was purified by silica gel column chromatography (eluting solvent: hexane-ethyl acetate), to give 12.8 g of ethyl 3-(3-[(tert-butoxycarbonyl)amino]methyl-4-methoxyphenyl)-3-hydroxy-2-isopropoxypropanoate (erythro/threo mixture) as a colorless oil.

$^1$H-NMR(CDCl$_3$) δ:0.99(d,J=6.1 Hz,3H) 1.15(d,J=6.1 Hz,3H) 1.19(t,J=7.6 Hz,3H) 1.44(s,9H) 2.91(d,J=5.2 Hz,1H) 3.43(sept,J=6.1 Hz,1H) 3.83(s,3H) 4.03(d,J=6.3 Hz,1H) 4.12(q,J=7.6 Hz,2H) 4.29(d,J=6.6 Hz,2H) 4.86(dd, J=5.2,6.3 Hz,1H) 4.99(t,J=6.6 Hz,1H) 6.81(d,J=8.7 Hz,1H) 7.23–7.29(m,2H) δ:1.11(t,J=6.9 Hz,3H) 1.17(d,J=6.1, Hz,3H) 1.19(d,J=6.1 Hz,3H) 1.44(s,9H) 3.00(d,J=4.4 Hz,1H) 3.63(sept,J=6.1 Hz,1H) 3.83(s,3H) 3.95(d,J=5.9 Hz,1H) 4.08(q,J=6.9 Hz,2H) 4.29(d,J=6.6 Hz,2H) 4.80(dd, J=4.4,5.9 Hz,1H) 4.99(t,J=6.6 Hz,1H) 6.81(d,J=8.7 Hz,1H) 7.23–7.29(m,2H)

Production Example 31e)

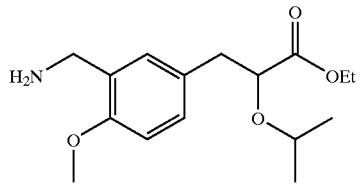

24.7 g of ethyl 3-(3-[(tert-butoxycarbonyl)amino]methyl-4-methoxyphenyl)-3-hydroxy-2-isopropoxypropanoate (erythro/threo mixture) was dissolved in 400 ml trifluoroacetic acid, and 96 ml triethylsilane was added, and the mixture was stirred for 38 hours. The solvent was evapoarated, and the residue was dissolved in 300 ml of 3 N hydrochloric acid and 200 ml hexane. The aqueous layer was washed with 100 ml hexane and basified with 5N sodium hydroxide and extracted 4 times with 200 ml dichloromethane. The organic layers were combined, dried over anhydrous magnesium sulfate and the solvent was evapoarated, to give 13.0 g of ethyl 3-[3-(aminoethyl)-4-methoxyphenyl]-2-isopropoxypropanoate identical in TLC and $^1$H-NMR to the compound obtained in Production Example 2c) as a pale yellow oil.

Example 31f)

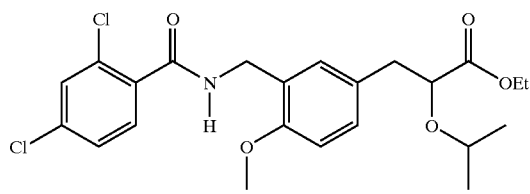

A solution of 15.9 g 2,4-dichlorobenzoyl chloride in tetrahydrofuran (15 ml) was added dropwise to a solution of 18.67 g ethyl 3-[3-(aminomethyl)-4-methoxyphenyl]-2-isopropoxypropanoate and 7.7 g triethylamine in diethyl ether (300 ml) under ice-cooling. After stirring under ice-cooling for 30 minutes and further at room temperature for 30 minutes, the reaction solution was poured into 500 ml water and extracted with 300 ml ethyl acetate. The organic layer was successively washed with 200 ml saturated aqueous sodium bisulfate, 200 ml saturated sodium hydrogencarbonate and 200 ml brine, dried over anhydrous magnesium sulfate and the solvent was evapoarated. The residue was purified by silica gel column chromatography (eluting solvent: hexane-ethyl acetate), to give 28.2 g of ethyl 3-(3-{[(2,4-dichlorobenzoyl)amino]methyl}-4-methoxyphenyl)-2-isopropoxypropanoate identical in TLC and $^1$H-NMR to the compound obtained in Example 31g) as a colorless solid.

Example 31g)

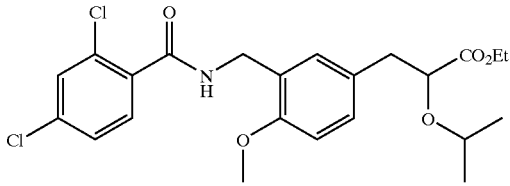

Ethyl 3-[3-(aminomethyl)-4-methoxyphenyl]-2-isopropoxypropanoate and 2,4-dichlorobenzoic acid were treated in the same manner as in Example 19d), to give ethyl 3-(3-{[(2,4-dichlorobenzoyl)amino]methyl}-4-methoxyphenyl)-2-isopropoxypropanoate.

$^1$H-NMR(CDCl$_3$) δ:0.95 (d, J=6.0 Hz, 3H) 1.14 (d, J=6.0 Hz, 3H) 1.23 (t, J=6.8 Hz, 3H) 2.87(dd,J=8.4, 13.6 Hz, 1H) 2.94 (dd, J=4.8, 13.6 Hz, 1H) 3.50 (sept, J=6.0 Hz, 1H) 3.84 (s, 3H) 4.01(dd, J=4.8, 8.4 Hz, 1H) 4.05–4.20 (m, 2H) 4.61 (d, J=5.6 Hz, 2H) 6.74–6.84(m,1H) 6.79(d,J=8.4 Hz,1H) 7.16(dd,J=2.0,8.4 Hz,1H) 7.22(d,J=2.0 Hz,1H) 7.29(dd,J=2.0,8.4 Hz,1H) 7.39(d,J=2.0 Hz,1H) 7.64(d,J=8.0 Hz,1H)

Example 31h)

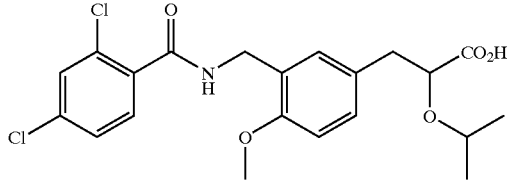

3-(3-{[(2,4-Dichlorobenzoyl)amino]methyl}-4-methoxyphenyl)-2-isopropoxypropanoic acid was obtained by the same treatment as in Example 1d).

$^1$H-NMR (CDCl$_3$) δ:1.02 (d, J=6.0 Hz, 3H) 1.16 (d, J=6.0 Hz, 3H) 2.91 (dd, J=7.2,14 Hz, 1H) 3.04 (dd, J=4.0, 14 Hz, 1H) 3.56 (sept, J=6.0 Hz, 1H) 3.84 (s, 3H) 4.09 (dd, J=4.4, 7.6 Hz, 1H) 4.60 (d, J=6.0 Hz, 2H) 6.81 (d,J=8.4 Hz, 1H) 6.83tm, 1H) 7.16 (dd, J=2.4, 8.4 Hz, 1H) 7.23 (d, J=2.0 Hz, 1H) 7.29 (dd, J=2.0, 8.4 Hz, 1H) 7.39 (d, J=2.0 Hz,1H) 7.64 (d, J=8.4 Hz, 1H)

Example 31i)

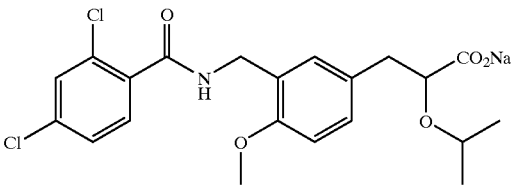

1.0 g of 3-(3-{[(2,4-dichlorobenzoyl)amino]methyl}-4-methoxyphenyl)-2-isopropoxypropanoic acid was dissolved in 5 ml ethanol, and 2.3 ml of 1 N aqueous sodium hydroxide solution was added thereto, and the solvent was removed, to give sodium 3-(3-{[(2,4-dichlorobenzoyl)amino]methyl}-4-methoxyphenyl)-2-isopropoxypropanoate was obtained.

$^1$H-NMR(DMSO-d$_6$) δ: 0.79 (d, J=6.0 Hz, 3H) 0.97 (d, J=6.0 Hz, 3H) 2.51 (dd, J=9.2, 13.6 Hz, 1H) 2.79 (dd, J=4.0, 13.6 Hz, 1H) 3.48 (sept, J=6.0 Hz, 1H) 3.63 (dd,J=3.6, 8.8 Hz, 1H) 3.75 (s,3H) 4.35 (d, J=6.0 Hz, 2H) 6.82 (d, J=8.4 Hz, 1H) 7.07 (d, J=7.6 Hz, 1H) 7.15 (s, 1H) 7.48 (s, 2H) 7.67 (s, 1H) 8.87 (t, J=6.0 Hz, 1H)

Example 32

Example 32a)

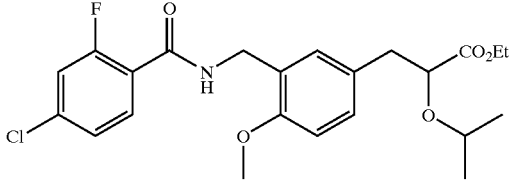

Ethyl 3-[3-(aminomethyl)-4-methoxyphenyl]-2-isopropoxypropanoate and 4-chloro-2-fluorobenzoic acid were treated in the same manner as in Example 19d), to give ethyl 3-(3-{[(4-chloro-2-fluorobenzoyl)amino]methyl}-4-methoxyphenyl)-2-isopropoxypropanoate.

$^1$H-NMR(CDCl$_3$) δ: 0.95 (d, J=6.0 Hz, 3H) 1.13 (d, J=6.0 Hz, 3H) 1.22 (t, J=7.2 Hz, 3H) 2.86 (dd, J=8.0, 14 Hz, 1H) 2.93 (dd, J=4.8, 14 Hz, 1H) 3.49 (sept, J=6.0 Hz, 1H) 3.86

(s, 3H) 4.00 (dd, J=5.2, 8.0 Hz, 1H) 4.05–4.25 (m, 2H) 4.62 (d, J=5.6 Hz, 2H) 6.80 (d, J=8.4 Hz, 1H) 7.10–7.20 (m, 2H) 7.20(d, J=2.0 Hz,1H) 7.23 (dd, J=2.0, 8.4 Hz, 1H) 7.2–7.35 (m, 1H) 8.06 (t, J=8.4 Hz, 1H)

Example 32b)

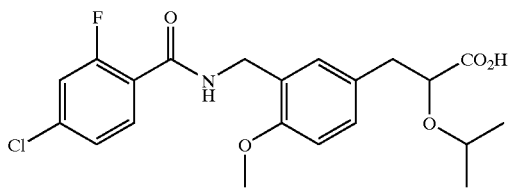

3-(3-{[(4-Chloro-2-fluorobenzoyl)amino]methyl}-4-methoxyphenyl)-2-isopropoxypropanoic acid was obtained in the same method as in Example 1d).

¹H-NMR(CDCl₃) δ: 1.01 (d, J=6.0 Hz, 3H) 1.15 (d, J=6.0 Hz, 3H) 2.90 (dd, J=7.6, 14 Hz, 1H) 3.04 (dd, J=4.0, 14 Hz, 1H) 3.55 (sept, J=6.0 Hz, 1H) 3.87 (s, 3H) 4.09 (dd, 7.6 Hz, 1H) 4.62 (d, J=5.6 Hz, 2H) 6.82 (d, J=8.0 Hz, 1H) 7.08–7.18 (m, 2H) 7.16–7.28 (m, 2H) 7.24–7.38 (m, 1H) 8.05 (t, J=8.4 Hz, 1H)

Example 32b)

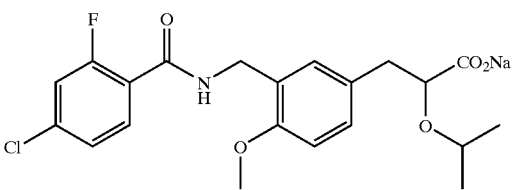

Sodium 3-(3-{[(4-chloro-2-fluorobenzoyl)amino]methyl}-4-methoxyphenyl)-2-isopropoxypropanoate was obtained in the same method as in Example 31c).

¹H-NMR(DMSO-d₆) δ: 0.77(d, J=6.4 Hz, 3H) 0.95(d, J=6.0 Hz, 3H) 2.53(dd, J=9.2, 14 Hz, 1H) 2.79(dd, J=3.2, 14 Hz, 1H) 3.46(sept, J=6.0 Hz, 1H) 3.64(dd, J=3.6, 9.2 Hz, 1H) 3.76(s, 3H) 4.38(t, J=5.2 Hz, 2H) 6.82(d, J=8.4 Hz, 1H) 7.07 (d, J=8.8 Hz, 1H) 7.10(s, 1H) 7.36(d, J=8.4 Hz, 1H) 7.53(d, J=10 Hz, 1H) 7.67(t, J=8 Hz, 1H) 8.76(m, 1H)

Example 33

Example 33a)

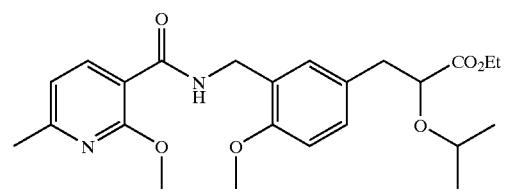

Ethyl 3-[3-(aminomethyl)-4-methoxyphenyl]-2-isopropoxy propanoate and 2-methoxy-6-methylnicotinic acid were treated in the same method as in Example 19d), to give ethyl 2-isopropoxy-3-[4-methoxy-3-({[(2-methoxy-6-methyl-3-pyridyl)carbonyl]amino}methyl)phenyl]propanoate.

¹H-NMR(CDCl₃) δ: 0.95 (d, J=6.0 Hz, 3H) 1.12 (d, J=6.0 Hz, 3H) 1.21 (t, J=7.2 Hz, 3H) 2.47 (s, 3H) 2.86 (dd, J=8.4,

14 Hz, 1H) 2.93 (dd, J=5.2, 14 Hz, 1H) 3.49 (sept, J=6.0 Hz, 1H) 3.89 (s, 3H) 4.00 (dd, J=4.8, 8.0 Hz, 1H) 4.04 (s, 3H) 4.1–4.2 (m, 2H) 4.62 (d, J=6.0 Hz, 2H) 6.80 (d, J=8.4 Hz, 1H) 6.86 (d, J=7.6 Hz, 1H) 7.14 (dd, J=2.0, 8.0 Hz, 1H) 7.20 (d, J=2.0 Hz, 1H) 8.39 (d, J=7.6 Hz, 1H) 8.42 (m, 1H)

Example 33b)

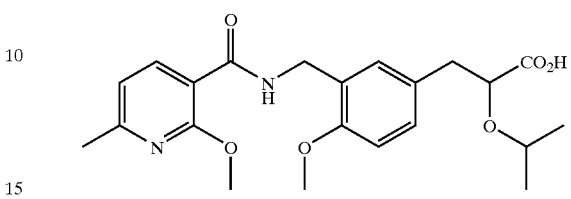

2-Isopropoxy-3-[4-methoxy-3-({[(2-methoxy-6-methyl-3-pyridyl)carbonyl]amino}methyl)phenyl]propanoic acid was obtained in the same method as in Example 1d).

¹H-NMR(CDCl₃) δ: 1.03 (d, J=6.0 Hz, 3H) 1.14 (d, J=6.4 Hz, 3H) 2.47 (s, 3H) 2.90 (dd, J=7.2, 14 Hz, 1H) 3.04 (dd, J=4.4, 14 Hz, 1H) 3.56 (sept, J=6.4 Hz, 1H) 3.89 (s, 3H) 4.06 (s, 3H) 4.0–4.15 (m, 1H) 4.61 (d, J=4.0 Hz, 2H) 6.81 (d, J=8.4 Hz, 1H) 6.86 (d, J=7.6 Hz, 1H) 7.12 (dd, J=2.0, 8.4 Hz, 1H) 7.20 (d, J=2.4 Hz, 1H) 8.37 (d, J=7.6 Hz, 1H) 8.48 (m, 1H)

Example 34

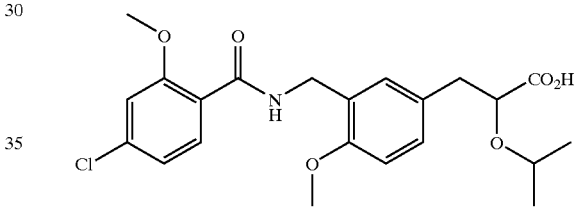

Ethyl 3-[3-(aminomethyl)-4-methoxyphenyl]-2-isopropoxypropanoate and 4-chloro-2-methoxybenzoic acid were treated in the same manners as in Example 20d) and then in Example 1d), to give 3-(3-{[(4-chloro-2-methoxybenzoyl)amino]methyl}-4-methoxyphenyl)-2-isopropoxypropanoic acid.

¹H-NMR(CDCl₃) δ: 1.02 (d, J=6.0 Hz, 3H) 1.14 (d, J=6.0 Hz, 3H) 2.90 (dd, J=7.6, 14 Hz, 1H) 3.03 (dd, J=4.4, 14 Hz, 1H) 3.56 (sept, J=6.0 Hz, 1H) 3.88 (s, 3H) 3.94 (s, 3H) 4.05–4.15 (m, 1H) 4.61 (dd, J=2.0, 6.0 Hz, 2H) 6.81 (d, J=8.4 Hz, 1H) 6.95 (d, J=2.0 Hz, 1H) 7.05 (dd, J=2.0, 8.4 Hz, 1H) 7.13 (dd, J=2.0, 8.4 Hz, 1H) 7.20 (d, J=2.0 Hz, 1H) 8.14 (d, J=8.4 Hz, 1H) 8.28 (t, J=5.6 Hz, 1H)

Example 35

Example 35d)

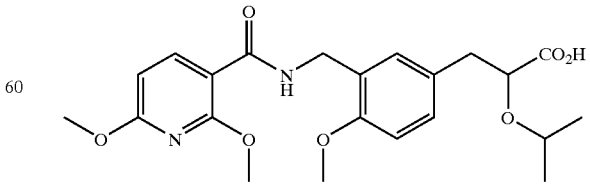

Ethyl 3-[3-(aminomethyl)-4-methoxyphenyl[-2-isopropoxy propanoate and 2,6-dimethoxynicotinic acid were treated in the same manners as in Example 20d) and then in Example 1d), to give 3-[3-({[(2,6-dimethoxy-3-pyridyl)carbonyl]amino}methyl)-4-methoxyphenyl]-2-isopropoxypropanoic acid.

$^1$H-NMR(CDCl$_3$) δ: 1.00 (d, J=6.4 Hz, 3H) 1.13 (d, J=6.4 Hz, 3H) 2.89 (dd, J=7.6, 14 Hz, 1H) 3.03 (dd, J=4.4, 14 Hz, 1H) 3.55 (sept, J=6.0 Hz, 1H) 3.88 (s, 3H) 3.95 (s, 3H) 4.07 (s, 3H) 3.8–4.2 (m, 1H) 4.60 (dd, J=1.6, 6.0 Hz, 2H) 6.41 (d, J=8.4 Hz, 1H) 6.80 (d, J=8.4 Hz, 1H) 7.13 (dd, J=2.0, 8.4 Hz, 1H) 7.21 (d, J=2.0 Hz, 1H) 8.32 (m, 1H) 8.41 (d, J=8.4 Hz, 1H)

Example 36

Example 36a)

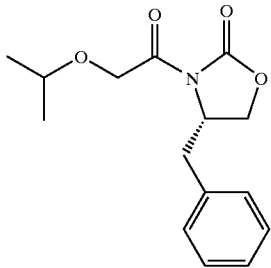

A solution of 98 g 2-isopropoxyacetic acid and 360 ml triethylamine in tetrahydrofuran (4 L) was cooled at –25° C., and 92 ml 2,2-dimethylpropanoyl chloride was added dropwise, and the reaction solution was stirred for 5 hours at –20° C. 50 g of anhydrous lithium chloride and 120 g of (4S)-4-benzyl-1,3-oxazolone-2-one were added sequentially, then the mixture was further stirred overnight at room temperature, the reaction solution was filtered and the filtrate was evaporated. The residue was dissolved in 2 L ethyl acetate, washed with saturated aqueous sodium hydrogencarbonate, dried over anhydrous magnesium sulfate and the solvent was evapoarated. The residue was purified by silica gel column chromatography (eluting solvent: hexane-ethyl acetate), to give 106.6 g of (4S)-4-benzyl-3-(2-isopropoxyacetyl)-1,3-oxazolone-2-one as a colorless oil.

$^1$H-NMR(CDCl$_3$) δ:1.17(d,J=6.0 Hz,6H) 2.81(dd,J=9.5, 13.4 Hz,1H) 3.35(dd,J=3.2,13.4 Hz,1H) 3.74(sept,J=6.0 Hz,1H)) 4.24(dd,J=3.5,9.3 Hz) 4.29(t,J=9.3 Hz,1H) 4.65(d, J=19.5 Hz,1H) 4.69(m,1H) 4.70(d,J=19.5 Hz,1H) 7.22(d,J= 7.2 Hz,2H) 7.30–7.45(m,3H)

Example 36b)

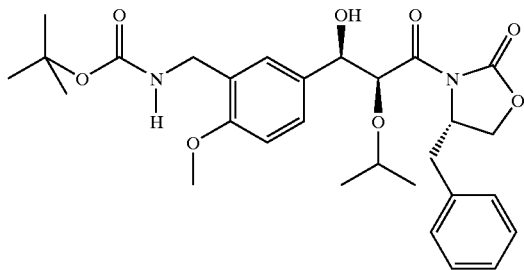

A solution of 127.4 g of (4S)-4-benzyl-3-(2-isopropoxyacetyl)-1,3-oxazolone-2-one in toluene (4 L) was divided into 2 portions of equal volume and cooled at –75° C. Then, 28.0 g of triethylamine was added to each solution. 232 ml dibutyl boron triflate (1 M solution in dichloromethane) was added dropwise at such a rate that the internal temperature did not exceed –70° C. After the dropwise addition, the mixture was stirred for 50 minutes and then the internal temperature was raised to 0° C., and the mixture was further stirred for 50 minutes and cooled again at –75° C. To the reaction solution was added via a cannula a solution of tert-butyl N-(5-formyl-2-methoxybenzyl) carbamate in dichloromethane (1.4 L) previously cooled at about –70° C., followed by stirring at –75° C. for 30 minutes. Then, the internal temperature was elevated at a rate of 10° C./10 minutes to 0° C. over about 1 hour. After stirring at 0° C. for 75 minutes, a mixture of 1.21 L methanol, 0.605 L buffer pH 7 (sodium dihydrogen phosphate-citric acid) and 0.262 L hydrogen peroxide (30% aqueous solution) was added. The two reaction solutions were combined, poured into 9 L water and extracted with 1 L dichloromethane. The organic layer was washed with 4 L brine, and then the aqueous layers were combined and extracted with 4 L ethyl acetate. All the organic layers were combined, dried over anhydrous magnesium sulfate and the solvent was evapoarated. The residue was purified by silica gel column chromatography (eluting solvent: hexane-ethyl acetate), to give 111.0 g of tert-butyl N-(5-(1R,2S)-3-[(4S)-4-benzyl-2-oxo-1,3-oxazolane-3-yl]-1-hydroxy-2-isopropoxy-3-oxopropyl-2-methoxybenzyl)carbamate as a colorless solid.

$^1$H-NMR(CDCl$_3$) δ:1.17(d,J=6.2 Hz,3H) 1.21(d,J=6.2 Hz,3H) 1.43(s,9H) 2.75(dd,J=9.6,13.2 Hz,1H) 3.02–3.15 (br.s,1H) 3.24(dd,J=3.6,13.2 Hz,1H) 3.64–3.73(m,2H) 3.83 (s,3H) 4.02(d,J=8.2 Hz,1H) 4.23(dd,J=6.2,15.6 Hz,1H) 4.31 (dd,J=6.4,15.6 Hz,1H) 4.46(m,1H) 4.78(d,J=5.6 Hz,1H) 4.99(m,1H) 5.42(d,J=5.6 Hz,1H) 6.83(d,J=8.3 Hz,1H) 7.19 (d,J=7.2 Hz,2H) 7.26–7.39(m,5H)

Production Example 36c)

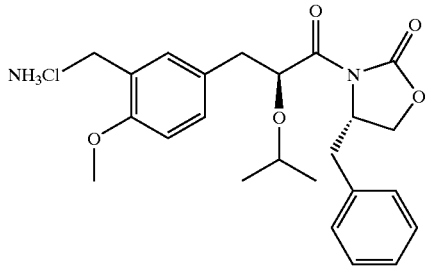

8.96 g of tert-butyl N-(5-(1R,2S)-3-[(4S)-4-benzyl-2-oxo-1,3-oxazolane-3-yl]-1-hydroxy-2-isopropoxy-3-oxopropyl-2-methoxybenzyl)carbamate was reduced in the same manner as in Production Example 31e). Then, to the crude product was added 50 ml of 4N hydrochloric acid-ethyl acetate solution. After evaporating the solvent, the residue was suspended in diisopropyl ether-hexane. The solid was collected by filtration and washed with the above solvent, to give 7.89 g of (4S)-3-(2S)-3-[3-(aminomethyl)-4-methoxyphenyl]-2-isopropoxypropanoyl-4-benzyl-1,3-oxazolane-2-one hydrochloride as a colorless solid.

$^1$H-NMR(CDCl$_3$) δ:1.00(d,J=6.3 Hz,3H) 1.14(d,J=6.3 Hz,3H) 2.77–2.85(m,2H) 2.94(dd,J=3.5,11.9 Hz,1H) 3.28 (dd,J=1.7,12.8 Hz,1H) 3.50(sept,J=6.3 Hz,1H) 3.82(s,3H) 4.10–4.19(m,4H) 4.64(m,1H) 5.28(dd,J=3.5,7.9 Hz,1H) 6.81(d,J=8.4 Hz,1H) 7.20(d,J=7.0 Hz,2H) 7.25–7.34(m,5H) 8.25(br.s,3H)

Example 36d)

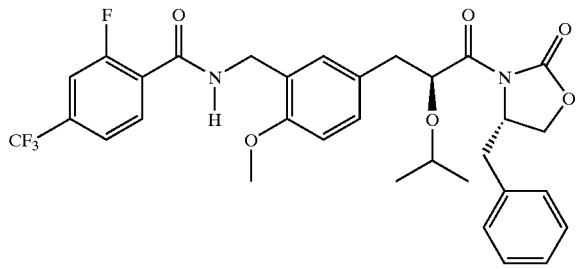

7.66 g of (4S)-3-(2S)-3-[3-(aminomethyl)-4-methoxyphenyl]-2-isopropoxypropanoyl-4-benzyl-1,3-oxazolane-2-one hydrochloride was amidated in the same manner as in Production Example 31f). Then, the crude product was dissolved in 20 ml ethyl acetate under refluxing, followed by cooling to room temperature. 60 ml diisopropyl ether and 120 ml hexane were successively added thereto, and the resulting precipitates were collected by filtration, to give 6.46 g of N1-(5-(2S)-3-[(4S)-4-benzyl-2-oxo-1,3-oxazolane-3-yl]-2-isopropoxy-3-oxopropyl-2-methoxybenzyl)-2-fluoro-4-(trifluoromethyl)benzaldehyde as a colorless solid.

$^1$H-NMR(CDCl$_3$) δ:1.04(d,J=6.2 Hz,3H) 1.16(d,J=6.2 Hz,3H) 2.75(dd,J=10.1,12.6 Hz,1H) 2.88(dd,J=7.9,13.9 Hz,1H) 2.93(dd,J=4.7,13.9 Hz,1H) 3.32(dd,J=3.5,12.6 Hz,1H) 3.52(sept,J=6.2 Hz,1H) 3.86(s,3H) 3.98(t,J=8.5 Hz,1H) 4.11(dd,J=2.6,8.5 Hz,1H) 4.56(m,1H) 4.65(d,J=5.9 Hz,2H) 5.34(dd,J=4.7,7.9 Hz,1H) 6.8(d,J=8.7 Hz,1H) 7.20–7.38(m,8H) 7.56(d,J=8.7 Hz,1H),8.34(t,J=8.7 Hz,1H)

Example 36e)

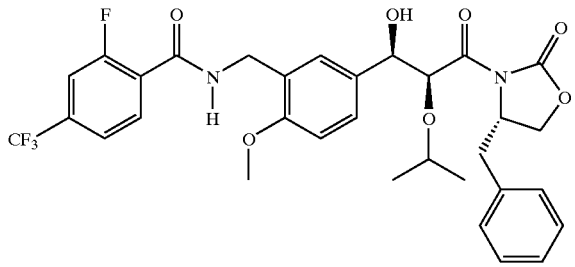

From 1.39 g of (4S)-4-benzyl-3-(2-isopropoxyacetyl)-1,3-oxazolone-2-one and 0.89 g of N1-(5-formyl-2-methoxybenzyl)-2-fluoro-4-(trifluoromethyl)benzamide, 1.36 g of N1-(5-(2S)-3-[(4S)-4-benzyl-2-oxo-1,3-oxazolane-3-yl]-1-hydroxy-2-isopropoxy-3-oxopropyl-2-methoxybenzyl)-2-fluoro-4-(trifluoromethyl)benzamide was obtained as a colorless solid in the same manner as in Production Example 36b).

$^1$H-NMR(CDCl$_3$) δ:1.15(d,J=6.0 Hz,3H) 1.20(d,J=3 Hz,3H) 2.67(dd,J=9.6,13.4 Hz,1H) 3.05–3.14(br.s,1H) 3.25 (dd,J=3.8,13.4 Hz,1H) 3.61(t,J=8.6 Hz,1H) 3.67(sept,J=6.0 Hz,1H) 3.86(s,3H) 3.93(dd,J=1.7,8.6 Hz,1H) 4.44(m,1H) 4.60(dd,J=5.2,14.1 Hz,1H) 4.66(dd,J=5.2,14.1 Hz) 4.79(d, J=5.8 Hz,1H) 5.42(d,J=5.8 Hz,1H) 6.88(d,J=8.7 Hz,1H) 7.19(d,J=7.1 Hz,2H) 7.27–7.33(m,4H) 7.36(dd,J=0.8,11.1 Hz,1H) 7.39(dd,J=2.0,8.0 Hz,1H) 7.44(d,J=7.7 Hz,1H) 8.03 (t,J=7.7 Hz,1H)

Example 36f)

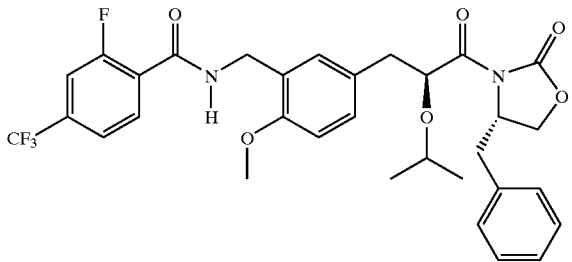

From 1.36 g of N1-(5-(2S)-3-[(4S)-4-benzyl-2-oxo-1,3-oxazolane-3-yl]-1-hydroxy-2-isopropoxy-3-oxopropyl-2-methoxybenzyl)-2-fluoro-4-(trifluoromethyl)benzamide, 1.30 g of N1-(5-(2S)-3-[(4S)-4-benzyl-2-oxo-1,3-oxazolane-3-yl]-2-isopropoxy-3-oxopropyl-2-methoxybenzyl)-2-fluoro-4-(trifluoromethyl)benzamide which was identical in TLC and $^1$H-NMR to the compound obtained in Production Example 36d) was obtained as a colorless solid in the same manner as in Example 31e).

Example 36g)

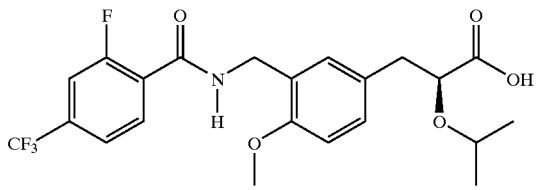

From 6.46 g of N1-(5-(2S)-3-[(4S)-4-benzyl-2-oxo-1,3-oxazolane-3-yl]-2-isopropoxy-3-oxopropyl-2-methoxybenzyl)-2-fluoro-4-(trifluoromethyl)benzamide, 4.81 g of (2S)-3-[3-([2-fluoro-4-(trifluoromethyl)benzoyl] aminomethyl)-4-methoxyphenyl]-2-isopropoxypropanoic acid which was identical in TLC and $^1$H-NMR to the compound obtained in Production Example 6a) was obtained as a colorless oil in the same manner as in Example 37c) Purity by HPLC analysis: 97.7%, optical purity: 96.8% e.e. (OD column; flow rate 0.5 ml/min; 2-propanol: hexane:trifluoroacetic acid=700:300:1).

Example 37

Production Example 37a)

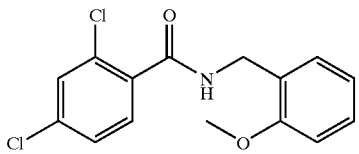

45 mL 2,4-dichlorobenzoyl chloride was added dropwise over 1.5 hours into a solution of 50 ml 2-methoxybenzylamine and 123 ml pyridine in N,N-dimethylformamide (400 mL) at 5 to 10° C., followed by stirring at room temperature for 16 hours. The reaction solution was diluted with ethyl acetate, saturated aqueous ammonium chloride solution and 1N aqueous sodium hydroxide solution. The organic layer was washed with 1N aqueous sodium hydroxide solution, 1 N hydrochloric acid (×2), saturated aqueous ammonium chloride solution (×2) and brine, dried over anhydrous sodium sulfate and concentrated. The residue was suspended in diisopropyl ether (300 mL) and diethyl ether (500 mL). The solid was collected by filtration and washed with diethyl ether, to give 81.1 g of N1-(2-methoxybenzyl)-2,4-dichlorobenzamide as a pale yellow solid.

$^1$H-NMR(CDCl$_3$) δ: 3.87 (s, 3H) 4.64 (d, J=6.0 Hz, 2H) 6.82 (br, 1H) 6.89 (d, J=8.4 Hz, 1H) 6.92–6.98 (m, 1H) 7.26–7.32 (m, 2H) 7.35 (dd, J=2.4, 7.6 Hz, 1H) 7.40 (d, J=2.4 Hz, 1H) 7.65 (d, J=8.4 Hz, 1H)

Production Example 37b)

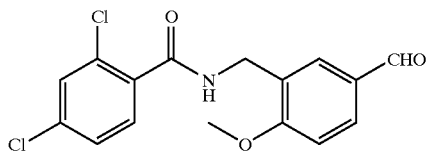

9.04 g of hexamethylene tetramine was added to a solution of 10.0 g N1-(2-methoxybenzyl)-2,4-dichlorobenzamide in trifluoroacetic acid (200 mL), followed by stirring at 50° C. for 23 hours. The reaction solution was left and cooled to room temperature and then concentrated. The residue was diluted with ice-water and adjusted to pH 11 to 12 with 1N aqueous sodium hydroxide solution. The solution was extracted with ethyl acetate. The organic layer was washed with 1 N aqueous sodium hydroxide solution (×3), 1 N hydrochloric acid (×2) and brine, dried over anhydrous sodium sulfate and filtered thorough 100 g silica gel. After concentrating the filtrate, the residue was suspended in ethyl acetate. The solid was collected by filtration and washed with ethyl acetate, to give 7.15 g of N1-(5-formyl-2-methoxybenzyl)-2,4-dichlorobenzamide as a colorless solid.

$^1$H-NMR(CDCl$_3$) δ: 3.97 (s, 3H) 4.68 (d, J=6.0 Hz, 2H) 6.81 (br, 1H) 7.01 (d, J=8.4 Hz, 1H) 7.31 (dd, J=2.0, 8.4 Hz, 1H) 7.41 (d, J=2.0 Hz, 1H) 7.68 (d, J=8.4 Hz, 1H) 7.85 (dd, J=2.0, 8.4 Hz, 1H) 7.90 (d, J=2.0 Hz, 1H) 9.88 (s, 1H)

Example 37c)

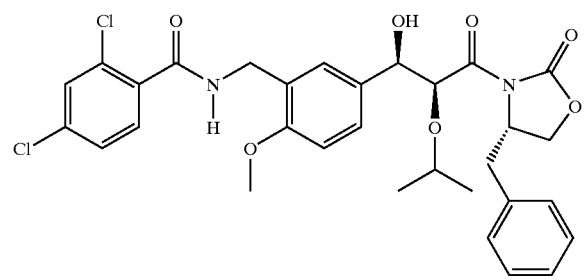

From 125.0 g of (4S)-4-benzyl-3-(2-isopropoxyacetyl)-1,3-oxazolone-2-one and 101.9 g of N1-(5-formyl-2-methoxybenzyl)-2,4-dichlorobenzamide, 167.0 g of N1-(5-(2S)-3-[(4S)-4-benzyl-2-oxo-1,3-oxazolane-3-yl]-1-hydroxy-2-isopropoxy-3-oxopropyl-2-methoxybenzyl)-2,4-dichlorobenzamide was obtained as a colorless solid in the same manner as in Example 36b).

$^1$H-NMR(CDCl$_3$) δ:1.15(d,J=6.2 Hz,3H) 1.20(d,J=6.2 Hz,3H) 2.71(dd,J=9.5,14.1 Hz,1H) 3.06–3.15(br.s,1H) 3.25 (dd,J=3.2,14.1 Hz,1H) 3.68(sept,J=6.2 Hz,1H) 3.69(dd,J= 7.8,8.5 Hz,1H) 3.84(s,3H) 3.97(dd,J=2.1,8.5 Hz,1H) 4.44 (m,1H) 4.58(dd,J=5.3,13.9 Hz,H) 4.63(dd,J=5.3,13.9 Hz,1H) 4.79(d,J=5.6 Hz,1H) 5.40(d,J=5.6 Hz,1H) 6.73(t,J= 5.3 Hz,1H) 6.85(d,J=8.2 Hz,1H) 7.16(d,J=7.0 Hz,2H) 7.25–7.34(m,5H) 7.37(dd,J=1.9,8.2 Hz,1H) 7.40(d,J=1.9 Hz,1H) 7.58(d,J=8.2 Hz,1H)

Production Example 37d)

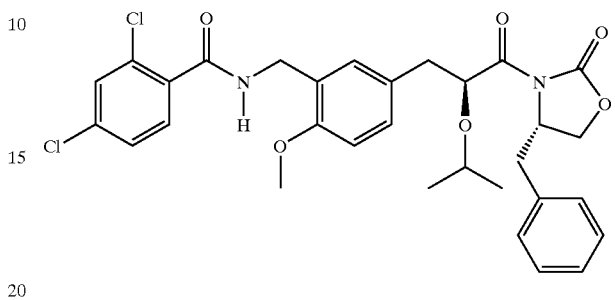

From 167 g of N1-(5-(2S)-3-[(4S)-4-benzyl-2-oxo-1,3-oxazolane-3-yl]-1-hydroxy-2-isopropoxy-3-oxopropyl-2-methoxybenzyl)-2,4-dichlorobenzamide, a crude product was obtained in the same manner as in Production Example 31e). This product was dissolved in 550 ml ethyl acetate under reflux and cooled to room temperature, and 550 ml diisopropyl ether and 800 ml hexane were successively added thereto. The precipitates were collected by filtration, to give 119.7 g of N1-(5-(2S)-3-[(4S)-4-benzyl-2-oxo-1,3-oxazolane-3-yl]-2-isopropoxy-3-oxopropyl-2-methoxybenzyl)-2,4-dichlorobenzamide as a colorless solid.

$^1$H-NMR(CDCl$_3$) δ:1.04(d,J=6.2 Hz,3H) 1.17(d,J=6.2 Hz,1H) 2.96(dd,J=9.1,13.3 Hz,1H) 2.89(dd,J=7.8,13.2 Hz,1H) 2.94(dd,J=5.3,13.2 Hz,1H) 3.30(dd,J=3.1,13.3 Hz,1H) 3.53(sept,J=6.2 Hz,1H) 3.84(s,3H) 4.02(t,J=8.4 Hz,1H) 4.11(dd,J=1.6,8.4 Hz,1H) 4.57(m,1H) 4.59(dd,J= 6.2,14.3 Hz,1H) 4.63(dd,J=6.2,14.3 Hz,1H) 5.34(dd,J=5.3, 7.8 Hz,1H) 6.75(t,J=6.2 Hz,1H) 6.80(d,J=8.2 Hz,1H) 7.19 (d,J=8.3 Hz,2H) 7.22–7.33(m,6H) 7.40(d,J=2.8 Hz,1H) 7.63 (d,J=10.3 Hz,1H)

Production Example 37e)

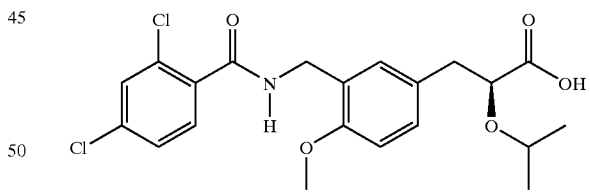

400 ml water was added to a solution of 124.9 g N1-(5-(2S)-3-[(4S)-4-benzyl-2-oxo-1,3-oxazolane-3-yl]-2-isopropoxy-3-oxopropyl-2-methoxybenzyl)-2,4-dichlorobenzamide in tetrahydrofuran (1.6 L), and the mixture was cooled to −10° C. Then, 184 ml of 30% hydrogen peroxide and a solution of 20.3 g lithium hydroxide in water (150 ml) were successively added thereto, followed by stirring at 4° C. for 24 hours. After the solution was cooled again to −10° C., 1.5 L of 2 M aqueous sodium sulfite was added thereto, adjusted to pH 2 to 3 with 5N hydrochloric acid and extracted with 1.5 L ethyl acetate. The organic layer was dried over anhydrous magnesium sulfate and the solvent was evaporated. The residue was dissolved in 1 N sodium hydroxide, and the aqueous layer was extracted 4 times with a mixed solvent of diethyl ether-dichloromethane (4:1). The organic layers were combined, and the solvent was evapoarated. The residue was recrystallized from ethyl acetate-hexane, and 33.7 g of (4S)-4-benzyl-3-(2-isopropoxyacetyl)-1,3-oxazolone-2-one was recovered. The aqueous layer was adjusted to pH 2 to 3 with 5N hydrochloric acid and extracted with 1.5 L and 0.5 L dichloromethane. The organic layers were combined, dried over anhydrous magnesium sulfate and the solvent was evaporated, to give 87.7 g of (2S)-3-[3-([2,4-dichlorobenzoyl]aminomethyl)-4-methoxyphenyl]-2-isopropoxypropanoic acid which was identical in TLC and $^1$H-NMR to the compound obtained in Production Example 31b). Purity by HPLC analysis: 98.6% (OD column; flow rate 0.5 ml/min; 2-propanol:hexane:trifluoroacetic acid= 700:300:1). The compound was purified by silica gel column chromatography (eluting solvent hexane-ethyl acetate) and then recrystallized from 410 ml ethyl acetate and 410 ml heptane, to give 61.6 g colorless solid (purity by HPLC analysis: 99.8%, optical purity: 99.7% e.e.).

Example 38

Production Example 38a)

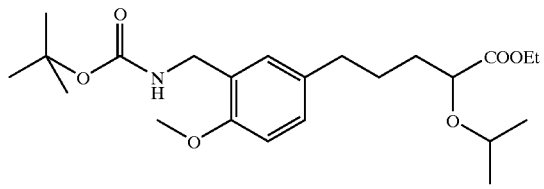

A suspension of 2.75 g tert-butyl N-(5-formyl-2-methoxybenzyl)carbamate and 4.73 g (triphenylphosphoranilidene)acetaldehyde in toluene (50 mL) was stirred at 80° C. for 16 hours. The reaction solution was left and cooled to room temperature, and the insoluble matters were filtered off through silica gel, and the filtrate was concentrated. Using 2.47 g of the resulting residue, 630 mg of ethyl 5-(3-{[(tert-butoxycarbonyl)amino]methyl}-4-methoxyphenyl)-2-isopropoxypentanoate was obtained as a colorless oil in the same manners as in Production Example 1a) and Production Example 1b).

$^1$H-NMR(CDCl$_3$) δ: 1.13 (d, J=6.0 Hz, 3H) 1.19 (d, J=6.0 Hz, 3H) 1.27 (t, J=7.2 Hz, 3H) 1.44 (s, 9H) 1.50–1.80 (m, 4H) 2.55 (t, J=7.2 Hz, 2H) 3.57 (sept, J=6.0 Hz, 1H) 3.81 (s, 3H) 3.88 (dd, J=4.8, 7.6 Hz, 1H) 4.19 (q, J=7.2 Hz, 2H) 4.27 (d, J=5.6 Hz, 2H) 5.01 (br, 1H) 6.76 (d, J=8.0 Hz, 1H) 7.00–7.08 (m, 2H)

Example 38b)

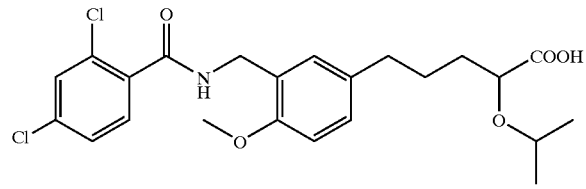

2 ml of 4N HCl/dioxane was added to 50 mg of ethyl 5-(3-{[(tert-butoxycarbonyl)amino]methyl}-4-methoxyphenyl)-2-isopropoxypentanoate, followed by stirring at room temperature for 3.5 hours. After the reaction solution was concentrated, the residue was dissolved in 2 mL N,N-dimethylformamide, and to 1 ml thereof were added 12 mg of 2,4-dichlorobenzoic acid, 9 μL diethyl cyanophosphonate and 17 μL triethylamine, followed by stirring at room temperature for 17 hours. The reaction solution was diluted with water and extracted with ethyl acetate. The organic layer was concentrated, and then the residue was dissolved in 0.4 mL methanol. 0.1 mL of 5N aqueous sodium hydroxide solution was added, and the mixture was stirred at room temperature for 1 hour. The reaction solution was concentrated and neutralized with 1 N hydrochloric acid. After extracting with ethyl acetate, the extract was purified by HPLC on a reverse phase column with a water-acetonitrile-trifluoroacetic acid system as an eluting solvent, to give 5.02 mg of 5-(3-{[(2,4-dichlorobenzoyl)amino]methyl}-4-methoxyphenyl)-2-isopropoxypentanoic acid.

MS m/e (ESI) 468 (MH$^+$)

Example 39

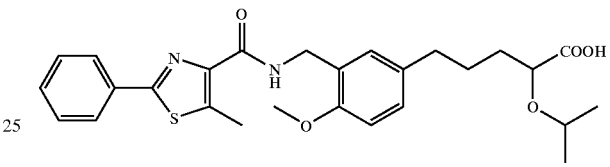

2-Isopropoxy-5-[4-methoxy-3-({[(5-methyl-2-phenyl-1,3-thiazole-4-yl)carbonyl]amino}methyl)phenyl]pentanoic acid was obtained in the same method as in Example 38 from ethyl 5-(3-{[(tert-butoxycarbonyl)amino]methyl}-4-methoxyphenyl)-2-isopropoxypentanoate.

MS m/e (ESI) 497 (MH$^+$)

Example 40

Production Example 40a)

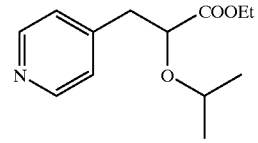

Using 4.0 g of 4-pyridine carboxyaldehyde, 4.88 g of ethyl 2-isopropoxy-3-(4-pyridyl)propanoate was obtained as a colorless oil in the same methods as in Production Example 1a) and Production Example 1b).

$^1$H-NMR(CDCl$_1$) δ: 0.93 (d, J=6.0 Hz, 3H) 1.15 (d, J=6.0 Hz, 3H) 1.26 (t, J=7.2 Hz, 3H) 2.92 (dd, J=8.8, 13.6 Hz, 1H) 3.00 (dd, J=4.4, 13.6 Hz, 1H) 3.52 (sept, J=6.0 Hz, 1H) 4.06 (dd, J=4.4, 8.8 Hz, 1H) 4.15–4.24 (m, 2H) 7.19 (dd, J=1.6, 4.4 Hz, 2H) 8.51 (dd, J=1.6, 4.4 Hz, 2H)

Production Example 40b)

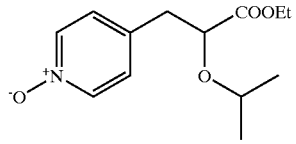

6.0 g of m-chloroperbenzoic acid was added to a solution of 4.88 g ethyl 2-isopropoxy-3-(4-pyridyl)propanoate in dichloromethane (50 mL), followed by stirring at room temperature for 1.5 hours. After the reaction solution was diluted with saturated aqueous sodium hydrogencarbonate solution, the aqueous layer was extracted with dichloromethane for 3 times. The combined organic layer was dried over anhydrous sodium sulfate and then concentrated, to give 6.40 g crude 4-(3-ethoxy-2-isopropoxy-3-oxopropyl)-1-pyridinium oleate as a yellow oil.

$^1$H-NMR(CDCl$_3$) δ: 0.96 (d, J=6.0 Hz, 3H) 1.16 (d, J=6.0 Hz, 3H) 1.27 (t, J=7.2 Hz, 3H) 2.93 (dd, J=8.8, 14.0 Hz, 1H) 3.00 (dd, J=4.0, 14.0 Hz, 1H) 3.55 (sept, J=6.0 Hz, 1H) 4.03 (dd, J=4.0, 8.8 Hz, 1H) 4.16–4.25 (m, 2H) 7.20–7.25 (m, 2H) 8.16–8.21 (m, 2H)

Production Example 40c)

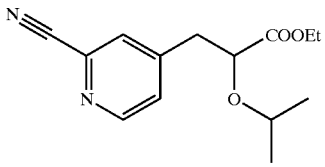

2.3 mL dimethyl carbamyl chloride was added dropwise over 40 minutes into a solution of 6.40 g crude 4-(3-ethoxy-2-isopropoxy-3-oxopropyl)-1-pyridinium oleate and 3.3 mL trimethylsilyl cyanide in dichloromethane (60 mL), followed by stirring for 11.5 hours. 10% aqueous potassium carbonate was added to the reaction solution, followed by stirring at room temperature for 30 minutes. The organic layer was dried over anhydrous sodium sulfate and concentrated. The residue was purified by silica gel flash column chromatography, to give 3.87 g of ethyl 3-(2-cyano-4-pyridyl)-2-isopropoxypropanoate as a pale yellow oil.

$^1$H-NMR(CDCl$_3$) δ: 0.94 (d, J=6.0 Hz, 3H) 1.17 (d, J=6.0 Hz, 3H) 1.28 (t, J=7.2 Hz, 3H) 2.99 (dd, J=8.8, 14.0 Hz, 1H) 3.06 (dd, J=4.0, 14.0 Hz, 1H) 3.56 (sept, J=6.0 Hz, 1H) 4.06 (dd, J=4.0, 8.8 Hz, 1H) 4.17–4.26 (m, 2H) 7.43 (dd, J=1.6, 5.0 Hz, 1H) 7.63 (dd, J=0.8, 1.6 Hz, 1H) 8.61 (dd, J=0.8, 5.0 Hz, 2H)

Production Example 40d)

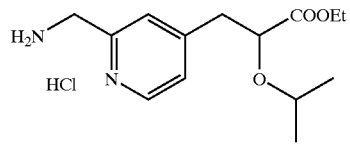

1.0 g of ethyl 3-(2-cyano-4-pyridyl)-2-isopropoxypropanoate was dissolved in 70 mL ethanol, and 1.9 mL conc. hydrochloric acid and 0.9 g of 10% palladium-carbon were added thereto, and the mixture was stirred at room temperature for 2 hours in a hydrogen atmosphere. After the catalyst was filtered off and the solvent was evaporated, the reaction product was subjected to azeotropic distillation with ethyl acetate and toluene, to give 1.21 g of ethyl 3-[2-(aminomethyl)-4-pyridyl]-2-isopropoxypropanoate hydrochloride was obtained as a crude product.

$^1$H-NMR(DMSO-d$_6$) δ: 0.90 (d, J=6.0 Hz, 3H) 1.07 (d, J=6.0 Hz, 3H) 1.19 (t, J=7.2 Hz, 3H) 2.96 (dd, J=8.8, 14.0 Hz, 1H) 3.08 (dd, J=4.4, 8.8 Hz, 1H) 3.55 (sept, J=6.0 Hz, 1H) 4.13 (q, J=7.2 Hz, 2H) 4.25 (br, 2H) 4.31 (dd, J=4.4, 8.8 Hz, 1H) 7.52 (d, J=5.2 Hz, 1H) 7.97 (s, 1H) 8.63 (d, J=5.2 Hz, 1H) 8.66–8.83 (m, 3H)

Example 40e)

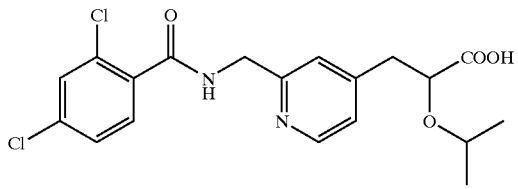

CF3COOH 3-(2-{[(2,4-Dichlorobenzoyl)amino]methyl}-4-pyridyl)-2-isopropoxypropanoate trifluoroacetate was obtained from ethyl 3-[2-(aminomethyl)-4-pyridyl]-2-isopropoxypropanoate hydrochloride in the same manners as in Example 19d) and Example 19e).

$^1$H-NMR(CDCl3) δ: 1.07 (d, J=6.0 Hz, 3H) 1.17 (d, J=6.0 Hz, 3H) 3.27 (d, J=5.6 Hz, 2H) 3.69 (sept, J=6.0 Hz, 1H) 4.30 (t, J=5.6 Hz, 1H) 4.80–4.91 (m, 2H) 7.27 (dd, J=72.0, 7.8 Hz, 1H) 7.39(d, J=2.0 Hz, 1H) 7.48(d, J=7.8 Hz, 1H) 7.68(dd, J=1.6, 6.0 Hz, 1H) 7.93 (d, J=1.6 Hz, 1H) 8.56 (d, J=6.0 Hz, 1H) 8.60 (t, J=6.0 Hz, 1H)

MS m/e (ESI) 440 (MH$^+$)

Example 41

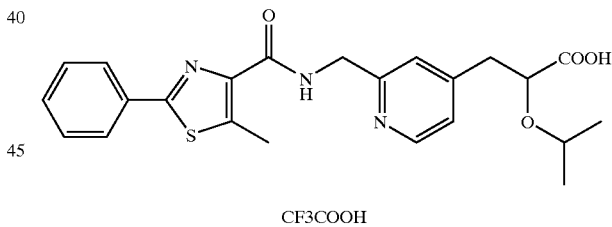

CF3COOH

2-Iopropoxy-3-[2-({[(5-methyl-2-phenyl-1,3-thiazol-4-yl)carbonyl]amino}methyl)-4-pyridyl]propanoic acid trifluoroacetate was obtained from ethyl 3-[2-(aminomethyl)-4-pyridyl]-2-isopropoxypropanoate hydrochloride in the same methods as in Example 19d) and Example 19e).

$^1$H-NMR(CDCl$_3$) δ: 1.07 (d, J=6.0 Hz, 3H) 1.19 (d, J=6.0 Hz, 3H) 2.72 (s, 3H) 3.28 (d, J=6.0 Hz, 2H) 3.71 (sept, J=6.0 Hz, 1H) 4.31 (t, J=5.6 Hz, 1H) 4.84 (dd, J=2.8,5.6 Hz, 2H) 7.41–7.49 (m, 3H) 7.68 (dd, J=2.0, 6.0 Hz, 1H) 7.88–7.93 (m, 2H) 7.94(d, J=1.2 Hz, 1H) 8.57(d, J=6.0 Hz, 1H) 8.74 (t, J=6.0 Hz, 1H)

MS m/e (ESI) 411 (MH$^+$)

Example 42

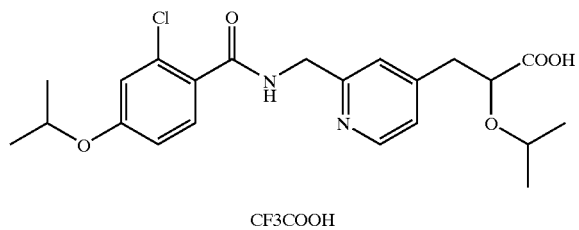

CF3COOH 3-(2-{[(2-Chloro-4-isopropoxybenzoyl)amino]methyl}-4-pyridyl)-2-isopropoxypropanoate trifluoroacetate was obtained from ethyl 3-[2-(aminomethyl)-4-pyridyl]-2-isopropoxypropanoate hydrochloride in the same method as in Example 19d) and Example 19e).

MS m/e (ESI) 435 (MH$^+$)

Example 43

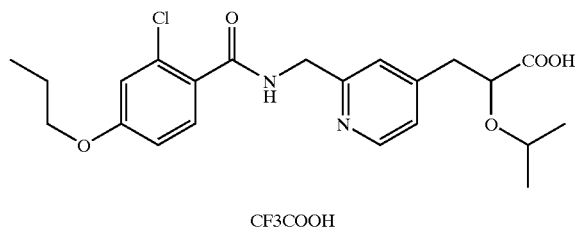

CF3COOH 3-(2-{[(2-chloro-4-propoxybenzoyl)amino]methyl}-4-pyridyl)-2-isopropoxypropanoate trifluoroacetate was obtained from ethyl 3-[2-(aminomethyl)-4-pyridyl]-2-isopropoxypropanoate hydrochloride in the same method as in Example 19d) and Example 19e).

MS m/e (ESI) 435 (MH$^+$)

Example 44

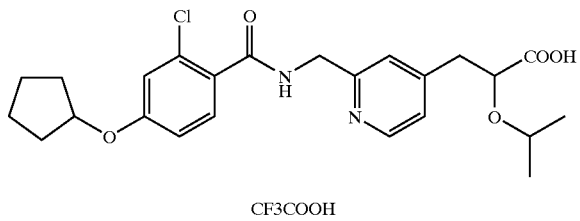

CF3COOH

3-[2-({[2-Chloro-4-(cyclopentyloxy)benzoyl]amino}methyl)-4-pyridyl]-2-isopropoxypropanoate trifluoroacetate was obtained from ethyl 3-[2-(aminomethyl)-4-pyridyl]-2-isopropoxypropanoate hydrochloride in the same method as in Example 19d) and Example 19e). MS m/e (ESI) 461 (MH$^+$)

Example 45

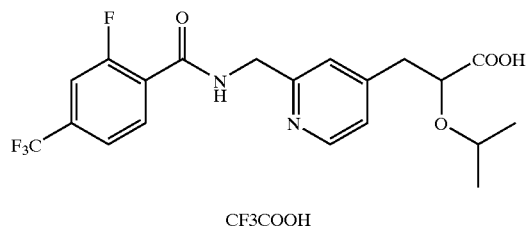

CF3COOH

Ethyl 3-[2-({[2-Fluoro-4-(trifluoromethyl)benzoyl]amino}methyl)-4-pyridyl]-2-isopropoxypropanoate trifluoroacetate was obtained from ethyl 3-[2-(aminomethyl)-4-pyridyl]-2-isopropoxypropanoate hydrochloride in the same method as in Example 19d) and Example 19e)

MS m/e (ESI) 429 (MH$^+$)

Example 46

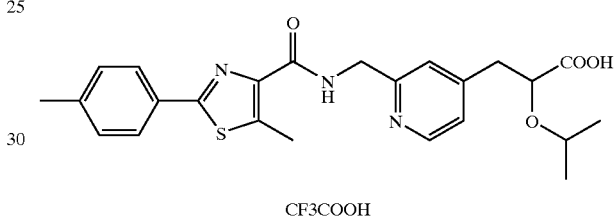

CF3COOH

2-Isopropoxy-3-{2-[({[5-methyl-2-(4-methylphenyl)-1,3-thiazole-4-yl]carbonyl}amino)methyl]-4-pyridyl}propanoic acid trifluoroacetate was obtained from ethyl 3-[2-(aminomethyl)-4-pyridyl]-2-isopropoxypropanoate hydrochloride in the same methods as in Example 19d) and Example 19e).

MS m/e (ESI) 454 (MH$^+$)

Example 47

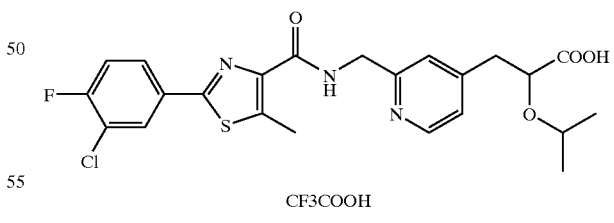

CF3COOH

3-{2-[({[2-(3-Chloro-4-fluorophenyl)-5-methyl-1,3-thiazole-4-yl]carbonyl}amino)methyl]-4-pyridyl}-2-isopropoxypropanoate trifluoroacetate was obtained from ethyl 3-[2-(aminomethyl)-4-pyridyl]-2-isopropoxypropanoate hydrochloride in the same methods as in Example 19d) and Example 19e).

MS m/e (ESI) 492 (MH$^+$)

Example 48

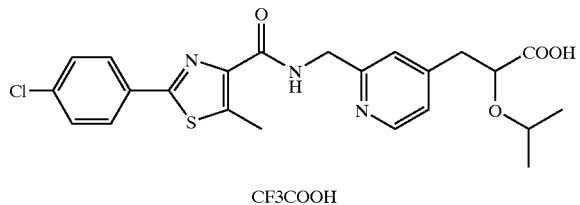

CF3COOH

3-{2-[({[2-(4-Chlorophenyl)-5-methyl-1,3-thiazol-4-yl]carbonyl}amino)methyl]-4-pyridyl}-2-isopropoxypropanoic acid trifluoroacetate was obtained from ethyl 3-[2-(aminomethyl)-4-pyridyl]-2-isopropoxypropanoate hydrochloride in the same methods as in Example 19d) and Example 19e).

MS m/e (ESI) 474 (MH$^+$)

Example 49

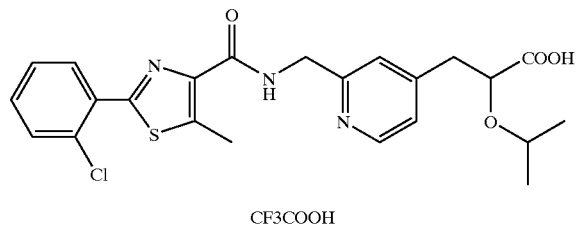

CF3COOH

3-{2-[({[2-(2-Chlorophenyl)-5-methyl-1,3-thiazole-4-yl]carbonyl}amino)methyl]-4-pyridyl}-2-isopropoxypropanoic acid trifluoroacetate was obtained from ethyl 3-[2-(aminomethyl)-4-pyridyl]-2-isopropoxypropanoate hydrochloride in the same methods as in Example 19d) and Example 19e).

MS m/e (ESI) 474 (MH$^+$)

Example 50

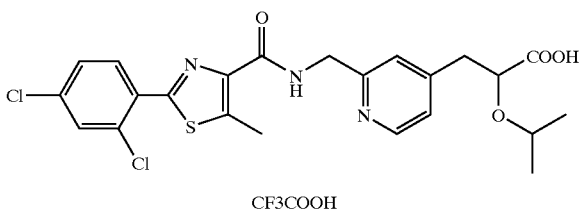

CF3COOH

3-{2-[({[2-(2,4-Dichlorophenyl)-5-methyl-1,3-thiazole-4-yl]carbonyl}amino)methyl]-4-pyridyl}-2-isopropoxypropanoic acid trifluoroacetate was obtained from ethyl 3-[2-(aminomethyl)-4-pyridyl]-2-isopropoxypropanoate hydrochloride in the same methods as in Example 19d) and Example 19e).

MS m/e (ESI) 508 (MH$^+$)

Example 51

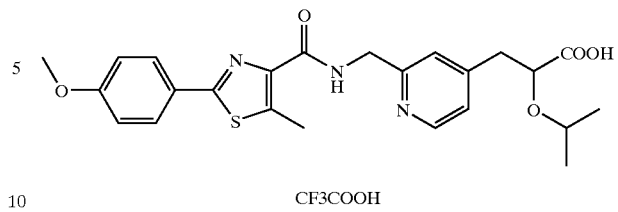

CF3COOH

2-Isopropoxy-3-{2-[({[2-(4-methoxyphenyl)-5-methyl-1,3-thiazole-4-yl]carbonyl}amino)methyl]-4-pyridyl}propanoate trifluoroacetate was obtained from ethyl 3-[2-(aminomethyl)-4-pyridyl]-2-isopropoxypropanoate hydrochloride in the same methods as in Example 19d) and Example 19e).

MS m/e (ESI) 470 (MH$^+$)

Example 52

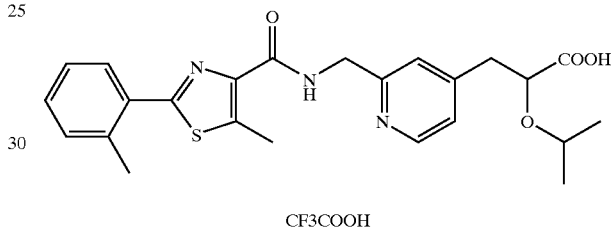

CF3COOH

2-Isopropoxy-3-{2-[({[5-methyl-2-(2-methoxyphenyl)-1,3-thiazole-4-yl]carbonyl}amino)methyl]-4-pyridyl}propanoic acid trifluoroacetate was obtained from ethyl 3-[2-(aminomethyl)-4-pyridyl]-2-isopropoxypropanoate hydrochloride in the same methods as in Example 19d) and Example 19e).

MS m/e (ESI) 454 (MH$^+$)

Example 53

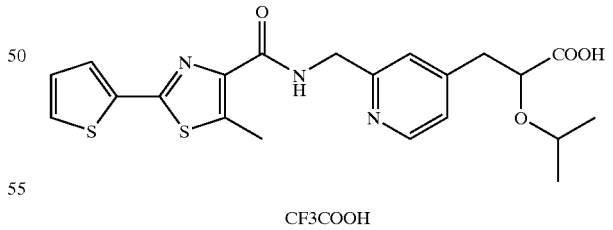

CF3COOH

2-Isopropoxy-3-{2-[({[5-methyl-2-(2-thienyl)-1,3-thiazole-4-yl]carbonyl}amino)methyl]-4-pyridyl}propanoate trifluoroacetate was obtained from ethyl 3-[2-(aminomethyl)-4-pyridyl]-2-isopropoxypropanoate hydrochloride in the same methods as in Example 19d) and Example 19e).

MS m/e (ESI) 446 (MH$^+$)

Example 54

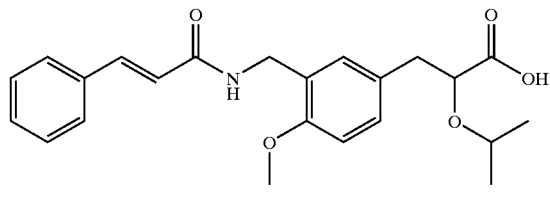

Using cinnamic acid, 2-isopropoxy-3-[4-methoxy-3-([(E)-3-phenyl-2-propenoyl]aminomethyl)phenyl]propionic acid was obtained in the same methods as in Example 19d) and Example 19e).

MS m/e (ESI) 398 (MH$^+$)

Example 55

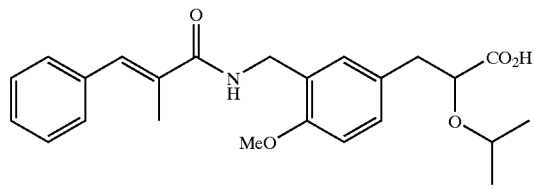

2-Isopropoxy-3-[4-methoxy-3-([(E)-2-methyl-3-phenyl-2-propenoyl]aminomethyl)phenyl]propionic acid was obtained in the same method as in Example 54.

$^1$H-NMR(CDCl$_3$) δ: 1.07 (d, J=6.0 Hz, 3H) 1.17 (d, J=6.0 Hz, 3H) 2.09 (d, J=1.2 Hz, 3H) 2.92 (dd, J=7.2, 13.6 Hz, 1H) 3.07 (dd, J=4.4, 14.0 Hz, 1H) 3.60 (sept, J=6.0 Hz, 1H) 3.87 (s, 3H) 4.12 (dd, J=4.4, 7.2 Hz, 1H) 4.54 (d, J=5.6 Hz, 2H) 6.46 (br, 1H) 6.82 (d, J=8.4 Hz, 1H) 7.15 (dd, J=2.0, 8.4 Hz, 1H) 7.22 (d, J=2.4 Hz, 1H) 7.26–7.39 (m, 6H)

MS m/e(ESI) 412 (MH$^+$)

Example 56

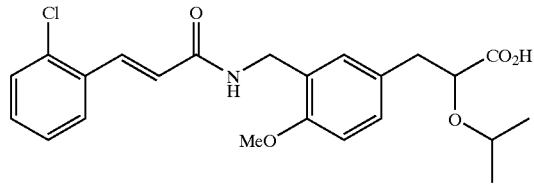

2-Isopropoxy-3-[4-methoxy-3-([(E)-3-(2-chlorophenyl-2-propenoyl]aminomethyl)phenyl]propionic acid was obtained in the same method as in Example 54.

$^1$H-NMR(CDCl$_3$) δ: 1.07 (d, J=6.0 Hz, 3H) 1.17 (d, J=6.0 Hz, 3H) 2.92 (dd, J=7.2, 13.6 Hz, 1H) 3.05 (dd, J=4.4, 14.0 Hz, 1H) 3.57 (sept, J=6.0 Hz, 1H) 3.86 (s, 3H) 4.11 (t, J=4.4 Hz, 1H) 4.54 (d, J=5.6 Hz, 2H) 6.22 (br, 1H) 6.40 (d, J=16.0 Hz, 1H) 6.81 (d, J=8.4 Hz, 1H) 7.14 (d, J=8.0 Hz, 1H) 7.21–7.27 (m, 2H) 7.40 (d, J=2.0, 7.6 Hz, 1H) 7.56 (d, J=7.6 Hz, 1H) 7.97 (d, J=16.0 Hz, 1H)

MS m/e(ESI) 432 (MH$^+$)

Example 57

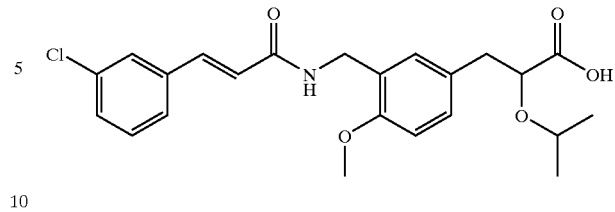

2-Isopropoxy-3-[4-methoxy-3-([(E)-3-(3-chlorophenyl-2-propenoyl]aminomethyl)phenyl]propionic acid was obtained in the same method as in Example 54.

MS m/e(ESI) 432 (MH$^+$)

Example 58

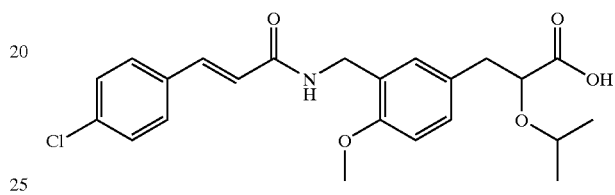

2-Isopropoxy-3-[4-methoxy-3-([(E)-3-(4-chlorophenyl-2-propenoyl]aminomethyl)phenyl]propionic acid was obtained in the same method as in Example 54.

MS m/e(ESI) 432 (MH$^+$)

Example 59

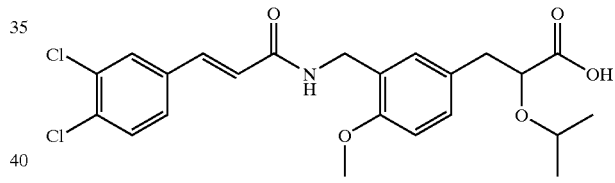

2-Isopropoxy-3-[4-methoxy-3-([(E)-3-(3,4-dichlorophenyl-2-propenoyl]aminomethyl)phenyl] propionic acid was obtained in the same method as in Example 54.

MS m/e(ESI) 466 (MH$^+$)

Example 60

Production Example 60a)

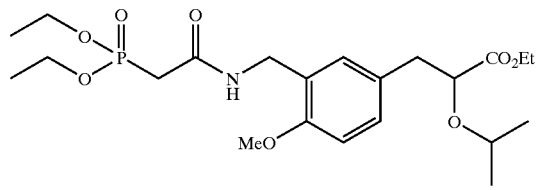

600 mg diethylphosphonoacetic acid and 969 mg of ethyl 3-[3-(aminomethyl)-4-methoxyphenyl]-2-isopropoxypropionate were dissolved in 10 ml N,N-dimethylformamide, followed by the successive addition of 470 μl diethyl cyanophosphonate and 1.07 ml triethylamine. The mixture was stirred overnight at room temperature, and the reaction mixture was diluted with ethyl acetate. The organic layer was washed with water and brine, dried over anhydrous magnesium sulfate and the solvent was evaporated. Thus, 1.387 g of ethyl 3-[3-([2-(diethoxyphosphoryl)acetyl]aminomethyl)-4-methoxyphenyl]-2-isopropoxypropionate was obtained.

$^1$H-NMR(CDCl$_3$) δ:0.97(d, J=6.0 Hz, 3H) 1.15 (d, J=6.0 Hz, 3H) 1.23–1.30 (m, 9H) 2.84 (d, J=20.4 Hz, 2H) 2.85–2.94 (m, 2H) 3.48 (sept, J=6.0 Hz, 1H) 3.84 (s, 3H) 4.00 (dd, J=4.8, 8.4 Hz, 1H) 4.03–4.21 (m, 6H) 4.43 (d, J=6.0 Hz, 2H) 6.77 (d, J=8.0 Hz, 1H) 7.12–7.15 (m, 2H)

Example 60b)

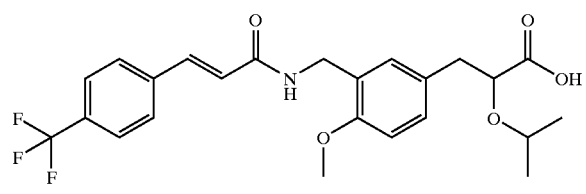

15 mg of ethyl 3-[3-([2-(diethoxyphospholyl)acetyl]aminomethyl)-4-methoxyphenyl]-2-isopropoxypropionate was dissolved in 0.4 ml tetrahydrofuran. About 3 mg of lithium hydride was added thereto, followed by stirring at room temperature for 0.5 hour. A solution of 10 mg 4-(trifluoromethyl)benzaldehyde in N,N-dimethylformamide (0.1 ml) was added thereto. After stirring at room temperature for 1 hour, 0.5 ml methanol and 0.1 ml of 5N sodium hydroxide were added thereto, the mixture was stirred overnight at room temperature. Then, 1N hydrochloric acid was added thereto which was then extracted with ethyl acetate, and the solvent was evaporated. The residue was purified by HPLC, to give 9.26 mg of 2-isopropoxy-3-4-methoxy-3-[(((E)-3-[4-(trifluoromethyl)phenyl]-2-propenoylamino)methyl]phenylpropionic acid.

MS m/e(ESI) 466 (MH$^+$)

Example 61

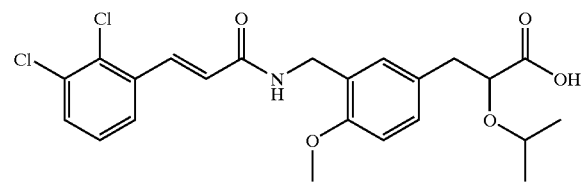

2-Isopropoxy-3-[4-methoxy-3-([(E)-3-(2,3-dichlorophenyl-2-propenoyl]aminomethyl)phenyl]propionic acid was obtained in the same method as in Example 60.

MS m/e(ESI) 466 (MH$^+$)

Example 62

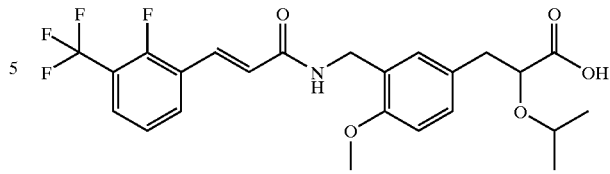

2-Isopropoxy-3-4-methoxy-3-([(E)-3-(2-fluoro-3-(trifluoromethyl)phenyl]-2-propenoylamino)methyl]phenylpropionic acid was obtained in the same method as in Example 60.

MS m/e(ESI) 484(MH$^+$)

Example 63

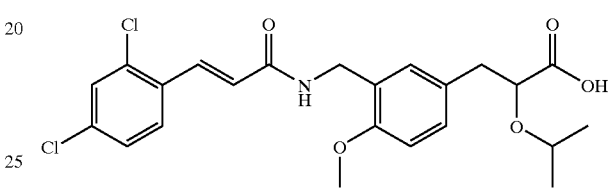

2-Isopropoxy-3-[4-methoxy-3-([(E)-3-(2,4-dichlorophenyl-2-propenoyl]aminomethyl)phenyl]propionic acid was obtained in the same method as in Example 60.

MS m/e(ESI) 466 (MH$^+$)

Example 64

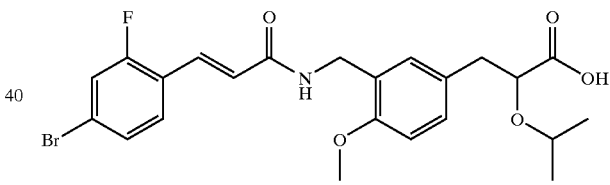

2-Isopropoxy-3-[4-methoxy-3-([(E)-3-(4-bromo-2-fluorophenyl-2-propenoyl]aminomethyl)phenyl]propionic acid was obtained in the same method as in Example 60.

MS m/e(ESI) 494 (MH$^+$)

Example 65

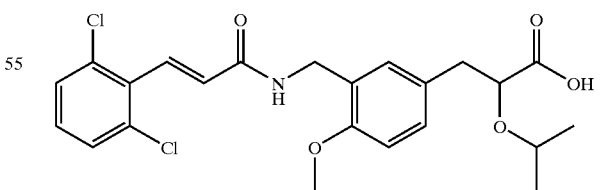

2-Isopropoxy-3-[4-methoxy-3-([(E)-3-(2,5-dichlorophenyl-2-propenoyl]aminomethyl)phenyl]propionic acid was obtained in the same method as in Example 60.

MS m/e(ESI) 466 (MH$^+$)

Example 66

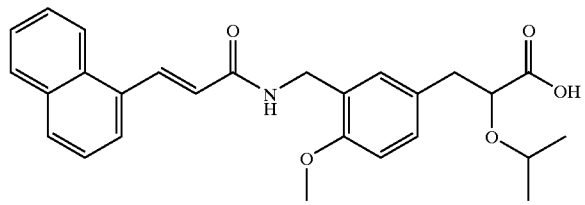

2-Isopropoxy-3-[4-methoxy-3-([(E)-3-(1-naphthyl)-2-propenoyl]aminomethyl)phenyl]propionic acid was obtained in the same method as in Example 60.

MS m/e (ESI) 448 (MH⁺)

Example 67

Production Example 67a)

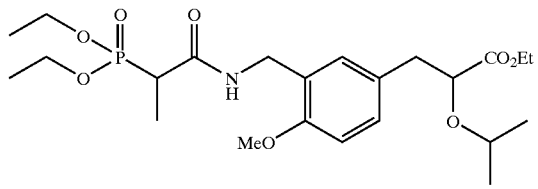

643 mg of 2-diethylphosphonopropionic acid and 973 mg of ethyl 3-[3-(aminomethyl)-4-methoxyphenyl]-2-isopropoxypropionate were dissolved in 10 ml N,N-dimethylformamide, and 470 μl diethyl cyanophosphonate and 1.07 ml triethylamine were successively added thereto. The mixture was stirred overnight at room temperature, and the reaction mixture was diluted with ethyl acetate. The organic layer was washed with water and brine, dried over anhydrous magnesium sulfate and the solvent was evaporated, to give 1.310 g of ethyl 3-[3-([2-(diethoxyphosphoryl)propanoyl]aminomethyl)-4-methoxyphenyl]-2-isopropoxypropionate.

$^1$H-NMR(CDCl$_3$) δ:0.97(d, J=6.0 Hz, 3H) 1.15 (d, J=6.0 Hz, 3H) 1.24–1.29 (m, 9H) 1.40 (dd, J=7.2, 17.6 Hz, 3H) 2.79–2.94 (m, 3H) 3.50 (sept, J=6.0 Hz, 1H) 3.84 (s, 3H) 3.98–4.2 (m, 7H) 4.43 (d, J=4.8 Hz, 2H) 6.77 (d, J=8.4 Hz, 1H) 7.12 (d, J=8.4 Hz, 1H) 7.16 (s, 1H)

Example 67b)

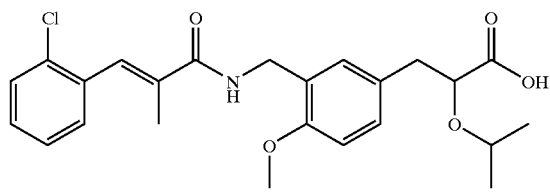

3-[3-([(E)-3-(2-chlorophenyl)-2-methyl-propenoyl]aminomethyl)-4-methoxyphenyl]-2-isopropoxypropionic acid was obtained in the same method as in Example 60.

MS m/e(ESI) 446 (MH⁺)

Example 68

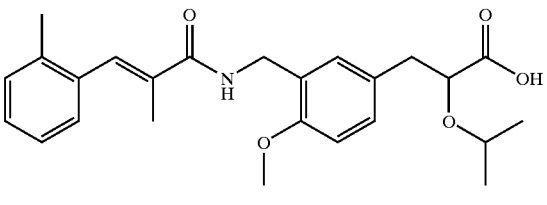

3-[3-([(E)-3-(2-methylphenyl)-2-methyl-propenoyl]aminomethyl)-4-methoxyphenyl]-2-isopropoxypropionic acid was obtained in the same method as in Example 60.

MS m/e(ESI) 426 (MH⁺)

Example 69

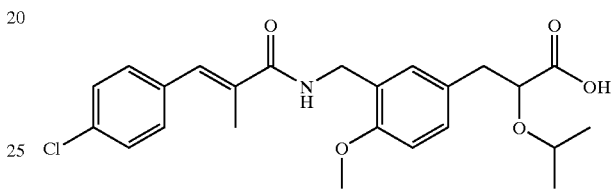

3-[3-([(E)-3-(4-chlorophenyl)-2-methyl-propenoyl]aminomethyl)-4-methoxyphenyl]-2-isopropoxypropionic acid was obtained in the same method as in Example 60.

MS m/e(ESI) 446 (MH⁺)

Example 70

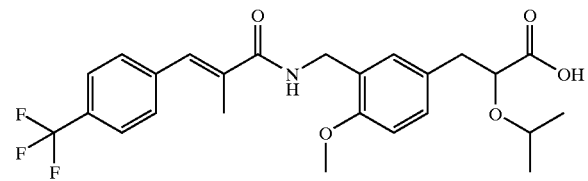

2-Isopropoxy-3-4-methoxy-3-[3-([(E)-2-methyl-3-[4-(trifluoromethyl)phenyl]-2-propenoylamino)methyl]phenylpropionic acid was obtained in the same method as in Example 60.

MS m/e(ESI) 480 (MH⁺)

Example 71

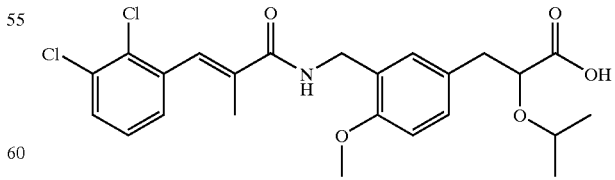

3-[3-([(E)-3-(2,3-Dichlorophenyl)-2-methyl-propenoyl]aminomethyl)-4-methoxyphenyl]-2-isopropoxypropionic acid was obtained in the same method as in Example 60.

MS m/e(ESI) 480 (MH⁺)

Example 72

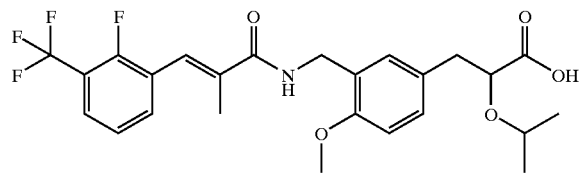

3-3-[((E)-3-[2-Fluoro-3-(trifluoromethyl)phenyl]-2-methyl-2-propenoylamino)methyl]-4-methoxyphenyl-2-isopropoxypropionic acid was obtained in the same method as in Example 60.

MS m/e(ESI) 498 (MH+)

Example 73

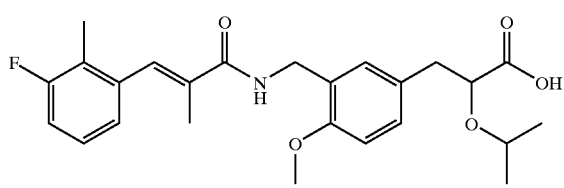

3-[3-([(E)-3-(3-Fluoro-2-methylphenyl)-2-methyl-propenoyl]aminomethyl)-4-methoxyphenyl]-2-isopropoxypropionic acid was obtained in the same method as in Example 60.

MS m/e(ESI) 444 (MH+)

Example 74

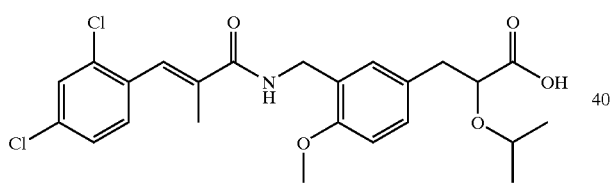

3-[3-([(E)-3-(2,4-Dichlorophenyl)-2-methyl-propenoyl]aminomethyl)-4-methoxyphenyl]-2-isopropoxypropionic acid was obtained in the same method as in Example 60.

MS m/e(ESI) 480 (MH+)

Example 75

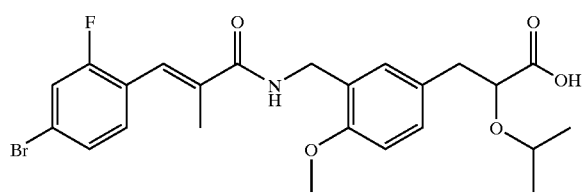

3-[3-([(E)-3-(2-Fluoro-4-bromophenyl)-2-methyl-propenoyl]aminomethyl)-4-methoxyphenyl]-2-isopropoxypropionic acid was obtained in the same method as in Example 60.

MS m/e(ESI) 510 (MH+)

Example 76

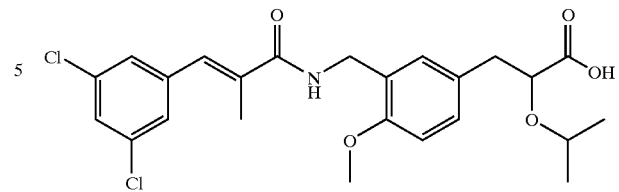

3-[3-([(E)-3-(3,4-Dichlorophenyl)-2-methyl-propenoyl]aminomethyl)-4-methoxyphenyl]-2-isopropoxypropionic acid was obtained in the same method as in Example 60.

MS m/e(ESI) 480 (MH+)

Example 77

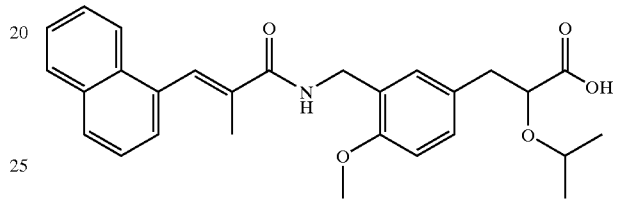

2-Isopropoxy-3-[4-methoxy-3-([(E)-2-methyl-3-(1-naphthyl)-2-propenoyl]aminomethyl)phenyl]propionic acid was obtained in the same method as in Example 60.

MS m/e(ESI) 462 (MH+)

Example 78

Production Example 78a)

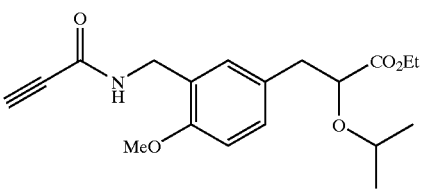

114 mg propiolic acid was dissolved in 8 ml tetrahydrofuran, and 13 mg lithium hydride and 140 μl ethyl chloroformate were successively added thereto, followed by stirring at room temperature for 1 hour. After adding the mixture to a solution of 489 mg ethyl 3-[3-(aminomethyl)-4-methoxyphenyl]-2-isopropoxypropionate in 2 ml tetrahydrofuran, 210 μl triethylamine was added thereto, followed by stirring overnight at room temperature. The reaction mixture was diluted with ethyl acetate, and the organic layer was washed with water and brine, dried over anhydrous magnesium sulfate and the solvent was evapoarated. The residue was purified by silica gel column chromatography, to give 230 mg of ethyl 2-isopropoxy-3-4-methoxy-3-[(propioylamino)methyl]phenylpropionate from fractions eluted with hexane-ethyl acetate (2:1→3:2).

$^1$H-NMR(CDCl$_3$) δ: 0.98(d, J=6.0 Hz, 3H) 1.16(d, J=6.0 Hz, 3H) 1.25(t, J=7.2 Hz, 3H) 2.76(s, 1H) 2.87(dd, J=8.4, 14.0 Hz, 1H) 2.94(dd, J=4.8, 14.0 Hz, 1H) 3.51 (sept, J=6.0 Hz, 1H) 3.85 (s, 3H) 4.01 (dd, J=5.2, 8.4 Hz, 1H) 4.12 (q, J=8.0 Hz, 2H) 4.45 (d, J=6.0 Hz, 2H) 6.35 (br,1H) 6.80 (d,J=8.0 Hz,1H) 7.13–7.18 (m,2H)

Example 78b)

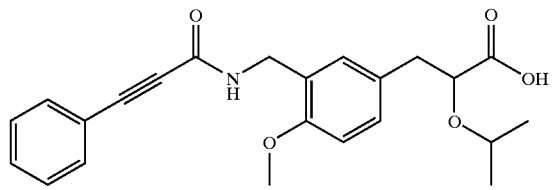

16 mg of ethyl 2-isopropoxy-3-4-methoxy-3-[(propioylamino)methyl]phenylpropionate was dissolved in 0.6 ml N,N-dimethylformamide. To the mixture were added 15 mg iodobenzene, 3 mg dichlorobistriphenyl phosphine palladium, 2 mg copper iodide, 3 mg lithium chloride and 0.1 ml triethylamine were added, followed by stirring in nitrogen atmosphere at room temperature overnight. Water was added to the reaction mixture which was then extracted with ethyl acetate, and the solvent was evaporated. To the residue were added 0.5 ml methanol and 0.1 ml of 5N sodium hydroxide, followed by stirring at room temperature overnight. The reaction mixture was acidified with 5N hydrochloric acid and extracted with ethyl acetate, and the solvent was evaporated. The residue was purified by HPLC, to give 1.91 mg of 2-isopropoxy-3-(4-methoxy-3-[(3-phenyl-2-propinoyl)amino]methylphenyl)propionic acid.

MS m/e(ESI) 397 (MH$^+$)

Example 79

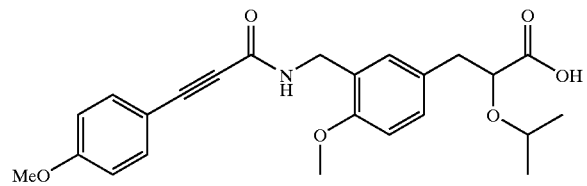

2-Isopropoxy-3-[4-methoxy-3-([3-(4-methoxyphenyl)-2-propinoyl]aminomethyl)phenyl]propionic acid was obtained in the same method as in Example 78.

MS m/e(ESI) 426 (MH$^+$)

Example 80

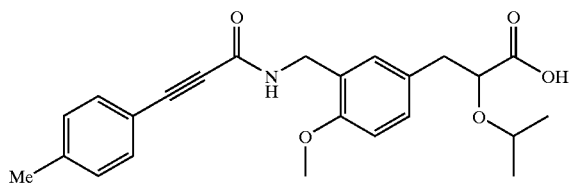

2-Isopropoxy-3-[4-methoxy-3-([3-(4-methylphenyl)-2-propinoyl]aminomethyl)phenyl]propionic acid was obtained in the same method as in Example 78.

MS m/e(ESI) 410 (MH$^+$)

Example 81

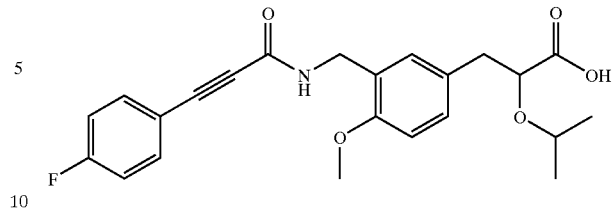

2-Isopropoxy-3-[4-methoxy-3-([3-(4-fluorophenyl)-2-propinoyl]aminomethyl)phenyl]propionic acid was obtained in the same method as in Example 78.

MS m/e(ESI) 414 (MH$^+$)

Example 82

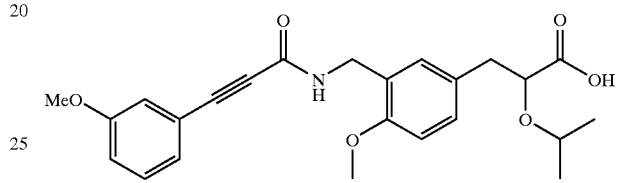

2-Isopropoxy-3-[4-methoxy-3-([3-(3-methoxyphenyl)-2-propinoyl]aminomethyl)phenyl]propionic acid was obtained in the same method as in Example 78.

MS m/e(ESI) 426 (MH$^+$)

Example 83

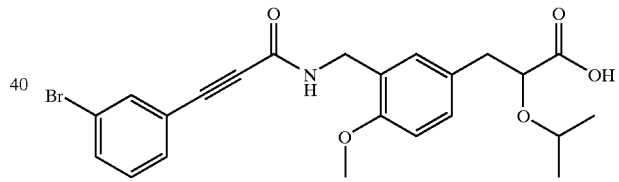

2-Isopropoxy-3-[4-methoxy-3-([3-(3-bromophenyl)-2-propinoyl]aminomethyl)phenyl]propionic acid was obtained in the same method as in Example 78.

MS m/e(ESI) 475 (MH$^+$)

Example 84

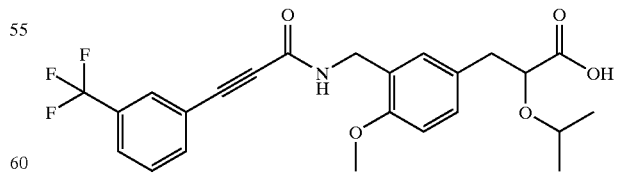

2-Isopropoxy-3-4-methoxy-3-([3-[3-(trifluoromethyl)phenyl]-2-propinoylaminomethyl]propionic acid was obtained in the same method as in Example 78.

MS m/e(ESI) 464 (MH$^+$)

Example 85

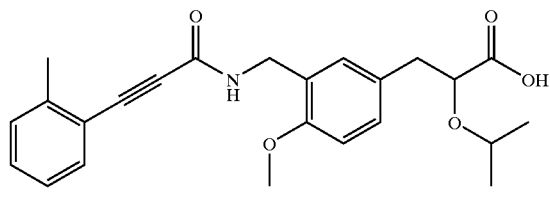

2-Isopropoxy-3-[4-methoxy-3-([3-(3-methylphenyl)-2-propinoyl]aminomethyl)phenyl]propionic acid was obtained in the same method as in Example 78.

MS m/e(ESI) 410 (MH$^+$)

Example 86

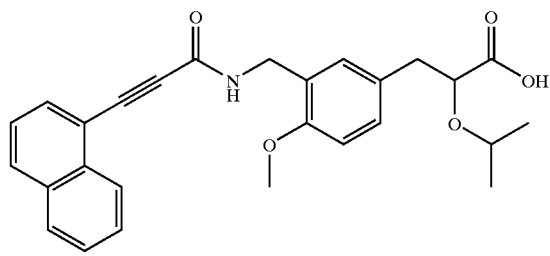

2-Isopropoxy-3-[4-methoxy-3-([3-(1-naphthyl)-2-propinoyl]aminomethyl)phenyl]propionic acid was obtained in the same method as in Example 78.

MS m/e(ESI) 446 (MH$^+$)

Example 87

Production Example 87a)

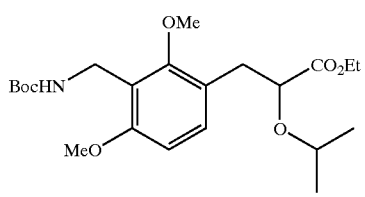

Using 3-bromo-2,6-dimethoxybenzaldehyde, ethyl 3-(3-[(tertiary butoxycarbonyl)amino]methyl-2,4-dimethoxyphenyl)-2-isopropoxypropionate was obtained in the same method as in Production Example 89e).

$^1$H-NMR(CDCl$_3$) δ: 0.96 (d, J=6.0 Hz, 3H) 1.15 (d, J=6.0 Hz, 3H) 1.23 (t, J=7.2 Hz, 3H) 1.44 (s, 9H) 2.87 (dd, J=8.4, 14.0 Hz, 1H) 2.98 (dd, J=5.6, 14.0 Hz, 1H) 3.51 (sept, J=6.4 Hz, 1H) 3.80 (s, 3H) 3.83 (s, 3H) 4.12–4.17 (m, 3H) 4.40 (d, J=5.2 Hz, 2H) 5.11 (br, 1H) 6.60 (d, J=8.8 Hz, 1H) 7.15 (d, J=8.8 Hz, 1H)

Example 87b)

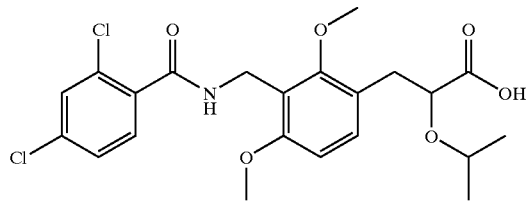

Using ethyl 3-(3-[(tertiary butoxycarbonyl)amino]methyl-2,4-dimethoxyphenyl)-2-isopropoxypropionate, 3-(3-[(2,4-dichlorobenzoyl)amino]methyl-2,4-dimethoxyphenyl)-2-isopropoxypropionic acid was obtained in the same method as in Example 38.

MS m/e(ESI) 470 (MH$^+$)

Example 88

Production Example 88a)

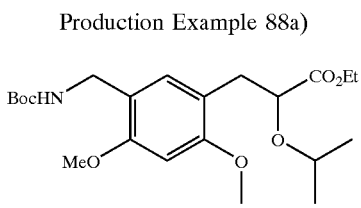

Using 5-bromo-2,4-dimethoxybenzaldehyde, ethyl 3-(3-[(tertiary butoxycarbonyl)amino]methyl-4,6-dimethoxyphenyl)-2-isopropoxypropionate was obtained in the same method as in Production Example 89e).

$^1$H-NMR(CDCl$_3$) δ: 0.98 (d, J=6.0 Hz, 3H) 1.14 (d, J=6.0 Hz, 3H) 1.26 (t, J=6.8 Hz, 3H) 1.43 (s, 9H) 2.86 (dd, J=8.8, 18.4 Hz, 1H) 2.98 (dd, J=6.4, 13.6 Hz, 1H) 3.51 (sept, J=6.4 Hz, 1H) 3.83 (s, 3H) 3.84 (s, 3H) 4.08–4.17 (m, 3H) 4.20 (brs, 2H) 4.94 (br, 1H) 6.40 (s, 1H) 7.02 (s, 1H)

Example 88b)

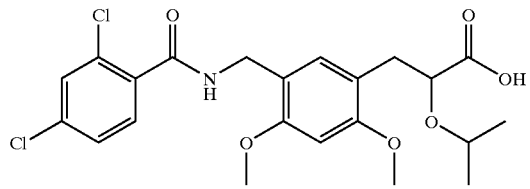

Using ethyl 3-(3-[(tertiary butoxycarbonyl)amino]methyl-4,6-dimethoxyphenyl)-2-isopropoxypropionate, 3-(5-[(2,4-dichlorobenzoyl)amino]methyl-2,4-dimethoxyphenyl)-2-isopropoxypropionic acid was obtained by treatment in the same method as in Example 38.

MS m/e(ESI) 470 (MH$^+$)

Example 89

Example 89a)

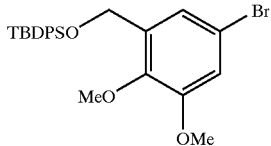

10.67 g of 5-bromo-2,3-dimethoxybenzaldehyde was dissolved in 100 ml tetrahydrofuran and 100 ml ethanol. 1 g of sodium borohydride was added thereto, followed by stirring overnight at room temperature. After adding 1 N hydrochloric acid thereto, the reaction solution was extracted with ethyl acetate, and the organic layer was washed with water and brine, dried over anhydrous magnesium sulfate and the solvent was evaporated, to give 10.27 g of 5-bromo-2,3-dimethoxybenzyl alcohol. 5.326 g of this crude product was dissolved in 50 ml N,N-dimethylformamide, and 1.8 g of imidazole and 5.9 g of tertiary butyl chlorodiphenyl silane were added, and the mixture was stirred overnight at room temperature. The reaction mixture was diluted with ethyl acetate, and the organic layer was washed with water and brine, dried over anhydrous magnesium sulfate and the solvent was evpoarated, to give 10.72 g of [(5-bromo-2,3-dimethoxybenzyl)oxy](tertiary butyl)diphenylsilane.

$^1$H-NMR(CDCl$_3$) δ: 1.10 (s, 9H) 3.63 (s, 3H) 3.84 (s, 3H) 4.76 (s,2H) 6.96 (d, J=2.0 Hz, 1H) 7.33 (d, J=1.6 Hz, 1H) 7.63–7.45 (m, 6H) 7.68–7.71 (m, 4H)

Production Example 89b)

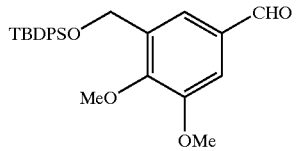

10.72 g of [(5-bromo-2,3-dimethoxybenzyl)oxy](tertiary butyl)diphenyl silane was dissolved in 100 ml tetrahydrofuran, followed by cooling at −78° C. in a nitrogen atmosphere. 16 ml butyl lithium (1.5 M solution in hexane) was added thereto, followed by stirring for 30 minutes. Then, 2.5 ml 4-formyl morpholine was added thereto. After stirrin at −78° C. for 1 hour, 1N hydrochloric acid was added thereto and the mixture was extracted with ethyl acetate. The organic layer was washed with water and brine, dride dried over anhydrous magnesium sulfate and the solvent was distilled away under reduced pressure. The residue was purified by silica gel column chromatography, and form fractions eluted with hexane-ethyl acetate (2:1→3:2), 9.4 g of 3-(1-(tertiary butyl)-1,1-diphenylsilyl]oxymethyl)-4,5-dimethoxybenzaldehyde was obtained.

$^1$H-NMR(CDCl$_3$) δ: 1.12 (s, 9H) 3.77 (s, 3H) 3.91 (s, 3H) 4.84 (s, 2H) 7.39–7.44 (m, 7H) 7.69–7.72 (m, 5H) 9.91 (s, 1H)

Production Example 89c)

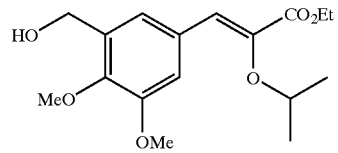

510 mg of diethyl 2-isopropoxyphosphonoacetate was dissolved in 20 ml tetrahydrofuran, and 370 mg of sodium hydride was added. After stirring at room temperature for 30 minutes, a solution of 3.485 g 3-([1-(tertiary butyl)-1,1-diphenylsilyl]oxymethyl)-4,5-dimethoxybenzaldehyde in 5 ml N,N-dimethylformamide was added thereto. After stirring overnight at room temperature, the reaction mixture was diluted with ethyl acetate. The organic layer was washed with water and brine, dried over anhydrous magnesium sulfate and the solvent was evapoarated, to give 5.01 g of ethyl (E,Z)-3-[[1-(tertiary butyl)-1,1-diphenylsilyl]oxymethyl]-4,5-dimethoxyphenyl]-2-isopropoxy-2-propionate. 5.01 g of this crude product was dissolved in 30 ml tetrahydrofuran, and 1 ml acetic acid and 10 ml tetrabutyl ammonium fluoride (1 M solution) were added successively. The reaction mixture was diluted with ethyl acetate, and the organic layer was washed with water and brine, dried over anhydrous magnesium sulfate. The residue was purified by silica gel column chromatography, and form fractions eluted with hexane-ethyl acetate (2:1→3:2), 2.209 g of ethyl (E,Z)-3-[hydroxymethyl)-4,5-dimethoxyphenyl]-2-isopropoxy-2-propionate was obtained.

$^1$H-NMR(CDCl$_3$) δ:1.24–1.39 (m, 9H) 3.84, 3.87 (each s, 3H) 3.89, 3.92 (each s, 3H) 4.16, 4.29 (each q, J=7.2 Hz, 2H) 4.27, 4.47 (each sept, J=6.0 Hz, 1H) 4.65, 4.67 (each s, 2H) 6.16, 6.94 (each s, 1H) 6.79 (s, 1H) 7.23, 7.67 (each d, J=2.0 Hz and 1.6 Hz, 1H)

Production Example 89d)

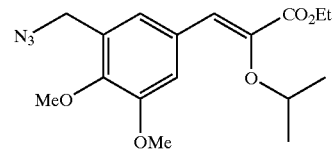

2.209 g of ethyl (E,Z)-3-[hydroxymethyl]-4,5-dimethoxyphenyl]-2-isopropoxy-2-propionate was dissolved in 15 ml toluene, and 1.6 ml diphenyl phosphoryl azide and 1.1 ml diazabicyclo[5.4.0]undecene were added, followed by stirring overnight at room temperature. Water was added to the reaction product and extracted with ethyl acetate. The organic layer was washed with brine, dried over anhydrous magnesium sulfate and the solvent was evapoarated. The residue was purified by silica gel column chromatography, and form fractions eluted with hexane-ethyl acetate (2:1→3:2), ethyl (E,Z)-3-[3-(azide methyl)-4,5-dimethoxyphenyl]-2-isopropoxy-2-propionate was obtained.

$^1$H-NMR(CDCl$_3$) δ:1.14 (t, =6.8 Hz, 3H) 1.30 (d, J=7.2 Hz, 3H) 1.35 (d, J=7.2 Hz, 3H) 3.84, 3.87 (each s, 3H) 3.90, 3.92 (each s, 3H) 4.16, 4.30 (each q, J=6.8 Hz, 2H) 4.35 (d, J=11.2 Hz, 2H) 4.50 (sept, J=6.4 Hz, 1H) 6.14, 6.93 (each s, 1H) 6.75, 6.72 (each d, J=2.0 Hz, 1H) 7.26, 7.64 (each d, J=2.0 Hz, 1H)

Production Example 89e)

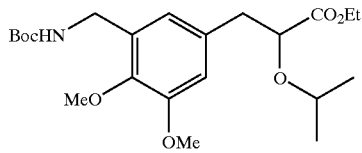

2.124 g of ethyl (E,Z)-3-[3-(methylazide)-4,5-dimethoxyphenyl]-2-isopropoxy-2-propionate was dissolved in 50 ml ethyl acetate. 1.5 g of tertiary butyl dicarbonate and 800 mg of 10% palladium-carbon were added thereto, followed by stirring for 20 hours at room temperature in a hydrogen atmosphere. The reaction mixture was filtered through Celite, and the filtrate was concentrated and the residue was purified by silica gel column chromatography, to give 1.93 g of ethyl 3-(3-[(tertiary butoxycarbonyl)amino]methyl-4,5-dimethoxyphenyl)-2-isopropoxypropionate from fractions eluted with hexane-ethyl acetate (5:1→4:1).

$^1$H-NMR(CDCl$_3$) δ: 0.97 (d, J=6.0 Hz, 3H) 1.16 (d, J=6.0 Hz, 3H) 1.26 (t, J=6.8 Hz, 3H) 1.44 (s, 9H) 2.87 (dd, J=8.4, 14.0 Hz, 1H) 2.94 (dd, J=4.8, 14.0 Hz, 1H) 3.51 (sept, J6.4 Hz, 1H) 3.82 (s, 3H) 3.84 (s, 3H) 4.02 (dd, J=4.8, 8.4 Hz, 1H) 4.13–4.22 (m, 2H) 4.29 (d, J=6.0 Hz, 2H) 4.94 (br, 1H) 6.76 (s, 1H) 6.78 (s, 1H)

Example 89f)

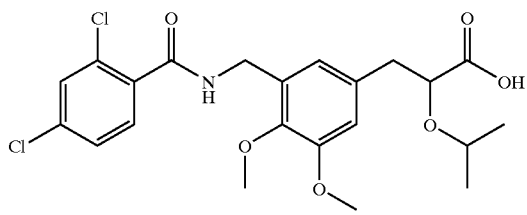

Ethyl 3-(3-[(tertiary butoxycarbonyl)amino]methyl-4,5-dimethoxyphenyl)-2-isopropoxypropionate was treated in the same manner as in Example 38, to give 3-(3-[(2,4-dichlorobenzoyl)amino]methyl-4,5-dimethoxyphenyl)-2-isopropoxypropionic acid.

MS m/e(ESI) 470 (MH$^+$)

Example 90

Example 90a)

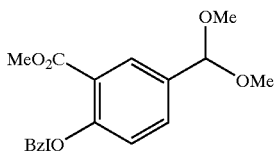

39.1 g of methyl 2-benzyloxy-5-formyl-benzoate was dissolved in 300 ml methanol. 60 ml trimethyl orthoformate and 2 g of p-toluenesulffonic acid were added thereto, followed by heating under reflux for 4 hours. After cooling to room temperature, 5 ml triethylamine was added thereto, and the mixture was evaporated. The residue was dissolved in ethyl acetate, successively washed with water and saturated aqueous sodium bicarbonate solution, dried over anhydrous magnesium sulfate and the solvent was evaporated, to give 39.08 g of methyl 2-(benzyloxy)-5-(dimethoxymethyl) benzoate.

$^1$H-NMR(CDCl$_3$) δ: 3.32 (6H, s) 3.88 (s, 3H) 5.19 (s, 2H) 5.37 (s, 1H) 7.03 (d, J=8.0 Hz, 1H) 7.33–7.41 (m, 3H) 7.47–7.53 (m, 3H) 7.91 (s, 1H)

Production Example 90b)

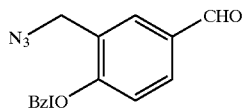

7 g of aluminum hydride was suspended in 200 ml tetrahydrofuran under ice-cooling, and a solution of 39.08 g of methyl 2-(benzyloxy)-5-(dimethoxymethyl)benzoate in 100 ml tetrahydrofuran was added thereto. After stirring for 5 minutes, water, 15% sodium hydroxide and water were added thereto and filtered. The filtrate was evapoarated, to give 35.15 g of 2-(benzyloxy)-5-(dimethoxymethyl)benzyl alcohol. This crude product was dissolved in 250 ml toluene, and 40 g of diphenyl phosphoryl azide and 22 ml diazabicylo [5.4.0]undecene were added, followed by stirring overnight at room temperature. Water was added to the reaction product, followed by extracting with ethyl acetate. The organic layer was washed with brine, dried over anhydrous magnesium sulfate and the solvent was evapoarated. The residue was purified by silica gel column chromatography, and from fractions eluted with hexane-ethyl acetate (15:1), 17.4 g of 4-(benzyloxy)-3-(azidomethyl) dimethoxymethylbenzene was obtained. This product was left for 1 month at room temperature and purified by silica gel column chromatography, and from fractions eluted with hexane-ethyl acetate (12:1), 9.39 g of 4-(benzyloxy)-3-(azidomethyl)benzaldehyde was obtained.

$^1$H-NMR(CDCl$_3$) δ: 4.48 (s, 2H) 5.22 (s, 2H) 7.90 (d, J=8.8 Hz, 1H) 7.37–7.45 (m, 5H) 7.84–7.86 (m, 2H) 9.90 (s, 1H)

Production Example 90c)

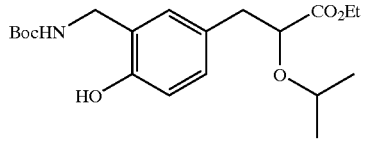

12.9 g of diethyl 2-isopropoxyphosphonoacetate was dissolved in 100 ml tetrahydrofuran, and 1.7 g of sodium hydride was added under ice-cooling. After stirring at room temperature for 30 minutes, a solution of 9.39 g of 3,4-(benzyloxy)-3-(azidomethyl)benzaldehyde in 20 ml N,N-dimethylformamide was added. After stirring at room temperature for 4 hours, the reaction mixture was diluted with ethyl acetate. The organic layer was washed successively with water and brine, dried over anhydrous magnesium sulfate and the solvent was evapoarated, to give 16.7 g of ethyl (E,Z)-3-[azidomethyl]-4-(benzyloxy)phenyl]-2-isopropoxy-2-propionate. 12.46 g of this crude product was dissolved in ethanol, and 8.3 g of tertiary butyl dicarbonate and 3 g of 10% palladium-carbon were added, followed by stirring at room temperature for 1.5 days in a hydrogen atmosphere. The reaction mixture was filtered through Celite, and the filtrate was concentrated. The residue was purified by silica gel column chromatography, and from fractions eluted with hexane-ethyl acetate (4:1), 6.2 g of ethyl 3-(3-[(tertiary butoxycarbonyl)amino]methyl-4-hydroxyphenyl)-2-isopropoxypropionate was obtained.

$^1$H-NMR(CDCl$_3$) δ: 0.99 (d, J=6.0 Hz, 3H) 1.15 (d, J=6.0 Hz, 3H) 1.23 (t, J=7.2 Hz, 3H) 1.44 (s, 9H) 2.84 (dd, J=8.4, 13.6 Hz, 1H) 2.90 (dd, J=5.0, 13.6 Hz, 1H) 3.50 (sept, J=6.4 Hz, 1H) 3.98 (dd, J=5.6, 8.4 Hz, 1H) 4.12 (q, J=6.8 Hz, 2H) 4.19 (d, J=6.4 Hz, 2H) 5.22 (br, 1H) 6.86 (d, J8.4 Hz, 1H) 6.94 (d, J=2.0 Hz, 1H) 7.08 (dd, =2.0, 8.0 Hz, 1H) 8.77 (br, 1H)

Production Example 90d)

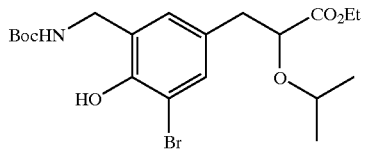

402 mg of ethyl 3-(3-[(tertiary butoxycarbonyl)amino]methyl-4-hydroxyphenyl)-2-isopropoxypropionate was dissolved in 5 ml acetonitrile, and 200 mg N-bromosuccimide was added. After stirring at room temperature for 1 hour, the reaction mixture was diluted with ethyl acetate. The organic layer was successively washed with water and brine, dried over anhydrous magnesium sulfate and the solvent was evapoarated. The residue was purified by silica gel column chromatography, and from fractions eluted with hexane-ethyl acetate (5:1), 433 mg of ethyl 3-(3-bromo-5-[(tertiary butoxycarbonyl)amino]methyl-4-hydroxyphenyl)-2-isopropoxypropionate was obtained.

$^1$H-NMR(CDCl$_3$) δ: 0.98 (d, J=6.0 Hz, 3H) 1.16 (d, J=6.0 Hz, 3H) 1.25 (t, J=6.8 Hz, 3H) 1.44 (s, 9H) 2.80 (dd, J=8.4, 13.6 Hz, 1H) 2.88 (dd, J=7.2, 14.0 Hz, 1H) 3.51 (sept, J=6.4 Hz, 1H) 3.97 (dd, J=4.8, 8.4 Hz, 1H) 4.16–4.22 (m, 2H) 4.24 (d, J=6.8 Hz, 2H) 5.20 (br, 1H) 6.96 (d, J=1.6 Hz, 1H) 7.35 (d, J=2.0 Hz, 1H) 8.45 (br, 1H)

Production Example 90e)

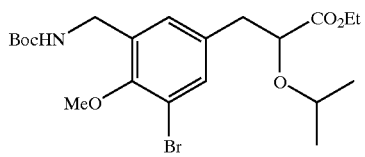

944 mg of ethyl 3-(3-bromo-5-[(tertiary butoxycarbonyl)amino]methyl-4-hydroxyphenyl)-2-isopropoxypropionate was dissolved in 5 ml N,N-dimethylformamide, and 0.15 ml iodomethane and 500 mg of potassium carbonate were successively added. After stirring at room temperature for 2 hours, the reaction mixture was diluted with ethyl acetate. The organic layer was washed with water and brine, dried over anhydrous magnesium sulfate and the solvent was evapoarated. The residue was purified by silica gel column chromatography, and from fractions eluted with hexane-ethyl acetate (4:1), 876 mg of ethyl 3-(3-bromo-5-[(tertiary butoxycarbonyl)amino]methyl-4-methoxyphenyl)-2-isopropoxypropionate was obtained.

$^1$H-NMR(CDCl$_3$) δ: 0.97 (d, J=6.0 Hz, 3H) 1.16 (d, J=6.0 Hz, 3H) 1.45 (s, 9H) 2.86 (dd, J=8.4, 14.0 Hz, 1H) 2.93 (dd, J=4.4, 14.0 Hz, 1H) 3.51 (sept, J=6.4 Hz, 1H) 3.74 (s, 3H) 3.84 (s, 3H) 4.02 (dd, J=4.8, 8.4 Hz, 1H) 4.34 (d, J=6.0 Hz, 2H) 4.95 (br, 1H) 7.12 (d, J=1.6 Hz, 1H) 7.37 (d, J=2.0 Hz, 1H)

Example 90f)

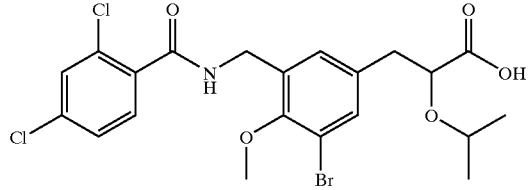

Ethyl 3-(3-bromo-5-[(tertiary butoxycarbonyl)amino]methyl-4-methoxyphenyl)-2-isopropoxypropionate was treated in the same method as in Example 38, to give 3-(3-bromo-5-[(2,4-dichlorobenzoyl)amino]methyl-4-methoxyphenyl)-2-isopropoxypropionic acid.

MS m/e(ESI) 520 (MH$^+$)

Example 91

Production Example 91a)

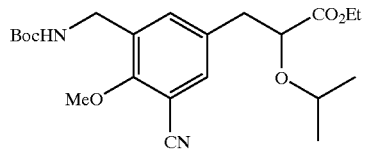

876 mg of ethyl 3-(3-bromo-5-[(tertiary butoxycarbonyl)amino]methyl-4-methoxyphenyl)-2-isopropoxypropionate was dissolved in 5 ml propionitrile, and 182 mg of sodium cyanide, 214 mg of tetrakistriphenylphosphine palladium and 70 mg of copper iodide were added, followed by heating under reflux overnight in a nitrogen atmosphere. The reaction mixture was cooled to room temperature, ethyl acetate was added thereto and filtered through Celite. The filtrate was evapoarated and the residue was purified by silica gel column chromatography, and from fractions eluted with hexane-ethyl acetate (4:1), 586 mg of ethyl 3-(3-cyano-5-[(tertiary butoxycarbonyl)amino]methyl-4-methoxyphenyl)-2-isopropoxypropionate was obtained.

$^1$H-NMR(CDCl$_3$) δ:0.95(d, J=6.0 Hz, 3H) 1.17(d, J=6.0 Hz, 3H) 1.27(t, J=6.8 Hz, 3H) 1.45 (s, 9H) 2.89 (dd, J=8.4, 14.0 Hz, 1H) 2.97 (dd, J=4.4, 14.0 Hz, 1H) 3.53 (sept, J=6.4 Hz, 1H) 4.00 (dd, J=4.8, 8.4 Hz, 1H) 4.07 (s, 3H) 4.21–4.27 (m, 2H) 4.30 (s, 2H) 4.94 (br, 1H) 7.40 (d, J=2.4 Hz, 1H) 7.42 (d, J=0.8 Hz, 1H)

Example 91b)

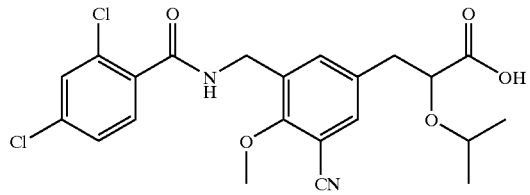

Ethyl 3-(3-cyano-5-[(tertiary butoxycarbonyl)amino]methyl-4-methoxyphenyl)-2-isopropoxypropionate was treated in the same method as in Example 38, to give 3-(3-cyano-5-[(2,4-dichlorobenzoyl)amino]methyl-4-methoxyphenyl)-2-isopropoxypropionic acid.

MS m/e(ESI) 465 (MH$^+$)

Example 92

Example 92a)

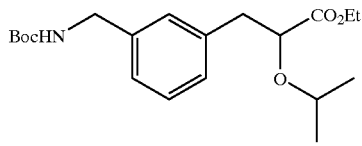

12 g of 5-bromo-2-chorobenzoic acid was dissolved in 60 ml tetrahydrofuran, and 148.3 g of borane-tetrahydrofuran complex (1 M solution in tetrahydrofuran) was added, followed by stirring at room temperature for 2.5 days. 1N hydrochloric acid was added, and the mixture was extracted with ethyl acetate. The organic layer was washed with water and brine, dried over anhydrous magnesium sulfate and the solvent was evapoarated, to give 11.46 g of 5-bromo-2-chlorobenzyl alcohol. This crude product was treated in the same method as in Production Example 89e), to give ethyl 3-(3-[(tertiary butoxycarbonyl)amino]methylphenyl)-2-isopropoxypropionate.

$^1$H-NMR(CDCl$_3$) δ: 0.95 (d, J=6.0 Hz, 3H) 1.15 (d, J=6.0 Hz, 3H) 1.24 (t, J=7.2 Hz, 3H) 1.46 (s, 9H) 2.93 (dd, J=8.4, 14.0 Hz, 1H) 3.07 (dd, J=4.8, 14.0 Hz, 1H) 3.49 (sept, J=6.4 Hz, 1H) 4.04 (dd, J=4.8, 8.4 Hz, 1H) 4.12–4.19 (m, 2H) 4.30 (d, J=5.2 Hz, 2H) 4.0 (br, 1H) 7.12–7.16 (m, 3H) 7.23 (d, J=8.0 Hz, 1H)

Example 92b)

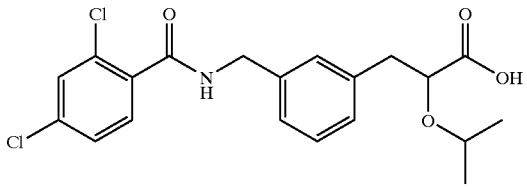

Ethyl 3-(3-[(tertiary butoxycarbonyl)amino]methylphenyl)-2-isopropoxypropionate was treated in the same method as in Example 38, to give 3-(3-[(2,4-dichlorobenzoyl)amino]methylphenyl)-2-isopropoxypropionic acid.

MS m/e(ESI) 410 (MH$^+$)

Example 93

Production Example 93a)

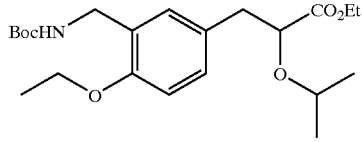

795 mg of ethyl 3-(3-[(tertiary butoxycarbonyl)amino]methyl-4-hydroxyphenyl)-2-isopropoxypropionic acid was dissolved in 2 ml N,N-dimethylformamide, and 0.3 ml iodoethane and 200 mg potassium carbonate were successively added. After stirring at 50° C. for 4 hours, the reaction mixture was diluted with ethyl acetate, The organic layer was washed with water and brine, dried over anhydrous magnesium sulfate and the solvent was evapoarated. The residue was purified by silica gel column chromatography, and from fractions eluted with hexane-ethyl acetate (8:1), 185 mg of ethyl 3-(3-[(tertiary butoxycarbonyl)amino]methyl-4-ethoxyphenyl)-2-isopropoxypropionate was obtained.

$^1$H-NMR(CDCl$_3$) δ: 0.96 (d, J=6.0 Hz, 3H) 1.15 (d, J=6.0 Hz, 3H) 1.24 (t, J=6.8 Hz, 3H) 1.42 (t, J=6.8 Hz, 3H) 1.45 (s, 9H) 2.86 (dd, J=8.4, 14.0 Hz, 1H) 2.93 (dd, J=4.8, 14.0 Hz, 1H) 3.49 (sept, J=6.4 Hz, 1H) 3.98–4.06 (m, 3H) 4.13–4.21 (m, 2H) 4.29 (d, J=5.2 Hz, 2H) 4.99 (br, 1H) 6.75 (d, J=8.4 Hz, 1H) 7.14 (d, J=8.8 Hz, 1H) 7.14 (s, 1H)

Example 93b)

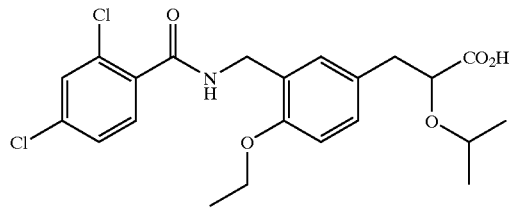

Ethyl 3-(3-[(tertiary butoxycarbonyl)amino]methyl-4-ethoxyphenyl)-2-isopropoxypropionate was treated in the same method as in Example 38, to give 3-(3-[(2,4-dichlorobenzoyl)amino]methyl-4-ethoxyphenyl)-2-isopropoxypropionic acid.

$^1$H-NMR(CDCl$_3$) δ: 1.06 (d, J=6.0 Hz, 3H) 1.17 (d, J=6.0 Hz, 3H) 1.45 (t, J=7.2 Hz, 3H) 2.92 (dd, J=8.0, 14.0 Hz, 1H) 3.07 (dd, J=4.4, 14.0 Hz, 1H) 3.58 (sept, J=6.0 Hz, 1H) 4.06–4.15 (m, 3H) 4.64 (d, J=6.0 Hz, 2H) 6.81 (d, J=8.4 Hz, 1H) 6.88 (br, 1H) 7.15 (dd, J=2.4,8.4 Hz, 1H) 7.27 (d, J=8.4 Hz, 2H) 7.42 (d, J=2.4 Hz, 1H) 7.68 (d, J=8.4 Hz, 1H)

MS m/e(ESI) 454 (MH$^+$)

Example 94

Production Example 94a)

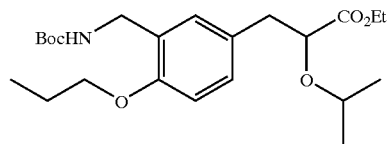

Ethyl 3-(3-[(tertiary butoxycarbonyl)amino]methyl-4-propoxyphenyl)-2-isopropoxypropionate was obtained in the same method as in Production Example 93.

$^1$H-NMR(CDCl$_3$) δ: 0.97 (d, J=6.0 Hz, 3H) 1.05 (t, J=6.8 Hz, 3H) 1.15 (d, J=6.0 Hz, 3H) 1.25 (t, J=6.8 Hz, 3H) 1.44 (s, 9H) 1.78–1.86 (m, 2H) 2.86 (dd, J=8.4, 14.0 Hz, 1H) 2.93 (dd, J=4.8, 14.0 Hz, 1H) 3.50 (sept, J=6.4 Hz, 1H) 3.93 (t, J=6.4 Hz, 2H) 4.00 (dd, J=4.8, 8.4 Hz, 1H) 4.14–4.21 (m, 2H) 4.30 (d, J=5.2 Hz, 2H) 4.98 (br, 1H) 6.75 (d, J=8.4 Hz, 1H) 7.09 (dd, J=2.0, 8.4 Hz, 1H) 7.13 (s, 1H)

Example 94b)

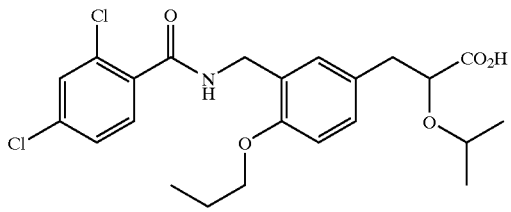

Ethyl 3-(3-[(tertiary butoxycarbonyl)amino]methyl-4-propoxyphenyl)-2-isopropoxypropionate was treated in the same method as in Example 38, to give 3-(3-[(2,4-dichlorobenzoyl)amino]methyl-4-propoxyphenyl)-2-isopropoxypropionic acid.

$^1$H-NMR(CDCl$_3$) δ:1.05(t, J=7.2 Hz, 3H) 1.06(d, J=6.0 Hz, 3H) 1.18(d, J=6.0 Hz, 3H) 1.80–1.87 (m, 2H) 2.91 (dd, J=8.0, 14.0 Hz, 1H) 3.07 (dd, J=4.4, 14.0 Hz, 1H) 3.59 (sept, J=6.0 Hz, 1H) 3.97 (t, J=7.2 Hz, 2H) 4.12 (dd, J=4.4, 8.0 Hz, 1H) 4.65 (d, J=6.0 Hz, 2H) 6.81–6.84 (m, 2H) 7.15 (dd, J=2.4, 8.4 Hz, 1H) 7.25 (d, J=2.4 Hz, 1H) 7.28–7.33 (m, 1H) 7.42 (d, J=2.4 Hz, 1H) 7.67 (d, J=9.6 Hz, 1H)

MS m/e(ESI) 470 (MH$^+$)

Example 95

Production Example 95a)

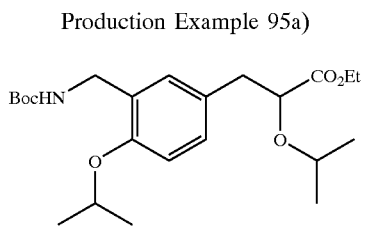

Ethyl 3-(3-[(tertiary butoxycarbonyl)amino]methyl-4-isopropoxyphenyl)-2-isopropoxypropionate was obtained in the same method as in Production Example 93.

$^1$H-NMR(CDCl$_3$) δ: 0.97 (d, J=6.0 Hz, 3H) 1.15 (d, J=6.0 Hz, 3H) 1.24 (t, J=6.8 Hz, 3H) 1.33 (d, J=6.0 Hz, 6H) 1.44 (s, 9H) 1.78–1.86 (m, 2H) 2.86 (dd, J=8.4, 14.0 Hz, 1H) 2.92 (dd, J=4.8, 14.0 Hz, 1H) 3.50 (sept, J=6.0 Hz, 1H) 4.00 (dd, J=4.8, 8.4 Hz, 1H) 4.13–4.21 (m, 2H) 4.26 (d, J=5.2 Hz, 2H) 4.54 (sept, J=6.0 Hz, 1H) 4.96 (br, 1H) 6.77 (d, J=8.4 Hz, 1H) 7.08 (dd, J=2.4, 8.4 Hz, 1H) 7.13 (s, 1H)

Example 95b)

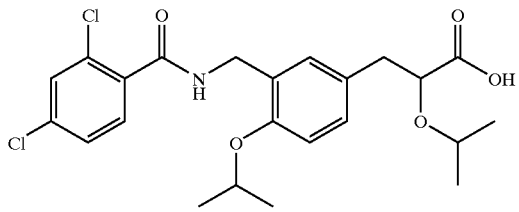

Ethyl 3-(3-[(tertiary butoxycarbonyl)amino]methyl-4-isopropoxyphenyl)-2-isopropoxypropionate was treated in the same method as in Example 38, to give 3-(3-[(2,4-dichlorobenzoyl)amino]methyl-4-isopropoxyphenyl)-2-isopropoxypropionic acid.

MS m/e(ESI) 470 (MH$^+$)

Example 96

Production Example 96a)

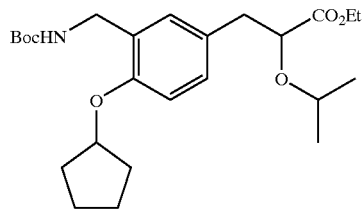

Ethyl 3-(3-[(tertiary butoxycarbonyl)amino]methyl-4-cyclopentyloxyphenyl)-2-isopropoxypropionate was obtained in the same method as in Production Example 93.

$^1$H-NMR(CDCl$_3$) δ: 0.97 (d, J=6.0 Hz, 3H) 1.15 (d, J=6.0 Hz; 3H) 1.24 (t, J=6.8 Hz, 3H) 1.44 (s, 9H) 1.63–1.65 (m, 2H) 1.75–1.90 (m, 6H) 2.85 (dd, J=8.4, 14.0 Hz, 1H) 2.92 (dd, J=4.8, 14.0 Hz, 1H) 3.50 (sept, J=6.0 Hz, 1H) 4.00 (dd, J=4.8, 8.4 Hz, 1H) 4.10–4.21 (m, 2H) 4.25 (d, J=5.2 Hz, 2H) 4.76–4.79 (m, 1H) 4.95 (br, 1H) 6.75 (d, J=8.4 Hz, 1H) 7.07 (d, J=8.4 Hz, 1H) 7.12 (s, 1H)

Example 96b)

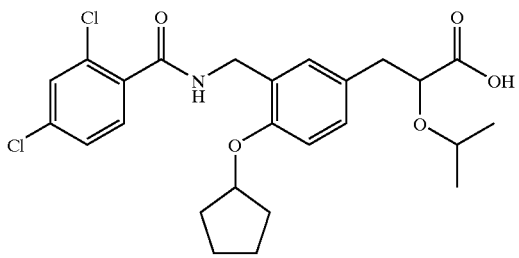

Ethyl 3-(3-[(tertiary butoxycarbonyl)amino]methyl-4-cyclopentyloxyphenyl)-2-isopropoxypropionate was treated in the same method as in Example 38, to give 3-(3-[(2,4-dichlorobenzoyl)amino]methyl-4-cyclopentyloxyphenyl)-2-isopropoxypropionic acid.

MS m/e(ESI) 494 (MH$^+$)

Example 97

Production Example 97a)

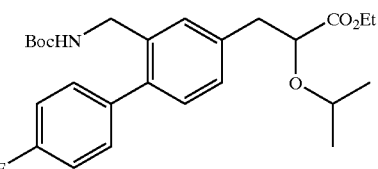

329 mg of ethyl 3-(3-[(tertiary butoxycarbonyl)amino]methyl-4-[(trifluoromethyl)sulfonyl]oxyphenyl)-2-isopropoxypropionate was dissolved in 4 ml toluene. 110 mg of 4-fluorophenylboric acid, 74 mg of tetrakistriphenyl phosphine palladium and 440 mg of potassium carbonate were added, followed by stirring overnight at 100° C. in a nitrogen atmosphere. The reaction mixture was diluted with ethyl acetate, filtered through Celite and the filtrate was evaporated. The residue was purified by silica gel column chromatography, and from fractions eluted with hexane-ethyl acetate (6:1), 262 mg of ethyl 3-(3-[(tertiary butoxycarbonyl)amino]methyl-4-[(trifluoromethyl) sulfonyl]oxyphenyl)-2-(4-fluorophenyl) phenylpropoxypropionate was obtained.

$^1$H-NMR(CDCl$_3$) δ: 1.01 (d, J=6.4 Hz, 3H) 1.18 (d, J=6.4 Hz, 3H) 1.26 (t, J=7.2 Hz, 3H) 1.43 (s, 9H) 2.99 (dd, J=8.8, 13.6 Hz, 1H) 3.04 (dd, J=5.6, 13.2 Hz, 1H) 3.56 (sept, J=6.4 Hz, 1H) 4.08–4.24 (m,5H) 4.60 (br 1H) 7.05–7.15 (m, 4H) 7.19–7.30 (m, 3H)

Example 97b)

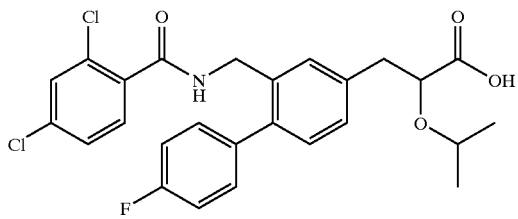

Ethyl 3-(3-[(tertiary butoxycarbonyl)amino]methyl-4-[(trifluoromethyl)sulfonyl]oxyphenyl)-2-(4-fluorophenyl) phenylpropoxypropionate was treated in the same method as in Example 38, to give 3-(3-[(2,4-dichlorobenzoyl)amino] methyl-4-(4-fluorophenyl)phenyl)-2-isopropoxypropionic acid.

MS m/e(ESI) 504 (MH$^+$)

Example 98

Production Example 98a)

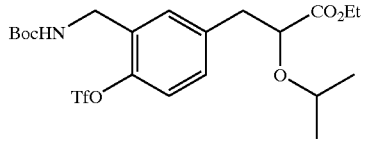

501 mg of ethyl 3-(3-[(tertiary butoxycarbonyl)amino] methyl-4-hydroxyphenyl)-2-isopropoxypropionate was dissolved in 7 ml pyridine, and 270 μL trifluoromethane sulfonic anhydride was added under ice-cooling. After stirring at room temperature for 1 hour, 100 μL trifluoromethane sulfonic anhydride was further added. The mixture was further stirred for 2 hours, then the reaction mixture was diluted with ethyl acetate. The organic layer was washed with 1N hydrochloric acid, water and brine, dried over anhydrous magnesium sulfate and the solvent was evapoarated, to give 663 mg of ethyl 3-(3-[(tertiary butoxycarbonyl)amino]methyl-4-[(trifluoromethyl) sulfonyl]oxyphenyl)-2-isopropoxypropionate.

$^1$H-NMR(CDCl$_3$) δ: 0.92 (d, J=6.0 Hz, 3H) 1.16 (d, J=6.0 Hz, 3H) 1.24 (t, J=6.8 Hz, 3H) 1.46 (s, 9H) 2.91–3.04 (m, 2H) 3.51 (sept, J=6.4 Hz, 1H) 4.02 (dd, J=4.4, 8.8 Hz, 1H) 4.16–4.23 (m, 2H) 4.40 (d, J=6.0 Hz, 2H) 4.95 (br, 1H) 7.17–7.20 (m, 1H) 7.24–7.25 (m, 1H) 7.40 (s, 1H)

Production Example 98b)

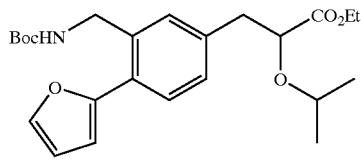

334 mg of ethyl 3-(3-[(tertiary butoxycarbonyl)amino] methyl-4-[(trifluoromethyl)sulfonyl]oxyphenyl)-2-isopropoxypropionate was dissolved in 4 ml dioxane. 280 mg of 2-tributylstannylfuran, 75 mg of tetrakistriphenylphosphine palladium and 83 mg of lithium chloride were added thereto, followed by stirring overnight at 80° C. in a nitrogen atmosphere. The reaction mixture was concentrated and the residue was purified by silica gel column chromatography, to give 180 mg of ethyl 3-(3-[(tertiary butoxycarbonyl)amino]methyl-4-[(trifluoromethyl) sulfonyl]oxyphenyl)-2-(2-furyl)propoxypropionate from fractions eluted with hexane-ethyl acetate (7:1).

$^1$H-NMR(CDCl$_3$) δ: 0.96 (d, J=6.0 Hz, 3H) 1.16 (d, J=6.4 Hz, 3H) 1.26 (t, J=6.8 Hz, 3H) 1.46 (s, 9H) 2.95 (dd, J=8.8, 13.6 Hz, 1H) 3.02 (dd, J=4.8, 14.0 Hz, 1H) 3.51 (sept, J=6.4 Hz, 1H) 4.06 (dd, J=4.8, 8.8 Hz, 1H) 4.19 (q, J=6.8 Hz, 2H) 4.47 (s, 2H) 4.95 (br 1H) 6.52 (d, J=20 Hz, 2H) 6.98 (s, 1H) 7.21 (d, J=8.4 Hz, 1H) 7.32 (s, 1H) 7.51–7.53 (m, 2H)

Example 98c)

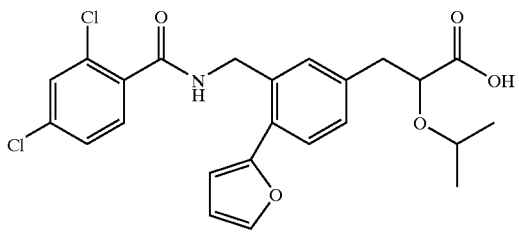

Ethyl 3-(3-[(tertiary butoxycarbonyl)amino]methyl-4-[(trifluoromethyl)sulfonyl]oxyphenyl)-2-(2-furyl) propoxypropionate was treated in the same method as in Example 38, to give 3-(3-[(2,4-dichlorobenzoyl)amino] methyl-4-(2-furyl)phenyl)-2-isopropoxypropionic acid.

MS m/e(ESI) 476 (MH$^+$)

Example 99

Production Example 99a)

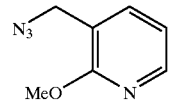

7.4 g of 2-methoxy-3-hydroxymethylpyridine was dissolved in 100 ml toluene, and 13.8 ml diphenyl phosphoryl azide and 9.5 ml diazabicyclo[5.4.0]undecene were added, and the mixture was stirred overnight at room temperature. Water was added to the reaction product which was then extracted with ethyl acetate. The organic layer was washed with brine, dried over anhydrous magnesium sulfate and the solvent was evaporated, to give 9.5 g of [(2-methoxy-3-pyridyl)methyl]azide.

¹H-NMR(CDCl₃) δ: 4.00 (s, 3H) 4.35 (s, 2H) 6.89–6.92 (m, 1H) 7.55–7.57 (m, 1H) 8.15–8.16 (m, 1H)

Production Example 99b)

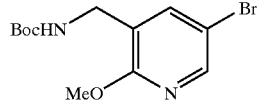

9.5 g of [(2-methoxy-3-pyridyl)methyl]azide was dissolved in 100 ml ethyl acetate, and 13 g of tertiary butyl dicarbonate and 3 g of 10% palladium-carbon were added, and the mixture was stirred at room temperature for 3 hours in a hydrogen atmosphere. The reaction mixture was filtered through Celite, and the filtrate was concentrated, and the residue was purified by silica gel column chromatography, and from fractions eluted with hexane-ethyl acetate (5:1→44:1), 6.84 g of tertiary butyl N-[(2-methoxy-3-pyridyl)methyl]carbamate was obtained. 2.916 g of this crude product was dissolved in 30 ml acetonitrile, and 2.19 g of N-bromosuccimide was added. After stirring at room temperature for 3 days, the solvent was evaporated and the residue was dissolved in ethyl acetate. The organic layer was successively washed with water and brine, dried over anhydrous magnesium sulfate and the solvent was evaporated. The residue was washed with a mixed solvent of diethyl ether, ethyl acetate and hexane, to give 1.185 g of N-[(5-bromo-2-methoxy-3-pyridyl)methyl]carbamate.

¹H-NMR(CDCl₃) δ: 1.44 (s, 9H) 3.94 (s, 3H) 4.22 (d, J=6.0 Hz, 2H) 5.02 (br, 1H) 7.62 (s, 1H) 8.01 (s, 1H)

Production Example 99c)

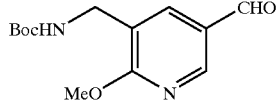

1.009 g of N-[(5-bromo-2-methoxy-3-pyridyl)methyl] carbamate, 45 mg of dichlorobistriphenylphosphine palladium, 325 mg of sodium formate and 17 mg of triphenylphosphine were dissolved in 3 ml anhydrous N,N-dimethylformamide, followed by stirring at 110° C. for 2.5 hours in a carbon monoxide atmosphere. The reaction mixture was diluted with ethyl acetate, and the organic layer was washed with water and saturated aqueous sodium bicarbonate solution, dried over anhydrous magnesium sulfate and the solvent was evaporated. The residue was purified by silica gel column chromatography, to give 401 mg of tertiary butyl N-[(5-formyl-2-methoxy-3-pyridyl)methyl]carbamate was obtained from fractions eluted with hexane-ethyl acetate (3.5:1).

¹H-NMR(CDCl₃) δ: 1.46 (s, 9H) 4.08 (s, 3H) 4.31 (d, J=6.0 Hz, 2H) 5.02 (br, 1H) 8.01 (d, J=2.4 Hz, 1H) 8.54 (d, J=2.0 Hz, 1H)

Production Example 99d)

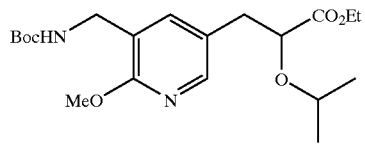

510 mg of diethyl ethyl-2-isopropoxyphosphonoacetate was dissolved in 5 ml tetrahydrofuran, and 70 mg of sodium hydride was added. After stirring at room temperature for 15 minutes, a solution of 401 mg N-[(5-formyl-2-methoxy-3-pyridyl)methyl]carbamate in 2 ml N,N-dimethylformamide was added thereto. The mixture was stirred at room temperature for 15 minutes, and the reaction mixture was diluted with ethyl acetate. The organic layer was washed with water and brine, dried over anhydrous magnesium sulfate and the solvent was evaporated. The residue was dissolved in 8 ml ethyl acetate and 2 ml ethanol, and 200 mg of 10% palladium-carbon was added, and the mixture was stirred overnight at room temperature in a hydrogen atmosphere. The reaction mixture was filtered through Celite, the filtrate was concentrated and the residue was purified by silica gel column chromatography, and from fractions eluted with hexane-ethyl acetate (4:1→2.5:1), 514 mg of ethyl 3-(5-[(tertiary butoxycarbonyl)amino]methyl-6-methoxy-3-pyridyl)-2-isopropoxypropionate was obtained.

¹H-NMR(CDCl₃) δ: 0.96 (d, J=6.0 Hz, 3H) 1.16 (d, J=6.0 Hz, 3H) 1.27 (t, J=7.2 Hz, 3H) 1.45 (s, 9H) 2.85 (dd, J=8.4, 14.0 Hz, 1H) 2.92 (dd, J=4.8, 14.0 Hz, 1H) 3.52 (sept, J=6.0 Hz) 3.96 (s, 3H) 3.99 (dd, J=4.8, 8.4 Hz, 1H) 4.17–4.24 (m, 4H) 5.03 (br, 1H) 7.47 (s, 1H) 7.93 (d, J=2.0 Hz, 1H)

Example 99e)

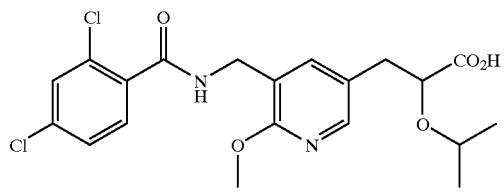

Ethyl 3-(5-[(tertiary butoxycarbonyl)amino]methyl-6-methoxy-3-pyridyl)-2-isopropoxypropionate was treated in the same method as in Example 38, to give 3-(5-[(2,4-dichlorobenzoyl)amino]methyl-6-methoxy-3-pyridyl)-2-isopropoxypropionic acid.

MS m/e(ESI) 441 (MH⁺)

Example 100

Production Example 100a)

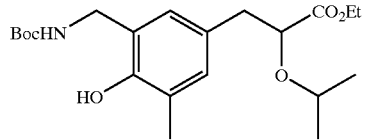

253 mg of ethyl 3-(3-bromo-5-[(tertiary butoxycarbonyl)amino]methyl-4-hydroxyphenyl)-2-isopropoxypropionate was dissolved in 3 ml acetonitrile, and 157 mg of N-iodosuccinimide was added thereto. After stirring at room temperature for 2.5 hours, the reaction mixture was diluted with ethyl acetate. The organic layer was washed with water and saturated aqueous sodium thiosulfate, dried over anhydrous magnesium sulfate and the solvent was evaporated. The residue was purified by silica gel column chromatography, to give 100 mg of ethyl 3-(3-iodo-5-[(tertiary butoxycarbonyl)amino]methyl-4-hydroxyphenyl)-2-isopropoxypropionate was obtained from fractions eluted with hexane-ethyl acetate (4:1).

¹H-NMR(CDCl₃) δ: 0.99 (d, J=6.0 Hz, 3H) 1.16 (d, J=6.0 Hz, 3H) 1.24 (t, J=6.8 Hz, 3H) 1.44 (s, 9H) 2.80 (dd, J=8.0, 13.6 Hz, 1H) 2.86 (dd, J=5.6, 13.6 Hz, 1H) 3.50 (sept, J=6.4 Hz, 1H) 3.96 (dd, J=5.2, 8.8 Hz, 1H) 4.15–4.23 (m, 5H) 6.96 (d, J=1.6 Hz, 1H) 7.58 (d, J=1.6 Hz, 1H)

Production Example 100b)

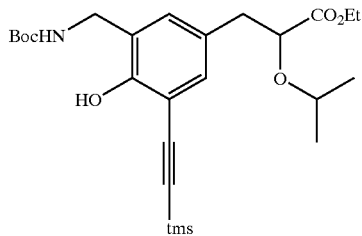

305 mg of ethyl 3-(3-iodo-5-[(tertiary butoxycarbonyl)amino]methyl-4-hydroxyphenyl)-2-isopropoxypropionate was dissolved in 3 ml N,N-dimethylformamide. 120 mg of trimethyl silyl acetylene, 70 mg of tetrakistriphenylphosphine palladium, 11.5 mg of copper iodide and 0.5 ml triethylamine were added thereto, followed by stirring overnight at room temperature. The reaction mixture was diluted with ethyl acetate, and the organic layer was washed with water and saturated ammonium chloride solution, dried over anhydrous magnesium sulfate and the solvent was evpoarated. The residue was purified by silica gel column chromatography, and from fractions eluted with hexane-ethyl acetate (6:1), 165 mg of ethyl 3-3-[(tertiary butoxycarbonyl)amino]methyl-4-hydroxy-5-[2-(1,1,1-trimethylsilyl)-1-ethynyl]phenyl-2-isopropoxypropionate was obtained.

¹H-NMR(CDCl₃) δ: 0.27 (s, 9H) 0.96 (d, J=6.0 Hz, 3H) 1.15 (d, J=6.4 Hz, 3H) 1.24 (t, J=7.2 Hz, 3H) 1.44 (s, 9H) 2.80 (dd, J=9.2, 14.4 Hz, 1H) 2.88 (dd, J=5.2, 14.0 Hz, 1H) 3.49 (sept, J=6.4 Hz, 1H) 3.96 (dd, J=4.8, 8.8 Hz, 1H) 4.13–4.21 (m, 3H) 4.24 (d, J=6.0 Hz, 2H) 5.11 (br, 1H) 7.05 (d, J=1.6 Hz, 1H) 7.19 (d, J=2.4 Hz, 1H)

Production Example 100c)

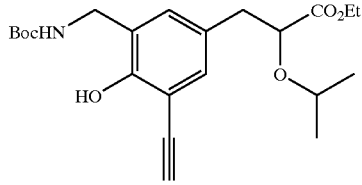

165 mg of ethyl 3-3-[(tertiary butoxycarbonyl)amino]methyl-4-hydroxy-5-[2-(1,1,1-trimethylsilyl)-1-ethynyl]phenyl-2-isopropoxypropionate was dissolved in 2 ml tetrahydrofuran, and 40 μl acetic acid and 0.5 ml tetrabutyl ammonium fluoride (1 M solution in tetrahydrofuran) were added thereto, followed by stirring at room temperature for 1 hour. The reaction mixture was diluted with ethyl acetate, and the organic layer was washed with water and saturated aqueous sodium bicarbonate solution, dried over anhydrous magnesium sulfate and the solvent was evpoarated. The residue was purified by silica gel column chromatography, to give 122 mg of ethyl 3-3-[(tertiary butoxycarbonyl)amino]methyl-4-hydroxy-5-(1-ethynyl)phenyl-2-isopropoxypropionate from fractions eluted with hexane-ethyl acetate (3:1).

¹H-NMR(CDCl₃) δ: 0.97 (d, J=6.0 Hz, 3H) 1.15 (d, J=6.4 Hz, 3H) 1.26 (t, J=7.2 Hz, 3H) 1.44 (s, 9H) 2.81 (dd, J=9.2, 14.4 Hz, 1H) 2.88 (dd, J=5.2, 14.0 Hz, 1H) 3.36 (s, 1H) 3.50 (sept, J=6.4 Hz, 1H) 3.97 (dd, J=4.8, 8.8 Hz, 1H) 4.15–4.22 (m, 2H) 4.23 (d, J=6.8 Hz, 2H) 7.04 (s, 1H) 7.20 (s, 1H)

Production Example 100d)

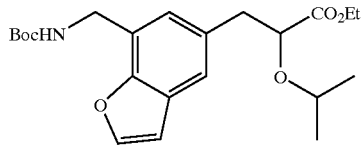

121 mg of ethyl 3-3-[(tertiary butoxycarbonyl)amino]methyl-4-hydroxy-5-(1-ethynyl)phenyl-2-isopropoxypropionate was dissolved in 2 ml N,N-dimethylformamide, and 50 mg potassium carbonate was added. After stirring overnight at 60–70° C., the reaction mixture was diluted with ethyl acetate. The organic layer was washed with water and brine, dried over anhydrous magnesium sulfate and the solvent was evaporated. The residue was purified by silica gel column chromatography, and from fractions eluted with hexane-ethyl acetate (6:1), 57 mg of ethyl 3-(7-[(tertiary butoxycarbonyl)amino]methylbenzo[b]furan-5-yl)-2-isopropoxypropionate was obtained.

¹H-NMR(CDCl₃) δ: 0.94 (d, J=6.0 Hz, 3H) 1.15 (d, J=6.0 Hz, 3H) 1.23 (t, J=6.8 Hz, 3H) 1.46 (s, 9H) 3.01 (dd, J=8.8, 14.0 Hz, 1H) 3.08 (dd, J=5.2, 14.0 Hz, 1H) 3.49 (sept, J=6.4 Hz, 1H) 4.07 (dd,J=5.2, 8.4 Hz, 1H) 4.12–4.19 (m, 2H) 4.60 (brs, 2H) 5.01 (br, 1H) 6.72 (s, 1H) 7.13 (s, 1H) 7.39 (d, J=1.6 Hz, 1H) 7.61 (d, J=2.0 Hz,1H)

Example 100e)

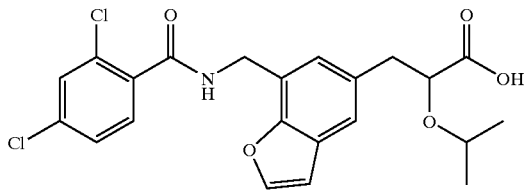

Ethyl 3-(7-[(tertiary butoxycarbonyl)amino]methylbenzo[b]furan-5-yl)-2-isopropoxypropionate was treated in the same method as in Example 38, to give 3-(7-[(2,4-dichlorobenzoyl)amino]methylbenzo[b]furan-5-yl)-2-isopropoxypropionic acid.

MS m/e (ESI) 451 (MH⁺)

Example 101

Production Example 101a)

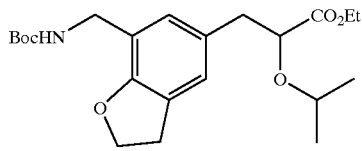

29 mg of ethyl 3-(7-[(tertiary butoxycarbonyl)amino]methylbenzo[b]furan-5-yl)-2-isopropoxypropionate was dissolved in ethanol, and 30 mg of 10% palladium-carbon was added, and the mixture was stirred at room temperature for 3 days in a hydrogen atmosphere. The reaction mixture was filtered through Celite, and the filtrate was concentrated, to give 27 mg of ethyl 3-(7-[(tertiary butoxycarbonyl)amino]methyl-2,3-dihydrobenzo[b]furan-5-yl)-2-isopropoxypropionate.

$^1$H-NMR(CDCl$_3$) δ: 0.99 (d, J=6.0 Hz, 3H) 1.15 (d, J=6.0 Hz, 3H) 1.25 (t, J=6.8 Hz, 3H) 1.45 (s, 9H) 2.85 (dd, J=8.4, 14.0 Hz, 1H) 2.92 (dd, J=4.8, 14.0 Hz, 1H) 3.17 (t, J=5.2 Hz, 2H) 3.50 (sept, J=6.0 Hz, 1H) 3.98 (dd, J=4.8, 8.4 Hz, 1H) 4.13–4.20 (m, 2H) 4.24 (brs, 2H) 4.57 (t, J=5.2 Hz, 2H) 4.97 (br, 1H) 6.91 (s, 1H) 7.00 (s, 1H)

Example 101b)

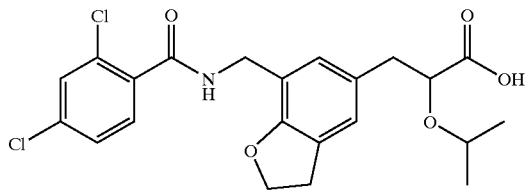

Ethyl 3-(7-[(tertiary butoxycarbonyl)amino]methyl-2,3-dihydrobenzo[b]furan-5-yl)-2-isopropoxypropionate was treated in the same method as in Example 38, to give 3-(7-[(2,4-dichlorobenzoyl)amino]methyl-2,3-dihydrobenzo[b]furan-5-yl)-2-isopropoxypropionic acid.

MS m/e(ESI) 481 (MH$^+$)

Example 102

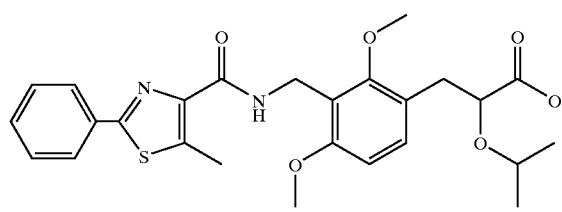

3-[2,4-Dimethoxy-3-([(5-methyl-2-phenyl-1,3-thiazole-4-yl)carbonyl]aminomethyl)phenyl]-2-isopropoxypropionic acid was obtained by treatment in the same method as in Example 87.

MS m/e(ESI) 499 (MH$^+$)

Example 103

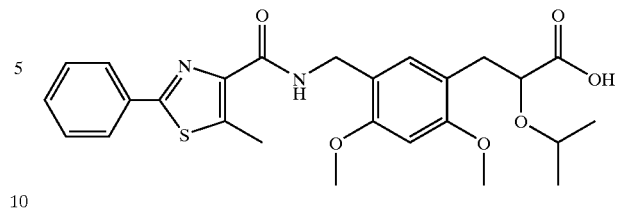

3-[2,4-Dimethoxy-5-([(5-methyl-2-phenyl-1,3-thiazole-4-yl)carbonyl]aminomethyl)phenyl]-2-isopropoxypropionic acid was obtained by treatment in the same method as in Example 88.

MS m/e(ESI) 499 (MH$^+$)

Example 104

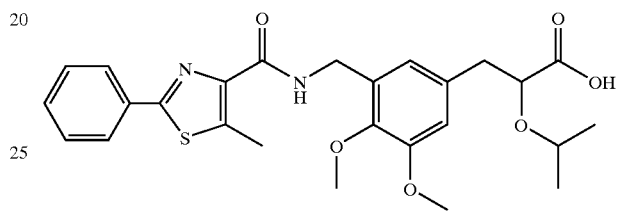

3-[3,4-Dimethoxy-5-([(5-methyl-2-phenyl-1,3-thiazole-4-yl)carbonyl]aminomethyl)phenyl]-2-isopropoxypropionic acid was obtained by treatment in the same method as in Example 89.

MS m/e(ESI) 499 (MH$^+$)

Example 105

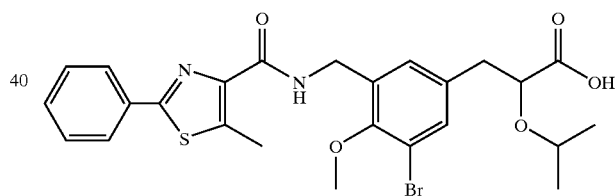

3-[3-Bromo-4-methoxy-5-([(5-methyl-2-phenyl-1,3-thiazole-4-yl)carbonyl]aminomethyl)phenyl]-2-isopropoxypropionic acid was obtained by treatment in the same method as in Example 90.

MS m/e(ESI) 548 (MH$^+$)

Example 106

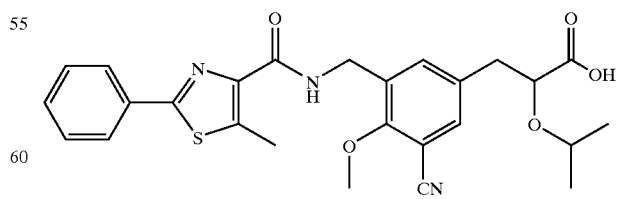

3-[3-Cyano-4-methoxy-5-([(5-methyl-2-phenyl-1,3-thiazole-4-yl)carbonyl]aminomethyl)phenyl]-2-isopropoxypropionic acid was obtained by treatment in the same method as in Example 91.

MS m/e(ESI) 494 (MH⁺)

Example 107

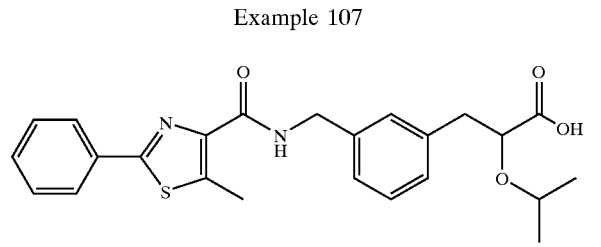

2-Isopropoxy-3-[3-([(5-methyl-2-phenyl-1,3-thiazole-4-yl)carbonyl]aminomethyl)phenyl]]propionic acid was obtained by treatment in the same method as in Example 92.

MS m/e(ESI) 439 (MH⁺)

Example 108

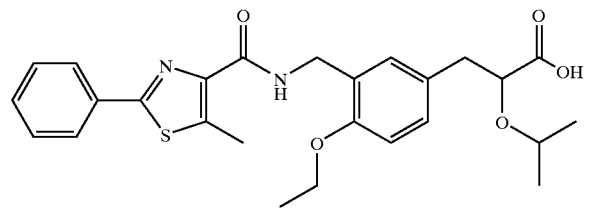

3-[4-Ethoxy-3-([(5-methyl-2-phenyl-1,3-thiazole-4-yl)carbonyl]aminomethyl)phenyl]-2-isopropoxypropionic acid was obtained by treatment in the same method as in Example 93.

MS m/e(ESI) 483 (MH⁺)

Example 109

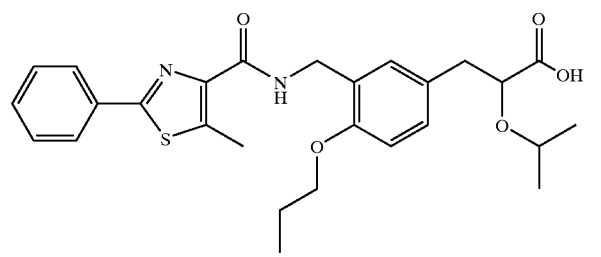

3-[4-Propoxy-3-([(5-methyl-2-phenyl-1,3-thiazole-4-yl)carbonyl]aminomethyl)phenyl]-2-isopropoxypropionic acid was obtained by treatment in the same method as in Example 94.

MS m/e(ESI) 497 (MH⁺)

Example 110

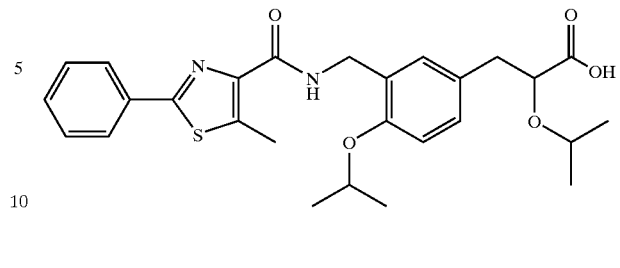

3-[4-Isopropoxy-3-([(5-methyl-2-phenyl-1,3-thiazole-4-yl)carbonyl]aminomethyl)phenyl]-2-isopropoxypropionic acid was obtained by treatment in the same method as in Example 95.

MS m/e(ESI) 497 (MH⁺)

Example 111

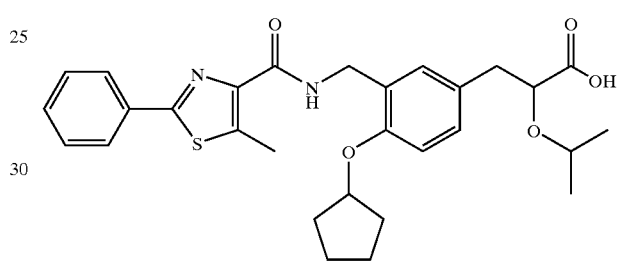

3-[4-Cyclopentyloxy-3-([(5-methyl-2-phenyl-1,3-thiazole-4-yl)carbonyl]aminomethyl)phenyl]-2-isopropoxypropionic acid was obtained by treatment in the same method as in Example 96.

MS m/e(ESI) 523 (MH⁺)

Example 112

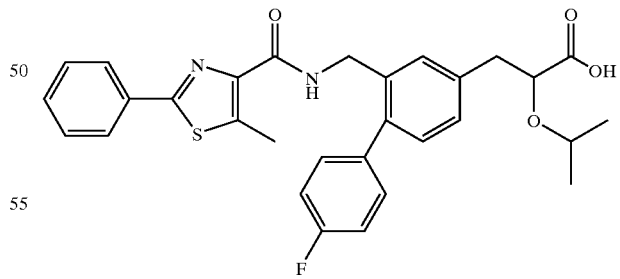

3-[4-(4-Fluorophenyl)-3-([(5-methyl-2-phenyl-1,3-thiazole-4-yl)carbonyl]aminomethyl)phenyl]-2-isopropoxypropionic acid was obtained by treatment in the same method as in Example 97.

MS m/e(ESI) 533 (MH⁺)

Example 113

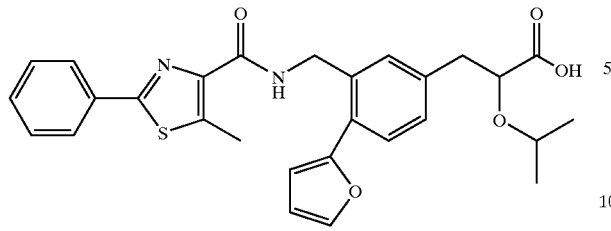

3-[4-(4-Furyl)-3-([[(5-methyl-2-phenyl-1,3-thiazole-4-yl)carbonyl]aminomethyl)phenyl]-2-isopropoxypropionic acid was obtained by treatment in the same method as in Example 98.

MS m/e(ESI) 505 (MH+)

Example 114

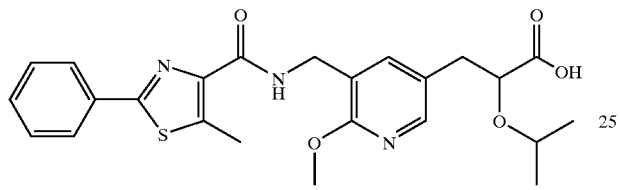

2-Isopropoxy-3-[6-methoxy-5-([(5-methyl-2-phenyl-1,3-thiazole-4-yl)carbonyl]aminomethyl)-3-pyridyl]propionic acid was obtained by treatment in the same method as in Example 99.

MS m/e(ESI) 470 (MH+)

Example 115

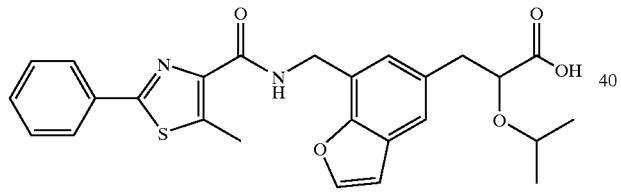

2-Isopropoxy-3-[7-([[(5-methyl-2-phenyl-1,3-thiazole-4-yl)carbonyl]aminomethyl)benzo[b]furan-5-yl)propionic acid was obtained by treatment in the same method as in Example 100.

MS m/e(ESI) 479 (MH+)

Example 116

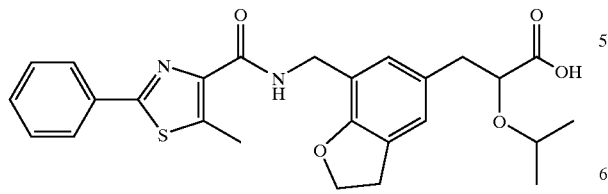

2-Isopropoxy-3-[7-([[(5-methyl-2-phenyl-1,3-thiazole-4-yl)carbonyl]aminomethyl)-2,3-dihydrobenzo[b]furan-5-yl]propionic acid was obtained by treatment in the same method as in Example 101.

MS m/e(ESI) 480 (MH+)

Example 117

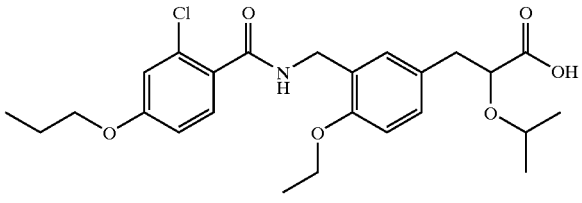

3-(3-([[(2-Chloro-4-propoxybenzoyl)amino]methyl-4-ethoxyphenyl)-2-isopropoxypropionic acid was obtained by treatment in the same method as in Example 93.

MS m/e(ESI) 498 (MH+)

Example 118

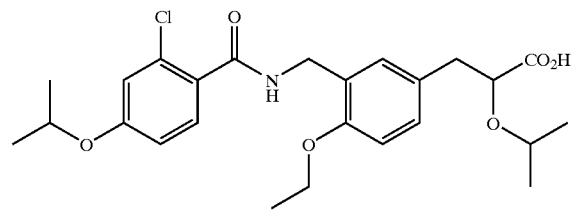

3-(3-([[(2-Chloro-4-isopropoxybenzoyl)amino]methyl-4-ethoxyphenyl)-2-isopropoxypropionic acid was obtained by treatment in the same method as in Example 93.

$^1$H-NMR(CDCl$_3$) δ: 1.04 (d, J=6.0 Hz, 3H) 1.15 (d, J=6.0 Hz, 3H) 1.34 (d, J=6.0 Hz, 6H) 1.43 (t, J=7.2 Hz, 3H) 2.90 (dd, J=8.0, 14.0 Hz, 1H) 3.06 (dd, J=4.4, 14.0 Hz, 1H) 3.57 (sept, J=6.0 Hz, 1H) 4.06 (q, J=7.2 Hz, 2H) 4.11 (dd, J=4.4, 8.0 Hz, 1H) 4.56 (sept, J=6.0 Hz, 1H) 4.62 (d, J=5.6 Hz, 2H) 6.79 (d, J=8.8 Hz, 1H) 6.81 (dd, J=2.4,8.4 Hz, 1H) 6.87 (d, J=2.8 Hz, 1H) 7.07 (br, 1H) 7.12 (dd, J=2.4, 8.4 Hz, 1H) 7.23 (d, J=2.4 Hz, 1H) 7.74 (d, J=8.4 Hz, 1H)

MS m/e(ESI) 478 (MH+)

Example 119

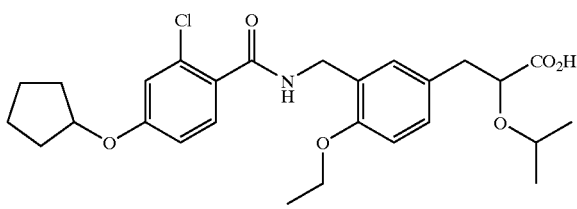

3-(3-([[(2-Chloro-4-cyclopentyloxybenzoyl)amino]methyl-4-ethoxyphenyl)-2-isopropoxypropionic acid was obtained by treatment in the same method as in Example 93.

$^1$H-NMR(CDCl$_3$) δ: 1.04 (d, J=6.0 Hz, 3H) 1.15 (d, J=6.0 Hz, 3H) 1.43 (t, J=7.2 Hz, 3H) 1.61–1.65 (m, 2H) 1.74–1.94 (m, 6H) 2.90 (dd, J=8.0, 14.0 Hz, 1H) 3.05 (dd, J=4.4, 14.0 Hz, 1H) 3.57 (sept, J=6.0 Hz, 1H) 4.06 (q, J=7.2 Hz, 2H) 4.10 (dd, J=4.4, 8.0 Hz, 1H) 4.62 (d, J=5.6 Hz, 2H) 4.74–4.77 (m, 1H) 6.78 (d, J=8.0 Hz, 1H) 6.80 (dd, J=2.4, 8.4 Hz, 1H) 6.86 (d, J=2.4 Hz, 1H) 7.08 (brt, J=5.6 Hz, 1H) 7.12 (dd, J=2.4, 8.4 Hz, 1H) 7.23 (d, J=2.4 Hz, 1H) 7.73 (d, J=8.4 Hz, 1H)

MS m/e(ESI) 504 (MH+)

Example 120

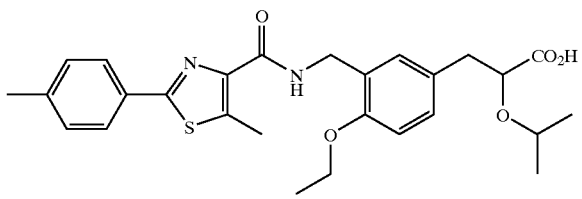

3-3-[([2-(4-Methylphenyl)-5-methyl-1,3-thiazole-4-yl]carbonylamino)methyl]-4-ethoxyphenyl-2-isopropoxypropionic acid was obtained by treatment in the same method as in Example 93.

$^{1}$H-NMR(CDCl$_3$) δ: 1.06 (d, J=6.0 Hz, 3H) 1.17 (d, J=6.0 Hz, 3H) 1.48 (t, J=7.2 Hz, 3H) 2.04 (s, 3H) 2.71 (s, 3H) 2.92 (dd, J=8.0, 14.0 Hz, 1H) 3.06 (dd, J=4.4, 14.0 Hz, 1H) 3.59 (sept, J=6.0 Hz, 1H) 4.08–4.13 (m, 3H) 4.59 (d, J=5.6 Hz, 2H) 4.74–4.77 (m, 1H) 6.53 (brt, J=6.4 Hz, 1H) 6.81 (d, J=8.4 Hz, 1H) 7.13 (dd, J=2.4, 8.4 Hz, 1H) 7.21 (d, J=2.4 Hz, 1H) 7.24 (d, J=8.0 Hz, 2H) 7.80 (d, J=8.4 Hz, 2H)

MS m/e(ESI) 497 (MH$^+$)

Example 121

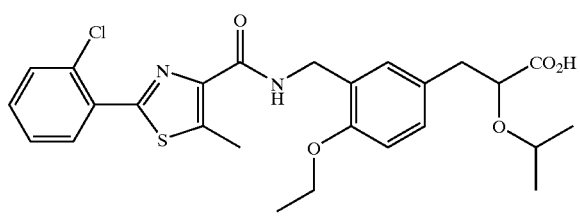

3-3-[([2-(2-Chlorophenyl)-5-methyl-1,3-thiazole-4-yl]carbonylamino)methyl]-4-ethoxyphenyl-2-isopropoxypropionic acid was obtained by treatment in the same method as in Example 93.

$^{1}$H-NMR(CDCl$_3$) δ: 1.06 (d, J=6.0 Hz, 3H) 1.17 (d, J=6.0 Hz, 3H) 1.48 (t, J=7.2 Hz, 3H) 2.75 (s, 3H) 2.92 (dd, J=8.0, 14.0 Hz, 1H) 3.06 (dd, J=4.4, 14.0 Hz, 1H) 3.59 (sept, J=6.0 Hz, 1H) 4.08–4.13 (m, 3H) 4.60 (d, J=6.0 Hz, 2H) 6.61 (brt, J=6.4 Hz, 1H) 6.82 (d, J=8.4 Hz, 1H) 7.14 (dd, J=2.4, 8.4 Hz, 1H) 7.22 (d, J=2.4 Hz, 1H) 7.35–7.40 (m, 1H) 7.48–7.51 (m, 1H) 8.24–8.27 (m, 1H)

MS m/e(ESI) 516 (MH$^+$)

Example 122

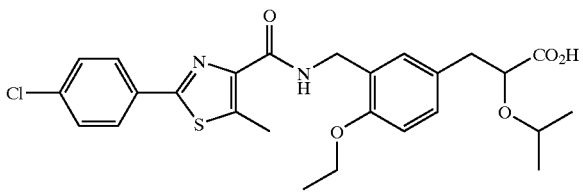

3-3-[([2-(4-Chlorophenyl)-5-methyl-1,3-thiazole-4-yl]carbonylamino)methyl]-4-ethoxyphenyl-2-isopropoxypropionic acid was obtained by treatment in the same method as in Example 93.

$^{1}$H-NMR(CDCl$_3$) δ: 1.06 (d, J=6.0 Hz, 3H) 1.17 (d, J=6.0 Hz, 3H) 1.48 (t, J=7.2 Hz, 3H) 2.71 (s, 3H) 2.92 (dd, J=8.0, 14.0 Hz, 1H) 3.06 (dd, J=4.4, 14.0 Hz, 1H) 3.59 (sept, J=6.0 Hz, 1H) 4.08–4.13 (m, 3H) 4.59 (d, J=6.0 Hz, 2H) 6.54 (brt, J=5.6 Hz, 1H) 6.82 (d, J=8.4 Hz, 1H) 7.14 (dd, J=2.4, 8.4 Hz, 1H) 7.21 (d, J=2.4 Hz, 1H) 7.41 (d, J=8.8 Hz, 2H) 7.86 (d, J=8.8 Hz, 2H)

MS m/e(ESI) 516 (MH$^+$)

Example 123

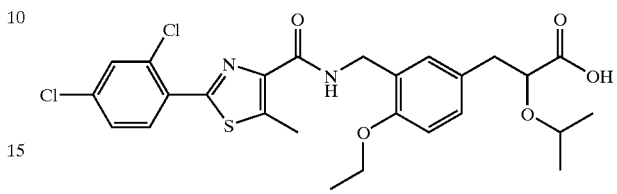

3-3-[([2-(2,4-Dichlorophenyl)-5-methyl-1,3-thiazole-4-yl]carbonylamino)methyl]-4-ethoxyphenyl-2-isopropoxypropionic acid was obtained by treatment in the same method as in Example 93.

MS m/e(ESI) 551 (MH$^+$)

Example 124

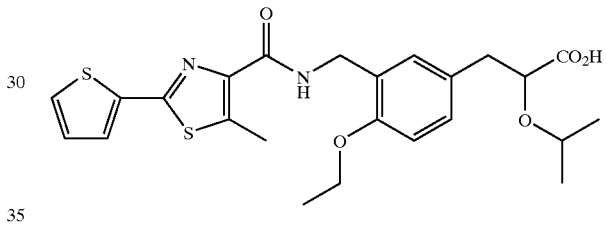

3-4-Ethoxy-3-[([5-methyl-2-(2-thienyl)-1,3-thiazole-4-yl]carbonylamino)methyl]phenyl-2-isopropoxypropionic acid was obtained by treatment in the same method as in Example 93.

$^{1}$H-NMR(CDCl$_3$) δ: 1.06 (d, J=6.0 Hz, 3H) 1.17 (d, J=6.0 Hz, 3H) 1.47 (t, J=7.2 Hz, 3H) 2.05 (s, 3H) 2.92 (dd, J=8.0, 14.0 Hz, 1H) 3.06 (dd, J=4.4, 14.0 Hz, 1H) 3.57 (sept, J=6.0 Hz, 1H) 4.08–4.13 (m, 3H) 4.58 (d, J=5.6 Hz, 2H) 6.50 (br, 1H) 6.82 (d, J=8.0 Hz, 1H) 7.09 (dd, J=3.6, 5.2 Hz, 1H) 7.13 (dd, J=2.4, 8.0 Hz, 1H) 7.21 (d, J=2.0 Hz, 1H) 7.48 (ddd, J=1.2, 5.2, 33.6 Hz, 1H)

MS m/e(ESI) 489 (MH$^+$)

Example 125

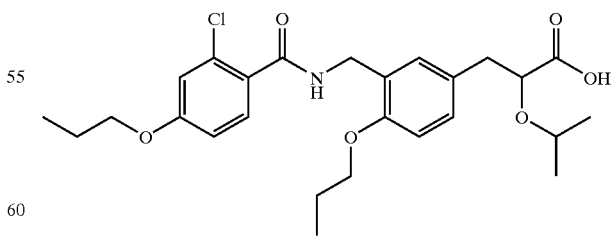

3-(3-[(2-Chloro-4-propoxybenzoyl)amino]methyl-4-propoxyphenyl)-2-isopropoxypropionic acid was obtained by treatment in the same method as in Example 94.

MS m/e(ESI) 492 (MH$^+$)

Example 126

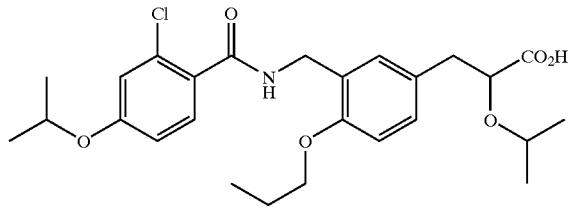

3-(3-([(2-Chloro-4-propoxybenzoyl)amino]methyl-4-isopropoxyphenyl)-2-isopropoxypropionic acid was obtained in the same treatment as in Example 94.

$^1$H-NMR(CDCl$_3$) δ: 1.04 (d, J=6.0 Hz, 3H) 1.05 (t, J=7.2 Hz, 3H) 1.16 (d, J=6.0 Hz, 3H) 1.33 (d, J=6.0 Hz, 6H) 1.79–1.87 (m, 2H) 2.90 (dd, J=8.0, 14.0 Hz, 1H) 3.06 (dd, J=4.4, 14.0 Hz, 1H) 3.57 (sept, J=6.0 Hz, 1H) 3.95 (t, J=7.2 Hz, 2H) 4.11 (dd, J=4.4, 8.0 Hz, 1H) 4.56 (sept, J=6.0 Hz, 1H) 4.63 (d, J=7.0 Hz, 2H) 6.79 (d, J=8.8 Hz, 1H) 6.81 (dd, J=2.4, 8.8 Hz, 1H) 6.86 (d, J=2.8 Hz, 1H) 6.99 (br, 1H) 7.11 (dd, J=2.4, 8.4 Hz, 1H) 7.23 (d, J=2.0 Hz, 1H) 7.72 (d, J=8.4 Hz, 1H)

MS m/e(ESI) 492 (MH$^+$)

Example 127

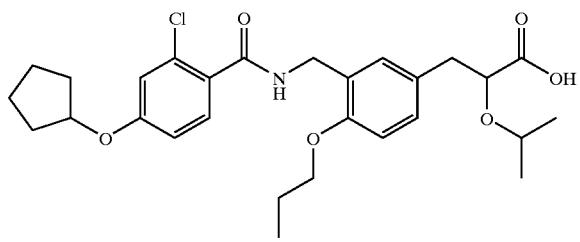

3-(3-[(2-Chloro-4-cyclopentyloxybenzoyl)amino]methyl-4-propoxyphenyl)-2-isopropoxypropionic acid was obtained in the same treatment as in Example 94.

MS m/e(ESI) 518 (MH$^+$)

Example 128

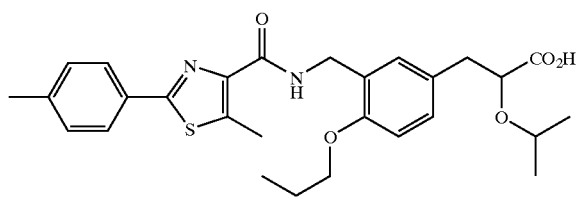

3-3-[([2-(4-Methylphenyl)-5-methyl-1,3-thiazole-4-yl]carbonylamino)methyl]-4-propoxyphenyl-2-isopropoxypropionic acid was obtained in the same treatment as in Example 94.

$^1$H-NMR(CDCl$_3$) δ: 1.06 (d, J=6.0 Hz, 3H) 1.09 (t, J=7.2 Hz, 3H) 1.17 (d, J=6.0 Hz, 3H) 1.82–1.91 (m, 2H) 2.40 (s, 3H) 2.71 (s, 3H) 2.92 (dd, J=8.0, 14.0 Hz, 1H) 3.06 (dd, J=4.4, 14.0 Hz, 1H) 3.59 (sept, J=6.0 Hz, 1H) 3.99 (t, J=6.8 Hz, 2H) 4.12 (dd, J=4.4, 8.0 Hz, 1H) 4.59 (d, J=6.0 Hz, 2H) 6.46 (brt, J=6.4 Hz, 1H) 6.82 (d, J=8.2 Hz, 1H) 7.14 (dd, J=2.4, 8.8 Hz, 1H) 7.22 (d, J=2.4 Hz, 1H) 7.24 (d, J=8.0 Hz, 2H) 7.80 (d, J=8.4 Hz, 2H)

MS m/e(ESI) 511 (MH$^+$)

Example 129

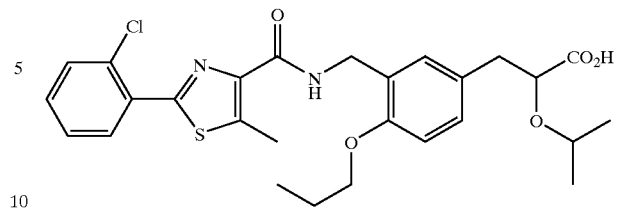

3-3-[([2-(2-Chlorophenyl)-5-methyl-1,3-thiazole-4-yl]carbonylamino)methyl]-4-propoxyphenyl-2-isopropoxypropionic acid was obtained by treatment in the same method as in Example 94.

$^1$H-NMR(CDCl$_3$) δ: 1.07 (d, J=6.0 Hz, 3H) 1.09 (t, J=7.6 Hz, 3H) 1.17 (d, J=6.0 Hz, 3H) 1.85–1.91 (m, 2H) 2.74 (s, 3H) 2.92 (dd, J=8.0, 14.0 Hz, 1H) 3.06 (dd, J=4.4, 14.0 Hz, 1H) 3.59 (sept, J=6.0 Hz, 1H) 3.99 (t, J=6.4 Hz, 2H) 4.12 (dd, J=4.4, 8.0 Hz, 1H) 4.60 (d, J=6.0 Hz, 2H) 6.57 (brt, J=6.4 Hz, 1H) 6.82 (d, J=8.4 Hz, 1H) 7.14 (dd, J=2.4, 8.4 Hz, 1H) 7.22 (d, J=2.4 Hz, 1H) 7.35–7.40 (m, 2H) 7.48–7.51 (m, 1H) 8.24–8.27 (m, 1H)

MS m/e(ESI) 531 (MH$^+$)

Example 130

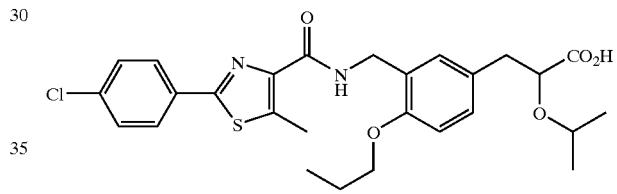

3-3-[([2-(4-Chlorophenyl)-5-methyl-1,3-thiazole-4-yl]carbonylamino)methyl]-4-propoxyphenyl-2-isopropoxypropionic acid was obtained by treatment in the same method as in Example 94.

$^1$H-NMR(CDCl$_3$) δ: 1.06 (d, J=6.0 Hz, 3H) 1.08 (t, J=7.6 Hz; 3H) 1.17 (d, J=6.0 Hz, 3H) 1.84–1.89 (m, 2H) 2.70 (s, 3H) 2.92 (dd, J=8.0, 14.0 Hz, 1H) 3.05 (dd, J=4.4, 14.0 Hz, 1H) 3.60 (sept, J=6.0 Hz, 1H) 3.99 (t, J=6.4 Hz, 2H) 4.12 (dd, J=4.4, 8.0 Hz, 1H) 4.59 (d, J=5.6 Hz, 2H) 6.49 (brt, J=6.4 Hz, 1H) 6.82 (d, J=8.4 Hz, 1H) 7.14 (dd, J=2.4, 8.4 Hz, 1H) 7.21 (d, J=2.4 Hz, 1H) 7.41 (d. J=8.8 Hz, 2H) 7.85 (d, J=8.8 Hz, 2H)

MS m/e(ESI) 531 (MH$^+$)

Example 131

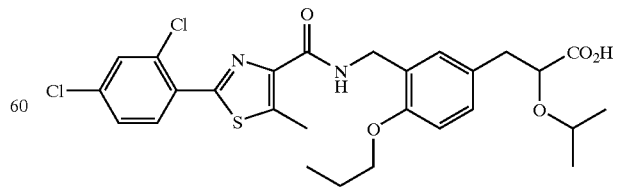

3-3-[([(2-(2,4-Dichlorophenyl)-5-methyl-1,3-thiazole-4-yl]carbonylamino)methyl]-4-propoxyphenyl-2- isopropoxypropionic acid was obtained by treatment in the same method as in Example 94.

¹H-NMR(CDCl₃) δ: 1.07 (d, J=6.0 Hz, 3H) 1.07 (t, J=7.2 Hz, 3H) 1.17 (d, J=6.0 Hz, 3H) 1.83–1.92 (m, 2H) 2.73 (s, 3H) 2.92 (dd, J=7.2, 14.0 Hz, 1H) 3.06 (dd, J=4.0, 14.0 Hz, 1H) 3.60 (sept, J=6.0 Hz, 1H) 3.99 (t, J=6.4 Hz, 2H) 4.12 (dd, J=4.4, 8.0 Hz, 1H) 4.60 (d, J=5.6 Hz, 2H) 6.55 (brt, J=6.4 Hz, 1H) 6.82 (d, J=8.4 Hz, 1H) 7.14 (dd, J=2.4, 8.4 Hz, 1H) 7.22 (d, J=2.4 Hz, 1H) 7.36 (dd, J=2.4, 8.8 Hz, 1H) 7.51 (d, J=2.0 Hz, 1H) 8.26 (d, J=8.4 Hz, 1H)

MS m/e(ESI) 565 (MH⁺)

Example 132

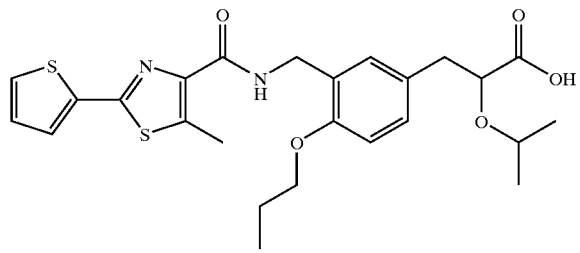

3-4-Propoxy-3-[([5-methyl-2-(2-thienyl)-1,3-thiazole-4-yl]carbonylamino)methyl]phenyl-2-isopropoxypropionic acid was obtained by treatment in the same method as in Example 94.

MS m/e(ESI) 503 (MH⁺)

Example 133

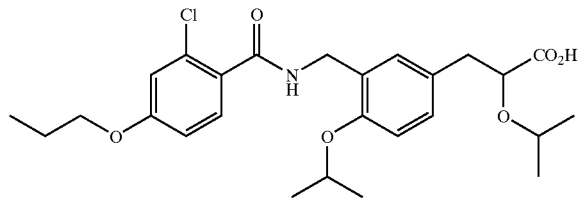

3-(3-[(2-Chloro-4-propoxybenzoyl)amino]methyl-4-isopropoxyphenyl)-2-isopropoxypropionic acid was obtained by treatment in the same method as in Example 95.

¹H-NMR(CDCl₃) δ: 1.03 (t, J=7.2 Hz, 3H) 1.04 (d, J=6.0 Hz, 3H) 1.16 (d, J=6.0 Hz, 3H) 1.35 (d, J=6.0 Hz, 6H) 1.78–1.83 (m, 2H) 2.90 (dd, J=7.2, 14.0 Hz, 1H) 3.05 (dd, J=4.0, 14.0 Hz, 1H) 3.57 (sept, J=6.0 Hz, 1H) 3.92 (t, J=6.4 Hz, 2H) 4.10 (dd, J=4.0, 7.2 Hz, 1H) 4.56–4.61 (m, 3H) 6.80 (d, J=8.4 Hz, 1H) 6.83 (dd, J=2.4, 8.4 Hz, 1H) 6.89 (d, J=2.4 Hz, 1H) 7.04 (brt, J=5.2 Hz, 1H) 7.11 (dd, J=2.4, 8.4 Hz, 1H) 7.23 (d, J=2.4 Hz, 1H) 7.74 (d, J=8.8 Hz, 1H)

MS m/e(ESI) 492 (MH⁺)

Example 134

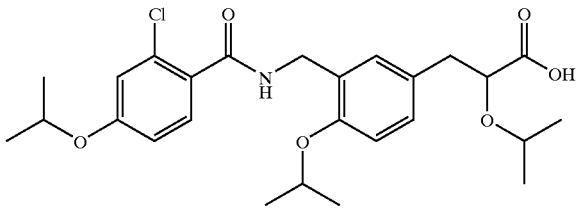

3-(3-[(2-Chloro-4-isopropoxybenzoyl)amino]methyl-4-isopropoxyphenyl)-2-isopropoxypropionic acid was obtained by treatment in the same method as in Example 95.

MS m/e(ESI) 492 (MH⁺)

Example 135

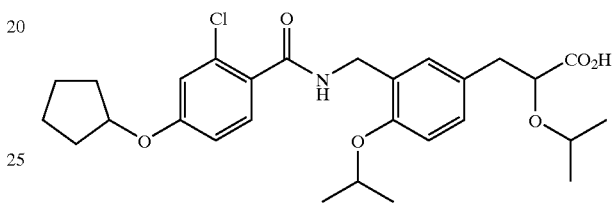

3-(3-[(2-Chloro-4-cyclopentyloxybenzoyl)amino]methyl-4-isopropoxyphenyl)-2-isopropoxypropionic acid was obtained by treatment in the same method as in Example 95.

¹H-NMR(CDCl₃) δ: 1.04 (d, J=6.0 Hz, 3H) 1.16 (d, J=6.0 Hz, 3H) 1.35 (d, J=6.0 Hz, 6H) 1.61–1.65 (m, 2H) 1.75–1.94 (m, 6H) 2.90 (dd, J=7.2, 14.0 Hz, 1H) 3.05 (dd, J=4.0, 14.0 Hz, 1H) 3.57 (sept, J=6.0 Hz, 1H) 4.10 (dd, J=4.0, 7.2 Hz, 1H) 4.60 (d, J=5.6 Hz, 3H) 4.76 (sept, J=6.0 Hz, 1H) 6.80 (d, J=8.8 Hz, 1H) 6.81 (d, J=8.8 Hz, 1H) 6.86 (d, J=2.4 Hz, 1H) 7.05 (brt, J=5.6 Hz, 1H) 7.11 (dd, J=2.4, 8.4 Hz, 1H) 7.23 (d, J=2.0 Hz, 2H) 7.73 td, J=8.8 Hz, 2H)

MS m/e(ESI) 518 (MH⁺)

Example 136

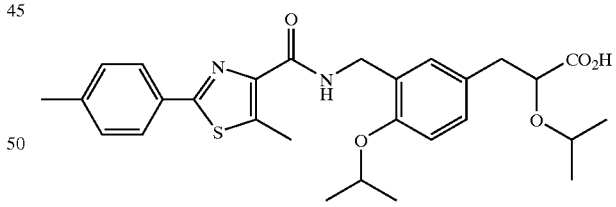

3-3-[([2-(4-Methylphenyl)-5-methyl-1,3-thiazole-4-yl)carbonylamino)methyl]-4-isopropoxyphenyl-2-isopropoxypropionic acid was obtained by treatment in the same method as in Example 95.

¹H-NMR(CDCl₃) δ: 1.06 (d, J=6.0 Hz, 3H) 1.17 (d, J=6.0 Hz, 3H) 1.39 (d, J=6.0 Hz, 6H) 2.40 (s, 3H) 2.71 (s, 3H) 2.91 (dd, J=7.2, 14.0 Hz, 1H) 3.05 (dd, J=4.0, 14.0 Hz, 1H) 3.59 (sept, J=6.0 Hz, 1H) 4.11 (dd, J=4.0, 7.2 Hz, 1H) 4.56 (d, J=5.6 Hz, 2H) 4.63 (sept, J=6.0 Hz, 1H) 6.53 (brt, J=5.6 Hz, 1H) 6.83 (d, J=8.4 Hz, 1H) 7.13 (dd, J=2.4, 8.4 Hz, 1H) 7.21 (d, J=2.4 Hz, 1H) 7.24 (d, J=8.4 Hz, 2H) 7.80 (d, J=8.4 Hz, 2H)

MS m/e(ESI) 511 (MH⁺)

Example 137

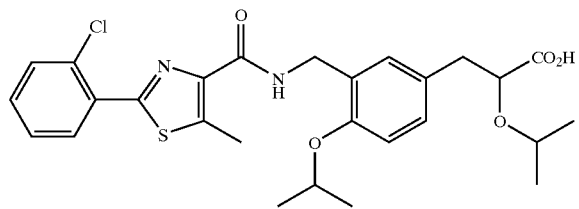

3-3-[([2-(2-Chlorophenyl)-5-methyl-1,3-thiazole-4-yl]carbonylamino)methyl]-4-isopropoxyphenyl-2-isopropoxypropionic acid was obtained by treatment in the same method as in Example 95.

$^1$H-NMR(CDCl$_3$) δ: 1.07 (d, J=6.0 Hz, 3H) 1.17 (d, J=6.0 Hz, 3H) 1.40 (d, J=6.0 Hz, 6H) 2.75 (s, 3H) 2.92 (dd, J=7.2, 14.0 Hz, 1H) 3.05 (dd, J=4.0, 14.0 Hz, 1H) 3.60 (sept, J=6.0 Hz, 1H) 4.12 (dd, J=4.0, 7.2 Hz, 1H) 4.58 (d, J=5.6 Hz, 2H) 4.64 (sept, J=6.0 Hz, 1H) 6.63 (brt, J=5.6 Hz, 1H) 6.83 (d, J=8.4 Hz, 1H) 7.13 (dd, J=2.4, 8.4 Hz, 1H) 7.21 (d, J=2.4 Hz, 1H) 7.35–7.39 (m,2H) 7.48–7.50 (m, 1H) 8.25–8.27 (m, 1H)

MS m/e(ESI) 531 (MH$^+$)

Example 138

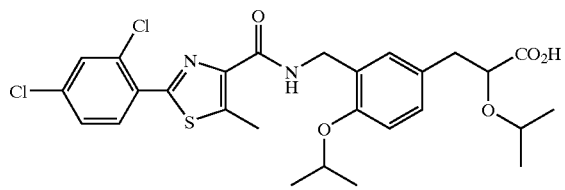

3-3-[([2-(2,4-Dichlorophenyl)-5-methyl-1,3-thiazole-4-yl)carbonylamino)methyl]-4-isopropoxyphenyl-2-isopropoxypropionic acid was obtained by treatment in the same method as in Example 95.

$^1$H-NMR (CDCl$_3$) δ: 1.07 (d, J=6.0 Hz, 3H) 1.17 (d, J=6.0 Hz, 3H) 1.40 (d, J=6.0 Hz, 6H) 2.74 (s, 3H) 2.92 (dd, J=7.2, 14.0 Hz, 1H) 3.05 (dd, J=4.0, 14.0 Hz, 1H) 3.60 (sept, J=6.0 Hz, 1H) 4.12 (dd, T=4.0, 7.2 Hz, 1H) 4.56 (d, J=5.6 Hz, 2H) 4.64 (sept, J=6.0 Hz, 1H) 6.63 (brt, J=5.6 Hz, 1H) 6.83 (d, J=8.4 Hz, 1H) 7.13 (dd, J=2.4, 8.4 Hz, 1H) 7.21 (d, J=2.4 Hz, 1H) 7.36 (dd, J=2.0, 8.4 Hz, 1H) 7.51 (d, J=2.4 Hz, 1H) 7.26 (d, J=8.8 Hz, 2H)

MS m/e(ESI) 565 (MH$^+$)

Example 139

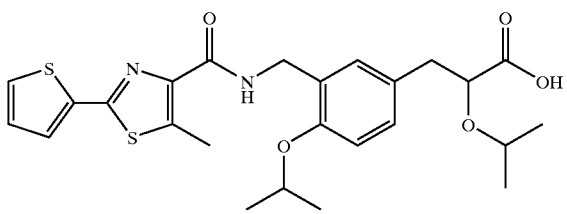

3-4-Isopropoxy-3-[([5-methyl-2-(2-thienyl)-1,3-thiazole-4-yl]carbonylamino)methyl]phenyl-2-isopropoxypropionic acid was obtained by treatment in the same method as in Example 95.

MS m/e(ESI) 503 (MH$^+$)

Example 140

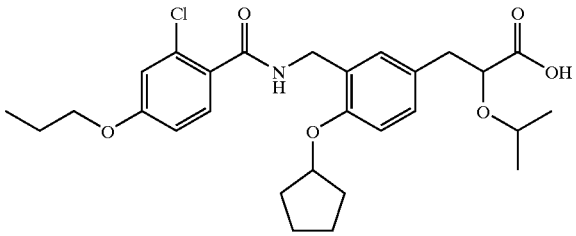

3-(3-[(2-Chloro-4-propoxybenzoyl)amino]methyl-4-cyclopentyloxyphenyl)-2-isopropoxypropionic acid was obtained by treatment in the same method as in Example 96.

MS m/e(ESI) 513 (MH$^+$)

Example 141

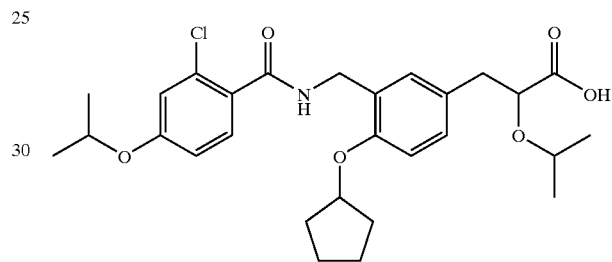

3-(3-[(2-Chloro-4-isopropoxybenzoyl)amino]methyl-4-cyclopentyloxyphenyl)-2-isopropoxypropionic acid was obtained by treatment in the same method as in Example 96.

MS m/e(ESI) 518 (MH$^+$)

Example 142

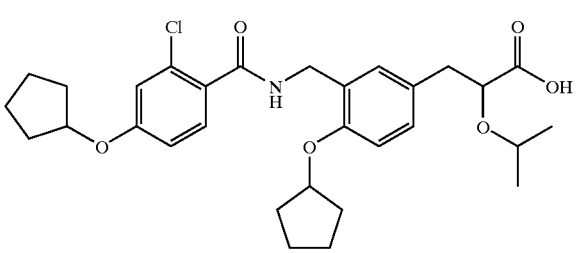

3-(3-[(2-Chloro-4-cyclopentyloxybenzoyl)amino]methyl-4-cyclopentyloxyphenyl)-2-isopropoxypropionic acid was obtained by treatment in the same method as in Example 96.

MS m/e(ESI) 544 (MH$^+$)

Example 143

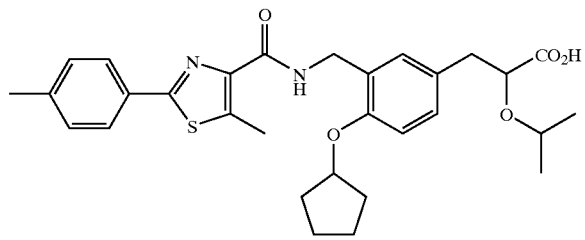

3-3-[([2-(4-Methylphenyl)-5-methyl-1,3-thiazole-4-yl]carbonylamino)methyl]-4-cyclopentyloxyphenyl-2-isopropoxypropionic acid was obtained by treatment in the same method as in Example 96.

$^1$H-NMR(CDCl$_3$) δ: 1.06 (d, J=6.0 Hz, 3H) 1.17 (d, J=6.0 Hz, 3H) 1.65–1.69 (m, 2H) 1.77–2.10 (m, 6H) 2.40 (s, 3H) 2.71 (s, 3H) 2.91 (dd, J=7.2, 14.0 Hz, 1H) 3.06 (dd, J=4.0, 14.0 Hz, 1H) 3.59 (sept, J=6.0 Hz, 1H) 4.11 (dd, J=4.0, 7.2 Hz, 1H) 4.54 (d, J=5.6 Hz, 2H) 4.82–4.85 (m, 1H) 6.44 (br, 1H) 6.82 (d, J=8.4 Hz, 1H) 7.12 (dd, J=2.4, 8.4 Hz, 1H) 7.20 (d, J=2.4 Hz, 1H) 7.24 (d, J=7.2 Hz, 2H) 7.80 (d, J=8.0 Hz, 2H)

MS m/e(ESI) 537 (MH$^+$)

Example 144

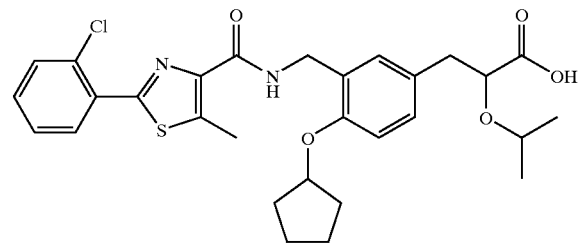

3-3-[([2-(2-Chlorophenyl)-5-methyl-1,3-thiazole-4-yl]carbonylamino)methyl]-4-cyclopentyloxyphenyl-2-isopropoxypropionic acid was obtained by treatment in the same method as in Example 96.

MS m/e(ESI) 557 (MH$^+$)

Example 145

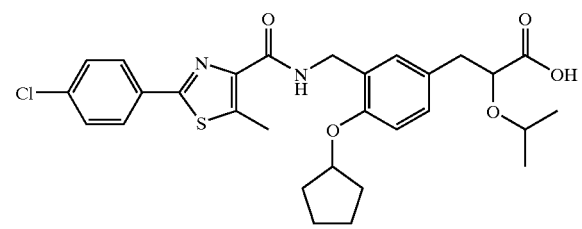

3-3-[([2-(4-Chlorophenyl)-5-methyl-1,3-thiazole-4-yl]carbonylamino)methyl]-4-cyclopentyloxyphenyl-2-isopropoxypropionic acid was obtained by treatment in the same method as in Example 96.

MS m/e(ESI) 557 (MH$^+$)

Example 146

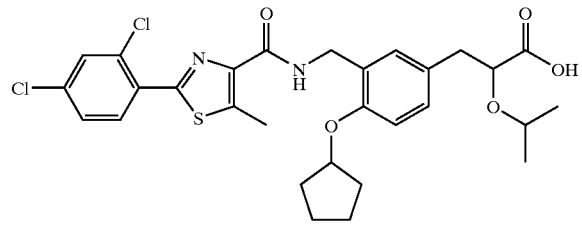

3-3-[([2-(2,4-Dichlorophenyl)-5-methyl-1,3-thiazole-4-yl]carbonylamino)methyl]-4-cyclopentyloxyphenyl-2-isopropoxypropionic acid was obtained by treatment in the same method as in Example 96.

MS m/e(ESI) 591 (MH$^+$)

Example 147

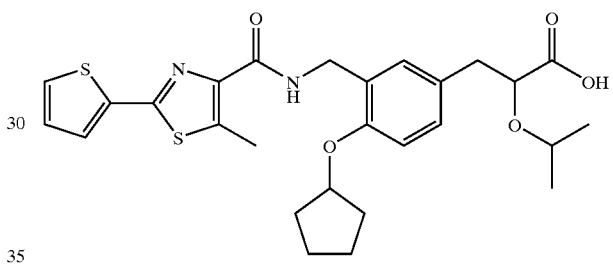

3-4-Cyclopentyloxy-3-[([5-methyl-2-(2-thienyl)-1,3-thiazole-4-yl]carbonylamino)methyl]phenyl-2-isopropoxypropionic acid was obtained by treatment in the same method as in Example 96.

MS m/e(ESI) 529 (MH$^+$)

Example 148

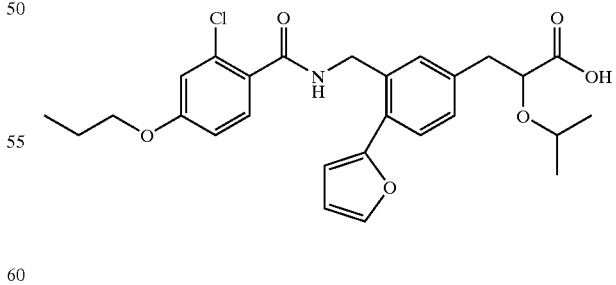

3-[3-[(2-Chloro-4-propoxybenzoyl)amino]methyl-4-(2-furyl)phenyl]-2-isopropoxypropionic acid was obtained by treatment in the same method as in Example 98.

MS m/e(ESI) 500 (MH$^+$)

Example 149

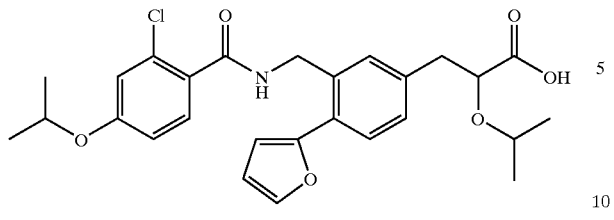

3-[3-[(2-Chloro-4-isopropoxybenzoyl)amino]methyl-4-(2-furyl)phenyl]-2-isopropoxypropionic acid was obtained by treatment in the same method as in Example 98.

MS m/e(ESI) 500 (MH⁺)

Example 150

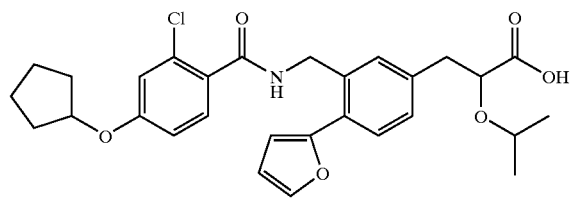

3-[3-[(2-Chloro-4-cyclopentyloxybenzoyl)amino]methyl-4-(2-furyl)phenyl]-2-isopropoxypropionic acid was obtained by treatment in the same method as in Example 98.

MS m/e(ESI) 526 (MH⁺)

Example 151

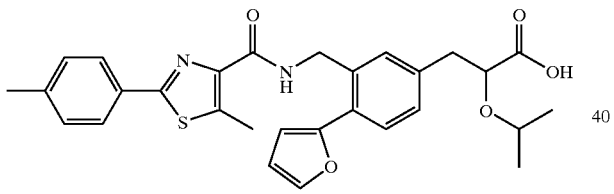

3-4-(2-Furyl)-3-[([5-methyl-2-(4-methylphenyl)-1,3-thiazole-4-yl]carbonylamino)methyl]phenyl-2-isopropoxypropionic acid was obtained by treatment in the same method as in Example 98.

MS m/e(ESI) 519 (MH⁺)

Example 152

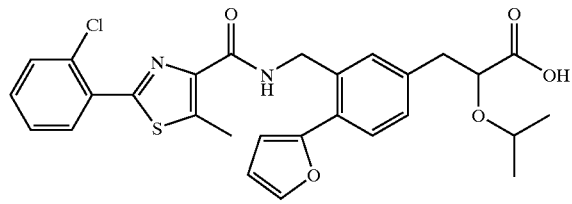

3-4-(2-Furyl)-3-[([5-methyl-2-(2-chlorophenyl)-1,3-thiazole-4-yl]carbonylamino)methyl]phenyl-2-isopropoxypropionic acid was obtained by treatment in the same method as in Example 98.

MS m/e(ESI) 539 (MH⁺)

Example 153

Production Example 153a)

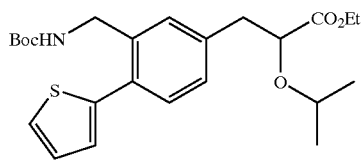

Ethyl 3-(3-[(tertiary butoxycarbonyl)amino]methyl-4-[(trifluoromethyl)sulfonyl]oxyphenyl)-2-(2-thienyl)propoxypropionate was obtained in the same manner as in Production Example 97.

$^1$H-NMR(CDCl$_3$) δ: 1.01 (d, J=6.0 Hz, 3H) 1.18 (d, J=6.4 Hz, 3H) 1.27 (t, J=7.2 Hz, 3H) 1.46 (s, 9H) 2.91–3.06 (m, 2H) 3.51 (sept, J=6.4 Hz, 1H) 4.10 (dd, J=4.8, 8.8 Hz, 1H) 4.16–4.24 (m, 2H) 4.40 (d, J=5.6 Hz, 2H) 4.69 (br 1H) 7.01 (d, J=6.0 Hz, 1H) 7.08 (d, J=5.2 Hz, 1H) 7.13–7.20 (m, 2H) 7.24–7.35 (m, 2H)

Example 153b)

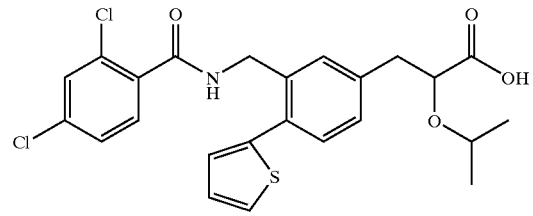

Ethyl 3-(3-[(tertiary butoxycarbonyl)amino]methyl-4-[(trifluoromethyl)sulfonyl]oxyphenyl)-2-(2-thienyl)propoxypropionate was treated in the same manner as in Example 98, to give 3-(3-[(2,4-dichlorobenzoyl)amino]methyl-4-(2-thienyl)phenyl)-2-isopropoxypropionic acid.

MS m/e(ESI) 492 (MH⁺)

Example 154

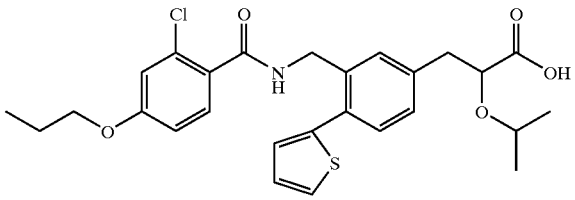

3-[3-([(2-Chloro-4-propoxybenzoyl)amino]methyl-4-(2-thienyl)phenyl)-2-isopropoxypropionic acid was obtained by treatment in the same manner as in Example 153.

MS m/e(ESI) 516 (MH⁺)

Example 155

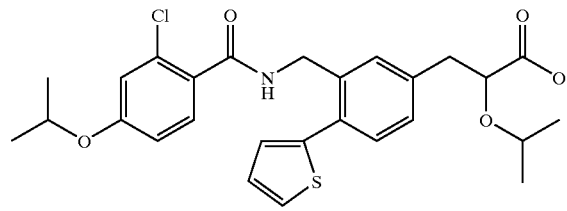

3-[3-([(2-Chloro-4-isopropoxybenzoyl)amino]methyl-4-(2-thienyl)phenyl)-2-isopropoxypropionic acid was obtained by treatment in the same manner as in Example 153.

MS m/e(ESI) 516 (MH⁺)

Example 156

Production Example 156a)

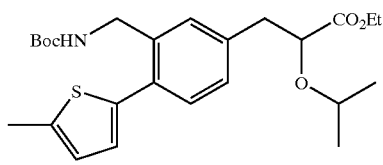

Ethyl 3-(3-[(tertiary butoxycarbonyl)amino]methyl-4-[(trifluoromethyl)sulfonyl]oxyphenyl)-2-(5-methyl-2-thienyl)propoxypropionate was obtained in the same method as in Production Example 97.

¹H-NMR(CDCl₃) δ: 1.01 (d, J=6.0 Hz, 3H) 1.17 (d, J=6.4 Hz, 3H) 1.25 (t, J=7.2 Hz, 3H) 1.46 (s, 9H) 2.51 (s, 3H) 2.91–3.05 (m, 2H) 3.51 (sept, J=6.4 Hz, 1H) 4.07 (dd, J=4.8, 8.8 Hz, 1H) 4.18–4.29 (m, 2H) 4.40 (br, 2H) 4.70 (br 1H) 6.73 (s, 1H) 7.11–7.19 (m, 2H) 7.23–7.30 (m, 2H)

Example 156b)

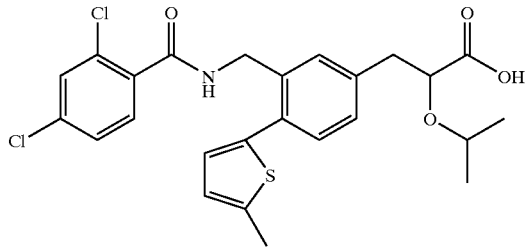

Ethyl 3-(3-[(tertiary butoxycarbonyl)amino]methyl-4-[(trifluoromethyl)sulfonyl]oxyphenyl)-2-(5-methyl-2-thienyl)propoxypropionate was treated in the same manner as in Example 153, to give 3-[3-[(2,4-dichlorobenzoyl)amino]methyl-4-(5-methyl-2-thienyl)phenyl]-2-isopropoxypropionic acid.

MS m/e(ESI) 506 (MH⁺)

Example 157

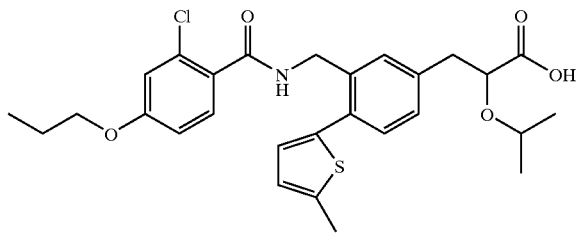

3-[3-([(2-Chloro-4-propoxybenzoyl)amino]methyl-4-(5-methyl-2-thienyl)phenyl]-2-isopropoxypropionic acid was obtained by treatment in the same manner as in Example 156.

MS m/e(ESI) 530 (MH⁺)

Example 158

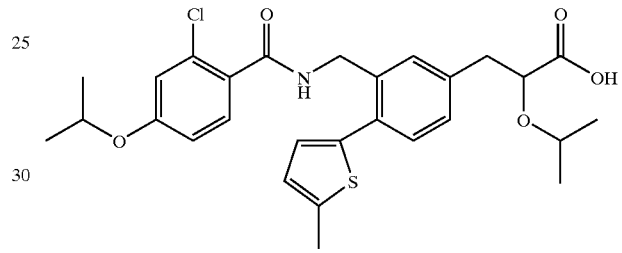

3-[3-[(2-Chloro-4-isopropoxybenzoyl)amino]methyl-4-(5-methyl-2-thienyl)phenyl]-2-isopropoxypropionic acid was obtained by treatment in the same manner as in Example 156.

MS m/e(ESI) 530 (MH⁺)

Example 159

Production Example 159a)

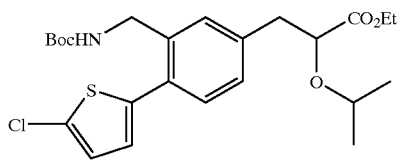

Ethyl 3-(3-[(tertiary butoxycarbonyl)amino]methyl-4-[(trifluoromethyl)sulfonyl]oxyphenyl)-2-(5-chloro-2-thienyl)propoxypropionate was obtained in the same method as in Production Example 97.

¹H-NMR(CDCl₃) δ: 1.00 (d, J=6.0 Hz, 3H) 1.17 (d, J=6.4 Hz, 3H) 1.25 (t, J=7.2 Hz, 3H) 1.45 (s, 9H) 2.51 (s, 3H) 2.91–3.05 (m, 2H) 3.50 (sept, J=6.0 Hz, 1H) 4.08 (dd, J=4.8, 8.8 Hz, 1H) 4.21–4.24 (m, 2H) 4.38–4.41 (m, 2H) 4.69 (br 1H) 6.78 (d, J=3.6 Hz, 1H) 7.17–7.20 (m, 2H) 7.25 (d, J=8.0 Hz, 1H) 7.31 (s, 1H)

Example 159b)

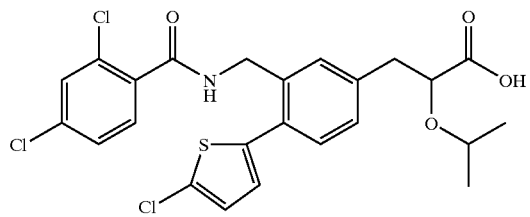

Ethyl 3-(3-[(tertiary butoxycarbonyl)amino]methyl-4-[(trifluoromethyl)sulfonyl]oxyphenyl)-2-(5-chloro-2-thienyl)propoxypropionate was treated in the same manner as in Example 153, to give 3-[3-[(2,4-dichlorobenzoyl)amino]methyl-4-(5-chloro-2-thienyl)phenyl]-2-isopropoxypropionic acid.

MS m/e(ESI) 526 (MH$^+$)

Example 160

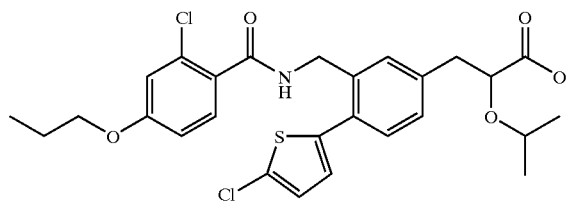

3-[3-[(2-Chloro-4-propoxybenzoyl)amino]methyl-4-(5-chloro-2-thienyl)phenyl]-2-isopropoxypropionic acid was obtained by treatment in the same manner as in Example 159.

MS m/e(ESI) 550 (MH$^+$)

Example 161

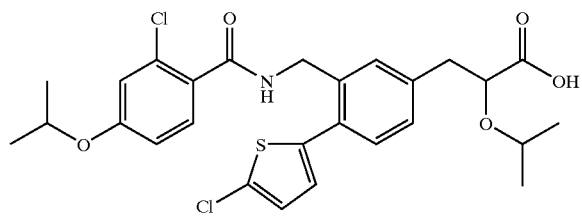

3-(3-[(2-Chloro-4-isopropoxybenzoyl)amino]methyl-4-(5-chloro-4-thienyl)phenyl)-2-isopropoxypropionic acid was obtained by treatment in the same manner as in Example 159.

MS m/e(ESI) 550 (MH$^+$)

Example 162

Production Example 162a)

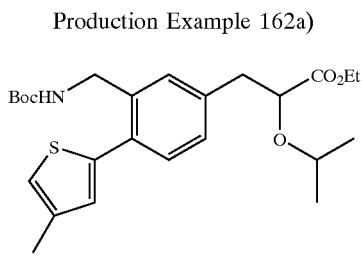

Ethyl 3-(3-[(tertiary butoxycarbonyl)amino]methyl-4-[(trifluoromethyl)sulfonyl]oxyphenyl)-2-(4-methyl-2-thienyl)propoxypropionate was obtained in the same method as in Production Example 97.

$^1$H-NMR(CDCl$_3$) δ: 1.00 (d, J=6.0 Hz, 3H) 1.17 (d, J=6.4 Hz, 3H) 1.26 (t, J=7.2 Hz, 3H) 1.45 (s, 9H) 2.29 (s, 3H) 2.94–3.05 (m, 2H) 3.54 (sept, J=6.0 Hz, 1H) 4.08 (dd, J=4.8, 8.8 Hz, 1H) 4.12–4.24 (m, 2H) 4.40 (br, 2H) 4.70 (br 1H) 6.82 (s, 1H) 7.14–7.19 (m, 2H) 7.28 (d, J=9.6 Hz, 1H) 7.31 (s, 1H)

Example 162b)

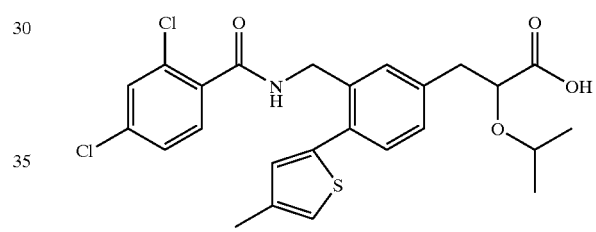

Ethyl 3-(3-[(tertiary butoxycarbonyl)amino]methyl-4-[(trifluoromethyl)sulfonyl]oxyphenyl)-2-(4-methyl-2-thienyl)propoxypropionate was treated in the same manner as in Example 153, to give 3-[3-[(2,4-dichlorobenzoyl)amino]methyl-4-(4-methyl-2-thienyl)phenyl]-2-isopropoxypropionic acid.

MS m/e(ESI) 506 (MH$^+$)

Example 163

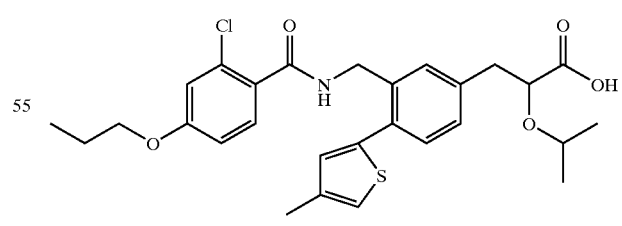

3-(3-[(2-Chloro-4-propoxybenzoyl)amino]methyl-4-(4-methyl-2-thienyl)phenyl]-2-isopropoxypropionic acid was obtained by treatment in the same manner as in Example 162.

MS m/e(ESI) 530 (MH$^+$)

Example 164

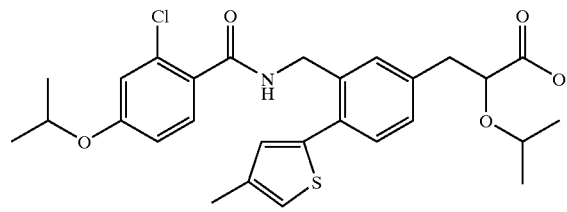

3-[(2-Chloro-4-isopropoxybenzoyl)amino]methyl-4-(4-methyl-2-thienyl)phenyl]-2-isopropoxypropionic acid was obtained by treatment in the same manner as in Example 162.

MS m/e(ESI) 530 (MH+)

Example 165

Production Example 165a)

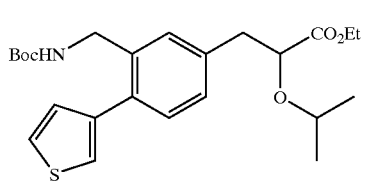

Ethyl 3-(3-[(tertiary butoxycarbonyl)amino]methyl-4-[(trifluoromethyl)sulfonyl]oxyphenyl)-2-(3-thienyl)propoxypropionate was obtained in the same method as in Production Example 97.

$^1$H-NMR(CDCl$_3$) δ: 1.01 (d, J=6.0 Hz, 3H) 1.17 (d, J=6.4 Hz, 3H) 1.27 (t, J=7.2 Hz, 3H) 1.44 (s, 9H) 2.95–3.06 (m, 2H) 3.55 (sept, J=6.0 Hz, 1H) 4.09 (dd, J=4.8, 8.8 Hz, 1H) 4.14–4.25 (m, 2H) 4.32 (d, J=5.6 Hz, 2H) 4.64 (br 1H) 7.10–7.11 (m, 1H) 7.18–7.25 (m, 3H) 7.30 (s, 1H) 7.37 (dd, J=2.1, 5.2 Hz, 1H)

Example 165b)

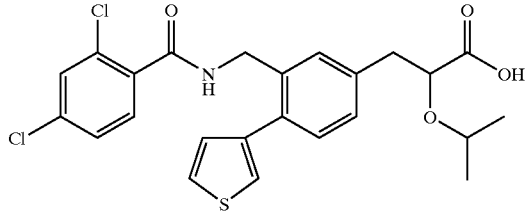

Ethyl 3-(3-[(tertiary butoxycarbonyl)amino]methyl-4-[(trifluoromethyl)sulfonyl]oxyphenyl)-2-(3-thienyl)propoxypropionate was treated in the same manner as in Example 153, to give 3-[3-[(2,4-dichlorobenzoyl)amino]methyl-4-(3-thienyl)phenyl]-2-isopropoxypropionic acid.

MS m/e(ESI) 492 (MH+)

Example 166

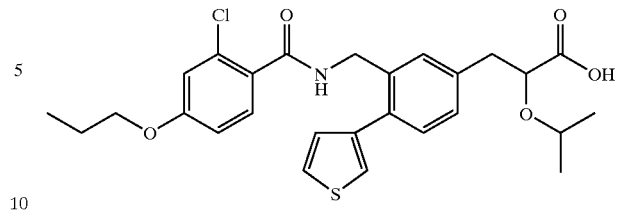

3-[3-[(2-Chloro-4-propoxybenzoyl)amino]methyl-4-(3-thienyl)phenyl]-2-isopropoxypropionic acid was obtained by treatment in the same manner as in Example 165.

MS m/e(ESI) 516 (MH+)

Example 167

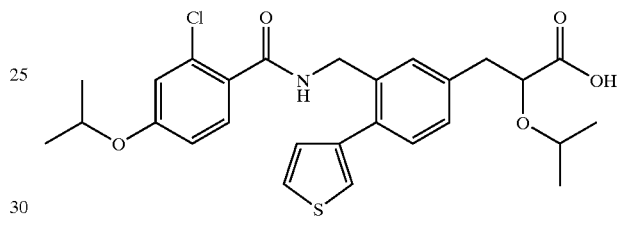

3-[3-[(2-Chloro-4-isopropoxybenzoyl)amino]methyl-4-(3-thienyl)phenyl)-2-isopropoxypropionic acid was obtained by treatment in the same manner as in Example 165.

MS m/e(ESI) 516 (MH+)

Example 168

Production Example 168a)

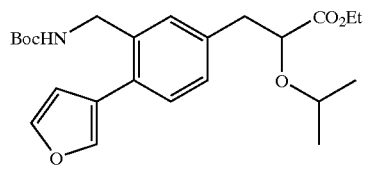

Ethyl 3-(3-[(tertiary butoxycarbonyl)amino]methyl-4-[(trifluoromethyl)sulfonyl]oxyphenyl)-2-(3-furyl)propoxypropionate was obtained in the same method as in Production Example 97.

$^1$H-NMR(CDCl$_3$) δ: 1.00 (d, J=6.0 Hz, 3H) 1.17 (d, J=6.0 Hz, 3H) 1.27 (t, J=7.2 Hz, 3H) 1.45 (s, 9H) 2.93–3.04 (m, 2H) 3.54 (sept, J=6.0 Hz, 1H) 4.08 (dd, J=6.8, 8.0 Hz, 1H) 4.18–4.26 (m, 2H) 4.30–4.41 (m, 2H) 4.67 (br 1H) 6.52 (d, J=4.0 Hz, 1H) 7.13–7.19 (m, 2H) 7.25–7.28 (m, 2H) 7.49 (d, J=4.0 Hz, 1H)

Example 168b)

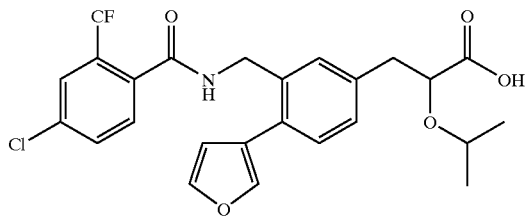

Ethyl 3-(3-[(tertiary butoxycarbonyl)amino]methyl-4-[(trifluoromethyl)sulfonyl]oxyphenyl)-2-(3-furyl)propoxypropionate was treated in the same manner as in Example 153), to give 3-[3-[(2,4-dichlorobenzoyl)amino]methyl-4-(3-furyl)phenyl]-2-isopropoxypropionic acid.

MS m/e(ESI) 476 (MH⁺)

Example 169

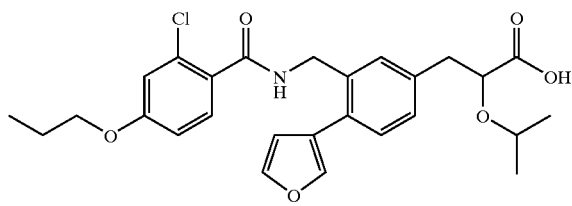

3-[3-[(2-Chloro-4-propoxybenzoyl)amino]methyl-4-(3-furyl)phenyl]-2-isopropoxypropionic acid was obtained by treatment in the same manner as in Example 168.

MS m/e(ESI) 500 (MH⁺)

Example 170

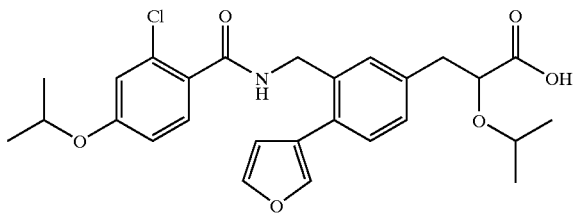

3-[3-[(2-Chloro-4-isopropoxybenzoyl)amino]methyl-4-(3-furyl)phenyl]-2-isopropoxypropionic acid was obtained by treatment in the same manner as in Example 168.

MS m/e(ESI) 500 (MH⁺)

Example 171

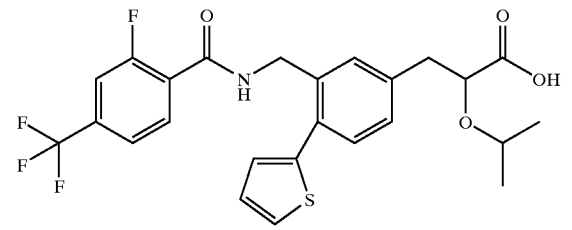

3-[3-([2-Fluoro-4-(trifluoromethyl)benzoyl]aminomethyl)-4-(2-thienyl)phenyl]-2-isopropoxypropionic acid was obtained by treatment in the same manner as in Example 153.

MS m/e(ESI) 510 (MH⁺)

Example 172

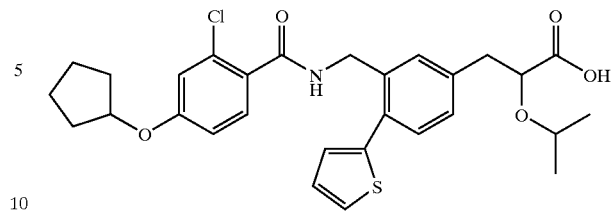

3-[3-[(2-Chloro-4-cyclopentyloxybenzoyl)amino]methyl-4-(2-thienyl)phenyl]-2-isopropoxypropionic acid was obtained by treatment in the same manner as in Example 153.

MS m/e(ESI) 542 (MH⁺)

Example 173

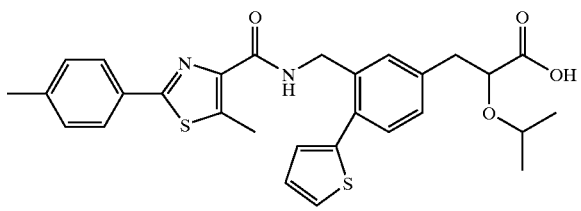

2-Isopropoxy-3-[3-([(5-methyl-2-(4-methylphenyl)-1,3-thiazole-4-yl]carbonylamino)methyl)-4-(2-thienyl)phenyl]propionic acid was obtained by treatment in the same manner as in Example 153.

MS m/e(ESI) 535 (MH⁺)

Example 174

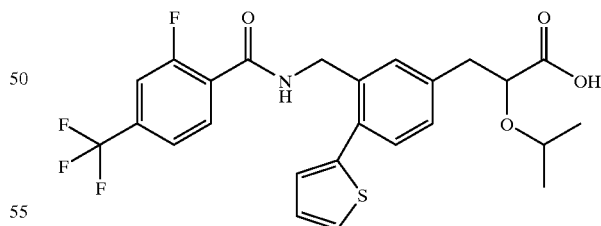

3-(3-[(2-Fluoro-4-(trifluoromethyl)benzoyl]aminomethyl)-4-(5-methyl-2-thienyl)phenyl]-2-isopropoxypropionic acid was obtained by treatment in the same manner as in Example 156.

MS m/e(ESI) 524 (MH⁺)

Example 175

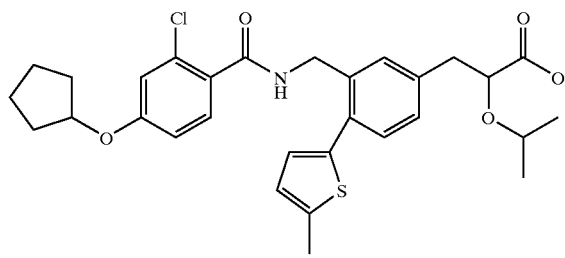

3-(3-[(2-Chloro-4-cyclopentyloxybenzoyl)amino]methyl-4-(5-methyl-2-thienyl)phenyl)-2-isopropoxypropionic acid was obtained by treatment in the same manner as in Example 156.

MS m/e(ESI) 556 (MH$^+$)

Example 176

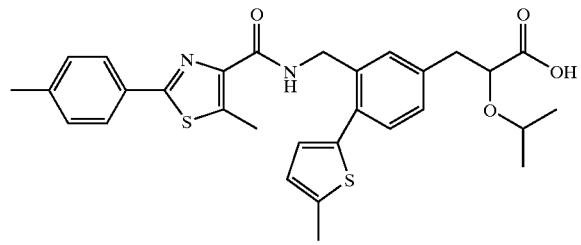

2-Isopropoxy-3-[3-[([5-methyl-2-(4-methylphenyl)-1,3-thiazole-4-yl]carbonylamino)methyl]-4-(5-methyl-2-thienyl)phenyl]propionic acid was obtained by treatment in the same manner as in Example 156.

MS m/e(ESI) 549 (MH$^+$)

Example 177

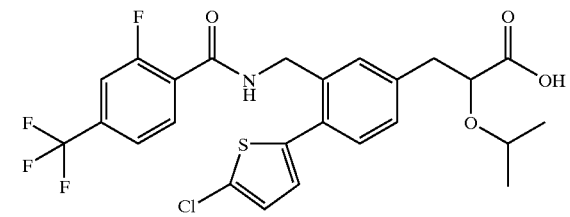

3-[3-[(2-Fluoro-4-(trifluoromethyl)benzoyl]aminomethyl]-4-(5-chloro-2-thienyl)phenyl]-2-isopropoxypropionic acid was obtained by treatment in the same manner as in Example 159.

MS m/e(ESI) 544 (MH$^+$)

Example 178

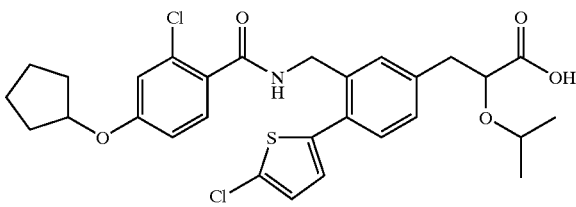

3-[3-[(2-Chloro-4-cyclopentyloxybenzoyl)amino]methyl-4-(5-chloro-2-thienyl)phenyl)-2-isopropoxypropionic acid was obtained by treatment in the same manner as in Example 159.

MS m/e(ESI) 576 (MH$^+$)

Example 179

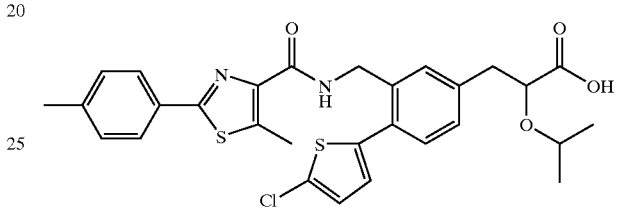

2-Isopropoxy-3-[3-([(5-methyl-2-(4-methylphenyl)-1,3-thiazole-4-yl]carbonylamino)methyl]-4-(5-chloro-2-thienyl)phenyl]propionic acid was obtained by treatment in the same manner as in Example 159.

MS m/e(ESI) 569 (MH$^+$)

Example 180

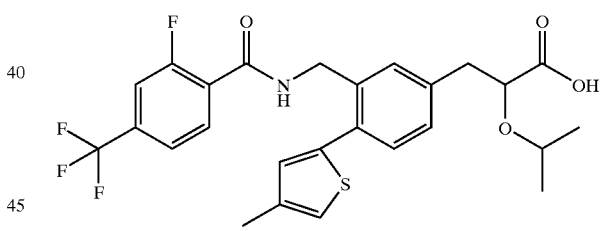

3-(3-[(2-Fluoro-4-(trifluoromethyl)benzoyl]aminomethyl)-4-(4-methyl-2-thienyl)phenyl]-2-isopropoxypropionic acid was obtained by treatment in the same manner as in Example 162.

MS m/e(ESI) 524 (MH$^+$)

Example 181

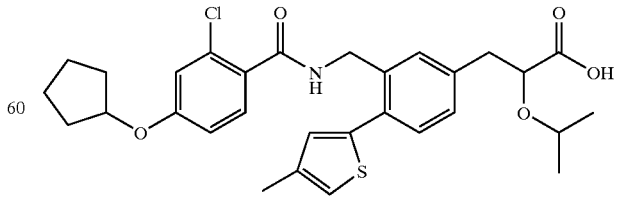

3-[3-[(2-Chloro-4-cyclopentyloxybenzoyl)amino]methyl-4-(4-methyl-2-thienyl)phenyl]-2- isopropoxypropionic acid was obtained by treatment in the same manner as in Example 162).

MS m/e(ESI) 556 (MH$^+$)

Example 182

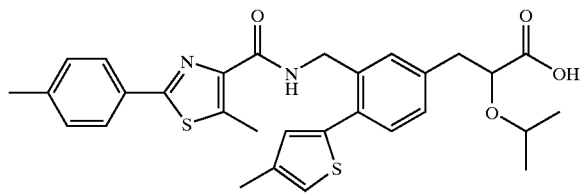

2-Isopropoxy-3-[3-[([5-methyl-2-(4-methylphenyl)-1,3-thiazole-4-yl]carbonylamino)methyl]-4-(4-methyl-2-thienyl)phenyl]propionic acid was obtained by treatment in the same manner as in Example 162.

MS m/e(ESI) 549 (MH$^+$)

Example 183

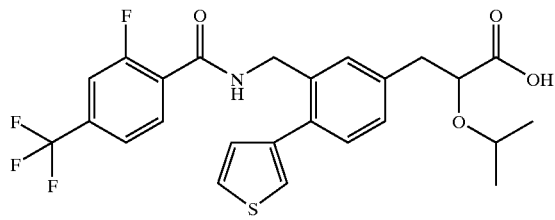

3-(3-([2-Fluoro-4-(trifluoromethyl)benzoyl]aminomethyl]-4-(3-thienyl)phenyl)-2-isopropoxypropionic acid was obtained by treatment in the same manner as in Example 165.

MS m/e(ESI) 510 (MH$^+$)

Example 184

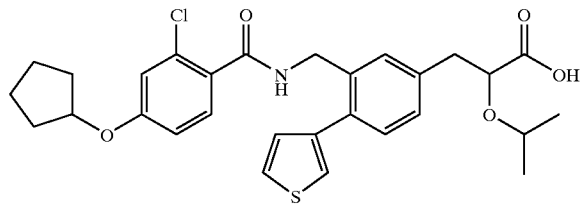

3-[3-[(2-Chloro-4-cyclopentyloxybenzoyl)amino]methyl-4-(3-thienyl)phenyl)-2-isopropoxypropionic acid was obtained by treatment in the same manner as in Example 165.

MS m/e(ESI) 542 (MH$^+$)

Example 185

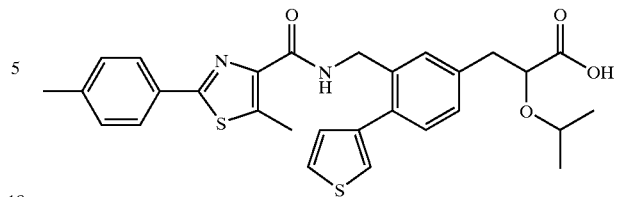

2-Isopropoxy-3-[3-[([5-methyl-2-(4-methylphenyl)-1,3-thiazole-4-yl]carbonylamino)methyl]-4-(3-thienyl)phenyl]propionic acid was obtained by treatment in the same manner as in Example 165.

MS m/e(ESI) 535 (MH$^+$)

Example 186

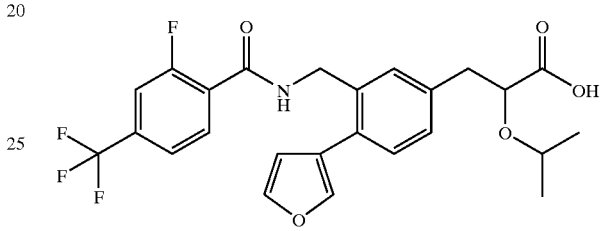

3-[3-(2-Fluoro-4-(trifluoromethyl)benzoyl]aminomethyl)-4-(3-furyl)phenyl]-2-isopropoxypropionic acid was obtained by treatment in the same manner as in Example 168.

MS m/e(ESI) 494 (MH$^+$)

Example 187

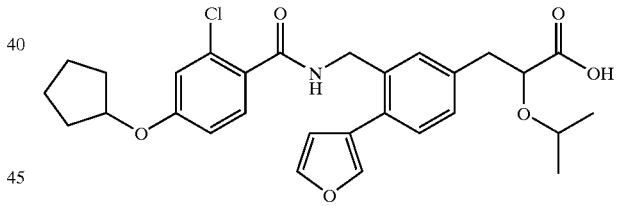

3-[3-[(2-Chloro-4-cyclopentyloxybenzoyl)amino]methyl-4-(3-furyl)phenyl]-2-isopropoxypropionic acid was obtained by treatment in the same manner as in Example 168.

MS m/e(ESI) 526 (MH$^+$)

Example 188

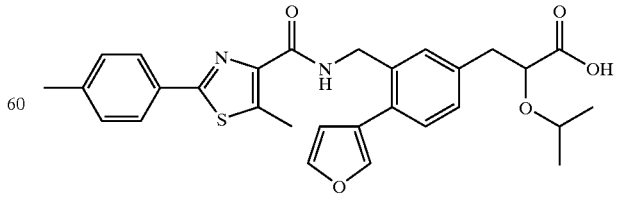

2-Isopropoxy-3-[3-[([5-methyl-2-(4-methylphenyl)-1,3-thiazole-4-yl]carbonylamino)methyl]-4-(3-furyl)phenyl]

propionic acid was obtained by treatment in the same manner as in Example 168.

MS m/e(ESI) 519 (MH⁺)

Example 189

Production Example 189a)

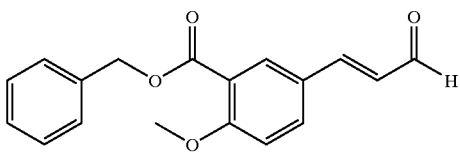

2.95 g of benzyl 5-formyl-2-methoxybenzoate and 5 g of triphenyl phosphoranilidene acetaldehyde were mixed in toluene, followed by stirring at 80° C. for 7 hours. The solvent was evaporated, and the residue was purified by silica gel column chromatography (hexane:ethyl acetate= 3:1), to give 2.0 g of benzyl 2-methoxy-5-(3-oxo-1-propenyl)benzoate (E-Z mixture) as a yellow solid.

¹H-NMR(CDCl₃) δ:3.95+3.97(s, 3H) 5.37(s, 2H) 6.61+6.64(s, J=8.0 Hz, 1H) 6.90–7.07(m, 2H) 7.33–7.47(m, 5H) 7.62+7.70(dd, J=2.0,8.0 Hz, 1H) 7.95+8.02(d, J=2.0 Hz, 1H)

Example 189b)

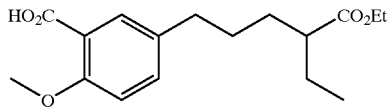

0.77 g of triethyl-2-phosphonobutyrate was dissolved in N,N-dimethylformamide, and 115 mg of sodium hydride was added and the mixture was stirred at room temperature for 1 hour. A solution of 0.6 g benzyl 2-methoxy-5-(3-oxo-1-propenyl)benzoate (E-Z mixture) in N,N-dimethylformamide was added thereto, followed by stirring at room temperature for 2 hours. Water and aqueous ammonium chloride solution were added to the reaction solution, followed by extracting with ethyl acetate The organic layer was extracted with brine, dried over anhydrous magnesium sulfate and evaporated. The residue was purified by silica gel column chromatography (hexane:ethyl acetate=8:1). The resulting product was dissolved in ethanol, and 10% palladium-carbon was added, and the atmosphere was replaced by hydrogen, and the solution was stirred at room temperature for 7 hours. The palladium-carbon was filtered off and the solvent was evaporated, to give 0.47 g of 5-[4-(ethoxycarbonyl)hexyl]-2-methoxybenzoic acid as a colorless oil.

¹H-NMR(CDCl₃) δ:0.50(t, J=8.0 Hz, 3H) 1.17(t, J=8.0 Hz, 3H) 1.38–1.58(m, 6H) 2.20(m, 1H) 2.54(t, J=8.0 Hz, 2H) 3.99(s, 3H) 4.07(q, J=8.0 Hz, 2H) 7.90(d, J=8.0 Hz, 1H) 7.29(dd, J=2.0, 8.0 Hz, 1H) 7.91(d, J=2.0 Hz, 1H)

Example 189c)

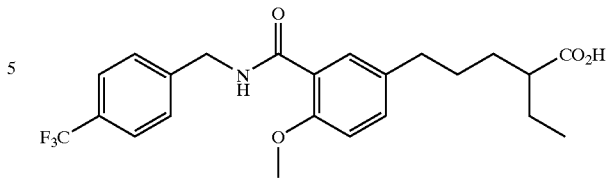

0.47 g of 5-[4-(ethoxycarbonyl)hexyl]-2-methoxybenzoic acid and 0.27 g of 4-(trifluoromethyl)benzylamine were reacted in the same methods as in Example 1c) and 1d), whereby 0.21 g of 2-ethyl-5-[4-methoxy-3-([4-(trifluoromethyl)benzyl]aminocarbonyl)phenyl]pentanoic acid was obtained as a colorless amorphous.

¹H-NMR(CDCl₃) δ:0.85(t, J=8.0 Hz, 3H) 1.42–1.59(m, 6H) 2.27(m, 1H) 2.53(m, 2H) 3.85(s, 3H) 4.66(d, J=6.0 Hz, 2H) 6.90(d, J=7.0 Hz, 1H) 7.26(m, 1H) 7.47(d, J=8.0 Hz, 2H) 7.59(d, J=8.0 Hz, 2H) 8.04(d, J=2.0 Hz, 1H) 8.34(bs, 1H)

Example 190

Production Example 190a)

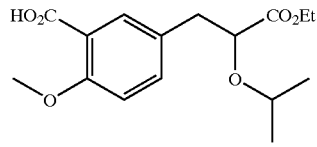

5-(5-Ethoxy-4-isopropoxy-5-oxopentyl)-2-methoxybenzoic acid was obtained in the same methods as in Production Example 189a) and Example 189a).

¹H-NMR(CDCl₃) δ:1.13(d, J=6.0 Hz, 3H) 1.19(d, J=6.0 Hz, 3H) 1.27(t, J=8.0 Hz, 3H) 1.54–1.74(m, 4H) 2.62(t, J=8.0 Hz, 2H) 3.58(sept, J=8.0 Hz, 1H) 3.88(m, 1H) 4.05(s, 3H) 4.18(q, J=8.0 Hz, 2H) 6.98(d, J=8.0 Hz, 1H) 7.37(dd, J=2.0,8.0 Hz, 1H) 8.00(d, J=2.0 Hz, 1H)

Example 190b)

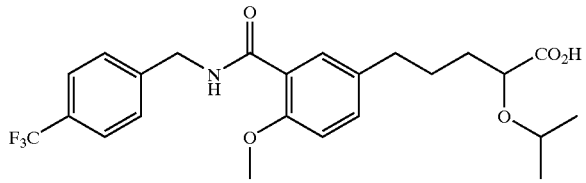

0.35 g of 5-(5-ethoxy-4-isopropoxy-5-oxopentyl)-2-methoxybenzoic acid and 0.18 g of 4-(trifluoromethyl)benzylamine were reacted in the same methods as in Examples 1c) and 1d), whereby 0.18 g of 5-3-[(benzylamino)carbonyl]-4-methoxyphenyl-1-isopropoxypentanoic acid was obtained as a colorless amorphous.

¹H-NMR(CDCl₃) δ:1.20(d, J=6.0 Hz, 3H) 1.21(d, J=6.0 Hz, 3H) 1.67–1.80(m, 4H) 2.63(t, J=8.0 Hz, 2H) 3.69(sept, J=6.0 Hz, 1H) 3.92(s, 3H) 3.96(m, 1H) 4.70(d, J=6.0 Hz, 2H) 6.98(d, J=8.0 Hz, 1H) 7.26(m, 1H) 7.47(d, J=8.0 Hz, 1H) 7.59(d, J=8.0 Hz, 2H) 8.04(d, J=2.0 Hz, 1H) 8.33(bs, 1H)

Example 191

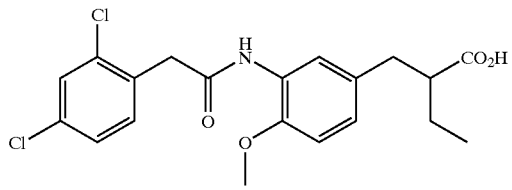

2-(4-Methoxy-3-{[2-(2,4-dichlorophenyl)acetyl]amino}benzyl)butanoic acid was obtained in the same method as in Example 17.

$^1$H-NMR(CDCl$_3$) δ:0.93(t, J=8.0 Hz, 3H) 1.55–1.64(m, 2H) 2.58(m, 1H) 2.68(dd, J=4.5,14.0 Hz, 1H) 2.89(dd, J=7.0, 14.0 Hz, 1H) 3.78(s, 3H) 3.82(s, 2H) 6.73(d, J=8.0 Hz, 1H) 6.84(dd, J=2.0, 8.0 Hz, 1H) 7.26(m, 1H) 7.35(d, J=8.0 Hz, 2H) 7.45(d, 2.0 Hz, 1H) 7.88(s, 1H) 8.19(d, J=2.0 Hz, 1H)

Example 192

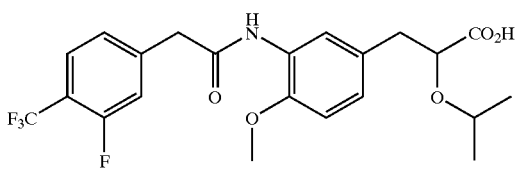

2-Isopropoxy-3-(4-methoxy-3-{[2-(3-fluoro)-4-trifluoromethyl)phenyl]acetyl}amino)phenylpropanoic acid was obtained by the same method as in Example 14.

$^1$H-NMR(CDCl$_3$) δ:1.06 (d, J=6.0 Hz, 3H) 1.65 (d, J=6.0 Hz, 3H) 2.90(dd, J=7.0, 14.0 Hz, 1H) 3.06(dd, J=4.5, 14.0 Hz, 1H) 3.58(sept, J=6.0 Hz, 1H) 3.78(s, 2H) 3.80(s, 3H) 4.13(m, 1H) 6.77(d, J=8.0 Hz, 1H) 6.92(dd, J=2.0, 8.0 Hz, 1H) 7.25(m, 2H) 7.61(t, J=8.0 Hz, 1H) 7.76(s, 1H) 8.24(d, J=2.0 Hz, 1H)

Example 193

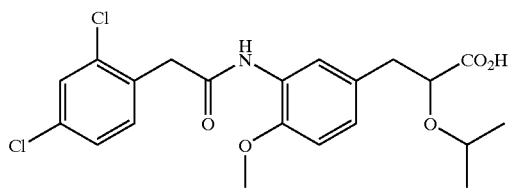

2-Isopropoxy-3-(4-methoxy-3-{[2-(2,4-dichlorophenyl)acetyl]amino)phenylpropionic acid was obtained by the same method as in Example 14.

$^1$H-NMR(CDCl$_3$) δ:1.06(d, J=6.0 Hz, 3H) 1.15(d, J=6.0 Hz, 3H) 2.88(dd, J=7.0, 14.0 Hz, 1H) 3.05(dd, J=4.5, 14.0 Hz, 1H) 3.57(sept, J=6.0 Hz, 1H) 3.80(s, 3H) 3.83(s, 2H) 4.12(m, 1H) 6.76(d, J=8.0 Hz, 1H) 6.90(dd, J=2.0, 8.0 Hz, 1H) 7.27(dd, J=2.0, 8.0 Hz, 1H) 7.36(d, J=8.0 Hz, 1H) 7.46(d, J=2.0 Hz, 1H) 7.86(s, 1H) 8.26(d, J=2.0 Hz, 1H)

Example 194

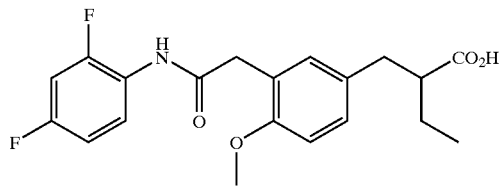

2-(4-Methoxy-3-{2-oxo-2-[2,4-difluoroanilino]ethyl}benzyl)butanoic acid was obtained by the same method as in Example 22.

$^1$H-NMR(CDCl$_3$) δ:0.95(t, J-8.0 Hz, 3H) 1.57–1.66(m, 2H) 2.57(m, 1H) 2.70(dd, J=7.0, 14.0 Hz, 1H) 2.89(dd, J=4.5, 14.0 Hz, 1H) 3.69(s, 2H) 3.92(s, 3H) 6.76–6.87(m, 3H) 7.09–7.12(m, 2H) 8.22–8.29(m, 2H)

Example 195

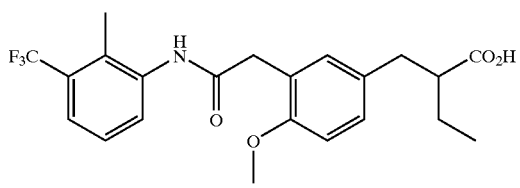

2-(4-Methoxy-3-{2-oxo-2-[2-methyl-4-(trifluoromethyl)anilino]ethyl}benzyl)butanoic acid was obtained by the same method as in Example 22.

$^1$H-NMR(CDCl$_3$) δ:0.96(t, J-8.0 Hz, 3H) 1.55–1.70(m, 2H) 2.10(m, 1H) 2.57(dd, J=4.5,14.0 Hz, 1H) 2.89(dd, J=7.0, 14.0 Hz, 1H) 3.73(s, 3H) 3.89(s, 2H) 6.88(d, J=8.0 Hz, 1H) 7;12–7.15(m, 2H) 7.26(t, J=8.0 Hz, 1H) 7.39(d, J=8.0 Hz, 2H) 7.63(s, 1H) 8.03 (d, J=8.0 Hz, 1H)

Example 196

Production Example 196a)

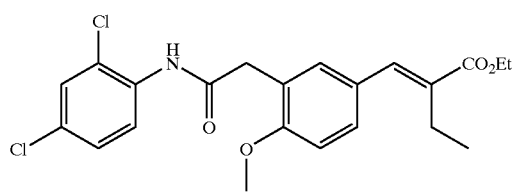

Ethyl 2-ethyl-3-(4-methoxy-3-{2-oxo-2-[2,4-dichloroanilino]ethyl}phenyl)-2-propenoate was obtained by the same method as in Examples 22a)–c).

$^1$H-NMR(CDCl$_3$) δ:1.17(t, J=8.0 Hz, 3H) 1.34(t, J=8.0 Hz, 3H) 2.56(q, J=8.0 Hz, 2H) 3.77(s, 3H) 3.96(s, 3H) 4.26(q, J=8.0 Hz, 2H) 6.98(d, J=8.0 Hz, 1H) 7.22(dd, J=2.0, 8.0 Hz, 1H) 7.31(d, J=8.0 Hz, 1H) 7.37(dd, J=2.0 Hz, 1H) 7.58(s, 1H) 8.22(bs, 1H) 8.37(d, J=8.0 Hz, 1H)

Example 196b)

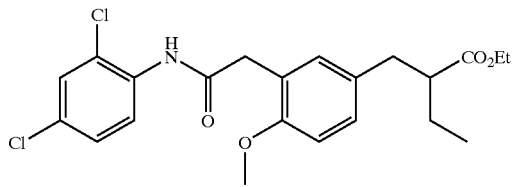

0.9 g of 2-ethyl-3-(4-methoxy-3-{2-oxo-2-[2,4-dichloroanilino]ethyl}phenyl)-2-propenoate was dissolved in 15 ml ethanol and 15 ml ethyl acetate, and 0.6 g of palladium-carbon poisoned with ethylene diamine was added. The reaction solution was stirred at room temperature for 5 hours in a hydrogen atmosphere, and then the palladium-carbon was filtered off, and the solvent was evaporated. The residue was purified by silica gel column chromatography, to give 0.44 g of ethyl 2-(4-methoxy-3-{2-oxo-2-[2,4-dichloroanilino]ethyl}benzyl)butanoate as a colorless oil.

$^1$H-NMR(CDCl$_3$) δ:0.90(t, J-8.0 Hz, 3H) 1.14(t, J-8.0 Hz, 3H) 1.50–1.68(m, 2H) 2.54(m, 2H) 2.68(dd, J=4.5, 14.0 Hz, 1H) 2.86(dd, J=4.5, 14.0 Hz, 1H) 3.72(s, 2H) 3.88(s, 3H) 4.05(q, J=8.0 Hz, 2H) 6.85(d, J=8.0 Hz, 1H) 7.10(m, 2H) 7.20(d, J=8.0 Hz, 1H) 7.26(d, J=8.0 Hz, 1H) 8.30(bs,1H) 8.37(d,J=8.0 Hz,1H)

Example 196c)

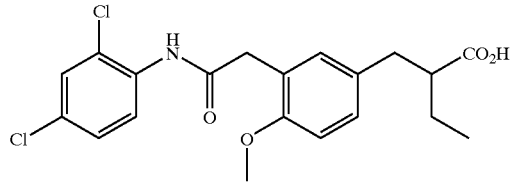

0.27 g of ethyl 2-(4-methoxy-3-{2-oxo-2-[2,4-dichloroanilino]ethyl}benzyl)butanoate was dissolved in 10 ml ethanol, and 1 ml of 5 N sodium hydroxide was added. After stirring the reaction solution at room temperature for 24 hours, water was added thereto and the aqueous layer was extracted with diethyl ether. The aqueous layer was acidified with hydrochloric acid and extracted with ethyl acetate. The ethyl acetate layer was washed with brine, dried over anhydrous magnesium sulfate and the solvent was evaporated, to give 2-(4-methoxy-3-{2-oxo-2-[2,4-dichloroanilino]ethyl}benzyl)butanoic acid as a colorless oil.

$^1$H-NMR(CDCl$_3$) δ:0.89(t, J-8.0 Hz, 3H) 1.49–1.62(m, 2H) 2.50(m, 2H) 2.64(dd, J=4.5, 14.0 Hz, 1H) 2.84(dd, J=4.5, 14.0 Hz, 1H) 3.72(s, 2H) 3.88(s, 3H) 6.80(d, J=8.0 Hz, 1H) 7.06(m, 2H) 7.12(dd, J=2.0, 8.0 Hz, 1H) 7.22(d, J=8.0 Hz, 1H) 8.23(s, 1H) 8.28(d, J=8.0 Hz, 1H)

Example 197

Production Example 197a)

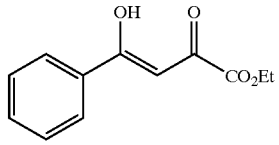

1 g of sodium hydride was suspended in tetrahydrofuran, and 3 g acetophenone dissolved in tetrahydrofuran was added, followed by stirring at room temperature for 30 minutes. Further, 3.7 g of diethyl oxazalate was added, and the mixture was heated under reflux for 1 hour. The reaction solution was ice-cooled, and water and aqueous ammonium chloride solution were added thereto, followed by extracting with ethyl acetate. The organic layer was washed with brine, dried over anhydrous magnesium sulfate and the solvent was evaporated. Diisopropyl ether was added to the residue, and the resulting crystals were filtered, to give 2.37 g of ethyl-(Z)-4-hydroxy-2-oxo-4-phenyl-3-butanoate.

$^1$H-NMR(DMSO-d$_6$) δ:1.15(t, J=8.0 Hz, 3H) 4.18(q, J=8.0 Hz, 2H) 6.55(s, 1H) 7.35–7.48(m, 3H) 7.80(m, 2H)

Production Example 197b)

0.67 g of ethyl-(Z)-4-hydroxy-2-oxo-4-phenyl-3-butanoate was dissolved in 10 ml acetic acid, and 0.17 g of methyl hydrazine was added. After heating under reflux the reaction solution for 2 hours, the acetic acid was evaporated. The residue was dissolved by adding ethyl acetate and tetrahydrofuran, then washed with aqueous sodium hydrogencarbonate solution and brine, dried over anhydrous magnesium sulfate and evaporated. The residue was purified by silica gel column chromatography, to give 0.12 g of ethyl 1-methyl-3-phenyl-1H-5-pyrazolecarboxylate from a fraction of hexane:ethyl acetate (9:1) and 0.55 g of ethyl 1-methyl-5-phenyl-1H-3-pyrazolecarboxylate from a fracton of hexane:ethyl acetate (4:1).

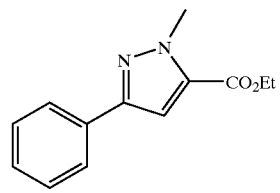

Ethyl 1-methyl-3-phenyl-1H-5-pyrazolecarboxylate $^1$H-NMR(CDCl$_3$) δ:1.42(t, J=8.0 Hz, 3H) 4.21(s, 3H) 4.38(q, J=8.0 Hz, 2H) 7.11(s, 1H) 7.32(t, J=8.0 Hz, 1H) 7.40(t, J=8.0 Hz, 2H) 8.79(d, J=8.0 Hz, 2H)

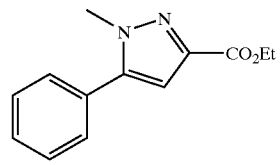

Ethyl 1-methyl-5-phenyl-1H-3-pyrazolecarboxylate $^1$H-NMR(CDCl$_3$) δ:1.41(t, J=8.0 Hz, 3H) 3.95(s, 3H) 4.43(q, J=8.0 Hz, 2H) 6.85(s, 1H) 7.40–7.53(m, 5H)

Production Example 197c)

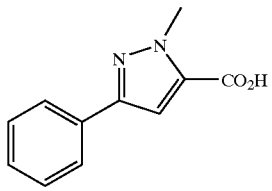

0.12 g of ethyl 1-methyl-3-phenyl-1H-5-pyrazolecarboxylate was dissolved in 5 ml ethanol. 1 ml of 5N aqueous sodium hydroxide solution was added thereto, followed by heating under reflux for 1 hour. The reaction solution was ice-cooled, neutralized with 2N hydrochloric acid and then extracted with ethyl acetate. The organic layer was washed with brine, dried over anhydrous magnesium sulfate and evaporated, to give 0.11 g of 1-methyl-3-phenyl-1H-5-pyrazolecarboxylic acid.

$^1$H-NMR(CDCl$_3$) δ: 4.22(s, 3H) 7.22(s, 1H) 7.33(t, J=8.0 Hz, 1H) 7.40(t, J=8.0 Hz, 2H) 8.80(d, J=8.0 Hz, 2H)

Example 197d)

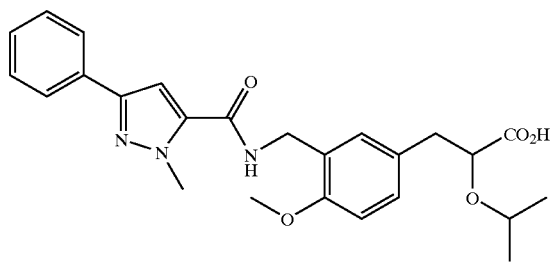

2-Isopropoxy-3-[4-methoxy-3-([(1-methyl-3-phenyl-1H-5-pyrazolyl)carbonyl]aminoethyl)phenyl]propanoic acid was obtained by the same method as in Examples 19d) and e).

$^1$H-NMR(CDCl$_3$) δ:1.06(d, J=6.0 Hz, 3H) 1.17 (d, J=6.0 Hz, 3H) 2.94(dd, J=7.0, 14.0 Hz, 1H) 3.06(dd, J=4.5, 14.0, 1H) 3.88(s, 3H) 4.12(dd, J=4.0, 7.0 Hz, 1H) 4.20(s, 3H) 4.57(d, J=6.0 Hz, 3H) 6.57(bs, 1H) 6.73(s, 1H) 6.84(d, J=2.0 Hz, 1H) 7.16(dd, J=2.0, 8.0 Hz, 1H) 7.22(d, J=2.0 Hz, 1H) 7.32(d, J=8.0 Hz, 1H) 7.39(m, 2H) 7.76(m, 2H)

Example 198

Production Example 198a)

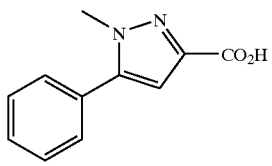

0.55 g of ethyl 1-methyl-5-phenyl-1H-3-pyrazolecarboxylate was dissolved in 10 ml ethanol. 2 ml of 5N aqueous sodium hydroxide solution was added thereto, followed by heating under reflux for 1 hour. The reaction mixture was ice-cooled, neutralized with 2N hydrochloric acid and then extracted with ethyl acetate. The organic layer was washed with brine, dried over anhydrous magnesium sulfate and evaporated, to give 0.5 g of 1-methyl-5-phenyl-1H-3-pyrazolecarboxylic acid.

$^1$H-NMR(CDCl$_3$) δ: 3.91 (s, 3H) 6.82(s, 1H) 7.34–7.45 (m, 5H)

Example 198b)

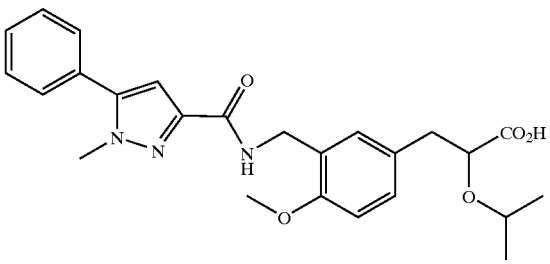

2-Isopropoxy-3-[4-methoxy-3-([(1-methyl-5-phenyl-1H-3-pyrazolyl)carbonyl]aminoethyl)phenyl]propanoic acid was obtained by the same method as in Examples 19d) and e).

$^1$H-NMR(CDCl$_3$) δ:1.04(d, J=6.0 Hz, 3H) 1.14(d, J=6.0 Hz, 3H) 2.90(dd, J=7.0, 14.0 Hz, 1H) 3.04(dd, J=4.5, 14.0, 1H) 3.55(sept, J=6.0 Hz, 1H) 3.86(s, 3H) 3.88(s, 3H) 4.09 (dd, J=4.0, 7.0 Hz, 1H) 4.60(d, J=6.0 Hz, 3H) 6.80(d, J=6.0 Hz, 1H) 6.84(s, 1H) 7.12(dd, J=2.0, 8.0 Hz, 1H) 7.23(d, J=2.0 Hz, 1H) 7.32(bs, 1H) 7.39–7.57(m, 5H)

Example 199

Production Example 199a)

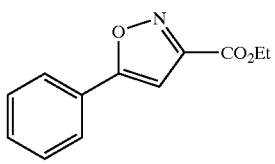

1 g of phenyl acetylene and 1.48 g of ethyl 2-chloro-2-hydroxyiminoacetate were dissolved in 20 ml chloroform, and 1.4 g of potassium carbonate was added thereto, and the mixture was stirred at room temperature for 16 hours. Water and aqueous ammonium chloride solution were added to the reaction solution, followed by extracting with ethyl acetate. The organic layer was washed with brine, dried over anhydrous magnesium sulfate and evaporated. The residue was purified by silica gel column chromatography (hexane:ethyl acetate=9:1), to give 1.2 g of ethyl 5-phenyl-4-isoxazole carboxylate.

$^1$H-NMR(CDCl$_3$) δ:1.35(t, J=8.0 Hz, 3H) 4.40(q, J=8.0 Hz, 2H) 6.85(s, 1H) 7.36–7.50(m, 3H) 7.68–7.80(m, 2H)

Production Example 199b)

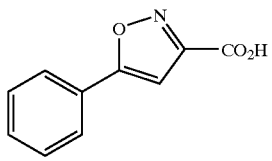

0.4 g of ethyl 5-phenyl-4-isoxazole carboxylate was dissolved in 10 ml ethanol, and 2 ml of 5N sodium hydroxide solution was added, and the mixture was stirred at room temperature for 1 hour. The reaction solution was neutralized with 2 N hydrochloric acid and then extracted with ethyl acetate. The organic layer was washed with brine, dried over anhydrous magnesium sulfate and evaporated, to give 0.25 g of 5-phenyl-3-isoxazolecarboxylic acid.

$^1$H-NMR(DMSO-d$_6$) δ: 7.32(s, 1H) 7.48–7.57(m, 3H) 7.92(m, 2H)

Example 199c)

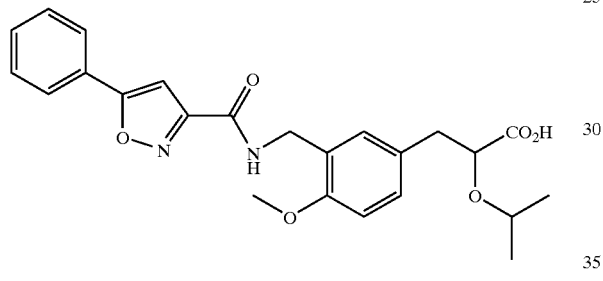

2-Isopropoxy-3-[4-methoxy-3-([(5-phenyl-3-isoxazolyl)carbonyl]aminoethyl)phenyl]propanoic acid was obtained by the same method as in Examples 19d) and e).

$^1$H-NMR(CDCl$_3$) δ:1.04(d, J=6.5 Hz, 3H) 1.16(d, J=6.5 Hz, 3H) 2.90(dd, J=7.0, 14.0 Hz, 1H) 3.06(dd, J=4.5, 14.0 Hz, 1H) 3.56(sept, J=6.0 Hz, 1H) 3.87(s, 3H) 4.10(dd, J=4.5, 7.0 Hz, 1H) 4.61(d, J=6.0 Hz, 2H) 6.82(d, J=8.0 Hz, 1H) 6.96(s, 1H) 7.15(dd, J=2.0, 8.0 Hz, 1H) 7.22(d, J=2.0 Hz, 1H) 7.36(bs, 1H) 7.47(m, 3H) 7.78(m, 2H)

Example 200

Production Example 200a)

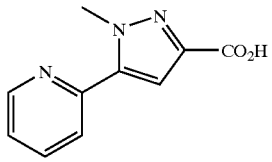

1-Methyl-5-(2-pyridyl)-1H-3-pyrazolecarboxylic acid was obtained by the same method as in Production Examples 197a), b) and 198.

$^1$H-NMR(DMSO-d$_6$) δ:4.18 (s, 3H) 7.22(s, 1H) 7.40(t, J=6.0 Hz, 1H) 7.85–7.94(m, 2H) 8.68(d, J=4.0 Hz, 1H) 12.75(s, 1H)

Example 200b)

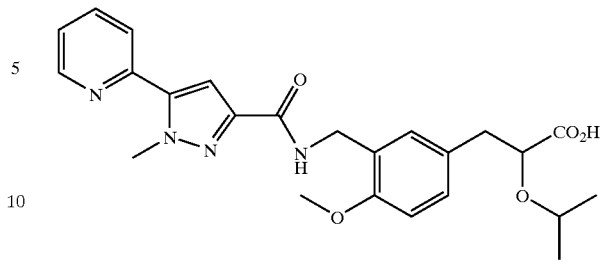

2-Isopropoxy-3-4-methoxy-3-[([1-methyl-5-(2-pyridyl)-1H-3-pyrazolyl]carbonylamino)methyl]phenylpropanoic acid was obtained by the same method as in Examples 19d) and e).

$^1$H-NMR(CDCl$_3$) δ:1.03(d, J=6.5 Hz, 3H) 1.34(d, J=6.5 Hz, 3H) 2.90(dd, J=7.0, 14.0 Hz, 1H) 3.05(dd, J=4.5, 14.0 Hz, 1H) 3.55(sept, J=6.0 Hz, 1H) 3.87(s, 3H) 4.09(dd, J=4.5, 7.0 Hz, 1H) 4.24(s, 3H) 4.60(d, J=6.0 Hz, 2H) 6.81(d, J=8.0 Hz, 1H) 7.14(m, 2H) 7.23(m, 2H) 7.34(bs, 1H) 7.64(d, J=8.0 Hz, 1H) 7.85(bs, 1H) 8.70(d, J=4.0 Hz, 1H)

Example 201

Production Example 201a)

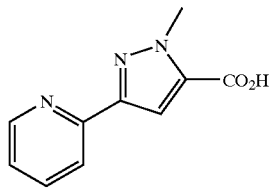

1-Methyl-3-(2-pyridyl)-1H-5-pyrazolecarboxylic acid was obtained by the same method as in Production Examples 197a)–c).

$^1$H-NMR(DMSO-d$_6$) δ:4.13(s, 3H) 7.26(s, 1H) 7.32(dd, J=4.0, 8.0 Hz, 1H) 7.82(t, J=8.0 Hz, 1H) 7.91(d, J=8.0 Hz, 1H) 8.57(d,J=4.0 Hz,1H)

Production Example 201b)

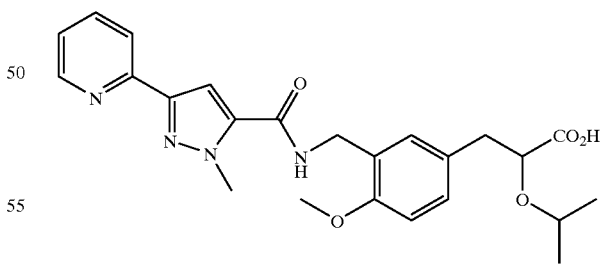

2-Isopropoxy-3-4-methoxy-3-[([1-methyl-3-(2-pyridyl)-1H-5-pyrazolyl]carbonylamino)methyl]phenylpropanoic acid was obtained by the same method as in Examples 19d) and e).

$^1$H-NMR(CDCl$_3$) δ:1.03(d, J=6.5 Hz, 3H) 1.10(d, J=6.5 Hz, 3H) 2.75–3.00(m, 2H) 3.57(sept, J=6.0 Hz, 1H) 3.81(s, 3H) 4.05(dd, J=4.5, 7.0 Hz, 1H) 4.21(s, 3H) 4.52(d, J=6.0 Hz, 2H) 6.75(d, J=8.0 Hz, 1H) 7.08(m, 2H) 7.15(bs, 1H)

7.45(bs, 1H) 7.84(s, 1H) 8.04(t, J=8.0 Hz, 1H) 8.24(d, J=8.0 Hz, 1H) 8.70(d, J=4.0 Hz, 1H)

Example 202

Production Example 202a)

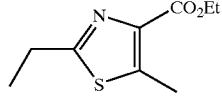

2.33 ml ethyl 2-chloroacetoacetate and 1.5 g thiopropionamide were dissolved in 30 ml ethanol, followed by stirring at room temperature for 16 hours. The reaction solution was ice-cooled and water was added thereto, followed by extracting with ethyl acetate. The organic layer was washed with brine, dried over anhydrous magnesium sulfate and evaporated. The residue was purified by silica gel column chromatography (hexane:ethyl acetate=14:1), to give 0.8 g of ethyl 2-ethyl-5-methyl-1,3-thiazole-4-carboxylate.

$^1$H-NMR(CDCl$_3$) δ:1.34–1.60(m,6H) 2.98(q,J=8.0 Hz,2H) 3.70(s,3H) 4.29(q,J=8.0 Hz,2H)

Production Example 202b)

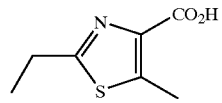

8 g of ethyl 2-ethyl-5-methyl-1,3-thiazole-4-carboxylate was dissolved in 10 ml ethanol. 2 ml of 5N sodium hydroxide was added, followed by heating under reflux for 1 hour. The reaction solution was ice-cooled and neutralized with 2N hydrochloric acid, followed by extracting with ethyl acetate. The organic layer was washed with brine, dried over anhydrous magnesium sulfate and evapoarated, to give 0.8 g of 2-ethyl-5-methyl-1,3-thiazole-4-carboxylic acid.

$^1$H-NMR(CDCl$_3$) δ:1.40(t,J=8.0 Hz,3H) 3.74(s,3H) 4.03 (q,J=8.0 Hz,2H)

Example 202c)

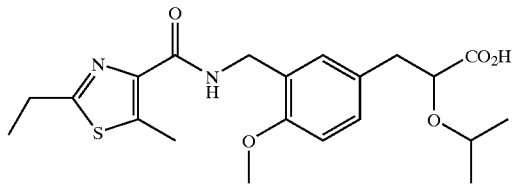

3-[3-([[(2-Ethyl-5-methyl-1,3-thiazole-4-yl)carbonyl] aminoethyl)-4-methoxyphenyl]-2-isopropoxypropanoic acid was obtained by the same method as in Production Examples 19d) and e).

$^1$H-NMR(CDCl$_3$) δ:0.98(d, J=6.5 Hz, 3H) 1.10(d, J=6.5 Hz, 3H) 1.30(t, J=8.0 Hz, 3H) 2.56(s, 3H) 2.82–3.01(m, 4H) 3.51(sept, J=6.0 Hz, 1H) 3.80(s, 3H) 4.04(dd, J=4.5, 7.0 Hz, 1H) 4.48d, J=6.0 Hz, 2H) 6.31(bs, 1H) 6.75(d, J=8.0 Hz, 1H) 6.08(dd, J=2.0, 8.0 Hz, 1H) 7.13(d, J=2.0 Hz,1H)

Example 203

Production Example 203a)

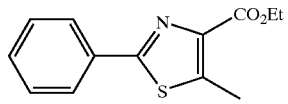

10 ml ethyl 2-chloroacetacetate and 10 g thiobenzamide were dissolved in 100 ml ethanol, followed by heating under reflux for 4 hours. The reaction solution was ice-cooled and water was added thereto, followed by extracting with ethyl acetate. The organic layer was washed with brine, dried over anhydrous magnesium sulfate and evaporated. The residue was purified by silica gel column chromatography (hexane:ethyl acetate=14:1), to give 17 g of ethyl 5-methyl-2-phenyl-1,3-thiazole-4-carboxylate.

$^1$H-NMR(CDCl$_3$) δ:1.39(t, J=8.0 Hz, 3H) 2.78(s, 3H) 4.35(q, J=8.0 Hz, 2H) 7.45(m, 3H) 7.95(m, 2H)

Production Example 203b)

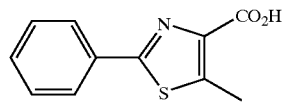

0.8 g of ethyl 5-methyl-2-phenyl-1,3-thiazole-4-carboxylate was dissolved in 10 ml ethanol. 2 ml of 5N sodium hydroxide was added thereto, followed by heating under reflux for 1 hour. The reaction solution was ice-cooled and neutralized with 2N hydrochloric acid, followed by extracting with ethyl acetate. The organic layer was washed with brine, dried over anhydrous magnesium sulfate and evaporated, to give 0.8 g of 5-methyl-2-phenyl-1,3-thiazole-4-carboxylic-acid.

$^1$H-NMR(DMSO-d$_6$) δ:2.66(s, 3H) 7.52 (m, 3H) 7.96(m, 2H)

Example 203c)

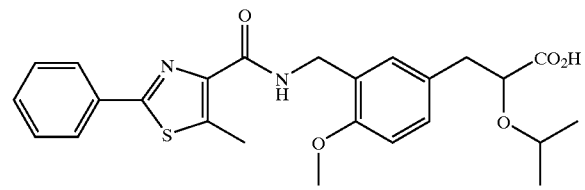

2-Isopropoxy-3-[4-methoxy-3-([(5-methyl-2-phenyl-1,3-thiazole-4-yl)carbonyl]aminoethyl)phenyl]propanoic acid was obtained by the same method as in Examples 19d) and e).

$^1$H-NMR(CDCl$_3$) δ:0.99 (d, J=6.5 Hz, 3H) 1.10(d, J=6.5 Hz, 3H) 2.65(s, 3H) 2.86(dd, J=7.0, 14.0 Hz, 1H) 3.00(dd, J=4.5, 14.0 Hz, 1H) 3.52(sept, J=6.0 Hz, 1H) 3.82(s, 3H) 4.05(dd, J=4.5, 7.0 Hz, 1H) 4.51(d, J=6.0 Hz, 2H) 6.42(bs, 1H) 6.77(d, J=8 .0 Hz, 1H) 7.09(dd, J=2.0, 8.0 Hz, 1H) 7.16(d, J=2.0 Hz, 1H) 7.37(m, 3H) 7.85 (m, 2H)

Example 204

Example 204a)

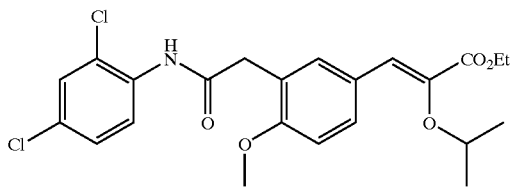

3.1 g of N-(2,4-dichlorophenyl)-2-(5-formyl-2-methoxyphenyl)acetamide and 3.3 g of ethyl 2-(diethylphosphoryl)-2-ethylacetate were treated by the same method as in Example 1a), to give 2.6 g of 2-ethyl-3-(4-methoxy-3-{2-oxo-2-[2,4-dichloroanilino]ethyl}phenyl)-2-propenoate.

$^1$H-NMR(CDCl$_3$) δ:1.26(d, J=6.0 Hz, 6H) 1.35(t, J=8.0 Hz, 3H) 3.75(s, 2H) 3.94 (s, 3H) 4.27 (q, J=8.0 Hz, 2H) 4.41 (sept, J=6.0 Hz, 1H) 6.95 (m, 2H) 7.20 (d, J=8.0 Hz, 1H) 7.30(d, J=8.0 Hz, 1H) 7.79(d, J=2.0 Hz, 1H) 7.85(dd, J=2.0, 8.0 Hz, 1H) 8.18(bs, 1H) 8.38(d, J=8.0 Hz, 1H)

Example 204b)

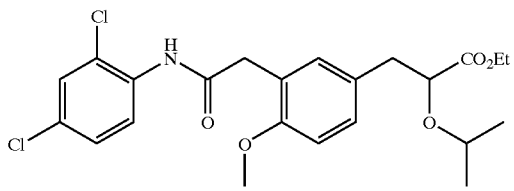

By the same method as in Example 196b), 0.3 g of ethyl 2-(4-methoxy-3-{2-oxo-2-[2,4-dichloroanilino]ethyl}benzyl)butanoate was obtained from 2 g of 2-ethyl-3-(4-methoxy-3-{2-oxo-2-[2,4-dichloroanilino]ethyl}phenyl)-2-propenoate.

$^1$H-NMR(CDCl$_3$) δ: 0.88(d, J=6.0 Hz, 3H) 1.06(d, J=6.0 Hz, 3H) 1.15(t, J=8.0 Hz, 3H) 2.85(m, 2H) 3.43(sept, J=6.0 Hz, 1H) 3.65(s, 3H) 3.82(s, 3H) 3.94(dd, J=4.0, 8.0 Hz, 1H) 4.09(q, J=8.0 Hz, 2H) 6.80(d, J=8.0 Hz, 1H) 7.13(m, 3H) 7.23(d, J=8.0 Hz, 1H) 8.22(s, 1H) 8.28(d,J=8.0 Hz,1H)

Example 204c)

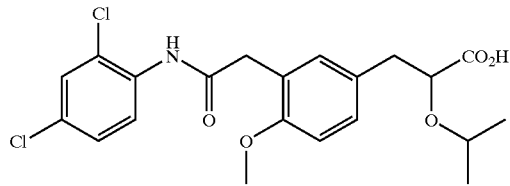

0.3 g of ethyl 2-(4-methoxy-3-{2-oxo-2-[2,4-dichloroanilino]ethyl}benzyl)butanoate was dissolved in 10 ml ethanol, followed by adding 1 ml of 5N sodium hydroxide. The reaction solution was heated under reflux for 10 minutes, and then acidified with 1N hydrochloric acid under ice-cooling. The aqueous layer was extracted with ethyl acetate and washed with brine. The organic layer was dried over anhydrous magnesium sulfate and the solvent was evaporated, to give 0.19 g of 2-(4-methoxy-3-{2-oxo-2-[4-(trifluoromethyl)anilino]ethyl}benzyl)butanoic acid.

$^1$H-NMR(CDCl$_3$) δ: 0.95(d, J=6.0 Hz, 3H) 1.08(d, J=6.0 Hz, 3H) 2.86(.dd, J=7.0, 14.0 Hz, 1H) 3.00(dd, J=4.5, 14.0 Hz, 1H) 3.49(sept, J=6.0 Hz, 1H) 3.67(s, 3H) 3.84(s, 3H) 4.04(dd, J=4.5, 7.0 Hz, 1H) 6.82 (d, J=8.0 Hz, 1H) 7.12(m, 3H) 7.23(d, J=8.0 Hz, 1H) 8.20(s, 1H) 8.28(d,J=8.0 Hz,1H)

Example 205

Production Example 205a)

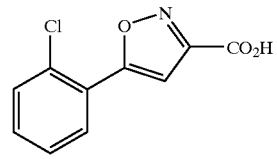

5-(2-Chlorophenyl)-4-isoxazolecarboxylic acid was obtained by the same method as in Production Example 199.

$^1$H-NMR(CDCl$_3$) δ:7.40(s,1H) 7.43(m,2H) 7.56 (m, 1H) 8.00(dd,J=2.0,8.0 Hz,1H)

Example 205b)

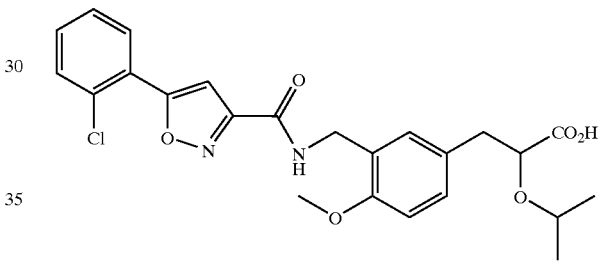

3-3-[([5-(2-Chlorophenyl)-3-isoxazolyl]carbonylamino)methyl]-4-methoxyphenyl-2-isopropoxypropanoic acid was obtained by the same method as in Examples 19d) and e).

$^1$H-NMR(CDCl$_3$) δ: 0.98(d, J=6.0 Hz, 3H) 1.09(d, J=6.0 Hz, 3H) 2.84(dd, J=7.0, 14.0 Hz, 1H) 3.00(dd, J=4.5, 14.0 Hz, 1H) 3.50(sept, J=6.0 Hz, 1H) 3.81(s, 3H) 4.05(dd, J=4.5, 7.0 Hz, 1H) 4.46(d, J=7.0 Hz,2H) 6.76 (d, J=8.0 Hz, 1H) 7.08(dd, J=2.0, 8.0 Hz, 1H) 7.16(d, J=2.0 Hz, 1H) 7.29–7.35 (m, 2H) 7.46(dd, J=4.0, 7.5 Hz, 1H) 7.85(dd,J=4.0,7.5 Hz,1H)

Example 206

Production Example 206a)

2 ml ethyl 2,4-dioxovalerate and 1.2 g phenyl hydrazine were dissolved in 20 ml acetic acid, followed by stirring at 100° C. for 2 hours. After evaporating acetic acid, ethyl acetate was added to the residue. The mixture was washed with aqueous sodium hydrogencarbonate solution and brine, dried over anhydrous magnesium sulfate and evaporated. The residue was subjected to silica gel column chromatography, to give 0.37 g of ethyl 3-methyl-1-phenyl-1H-5-pyrazolecarboxylate with hexane:ethyl acetate (14:1) and 0.46 g of ethyl 5-methyl-1-phenyl-1H-3-pyrazolecarboxylate with hexane:ethyl acetate (9:1).

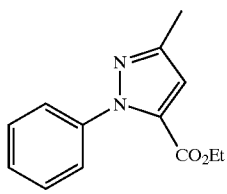

Ethyl 3-methyl-1-phenyl-1H-5-pyrazolecarboxylate
¹H-NMR(CDCl₃) δ:1.22(t, J=8.0 Hz, 3H) 2.35 (s, 3H) 4.22(q, J=8.0 Hz, 2H) 6.80(s, 1H) 7.42(m, 5H)

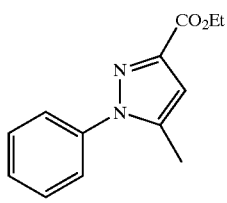

Ethyl 5-methyl-1-phenyl-1H-3-pyrazolecarboxylate
¹H-NMR(CDCl₃) δ:1.39 (t, J=8.0 Hz, 3H) 2.34 (s, 3H) 4.41(q, J=8.0 Hz, 2H) 6.74(s, 1H) 7.40–7.50(m, 5H)

Production Example 206b)

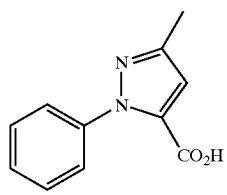

0.37 g of ethyl 3-methyl-1-phenyl-1H-5-pyrazolecarboxylate was dissolved in 10 ml ethanol, and 1 ml of 5N sodium hydroxide was added, followed by heating under reflux for 1 hour. The reaction solution was ice-cooled and neutralized with 2N hydrochloric acid, followed by extracting with ethyl acetate. The organic layer was washed with brine, dried over anhydrous magnesium sulfate and evaporated, to give 0.26 g of 3-methyl-1-phenyl-1H-5-pyrazolecarboxylic acid.
¹H-NMR(CDCl₃) δ: 2.35(s, 3H) 6.87(s, 1H) 7.40(m, 5H)

Example 206

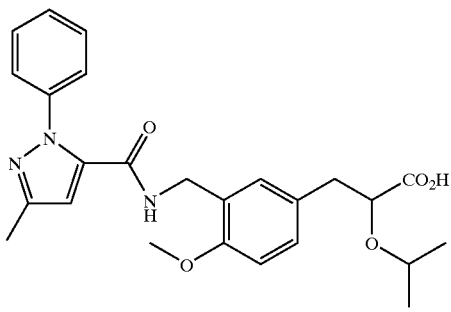

2-Isopropoxy-3-[4-methoxy-3-([(3-methyl-1-phenyl-1H-5-pyrazolyl)carbonyl]aminoethyl)phenyl]propanoic acid was obtained by the same method as in Examples 19d) and e).

¹H-NMR(CDCl₃) δ: 0.98(d, J=6.0 Hz, 3H) 1.09(d, J=6.0 Hz, 3H) 2.62(s, 3H) 2.84(dd, J=7.0, 14.0 Hz, 1H) 2.96(dd, J=4.5, 14.0 Hz, 1H) 3.51(sept, J=6.0 Hz, 1H) 3.64(s, 3H) 4.03(dd, J=4.5, 7.0 Hz, 1H) 4.38(d, J=7.0 Hz,2H) 6.23(bs, 1H) 6.67(d, J=8.0 Hz, 1H) 7.05–7.08(m, 2H) 7.24–7.32(m, 5H)

Example 207

Production Example 207a

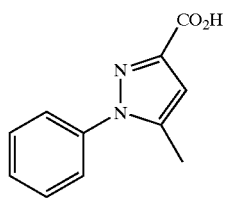

5-Methyl-1-phenyl-1H-3-pyrazolecarboxylic acid was obtained by the same method as in Production Example 206b).
¹H-NMR(CDCl₃) δ: 2.35(s, 3H) 6.79(s, 1H) 7.42–7.52(m, 5H)

Example 207b

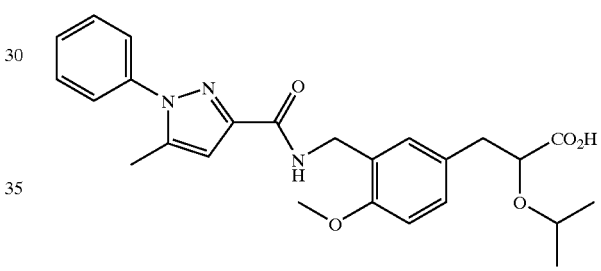

2-Isopropoxy-3-[4-methoxy-3-([(5-methyl-1-phenyl-1H-3-pyrazolyl)carbonyl]aminoethyl)phenyl]propanoic acid was obtained by the same method as in Examples 19d) and e).
¹H-NMR(CDCl₃) δ: 0.96(d, J=6.0 Hz, 3H) 1.09(d, J=6.0 Hz, 3H) 2.60(s, 3H) 2.82(dd, J=7.0, 14.0 Hz, 1H) 2.97(dd, J=4.5, 14.0 Hz, 1H) 3.47(sept, J=6.0 Hz, 1H) 3.76(s, 3H) 4.01(dd, J=4.5, 7.0 Hz, 1H) 4.51(d, J=7.0 Hz,2H) 6.67(s, 1H) 6.71(d, J=8.0 Hz, 1H) 7.04(dd, J=8.0, 2.0 Hz, 1H) 7.15(d, J=2.0 Hz, 1H) 7.27(bs,1H) 7.35–7.38(m, 3H) 7.41–7.46(m, 2H)

Example 208

Example 208a

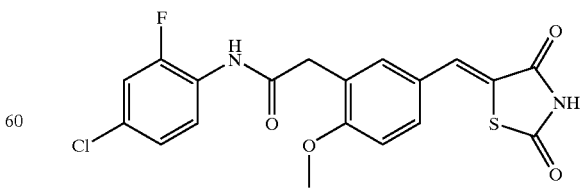

N1-{5-[(2,4-dioxo-1,3-thiazolane-5-ilydene)methyl]-2-methoxybenzyl}-2-fluoro-4-chlorobenzamide was obtained by the same method as in Examples 28a)–c).

¹H-NMR(DMSO-d₆) δ:3.74(s, 2H) 3.85(s, 3H) 7.12(d, J=8.0 Hz, 1H) 7.23(d, J=8.0 Hz, 1H) 7.44(bs, 1H) 7.50(t, J=8.0 Hz, 1H) 7.66(s, 1H) 7.90 t, J=8.0 Hz, 1H) 9.98(s, 1H)

Example 208b

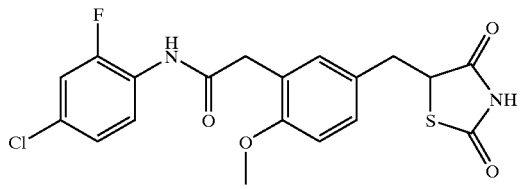

0.3 g of N1-{5-[(2,4-dioxo-1,3-thiazolane-5-ilydene)methyl]-2-methoxybenzyl}-2-fluoro-4-chlorobenzamide was dissolved in 20 ml methanol, followed by adding 20 mg iodine. While heating under reflux the reaction solution, 400 mg magnesium was added in 10 portions at 10 minutes intervals. The reaction solution was ice-cooled and acidified with 2N hydrochloric acid, followed by extracting with dichloromethane. The organic layer was washed with brine, dried over anhydrous magnesium sulfate and evaporated. Diisopropyl ether was added to the residue and the resulting crystals were filtered, to give 80 mg of N1-(4-chloro-2-fluorophenyl)-2-2-methoxy-5-[(2-methylene-4-oxo-1,3-thiazolane-5-yl)methyl]phenylacetamide.

¹H-NMR(DMSO-d₆) δ:2.99(dd, J=10.0, 14.0 Hz, 1H) 3.27(m, 1H) 3.65(s, 2H) 3.73(s, 3H) 4.81(m, 1H) 6.91(d, J=8.0 Hz, 1H) 7.08–7.11(m, 2H) 7.22(m, 1H) 7.47(m, 1H) 7.89(m, 1H) 9.84(s, 1H)

Example 209

Production Example 209a

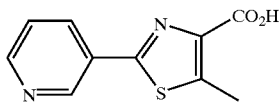

5-Methyl-2-(3-pyridyl)-1,3-thiazole-4-carboxylic acid was obtained by the same method as in Production Example 203.

¹H-NMR(CDCl₃) δ:2.67(s, 3H) 7.54(dd, J=4.0, 8.0 Hz, 1H) 8.31(d, J=8.0 Hz, 1H) 8.70(d, J=4.0 Hz, 1H) 9.51(s, 1H)

Example 209b

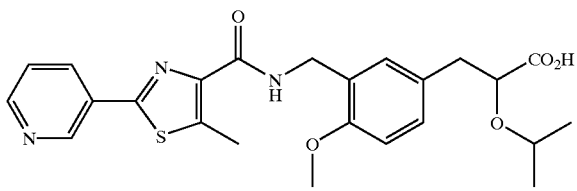

2-Isopropoxy-3-4-methoxy-3-[([5-methyl-2-(3-pyridyl)-1,3-thiazole-4-yl]carbonylamino)methyl]phenylpropanoic acid was obtained by the same method as in Production Examples 19d) and e).

¹H-NMR(CDCl₃) δ: 1.01(d, J=6.0 Hz, 3H) 1.11(d, J=6.0 Hz, 3H) 2.66(s, 3H) 2.87(dd, J=7.0, 14.0 Hz, 1H) 2.99(dd, J=4.5, 14.0 Hz, 1H) 3.55(sept, J=6.0 Hz, 1H) 3.83(s, 3H) 4.06(dd, J=4.5, 7.0 Hz, 1H) 4.52(d, J=7.0 Hz,2H) 6.59(bs, 1H) 6.78(d, J=8.0 Hz, 1H) 6.91(s, 1H) 7.09–7.26(m, 2H) 7.40(m, 1H) 7.60(m, 1H) 8.56(d, J=7.0 Hz, 1H)

Example 210

Production Example 210a

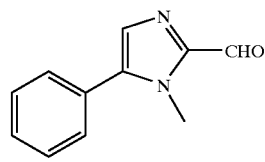

3.7 g of 1-methyl-3-phenylimidazole was dissolved in tetrahydrofuran, followed by adding dropwise 18.7 ml of n-butyl lithium (1.5 mol/l solution in hexane) thereinto under cooling at −50° C. After elevating the reaction temperature to −20° C., it was cooled again to −50° C. 3.6 ml N,N-dimethylformamide was added thereto and then the cooling device was removed and the reaction temperature was elevated to room temperature. Aqueous ammonium chloride solution was added to the reaction solution, followed by extracting with ethyl acetate. The ethyl acetate layer was washed with brine, dried over anhydrous magnesium sulfate and the solvent was evaporated. The residue was purified by silica gel column chromatography (hexane:ethyl acetate=3:1), to give 1.9 g of 1-methyl-5-phenyl-1H-2-imidazole carboxyaldehyde.

¹H-NMR(DMSO-d₆) δ:3.98(s, 3H) 7.28(t, J=8.0 Hz, 1H) 7.40(t, J=8.0 Hz, 2H) 8.82(d, J=8.0 Hz, 2H) 8.10(s, 1H) 9.75(s, 1H)

Production Example 210b

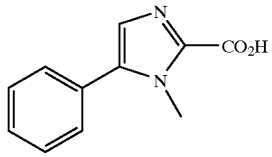

1 g of 1-methyl-5-phenyl-1H-2-imidazolecarboxyaldehyde was dissolved in 15 ml dimethyl sulfoxide, and 3 ml potassium hydrogen phosphate (1 mol/l) was added. An aqueous solution of 1.5 g sodium chlorite was added, followed by stirring at room temperature for 20 minutes. Water was added to the reaction solution, followed by extracting with ethyl acetate. The ethyl acetate layer was washed with brine, dried over anhydrous magnesium sulfate and evaporated. The residue was purified by silica gel column chromatography (hexane:ethyl acetate= 3:1→1:4→ethyl acetate:methanol=3:1), to give 90 mg 1-methyl-5-phenyl-1H-2-imidazolecarboxylic acid.

¹H-NMR(DMSO-d₆) δ:4.00(s, 3H) 7.26(t, J=8.0 Hz, 1H) 7.42(t, J=8.0 Hz, 2H) 7.75(s, 1H) 8.82(d, J=8.0 Hz, 2H)

Example 210c

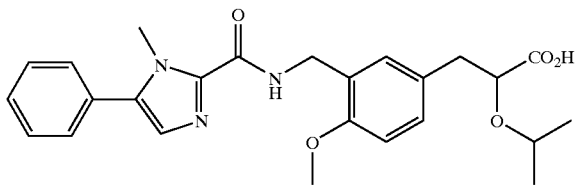

2-Isopropoxy-3-[4-methoxy-3-([(1-methyl-5-phenyl-1H-2-imidazolyl)carbonyl]aminoethyl)phenyl]propanoic acid was obtained by the same method as in Examples 19d) and e).

$^1$H-NMR(CDCl$_3$) δ: 0.97(d, J=6.0 Hz, 3H) 1.06(d, J=6.0 Hz, 3H) 2.84(dd, J=7.0, 14.0 Hz, 1H) 2.97(dd, J=4.5, 14.0 Hz, 1H) 3.48(sept, J=6.0 Hz, 1H) 3.81(s, 3H) 4.02(m, 1H) 4.03(s, 3H) 4.52(d, J=7.0 Hz,2H) 6.75(d, J=8.0 Hz, 1H) 6.91(s, 1H) 7.06(dd, J=2.0, 8.0 Hz, 1H) 7.16(m, 2H) 7.21(m, 1H) 7.31(t, J=7.5 Hz, 2H) 7.68(d, J=7.5 Hz, 2H)

Example 211

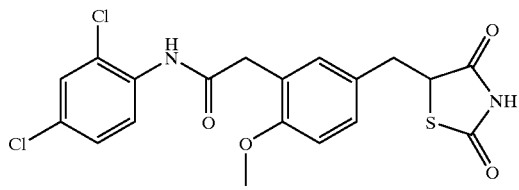

N1-(2,4-dichlorophenyl)-2-2-methoxy-5-[(2-methylene-4-oxo-1,3-thiazolane-5-yl)methyl]phenylacetamide was obtained by the same method as in Examples 28a)–c), 208a) and b).

$^1$H-NMR(DMSO-d$_6$) δ:3.00(dd, J=10.0, 14.0 Hz, 1H) 3.32(m, 1H) 3.65(s, 2H) 3.76(s,3H) 4.82(dd,J=4.5,10.0 Hz,1H) 6.93(d, J=8.0 Hz, 1H) 7.11(m, 2H) 7.38(dd, J=2.5, 8.0 Hz, 1H) 7.64(d, J=2.5 Hz, 1H) 7.80(d, J=8.0 Hz, 1H) 9.42(s, 1H)

Example 212

Production Example 212a

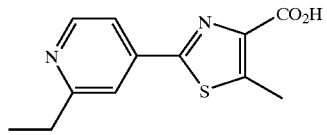

2-(2-Ethyl-4-pyridyl)-5-methyl-1,3-thiazole-4-carboxylic acid was obtained by the same method as in Production Example 203.

$^1$H-NMR(DMSO-d$_6$) δ:1.23(t, J=8.0 Hz, 3H) 2.69(s, 3H) 2.83(q, J=8.0 Hz, 2H) 7.70(d, J=6.0 Hz, 1H) 7.78(s, 1H) 8.60(d, J=6.0 Hz, 1H)

Example 212b

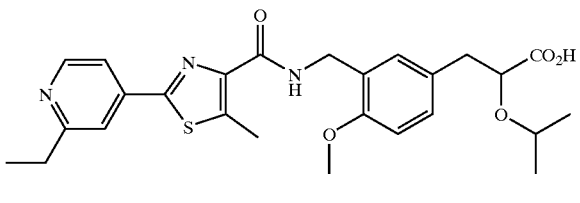

3-3-[([2-(2-ethyl-4-pyridyl)-5-methyl-1,3-thiazole-4-yl]carbonylamino)methyl]-4-methoxyphenyl-2-isopropoxypropanoic acid was obtained by the same method as in Examples 19d) and e).

$^1$H-NMR(CDCl$_3$) δ: 1.07(d, J=6.0 Hz, 3H) 1.18(d, J=6.0 Hz, 3H) 1.37(d, J=7.5 Hz, 3H) 2.72(s, 3H) 2.94(m, 3H) 3.06(dd, J=4.5, 14.0 Hz, 1H) 3.61(sept, J=6.0 Hz, 1H) 3.89(s, 3H) 4.12(dd, J=4.5, 7.0 Hz, 1H) 4.59(d, J=7.0 Hz, 2H) 6.55(bs, 1H) 6.84(d, J=7.0 Hz, 1H) 7.18(d, J=7.0 Hz, 1H) 7.22(s, 1H) 7.63(m, 1H) 7.72(s, 1H) 8.62(d, J=5.0 Hz, 1H)

Example 213

Production Example 213a

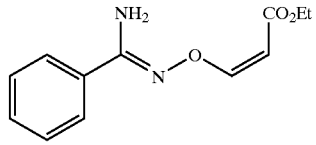

6.7 g of benzamidoxime and 5 ml ethyl propiolate were dissolved in 5 ml methanol and heated under reflux for 3 hours. The solvent was evaporated and the residue was purified by silica gel column chromatography (hexane:ethyl acetate=10:1), to give 4.5 g of ethyl (Z)-3-([(Z)-1-amino-1-phenylmethylidene]aminoxy)-2-propenoate.

$^1$H-NMR(CDCl$_3$) δ: 1.30(t, J=8.0 Hz, 3H) 4.17(q, J=8.0 Hz, 2H) 4.90(d, J=6.0 Hz, 1H) 5.25(bs, 2H) 7.38(d, J=6.0 Hz, 1H) 7.40–7.50(m, 3H) 7.65(m, 2H)

Production Example 213b

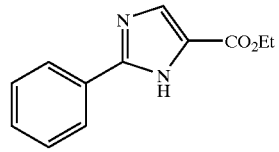

4.5 g of (Z)-3-([(Z)-1-amino-1-phenylmethylidene]aminoxy)-2-propenoate was dissolved in 30 ml diphenyl ether and heated at 200° C. for 5 hours. Hexane was added to the reaction mixture, and the resulting solid was filtered and purified by silica gel column chromatography (hexane:ethyl acetate=1:1→dichloromethane:methanol=50:1), to give 3.5 g of ethyl 2-phenyl-1H-5-imidazolecarboxylate.

$^1$H-NMR(CDCl$_3$) δ: 1.39(t, J=8.0 Hz, 3H) 4.38(q, J=8.0 Hz, 2H) 7.43(m,3H) 7.78(s, 1H) 7.90(m, 2H)

Production Example 213c 3.5 g of ethyl 2-phenyl-1H-5-imidazolecarboxylate was dissolved in 30 ml N,N-dimethylformamide. 0.71 g of sodium hydride was added thereto under ice-cooling, followed by stirring at room temperature for 1 hour. The reaction solution was ice-cooled again and 1.5 ml methyl iodide was added, followed by stirring at room temperature for 30 minutes. Water and aqueous ammonium chloride solution were added to the reaction solution, followed by extracting with ethyl acetate. The ethyl acetate layer was washed with brine, dried over anhydrous magnesium sulfate and evaporated. The residue was purified by silica gel column chromatography, to give 0.6 g of ethyl 1-methyl-2-phenyl-1H-4-imidazole carboxylate with hexane:ethyl acetate=8:1 and 2.2 g of ethyl 1-methyl-2-phenyl-1H-5-imidazolecarboxylate with hexane:ethyl acetate=1:1.

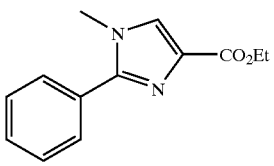

Ethyl 1-methyl-2-phenyl-1H-4-imidazolecarboxylate $^1$H-NMR(CDCl$_3$) δ: 1.37(t, J=8.0 Hz, 3H) 3.94(s, 3H) 4.34(q, J=8.0 Hz, 2H) 7.46(m, 3H) 7.60(m, 2H) 7.83(s, 1H)

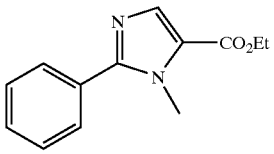

Ethyl 1-methyl-2-phenyl-1H-5-imidazolecarboxylate $^1$H-NMR(CDCl$_3$) δ: 1.39(t, J=8.0 Hz, 3H) 3.77(s, 3H) 4.39(q, J=8.0 Hz, 2H) 7.45(m, 3H) 7.64(m, 2H) 7.68(s, 1H)

Production Example 213d

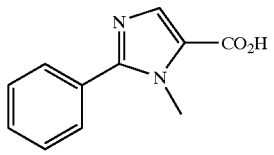

2.2 g of ethyl 1-methyl-2-phenyl-1H-5-imidazolecarboxylate was dissolved in 20 ml ethanol and 2 ml of 5N sodium hydroxide was added, followed by heating under reflux for 1 hour. The reaction solution was ice-cooled and neutralized with 2N hydrochloric acid, followed by extracting with a mixed solvent of ethyl acetate and tetrahydrofuran. The organic layer was washed with brine, dried over anhydrous magnesium sulfate and evaporated, to give 1.1 g of 1-methyl-2-phenyl-1H-5-imidazolecarboxylic acid.

$^1$H-NMR(CDCl$_3$) δ: 3.77(s, 3H) 7.52(m, 3H) 7.71(m, 2H) 8.06(s, 1H)

Example 213e

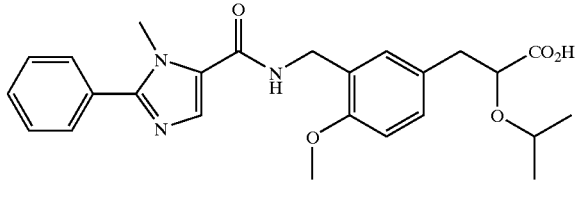

2-Isopropoxy-3-[4-methoxy-3-([(1-methyl-2-phenyl-1H-5-imidazolyl)carbonyl]aminoethyl)phenyl]propanoic acid was obtained by the same method as in Examples 19d) and e).

$^1$H-NMR(CDCl$_3$) δ: 0.82(d, J=6.0 Hz, 3H) 0.97(d, J=6.0 Hz, 3H) 2.66(dd, J=7.0, 14.0 Hz, 1H) 2.79(dd, J=4.5, 14.0 Hz, 1H) 3.41(sept, J=6.0 Hz, 1H) 3.76(s, 3H) 3.78(s, 3H) 3.91(dd, J=4.5, 7.0 Hz, 1H) 4.37 (d, J=7.0 Hz,2H) 6.87(d, J=8.0 Hz, 1H) 7.05–7.08(m, 2H) 7.46–7.53(m, 3H) 7.72(d, J=6.5 Hz, 1H) 7.82(s, 1H) 8.13(bs, 1H)

Example 214

Production Example 214a

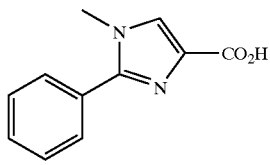

0.6 g of ethyl 1-methyl-2-phenyl-1H-4-imidazolecarboxylate was dissolved in 10 ml ethanol and 1 ml of 5N sodium hydroxide was added, followed by heating under reflux for 1 hour. The reaction solution was ice-cooled and neutralized with 2N hydrochloric acid, followed by extracting with ethyl acetate and tetrahydrofuran. The organic layer was washed with brine, dried over anhydrous magnesium sulfate and evaporated, to give 0.5 g of 1-methyl-2-phenyl-1H-4-imidazolecarboxylic acid.

$^1$H-NMR(CDCl$_3$) δ: 3.86(s, 3H) 7.52(m, 3H) 7.68(m, 2H) 7.83(s, 1H)

Example 214b

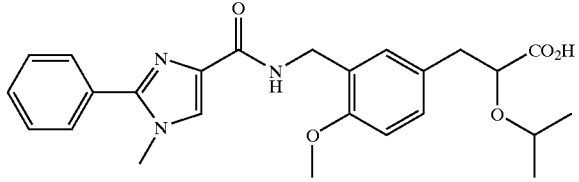

2-Isopropoxy-3-[4-methoxy-3-([(1-methyl-2-phenyl-1H-4-imidazolyl)carbonyl]aminoethyl)phenyl]propanoic acid was obtained by the same method as in Examples 19d) and e).

$^1$H-NMR(CDCl$_3$) δ: 0.84(d, J=6.0 Hz, 3H) 0.99(d, J=6.0 Hz, 3H) 2.70(dd, J=7.0, 14.0 Hz, 1H) 2.84(dd, J=4.5, 14.0 Hz, 1H) 3.44(sept, J=6.0 Hz, 1H) 3.79(s, 3H) 3.90(s, 3H) 3.96(dd, J=4.5, 7.0 Hz, 1H) 4.40 (d, J=7.0 Hz, 2H) 6.90(d, J=8.0 Hz, 1H) 7.11(m, 2H) 7.56–7.64(m, 3H) 7.70–7.76(m, 1H) 8.10(s, 1H) 8.97(bs, 1H)

Example 215

Production Example 215a

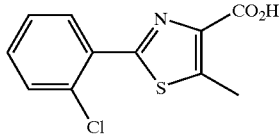

2-(2-Chlorophenyl)-5-methyl-1,3-thiazole-4-carboxylic acid was obtained by the same method as in Production Example 203.

$^1$H-NMR(DMSO-d$_6$) δ:2.68(s, 3H) 7.48–7.55(m, 2H) 7.65(d, J=8.0 Hz, 1H) 8.24(dd, J=2.0, 8.0 Hz, 1H) 13.50(bs, 1H)

Example 215b

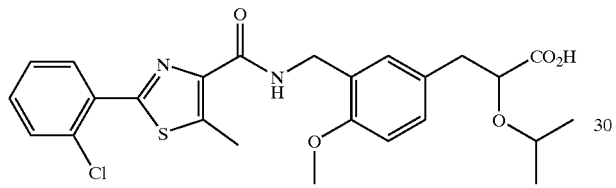

3-3-[([2-(2-Chlorophenyl)-5-methyl-1,3-thiazolane-4-yl]carbonylamino)methyl]-4-methoxyphenyl-2-isopropoxycarboxylic acid was obtained by the same method as in Example 38.

$^1$H-NMR(CDCl$_3$) δ: 1.07(d, J=6.0 Hz, 3H) 1.17(d, J=6.0 Hz, 3H) 2.74(s, 3H) 2.93(dd, J=7.0, 14.0 Hz, 1H) 3.07(dd, J=4.5, 14.0 Hz, 1H) 3.60(sept, J=6.0 Hz, 1H) 3.89(s, 3H) 4.13(dd, J=4.5, 7.0 Hz, 1H) 4.59 (d, J=7.0 Hz, 2H) 6.84(d, J=8.0 Hz, 1H) 7.16(dd, J=2.0, 8.0 Hz, 1H) 7.23(d, J=2.0 Hz, 1H) 7.35–7.38(m, 2H) 7.48–7.51(m, 1H) 8.23–8.26(m, 1H)

Example 216

Production Example 216a

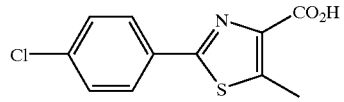

2-(4-Chlorophenyl)-5-methyl-1,3-thiazole-4-carboxylic acid was obtained by the same method as in Production Example 203.

$^1$H-NMR(DMSO-d$_6$) δ:2.66(s, 3H) 7.56(d, J=8.0 Hz, 2H) 7.98(d, J=8.0 Hz, 2H)

Example 216b

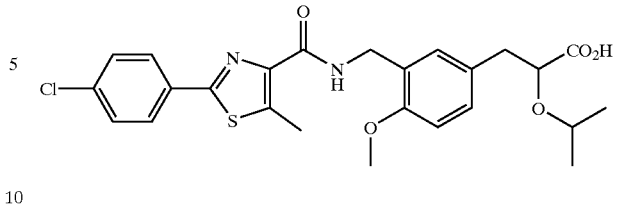

3-3-[([2-(4-Chlorophenyl)-5-methyl-1,3-thiazolane-4-yl]carbonylamino)methyl]-4-methoxyphenyl-2-isopropoxycarboxylic acid was obtained by the same method as in Example 38.

$^1$H-NMR(CDCl$_3$) δ: 1.07(d, J=6.0 Hz, 3H) 1.17(d, J=6.0 Hz, 3H) 2.70(s, 3H) 2.93(dd, J=7.0, 14.0 Hz, 1H) 3.06(dd, J=4.5, 14.0 Hz, 1H) 3.60(sept, J=6.0 Hz, 1H) 3.90(s, 3H) 4.13(dd, J=4.5, 7.0 Hz, 1H) 4.58 (d, J=7.0 Hz, 2H) 6.52(bs, 1H) 6.84(d, J=8.0 Hz, 1H) 7.16(dd, J=2.0, 8.0 Hz, 1H) 7.22(d, J=2.0 Hz, 1H) 7.41(d, J=9.0 Hz, 2H) 7.86(d, J=9.0 Hz, 2H)

Example 217

Production Example 217a

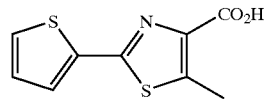

5-Methyl-2-(2-thienyl)-1,3-thiazole-4-carboxylic acid was obtained by the same method as in Production Example 203.

$^1$H-NMR(DMSO-d$_6$) δ:2.60(s, 3H) 7.08(dd, J=4.0, 5.0 Hz, 1H) 7.77(d, J=8.0 Hz, 1H) 7.80(d, J=5.0 Hz, 1H) 38(bs, 1H)

Example 217b

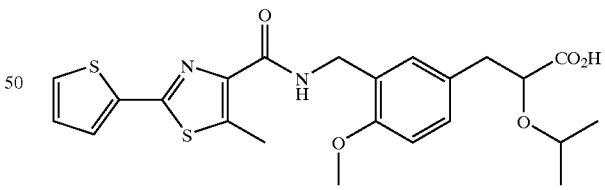

2-Isopropoxy-3-4-methoxy-3-[([5-methyl-2-(2-thienyl)-1,3-thiazole-4-yl]carbonylamino)methyl]phenylpropanoic acid was obtained by the same method as in Example 38.

$^1$H-NMR(CDCl$_3$) δ:1.05(d,J=6.0 Hz,3H) 1.17(d,J=6.0 Hz,3H) 2.67(s,3H) 2.93(dd,J=7.0,14.0 Hz, 1H) 3.06(dd, J=4.5, 14.0 Hz, 1H) 3.59(sept, J=6.0 Hz, 1H) 3.89(s, 3H) 4.11(dd, J=4.5, 7.0 Hz, 1H) 4.57 (d, J=7.0 Hz, 2H) 6.49(bs, 1H) 6.83(d, J=8.0 Hz, 1H) 7.08(dd, J=4.0, 5.0 Hz, 1H) 7.17(dd, J=2.0, 8.0 Hz, 1H) 7.22(d, J=2.0 Hz, 1H) 7.43(dd, J=1.0, 5.0 Hz, 1H) 7.52(dd, J=1.0, 4.0 Hz, 1H)

Example 218

Production Example 218a

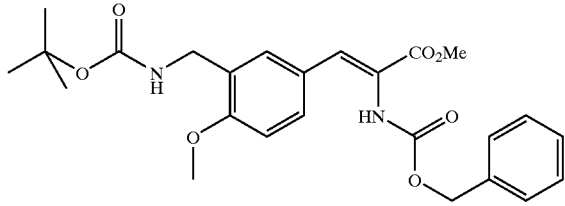

20.6 g of (±)-Z-α-(phosphonoglycinetrimethyl ester was dissolved in 200 ml dichloromethane, followed by adding 8.9 ml of 1,8-diazabicyclo[5.4.0]-7-undecene. After stirring the reaction solution at room temperature for 15 minutes, tert-butyl-N-(5-formyl-2-methoxybenzyl)carbamate dissolved in 50 ml dichloromethane was added, followed by stirring at room temperature for 16 hours. The reaction solution was ice-cooled and water was added, followed by extracting with ethyl acetate. The organic layer was washed brine, dried over anhydrous magnesium sulfate and evaporated. The residue was purified by silica gel column chromatography (hexane:ethyl acetate=3:1), to give 21 g of methyl (Z)-2-[(benzyloxy)carbonyl]amino-3-(3-[(tert-butoxycarbonyl)amino]methyl-4-methoxyphenyl)-2-propenoate.

$^1$H-NMR(CDCl$_3$) δ:1.44(s, 9H) 3.80(s, 3H) 3.86(s, 3H) 4.25(s, 2H) 4.90(bs, 1H) 5.13(s, 2H) 6.78(d, J=8.0 Hz, 1H) 7.35(m, 5H) 7.42(m, 1H) 7.49(m,1H)

Production Example 218b

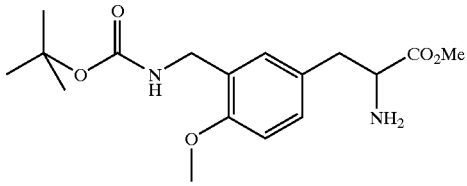

5 g of methyl (Z)-2-[(benzyloxy)carbonyl]amino-3-(3-[(tert-butoxycarbonyl)amino]methyl-4-methoxyphenyl)-2-propenoate was dissolved in methanol. 0.7 g of 10% palladium-carbon was added thereto, followed by stirring for 16 hours in a hydrogen atmosphere. The reaction solution was filtered and evaporated. The residue was purified by silica gel column chromatography (ethyl acetate), to give 3.4 g of methyl 2-amino-3-(3-[(tert-butoxycarbonyl)amino]methyl-4-methoxyphenyl)propanoate was obtained.

$^1$H-NMR(CDCl$_3$) δ:1.43(s,9H) 2.80(dd,J=7 0,14.0 Hz,1H) 3.69(dd,J=4.5,14.0 Hz,1H) 3.72(s,3H) 3.82(s,3H) 4.27(d,J=6.0 Hz,2H) 5.00(bs,1H) 6.79(d,J=8.0 Hz,1H) 7.06 (m,2H)

Production Example 218c

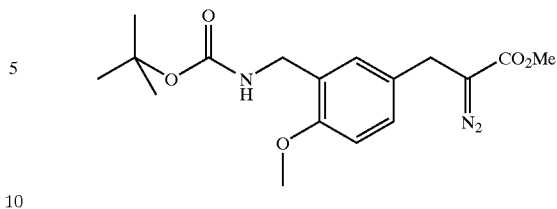

3.4 g of methyl 2-amino-3-(3-[(tert-butoxycarbonyl) amino]methyl-4-methoxyphenyl) propanoate was dissolved in 30 ml chloroform, and 1.7 ml acetic acid and 1.35 ml isoamyl nitrite were added, followed by stirring at 60° C. for 20 minutes. The reaction solution was ice-cooled and water was added thereto, followed by extracting with dichloromethane. The organic layer was washed with brine, dried over anhydrous magnesium sulfate and then evaporated. The residue was purified by silica gel column chromatography (hexane:ethyl acetate=9:1), to give 2.5 g of 1-[1-(3-[(tert-butoxycarbonyl)amino]methyl-4-methoxybenzyl)-2-methoxy-2-oxoethyl]-1-diazine-1-ium.

$^1$H-NMR(CDCl$_3$) δ:1.43(s,9H) 3.78(s,3H) 3.82(s,3H) 4.27(d,J=6.0 Hz,1H) 5.00(bs,1H) 6.79(d,J=8.0 Hz,1H) 7.11 (m,2H)

Example 218d

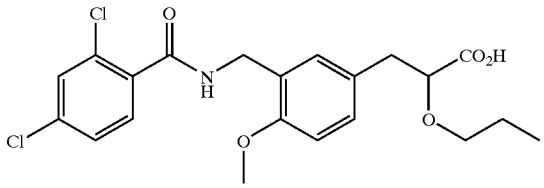

2 g of 1-[1-(3-[(tert-butoxycarbonyl)amino]methyl-4-methoxybenzyl)-2-methoxy-2-oxoethyl]-1-diazine-1-ium was dissolved in 30 ml n-propanol, followed by adding 25 mg of rhodium (II) acetate. After stirring at room temperature for 1 hour, it was evaporated. The residue was purified by silica gel column chromatography (hexane:ethyl acetate= 9:1). The resulting product was treated by the same method as in Example 38, to give 3-(3-[(2,4-dichlorobenzoyl) amino]methyl-4-methoxyphenyl)-2-propoxypropanoic acid was obtained.

$^1$H-NMR(CDCl$_3$) δ: 0.87(d, J=8.0 Hz, 3H) 1.58(q, J=8.0 Hz, 2H) 2.97(dd, J=7.0, 14.0 Hz, 1H) 3.09(dd, J=4.5, 14.0 Hz, 1H) 3.38(m, 1H) 3.52(m, 1H) 3.85(s, 3H) 4.07(dd, J=4.5, 7.0 Hz, 1H) 4.60(d, J=7.0 Hz,2H) 6.82(m, 2H) 7.16(dd, J=2.0, 8.0 Hz, 1H) 7.30(dd, J=2.0, 8.0 Hz, 1H) 7.40(d, J=2.0 Hz, 1H) 7.40(d, J=2.0 Hz, 1H) 7.65(d, J=8.0 Hz, 1H)

Example 219

Production Example 219a

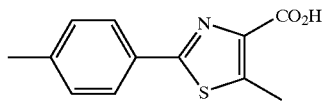

2-(4-Methylphenyl)-5-methyl-1,3-thiazole-4-carboxylic acid was obtained by the same method as in Production Example 203.

¹H-NMR(CDCl₃) δ:2.40(s,3H) 2.77(s,3H) 7.25(d,J=8.0 Hz,2H) 7.85(d,J=8.0 Hz,2H)

Example 219b

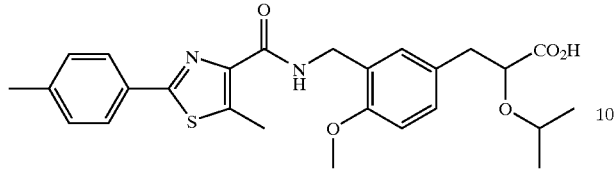

3-3-[([2-(4-Methylphenyl)-5-methyl-1,3-thiazole-4-yl]carbonylamino)methyl]-4-methoxyphenyl-2-isopropoxycarboxylic acid was obtained by the same method as in Example 38.

¹H-NMR(CDCl₃) δ: 1.07 (d, J=6.0 Hz, 3H) 1.17(d, J=6.0 Hz, 3H) 2.40(s, 3H) 2.70(s, 3H) 2.93(dd, J=7.0, 14.0 Hz, 1H) 3.07(dd, J=4.5, 14.0 Hz, 1H) 3.60(sept, J=6.0 Hz, 1H) 3.89(s, 3H) 4.13(dd, J=4.5, 7.0 Hz, 1H) 4.58 (d, J=7.0 Hz, 2H) 6.49(bs, 1H) 6.84(d, J=8.0 Hz, 1H) 7.16(dd, J=2.0, 8.0 Hz, 1H) 7.22 (d,J=2.0 Hz,1H) 7.24(d,J=8.0 Hz,2H) 7.81(d, J=8.0 Hz,2H)

Example 220

Production Example 220a

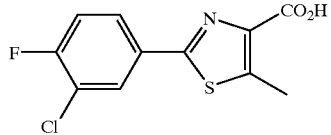

2-(3-Chloro-4-fluorophenyl)-5-methyl-1,3-thiazole-4-carboxylic acid was obtained by the same method as in Production Example 203.

¹H-NMR(CDCl₃) δ:2.80(s, 3H) 7.23(d, J=8.0 Hz, 1H) 7.84 (m, 1H) 8.09(dd, J=2.0, 8.0 Hz, 1H)

Example 220b

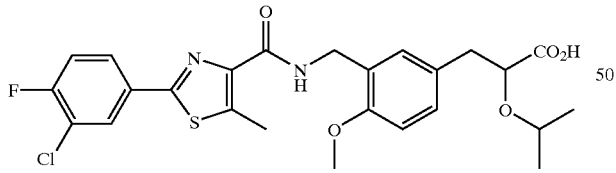

3-3-[([2-(3-Chloro-4-fluorophenyl)-5-methyl-1,3-thiazole-4-yl]carbonylamino)methyl]-4-methoxyphenyl-2-isopropoxycarboxylic acid was obtained by the same method as in Example 38.

¹H-NMR(CDCl₃) δ: 1.07(d, J=6.0 Hz, 3H) 1.18(d, J=6.0 Hz, 3H) 2.70(s, 3H) 2.94(dd, J=7.0, 14.0 Hz, 1H) 3.07(dd, J=4.5, 14.0 Hz, 1H) 3.61(sept, J=6.0 Hz, 1H) 3.89(s, 3H) 4.13(dd, J=4.5, 7.0 Hz, 1H) 4.58 (d, J=7.0 Hz, 2H) 6.52(bs, 1H) 6.84(d, J=8.0 Hz, 1H) 7.17(dd, J=2.0, 8.0 Hz, 1H) 7.21–7.23(m, 2H) 7.76–7.80(m, 1H) 8.02(dd, J=2.0, 8.0 Hz, 1H)

Example 221

Production Example 221a

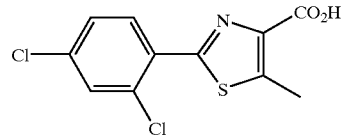

2-(2,4-Dichlorophenyl)-5-methyl-1,3-thiazole-4-carboxylic acid was obtained by the same method as in Production Example 203.

¹H-NMR(DMSO-d₆) δ:2.67(s, 3H) 7.60(dd, J=2.0, 8.0 Hz, 1H) 7.86(d, J=2.0 Hz, 1H) 8.28(d, J=8.0 Hz, 1H)

Example 221b

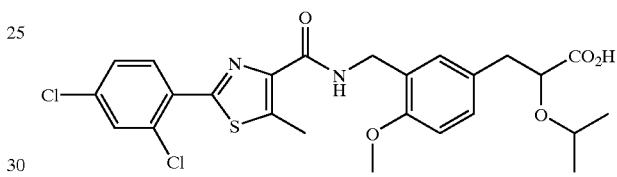

3-3-[([2-(2,4-Dichlorophenyl)-5-methyl-1,3-thiazole-4-yl]carbonylamino)methyl]-4-methoxyphenyl-2-isopropoxycarboxylic acid was obtained by the same method as in Example 38.

¹H-NMR(CDCl₃) δ: 1.07(d, J=6.0 Hz, 3H) 1.17(d, J=6.0 Hz, 3H) 2.72(s, 3H) 2.94(dd, J=7.0, 14.0 Hz, 1H) 3.07(dd, J=4.5, 14.0 Hz, 1H) 3.60(sept, J=6.0 Hz, 1H) 3.89(s, 3H) 4.13(dd, J=4.5, 7.0 Hz, 1H) 4.59 (d, J=7.0 Hz,2H) 6.52(bs, 1H) 6.84(d, J=8.0 Hz, 1H) 7.17(dd, J=2.0, 8.0 Hz, 1H)7.23 (d, J=2.0 Hz, 1H) 7.36(dd, J=2.0, 8.0 Hz, 1H) 7.51(d, J=2.0 Hz, 1H) 8.24(d, J=8.0 Hz, 1H)

Example 222

Production Example 222a

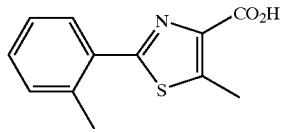

2-(2-Methylphenyl)-5-methyl-1,3-thiazole-4-carboxylic acid was obtained by the same method as in Production Example 203.

¹H-NMR(CDCl₃) δ:2.61(s, 3H) 2.82(s, 3H), 7.27–7.33 (m, 2H) 7.37(d, J=8.0 Hz, 1H) 7.80(d, J=8.0 Hz, 1H)

Example 222b

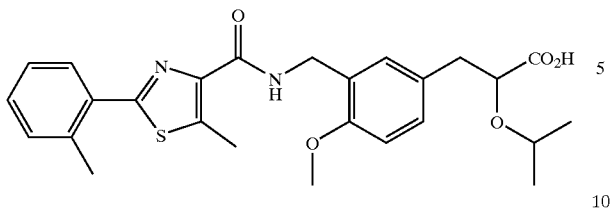

3-3-[([2-(2-Methylphenyl)-5-methyl-1,3-thiazole-4-yl] carbonylamino)methyl]-4-methoxyphenyl-2-isopropoxycarboxylic acid was obtained by the same method as in Example 38.

$^1$H-NMR(CDCl$_3$) δ: 1.07(d, J=6.0 Hz, 3H) 1.17(d, J=6.0 Hz, 3H) 2.57(s, 3H) 2.72(s, 3H) 2.94(dd, J=7.0, 14.0 Hz, 1H) 3.07(dd, J=4.5, 14.0 Hz, 1H) 3.60(sept, J=6.0 Hz, 1H) 3.89(s, 3H) 4.12(dd, J=4.5, 7.0 Hz, 1H) 4.59 (d, J=7.0 Hz,2H) 6.51(bs, 1H) 6.84(d, J=8.0 Hz, 1H) 7.16(dd, J=2.0, 8.0 Hz, 1H) 7.24(d, J=2.0 Hz, 1H) 7.26–7.38(m, 3H) 7.70 (dd, J=2.0, 8.0 Hz, 1H)

Example 223

Production Example 223a

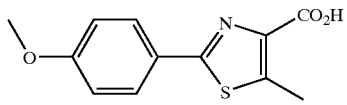

2-(4-Methylphenyl)-5-methyl-1,3-thiazole-4-carboxylic acid was obtained by the same method as in Production Example 203.

$^1$H-NMR(DMSO-d$_6$) δ:2.63(s,3H) 3.80(s,3H) 7.04(d,J=8.0 Hz,2H) 7.90(d,J=8.0 Hz,2H)

Example 223b

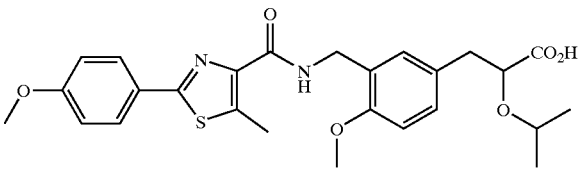

3-3-[([2-(4-Methylphenyl)-5-methyl-1,3-thiazole-4-yl] carbonylamino)methyl]-4-methoxyphenyl-2-isopropoxycarboxylic acid was obtained by the same method as in Example 38.

$^1$H-NMR(CDCl$_3$) δ: 0.1.05(d, J=6.0 Hz, 3H) 1.17(d, J=6.0 Hz, 3H) 2.69(s, 3H) 2.93(dd, J=7.0, 14.0 Hz, 1H) 3.05(dd, J=4.5, 14.0 Hz, 1H) 3.59(sept, J=6.0 Hz, 1H) 3.86(s, 3H) 3.89(s, 3H) 4.12(dd, J=4.5, 7.0 Hz, 1H) 4.58(d, J=7.0 Hz,2H) 6.49(bs, 1H) 6.83(d, J=8.0 Hz, 1H) 6.94(d, J=8.0 Hz, 2H) 7.17(dd, J=2.0, 8.0 Hz, 1H) 7.22(d, J=2.0 Hz, 1H) 7.86(d, J=8.0 Hz, 2H)

Example 224

Production Example 224a

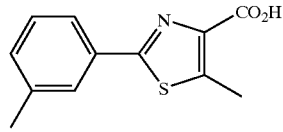

2-(3-Methylphenyl)-5-methyl-1,3-thiazole-4-carboxylic acid was obtained by the same method as in Production Example 203.

$^1$H-NMR(CDCl$_3$) δ:2.42(s, 3H) 2.81(s, 3H) 7.32(m, 2H) 7.76(dd, J=2.0, 8.0 Hz, 1H) 7.82(d, J=2.0 Hz, 1H)

Example 224b

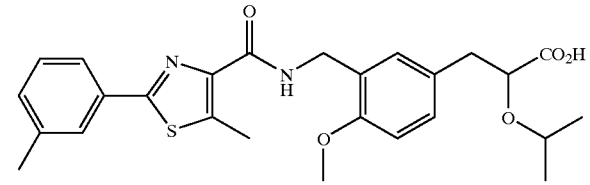

3-3-[([2-(3-Methylphenyl)-5-methyl-1,3-thiazole-4-yl] carbonylamino)methyl]-4-methoxyphenyl-2-isopropoxycarboxylic acid was obtained by the same method as in Example 38.

$^1$H-NMR(CDCl$_3$) δ: 1.07(d, J=6.0 Hz, 3H) 1.17(d, J=6.0 Hz, 3H) 2.41(s, 3H) 2.71(s, 3H) 2.93(dd, J=7.0, 14.0 Hz, 1H) 3.06(dd, J=4.5, 14.0 Hz, 1H) 3.60(sept, J=6.0 Hz, 1H) 3.89(s, 3H) 4.12 (dd, J=4.5, 7.0 Hz, 1H) 4.58 (d, J=7.0 Hz,2H) 6.49(bs, 1H) 6.84(d, J=8.0 Hz, 1H) 7.17(dd, J=2.0, 8.0 Hz, 1H) 7.23(d, J=2.0 Hz, 1H) 7.25–7.34(m, 2H) 7.70(d, J=8.0 Hz, 2H) 7.76(bs, 1H)

Example 225

Production Example 225a

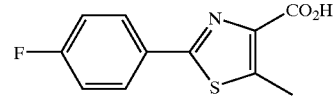

2-(4-Fluorophenyl)-5-methyl-1,3-thiazole-4-carboxylic acid was obtained by the same method as in Production Example 203.

$^1$H-NMR(CDCl$_3$) δ:2.85(s, 3H) 7.16(t, J=8.0 Hz, 1H) 7.87(t, J=8.0 Hz, 1H)

Example 225b

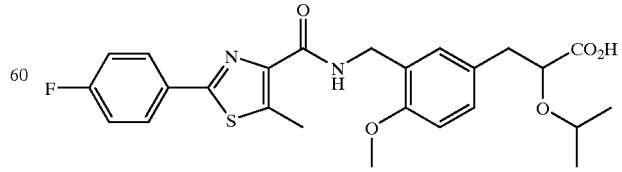

3-3-[([2-(4-Fluorophenyl)-5-methyl-1,3-thiazole-4-yl] carbonylamino)methyl]-4-methoxyphenyl-2- isopropoxycarboxylic acid was obtained by the same method as in Example 38.

MSm/e(ESI) (MH⁺) 487

Example 226

Production Example 226a

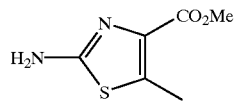

20 g of methyl dichloroacetate and 8 g of acetaldehyde were dissolved in 50 ml anhydrous diethyl ether, followed by adding dropwise 25 g of 28% sodium methylate thereinto under ice-cooling. After stirring the reaction solution for 2 hours under ice-cooling, water and brine, followed by extracting with diethyl ether. The organic layer was dried over anhydrous magnesium sulfate and then evaporated. The residue was dissolved in 60 ml methanol and 8.5 g of thiourea was added thereto, followed by heating under reflux for 4 hours. The reaction solution was ice-cooled and adjusted to pH 9 by adding water and an aqueous ammonia thereto, followed by extracting with dichloromethane. The organic layer was dried over anhydrous magnesium sulfate and evaporated. The residue was purified by silica gel column chromatography (hexane:ethyl acetate=4:1→1:1), to give 2.8 g of methyl 2-amino-5-methyl-1,3-thiazole-4-carboxylate.

$^1$H-NMR(CDCl$_3$) δ:2.61(s, 3H) 3.88(s, 3H) 5.02(bs, 2H)

Production Example 226b

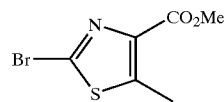

2.8 g of methyl 2-amino-5-methyl-1,3-thiazole-4-carboxylate was dissolved in 30 ml methanol and 7 ml hydrobromic acid, followed by adding dropwise an aqueous solution of 1.2 g sodium nitrite thereinto under ice-cooling. After stirring the reaction solution under ice-cooling for 30 minutes, a solution, previously heated at 60° C., of 1.3 g cuprous bromide in 7 ml hydrobromic acid was added thereto, followed by stirring at 60° C. for 1 hour. The reaction solution was ice-cooled and water was-added, followed by extracting with diethyl ether. The organic layer was extracted with brine, dried over anhydrous magnesium sulfate and evaporated, to give 0.47 g of methyl 2-bromo-5-methyl-1,3-thiazole-4-carboxylate.

$^1$H-NMR(CDCl$_3$) δ:2.74(s, 3H) 3.93(s, 3H)

Production Example 226c

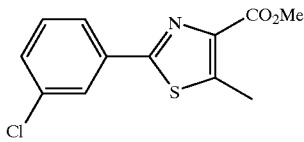

0.3 g of methyl 2-bromo-5-methyl-1,3-thiazole-4-carboxylate and 0.2 g of 3-chlorophenylboric acid were dissolved in toluene, and 0.15 g of tetrakistriphenyl phosphine and 0.7 g of potassium carbonate were added. The reaction solution was heated under reflux for 4 hours in a nitrogen atmosphere. The reaction solution was cooled, filtered through Celite and evapoarated. The residue was purified by silica gel column chromatography, to give 0.2 g of methyl 2-(3-methylphenyl)-5-methyl-1,3-thiazole-4-carboxylate.

$^1$H-NMR(CDCl$_3$) δ:2.83(s, 3H) 3.97(s, 3H) 7.38(m, 2H) 7.77(dd, J=2.0, 8.0 Hz, 1H) 7.94(d, J=2.0 Hz, 1H)

Production Example 226d

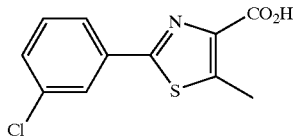

0.2 g of methyl 2-(3-methylphenyl)-5-methyl-1,3-thiazole-4-carboxylate was dissolved in 10 ml methanol, 1 ml of 5N sodium hydroxide was added, and the mixture was heated under reflux for 1 hour. The reaction solution was ice-cooled and neutralized with 2N hydrochloric acid, followed by extracting with ethyl acetate. The organic layer was washed with brine, dried over anhydrous magnesium sulfate and evaporated, to give 0.2 g of 2-(3-methylphenyl)-5-methyl-1,3-thiazole-4-carboxylic acid.

$^1$H-NMR(DMSO-d$_6$) δ:2.73(s,3H) 7.55(m,2H) 7.83(d,J=8.0 Hz,1H) 7.93(d,J=2.0 Hz,1H)

Example 226e

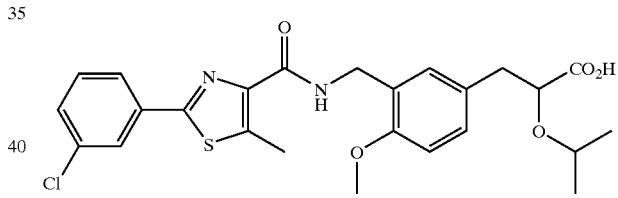

3-3-[([2-(3-Methylphenyl)-5-methyl-1,3-thiazole-4-yl]carbonylamino)methyl]-4-methoxyphenyl-2-isopropoxycarboxylic acid was obtained by the same method as in Example 38.

MSm/e(ESI) 503(MH⁺)

Example 227

Production Example 227a

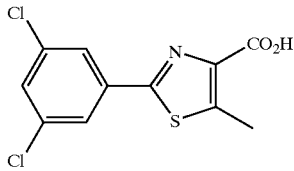

2-(3-5-Dichlorophenyl)-5-methyl-1,3-thiazole-4-carboxylic acid was obtained by the same method as in Production Example 226.

$^1$H-NMR(DMSO-d$_6$) δ:2.74(s, 3H) 8.75(s, 1H) 8.90(s, 2H)

Example 227b)

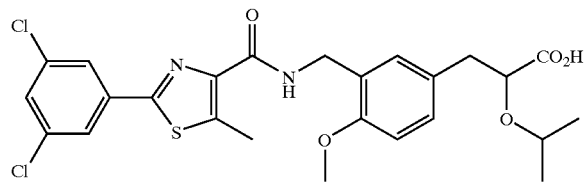

3-3-[([2-(3-5-Dichlorophenyl)-5-methyl-1,3-thiazole-4-yl]carbonylamino)methyl]-4-methoxyphenyl-2-isopropoxycarboxylic acid was obtained by the same method as in Example 38.

MSm/e(ESI) 537(MH$^+$)

Example 228

Production Example 228a

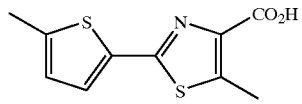

5-Methyl-2-(5-methyl-2-thienyl)-1,3-thiazole-4-carboxylic acid was obtained by the same method as in Production Example 226.

$^1$H-NMR(CDCl$_3$) δ:2.53(s,3H) 2.81(s,3H) 6.74(d,J=5.0 Hz,1H) 7.28(d, J=5.0 Hz, 1H)

Example 228b

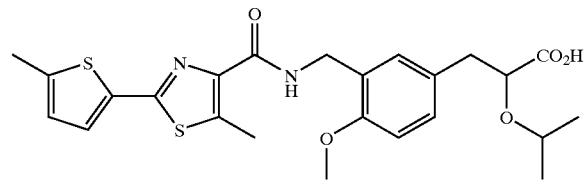

2-Isopropoxy-3-4-methoxy-3-[([5-methyl-2-(5-methyl-2-thienyl)-1,3-thiazole-4-yl]carbonylamino)methyl]phenylpropanonic acid was obtained by the same method as in Example 38.

MSm/e(ESI) 489(MH$^+$)

Example 229

Production Example 229a

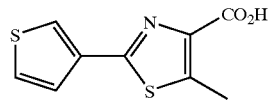

5-Methyl-2-(3-thienyl)-1,3-thiazole-4-carboxylic acid was obtained by the same method as in Production Example 226.

$^1$H-NMR(CDCl$_3$) δ:2.84(s, 3H) 7.41(dd, J=1.0, 5.0 Hz, 1H) 7.50(d, J=1.0 Hz, 1H) 7.81 (d, J=5.0 Hz, 1H)

Example 229b

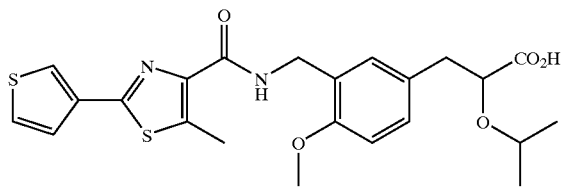

2-Isopropoxy-3-4-methoxy-3-[([5-methyl-2-(3-thienyl)-1,3-thiazole-4-yl]carbonylamino)methyl]phenylpropanonic acid was obtained by the same method as in Example 38.

MSm/e(ESI) 475(MH$^+$)

Example 230

Production Example 230a

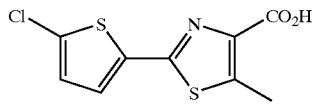

2-(5-Chloro-2-thienyl)-5-methyl-1,3-thiazole-4-carboxylic acid was obtained by the same method as in Production Example 226.

$^1$H-NMR(CDCl$_3$) δ:2.83(s, 3H) 6.92(d, J=5.0 Hz, 1H) 7.24 (d, J=5.0 Hz, 1H)

Example 230b

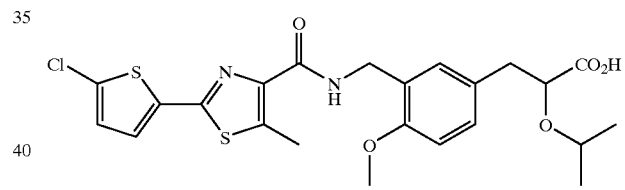

3-3-[([2-(5-Chloro-2-thienyl)-5-methyl-1,3-thiazole-4-yl]carbonylamino)methyl]-4-methoxyphenyl-2-isopropoxycarboxylic acid was obtained by the same method as in Example 38.

MSm/e(ESI) 509(MH$^+$)

Example 231

Production Example 231a

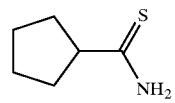

2 g of 1-cyclopentane carboxamide was dissolved in tetrahydrofuran, and 4.3 g Lawesson's reagent was added, and the mixture was stirred at room temperature for 16 hours. After the reaction solution was evaporated, the residue was purified by silica gel column chromatography, to give 1.8 g of 1-cyclopentane carbothioamide.

$^1$H-NMR(CDCl$_3$) δ:1.64(m, 2H) 1.78–1.94(m, 4H) 2.00 (m, 2H) 2.95(qui, J=6.0 Hz, 1H) 6.86(bs, 1H) 7.50(bs, 1H)

Production Example 231b

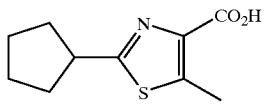

Ethyl 2-chloroacetoacetate and 1-cyclopentane carbothioamide were treated as the starting materials by the same method as in Production Example 203, to give 2-cyclopentyl-5-methyl-1,3-thiazole-4-carboxylic acid.

$^1$H-NMR(CDCl$_3$) δ:1.70–1.88(m, 6H) 2.20(m, 2H) 2.72 (s, 3H) 3.42(qui, J=6.0 Hz,1H)

Example 231c

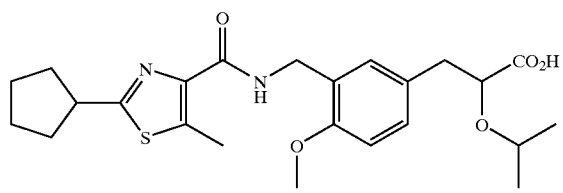

3-[3-([(2-Cyclopentyl-5-methyl-1,3-thiazole-4-yl) carbonyl]aminomethyl])-4-methoxyphenyl]-2-isopropoxypropanoic acid was obtained by the same method as in Example 38.

MSm/e(ESI) 461(MH$^+$)

Example 232

Production Example 232a

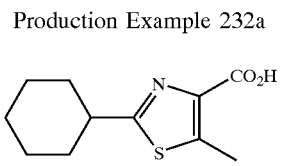

2-Cyclohexyl-5-methyl-1,3-thiazole-4-carboxylic acid was obtained by the same method as in Production Example 231.

$^1$H-NMR(CDCl$_3$) δ:1.25–1.55(m, 5H) 1.75(m, 1H) 1.86 (m, 2H) 0.213(m, 2H) 2.72(s, 3H) 2.96(qui, J=6.0 Hz, 1H)

Example 232b

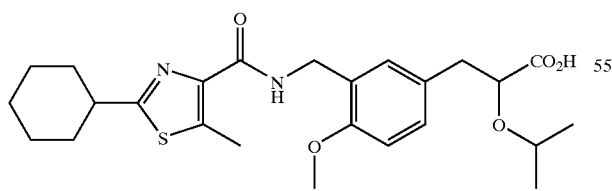

3-[3-([(2-Cyclohexyl-5-methyl-1,3-thiazole-4-yl) carbonyl]aminomethyl])-4-methoxyphenyl]-2-isopropoxypropanoic acid was obtained by the same method as in Example 38.

MSm/e(ESI) (MH$^+$) 475

Example 233

Production Example 233a

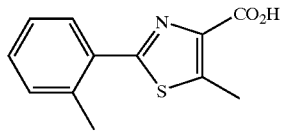

2-(2-Methylphenyl)-5-methyl-1,3-thiazole-4-carboxylic acid was obtained by the same method as in Production Example 231.

$^1$H-NMR(CDCl$_3$) δ:2.61(s, 3H) 2.82(s, 3H) 7.30(m, 2H) 7.37(d, J=8.0 Hz, 1H) 7.80(dd, J=2.0, 8.0 Hz, 1H)

Example 233b

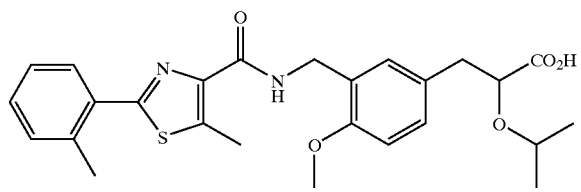

3-3-[([2-(2-Methylphenyl)-5-methyl-1,3-thiazole-4-yl] carbonylamino)methyl]-4-methoxyphenyl-2-isopropoxycarboxylic acid was obtained by the same method as in Example 38.

MSm/e(ESI) 482(MH$^+$)

Example 234

Production Example 234a

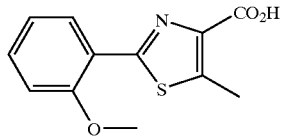

2-(2-Methoxyphenyl)-5-methyl-1,3-thiazole-4-carboxylic acid was obtained by the same method as in Production Example 231.

$^1$H-NMR(DMSO-d$_6$) δ:2.66(s,3H) 4.02(s,3H) 7.10(t,J= 8.0 Hz,1H) 7.25(d,J=8.0 Hz,1H) 7.55(t, J=8.0 Hz, 1H) 8.28(d, J=8.0 Hz, 1H)

Example 234b

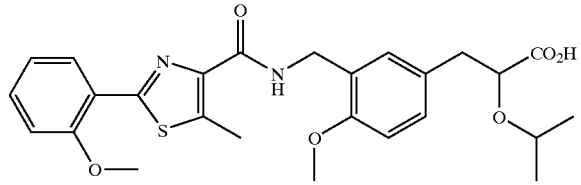

3-3-[([2-(2-Methoxyphenyl)-5-methyl-1,3-thiazole-4-yl] carbonylamino)methyl]-4-methoxyphenyl-2-isopropoxycarboxylic acid was obtained by the same method as in Example 38.

MSm/e(ESI) 498(MH+)

Example 235

Production Example 235a

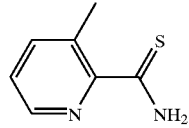

2 g of 2-cyano-3-methylpyridine was dissolved in 30 ml pyridine and 12 ml triethylamine, and a hydrogen sulfide gas was bubbled for 2 hours. The reaction solution was stirred at 50° C. for 2 hours in a sealed tube and then evaporated. The residue was purified by silica gel column chromatography (hexane:ethyl acetate=1:1), to give 2.6 g of 3-methyl-2-pyridine carbothioamide.

$^1$H-NMR(CDCl$_3$) δ:2.76(s,3H) 7.28(m,1H) 7.62(d,J=8.0 Hz,1H) 8.37 (d,J=4. 0 Hz, 1H)

Production Example 235b

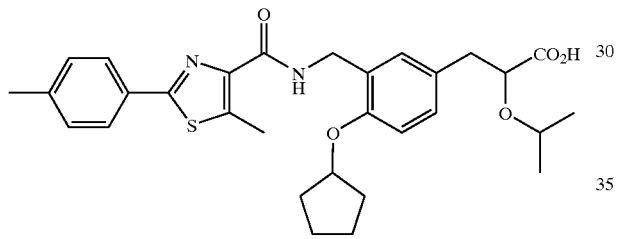

Ethyl 2-chloroacetacetate and 3-methyl-2-pyridinecarbothioamide were treated as the starting materials by the same method as in Production Example 203, to give 5-methyl-2-(3-methyl-2-pyridyl)-1,3-thiazole-4-carboxylic acid.

$^1$H-NMR(DMSO-d$_6$) δ:2.66 (s, 3H) 2.71(s, 3H) 7.42(dd, J=4.0, 8.0 Hz, 1H) 7.80(d, J=8.0 Hz, 1H) 8.44(d, J=4.0 Hz, 1H)

Example 235c

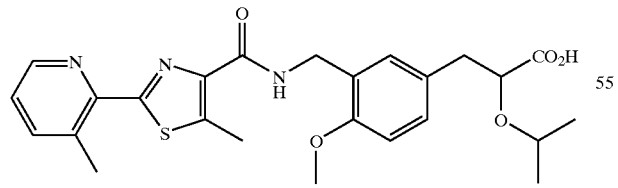

3-3-[([2-(3-Methyl-2-pyridyl)-5-methyl-1,3-thiazole-4-yl]carbonylamino)methyl]-4-methoxyphenyl-2-isopropoxypropanoic acid was obtained by the same method as in Example 38.

MSm/e(ESI) 484(MH+)

Example 236

Production Example 236a

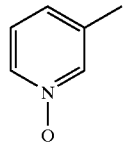

2 g of 3-picoline was dissolved in 30 ml dichloromethane, and 5.6 g of m-chlorobenzoic acid was added, and the mixture was stirred at room temperature for 16 hours. The reaction solution was evaporated, and the residue was purified by silica gel column chromatography (ethyl acetate:methanol=4:1), to give 2.4 g of 3-pyridine N-oxide.

$^1$H-NMR(CDCl$_3$) δ:2.31(s,3H) 7.10(d,J=8.0 Hz,1H) 7.17 (dd,J=4.0,8.0 Hz,1H) 8.07(m,2H)

Production Example 236b

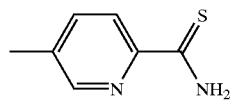

2.4 g of 3-pyridine N-oxide was dissolved in 30 ml acetonitrile, and 3.5 ml trimethylsilyl cyanide and 2.4 ml dimethylcarbamoyl chloride were added, and the mixture was heated under reflux for 2 hours. The reaction solution was ice-cooled, and water was added, followed by extracting with ethyl acetate. The organic layer was washed with brine, dried over anhydrous magnesium sulfate and evapoarated. The residue was purified by silica gel column chromatography (hexane:ethyl acetate=1:1), and it was treated according to Production Example 235a), to give 0.2 g of 5-methyl-2-pyridinecarbothioamide.

$^1$H-NMR(CDCl$_3$) δ:2.41(s,3H) 7.63 (d,J=8.0 Hz, 1H) 8.34(bs, 1H) 8.60(d,J=8.0 Hz,1H)

Production Example 236c

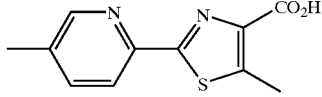

2-Chloroacetacetic acid and 5-methyl-2-pyridinecarbothioamide were treated as the starting materials by the same method as in Production Example 203, to give 2-(5-ethyl-2-pyridyl)-5-methyl-1,3-thiazole-4-carboxylic acid.

$^1$H-NMR(DMSO-d$_6$) δ:2.35(s, 3H) 2.65(s, 3H) 7.78(dd, J=2.0, 8.0 Hz, 1H) 8.02(d, J=8.0 Hz, 1H) 8.48(d, J=2.0 Hz, 1H)

Example 236d

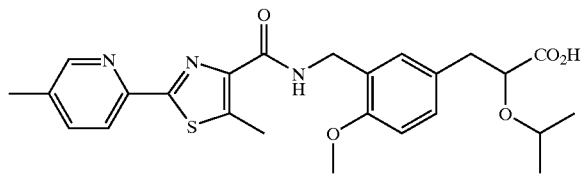

3-3-[([2-(5-Methyl-2-pyridyl)-5-methyl-1,3-thiazole-4-yl]carbonylamino)methyl]-4-methoxyphenyl-2-isopropoxypropanoic acid was obtained by the same method as in Example 38

MSm/e(ESI) 484 (MH$^+$)

Example 237

Production Example 237a

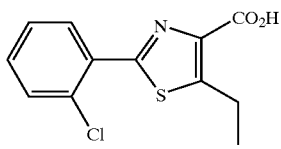

2-(2-Chlorophenyl)-5-ethyl-1,3-thiazole-4-carboxylic acid was obtained by the same method as in Production Example 203.

$^1$H-NMR(CDCl$_3$) δ:1.37(t, J=8.0 Hz, 3H) 3.24(q, H=8.0 Hz, 2H) 7.40(m, 2H) 7.52(m, 1H) 8.35(m, 1H)

Example 237b

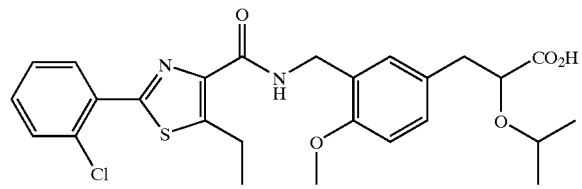

3-3-[([2-(2-Chlorophenyl)-5-ethyl-1,3-thiazole-4-yl]carbonylamino)methyl]-4-methoxyphenyl-2-isopropoxycarboxylic acid was obtained by the same method as in Example 38.

MSm/e(ESI) 517(MH$^+$)

Example 238

Production Example 238a

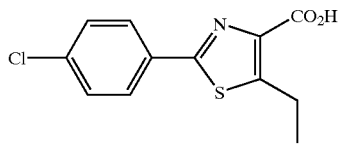

2-(4-Chlorophenyl)-5-ethyl-1,3-thiazole-4-carboxylic acid was obtained by the same method as in Production Example 203.

$^1$H-NMR(DMSO-d$_6$) δ:1.23(t,J=8.0 Hz,3H) 3.08(q,H=8.0 Hz,2H) 7.57(d,J=8.0 Hz,2H) 8.00(d,J=8.0 Hz,2H)

Example 238b

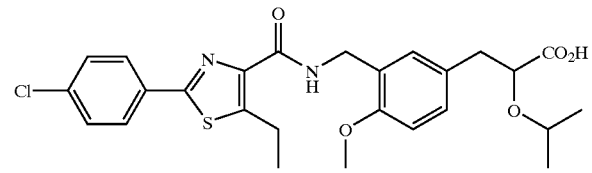

3-3-[([2-(4-Chlorophenyl)-5-ethyl-1,3-thiazole-4-yl]carbonylamino)methyl]-4-methoxyphenyl-2-isopropoxycarboxylic acid was obtained by the same method as in Example 38.

MSm/e(ESI) 517(MH$^+$)

Example 239

Production Example 239a

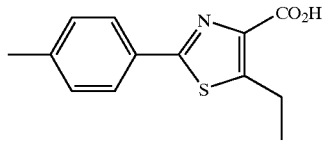

2-(4-Methylphenyl)-5-ethyl-1,3-thiazole-4-carboxylic acid was obtained by the same method as in Production Example 203.

$^1$H-NMR(DMSO-d$_6$) δ:1.23(t, J=8.0 Hz, 3H) 2.35(s, 3H) 3.07(q, H=8.0 Hz, 2H) 7.30(d, J=8.0 Hz, 2H) 7.86(d, J=8.0 Hz, 2H)

Example 239b

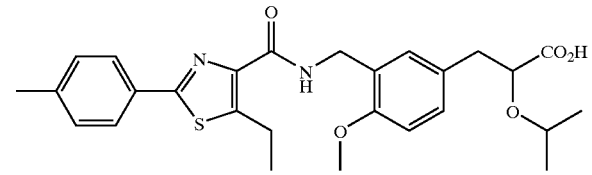

3-3-[([2-(4-Methylphenyl)-5-ethyl-1,3-thiazole-4-yl]carbonylamino)methyl]-4-methoxyphenyl-2-isopropoxycarboxylic acid was obtained by the same method as in Example 38.

MSm/e(ESI) 497(MH$^+$)

Example 240

Production Example 240a

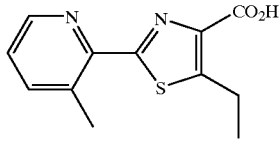

5-Ethyl-2-(3-methyl-2-pyridyl)-1,3-thiazole-4-carboxylic acid was obtained by the same method as in Production Example 235.

$^1$H-NMR(DMSO-d$_6$) δ:1.27(t, J=8.0 Hz, 3H) 2.74(s, 3H) 3.10(q, H=8.0 Hz, 2H) 7.42(dd, J=4. 0, 8.0 Hz, 1H) 7.81(d, J=8.0 Hz, 1H) 8.48(d, J=4.0 Hz,1H)

Example 240b

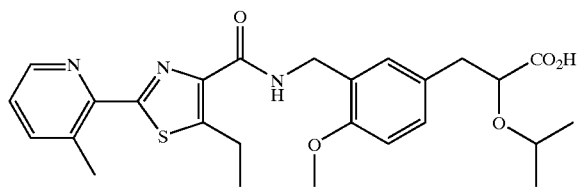

3-3-[([2-(3-Methyl-2-pyridyl)-5-ethyl-1,3-thiazole-4-yl]carbonylamino)methyl]-4-methoxyphenyl-2-isopropoxypropanoic acid was obtained by the same method as in Example 38.

MSm/e(ESI) 498(MH$^+$)

Example 241

Production Example 241a

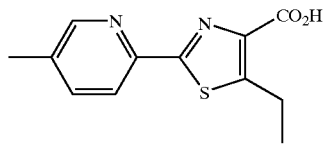

2-(5-Methyl-2-pyridyl)-5-ethyl-1,3-thiazole-4-carboxylic acid was obtained by the same method as in Production Examples 236 a)–c).

$^1$H-NMR(DMSO-d$_6$) δ:1.24(t, J=8.0 Hz, 3H) 2.35(s, 3H) 3.09(q, H=8.0 Hz, 2H) 7.79(d, J=8.0 Hz, 1H) 7.81(d, J=8.0 Hz, 1H) 8.49(s, 1H)

Example 241b

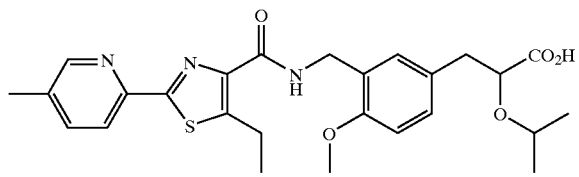

3-3-[([2-(5-Methyl-2-pyridyl)-5-ethyl-1,3-thiazole-4-yl]carbonylamino)methyl]-4-methoxyphenyl-2-isopropoxypropanoic acid was obtained by the same method as in Example 38.

MSm/e(ESI) 498(MH$^+$)

Example 242

Production Example 242a

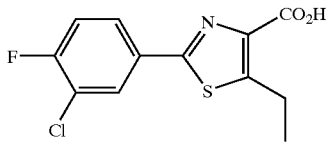

2-(3-Chloro-4-fluorophenyl)-5-ethyl-1,3-thiazole-4-carboxylic acid was obtained by the same method as in Production Example 203.

$^1$H-NMR(CDCl$_3$) δ:1.35(t, J=8.0 Hz, 3H) 3.20(q, H=8.0 Hz, 2H) 7.21(d, J=8.0 Hz, 1H) 7.83(m, 1H) 8.10(dd, J=2.0, 8.0 Hz, 1H)

Example 242b

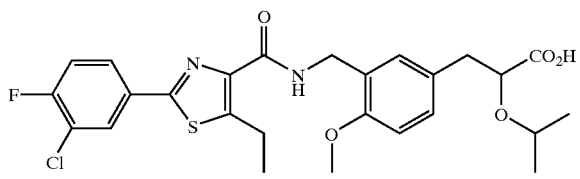

3-3-[([2-(3-Chloro-4-fluorophenyl)-5-ethyl-1,3-thiazole-4-yl]carbonylamino)methyl]-4-methoxyphenyl-2-isopropoxycarboxylic acid was obtained by the same method as in Example 38.

MSm/e(ESI) 535(MH$^+$)

Example 243

Production Example 243a

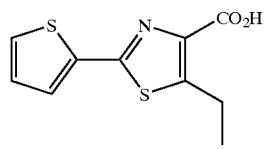

5-Ethyl-2-(2-thienyl)-1,3-thiazole-4-carboxylic acid was obtained by the same method as in Production Example 203.

$^1$H-NMR(CDCl$_3$) δ:1.33(t, J=8.0 Hz, 3H) 3.18(q, H=8.0 Hz, 2H) 7.10(dd, J=4.0, 5.0 Hz, 1H) 7.47(d, J=4.0 Hz, 1H) 7.60(d, J=5.0 Hz, 1H)

Example 243b

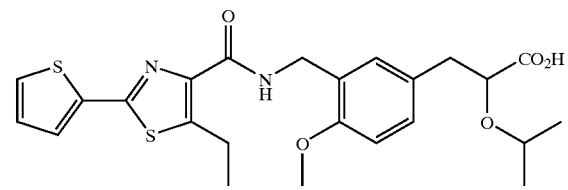

2-Isopropoxy-3-4-methoxy-3-[([5-ethyl-2-(2-thienyl)-1,3-thiazole-4-yl]carbonylamino)methyl]phenylpropanoic acid was obtained by the same method as in Example 38.

MSm/e(ESI) 489(MH$^+$)

Example 244

Example 244a

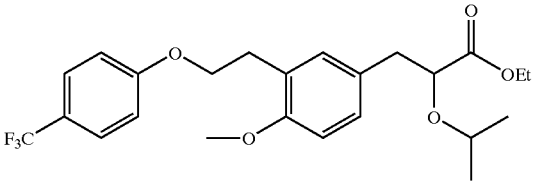

Using 4-methoxy-3-{2-[4-(trifluoromethyl)phenoxy]ethyl}benzaldehyde, ethyl 2-isopropoxy-3-(4-methoxy-3-2-[4-(trifluoromethyl)phenoxy]ethylphenyl)propanoate was obtained by the same method as in Production Example 1a) and then in Production Example 1b).

¹H-NMR(CDCl₃) δ: 0.96 (d, J=6.0 Hz, 3H) 1.15 (d, J=6.0 Hz, 3H) 1.23 (t, J=7.2 Hz, 3H) 2.79 (dd, J=8.4, 14.0 Hz, 1H) 2.95 (dd, J=4.8, 14.0 Hz, 1H) 3.08 (t, J=7.6 Hz, 2H) 3.50 (sept, J=6.0 Hz, 1H) 3.82 (s, 3H) 4.00 (dd, J=4.8, 8.4 Hz, 1H) 4.15–4.20 (m, 4H) 6.78 (d, J=8.0 Hz, 1H) 6.96 (d, J=8.8 Hz, 2H) 7.09 (s, 1H) 7.10 (d, J=8.0 Hz, 1H) 7.52 (d, J=8.8 Hz, 2H)

Example 244b

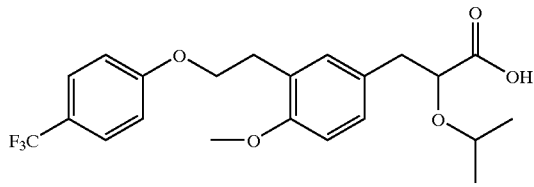

Ethyl 2-isopropoxy-3-(4-methoxy-3-2-[4-(trifluoromethyl)phenoxy]ethylphenyl)propanoate was treated in the same method as in Example 1e), to give 2-isopropoxy-3-(4-methoxy-3-2-[4-(trifluoromethyl)phenoxy)ethylphenyl)propanoic acid.

¹H-NMR(CDCl₃) δ: 1.02 (d, J=6.0 Hz, 3H) 1.15 (d, J=6.0 Hz, 3H) 2.89 (dd, J=7.6, 14.0 Hz, 1H) 3.07(dd, J=4.0, 14.0 Hz, 1H) 3.09 (t, J=7.6 Hz, 2H) 3.56 (sept, J=6.0 Hz, 1H) 3.83 (s, 3H) 4.10 (dd, J=4.0, 7.6 Hz, 1H) 4.17 (t, J=7.6 Hz, 2H) 6.80 (d, J=8.0 Hz, 1H) 6.96 (d, J=8.8 Hz, 2H) 7.09 (s, 1H) 7.09 (d, J=8.0 Hz, 1H) 7.52 (d, J=8.8 Hz, 2H)

Example 245

Example 245a

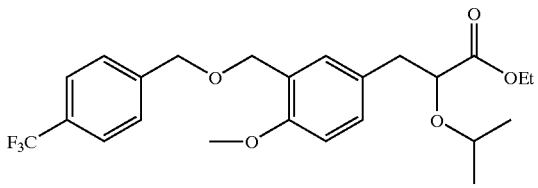

Using 4-methoxy-3-({[4-(trifluoromethyl)benzyl]oxy}methyl)benzaldehyde, ethyl 2-isopropoxy-3-[4-methoxy-3-([4-(trifluoromethyl)benzyl]oxymethyl)phenyl]propanoate was obtained by the same method as in Production Example 1a) and then in Production Example 1b).

¹H-NMR(CDCl₃) δ: 0.96 (d, J=6.0 Hz, 3H) 1.15 (d, J=6.0 Hz, 3H) 1.23 (t, J=7.2 Hz, 3H) 2.79 (dd, J=8.4, 14.0 Hz, 1H) 2.95 (dd, J=4.8, 14.0 Hz, 1H) 3.50 (sept, J=6.0 Hz, 1H) 3.82 (s, 3H) 4.00 (dd, J=4.8, 8.4 Hz, 1H) 4.15–4.20 (m, 2H) 4.58 (s, 2H) 4.64 (s, 2H) 6.79 (d, J=8.0 Hz, 1H) 7.16 (dd, J=2.4, 8.0 Hz, 1H) 7.28 (d, J=2.4 Hz, 1H) 7.49 (d, J=8.0 Hz, 2H) 7.60 (d, J=8.4 Hz, 2H)

Example 245b

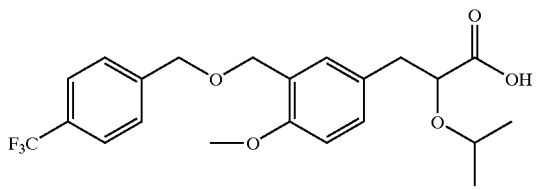

Ethyl 2-isopropoxy-3-[4-methoxy-3-([4-(trifluoromethyl)benzyl]oxymethyl)phenyl]propanoate was treated in the same method as in Example 1e), to give 2-isopropoxy-3-[4-methoxy-3-([4-(trifluoromethyl)benzyl]oxymethyl)phenyl]propanoic acid.

¹H-NMR(CDCl₃) δ: 1.02 (d, J=6.0 Hz, 3H) 1.15 (d, J=6.0 Hz, 3H) 2.92 (dd, J=7.6, 14.9 Hz, 1H) 3.09(dd, J=4.0, 14.0 Hz, 1H) 3.56 (sept, J=6.0 Hz, 1H) 3.81 (s, 3H) 4.12 (dd, J=4.0, 7.6 Hz, 1H) 4.59 (s, 2H) 4.64 (s, 2H) 6.80 (d, J=8.0 Hz, 1H) 7.14 (dd, J=2.4, 8.0 Hz, 1H) 7.28 (d, J=2.4 Hz, 1H) 7.50 (d, J=8.4 Hz, 2H) 7.60 (d, J=8.4 Hz, 2H)

Example 246

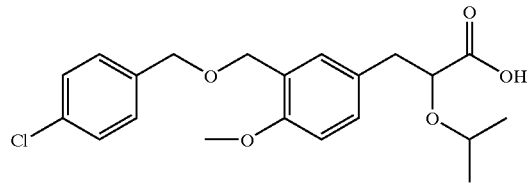

40 mg of sodium hydride was dissolved in 2 ml tetrahydrofuran and a solution of 0.51 g ethyl 3-[3-(hydroxymethyl)-4-methoxyphenyl]-2-isopropoxypropanoate in tetrahydrofuran (1 ml) and 0.25 mg 4-chlorobenzyl bromide were successively added thereto, followed by stirring at room temperature for 15 hours. The reaction solution was ice-cooled and neutralized with 1N hydrochloric acid, followed by extracting with ethyl acetate. The organic layer was washed with brine, dried over anhydrous magnesium sulfate and the solvent was evaporated. The residue was subjected to silica gel column chromatography, and from fractions eluted with hexane-ethyl acetate (4:1), 0.19 g product was obtained. 0.19 g of the resulting product was treated in the same method as in Example 1e), to give 0.17 g of 3-(3-[(4-chloromethyl)oxy]methyl-4-methoxyphenyl)-2-isopropoxypropanoic acid.

¹H-NMR(CDCl₃) δ: 1.02 (d, J=6.0 Hz, 3H) 1.15 (d, J=6.0 Hz, 3H) 2.92 (dd, J=7.6, 14.0 Hz, 1H) 3.09(dd, J=4.0, 14.0 Hz, 1H) 3.56 (sept, J=6.0 Hz, 1H) 3.81 (s, 3H) 4.12 (dd, J=4.0, 7.6 Hz, 1H) 4.59 (s, 2H) 4.60 (s, 2H) 6.80 (d, J=8.0 Hz, 1H) 7.13 (dd, J=2.4, 8.0 Hz, 1H) 7.27 (d, J=2.4 Hz, 1H) 7.32 (s, 4H)

Example 247

Production Example 247a

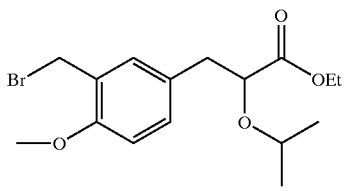

2.2 g of ethyl 3-[3-(hydroxymethyl)-4-methoxyphenyl]-2-isopropoxypropanoate was dissolved in 15 ml dimethoxyethane. 1.2 ml phosphorus tribromide was added thereto under ice-cooling, followed by stirring at room temperature for 4 hours. The reaction solution was diluted with ether and washed with water. The organic layer was washed with brine, dried over anhydrous magnesium sulfate and the solvent was evaporated. The residue was subjected to silica gel column chromatography, to give 2.6 g of ethyl 3-[3-(bromomethyl)-4-methoxyphenyl]-2-isopropoxypropanoate from fractions eluted with hexane-ethyl acetate (4:1).

$^1$H-NMR(CDCl$_3$) δ: 0.97 (d, J=6.0 Hz, 3H) 1.15 (d, J=6.0 Hz, 3H) 1.24 (t, J=7.2 Hz, 3H) 2.88(dd, J=8.4, 14.0 Hz, 1H) 2.95(dd, J=5.2, 14.0 Hz, 1H) 3.50(sept, J=6.0 Hz, 1H) 3.87(s, 3H) 4.00(dd, J=5.2, 8.4 Hz, 1H) 4.11–4.21(m, 2H) 4.53(d, J=2.4 Hz, 2H) 6.79(d, J=8.8 Hz, 1H) 7.08(d, J=8.8 Hz, 1H) 7.12(s, 1H)

Production Example 247b

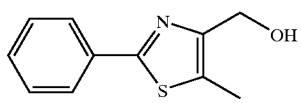

87 mg of lithium aluminum hydride was dissolved in 7.5 ml tetrahydrofuran. Under ice-cooling, a solution of 0.50 g ethyl 5-methyl-2-phenyl-1,3-thiazole-4-carboxylate in tetrahydrofuran (2.5 ml) was added thereto, followed by stirring at room temperature for 3 hours. The reaction solution was ice-cooled and 1N hydrochloric acid was added thereto, followed by extracting with ethyl acetate. The organic layer was washed with brine, dried over anhydrous magnesium sulfate and the solvent was evaporated. The residue was subjected to silica gel column chromatography, to give, 0.42 g of (5-methyl-2-phenyl-1,3-thiazole-4-yl)methanol from fractions eluted with hexane-ethyl acetate (2:1).

$^1$H-NMR(CDCl$_3$) δ:2.46(s,3H) 4.82(s,2H) 7.50–7.53(m, 3H) 7:88–7.91(m,2H)

Example 247c

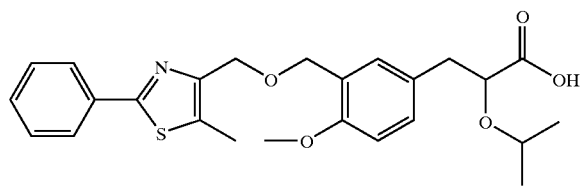

24 mg of sodium hydride was dissolved in 2 ml tetrahydrofuran. Under ice-cooling, a solution of 0.19 g of 3-[3-(bromomethyl)-4-methoxyphenyl]-2-isopropoxypropanoate in tetrahydrofuran (1 ml) and a solution of 0.12 mg of (5-methyl-2-phenyl-1,3-thiazole-4-yl)methanol in tetrahydrofuran (1 ml) were successively added thereto, followed by stirring at room temperature for 15 hours. 2 ml of 1N aqueous sodium hydroxide solution was added to the reaction solution, followed by stirring at room temperature for 2 hours. The reaction solution was ice-cooled and neutralized with 1N hydrochloric acid, followed by extracting with ethyl acetate. After concentrating the organic layer, the residue was purified by HPLC on a reverse phase column in a water-acetonitrile-trifluoroacetic acid system as the eluting solvent, to give 0.13 g of 2-isopropoxy-3-(4-methoxy-3-[(5-methyl-2-phenyl-1,3-thiazole-4-yl)methoxy]methylphenyl)propanoic acid.

MS m/e (ESI) 454(MH$^+$)

Example 248

Production Example 248a

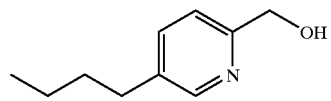

Using fusaric acid, (5-butyl-2-pyridyl)methanol was obtained in the same method as in Production Example 247b).

$^1$H-NMR(CDCl$_3$) δ: 0.93 (t, J=8.0 Hz, 3H) 1.31–1.40 (m, 2H) 1.56–1.65 (m, 2H) 2.63 (t, J=8.0 Hz, 2H) 4.73 (s, 2H) 7.14 (d, J=8.0 Hz, 1H) 7.50 (d, J=8.0 Hz, 1H) 8.39 (s, 1H)

Example 248b

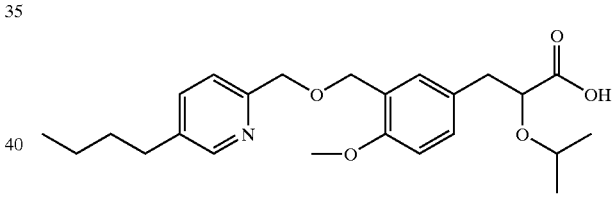

Using (5-butyl-2-pyridyl)methanol and 3-[3-(bromomethyl)-4-methoxyphenyl]-2-isopropoxypropanoate, 3-(3-[(5-butyl-2-pyridyl)methoxy]methyl-4-methoxyphenyl)-2-isopropoxypropanoic acid was obtained in the same method as in Example 247).

MS m/e (ESI) 416(MH$^+$)

Example 249

Production Example 249a

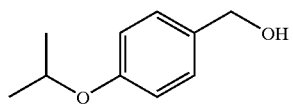

Using 4-isopropoxybenzoic acid, (4-isopropoxyphenyl)methanol was obtained in the same method as in Production Example 247b).

$^1$H-NMR(CDCl$_3$) δ: 1.34 (d, J=6.4 Hz, 6H) 4.55 (sept, J=6.4 Hz, 1H) 4.62 (s, 2H) 6.87 (d, J=8.8 Hz, 2H) 7.22 (d, J=8.8 Hz, 2H)

Example 249b

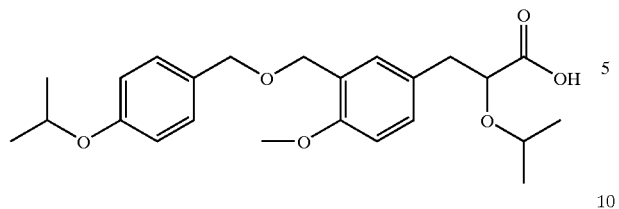

Using (4-isopropoxyphenyl)methanol and 3-[3-(bromomethyl)-4-methoxyphenyl]-2-isopropoxypropanoate, 2-isopropoxy-3-(3-[(4-isopropoxybenzyl)oxy]methyl-4-methoxy)propanoic acid was obtained in the same method as in Production Example 247).

MS m/e (ESI) 417(MH$^+$)

Example 250

Production Example 250a

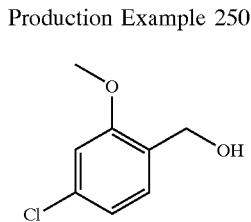

Using 4-chloro-2-methoxybenzoic acid, (4-chloro-2-methoxyphenyl)methanol was obtained in the same method as in Production Example 247b.

$^1$H-NMR(CDCl$_3$) δ: 3.83 (s, 3H) 4.62 (s, 2H) 6.85 (s, 1H) 6.94 (d, J=8.0 Hz, 1H) 7.20 (d, J=8.0 Hz, 1H)

Example 250b

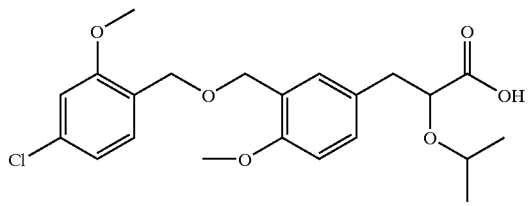

Using (4-chloro-2-methoxyphenyl)methanol and 3-[3-(bromomethyl)-4-methoxyphenyl]-2-isopropoxypropanoate, 3-(3-[(4-chloro-2-methoxybenzyl)oxy]methyl-4-methoxyphenyl)-2-isopropoxypropanoic acid was obtained in the same method as in Example 247).

MS m/e (ESI) 423(MH$^+$)

Example 251

Production Example 251a

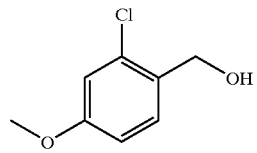

Using 2-chloro-4-methoxybenzoic acid, (2-chloro-4-methoxyphenyl)methanol was obtained in the same method as in Production Example 247b.

$^1$H-NMR(CDCl$_3$) δ: 3.80 (s, 3H) 4.70 (s, 2H) 6.80 (d, J=8.0 Hz, 1H) 6.95 (s, 1H) 7.37 (d, J=8.0 Hz, 1H)

Example 251b

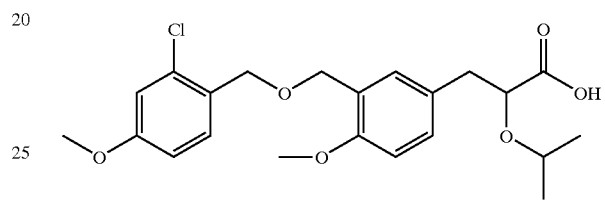

Using (2-chloro-4-methoxyphenyl)methanol and 3-[3-(bromomethyl)-4-methoxyphenyl]-2-isopropoxypropanoate, 3-(3-[(2-chloro-4-methoxybenzyl)oxy]methyl-4-methoxyphenyl)-2-isopropoxy propanoic acid was obtained in the same method as in Example 247).

MS m/e (ESI) 423(MH$^+$)

Example 252

Production Example 252a

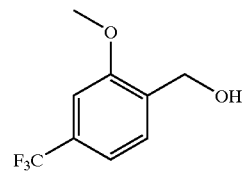

Using 2-methoxy-4-(trifluoromethyl)benzoic acid, [2-methoxy-4-(trifluoromethyl)phenyl]methanol was obtained in the same method as in Production Example 247b).

$^1$H-NMR(CDCl$_3$) δ: 3.92 (s, 3H) 4.72 (s, 2H) 7.08 (s, 1H) 7.22 (d, J=8.0 Hz, 1H) 7.42 (d, J=8.0 Hz, 1H) sample 252b)

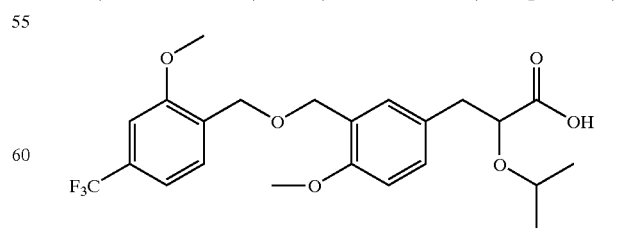

Using (2-chloro-4-methoxyphenyl)methanol and 3-[3-(bromomethyl)-4-methoxyphenyl]-2-isopropoxypropanoate, 3-(3-([2-fluoro-4-(trifluoromethyl)

benzyl]oxymethyl)-4-methoxyphenyl]-2-isopropoxypropanoic acid was obtained in the same method as in Example 247).

MS m/e (ESI) 457(MH⁺)

Example 253

Production Example 253a

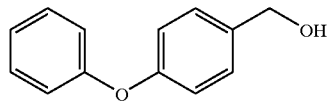

Using 4-phenoxybenzoic acid, (4-phenoxyphenyl) methanol was obtained in the same method as in Production Example 247b).

¹H-NMR(CDCl₃) δ:4.72(s,2H) 7.00–7.02(m,4H) 7.12(t, J=8.0 Hz,1H) 7.30–7.38(m,4H)

Example 253b

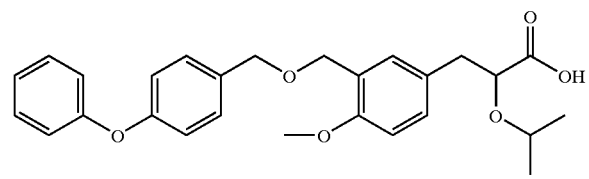

Using (4-phenoxyphenyl)methanol and 3-[3-(bromomethyl)-4-methoxyphenyl]-2-isopropoxypropanoate, 2-isopropoxy-3-(4-methoxy-3-[(4-phenoxybenzyl)oxy]methylphenyl)propanoic acid was obtained in the same method as in Example 247).

MS m/e (ESI) 451(MH⁺)

Example 254

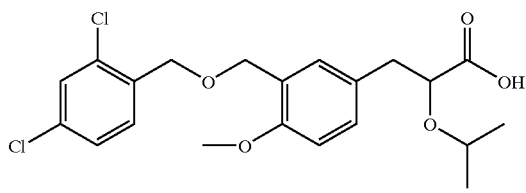

Using 2,4-dichlorobenzyl alcohol and 3-[3-(bromomethyl)-4-methoxyphenyl]-2-isopropoxypropanoate, 3-(3-[(2,4-dichlorobenzyl)oxy]methyl-4-methoxyphenyl)-2-isopropoxypropanoic acid was obtained in the same method as in Example 247).

MS m/e (ESI) 427(MH⁺)

Example 255

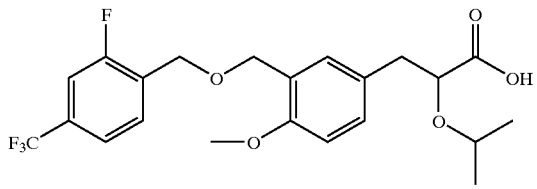

Using 2-fluoro-4-(trifluoromethyl)benzyl alcohol and 3-[3-(bromomethyl)-4-methoxyphenyl]-2-isopropoxypropanoate, 3-[3-([2-fluoro-4-(trifluoromethyl) benzyl]oxymethyl)-4-methoxyphenyl]-2-isopropoxypropanoic acid was obtained in the same method as in Example 247).

MS m/e (ESI) 445(MH⁺)

Example 256

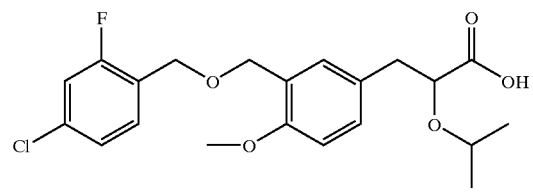

Using 4-chloro-2-fluorobenzyl alcohol and 3-[3-(bromomethyl)-4-methoxyphenyl]-2-isopropoxy propanoate, 3-(3-[(4-chloro-2-fluorobenzyl)oxy]methyl-4-methoxyphenyl)-2-isopropoxypropanoic acid was obtained in the same method as in Example 247).

MS m/e (ESI) 411(MH⁺)

Example 257

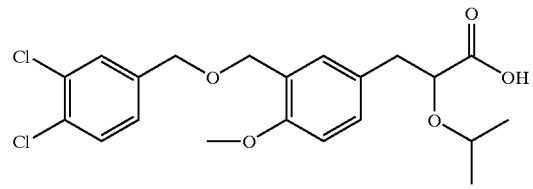

Using 3,4-dichlorobenzyl alcohol and 3-[3-(bromomethyl)-4-methoxyphenyl]-2-isopropoxypropanoate, 3-(3-[(3,4-dichlorobenzyl)oxy]methyl-4-methoxyphenyl)-2-isopropoxypropanoic acid was obtained in the same method as in Example 247).

MS m/e (ESI) 427(MH⁺)

Example 258

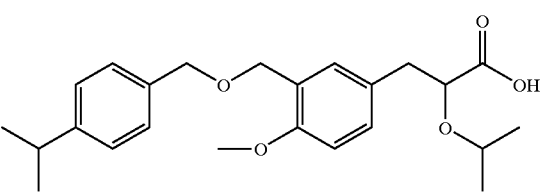

Using 4-isopropylbenzyl alcohol and 3-[3-(bromomethyl)-4-methoxyphenyl]-2- isopropoxypropanoate, 2-isopropoxy-3-(3-[(4-isopropoxybenzyl)oxy]methyl-4-methoxyphenyl)propanoic acid was obtained in the same method as in Example 247).

MS m/e (ESI) 401(MH⁺)

Example 259

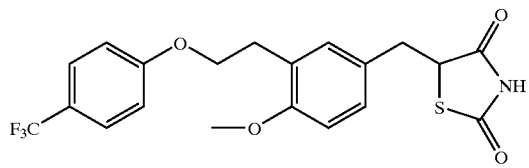

Using 4-methoxy-3-{2-[4-(trifluoromethyl)phenoxy]ethyl}benzaldehyde and 2,4-thiazolidine dione, 5-(4-methoxy-3-2-[4-(trifluoromethyl)phenoxy]ethylbenzyl)-1,3-thiazolane-2,4-dione was obtained in the same method as in Production Example 27c) and then in Example 29).

¹H-NMR(DMSO-d₆) δ: 3.09 (t, J=7.2 Hz, 2H) 3.10 (dd, J=9.2, 14.0 Hz, 1H) 3.45 (dd, J=4.0, 14.0 Hz, 1H) 3.83 (s, 3H) 4.17 (t, J=7.6 Hz, 2H) 4.49 (dd, J=4.0, 9.2 Hz, 1H) 6.82 (d, J=8.0 Hz, 1H) 6.96 (d, J=8.8 Hz, 2H) 7.08–7.10 (m,2H) 7.52 (d,J=8.8 Hz,2H) 8.37 (brs,1H)

Example 260

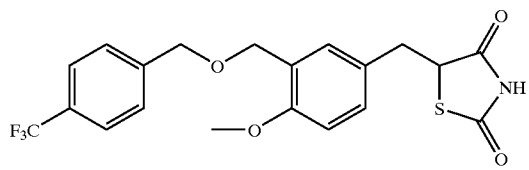

Using 4-methoxy-3-({[-4-(trifluoromethyl)benzyl]oxy}methyl)benzaldehyde and 2,4-thiazolidinedione, 5-[4-methoxy-3-([4-(trifluoromethyl)benzyl]oxymethyl)benzyl]-1,3-thiazolane-2,4-dione was obtained in the same method as in Production Example 27c) and then in Example 29).

¹H-NMR(DMSO-d₆) δ: 3.11 (dd, J=10.0, 14.0 Hz, 1H) 3.47 (dd, J=4.0, 14.0 Hz, 1H) 3.82 (s, 3H) 4.51 (dd, J=4.0, 9.2 Hz, 1H) 4.58 (s, 2H) 4.66 (s, 2H) 6.82 (d, J=8.0 Hz, 1H) 7.12 (dd, J=2.4, 8.0 Hz, 1H) 7.24–7.28 (m, 1H) 7.50 (d, J=8.0 Hz, 2H) 7.61 (d, J=8.0 Hz, 2H) 8.10 (brs, 1H)

Example 261

Production Example 261a

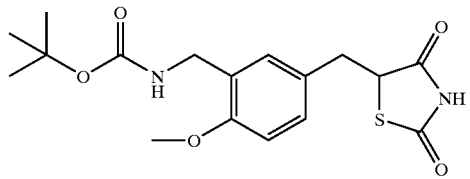

7.7 g of tert-butyl N-(5-formyl-2-methoxybenzyl)carbamate and 3.4 g of 2,4-thiazolidinedione were dissolved in 100 ml toluene, and 0.28 g piperidine and 0.24 g acetic acid were added, and the mixture was heated under reflux for 3 hours with Dean-Stark apparatus. After cooling the reaction solution to room temperature, the resulting crystals were collected by filtration, washed with toluene and then dried under reduced pressure, to give tert-butyl N-5-[(2,4-dioxo-1,3-thiazolane-5-ylidene)methyl]-2-methoxybenzylcarbamate. Then, the resulting tert-butyl N-5-[(2,4-dioxo-1,3-thiazolane-5-ylidene)methyl]-2-methoxybenzylcarbamate was dissolved in 80 ml dimethylformamide, and 8.0 g of 10% palladium carbon was added, and the mixture was stirred at 50° C. under pressure at 15 kg/cm² hydrogen for 20 minutes. The catalyst was filtered and the solvent was evaporated Then, water was added thereto, followed by extracting with ethyl acetate. The organic layer was washed with brine, dried over anhydrous magnesium sulfate and the solvent was evaporated. The residue was subjected to silica gel column chromatography, and from fractions eluted with hexane-ethyl acetate (1:1), 8.2 g of tert-butyl N-5-[(2,4-dioxo-1,3-thiazolane-5-yl)methyl]-2-methoxybenzylcarbamate was obtained.

¹H-NMR(CDCl₃) δ: 1.45(s,9H) 3.11(dd,J=9.2, 14.0 Hz, 1H) 3.42 (dd, J=3.6, 14.0 Hz, 1H) 3.83 (s, 3H) 4.26 (d, J=6.0 Hz, 2H) 4.50 (dd, J=3.6, 9.2 Hz, 1H) 5.00–5.08 (m, 1H) 6.79 (d, J=8.0 Hz, 1H) 7.09–7.13 (m, 2H) 8.28–8.33 (m, 1H)

Example 261b

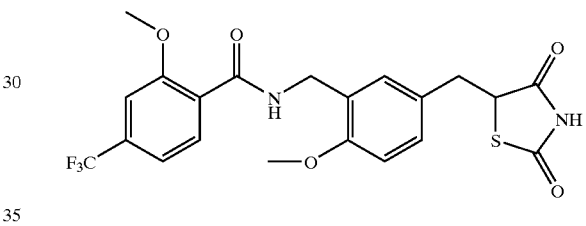

40 ml of 4 M HCl-dioxane was added to 8.2 g of tert-butyl N-5-[(2,4-dioxo-1,3-thiazolane-5-yl)methyl]-2-methoxybenzylcarbamate, foollowed by stirring for 1 hour. The reaction solution was concentrated and dried under reduced pressure, to give 6.0 g of tert-butyl N-5-[(2,4-dioxo-1,3-thiazolane-5-yl)methyl]-2-methoxybenzylamine hydrochloride. Then, 0.20 g of the resulting tert-butyl N-5-[(2,4-dioxo-1,3-thiazolane-5-yl)methyl]-2-methoxybenzylamine hydrochloride and 0.15 g of 2-methoxy-4-(trifluoromethyl)benzoic acid were dissolved in 2.5 ml dimethylformamide, and 0.11 ml diethyl cyanophosphonate and 0.10 ml triethylamine were added under ice-cooling. After stirring at room temperature for 16 hours, the reaction solution was diluted with water and extracted with ethyl acetate. The organic layer was successively washed with 1N hydrochloric acid and brine, dried over anhydrous magnesium sulfate and the solvent was evaporated. The residue was subjected to silica gel column chromatography, and from fractions eluted with hexane-ethyl acetate (2:1), 0.18 g of N1-5-[(2,4-dioxo-1,3-thiazolane-5-yl)methyl]-2-methoxybenzyl-2-methoxy-4-(trifluoromethyl)benzamide was obtained.

¹H-NMR(DMSO-d₆) δ: 2.99 (dd, J=9.6, 14.0 Hz, 1H) 3.28 (dd, J=4.0, 14.0 Hz, 1H) 3.79 (s, 3H) 3.97 (s, 3H) 4.42 (d, J=6.0 Hz, 2H) 4.79 (dd, J=4.0, 9.6 Hz, 1H) 6.93 (d, J=8.4 Hz, 1H) 7.08–7.13 (m, 2H) 7.37 (d, J=8.0 Hz, 1H) 7.42 (s, 1H) 7.84 (d, J=8.0 Hz, 1H) 8.64 (t, J=6.0 Hz, 1H) 12.02 (brs, 1H)

Example 262

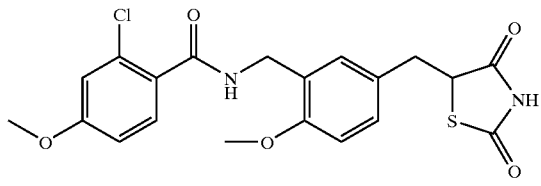

Using 2-chloro-4-methoxybenzoic acid and tert-butyl N-5-[(2,4-dioxo-1,3-thiazolane-5-yl)methyl]-2-methoxybenzylamine hydrochloride, N1-5-[(2,4-dioxo-1,3-thiazolane-5-yl)methyl]-2-methoxybenzyl-2-chloro-4-methoxybenzamide was obtained in the same method as in Example 261).

$^1$H-NMR(DMSO-$d_6$) δ: 2.99 (dd, J=9.6, 14.0 Hz, 1H) 3.28 (dd, J=4.0, 14.0 Hz, 1H) 3.78 (s, 3H) 3.79 (s, 3H) 4.42 (d, J=6.0 Hz, 2H) 4.79 (dd, J=4.0, 9.6 Hz, 1H) 6.93 (d, J=8.4 Hz, 1H) 6.94–6.96 (m, 1H) 7.06 (d, J=2.4 Hz, 1H) 7.08–7.13 (m, 2H) 7.43 (d, J=8.0 Hz, 1H) 8.64 (t, J=6.0 Hz, 1H) 12.02 (brs, 1H)

Example 263

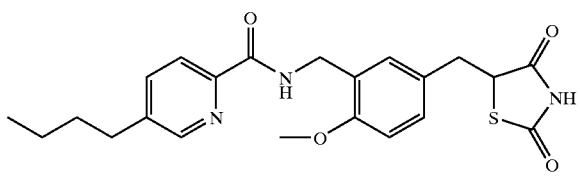

Using fusaric acid and tert-butyl N-5-[(2,4-dioxo-1,3-thiazolane-5-yl)methyl]-2-methoxybenzylamine hydrochloride, N2-5-[(2,4-dioxo-1,3-thiazolane-5-yl)methyl]-2-methoxybenzyl-5-butyl-2-pyridinecarboxyamide was obtained in the same method as in Example 261)

$^1$H-NMR(DMSO-$d_6$) δ: 0.89 (t, J=7.2 Hz, 3H) 1.25–1.33 (m, 2H) 1.53–1.60 (m, 2H) 2.67 (t, J=8.0 Hz, 2H) 2.99 (dd, J=9.6, 14.0 Hz, 1H) 3.28 (dd, J=4.0, 14.0 Hz, 1H) 3.79 (s, 3H) 4.42 (d, J=6.0 Hz, 2H) 4.77 (dd, J=4.0, 9.6 Hz, 1H) 6.93 (d, J=8.4 Hz, 1H) 7.03 (d, J=2.4 Hz, 1H) 7.10 (dd, J=2.4, 8.4 Hz, 1H) 7.81 (dd, J=2.0, 8.0 Hz, 1H) 7.95 (d, J=8.0 Hz, 1H) 8.49 (d, J=2.0 Hz, 1H) 8.89(t, J=6.0 Hz, 1H) 12.02 (brs, 1H)

Example 264

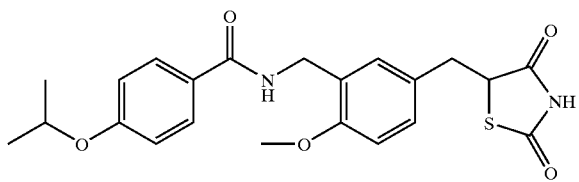

Using 4-isopropoxybenzoic acid and tert-butyl N-5-[(2,4-dioxo-1,3-thiazolane-5-yl)methyl]-2-methoxybenzylamine hydrochloride, N1-5-[(2,4-dioxo-1,3-thiazolane-5-yl)methyl]-2-methoxybenzyl-4-isopropoxybenzamide was obtained in the same method as in Example 261).

$^1$H-NMR(DMSO-$d_6$) δ: 1.26 (d, J=6.0 Hz, 6H) 2.99 (dd, J=9.6, 14.0 Hz, 1H) 3.28 (dd, J=4.0, 14.0 Hz, 1H) 3.79 (s, 3H) 4.42 (d, J=6.0 Hz, 2H) 4.69 (sept, J=6.0 Hz, 1H)4.79 (dd, J=4.0, 9.6 Hz, 1H) 6.93 (d, J=8.4 Hz, 1H) 6.95 (d, J=8.4 Hz, 2H) 7.03 (s, 1H) 7.08 (d, J=8.4 Hz, 1H) 7.84 (d, J=8.4 Hz, 2H) 8.63 (t, J=6.0 Hz, 1H) 12.02 (brs, 1H)

Example 265

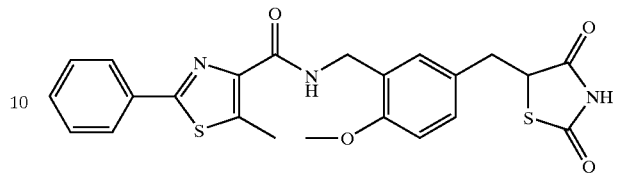

Using 5-methyl-2-phenyl-1,3-thiazole-4-carboxylic acid and tert-butyl N-5-[(2,4-dioxo-1,3-thiazolane-5-yl)methyl]-2-methoxybenzylamine hydrochloride, N4-5-[(2,4-dioxo-1,3-thiazolane-5-yl)methyl]-2-methoxybenzyl-5-methyl-2-phenyl-1,3-thiazole-4-carboxyamide was obtained in the same method as in Example 261).

$^1$H-NMR(DMSO-$d_6$) δ: 2.61(s, 3H) 2.99 (dd, J=9.6, 14.0 Hz, 1H) 3.28 (dd, J=4.0, 14.0 Hz, 1H) 3.79 (s, 3H) 4.37 (m, 2H) 4.77 (dd, J=4.0, 9.6 Hz, 1H) 6.93 (d, J=8.4 Hz, 1H) 7.08–7.13 (m, 2H) 7.46–7.52 (m, 3H) 7.90–7.95 (m, 2H) 8.61 (m, 1H) 12.02 (brs, 1H)

Example 266

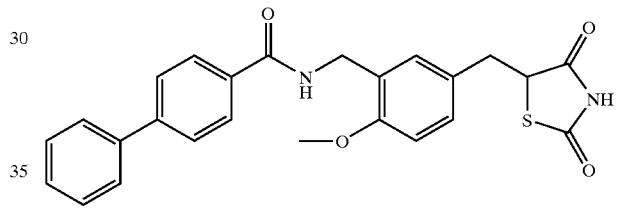

Using 4-phenylbenzoic acid and tert-butyl N-5-[(2,4-dioxo-1,3-thiazolane-5-yl)methyl]-2-methoxybenzylamine hydrochloride, N1-5-[(2,4-dioxo-1,3-thiazolane-5-yl)methyl]-2-methoxybenzyl-4-phenylbenzamide was obtained in the same method as in Example 261).

$^1$H-NMR(DMSO-$d_6$) δ: 2.99 (dd, J=9.6, 14.0 Hz, 1H) 3.28 (dd, J=4.0, 14.0 Hz, 1H) 3.79 (s, 3H) 4.42 (d, J=6.0 Hz, 2H) 4.77 (dd, J=4.0, 9.6 Hz, 1H) 6.93 (d, J=8.4 Hz, 1H) 7.08–7.13 (m, 2H) 7.39 (t, J=7.2 Hz, 1H) 7.48 (t, J=7.6 Hz, 2H) 7.72 (d, J=7.6 Hz, 2H) 7.76 (d, J=8.0 Hz, 2H) 7.99 (d, J=8.0 Hz, 2H) 8.87 (t, J=6.0 Hz, 1H) 12.02 (brs, 1H)

Example 267

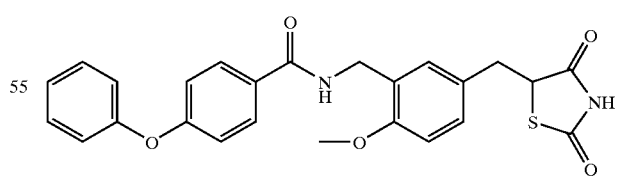

Using 4-phenoxybenzoic acid and tert-butyl N-5-[(2,4-dioxo-1,3-thiazolane-5-yl)methyl]-2-methoxybenzylamine hydrochloride, N1-5-[(2,4-dioxo-1,3-thiazolane-5-yl)methyl]-2-methoxybenzyl-4-phenoxybenzamide was obtained in the same method as in Example 261).

$^1$H-NMR(DMSO-$d_6$) δ: 2.99(dd, J=9.6, 14.0 Hz, 1H) 3.28(dd, J=4.0, 14.0 Hz, 1H) 3.79(s, 3H) 4.42(d, J=6.0 Hz, 2H) 4.77(dd, J=4.0, 9.6 Hz, 1H) 6.93(d, J=8.4 Hz, 1H) 7.02(d, J=8.8 Hz, 2H) 7.05–7.10(m, 4H) 7.20(t, J=8.0 Hz, 1H) 7.43(t, J=8.0 Hz, 2H) 7.92(d, J=8.8 Hz, 2H) 8.76(t, J=6.0 Hz, 1H) 12.02(brs, 1H)

Example 268

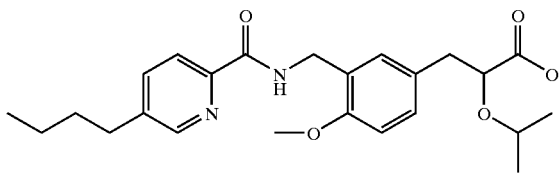

Using fusaric acid and ethyl 3-[3-(aminomethyl)-4-methoxyphenyl]-2-isopropoxypropanoate, 3-[3-t[t5-butyl-2-pyridyl)carbonyl]aminomethyl)-4-methoxyphenyl]-2-isopropoxypropanoic acid was obtained in the same method as in Example 19d) and then in Example 19e)

$^1$H-NMR(CDCl$_3$) δ: 0.93 (t, J=8.0 Hz, 3H) 1.00 (d, J=6.0 Hz, 3H) 1.12 (d, J=6.0 Hz, 3H) 1.31–1.40 (m, 2H) 1.56–1.65 (m, 2H) 2.66 (t, J=8.0 Hz, 2H) 2.88 (dd, J=8.0, 14.0 Hz, 1H) 3.04 (dd, J=4.4, 14.0 Hz, 1H) 3.53 (sept, J=6.0 Hz, 1H) 3.87 (s, 3H) 4.08 (dd, J=4.4, 8.0 Hz, 1H) 4.63 (d, J=6.4 Hz, 2H) 6.80 (d, J=8.0 Hz, 1H) 7.12 (dd, J=2.4, 8.0 Hz, 1H) 7.22 (d, J=2.4 Hz, 1H) 7.63 (dd, J=1.6, 8.0 Hz, 1H) 8.10 (d, J=8.0 Hz, 1H) 8.35 (d, J=1.6 Hz, 1H)

Example 269

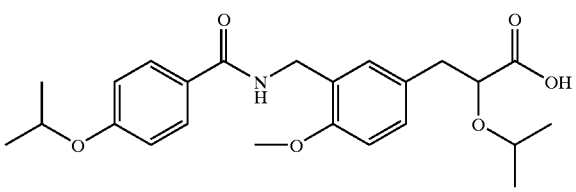

Using 4-isopropoxybenzoic acid and ethyl 3-[3-(aminomethyl)-4-methoxyphenyl]-2-isopropoxypropanoate, 2-isopropoxy-3-[3-[(4-isopropoxybenzoyl)amino]methyl-4-methoxyphenyl)propanoic acid was obtained in the same manner as in Example 19d) and then in Example 19e).

$^1$H-NMR(CDCl$_3$) δ: 1.02 (d, J=6.0 Hz, 3H) 1.15 (d, J=6.0 Hz, 3H) 1.34 (d, J=6.4 Hz, 6H) 2.90 (dd, J=8.0, 14.0 Hz, 1H) 3.05 (dd, J=4.4, 14.0 Hz, 1H) 3.57 (sept, J=6.0 Hz, 1H) 3.86 (s, 3H) 4.10 (dd, J=4.4, 8.0 Hz, 1H) 4.58 (d, J=6.0 Hz, 2H) 4.59–4.61 (m, 1H) 6.55–6.61 (m, 1H) 6.80 (d, J=8.0 Hz, 1H) 6.87 (d, J=8.8 Hz, 2H) 7.13 (dd, J=2.0, 8.0 Hz, 1H) 7.22 (d, J=2.0 Hz, 1H) 7.69 (d, J=8.8 Hz, 2H)

Example 270

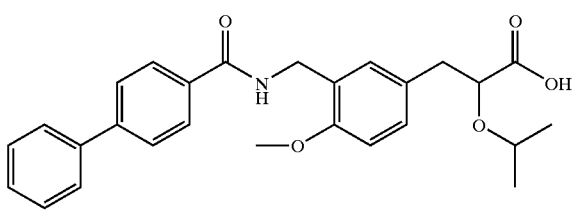

Using 4-phenylbenzoic acid and ethyl 3-[3-(aminomethyl)-4-methoxyphenyl]-2-isopropoxypropanoate, 2-isopropoxy-3-(4-methoxy-3-[(4-phenylbenzoyl)amino]methylphenyl)propanoic acid was obtained in the same method as in Example 19d) and then in Example 19e).

$^1$H-NMR(CDCl$_3$) δ: 1.03 (d, J=6.0 Hz, 3H) 1.15 (d, J=6.0 Hz, 3H) 2.92 (dd, J=8.0, 14.0 Hz, 1H) 3.06 (dd, J=4.4, 14.0 Hz, 1H) 3.58 (sept, J=6.0 Hz, 1H) 3.88 (s, 3H) 4.11 (dd, J=4.4, 8.0 Hz, 1H) 4.63 (d, J=6.4 Hz, 2H) 6.68–6.73 (m, 1H) 6.82 (d, J=8.0 Hz, 1H) 7.15 (dd, J=2.0, 8.0 Hz, 1H) 7.24 (d, J=2.0 Hz, 1H) 7.35–7.40 (m, 1H) 7.46 (t, J=7.2 Hz, 2H) 7.59 (d, J=7.2 Hz, 2H) 7.64 (d, J=8.0 Hz, 2H) 7.82 (d, J=8.0 Hz, 2H)

Example 271

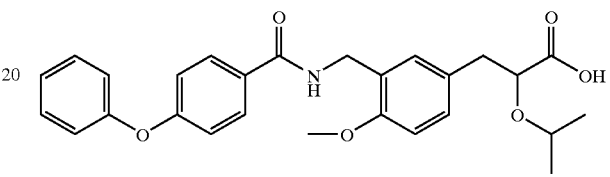

Using 4-phenoxybenzoic acid and ethyl 3-[3-(aminomethyl)-4-methoxyphenyl]-2-isopropoxypropanoate, 2-isopropoxy-3-(4-methoxy-3-[(4-phenylbenzoyl)amino]methylphenyl)propanoic acid was obtained in the same method as in Example 19d) and then in Example 19e)

$^1$H-NMR(CDCl$_3$) δ: 1.04 (d, J=6.0 Hz, 3H) 1.15 (d, J=6.0 Hz, 3H) 2.91 (dd, J=8.0, 14.0 Hz, 1H) 3.04 (dd, J=4.4, 14.0 Hz, 1H) 3.57 (sept, J=6.0 Hz, 1H) 3.86 (s, 3H) 4.10 (dd, J=4.4, 8.0 Hz, 1H) 4.59 (d, J=6.0 Hz, 2H) 6.60–6.65(m, 1H) 6.81(d, J=8.0 Hz, 1H) 6.98 (d, J=8.0 Hz, 2H) 7.03(d, J=8.0 Hz, 2H) 7.13–7.18 (m, 2H) 7.22(d, J=2.0 Hz, 1H) 7.37(t, J=8.0 Hz, 2H) 7.72(d, J=8.0 Hz, 2H)

Example 272

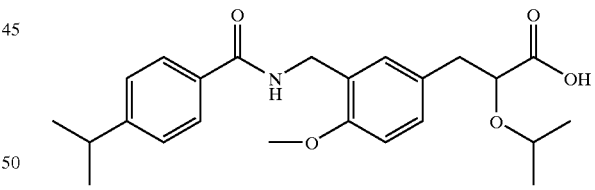

Using 4-isopropylbenzoic acid and ethyl 3-[3-(aminomethyl)-4-methoxyphenyl]-2-isopropoxypropanoate, 2-isopropoxy-3-(3-[(4-isopropylbenzoyl)amino]methyl-4-methoxyphenyl)propanoic acid was obtained in the same method as in Example 19d) and then in Example 19e).

$^1$H-NMR(CDCl$_3$) δ: 1.02 (d, J=6.0 Hz, 3H) 1.15 (d, J=6.0 Hz, 3H) 1.25 (d, J=6.0 Hz, 6H) 2.90 (dd, J=8.0, 14.0 Hz, 1H) 2.92 (sept, J=6.0 Hz, 1H) 3.04 (dd, J=4.4, 14.0 Hz, 1H) 3.56 (sept, J=6.0 Hz, 1H) 3.86 (s, 3H) 4.10 (dd, J=4.4, 8.0 Hz, 1H) 4.60 (d, J=6.0 Hz, 2H) 6.66–6.70 (m, 1H) 6.81 (d, J=8.0 Hz, 1H) 7.14 (dd, J=2.0, 8.0 Hz, 1H) 7.23 (d, J=2.0 Hz, 1H) 7.26 (d, J=8.0 Hz, 2H) 7.68 (d, J=8.0 Hz, 2H)

Example 273

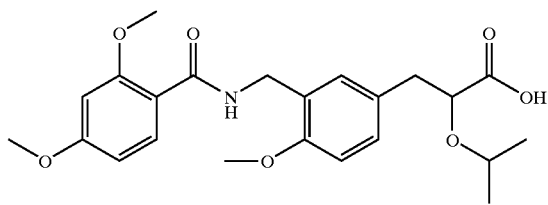

Using 2,4-dimethoxybenzoic acid and ethyl 3-[3-(aminomethyl)-4-methoxyphenyl]-2-isopropoxypropanoate, 3-(3-[(2,4-dimethoxybenzoyl)amino]methyl-4-methoxyphenyl)-2-isopropoxypropanoic acid was obtained in the same method as in Example 19d) and then in Example 19e).

$^1$H-NMR(CDCl$_3$) δ: 1.02 (d, J=6.0 Hz, 3H) 1.15 (d, J=6.0 Hz, 3H) 2.90 (dd, J=8.0, 14.0 Hz, 1H) 3.04 (dd, J=4.4, 14.0 Hz, 1H) 3.56 (sept, J=6.0 Hz, 1H) 3.85 (s, 3H) 3.88 (s, 3H) 3.92 (s, 3H) 4.09 (dd, J=4.4, 8.0 Hz, 1H) 4.61–4.63 (m, 2H) 6.47 (d, J=2.0 Hz, 1H) 6.59 (dd, J=2.0, 8.8 Hz, 1H) 6.81 (d, J=8.0 Hz, 1H) 7.13 (dd, J=2.0, 8.0 Hz, 1H) 7.22 (d, J=2.0 Hz, 1H) 8.19 (d, J=8.8 Hz, 1H) 8.34–8.39 (m, 1H)

Example 274

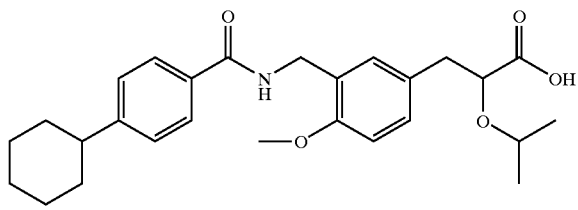

Using 4-cyclohexylbenzoic acid and ethyl 3-[3-([(tert-butoxycarbonyl)amino]methyl)-4-methoxyphenyl]-2-isopropoxypropanoate, 3-(3-[(4-cyclohexylbenzoyl)amino)methyl-4-methoxyphenyl)-2-isopropoxypropanoic acid was obtained in the same method as in Example 38).

MS m/e (ESI) 454(MH$^+$)

Example 275

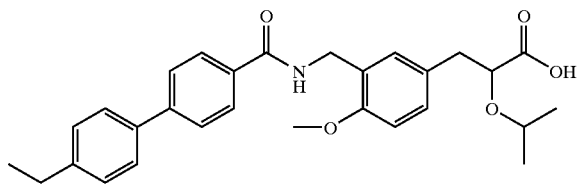

Using 4-(4'-ethylphenyl)benzoic acid and ethyl 3-[3-([(tert-butoxycarbonyl)amino]methyl)-4-methoxyphenyl]-2-isopropoxypropanoate, 2-isopropoxy-3-[4-methoxy-3-([4-(4'-ethylphenyl)benzoyl]amino)methylphenyl]propanoic acid was obtained in the same method as in Example 38).

MS m/e (ESI) 476(MH$^+$)

Example 276

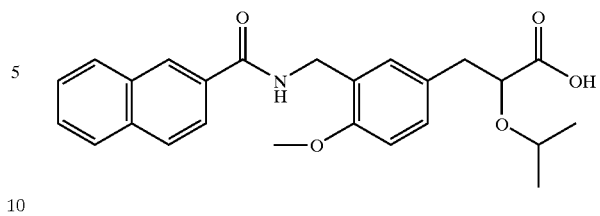

Using 2-naphthalene carboxylic acid and ethyl 3-[3-([(tert-butoxycarbonyl)amino]methyl)-4-methoxyphenyl]-2-isopropoxypropanoate, 2-isopropoxy-3-(4-methoxy-3-[(2-naphthylcarbonyl)amino]methylphenyl)propanoic acid was obtained in the same method as in Example 38).

MS m/e (ESI) 422(MH$^+$)

Example 277

Production Example 277a

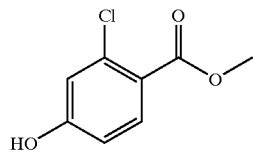

1.9 g of 2-chloro-4-hydroxybenzoic acid was dissolved in 20 ml dimethylformamide, and 1.8 g of methyl iodide and 1.2 g of potassium bicarbonate were added, and the mixture was stirred at room temperature for 3 hours. The reaction solution was diluted with water and then extracted with ethyl acetate. The organic layer was successively washed with 1N hydrochloric acid and brine, dried over anhydrous magnesium sulfate and the solvent was evaporated. The residue was subjected to silica gel column chromatography, and from fractions eluted with hexane-ethyl acetate (3:1), 1.7 g of methyl 2-chloro-4-hydroxybenzoate was obtained.

Production Example 277b

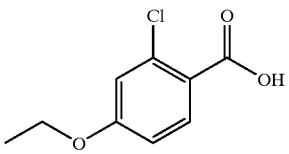

0.25 g of methyl 2-chloro-4-hydroxybenzoate was dissolved in 10 ml dimethylformamide, and 0.23 g of ethyl iodide and 0.21 g of potassium carbonate were added, and the mixture was stirred for 8 hours. After diluting the reaction mixture, it was extracted with ethyl acetate. The organic layer was successively washed with 1N hydrochloric acid and brine, dried over anhydrous magnesium sulfate and the solvent was evaporated. The residue was dissolved in 6 ml methanol, and 3 ml of 1 N sodium hydroxide was added, and the solution was stirred at room temperature for 6 hours. The reaction mixture was ice-cooled and neutralized with 1N hydrochloric acid, followed by extracting with ethyl acetate. The organic layer was washed with brine, dried over anhydrous sodium sulfate and the solvent was evaporated, to give 1.7 g of 2-chloro-4-ethoxybenzoic acid.

$^1$H-NMR(CDCl$_3$) δ: 1.43 (t, J=7.2 Hz, 3H) 4.10 (q, J=7.2 Hz, 2H) 6.84 (dd, J=2.8, 8.8 Hz, 1H) 6.99 (d, J=2.8 Hz, 1H) 8.03 (d, J=8.8 Hz, 1H)

Example 277c

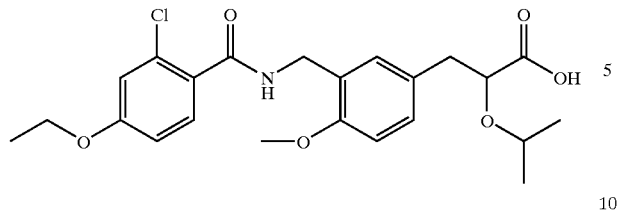

Using 2-chloro-4-ethoxybenzoic acid and 3-[3-([(tert-butoxycarbonyl)amino]methyl)-4-methoxyphenyl]-2-isopropoxypropanoate, 3-[3-([(2-chloro-4-ethoxybenzoyl)amino]methyl-4-methoxyphenyl)-2-isopropoxypropanoic acid was obtained in the same method as in Example 38).

MS m/e (ESI) 450(MH$^+$)

Example 278

Production Example 278a

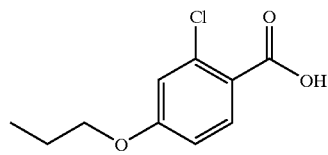

Using methyl 2-chloro-4-hydroxybenzoate and propyl iodide, 2-chloro-4-propoxybenzoic acid was obtained in the same manner as in Example 277b).

$^1$H-NMR(CDCl$_3$) δ: 1.05 (t, J=7.2 Hz, 3H) 1.80–1.86 (m, 2H) 3.98 (t, J=6.4 Hz, 2H) 6.84(dd, J=2.8, 8.8 Hz, 1H) 6.99(d, J=2.8 Hz, 1H) 8.03(d, J=8.8 Hz, 1H)

Example 278b

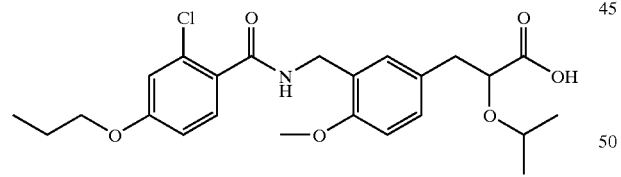

Using 2-chloro-4-propoxybenzoic acid and 3-[3-([(tert-butoxycarbonyl)amino]methyl)-4-methoxyphenyl]-1-2-isopropoxypropanoate, 3-(3-[(2-chloro-4-propoxybenzoyl)amino]methyl-4-methoxyphenyl)-2-isopropoxypropanoic acid was obtained in the same method as in Example 38).

$^1$H-NMR(CDCl$_3$) δ: 1.03(t, J=7.2 Hz, 3H) 1.04(d, J=6.0 Hz, 3H) 1.16 (d, J=6.0 Hz, 3H) 1.76–1.85 (m, 2H) 2.91 (dd, J=8.0, 14.0 Hz, 1H) 3.06 (dd, J=4.4, 14.0 Hz, 1H) 3.57 (sept, J=6.0 Hz, 1H) 3.85 (s, 3H) 3.92 (t, J=6.4 Hz, 2H) 4.10(dd, J=4.4, 8.0 Hz, 1H) 4.61(d, J=6.0 Hz, 2H) 6.80–6.89(m, 3H) 6.95–7.02(m, 1H) 7.14(dd, J=2.0, 8.0 Hz, 1H) 7.24(d, J=2.0 Hz, 1H) 7.74(d, J=8.8 Hz, 1H)

Example 279

Production Example 279a

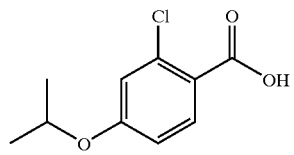

Using methyl 2-chloro-4-hydroxybenzoate and isopropyl iodide, 2-chloro-4-isopropoxybenzoic acid was obtained in the same method as in Production Example 277b).

$^1$H-NMR(CDCl$_3$) δ: 1.37 (d, J=6.0 Hz, 6H) 4.62 (sept, J=6.0 Hz, 1H) 6.81 (dd, J'2.8, 8.8 Hz, 1H) 6.99 (d, J=2.8 Hz, 1H) 8.02 (d, J=8.8 Hz, 1H)

Example 279b

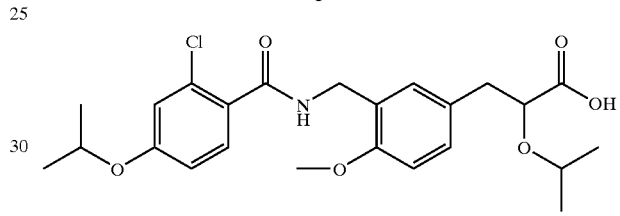

Using 2-chloro-4-isopropoxybenzoic acid and 3-(3-([(tert-butoxycarbonyl)amino]methyl)-4-methoxyphenyl]-2-isopropoxypropanoate, 3-(3-[(2-chloro-4-isopropoxybenzoyl)amino]methyl-4-methoxyphenyl)-2-isopropoxypropanoic acid was obtained in the same method as in Example 38).

MS m/e (ESI) 464(MH$^+$)

Example 280

Production Example 280a

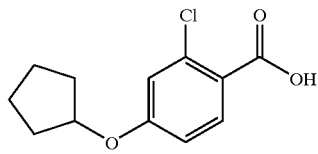

Using methyl 2-chloro-4-hydroxybenzoate and cyclopentyl bromide, 2-chloro-4-cyclopentyloxybenzoic acid was obtained in the same manner as in Example 277b).

$^1$H-NMR(CDCl$_3$) δ: 1.76–1.98 (m, 8H) 4.78–4.82 (m, 1H) 6.81 (dd, J=2.8, 8.8 Hz, 1H) 6.99 (d, J=2.8 Hz, 1H) 8.02 (d, J=8.8 Hz, 1H)

Example 280b

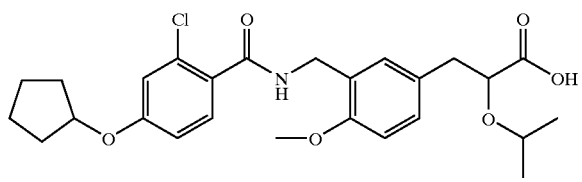

Using 2-chloro-4-cyclopentyloxybenzoic acid and 3-[3-([(tert-butoxycarbonyl)amino]methyl)-4-methoxyphenyl]-2-isopropoxypropanoate, 3-(3-[(2-chloro-4-cyclopentyloxybenzoyl)amino]methyl-4-methoxyphenyl)-2-isopropoxypropanoic acid was obtained in the same method as in Example 38).

$^1$H-NMR(CDCl$_3$) δ: 1.03 (d, J=6.0 Hz, 3H) 1.15 (d, J=6.0 Hz, 3H) 1.72–1.95 (m, 8H) 2.91 (dd, J=8.0, 14.0 Hz, 1H) 3.05 (dd, J=4.4, 14.0 Hz, 1H) 3.56 (sept, J=6.0 Hz, 1H) 3.85 (s, 3H) 4.10 (dd, J=4.4, 8.0 Hz, 1H) 4.60 (d, J=6.0 Hz, 2H) 4.74–4.77 (m, 1H) 6.79–6.86 (m, 3H) 6.95–7.01 (m, 1H) 7.14 (dd, J=2.0, 8.0 Hz, 1H) 7.24 (d, J=2.0 Hz, 1H) 7.73 (d, J=8.8 Hz, 1H)

Example 281

Production Example 281a

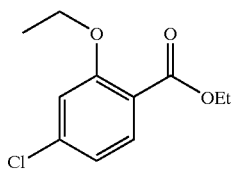

5.0 g of 4-chloro-2-hydroxybenzoic acid was dissolved in 25 ml dimethylformamide, and 14.5 g of ethyl iodide and 12 g of potassium carbonate were added thereto, followed by stirring at 70° C. for 8 hours. The reaction solution was diluted with water and then extracted with ethyl acetate. The organic layer was successively washed with 1N hydrochloric acid and brine, dried over anhydrous magnesium sulfate and the solvent was evaporated. The residue was subjected to silica gel column chromatography, and from fractions eluted with hexane-ethyl acetate (2:1), 3.8 g of ethyl 4-chloro-2-ethoxybenzoate was obtained.

$^1$H-NMR(CDCl$_3$) δ: 1.48 (t, J=7.2 Hz, 3H) 1.59 (t, J=7.2 Hz, 3H) 4.10 (q, J=7.2 Hz, 2H) 4.33 (q, J=7.2 Hz, 2H) 6.92 (d, J=2.0 Hz, 1H) 6.94 (dd, J=2.0, 8.8 Hz, 1H) 7.73 (d, J=8.8 Hz, 1H)

Production Example 281b

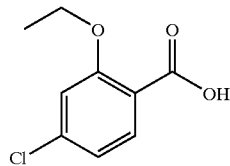

0.2 g of ethyl 4-chloro-2-ethoxybenzoate was dissolved in 5 ml methanol, and 2 ml of 1N sodium hydroxide was added, and the mixture was stirred at room temperature for 6 hours. The reaction mixture was ice-cooled and neutralized with 1N hydrochloric acid, followed by extracting with ethyl acetate. The organic layer was washed with brine, dried over anhydrous sodium sulfate and the solvent was evaporated, to give 0.20 g of 4-chloro-2-ethoxybenzoic acid.

$^1$H-NMR(CDCl$_3$) δ: 1.59 (t, J=7.2 Hz, 3H) 4.33 (q, J=7.2 Hz, 2H) 7.04 (d, J=2.0 Hz, 1H) 7.13 (dd, J=2.0, 8.8 Hz, 1H) 8.13 (d, J=8.8 Hz, 1H)

Example 281c

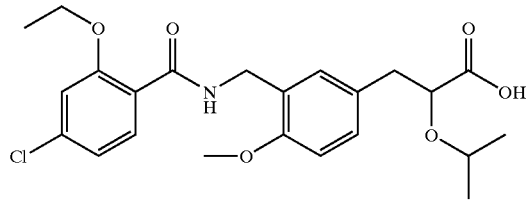

Using 4-chloro-2-ethoxybenzoic acid and 3-[3-([(tert-butoxycarbonyl)amino)methyl]-4-methoxyphenyl]-2-isopropoxypropanoate, 3-(3-[(4-chloro-2-ethoxybenzoyl)amino]methyl-4-methoxyphenyl)-2-isopropoxypropanoic acid was obtained in the same method as in Example 38).

MS m/e (ESI) 450(MH$^+$)

Example 282

Production Example 282a

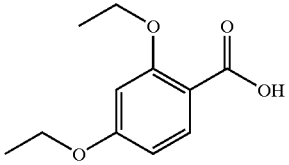

Using 2,4-dihydroxybenzoic acid and ethyl iodide, 2,4-diethoxybenzoic acid was obtained in the same method as in Production Example 281a) and then in Production Example 281b)

$^1$H-NMR(CDCl$_3$) δ: 1.45 (t, J=7.2 Hz, 3H) 1.56 (t, J=7.2 Hz, 3H) 4.10 (q, J=7.2 Hz, 2H) 4.28 (q, J=7.2 Hz, 2H) 6.51 (d, J=2.0 Hz, 1H) 6.62 (dd, J=2.0, 8.8 Hz, 1H) 8.12 (d, J=8.8 Hz, 1H)

Example 282b

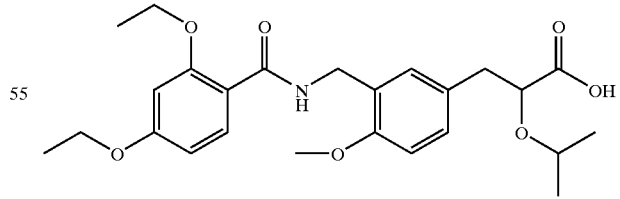

Using 2,4-diethoxybenzoic acid and 3-[3-([(tert-butoxycarbonyl)amino]methyl)-4-methoxyphenyl)-2-isopropoxypropanoate, 3-(3-[(2,4-diethoxybenzoyl)amino]methyl-4-methoxyphenyl)-2-isopropoxypropanoic acid was obtained in the same method as in Example 38).

MS m/e (ESI) 460(MH$^+$)

Example 283

Production Example 283a

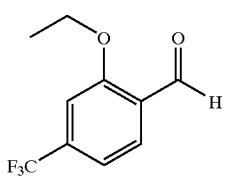

0.80 g of 2-hydroxy-4-(trifluoromethyl)benzaldehyde was dissolved in 8 ml dimethylformamide, and 0.78 g of ethyl iodide and 0.69 g of potassium carbonate were added, and the mixture was stirred at 70° C. for 2 hours. The reaction solution was diluted with water and then extracted with ethyl acetate. The organic layer was successively washed with 1N hydrochloric acid and brine, dried over anhydrous magnesium sulfate and the solvent was evaporated. The residue was subjected to silica gel column chromatography, and from fractions eluted with hexane-ethyl acetate (5:1), 0.60 g of 2-ethoxy-4-(trifluoromethyl)benzaldehyde was obtained.

$^1$H-NMR(CDCl$_3$) δ: 1.57 (t, J=7.2 Hz, 3H) 4.22 (q, J=7.2 Hz, 2H) 7.22 (s, 1H) 7.29 (d, J=8.0 Hz, 1H) 7.93 (d, J=8.0 Hz, 1H) 10.50 (s,1H) Production Example 283b

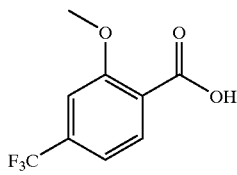

0.60 g of 2-ethoxy-4-(trifluoromethyl)benzaldehyde was dissolved in 5 ml dimethyl sulfoxide and an aqueous solution (1 ml) of 67 mg sodium dihydrogen phosphate, and an aqueous solution (3 ml) of 0.35 g sodium chlorite was added dropwise. After stirring at room temperature for 12 hours, water was added thereto, followed by extracting with ethyl acetate. The extract was washed with brine, dried over anhydrous magnesium sulfate and the solvent was evaporated. The residue was subjected to silica gel column chromatography, and from fractions eluted with hexane-ethyl acetate (2:1), 0.55 g of 2-ethoxy-4-(trifluoromethyl) benzoic acid was obtained.

$^1$H-NMR(CDCl$_3$) δ: 1.61 (t, J=7.2 Hz, 3H) 4.40 (q, J=7.2 Hz, 2H) 7.28 (s, 1H) 7.40 (d, J=8.0 Hz, 1H) 8.30 (d, J=8.0 Hz, 1H)

Example 283c

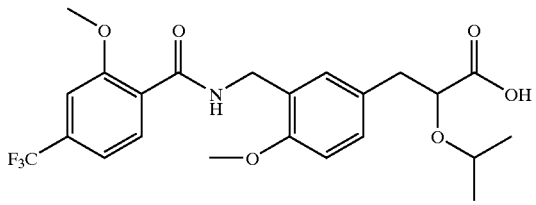

Using 2-ethoxy-4-(trifluoromethyl)benzoic acid and 3-[3-([(tert-butoxycarbonyl)amino]methyl)-4-methoxyphenyl]-2-isopropoxypropanoate, 3-(3-[(2-ethoxy-4-(trifluoromethyl)benzoyl]aminomethyl)-4-methoxyphenyl]-2-isopropoxypropanoic acid was obtained in the same method as in Example 38).

MS m/e (ESI) 484 (MH$^+$)

Example 284

Production Example 284a

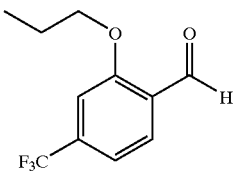

Using 2-hydroxy-4-(trifluoromethyl)benzaldehyde and propyl iodide, 2-propoxy-4-(trifluoromethyl)benzaldehyde was obtained in the same method as in Production Example 283a).

$^1$H-NMR(CDCl$_3$) δ: 1.11 (t, J=7.2 Hz, 3H) 1.88–1.96 (m, 2H) 4.10 (t, J=7.2 Hz, 2H) 7.22(s, 1H) 7.29(d, J=8.0 Hz, 1H) 7.93 (d, J=8.0 Hz, 1H) 10.50 (s, 1H)

Production Example 284b

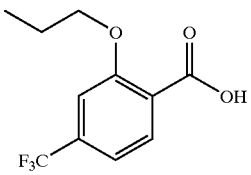

Using 2-propoxy-4-(trifluoromethyl)benzaldehyde, 2-propoxy-4-(trifluoromethyl)benzoic acid was obtained in the same method as in Production Example 283b).

$^1$H-NMR(CDCl$_3$) δ: 1.15 (t, J=7.2 Hz, 3H) 1.94–2.04 (m, 2H) 4.30 (t, J=7.2 Hz, 2H) 7.28 (s, 1H) 7.40 (d, J=8.0 Hz, 1H) 8.30 (d, J=8.0 Hz, 1H)

Example 284c

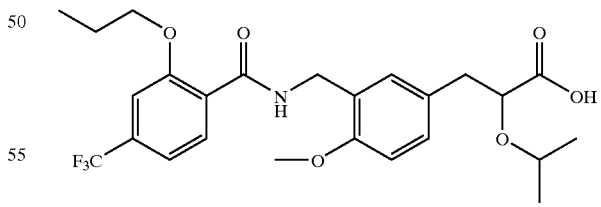

Using 2-propoxy-4-(trifluoromethyl)benzoic acid and 3-[3-([(tert-butoxycarbonyl)amino]methyl)-4-methoxyphenyl]-2-isopropoxypropanoate, 2-isopropoxy-3-[4-methoxy-3-([2-propoxy-4-(trifluoromethyl)benzoyl] aminomethyl)phenyl]propanoic acid was obtained in the same method as in Example 38).

MS m/e (ESI) 498(MH$^+$)

Example 285

Production Example 285a

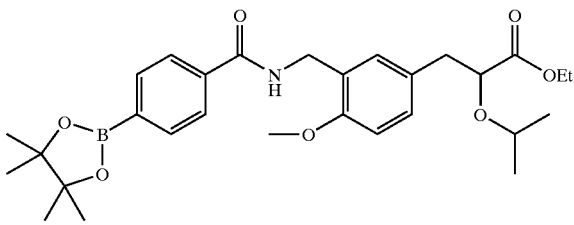

Using 4-bromobenzoic acid and ethyl 3-[3-(aminomethyl)-4-methoxyphenyl]-2-isopropoxypropanoate, ethyl 3-[3-([4-bromobenzoyl]amino)methyl]-4-methoxyphenyl)-2-isopropoxypropanoate was obtained in the same method as in Example 19d). Then, 1.1 g of the resulting ethyl 3-[3-([4-bromobenzoyl]amino)methyl]-4-methoxyphenyl)-2-isopropoxypropanoate, 0.64 g of bis(pinacolate)diboron, 56 mg of 1,1-bis(diphenylphosphino)ferrocene dichloropalladium and 0.68 g of potassium acetate were dissolved in 20 ml dimethyl sulfoxide, followed by stirring at 80° C. for 1 hour in a nitrogen atmosphere. After cooling the reaction solution to room temperature, ethyl acetate and water were added thereto. The mixture was filtered through Celite, and the mother liquor was extracted with ethyl acetate. The organic layer was washed with brine, dried over anhydrous magnesium sulfate and the solvent was evaporated. The residue was subjected to silica gel column chromatography, and from fractions eluted with hexane-ethyl acetate (1:1), 1.23 g of 2-isopropoxy-3-[4-methoxy-3-([4-(4,4,5,5-tetramethyl-1,3,2-dioxaborolane-2-yl)benzoyl]aminomethyl)phenyl]propanoate was obtained.

$^1$H-NMR(CDCl$_3$) δ: 0.96 (t, J=6.4 Hz, 3H) 1.14 (d, J=6.4 Hz, 3H) 1.21–1.27 (m, 3H) 1.35 (s, 12H) 2.88 (dd, J=8.4, 14.0 Hz, 1H) 2.94 (dd, J=4.8, 14.0 Hz, 1H) 3.50 (sept, J=6.4 Hz, 1H) 3.86 (s, 3H) 4.02 (dd, J=4.8, 8.4 Hz, 1H) 4.14–4.19 (m, 2H) 4.62 (d, J=5.6 Hz, 2H) 6.65–6.70 (m, 1H) 6.81 (d, J=8.4 Hz, 1H) 7.16 (dd, J=2.4, 8.4 Hz, 1H) 7.22 (d, J=2.4 Hz, 1H) 7.73 (d, J=8.0 Hz, 2H) 7.85 (d, J=8.0 Hz, 2H)

Example 285b

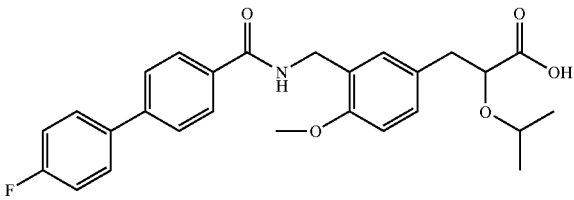

53 mg of ethyl 2-isopropoxy-3-[4-methoxy-3-([4-(4,4,5,5-tetramethyl-1,3,2-dioxaborolane-2-yl)benzoyl]aminomethyl)phenyl]propanoate, 21 mg of 4-bromofluorobenzene, 5.7 mg of 1,1-bis(diphenylphosphino)ferrocene dichloropalladium and 55 mg of potassium carbonate were dissolved in 1.5 ml dimethoxyethane, followed by stirring at 80° C. for 2 hours in a nitrogen atmosphere. After cooling the reaction solution to room temperature, it was filtered through Celite, and the mother liquor was evaporated. The residue was dissolved in 2 ml ethanol, and then 1 ml of 1 N sodium hydroxide was added, and the mixture was stirred at room temperature for 6 hours. The reaction solution was neutralized with 1N hydrochloric acid and extracted with ethyl acetate. The organic layer was concentrated and purified by HPLC on a reverse phase column in a water-acetonitrile-trifluoroacetic acid system as the eluting solvent, to give 19 mg of 2-isopropoxy-3-4-[methoxy-3-[(4-(4'-fluorophenyl)benzoyl]amino)methylphenyl]propanoic acid.

MS m/e (ESI) 466(MH$^+$)

Example 286

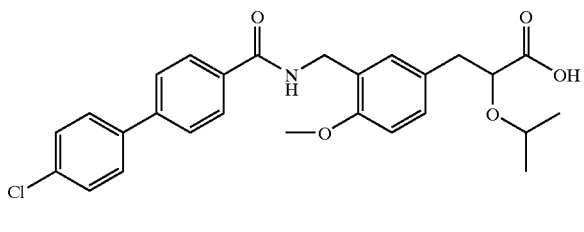

Using ethyl 2-isopropoxy-3-[4-methoxy-3-([4-(4,4,5,5-tetramethyl-1,3,2-dioxaborolane-2-yl)benzoyl]aminomethyl)phenyl]propanoate and 4-bromochlorobenzene, 2-isopropoxy-3-4-[methoxy-3-[(4-(4'-chlorophenyl)benzoyl]amino)methylphenyl]propanoic acid was obtained in the same method as in Example 285).

MS m/e (ESI) 482(MH$^+$)

Example 287

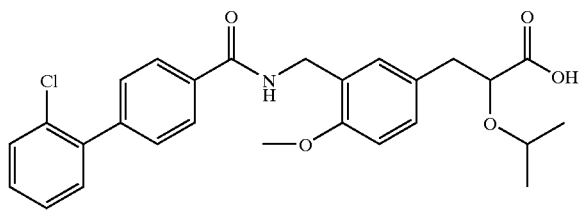

Using ethyl 2-isopropoxy-3-[4-methoxy-3-([4-(4,4,5,5-tetramethyl-1,3,2-dioxaborolane-2-yl)benzoyl]aminomethyl)phenyl]propanoate and 2-bromochlorobenzene, 2-isopropoxy-3-4-(methoxy-3-[(4-(2'-chlorophenyl)benzoyl]amino)methylphenyl]propanoic acid was obtained in the same method as in Example 285).

MS m/e (ESI) 482(MH$^+$)

Example 288

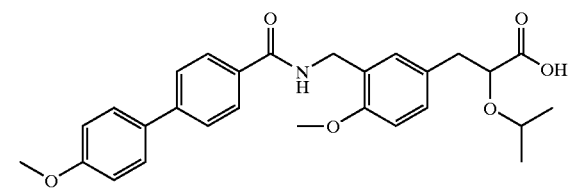

Using ethyl 2-isopropoxy-3-[4-methoxy-3-([4-(4,4,5,5-tetramethyl-1,3,2-dioxaborolane-2-yl)benzoyl]aminomethyl)phenyl]propanoate and 4-bromoanisole, 2-isopropoxy-3-4-[methoxy-3-[(4-(4'-methoxyphenyl)benzoyl]amino)methylphenyl]propanoic acid was obtained in the same method as in Example 285).

MS m/e (ESI) 478(MH$^+$)

Example 289

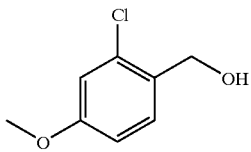

Using ethyl 2-isopropoxy-3-[4-methoxy-3-([4-(4,4,5,5-tetramethyl-1,3,2-dioxaborolane-2-yl)benzoyl]aminomethyl)phenyl]propanoate and 4-bromobenzotrifluoride, 2-isopropoxy-3-4-(methoxy-3-[(4-[4'-(trifluoromethyl)phenyl]benzoyl)amino]methylphenyl)propanoic acid was obtained in the same method as in Example 285).

MS m/e (ESI) 516(MH+)

Example 290

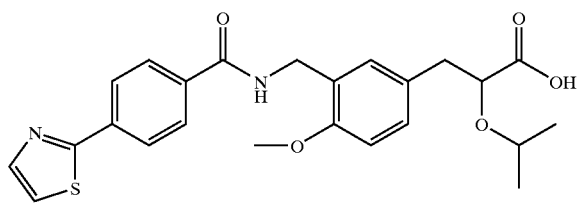

Using ethyl 2-isopropoxy-3-[4-methoxy-3-([4-(4,4,5,5-tetramethyl-1,3,2-dioxaborolane-2-yl)benzoyl]amino)methyl)phenyl]propanoate and 2-bromothiazole, 2-isopropoxy-3-[4-methoxy-3-[(4-(1,3-thiazole-2-yl)benzoyl]amino)methyl]phenyl]propanoic acid was obtained in the same method as in Example 285).

MS m/e (ESI) 455(MH+)

Example 291

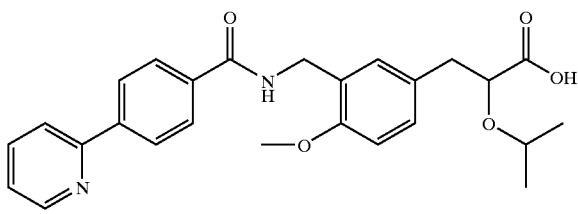

Using ethyl 2-isopropoxy-3-[4-methoxy-3-([4-(4,4,5,5-tetramethyl-1,3,2-dioxaborolane-2-yl)benzoyl]aminomethyl)phenyl]propanoate and 2-bromopyridine, 2-isopropoxy-3-[4-methoxy-3-[([4-(2-pyridyl)benzoyl]amino)methyl]phenyl)propanoic acid was obtained in the same method as in Example 285).

MS m/e (ESI) 449(MH+)

Example 292

Production Example 292a

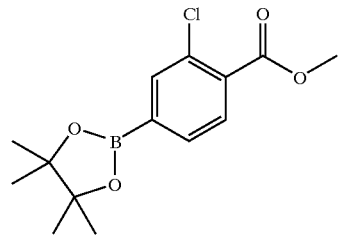

Using 1.0 g of 4-bromo-2-chlorobenzoic acid, 0.91 g of methyl 2-chloro-4-(4,4,5,5-tetramethyl-1,3,2-dioxaborolane-2-yl)benzoate was obtained in the same method as in Production Example 277a) and then in Production Example 285).

$^1$H-NMR(CDCl$_3$) δ: 1.25(s, 6H) 1.36 (s, 6H) 1.14 (d, J=6.4 Hz, 3H) 3.94 (s, 3H) 7.70 (d, J=8.0 Hz, 1H) 7.79 (d, J=8.0 Hz, 1H) 7.84 (s, 1H)

Production Example 292b

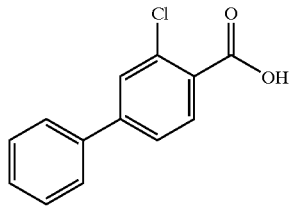

0.30 g of methyl 2-chloro-4-(4,4,5,5-tetramethyl-1,3,2-dioxaborolane-2-yl)benzoate, 0.19 g of bromobenzene, 57mg of 1,1-bis(diphenylphosphino)ferrocene dichloropalladium and 0.55 g of potassium carbonate were dissolved in 15 ml dimethoxyethane, and the mixture was heated under reflux for 1 hour. After cooling the reaction solution to room temperature, ethyl acetate and water were added thereto. The mixture was filtered through Celite, and the mother liquor was extracted with ethyl acetate. The organic layer was washed with brine, dried over anhydrous magnesium sulfate and the solvent was evaporated. The residue was subjected to silica gel column chromatography, and from fractions eluted with hexane-ethyl acetate (5:1), methyl 2-chloro-4-phenylbenzoate was obtained. Then, the resulting methyl 2-chloro-4-phenylbenzoate was dissolved in 4 ml methanol, and 2 ml of 1N sodium hydroxide was added, and the mixture was stirred at room temperature for 6 hours. The reaction mixture was ice-cooled and neutralized with 1N hydrochloric acid, followed by extracting with ethyl acetate. The organic layer was washed with brine, dried over anhydrous sodium sulfate and the solvent was evaporated, to give 0.12 g of 2-chloro-4-phenylbenzoic acid.

$^1$H-NMR(CDCl$_3$) δ: 7.44–7.52 (m, 3H) 7.56–7.63 (m, 3H) 7.73 (d, J=1.6 Hz, 3H) 8.05 (d, J=8.0 Hz, 1H)

Example 292c

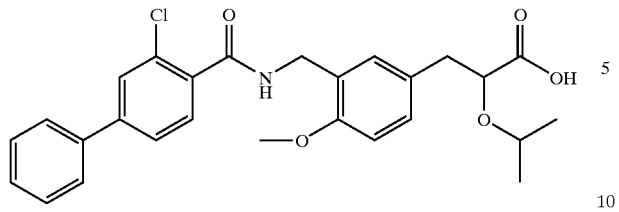

Using 2-chloro-4-phenylbenzoic acid and ethyl 3-[3-([(tert-butoxycarbonyl)amino]methyl)-4-methoxyphenyl]-2-isopropoxypropanoate, 3-(3-[(2-chloro-4-phenylbenzoyl)amino]methyl-4-methoxyphenyl)-2-isopropoxypropanoic acid was obtained in the same method as in Example 38).

MS m/e (ESI) 482(MH$^+$)

Example 293

Production Example 293a

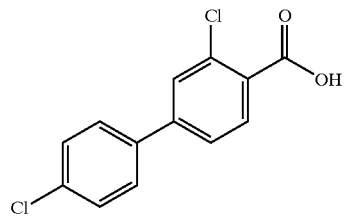

Using methyl 2-chloro-4-(4,4,5,5-tetramethyl-1,3,2-dioxaborolane-2-yl)benzoate and 4-bromochlorobenzene, 2-chloro-4-(4'-chlorophenyl)benzoic acid was obtained in the same method as in Production Example 292b).

$^1$H-NMR(DMSO-d$_6$) δ: 7.54(d,J=8.8 Hz,2H) 7.72(dd,J=1.6,8.0 Hz,2H) 7.78 (d, J=8.8 Hz, 2H) 7.84 (d, J=1.6 Hz, 2H) 7.87 (d, J=8.0 Hz,1H)

Example 293b

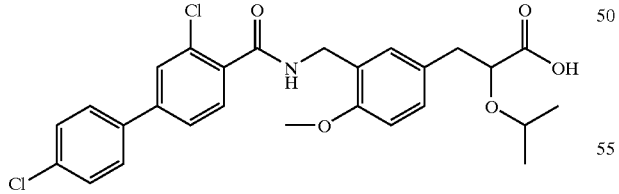

Using 2-chloro-4-(4'-chlorophenyl)benzoic acid and ethyl 3-[3-([(tert-butoxycarbonyl)amino]methyl)-4-methoxyphenyl]-2-isopropoxypropanoate, 3-(3-[2-chloro-4-(4'-chlorophenyl)benzoyl]aminomethyl)-4-methoxyphenyl]-2-isopropoxypropanoic acid was obtained in the same method as in Example 38).

MS m/e (ESI) 516(MH$^+$)

Example 294

Production Example 294a

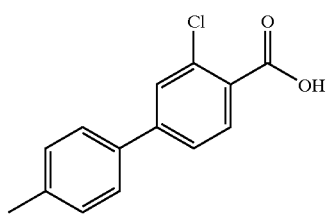

Using methyl 2-chloro-4-(4,4,5,5-tetramethyl-1,3,2-dioxaborolane-2-yl)benzoate and 4-bromotoluene, 2-chloro-6-4-(4'-methylphenyl)benzoic acid was obtained in the same method as in Production Example 292b).

$^1$H-NMR(CDCl$_3$) δ: 2.42 (s, 3H) 7.29 (d, J=8.0 Hz, 2H) 7.52 (d, J=8.0 Hz, 2H) 7.56 (dd, J=1.6, 8.4 Hz, 1H) 7.71 (d, J=1.6 Hz, 1H) 8.09 (d, J=8.4 Hz, 1H)

Example 294b

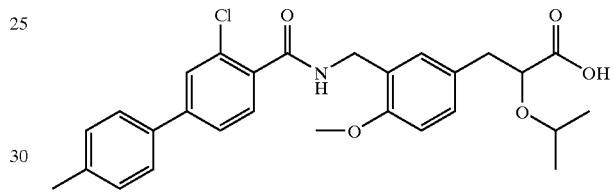

Using 2-chloro-4-(4'-methylphenyl)benzoic acid and ethyl 3-[3-([(tert-butoxycarbonyl)amino]methyl)-4-methoxyphenyl]-2-isopropoxypropanoate, 3-(3-[2-chloro-4-(4'-methylphenyl)benzoyl]aminomethyl)-4-methoxyphenyl]-2-isopropoxypropanoic acid was obtained in the same method as in Example 38).

MS m/e (ESI) 496(MH$^+$)

Example 295

Production Example 295a

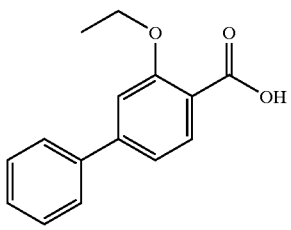

0.50 g of ethyl 4-chloro-2-ethoxybenzoate, 0.31 g of phenylboric acid, 85 mg of 1,1-bis(diphenylphosphino)ferrocene dichloronickel and 1.4 g of potassium phosphate were dissolved in 8 ml dioxane, followed by stirring at 95° C. for 1 hour in a nitrogen atmosphere. After cooling the reaction solution to room temperature, ethyl acetate and water were added thereto. The mixture was filtered through Celite, and the mother liquor was extracted with ethyl acetate. The organic layer was washed with brine, dried over anhydrous magnesium sulfate and the solvent was evaporated. The residue was subjected to silica gel column chromatography, and from fractions eluted with hexane-ethyl acetate (9:1), ethyl 2-ethoxy-4-phenylbenzoate was obtained. Then, the resulting ethyl 2-ethoxy-4-phenylbenzoate was dissolved in 4 ml ethanol, and 2 ml of 1N sodium hydroxide was added thereto, followed by stirring at room temperature for 6 hours. The reaction mixture was ice-cooled and neutralized with 1N hydrochloric acid, followed by extracting with ethyl acetate. The organic layer was washed with brine, dried over anhydrous sodium sulfate and the solvent was evaporated, to give 0.22 g of 2-ethoxy-4-phenylbenzoic acid.

$^1$H-NMR(CDCl$_3$) δ: 1.61 (t, J=7.2 Hz, 3H) 4.42 (q, J=7.2 Hz, 2H) 7.21 (d, J=1.6 Hz, 1H) 7.36 (dd, J=1.6, 8.4 Hz, 1H) 7.43–7.51 (m, 3H) 7.59–7.61 (m, 1H) 8.25 (d, J=8.4 Hz, 1H)

Example 295b

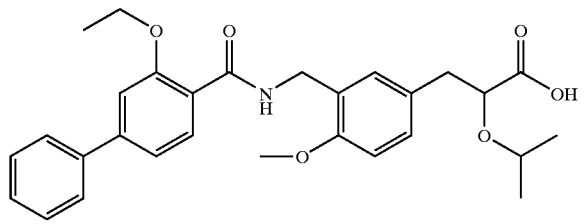

Using 2-ethoxy-4-phenylbenzoic acid and ethyl 3-[3-([(tert-butoxycarbonyl)amino]methyl)-4-methoxyphenyl]-2-isopropoxypropanoate, 3-(3-[(2-chloro-4-phenylbenzoyl)amino]methyl-4-methoxyphenyl)-2-isopropoxypropanoic acid was obtained in the same method as in Example 38).

MS m/e (ESI) 492(MH$^+$)

Example 296

Production Example 296a

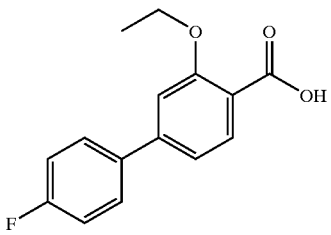

Using ethyl 4-chloro-2-ethoxybenzoate and 4-fluorobenzeneboric acid, 2-ethoxy-4-(4'-fluorophenyl) benzoic acid was obtained in the same method as in Production Example 295).

$^1$H-NMR(CDCl$_3$) δ: 1.61 (t, J=7.2 Hz, 3H) 4.42 (q, J=7.2 Hz, 2H) 7.15–7.20 (m, 3H) 7.30 (dd, J=1.6, 8.0 Hz, 1H) 7.55–7.59 (m, 2H) 8.24 (d, J=8.0 Hz, 1H)

Example 296b

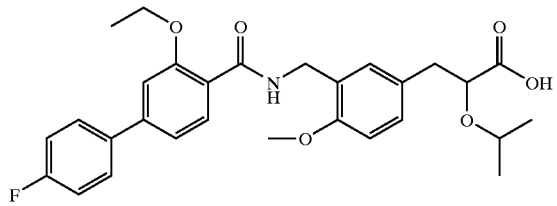

Using 2-ethoxy-4-(4'-fluorophenyl)benzoic acid and ethyl 3-[3-([(tert-butoxycarbonyl)amino]methyl)-4-methoxyphenyl]-2-isopropoxypropanoate, 3-(3-[2-ethoxy-4-(4'-fluorophenyl)benzoyl]aminomethyl)-4-methoxyphenyl]-2-isopropoxypropanoic acid was obtained in the same method as in Example 38 ).

MS m/e (ESI) 510(MH$^+$)

Example 297

Production Example 297a

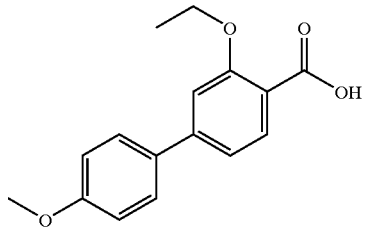

Using ethyl 4-chloro-2-ethoxybenzoate and 4-methoxybenzeneboric acid, 2-ethoxy-4-(4'-methoxyphenyl)benzoic acid was obtained in the same method as in Production Example 295.

$^1$H-NMR(CDCl$_3$) δ: 1.61 (t, J=7.2 Hz, 3H) 3.87 (s, 3H) 4.41 (q, J=7.2 Hz, 2H) 7.01 (d, J=8.0 Hz, 2H) 7.17 (d, J=1.6 Hz, 1H) 7.31 (dd, J=1.6, 8.4 Hz, 1H) 7.55 (d, J=8.0 Hz, 2H) 8.22 (d, J=8.4 Hz, 1H)

Example 297b

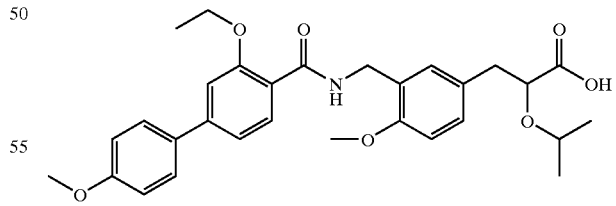

Using 2-ethoxy-4-(4'-methoxyphenyl)benzoic acid and ethyl 3-[3-([(tert-butoxycarbonyl)amino]methyl)-4-methoxyphenyl]-2-isopropoxypropanoate, 3-(3-[2-ethoxy-4-(4'-methoxyphenyl)benzoyl]aminomethyl)-4-methoxyphenyl]-2-isopropoxypropanoic acid was obtained in the same method as in Example 38.

MS m/e (ESI) 522(MH$^+$)

Example 298

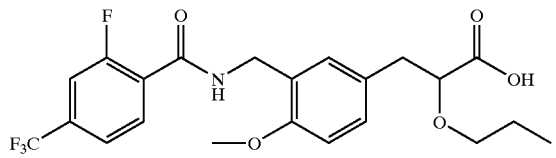

3-[3-([2-Fluoro-4-(trifluoromethyl)benzoyl]
aminomethyl)-4-methoxyphenyl]-2-propoxypropanoic acid
was obtained in the same method as in Example 218.

$^1$H-NMR(CDCl$_3$) δ: 0.86 (t, J=7.2 Hz, 3H) 1.51–1.61 (m, 2H) 2.97 (dd, J=8.0, 14.0 Hz, 1H) 3.07 (dd, J=4.4, 14.0 Hz, 1H) 3.35 (dt, J=6.4, 8.8 Hz, 1H) 3.50 (dt, J=6.4, 8.8 Hz, 1H) 3.89 (s, 3H) 4.04 (dd, J=4.4, 8.0 Hz, 1H) 4.64 (d, J=6.0 Hz, 2H) 6.82 (d, J=8.0 Hz, 1H) 7.17 (dd, J=2.0, 8.0 Hz, 1H) 7.22 (d, J=2.0 Hz, 1H) 7.38 (d, J=12.0 Hz, 1H) 7.37–7.45 (m, 1H) 7.52 (d, J=8.0 Hz, 1H) 8.23 (t, J=8.0 Hz, 1H)

Example 299

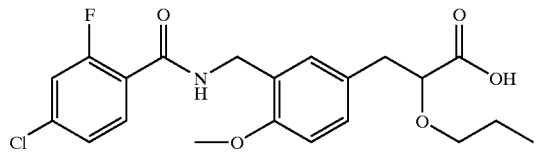

3-(3-[(4-Chloro-2-fluorobenzoyl)amino]methyl-4-methoxyphenyl)-2-propoxypropanoic acid was obtained in the same method as in Example 218.

MS m/e (ESI) 424(MH$^+$)

Example 300

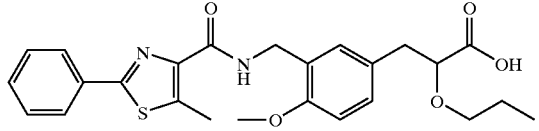

3-[4-Methoxy-3-([(5-methyl-2-phenyl-1,3-thiazole-4-yl)carbonyl]aminomethyl)phenyl]-2-propoxypropanoic acid was obtained in the same method as in Example 218.

MS m/e (ESI) 469(MH$^+$)

Example 301

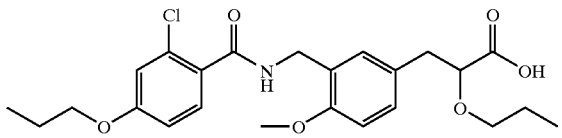

3-(3-[(2-Chloro-4-propoxy)amino]methyl-4-methoxyphenyl)-2-propoxypropanoic acid was obtained in the same method as in Example 218.

MS m/e (ESI) 464(MH$^+$)

Example 302

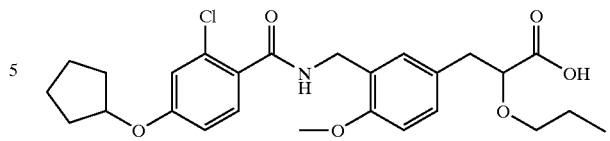

3-[3-([2-Chloro-4-(cyclopentyloxy)benzoyl]
aminomethyl)-4-methoxyphenyl]-2-propoxypropanoic acid was obtained in the same method as in Example 218.

MS m/e (ESI) 490(MH$^+$)

Example 303

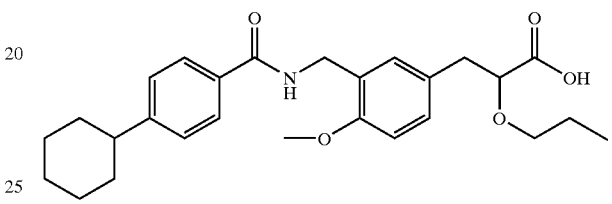

3-(3-[(4-Cyclohexylbenzoyl)amino]methyl-4-methoxyphenyl)-2-propoxypropanoic acid was obtained in the same method as in Example 218.

MS m/e (ESI) 454(MH$^+$)

Example 304

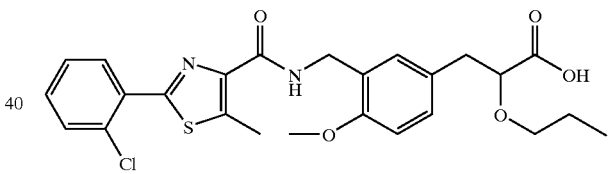

3-3-[([2-(2-Chlorophenyl)-5-methyl-1,3-thiazole-4-yl]carbonylamino)methyl]-4-methoxyphenyl-2-propoxypropanoic acid was obtained in the same method as in Example 218.

MS m/e (ESI) 503(MH$^+$)

Example 305

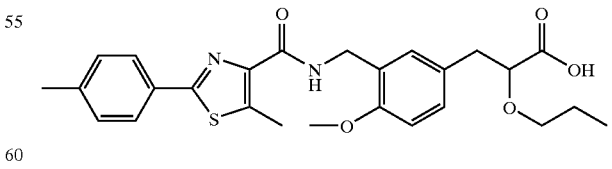

3-4-Methoxy-3-[([5-methyl-2-(4-methylphenyl)-1,3-thiazole-4-yl]carbonylamino)methyl phenyl-2-propoxypropanoic acid was obtained in the same method as in Example 218.

MS m/e (ESI) 483(MH$^+$)

Example 306

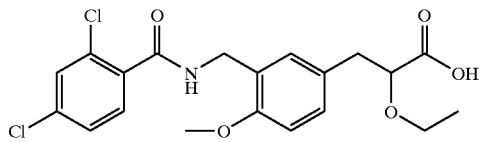

3-(3-[(2,4-Dichlorobenzoyl)amino]methyl-4-methoxyphenyl)-2-ethoxypropanoic acid was obtained in the same method as in Example 218.

MS m/e (ESI) 426(MH$^+$)

Example 307

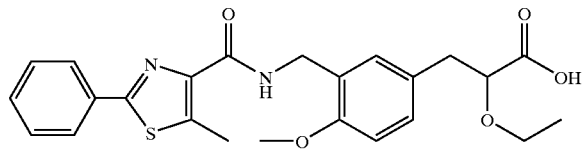

2-Ethoxy-3-[4-methoxy-3-([(5-methyl-2-phenyl-1,3-thiazole-4-yl)carbonyl]aminomethyl)phenyl]propanoic acid was obtained in the same method as in Example 218.

MS m/e (ESI) 455(MH$^+$)

Example 308

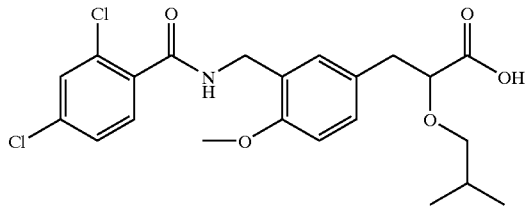

3-(3-[(2,4-Dichlorobenzoyl)amino]methyl-4-methoxyphenyl)-2-isobutoxypropanoic acid was obtained in the same method as in Example 218.

MS m/e (ESI) 454(MH$^+$)

Example 309

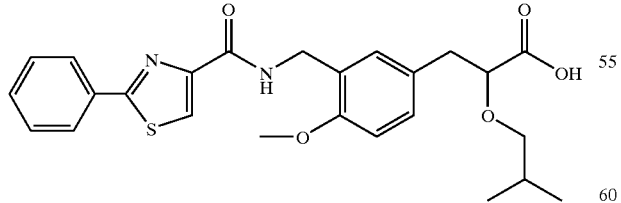

2-Isobutoxy-3-[4-methoxy-3-([(5-methyl-2-phenyl-1,3-thiazole-4-yl)carbonyl]aminomethyl)phenyl]propanoic acid was obtained in the same method as in Example 218.

MS m/e (ESI) 483(MH$^+$)

Example 310

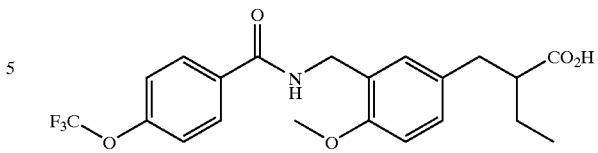

2-(4-Methoxy-3-([(4-(trifluoromethoxy)benzoyl]aminomethyl)benzyl]butanoic acid was obtained by treatment in the same manner as in Examples 1d) and 1e).

δ: 0.94 (t, J=7.2 Hz, 3H) 1.51–1.71 (m, 2H) 2.51–2.58 (m, 1H) 2.70 (dd, J=5.8, 14.0 Hz, 1H) 2.88 (dd, J=8.4, 14.0 Hz, 1H) 3.84 (s, 3H) 4.57 (d, J=5.6 Hz, 2H) 6.75 (t, J=5.6 Hz, 1H) 6.80 (d, J=8.4 Hz, 1H) 7.09(dd, J=2.0, 8.4 Hz, 1H) 7.15(d, J=2.0 Hz, 1H) 7.23(d, 8.4 Hz, 2H) 7.79(dt, J=2.0, 8.4 Hz, 2H)

Example 311

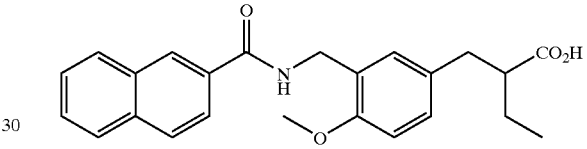

2-(4-Methoxy-3-[(2-naphthylcarbonyl)amino]methylbenzyl)butanoic acid was obtained by treatment in the same method as in Examples 1d) and 1e).

$^1$H-NMR(CDCl$_3$) δ: 0.96 (t, J=7.2 Hz, 3H) 2.53–2.62 (m, 1H) 2.73 (dd, J=5.8, 14.0 Hz, 1H) 2.89 (dd, J=8.6, 14.0 Hz, 1H) 2.89 (dd, J=8.6, 14.0 Hz, 1H) 3.87 (s, 3H) 4.64 (d, J=6.0 Hz, 2H) 6.82 (d, J=8.4 Hz, 1H) 6.85 (t, J=6.0 Hz, 1H) 7.10 (dd, 2.2, 8.4 Hz, 1H) 7.22 (d, J=2.2 Hz, 1H), 7.4–7.58 (m, 2H) 7.78–7.94 (m, 4H) 8.27 (s, 1H)

Example 312

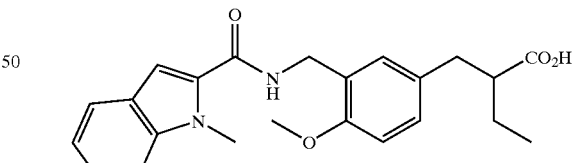

2-[4-Methoxy-3-([(1-methyl-1H-2-indolyl)carbonyl]aminomethyl)benzyl)butanoic acid was obtained by treatment in the same method as in Examples 1d) and 1e).

$^1$H-NMR(CDCl$_3$) δ: 0.95 (t, J=7.2 Hz, 3H) 1.51–1.62 (m, 2H) 2.53–2.62 (m, 1H) 2.72 (dd, J=6.4, 14.0 Hz, 1H) 2.89 (dd, J=4.4, 14.0 Hz, 1H) 3.86 (s, 3H) 4.04 (s, 3H) 4.57 (d, J=5.6 Hz, 2H) 6.77 (t, J=5.6 Hz, 1H) 6.79–6.83 (m, 2H) 7.06–7.18 (m, 3H) 7.27–7.33 (m, 1H) 7.37 (d, J=8.4 Hz, 1H) 7.61 (d, J=8.0 Hz, 1H)

Example 313

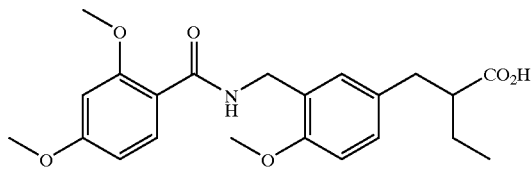

2-(3-[(2,4-Dimethoxybenzoyl)amino]-methyl-4-methoxybenzyl)butanoic acid was obtained by treatment in the same method as in Examples 1d) and 1e).

$^1$H-NMR(CDCl$_3$) δ: 0.94 (t, J=7.2 Hz, 3H) 1.50–1.71 (m, 2H) 2.49–2.58 (m, 1H) 2.70 (dd, J=6.0, 14.0 Hz, 1H) 2.86 (dd, J=4.4, 14.0 Hz, 1H) 3.84 (s, 3H) 3.86 (s, 3H) 3.90 (s, 3H) 4.59 (d, J=6.0 Hz, 1H) 4.60 (d, J=6.0 Hz, 1H) 6.46 (d, J=2.4 Hz, 1H) 6.58 (dd, J=2.4, 8.8 Hz, 1H) 6.78 (d, J=8.4 Hz, 1H) 7.05 (dd, J=2.4, 8.4 Hz, 1H) 7.17 (d, J=2.4 Hz, 1H) 8.16 (d, J=8.8 Hz, 1H) 8.35 (t, J=6.0 Hz, 1H)

Example 314

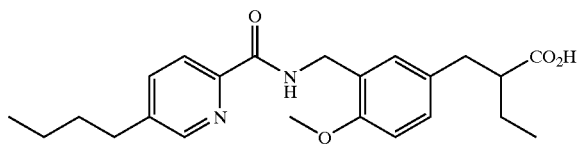

2-[3-([(5-Butyl-2-pyridyl)carbonyl]aminomethyl)-4-methoxybenzyl]butanoic acid was obtained by treatment in the same method as in Examples 1d) and 1e).

$^1$H-NMR(CDCl$_3$) δ: 0.90–1.00 (m, 6H) 1.30–1.42 (m, 2H) 1.50–1.71 (m, 4H) 2.50–2.59 (m, 1H) 2.65 (t, J=8.0 Hz, 2H) 2.70 (dd, J=6.4, 14.0 Hz, 1H) 2.86 (dd, J=8.4, 14.0 Hz, 1H) 3.86 (s, 3H) 4.61 (d, J=6.4 Hz, 2H) 6.78 (d, J=8.4 Hz, 1H) 7.06 (dd, J=2.4, 8.4 Hz, 1H) 7.17 (d, J=2.4 Hz, 1H) 7.62 (dd, J=2.0, 8.0 Hz, 1H) 8.10 (d, J=8.0 Hz, 1H) 8.35 (d, J=2.0 Hz, 1H) 8.42(t, J=6.4 Hz, 1H)

Example 315

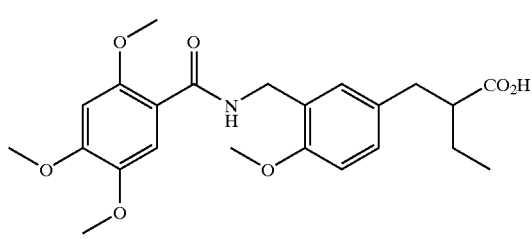

2-(4-Methoxy-3-[(2,4,5-trimethoxybenzoyl)amino]methylbenzyl)butanoic acid was obtained by treatment in the same method as in Examples 1d) and 1e)

$^1$H-NMR(CDCl$_3$) δ: 0.93 (t, J=7.6 Hz, 3H) 1.50–1.70 (m, 2H) 2.50–2.58 (m, 1H) 2.69 (dd, J=6.0, 13.6 Hz, 1H) 2.88 (dd, J=8.4, 13.6 Hz, 1H) 3.86 (s, 3H) 3.88 (s, 3H) 3.91 (s, 3H) 3.92 (s, 3H) 4.60 (d, J=6.0 Hz, 2H) 6.49 (s, 1H) 6.78 (d, J=8.0 Hz, 1H) 7.06 (dd, J=2.0, 8.0 Hz, 1H) 7.17 (d, J=2.0 Hz, 1H) 7.75 (s, 1H) 8.45 (t, J=6.0 Hz, 1H)

Example 316

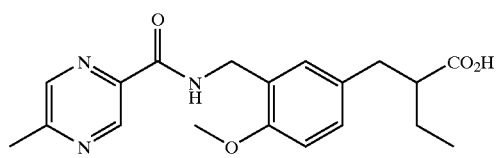

2-(3-[(2,4-Dimethoxybenzoylamino]methyl-4-methoxybenzyl)butanoic acid was obtained by treatment in the same method as in Examples 1d) and 1e).

$^1$H-NMR(CDCl$_3$) δ: 0.94 (t, J=7.2 Hz, 3H) 1.50–1.71 (m, 2H) 2.31 (s, 3H) 2.36 (s, 3H) 2.50–2.59 (m, 1H) 2.70 (dd, J=6.6, 14.0 Hz, 1H) 2.88 (dd, J=8.4, 14.0 Hz, 1H) 3.81 (s, 3H) 4.54 (d, J=6.0 Hz, 1H) 4.55 (d, J=6.0 Hz, 1H) 6.29(t, J=6.0 Hz, 1H) 6.78(d, J=8.6 Hz, 1H) 6.98(d, J=7.6 Hz, 1H) 7.00(s, 1H) 7.08(dd, J=2.0, 8.6 Hz, 1H) 7.18(d, J=2.0 Hz, 1H) 7.24 (d, J=7.6 Hz, 1H)

Example 317

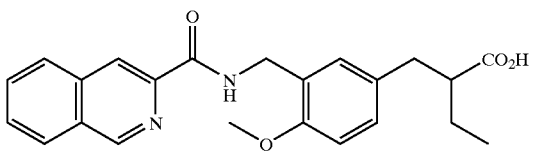

2-[4-Methoxy-3-([(5-methyl-2-pyrazinyl)carbonyl)aminomethyl)benzyl)butanoic acid was obtained by treatment in the same method as in Examples 1d) and 1e).

$^1$H-NMR(CDCl$_3$) δ: 0.94 (t, J=7.2 Hz, 3H) 1.50–1.70 (m, 2H) 2.50–2.58 (m, 1H) 2.69 (dd, J=6.8, 14.0 Hz, 1H) 2.88 (dd, J=8.4, 14.0 Hz, 1H) 3.85 (s, 3H) 4.61 (d, J=6.0 Hz, 2H) 6.79 (d, J=8.4 Hz, 1H) 7.08 (dd, J=2.0, 8.4 Hz, 1H) 7.15 (d, J=2.0 Hz, 1H) 8.21 (t, J=6.0 Hz, 1H) 8.36 (s, 1H) 9.26 (s, 1H)

Example 318

2-(4-Methoxy-3-[(2-quinolylcarbonyl)amino]methylbenzyl)butanoic acid was obtained by treatment in the same method as in Examples 1d) and 1e)

$^1$H-NMR (CDCl$_3$) δ: 0.93 (t, J=7.2 Hz, 3H) 1.50–1.70 (m, 2H) 2.51–2.60 (m, 1H) 2.70 (dd, J=6.4, 13.4 Hz, 1H) 2.89 (dd, J=8.6, 13.4 Hz, 1H) 3.87 (s, 3H) 4.68 (d, J=6.4 Hz, 2H) 6.80 (d, J=8.2 Hz, 1H) 7.07 (dd, J=2.2, 8.2 Hz, 1H) 7.21(d, J=2.2 Hz, 1H) 7.69(t, J=8.0 Hz, 1H) 7.76(t, J=8.0 Hz, 1H) 7.97(d, J=8.0 Hz, 1H) 8.01(d, J=8.0 Hz, 1H) 8.62(s, 1H) 8.67(t, J=6.4 Hz, 1H) 9.15(s, 1H)

Example 319

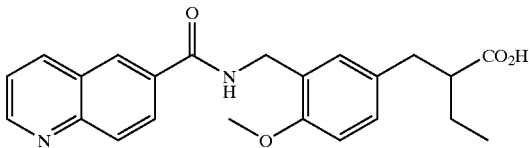

2-(4-Methoxy-3-[(6-quinolylcarbonyl)amino]methylbenzyl)butanoic acid was obtained by treatment in the same method as in Examples 1d) and 1e)

$^{1}$H-NMR(CDCl$_{3}$) δ: 0.91 (t, J=7.6 Hz, 3H) 1.47–1.70 (m, 2H) 2.47–2.56 (m, 1H) 2.69 (dd, J=6.0, 14.0 Hz, 1H) 2.84 (dd, J=8.8, 14.0 Hz, 1H) 3.79 (s, 3H) 4.57 (d, J=6.0 Hz, 2H) 6.75 (d, J=5.0 Hz, 1H) 6.84 (t, J=6.0 Hz, 1H) 7.05 (dd, J=2.0, 8.0 Hz, 1H) 7.17 (d, J=2.0 Hz, 1H) 7.34 (dd, J=4.4, 8.4 Hz, 1H) 7.88 (dd, J=2.0, 8.8 Hz, 1H) 7.96 (t, J=8.8 Hz, 1H) 8.06 (d, J=8.4 Hz, 1H) 8.10 (s, 1H) 8.86 (d, J=2.8 Hz, 1H)

Example 320

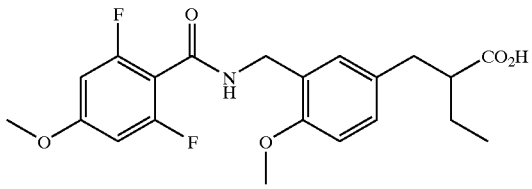

2-(3-[(2,6-Difluoro-4-methbxybenzoyl)amino]methyl-4-methoxybenzyl)butanoic acid was obtained.

$^{1}$H-NMR(CDCl$_{3}$) δ: 0.95(t, J=7.6 Hz, 3H) 1.53–1.71 (m, 2H) 2.52–2.59(m, 1H) 2.70(dd, J=6.6, 14.0 Hz, 1H) 2.88(dd, J=8.4, 14.0 Hz, 1H) 3.79(s, 3H) 3.83(s, 3H) 4.57(d, J=5.6 Hz, 1H) 4.57 (d, J=5.6 Hz, 1H) 6.44 (s, 1H) 6.46 (s, 1H) 6.78 (d, J=8.0 Hz, 1H) 7.07 (dd, J=2.0, 8.0 Hz, 1H) 7.17 (d, J=2.0 Hz, 1H)

Example 321

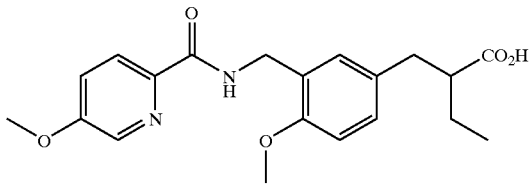

2-[4-Methoxy-3-([(5-methoxypyridyl-2-pyridyl)carbonyl]aminomethyl)benzyl]butanoic acid was obtained by treatment in the same method as in Examples 1d) and 1e).

$^{1}$H-NMR(CDCl$_{3}$) δ: 0.93 (t, J=7.2 Hz, 3H) 1.48–1.70 (m, 2H) 2.48–2.57 (m, 1H) 2.69 (dd, J=6.6, 13.6 Hz, 1H) 2.87 (dd, J=8.4, 13.6 Hz, 1H) 3.85 (s, 3H) 3.89 (s, 3H) 4.59 (d, J=6.0 Hz, 2H) 6.78 (d, J=8.0 Hz, 1H) 7.06 (dd, J=2.0, 8.0 Hz, 1H) 7.16 (d, J=2.0 Hz, 1H) 7.26 (dd, J=3.2, 8.4 Hz, 1H) 8.14 (d, J=8.4 Hz, 1H) 8.19 (d, J=3.2 Hz, 1H) 8.30 (t, J=6.0 Hz, 1H)

Example 322

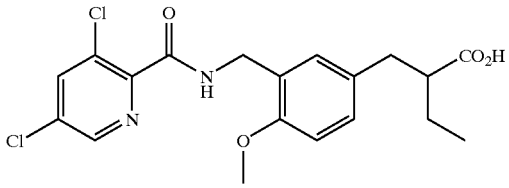

2-[3-([(3,5-Dichloro-2-pyridyl)carbonyl]aminomethyl)-4-methoxybenzyl]butanoic acid was obtained by treatment in the same method as in Examples 1d) and 1e).

$^{1}$H-NMR(CDCl$_{3}$) δ: 0.94(t, J=7.2 Hz, 3H) 1.51–1.70(m, 2H) 2.50–2.59(m, 1H) 2.69(dd, J=6.4, 13.6 Hz, 1H) 2.87(dd, J=8.4, 13.6 Hz, 1H) 3.85 (s, 3H) 4.57 (d, J=6.4 Hz, 2H) 6.78 (d, J=8.4 Hz, 1H) 7.07 (dd, J=2.2, 8.4 Hz, 1H) 7.16 (s, 1H) 7.82 (d, J=2.0 Hz, 1H) 8.09(t, J=6.4 Hz, 1H) 8.40(d, J=2.0 Hz, 1H)

Example 323

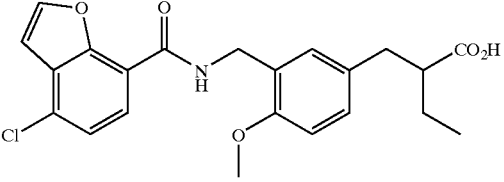

2-(3-([(4-Chlorobenzo[b]furan-7-yl)carbonyl]aminomethyl)-4-methoxybenzyl)butanoic acid was obtained by treatment in the same method as in Examples 1d) and 1e).

$^{1}$H-NMR(CDCl$_{3}$) δ: 0.94(t, J=7.2 Hz, 3H) 1.50–1.71 (m, 2H) 2.50–2.60 (m, 1H) 2.71(dd, J=6.0, 13.8 Hz, 1H) 2.87 (dd, J=8.8, 13.8 Hz, 1H) 3.89 (s, 3H) 4.69(d, J=6.0 Hz, 1H) 4.70 (d, J=6.0 Hz, 1H) 6.81 (d, J=8.4 Hz, 1H) 6.96 (d, J=2.0 Hz, 1H) 7.08 (dd, J=2.0, 8.4 Hz, 1H) 7.20 (d, J=2.0 Hz, 1H) 7.33 (d, J=8.0 Hz, 1H) 7.71 (d, J=2.0 Hz, 1H) 8.01 (t, J=6.0 Hz, 1H) 8.04 (d, J=8.0 Hz, 1H)

Example 324

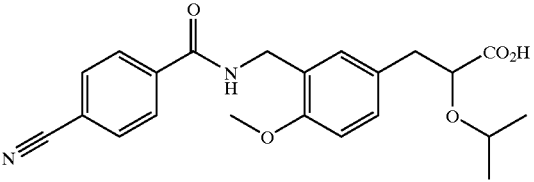

3-(3-[(4-Cyanobenzoyl)amino]methyl-4-methoxyphenyl)-2-isopropoxypropanoic acid was obtained by treatment in the same method as in Examples 1d) and 1e).

$^{1}$H-NMR(CDCl$_{3}$) δ: 1.04 (d, J=6.0 Hz, 3H) 1.16 (d, J=6.0 Hz, 3H) 2.92 (dd, J=7.2, 14.0 Hz, 1H) 3.03 (dd, J=4.4, 14.0 Hz, 1H) 3.59 (sept, J=6.0 Hz, 1H) 3.86(s, 3H) 4.11 (dd, J=4.4, 7.2 Hz, 1H) 4.60 (d, J=6.0 Hz, 2H) 6.77 (br, 1H) 6.82 (d, J=8.4 Hz, 1H) 7.16(dd, J=2.0, 8.4 Hz, 1H) 7.21 (d, J=2.0 Hz, 1H) 7.70(d, J=8.0 Hz, 2H) 7.84 (d, J=8.0 Hz, 2H)

Example 325

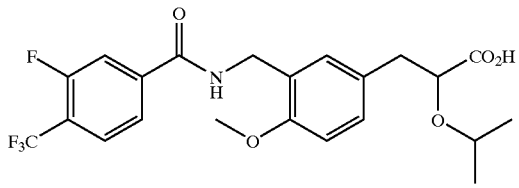

3-(3-([3-Fluoro-4-(trifluoromethyl)benzoyl]aminomethyl)-4-methoxyphenyl]-2-isopropoxypropanoic acid was obtained by treatment in the same method as in Examples 1d) and 1e).

$^1$H-NMR(CDCl$_3$) δ: 1.03(d, J=6.0 Hz, 3H) 1.16(d, J=6.0 Hz, 3H) 2.92(dd, J=7.4, 14.0 Hz, 1H) 3.03(dd, J=4.6, 14.0 Hz, 1H) 3.58 (sept, J=6.0 Hz, 1H) 3.87 (s, 3H) 4.11(dd, J=4.6, 7.4 Hz, 1H) 4.60(d, J=6.0 Hz, 2H) 6.75(br,1H) 6.83(d, J=8.4 Hz,1H) 7.17(dd,J=2.0,8.4 Hz, 1H) 7.21(d, J=2.0 Hz, 1H) 7.56–7.70(m, 3H)

Example 326

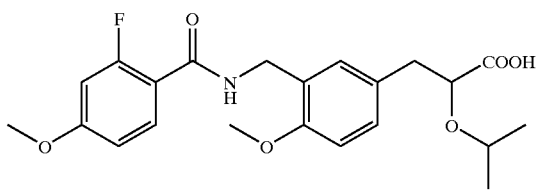

3-(3-[(2-Fluoro-4-methoxybenzoyl)amino]methyl-4-methoxyphenyl)-2-isopropoxypropanoic acid was obtained by treatment in the same method as in Examples 1d) and 1e).

$^1$H-NMR(CDCl$_3$) δ: 1.00 (d, J=6.0 Hz, 3H) 1.14 (d, J=6.0 Hz, 3H) 2.89 (dd, J=8.0, 14.0 Hz, 1H) 3.04 (dd, J=4.0, 14.0 Hz, 1H) 3.54 (sept, J=6.0 Hz, 1H) 3.83 (s, 3H) 3.86 (s, 3H) 4.09 (dd, J=4.0, 8.0 Hz, 1H) 4.62 (d, J=6.0 Hz, 2H) 6.59 (dd, J=2.4, 14.0 Hz, 1H) 6.77 (dd, J=2.4, 8.8 Hz, 1H) 6.81 (d, J=8.0 Hz, 1H) 7.13 (dd, J=2.0, 8.4 Hz, 1H) 7.21 (d, J=2.0 Hz, 1H) 7.27–7.36 (m, 1H) 8.05 (t, J=8.8 Hz, 1H)

Example 327

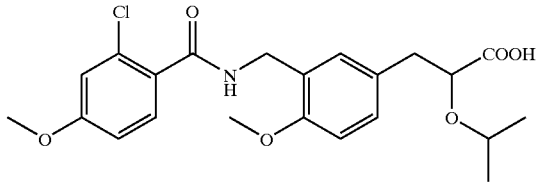

3-(3-[(2-Chloro-4-methoxybenzoyl)amino]methyl-4-methoxyphenyl)-2-isopropoxypropanoic acid was obtained by treatment in the same method as in Examples 1d) and 1e).

$^1$H-NMR(CDCl$_3$) δ: 1.02 (d, J=6.0 Hz, 3H) 1.15 (d, J=6.0 Hz, 3H) 2.90 (dd, J=7.6, 14.0 Hz, 1H) 3.05 (dd, J=4.4, 14.0 Hz, 1H) 3.56 (sept, J=6.0 Hz, 1H) 3.81 (s, 3H) 3.84 (s, 3H) 4.09 (dd, J=4.4, 7.6 Hz, 1H) 4.61 (d, J=5.6 Hz, 2H) 6.59 (dd, J=2.4, 14.0 Hz, 1H) 6.80 (d, J=8.4 Hz, 1H) 6.84 (dd, J=2.8, 8.8 Hz, 1H) 6.88 (d, J=2.8 Hz, 1H) 6.97 (t, J=5.6 Hz, 1H) 7.14 (dd, J=2.0, 8.4 Hz, 1H) 7.24 (d, J=2.0 Hz, 1H) 7.74 (d, J=8.8 Hz, 1H)

Example 328

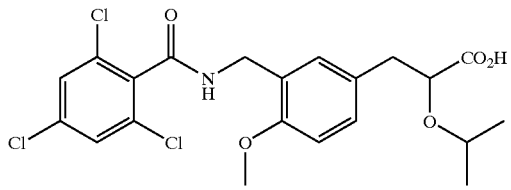

2-Isopropoxy-3-(4-methoxy-3-[(2,4,6-trichlorobenzoyl)amino]methylphenyl)propanoic acid was obtained by treatment in the same method as in Examples 1d) and 1e).

$^1$H-NMR(CDCl$_3$) δ: 1.04 (d, J=6.0 Hz, 3H) 1.16 (d, J=6.0 Hz, 3H) 2.91 (dd, J=7.6, 14.0 Hz, 1H) 3.05 (dd, J=4.4, 14.0 Hz, 1H) 3.57 (sept, J=6.0 Hz, 1H) 3.82 (s, 3H) 4.11 (dd, J=4.4, 7.6 Hz, 1H) 4.61 (d, J=6.0 Hz, 2H) 6.40 (br, 1H) 6.80 (d, J=8.4 Hz, 1H) 7.16 (dd, J=2.4, 8.4 Hz, 1H) 7.27 (d, J=2.4 Hz, 1H) 7.26 (s, 1H) 7.32 (s, 1H)

Example 329

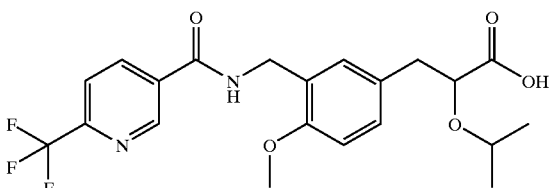

2-Isopropoxy-3-4-methoxy-3-[([6-(trifluoromethyl)-3-pyridyl]carbonylamino)methyl]phenylpropanoic acid was obtained by treatment in the same method as in Examples 1d) and 1e).

$^1$H-NMR(CDCl$_3$) δ: 1.05 (d, J=6.0 Hz, 3H) 1.16 (d, J=6.0 Hz, 3H) 2.93 (dd, J=7.2, 14.0 Hz, 1H) 3.04 (dd, J=4.4, 14.0 Hz, 1H) 3.59 (sept, J=6.0 Hz, 1H) 3.86 (s, 3H) 4.10 (dd, J=4.4, 7.2 Hz, 1H) 4.63 (d, J=6.0 Hz, 2H) 6.83 (d, J=8.4 Hz, 1H) 6.93 (bs, 1H) 7.17 (dd, J=2.0, 8.4 Hz, 1H) 7.22 (d, J=2.0 Hz, 1H) 7.75 (d, J=8.4 Hz, 1H) 8.29 (dd, J=1.2, 8.4 Hz, 1H) 9.02 (s, 1H)

Example 330

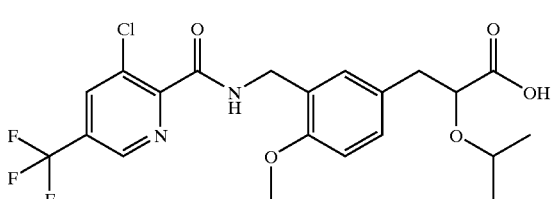

3-3-[([3-Chloro-5-(trifluoromethyl)-2-pyridyl]carbonylamino)methyl]-4-methoxyphenyl-2-isopropoxypropanoic acid was obtained.

$^1$H-NMR(CDCl$_3$) δ: 1.02 (d, J=6.0 Hz, 3H) 1.15 (d, J=6.0 Hz, 3H) 2.90 (dd, J=7.6, 14.0 Hz, 1H) 3.04 (dd, J=4.4, 14.0 Hz, 1H) 3.56 (sept, J=6.0 Hz, 1H) 3.86 (s, 3H) 4.09 (dd, J=4.4, 7.6 Hz, 1H) 4.61 (d, J=6.0 Hz, 2H) 6.82 (d, J=8.2 Hz, 1H) 7.15 (dd, J=2.0, 8.2 Hz, 1H) 7.23 (d, J=2.0 Hz, 1H) 8.05 (d, J=0.8 Hz, 1H) 8.14 (t, J=6.0 Hz, 1H) 8.70 (d, J=0.8 Hz, 1H)

Example 331

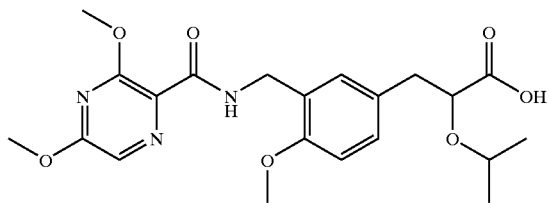

3-(3-[([2,4-Dimethoxy-5-pyrimidinyl)carbonyl]aminomethyl)-4-methoxyphenyl]-2-isopropoxypropanoic acid was obtained by treatment in the same method as in Examples 1d) and 1e).

¹H-NMR(CDCl₃) δ: 1.04 (d, J=6.0 Hz, 3H) 1.16 (d, J=6.0 Hz, 3H) 2.91 (dd, J=7.4, 14.0 Hz, 1H) 3.04 (dd, J=4.2, 14.0 Hz, 1H) 3.58 (sept, J=6.0 Hz, 1H) 3.89 (s, 3H) 4.10 (dd, J=4.2, 7.4 Hz, 1H) 4.60 (d, J=6.0 Hz, 2H) 6.82 (d, J=8.4 Hz, 1H) 7.14 (dd, J=2.0, 8.4 Hz, 1H) 7.19 (d, J=2.0 Hz, 1H) 7.96 (t, J=6.0 Hz, 1H) 9.10 (s, 1H)

Example 332

Production Example 332a

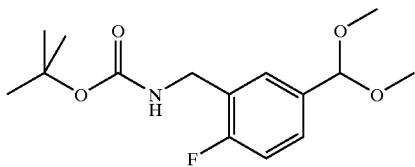

25 g of 3-bromo-4-fluorobenzaldehyde was dissolved in 300 ml methanol, then 40 g of trimethyl orthoformate and 3 g of p-toluenesulfonic acid were added, followed by heating under reflux for 6 hours. The reaction mixture was ice-cooled, and 5 g of sodium bicarbonate was added thereto. The reaction mixture was evaporated, and to the residue was added ethyl acetate. The organic layer was washed with water and brine, dried over anhydrous magnesium sulfate and the solvent was evaporated, to give 30 g of 2-bromo-4-(dimethoxymethyl)benzene was obtained. This crude product was dissolved in 300 ml tetrahydrofuran, followed by cooling to −78° C. in a nitrogen atmosphere. 60 ml butyl lithium (2.47 M solution in hexane) was added thereto. After stirring for 1 hr, 20 ml N,N-dimethylformamide was added thereto, and the mixture was heated to room temperature. Water was added to the reaction mixture, followed by extracting with ethyl acetate. The extract was dried over anhydrous magnesium sulfate and the solvent was evaporated, to give 25 g of 2-fluoro-5-(dimethoxymethyl) benzaldehyde. This crude product was dissolved in 200 ml ethanol, and 3.3 g of sodium borohydride was added under ice-cooling. After stirring at room temperature for 2 hours, water was added thereto and the mixture was extracted with ethyl acetate. The extract was dried over anhydrous magnesium sulfate and the solvent was evaporated, to give 25 g of 2-fluoro-5-(dimethoxymethyl)benzyl alcohol. This crude product was dissolved in 400 ml toluene, and 32 ml diphenyl phosphoryl azide and 22 ml diazabicyclo[5.4.0]undecene were added thereto, and the mixture was stirred at room temperature for 12 hours. Water was added to the reaction mixture, followed by extracting with ethyl acetate. The organic layer was washed with brine, dried over anhydrous magnesium sulfate and the solvent was evaporated, to give 30 g of 2-azidomethyl-4-(dimethoxymethyl)fluorobenzene. This crude product was dissolved in 500 ml tetrahydrofuran, and 50 ml water and 45 g triphenyl phosphine were added thereto, and the mixture was stirred at 50° C. for 3 hours. The solvent was evaporated, to give 70 g of 2-fluoro-5-(dimethoxymethyl)benzylamine. The crude product was dissolved in 200 ml N,N-dimethylformamide, and 55 g tertiary butyl dicarbonate and 43 ml triethylamine were added thereto, and the mixture was stirred at room temperature for 4 days. Water was added to the reaction mixture, followed by extracting with ethyl acetate. The organic layer was washed with brine, dried over anhydrous magnesium sulfate and the solvent was evaporated. The residue was subjected to silica gel column chromatography, and from fractions eluted with hexane-ethyl acetate (10:1→2:1), 30 g of tertiary butyl N-[5-(dimethoxymethyl)-2-fluorobenzyl]carbamate was obtained.

¹H-NMR(CDCl₃) δ: 1.44 (s, 9H) 3.30 (s, 6H) 4.36 (d, J=5.2 Hz, 2H) 4.90 (br, 1H) 5.34 (s, 1H) 7.02 (t, J=9.2 Hz, 1H) 7.16–7.46 (m,2H)

Production Example 332b

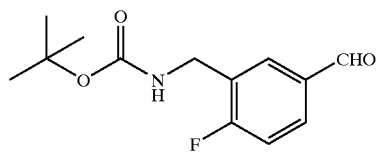

30 g of tertiary butyl N-(5-(dimethoxymethyl)-2-fluorobenzyl]carbamate was dissolved in 300 ml tetrahydrofuran, and 80 ml of 1 N hydrochloric acid was added thereto, and the mixture was stirred for 20 minutes under ice-cooling. Saturated aqueous sodium bicarbonate solution was added thereto, followed by extracting with ethyl acetate. The organic layer was washed with brine, dried over anhydrous magnesium sulfate and the solvent was evaporated, to give 25 g of tertiary butyl N-(2-fluoro-5-formyl)carbamate.

¹H-NMR(CDCl₃) δ: 1.45 (s, 9H) 4.43 (d, J=5.6 Hz, 2H) 4.98 (br, 1H) 7.19 (t, J=8.8 Hz, 1H) 7.79–7.85 (m, 1H) 7.90 (dd, J=2.0, 7.2 Hz, 1H)

Production Example 332c

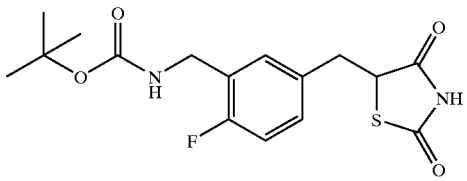

Tertiary butyl N-(2-fluoro-5-formyl)carbamate was treated in the same method as in Production Example 261, to give tertiary butyl N-5-[(2,4-dioxo-1,3-thiazolane-5-yl)methyl]-2-fluorobenzylcarbamate.

¹H-NMR(DMSO-d₆) δ: 1.38 (s, 9H) 3.06 (dd, J=9.2, 14.0 Hz, 1H) 3.34 (dd, J=4.0, 14.0 Hz, 1H) 4.12 (d, J=5.6 Hz, 2H) 4.81 (dd, J=4.0, 9.2 Hz, 1H) 7.05–7.20 (m, 2H) 7.35 (t, J=5.6 Hz, 1H) 7.93 (s, 1H)

Example 332d

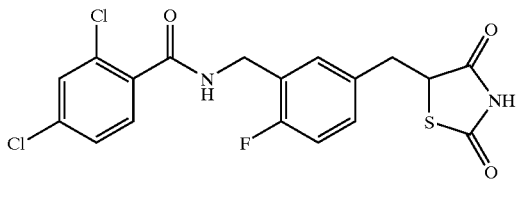

N1-5-[(2,4-Dioxo-1,3-thiazolane-5-yl)methyl]-2-fluorobenzyl-2,4-dichlorobenzamide was obtained by treatment in the same method as in Example 261.

$^1$H-NMR(CDCl$_3$) δ: 3.17 (dd, J=8.4, 14.4 Hz, 1H) 3.26 (dd, J=4.4, 14.4 Hz, 1H) 4.45 (dd, J=4.4, 8.4 Hz) 4.59 (d, J=36.0 Hz, 2H) 6.61 (br, 1H) 6.96 (t, J=9.2 Hz, 1H) 7.04–7.11 (m, 1H) 7.20–7.29 (m, 2H) 7.36 (d, J=2.0 Hz, 1H) 7.80 (d, J=8.4 Hz, 1H)

Example 333

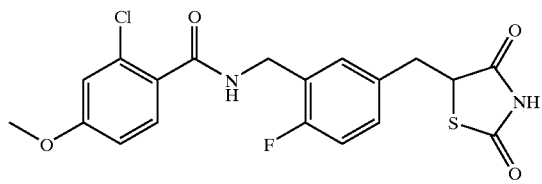

N1-5-[(2,4-Dioxo-1,3-thiazolane-5-yl)methyl]-2-fluorobenzyl-2-chloro-4-methoxybenzamide was obtained by treatment in the same method as in Example 261.

$^1$H-NMR(CDCl$_3$) δ: 3.15 (dd, J=8.6, 14.0 Hz, 1H) 3.32 (dd, J=4.2, 14.0 Hz, 1H) 3.76 (s, 3H) 4.44 (dd, J=4.2, 8.6 Hz, 1H) 4.59 (d, J=6.4 Hz, 2H) 6.76–6.86 (m, 3H) 6.95 (t, J=8.4 Hz, 1H) 7.03–7.08 (m, 1H) 7.27 (dd, J=2.0, 7.2 Hz, 1H) 7.69 (d, J=8.4Hz, 1H) 8.46 (br, 1H)

Example 334

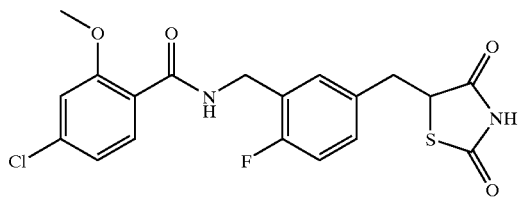

N1-5-[(2,4-Dioxo-1,3-thiazolane-5-yl)methyl]-2-fluorobenzyl-4-chloro-2-methoxybenzamide was obtained by treatment in the same method as in Example 261.

$^1$H-NMR(DMSO-d$_6$) δ: 3.07 (dd, J=8.8, 14.0 Hz, 1H) 3.34 (dd, J=4.4, 14.0 Hz, 1H) 3.90 (s, 3H) 4.47 (d, J=6.0 Hz, 2H) 4.82 (dd, J=4.4, 8.8 Hz, 1H) 7.00–7.30 (m, 5H) 7.70 (d, J=8.0 Hz, 1H) 8.63 (t, J=5.6 Hz, 1H) 12.03 (s, 1H)

Example 335

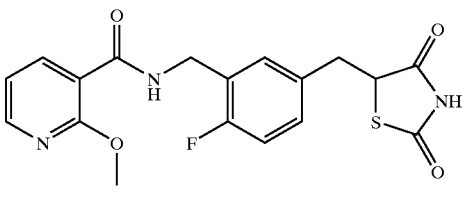

N3-5-[(2,4-Dioxo-1,3-thiazolane-5-yl)methyl]-2-fluorobenzyl-2-methoxynicotinamide was obtained by treatment in the same method as in Example 261.

$^1$H-NMR(CDCl$_3$) δ: 3.07 (dd, J=9.6, 14.0 Hz, 1H) 3.34 (dd, J=4.4, 14.0 Hz, 1H) 3.97 (s, 3H) 4.50 (d, J=6.0 Hz, 2H) 4.83 (dd, J=4.4, 9.2 Hz, 1H) 7.08–7.20 (m, 3H) 8.07–8.14 (m, 1H) 8.26–8.33 (m, 1H) 8.74 (t, J=6.0 Hz, 1H) 12.03 (s, 1H)

Example 336

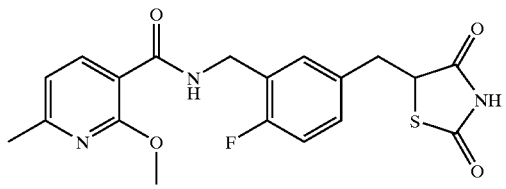

N3-5-[(2,4-Dioxo-1,3-thiazolane-5-yl)methyl]-2-fluorobenzyl-2-methoxy-6-methylnicotinamide was obtained by treatment in the same method as in Example 261.

$^1$H-NMR(CDCl$_3$) δ: 2.43 (3H, s) 3.07 (dd, J=9.4, 14.0 Hz, 1H) 3.40 (dd, J=4.0, 14.0 Hz, 1H) 3.96 (s, 3H) 4.49 (d, J=5.6 Hz, 2H) 4.82 (dd, J=4.0, 9.4 Hz, 1H) 6.94–7.00 (m, 1H) 7.10–7.30 (m, 3H) 8.02–8.10 (m, 1H) 8.64 (t, J=5.6 Hz, 1H) 12.02 (s, 1H)

Example 337

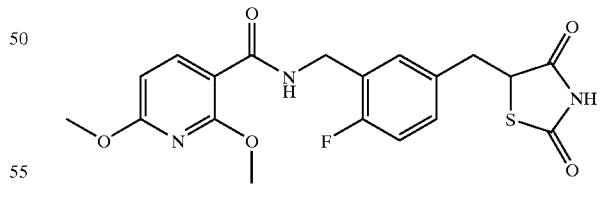

N3-5-[(2,4-Dioxo-1,3-thiazolane-5-yl)methyl]-2-fluorobenzyl-2,6-dimethoxynicotinamide was obtained by treatment in the same method as in Example 261.

$^1$H-NMR(CDCl$_3$) δ: 3.02–3.10 (m, 1H) 3.27–3.36 (m, 1H) 3.90 (d, J=2.0 Hz, 3H) 4.10 (d, J=2.0 Hz, 3H) 4.49 (d, J=5.6 Hz, 2H) 4.79–4.84 (m, 1H) 6.48 (d, J=8.0 Hz, 1H) 7.08–7.27 (m, 3H) 8.13 (d, J=8.0 Hz, 1H) 8.48 (t, J=5.6 Hz, 1H) 12.01 (s, 1H)

Example 338

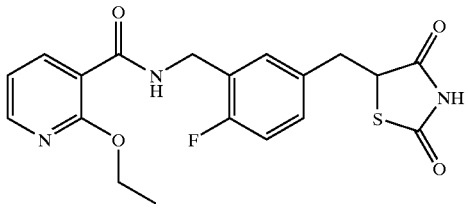

N3-5-[(2,4-Dioxo-1,3-thiazolane-5-yl)methyl]-2-fluorobenzyl-2-ethoxynicotinamide was obtained by treatment in the same method as in Example 261.

$^1$H-NMR(DMSO-d$_6$) δ: 1.33 (t, J=7.2 Hz, 3H) 3.07 (dd, J=9.6, 14.0 Hz, 1H) 3.35 (dd, J=4.4, 14.0 Hz, 1H) 4.43 (q, J=7.2 Hz, 2H) 4.49 (d, J=5.6 Hz, 2H) 4.85 (dd, J=4.4, 9.6 Hz, 1H) 7.06–7.30 (m, 4H) 8.12 (dd, J=2.0, 7.6 Hz, 1H) 8.27 (dd, J=2.0, 4.8 Hz, 1H) 8.63 (t, J=5.6 Hz, 1H)

Example 339

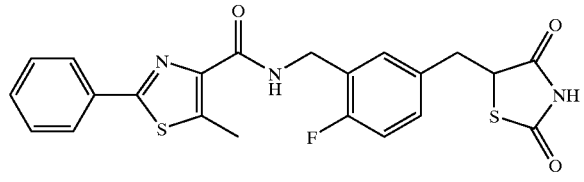

N4-5-[(2,4-Dioxo-1,3-thiazolane-5-yl)methyl]-2-fluorobenzyl-5-methyl-2-phenyl-1,3-thiazole-4-carboxamide was obtained by treatment in the same method as in Example 261.

$^1$H-NMR(DMSO-d$_6$) δ: 2.61 (s, 3H) 3.09 (dd, J=9.6, 14.0 Hz, 1H) 3.35 (dd, J=4.4, 14.0 Hz, 1H) 4.44 (d, J=5.6 Hz, 2H) 4.85 (dd, J=4.4, 9.6 Hz, 1H) 7.10–7.29 (m, 3H) 7.46–7.55 (m, 3H) 7.90–7.96 (m, 2H) 8.81 (t, J=5.6 Hz, 1H) 12.03(s, 1H)

Example 340

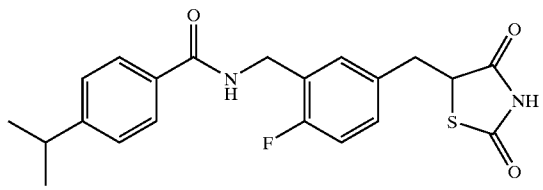

N1-5-[(2,4-Dioxo-1,3-thiazolane-5-yl)methyl]-2-fluorobenzyl-4-isopropylbenzamide was obtained by treatment in the same method as in Example 261.

$^1$H-NMR(CDCl$_3$) δ: 1.25 (d, J=7.2 Hz, 6H) 2.94 (sept, J=7.2 Hz, 1H) 3.19 (dd, J=8.8, 14.0 Hz, 1H) 3.36 (dd, J=4.4, 14.0 Hz, 1H) 4.50 (dd, J=4.4, 8.8 Hz, 1H) 4.64 (d, J=6.0 Hz, 2H) 6.61 (t, J=6.0 Hz, 1H) 7.00 (dd, J=8.6, 9.6 Hz, 1H) 7.08–7.14 (m, 1H) 7.25–7.35 (m, 3H) 7.68–7.74 (m, 2H) 9.04 (br, 1H)

Example 341

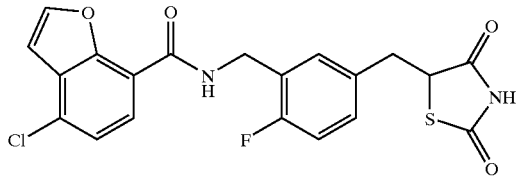

N7-5-[(2,4-Dioxo-1,3-thiazolane-5-yl)methyl]-2-fluorobenzyl-4-chlorobenzo[b]furan-7-carboxamide was obtained by treatment in the same method as in Example 261.

$^1$H-NMR(CDCl$_3$) δ: 3.19 (dd, J=8.8, 14.0 Hz, 1H) 3.39 (dd, J=4.4, 14.0 Hz, 1H) 4.50 (dd, J=4.4, 8.8 Hz, 1H) 4.76 (d, J=6.0 Hz, 2H) 6.98 (d, J=2.0 Hz, 1H) 7.03 (t, J=9.0 Hz, 1H) 7.10–7.16 (m, 1H) 7.30–7.42 (m, 2H) 7.77 (d, J=2.0 Hz, 1H) 7.83 (t, J=6.0 Hz, 1H) 8.06 (d, J=8.8 Hz, 1H)

Example 342

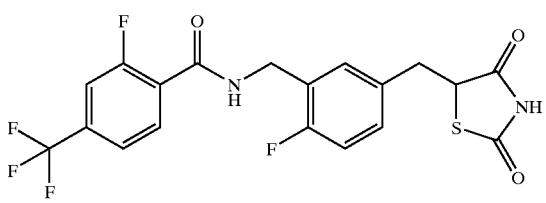

N1-5-[(2,4-Dioxo-1,3-thiazolane-5-yl)methyl]-2-fluorobenzyl-2-fluoro-4-(trifluoromethyl)benzamide was obtained by treatment in the same method as in Example 261.

$^1$H-NMR(CDCl$_3$) δ: 3.14 (dd, J=8.8, 14.0 Hz, 1H) 3.33 (dd, J=4.4, 14.0 Hz, 1H) 4.44 (dd, J=4.4, 8.8 Hz, 1H) 4.62 (d, J=5.6 Hz, 2H) 6.97 (t, J=9.0 Hz, 1H) 7.04–7.16 (m, 2H) 7.23(dd,J=2.2,7.2 Hz,1H) 7.35(d, J=11.6 Hz, 2H) 7.48(d, J=8.0 Hz, 1H) 8.17(t, J=8.0 Hz, 1H)

Example 343

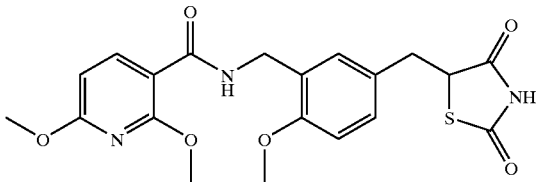

N3-5-[(2,4-Dioxo-1,3-thiazolane-5-yl)methyl]-2-methoxybenzyl-2,6-dimethoxynicotinamide was obtained by treatment in the same method as in Example 261.

$^1$H-NMR(DMSO-d$_6$) δ: 3.00 (dd, J=9.6, 14.0 Hz, 1H) 3.28 (dd, J=4.4, 14.0 Hz, 1H) 3.84 (s, 3H) 3.91 (s, 3H) 4.03 (s, 3H) 4.42 (d, J=5.6 Hz, 2H) 4.80 (dd, J=4.0, 9.6 Hz, 1H) 6.49 (d, J=8.4 Hz, 1H) 6.95 (d, J=8.4 Hz, 1H) 7.06–7.15 (m, 2H) 8.17 (d, J=8.4 Hz, 1H) 8.40 (t, J=5.6 Hz, 1H)

Example 344

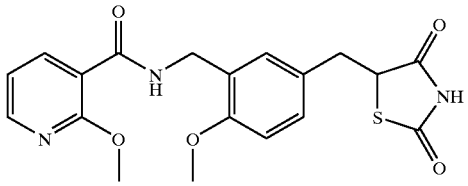

N3-5-[(2,4-Dioxo-1,3-thiazolane-5-yl)methyl]-2-methoxybenzyl-2-methoxynicotinamide was obtained by treatment in the same method as in Example 261.

¹H-NMR(DMSO-d₆) δ: 3.03 (dd, J=9.6, 14.0 Hz, 1H) 3.30 (dd, J=4.0, 14.0 Hz, 1H) 3.87 (s, 3H) 3.99 (s, 3H) 4.43 (d, J=6.0 Hz, 2H) 4.80 (dd, J=4.0, 9.6 Hz, 1H) 6.95 (d, J=8.8 Hz, 1H) 7.05–7.20 (m, 3H) 8.13–8.20 (m, 1H) 8.27–8.33 (m, 1H) 8.63 (t, J=6.0 Hz, 1H) 12.01 (br, 1H)

Example 345

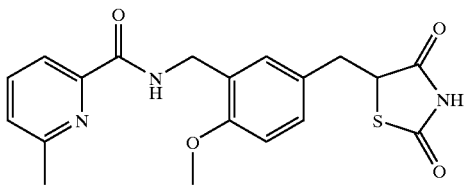

N2-5-[(2,4-Dioxo-1,3-thiazolane-5-yl)methyl]-2-methoxybenzyl-6-methyl-2-pyridinecarboxamide was obtained by treatment in the same method as in Example 261.

¹H-NMR(DMSO-d₆) δ: 2.54(s, 3H) 2.98(dd, J=9.6, 14.0 Hz, 1H) 3.24–3.31 (m, 1H) 3.82 (s, 3H) 4.44 (d, J=6.4 Hz, 2H) 4.79 (dd, J=4.4, 9.6 Hz, 1H) 6.95 (d, J=8.4 Hz, 1H) 7.05 (d, J=1.6 Hz, 1H) 7.11 (dd, J=1.6, 8.4 Hz, 1H) 7.45 (dd, J=1.6, 6.8 Hz, 1H) 7.80–7.90 (m, 2H) 8.85 (t, J=6.4 Hz, 1H) 11.99 (br, 1H)

Example 346

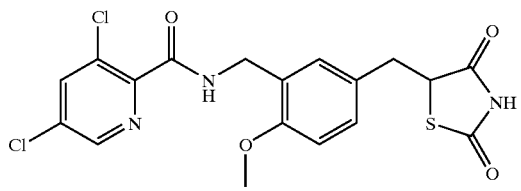

N2-5-[(2,4-Dioxo-1,3-thiazolane-5-yl)methyl]-2-methoxybenzyl-3,5-dichloro-2-pyridinecarboxamide was obtained by treatment in the same method as in Example 261.

¹H-NMR(DMSO-d₆) δ: 2.98(dd, J=9.6, 14.0 Hz, 1H) 3.30(dd, J=4.6, 14.0 Hz, 1H) 3.79 (s, 3H) 4.38 (d, J=6.0 Hz, 2H) 4.78 (dd, J=4.6, 9.6 Hz, 1H) 6.94 (d, J=8.2 Hz, 1H) 7.13(d, J=8.2 Hz, 1H) 7.15 (s, 1H) 8.35 (d, J=2.0 Hz, 1H) 8.64(s, 1H) 8.94 (t, J=6.0 Hz, 1H) 12.02 (br, 1H)

Example 347

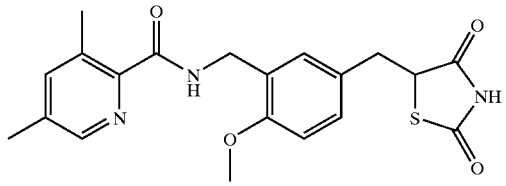

N2-5-[(2,4-Dioxo-1,3-thiazolane-5-yl)methyl]-2-methoxybenzyl-3,5-dimethyl-2-pyridinecarboxamide was obtained by treatment in the same method as in Example 261.

¹H-NMR(DMSO-d₆) δ: 2.31 (s, 3H) 2.52 (s, 3H) 2.97 (dd, J=9.6, 14.0 Hz, 1H) 3.28 (dd, J=3.8, 14.0 Hz, 1H) 3.80 (s, 3H) 4.38 (d, J=6.4 Hz, 2H) 4.77 (dd, J=3.8, 9.6 Hz, 1H) 6.93 (d, J=8.4 Hz, 1H) 7.06 (s, 1H) 7.10 (d, J=8.4 Hz, 1H) 7.55 (s, 1H) 8.28 (s, 1H) 8.79 (t, J=6.4 Hz, 1H)

Example 348

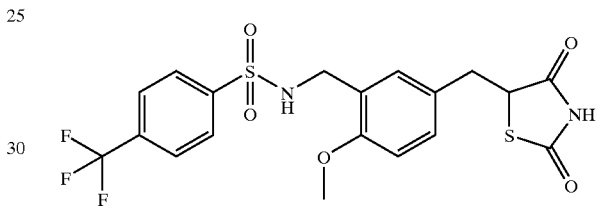

N1-5-[(2,4-Dioxo-1,3-thiazolane-5-yl)methyl]-2-methoxybenzyl-4-(trifluoromethyl)-1-benzenesulfamide was obtained by treatment in the same method as in Example 261.

¹H-NMR(DMSO-d₆) δ: 3.03 (dd, J=9.0, 14.0 Hz, 1H) 3.30 (dd, J=4.0, 14.0 Hz, 1H) 3.69 (s, 3H) 4.16 (d, J=6.4 Hz, 2H) 4.46 (dd, J=4.0, 9.6 Hz, 1H) 5.59 (t, J=6.4 Hz, 1H) 6.63 (d, J=8.4 Hz, 1H) 6.95 (d, J=2.0 Hz, 1H) 7.03 (dd, J=2.0, 8.4 Hz, 1H) 7.64 (d, J=8.4 Hz, 2H) 7.85 (d, J=8.4 Hz, 2H) 8.95 (s, 1H)

Example 349

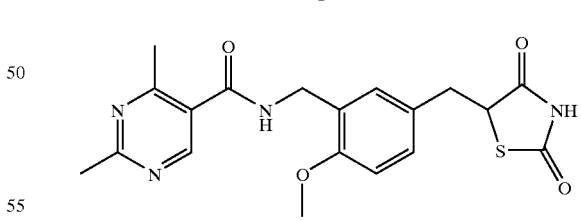

N5-5-[(2,4-Dioxo-1,3-thiazolane-5-yl)methyl]-2-methoxybenzyl-2,4-dimethyl-5-pyrimidinecarboxamide was obtained by treatment in the same method as in Example 261.

¹H-NMR (DMSO-d₆) δ: 3.14 (s, 6H) 3.03 (dd, J=9.6, 14.0 Hz, 1H) 3.30 (dd, J=4.4, 14.0 Hz, 1H) 3.79 (s, 3H) 4.36–4.40 (mn, 2H) 4.82 (dd, J=4.4, 9.6 Hz, 1H) 6.94 (d, J=8.8 Hz, 1H) 7.06–7.16 (m, 2H) 8.63 (s, 1H) 8.88 (t, J=5.6 Hz, 1H) 12.00 (br, 1H)

Example 350

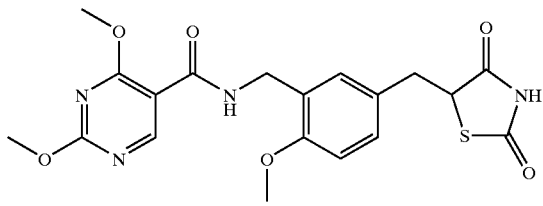

N5-5-[(2,4-Dioxo-1,3-thiazolane-5-yl)methyl]-2-methoxybenzyl-2,4-dimethyl-5-pyrimidinecarboxamide was obtained by treatment in the saine method as in Example 261.

$^1$H-NMR(DMSO-d$_6$) δ: 3.00 (dd, J=9.6, 14.0 Hz, 1H) 3.28 (dd, J=4.0, 14.0 Hz, 1H) 3.82 (s, 3H) 3.94 (s, 3H) 4.03 (s, 3H) 4.40 (d, J=6.0 Hz, 2H) 4.79 (dd, J=4.0, 9.6 Hz, 1H) 6.94 (d, J=8.4 Hz, 1H) 7.05–7.15 (m, 2H) 8.36 (t,J=6.0 Hz,1H) 8.72 (s,1H) 12.00 (br,1H)

Example 351

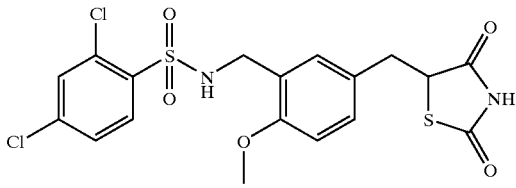

N1-5-[(2,4'-Dioxo-1,3-thiazolane-5-yl)methyl]-2-methoxybenzyl-2,4-dichloro-1-benzenesulfonamide was obtained by treatment in the same method as in Example 261.

$^1$H-NMR((DMSO-d$_6$) δ: 2.96 (dd, J=9.2, 14.4 Hz, 1H) 3.26 (dd, J=4.0, 14.4 Hz, 1H) 3.79 (s, 3H) 4.15 (d, J=5.6 Hz, 2H) 4.39 (dd, J=4.0, 9.2 Hz, 1H) 5.82 (t, J=5.6 Hz, 1H) 6.67 (d, J=8.4 Hz, 1H) 6.70 (s, 1H) 7.02 (d, J=8.4 Hz, 1H) 7.28 (d, J=8.4 Hz, 1H) 7.88 (d, J=8.4 Hz, 1H) 8.16 (br, 1H)

What is claimed is:

1. A compound represented by the following formula (I), a salt thereof, an ester thereof or a hydrate thereof

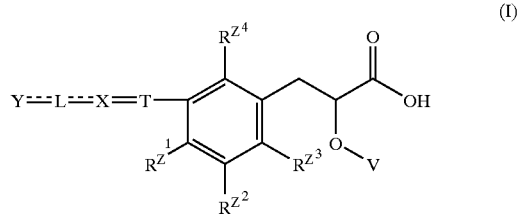

in the formula (I):

Y represents phenyl, pyridyl, pyrimidinyl, pyrazinyl, imidazolyl, pyrazolyl, oxazolyl, isoxazolyl, thiazolyl, benzofuryl, quinolyl, isoquinolyl or cycloalkyl group, which may have one or more substituents selected from the group consisting of a halogen atom, nitrile group, alkyl group, alkoxy group, halogenoalkyl group, cycloalkyl group, cycloalkyloxy group and aryl group;

L represents a single bond or a $C_{1-6}$ alkylene group, $C_{2-6}$ alkenylene group or $C_{2-6}$ alkynylene group, each of which may have one or more substituents selected from the group consisting of a halogen atom, nitrile group, alkyl group, alkoxy group, halogenoalkyl group, cycloalkyl group, cycloalkyloxy group and aryl group;

X represents oxygen atom or a group represented by the formula —CONH—, —NHCO—, —SO$_2$NH or —NHSO$_2$—;

T represents a single bond or a $C_{1-13}$ alkylene group, which may have one or more substituents selected from the group consisting of a halogen atom, nitrile group, alkyl group, alkoxy group, halogenoalkyl group, cycloalkyl group, cycloalkyloxy group and aryl group;

----- represents a single or double bond;

each of $R^{Z1}$, $R^{Z2}$, $R^{Z3}$ and $R^{Z4}$ is a hydrogen atom, a halogen atom, nitrile group, alkyl group, alkoxy group, halogenoalkyl group, cycloalkyl group, cycloalkyloxy group or aryl group, or $R_{Z1}$ and $R^{Z2}$ form a benzofuran ring together with the benzene ring bounded thereto; and V is a $C_{2-3}$ alkyl group;

provided that the case where T is a single bond, then X is not an oxygen atom and when T is a single bond, then X is not —NHCO— and L is not a $C_{1-6}$ alkylene group.

2. The compound according to claim 1, a salt thereof, an ester thereof or a hydrate thereof, wherein in the formula (I), $R^{Z1}$ is an alkoxy group, cycloalkyloxy group or aryl group.

3. The compound according to claim 1, a salt thereof, an ester thereof or a hydrate thereof, wherein in the formula (I), $R^{Z2}$, $R^{Z3}$ and $R^{Z4}$ are hydrogen atoms.

4. The compound according to claim 1, a salt thereof, an ester thereof or a hydrate thereof, wherein in the formula (I), V is an isopropyl group.

5. The compound according to claim 1, a salt thereof, an ester thereof or a hydrate thereof, wherein in the formula (I), Y is a phenyl, pyridyl, pyrimidinyl, imidazolyl, pyrazolyl, isoxazolyl or thiazolyl group.

6. The compound according to claim 1, a salt thereof, an ester thereof or a hydrate thereof, wherein in the formula (I), Y is a phenyl group.

7. The compound according to claim 1, a salt thereof, an ester thereof or a hydrate thereof, wherein in the formula (I), L is a single bond.

8. The compound according to claim 1, a salt thereof, an ester thereof or a hydrate thereof, wherein in the formula (I), X is a group represented by t he formula —CONH— or —NHCO—.

9. The compound according to claim 1, a salt thereof, an ester thereof or a hydrate thereof, wherein in the formula (I), X is a group represented by the formula —CONH—.

10. The compound according to claim 1, a salt thereof, an ester thereof or a hydrate thereof, wherein in the formula (I), T is a $C_{1-3}$ alkylene group.

11. The compound according to claim 1, 5, 6, 8, or 9, a salt thereof, an ester thereof or a hydrate thereof, wherein in the formula (I), X is a group represented by the formula —CONH—; and Y is a phenyl, pyridyl, pyrimidinyl, imidazolyl, pyrazolyl, isoxazolyl, thiazolyl group.

12. The compound according to claim 1, a salt thereof, an ester thereof or a hydrate thereof, wherein the compound represented by the formula (I) is one selected from the group consisting of:

(2S)-3-[3-([2,4-dichlorobenzoyl]aminomethyl)-4-methoxyphenyl]-2-isopropoxy propanoic acid and (2S)-3-[3-([2-fluoro-4-(trifluoromethyl)benzoyl]-aminomethyl)-4-methoxyphenyl)-2-isopropoxypropanoic acid.

13. The compound according to claim 1 or 12, a salt thereof, an ester thereof or a hydrate thereof, wherein the compound represented by the formula (I) is (2S)-3-[3-([2,4-dichlorobenzoyl]aminomethyl)-4-methoxyphenyl]-2-isopropoxy propanoic acid.

14. A pharmaceutical composition comprising a carboxylic acid compound represented by the following formula, a salt thereof, an ester thereof or a hydrate thereof

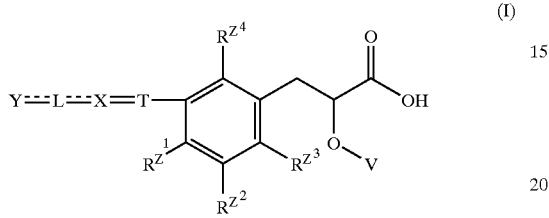

in the formula, Y represents phenyl, pyridyl, pyrimidinyl, pyrazinyl, imidazolyl, pyrazolyl, oxazolyl, isoxazolyl, thiazolyl, benzofuryl, quinolyl, isoquinolyl or cycloalkyl group, which may have one or more substituents selected from the group consisting of a halogen atom, nitrile group, alkyl group, alkoxy group, halogenoalkyl group, cycloalkyl group, cycloalkyloxy group and aryl group;

L represents a single bond or a $C_{1-6}$ alkylene group, $C_{2-6}$ alkenylene group or $C_{2-6}$ alkynylene group, each of which may have one or more substituents selected from the group consisting of a halogen atom, nitrile group, alkyl group, alkoxy group, halogenoalkyl group, cycloalkyl group, cycloalkyloxy group and aryl group;

X represents an oxygen atom or a group represented by the formula —CONH—, —NHCO—, —SO$_2$NH or —NHSO—;

T represents a single bond or a $C_{1-3}$ alkylene group, which may have one or more substituents selected from the group consisting of a halogen atom, nitrile group, alkyl group, alkoxy group, halogenbalkyl group, cycloalkyl group, cycloalkyloxy group and aryl group;

represents a single or double bond;

each of $R^{Z1}$, $R^{Z2}$, $R^{Z3}$ and $R^{Z4}$ is a hydrogen atom, a halogen atom, nitrile group, alkyl group, alkoxy group, halogenoalkyl group, cycloalkyl group, cycloalkyloxy group or aryl group, or $R^{Z1}$ and $R^{Z2}$ form a benzofuran ring together with the benzene ring bounded thereto; and V is a $C_{2-3}$ alkyl group;

provided that the case where T is a single bond, then X is not an oxygen atom and when T is a single bond, then X is not —NHCO— and L is not a $C_{1-6}$ alkylene group;

and a pharmaceutically acceptable carrier.

15. The pharmaceutical composition according to claim 14, which is based on PPAR α and γ dual agonism.

16. The pharmaceutical composition according to claim 14, which is based on PPAR α, β and γ triple agonism.

17. A method for treating diseases against which PPAR α and γ dual agonism or PPAR α, β and γ triple agonism is efficacious, by administering a pharmacologically effective amount of the compound according to claim 1, a salt thereof, an ester thereof or a hydrate thereof to a patient in need thereof.

18. The method of claim 17, wherein the disease is selected from the group consisting of diabetes mellitus and X syndromes.

19. A method of improving insulin resistance comprising administering an effective amount of the compound of claim 1 to a patient in need thereof.

* * * * *